US012435083B2

(12) United States Patent
Herlé et al.

(10) Patent No.: US 12,435,083 B2
(45) Date of Patent: Oct. 7, 2025

(54) CYCLOPROPYL-(HETERO)ARYL-SUBSTITUTED ETHYLSULPHONYL-PYRIDINE DERIVATIVES

(71) Applicants: BOEHRINGER INGELHEIM VETMEDICA GMBH, Ingelheim am Rhein (DE); NIHON NOHYAKU CO., LTD., Tokyo (JP)

(72) Inventors: Bart Herlé, Biberach an der Riss (DE); Hannes Fiepko Koolman, Biberach an der Riss (DE); Alan Long, Biberach an der Riss (DE); Robin Meier, Biberach an der Riss (DE); Ikki Yonemura, Osaka (JP); Julien Gagnepain, Ummendorf (DE)

(73) Assignees: Boehringer Ingelheim Vetmedica Gmbh, Ingelheim am Rhein (DE); Nihon Nohyaku Co., Ltd., Tokyo (JP)

( * ) Notice: Subject to any disclaimer, the term of this patent is extended or adjusted under 35 U.S.C. 154(b) by 70 days.

(21) Appl. No.: 17/930,882

(22) Filed: Sep. 9, 2022

(65) Prior Publication Data

US 2023/0234951 A1 Jul. 27, 2023

Related U.S. Application Data

(60) Provisional application No. 63/243,561, filed on Sep. 13, 2021.

(30) Foreign Application Priority Data

Sep. 23, 2021 (EP) .................................... 21198461

(51) Int. Cl.

| | |
|---|---|
| ***C07D 471/04*** | (2006.01) |
| ***C07D 401/04*** | (2006.01) |
| ***C07D 401/14*** | (2006.01) |
| ***C07D 413/04*** | (2006.01) |
| ***C07D 413/14*** | (2006.01) |
| ***C07D 417/04*** | (2006.01) |
| ***C07D 487/04*** | (2006.01) |
| ***C07D 498/04*** | (2006.01) |
| ***C07D 513/04*** | (2006.01) |

(52) U.S. Cl.

CPC ......... *C07D 471/04* (2013.01); *C07D 401/04* (2013.01); *C07D 401/14* (2013.01); *C07D 413/04* (2013.01); *C07D 413/14* (2013.01); *C07D 417/04* (2013.01); *C07D 487/04* (2013.01); *C07D 498/04* (2013.01); *C07D 513/04* (2013.01)

(58) Field of Classification Search

CPC .. C07D 471/04; C07D 401/04; C07D 401/14; C07D 413/04; C07D 413/14; C07D 417/04; C07D 487/04; C07D 498/04; C07D 513/04

See application file for complete search history.

(56) References Cited

U.S. PATENT DOCUMENTS

| | | | |
|---|---|---|---|
| 9,809,587 | B2 | 11/2017 | Stoller et al. |
| 2020/0045975 | A1 | 2/2020 | Sano et al. |
| 2020/0361940 | A1 | 11/2020 | Yamauchi et al. |

FOREIGN PATENT DOCUMENTS

| | | | | |
|---|---|---|---|---|
| EP | 4029570 A1 | 7/2022 | | |
| EP | 4029571 A1 | 7/2022 | | |
| JP | 2017526678 A | 9/2017 | | |
| JP | 2018076354 A | 5/2018 | | |
| WO | WO-2010021680 A2 * | 2/2010 | ......... C07D 491/107 | |
| WO | 2015071180 A1 | 5/2015 | | |
| WO | 2016039441 A1 | 3/2016 | | |
| WO | WO-2016030229 A1 * | 3/2016 | ............. A01N 43/90 | |
| WO | 2016059145 A1 | 4/2016 | | |
| WO | 2016071214 A1 | 5/2016 | | |

(Continued)

OTHER PUBLICATIONS

Wang Shuo, et al. Reductive Ring-Opening 1,3-Difunctionalizations of Arylcyclopropanes with Sodium Metal, SYNLETT, vol. 32, No. 02, Jan. 12, 2021 (Jan. 21, 2021), pp. 219-223, XP093008698, DE ISSN:0936-5214, DOI:10.1055/s-0040-1706538 compound 2 in Table 2.

(Continued)

*Primary Examiner* — Joseph K McKane
*Assistant Examiner* — Ashli Ariana Chicks
(74) *Attorney, Agent, or Firm* — Edell, Shapiro & Finnan, LLC

(57) ABSTRACT

The present invention relates to cyclopropyl-(hetero)aryl substituted ethylsulphonyl-pyridine derivatives of formula (1)

(I)

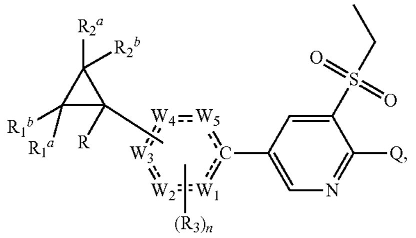

wherein the variables are as defined in the description and in the claims, which can be used as antiparasitic agents for the treatment, prevention and/or control of parasitic infections and/or infestations in animals.

32 Claims, No Drawings

(56) References Cited

FOREIGN PATENT DOCUMENTS

| | | | | |
|---|---|---|---|---|
| WO | 2017064628 | A1 | 4/2017 | |
| WO | 2017146221 | A1 | 8/2017 | |
| WO | 2018077565 | A1 | 5/2018 | |
| WO | 2018095795 | A1 | 5/2018 | |
| WO | 2018098499 | A1 | 5/2018 | |
| WO | 2018206348 | A1 | 11/2018 | |
| WO | 2019219689 | A1 | 11/2019 | |
| WO | 2019229089 | A1 | 12/2019 | |
| WO | 2019234158 | A1 | 12/2019 | |
| WO | 2020084075 | A1 | 4/2020 | |
| WO | 2020141136 | A1 | 7/2020 | |
| WO | 2020178789 | A1 | 9/2020 | |
| WO | 2020182577 | A1 | 9/2020 | |
| WO | WO-2021033141 | A1 * | 2/2021 | ........... C07D 401/04 |
| WO | 2021049595 | A1 | 3/2021 | |
| WO | 2021049596 | A1 | 3/2021 | |
| WO | 2021085370 | A1 | 5/2021 | |
| WO | 2022253841 | A1 | 12/2022 | |
| WO | 2023036934 | A1 | 3/2023 | |

OTHER PUBLICATIONS

Shyh-Ming Yang et al: :Discovery of Orally Bioavailable, Quinoline-Based Aldehyde Dehydrogenase 1A1 (ALDH1A1) Inhibitors with Potent Cellular Activity, Journal of Medicinal Chemistry, vol. 61, No. 11, May 16, 2018 (May 16, 2018), pp. 4883-4903, XP055536029, US issn: 0022-2623, DOI: 10.2021/acs.jmedchem.8b00270 compound in Scheme 2, step (e).

Abstract JP2018076354A.

Abstract WO2016039441A1.

Abstract WO2021085370A1.

* cited by examiner

CYCLOPROPYL-(HETERO)ARYL-SUBSTITUTED ETHYLSULPHONYL-PYRIDINE DERIVATIVES

INCORPORATION BY REFERENCE

All references cited herein, are incorporated by reference herein, in their entirety.

BACKGROUND OF THE INVENTION

A. Field of the Invention

The present invention relates to the field of animal health, in particular to new cyclopropyl-(hetero)aryl substituted ethylsulphonyl-pyridine derivatives as antiparasitic compounds as well as pharmaceutical compositions containing the same, and methods of using the same as antiparasitic agents for the treatment, prevention and/or control of parasitic infections and/or infestations in animals.

B. Background and Description of the Related Art

Animals, such as mammals and birds are often susceptible to parasite infestations/infections. These parasites may be ectoparasites, such as insects, and endoparasites such as filariae and other worms. Domesticated animals, such as cats and dogs, are often infested with one or more of the following ectoparasites: fleas (e.g. *Ctenocephalides* spp., such as *Ctenocephalides felis* and the like), ticks (e.g. *Rhipicephalus* spp., *Ixodes* spp., *Dermacentor* spp., Amblyoma spp., and the like), mites (e.g. *Demodex* spp., *Sarcoptes* spp., Otodectes spp., and the like), lice (e.g. *Trichodectes* spp., *Cheyletiella* spp., *Linognathus* spp. and the like), mosquitoes (*Aedes* spp., *Culex* spp., *Anopheles* spp. and the like) and flies (Hematobia spp.,*Musca* spp., *Stomoxys* spp., Dematobia spp., Cocliomyia spp. and the like).

Fleas are a particular problem because not only do they adversely affect the health of the animal or human, but they also cause a great deal of psychological stress. Moreover, fleas are also vectors of pathogenic agents in animals and humans, such as dog tapeworm (*Dipylidium caninum*).

Similarly, ticks are also harmful to the physical and psychological health of the animal or human. However, the most serious problem associated with ticks is that they are the vector of pathogenic agents in both humans and animals. Major diseases which are caused by ticks include borrelioses (Lyme disease caused by *Borrelia burgdorferi*), babesioses (or piroplasmoses caused by *Babesia* spp.) and rickettsioses (also known as Rocky Mountain spotted fever). Ticks also release toxins which cause inflammation or paralysis in the host. Occasionally, these toxins are fatal to the host.

Likewise, farm animals are also susceptible to parasite infestations. For example, cattle are affected by a large number of parasites. A parasite which is very prevalent among farm animals is the tick genus *Boophilus*, especially those of the species *microplus* (cattle tick), *decoloratus* and *annulatus*. Ticks, such as *Rhipicephalus microplus* (formerly *Boophilus microplus*), are particularly difficult to control because they live in the pasture where farm animals graze.

Currently available insecticidal and acaricidal treatments for animals do not always demonstrate good activity, good speed of action, or a long duration of action. Most treatments contain hazardous chemicals that can have serious consequences, including neurotoxicity and lethality from accidental ingestion. Persons applying these agents are generally advised to limit their exposure. Pet collars and tags have been utilized to overcome some problems, but these are susceptible to chewing, ingestion, and subsequent toxicological effects to the animal. Thus, current treatments achieve varying degrees of success, which depend partly on toxicity, method of administration, and efficacy. Additionally, some currently available agents are becoming ineffective due to parasitic resistance.

Further related art is as follows:

WO 2016/030229 discloses compounds and the agrochemically acceptable salts, stereoisomers, enantiomers, tautomers and N-oxides of those compounds, which can be used as insecticides and can be prepared in a manner known per se. This patent family also discloses one of the structurally closest prior art compounds designated as compound (C) below.

WO 2017/146221 and US 2020/0361940 disclose condensed heterocyclic compounds having bonded heterocycles and the salts of said compound. Further provided are an agricultural/horticultural insecticide having said compound as an active ingredient, and a method for using the agricultural/horticultural insecticide.

JP 2018/076354 discloses pest control compositions, which contain a compound represented by the formula and at least one component selected from group insecticides, acaricides, and nematicides, bactericides, plant growth regulators, phytotoxicity reducing agents, synergists, repellents, molluscicides, insect pheromone agents, herbicides, and microbial materials. This patent family also discloses one of the structurally closest prior art compounds designated as compound (D) below.

WO 2020/178789 discloses fused heterocyclic compound as well as methods for their preparation and use of the fused heterocyclic compounds as a pest control agent. This patent family also discloses one of the structurally closest prior art compounds designated as compound (B) below.

WO 2021/033141 discloses fused heterocyclic compounds as well as methods for their preparation and use of the compounds as a pest control agent. This patent family also discloses one of the structurally closest prior art compounds designated as compound (A) below.

WO 2021/049595 discloses condensed heterocyclic compounds having a substituted cyclopropane oxadiazole group or a salt thereof; an agricultural or horticultural pesticide having said compound or a salt thereof as an active component; an ectoparasite or endoparasite control agent for animals; and a method for using the same.

WO 2021/049596 discloses imidazopyridazine compounds having a substituted cyclopropane oxadiazole group or salts thereof; an agricultural and horticultural insecticide and an animal endo- and ecto-parasite controlling agent, which contain said compound or salts thereof as an active ingredient; and usage methods of the same.

Despite the availability of effective, broad spectrum antiparasitics, there remains a need for safer and more convenient, efficacious, and environmentally friendly products that will overcome the ever-present threat of resistance development. There is a need for improved antiparasitics, and in particular there is a need for improved insecticides and acaricides, particularly for use in animal health. Furthermore, there is a need for improved topical and oral products with convenient administration. Still further, there is a need for improved compositions which contains one or more active antiparasitics, which can be used to effectively treat against parasites. Such improvements would be particularly useful for the treatment of animals including companion animals (e.g., cats, dogs, llamas, and horses) and livestock (e.g., cattle, bison, swine, sheep, deer, elk, and goats).

Starting from the structurally closest prior art compounds (A), (B), (C) and (D) as depicted herein there is a need for improved antiparasitics that are more potent/efficacious against in particular ectoparasites fleas and/or ticks. It is important to note that compounds that show better activity versus ticks are more desirable in the animal health field, as ticks are more difficult to control than fleas.

SUMMARY OF THE INVENTION

The present invention solves the problems inherent in the related art and provides a distinct advance in the state of the art.

The present invention concerns a compound of formula (I)

(I)

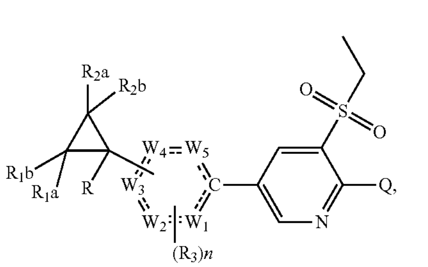

wherein:

- W1, W2, W3, W4, W5 are each independently N, C or C—H, wherein at most three of W1, W2, W3, W4, W5 are N;

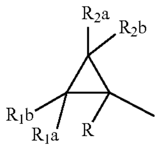

is attached to a C atom;

- R, R1a, R1b, R2a, R2b, R3 are each independently hydrogen, halogen, such as F, Cl, Br, I, $C_1$-$C_6$-alkyl, such as $CH_3$, $C_1$-$C_6$-haloalkyl, such as $CF_3$, $CHF_2$, $CH_2$—$CF_3$, $CH_2$—$CHF_2$, CH—$CH_2F$, $CF_2$—$CH_3$, $CH_2F$, $CF_2$—$CF_3$, $CF_2$—$CHF_2$, $C_3$-$C_5$-cycloalkyl, such as cyclopropyl, aryl, such as phenyl, $C_1$-$C_6$-alkoxy, such as methoxy, ethoxy, propoxy, $C_1$-$C_6$-haloalkoxy, such as O—$CF_3$, OH, CN, C(O)$OR_v$, $S(O)_r$($C_1$-$C_6$-alkyl), such as S—$CH_3$, S(O)—$CH_3$, $S(O)_2$—$CH_3$, $S(O)_r$—($C_1$-$C_6$-haloalkyl), such as S—$CF_3$, S(O)—$CF_3$, $S(O)_2$—$CF_3$, $S(O)_r$—R; $S(O)_2$—N($R_x$)($R_y$); S(O)—($R_w$)=N—$R_z$; and wherein R3, if present once or more times, in each occurrence is independently attached to a C atom; or wherein R together with R1a or R1b forms an unsubstituted or substituted carbocycle or an unsubstituted or substituted heterocycle, wherein preferably such carbocycle or heterocycle if substituted is independently substituted with one, two or three substituents each independently selected from the group consisting of: halogen, such as F, Cl, Br, I, alkyl, such as $CH_3$, $C_1$-$C_6$-haloalkyl, such as $CF_3$, $CHF_2$, $CH_2$—$CF_3$, $CH_2$—$CHF_2$, $CH_2$—$CH_2F$, $CF_2$—$CH_3$, $CH_2F$, $CF_2$—$CF_3$, $CF_2$—$CHF_2$, $C_3$-$C_5$-cycloalkyl, such as cyclopropyl, aryl, such as phenyl, $C_1$-$C_6$-alkoxy, such as methoxy, ethoxy, propoxy, $C_1$-$C_6$-haloalkoxy, such as O—$CF_3$, OH, CN, C(O)$OR_x$, $S(O)_r$—($C_1$-$C_6$-alkyl), such as S—$CH_3$, S(O)—$CH_3$, $S(O)_2$—$CH_3$, S(O)e-($C_1$-$C_6$-haloalkyl), such as S—$CF_3$, S(O)—$CF_3$, $S(O)_2$—$CF_3$;
- Q is selected from the group consisting of: Q1, Q2, Q3, wherein:
- Q1 is an unsubstituted or substituted monocyclic, preferably 5- or 6-membered, heteroaryl or heterocyclyl containing one, two or three heteroatoms, which are each independently selected from the group consisting of N, O, S, S(O), $S(O)_2$; wherein preferably QL if substituted is substituted with one, two, three or four substituents each independently selected from the group consisting of: halogen, such as F, Cl, Br, I, $C_1$-$C_6$-alkyl, such as methyl, ethyl, isopropyl, $C_2$-$C_6$-alkenyl, such as ethenyl, $CH_2$—CH=CH, $C_1$-$C_6$-haloalkyl, such as $CF_3$, $C_2F_5$, $CH_2$—$CHF_2$, $CH_2$—$CF_3$, $CHF_2$, $CF_2$—$CH_3$, $C_2$-$C_6$-haloalkenyl, such as CH=CF—$CF_3$, $C_1$-$C_6$-haloalkoxy, such as O—$CH_2$—$CF_3$, O—$CH_2$—$C_2F_5$, $C_3$-$C_5$-cycloalkyl, such as cyclopropyl, $C_3$-$C_5$-cycloalkyl-($C_1$-$C_6$-alkyl), such as cyclopropyl-methyl, $C_3$-$C_5$-cycloalkyl substituted with one or more halogens, such as cyclopropyl substituted with one or more F, $C_3$-$C_5$-cycloalkyl-($C_1$-$C_6$-haloalkyl), such as cyclopropyl-$CF_2$, C(O)—($C_1$-$C_6$-alkyl), such as C(O)-methyl, heterocyclyl, such as aziridinyl, oxetanyl, heteroaryl, such as pyridine or pyridine substituted with one or more $C_1$-$C_6$-haloalkyl or $C_1$-$C_6$-haloalkoxy, such as $CF_3$, $CH_2$—$CF_2$—$CF_3$, or O—$CH_2$—$CF_2$—$CF_3$, =O, S(O)$NR_xR_y$, such as S(O)NH—$CF_3$;
- Q2 is an unsubstituted or substituted fused bicyclic, preferably 9- or 10-membered, heteroaryl or heterocyclyl containing one, two, three, four or five heteroatoms, which are each independently selected from the group consisting of N, O, S, S(O), $S(O)_2$; wherein preferably Q2 if substituted is substituted with one, two, three, four, five or six substituents each independently selected from the group consisting of: halogen, such as F, Cl, Br, I, $C_1$-$C_6$-alkyl, such as methyl, ethyl, isopropyl, $C_2$-$C_6$-alkenyl, such as ethenyl, $CH_2$—CH=CH, $C_1$-$C_6$-haloalkyl, such as $CF_3$, $C_2F_5$, $CH_2$—$CHF_2$, $CH_2$—$CF_3$, $CHF_2$, $CF_2$—$CH_3$, $C_2$-$C_6$-haloalkenyl, such as CH=CF—$CF_3$, $C_1$-$C_6$-haloalkoxy, such as O—$CH_2$—$CF_3$, O—$CH_2$—$C_2F_5$, $C_3$-$C_x$-cycloalkyl, such as cyclopropyl, $C_3$-$C_5$-cycloalkyl-($C_1$-$C_6$-alkyl), such as cyclopropyl-methyl, $C_3$-$C_5$-cycloalkyl substituted with one or more halogens, such as cyclopropyl substituted with one or more F, $C_3$-$C_x$-cycloalkyl-($C_1$-$C_6$-haloalkyl), such as cyclopropyl-$CF_2$, C(O)—($C_1$-$C_6$-alkyl), such as C(O)-methyl, heterocyclyl, such as aziridinyl, oxetanyl, $S(O)_r$($C_1$-$C_6$-alkyl), such as S-methyl; S(O)-methyl, $S(O)_2$-methyl; $S(O)_s$—($C_1$-$C_6$-haloalkyl), such as S—$CF_3$, S(O)—$CF_3$, $S(O)_2$—$CF_3$, =O, S(O)$NR_xR_y$, such as S(O)NH—$CF_3$;
- Q3 is an unsubstituted or substituted fused tricyclic, preferably 12- or 13-membered, heteroaryl or heterocyclyl containing one, two, three, four, five, six or seven heteroatoms, which are each independently selected from the group consisting of N, O, S, S(O), $S(O)_2$; wherein preferably Q3 if substituted is substituted with one, two, three, four, five, six, seven or eight substituents each independently selected from the group consisting of: halogen, such as F, Cl, Br, I, $C_1$-$C_5$-alkyl, such as methyl, ethyl, isopropyl, $C_2$-$C_6$-alkenyl, such as ethenyl, $CH_2$—CH=CH, $C_1$-$C_6$-haloalkyl, such as $CF_3$, $C_2F_5$, $CH_2$—$CHF_2$, $CH_2$—$CF_3$, $CHF_2$, $CF_2$—$CH_3$, $C_2$-$C_5$-haloalkenyl, such as $CH{=}CF{-}CF_3$, $C_1$-$C_6$-haloalkoxy, such as $O{-}CH_2{-}CF_3$, $0{-}CH_2{-}C_2F_5$, $C_3$-$C_5$-cycloalkyl, such as cyclopropyl, $C_3$-$C_5$-cycloalkyl-($C_1$-$C_6$-alkyl), such as cyclopropyl-methyl, $C_3$-$C_5$-cycloalkyl substituted with one or more halogens, such as cyclopropyl substituted with one or more F, $C_3$-$C_5$-cycloalkyl-($C_1$-$C_6$-haloalkyl), such as cyclopropyl-$CF_2$, C(O)—($C_1$-$C_6$-alkyl), such as C(O)-methyl, heterocyclyl, such as aziridinyl, oxetanyl, $S(O)_r$—($C_1$-$C_6$-alkyl), such as S-methyl; S(O)-methyl, $S(O)_2$-methyl; $S(O)_s$($C_1$-$C_6$-haloalkyl), such as $S{-}CF_3$, $S(O){-}CF_3$, $S(O)_2{-}CF_3{=}0$, $S(O)NR_xR_y$, such as $S(O)NH{-}CF_3$;

$R_v$, $R_w$, $R_x$, $R_y$, $R_z$ in each occurrence are independently selected from the group consisting of: hydrogen, halogen, such as F, Cl, Br, I, $C_1$-$C_6$-alkyl, such as methyl, ethyl, $C_1$-$C_6$-haloalkyl, such as $CF_3$;

n is 0, 1, 2, 3, 4;

r, s, t in each occurrence are independently 0, 1 or 2;

the dashed bond (...) signifies a single or double bond;

or a pharmaceutically acceptable salt thereof;

with the proviso that the following compounds are excluded from the scope of the compound of formula (I):

(A)

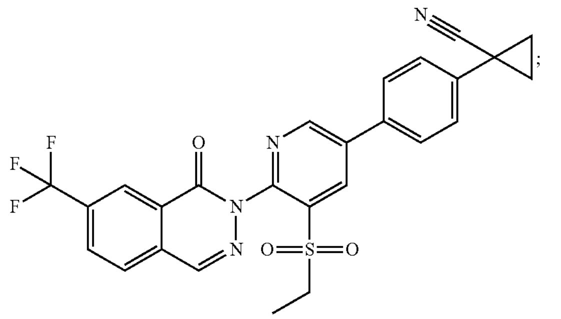

(B)

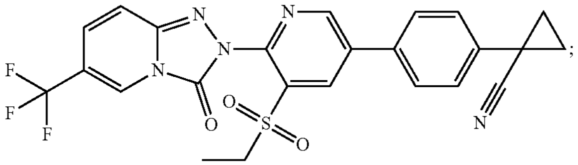

(C)

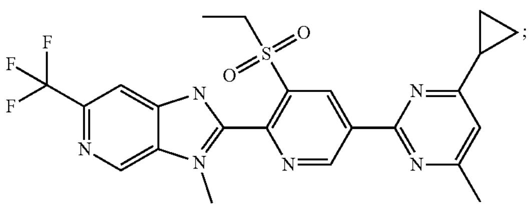

(D)

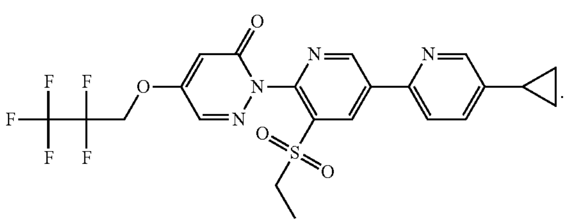

The present invention also concerns a compound of formula (I) as herein disclosed and/or claimed, wherein Q1, Q2, Q3 are independently selected from the group consisting of:

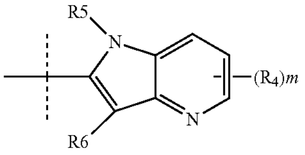

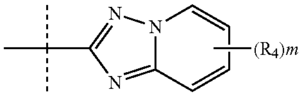

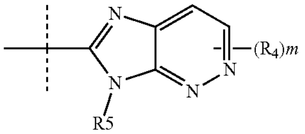

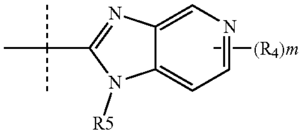

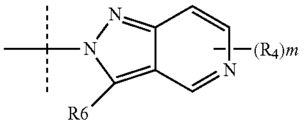

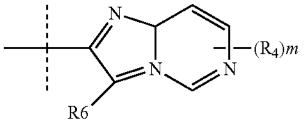

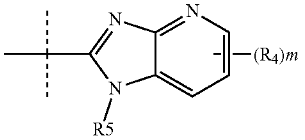

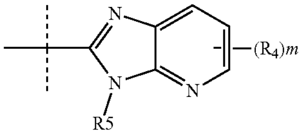

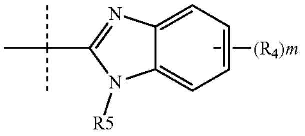

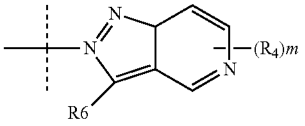

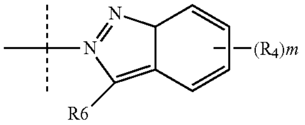

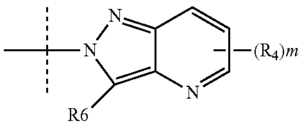

-continued
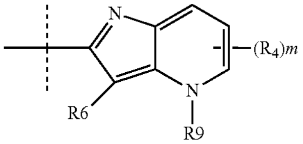
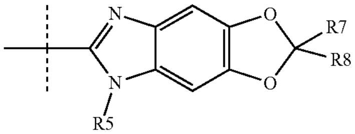
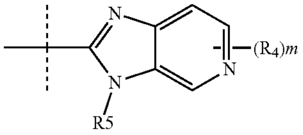
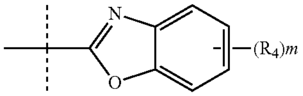
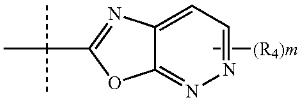
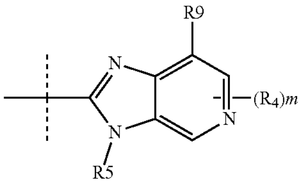
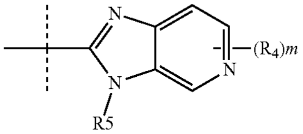
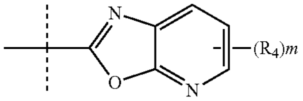
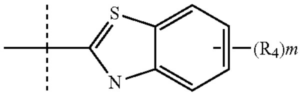
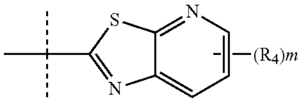
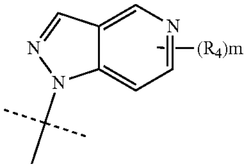
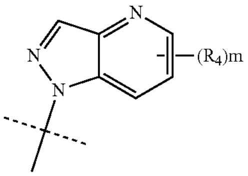
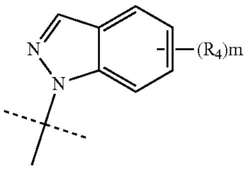
-continued
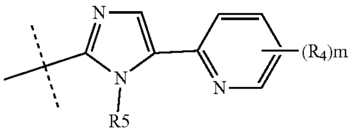
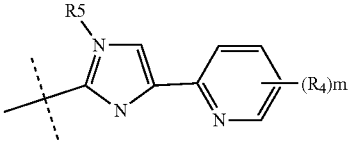
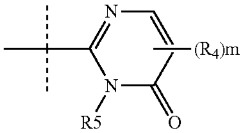
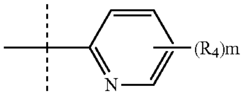
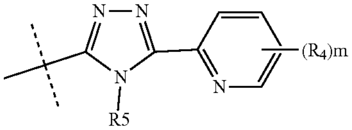
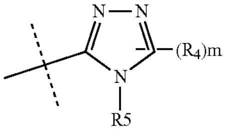
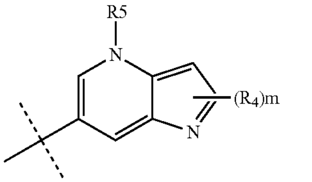
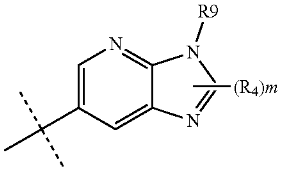
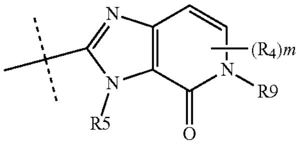
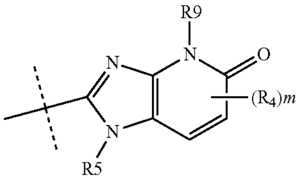
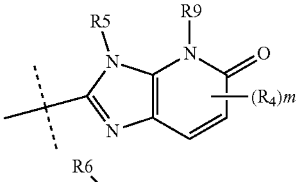
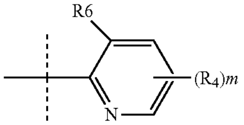

-continued

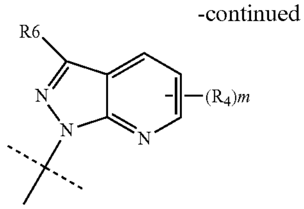

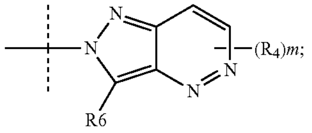

wherein:

R4 is $C_1$-$C_6$-haloalkyl, such as $CF_3$, $C_2F_5$, $C_2$-$C_6$-haloalkenyl, such as CH═CF—$CF_3$, $C_1$-$C_6$-haloalkoxy, such as O—$CH_2$—$CF_3$, 0—$CH_2$—$C_2F_5$, S(O)p-($C_1$-$C_6$-alkyl), such as S-methyl, S(O)-methyl; $S(O)_2$-methyl; $S(O)_q$—($C_1$-$C_6$-haloalkyl), such as S—$CF_3$, S(O)—$CF_3$, $S(O)_2$—$CF_3$, =O, wherein R4, if present once or more times, in each occurrence is independently attached to a C atom;

R5, R9 are each independently hydrogen, $C_1$-$C_6$-alkyl, such as methyl, ethyl, isopropyl, $C_2$-$C_6$-alkenyl, such as ethenyl, $C_1$-$C_6$-haloalkyl, such as $CF_3$, $CH_2$—$CHF_2$, $CH_2$—$CF_3$, $CHF_2$, $C_3$-$C_5$-cycloalkyl, such as cyclopropyl, $C_3$-$C_5$-cycloalkyl-alkyl, such as cyclopropylmethyl, $C_3$-$C_5$-cycloalkyl substituted with one or more haloalkyl, such as cyclopropyl substituted with one or more $CF_3$, Cr—$C_8$-cycloalkyl substituted with one or more halogens, such as cyclopropyl substituted with one or more F, C(O)—(CC-alkyl), such as C(O)-methyl, heterocyclyl, such as aziridinyl, oxetanyl, S(O) p-($C_1$-$C_6$-alkyl), such as S-methyl, S(O)-methyl; $S(O)_2$-methyl; $S(O)_q$—($C_1$-$C_6$-haloalkyl), such as S—$CF_3$, S(O)—$CF_3$, $S(O)_2$—$CF_3$;

R6, R7, R8 are each independently hydrogen, halogen, such as F, Cl, Br, I;

m is 0, 1 or 2;

p, q in each occurrence independently are 0, 1 or 2;

or a pharmaceutically acceptable salt thereof.

The present invention concerns a compound of formula (I) as herein disclosed and/or claimed, wherein the following Q radicals are excluded from the scope of the compound of formula (I):

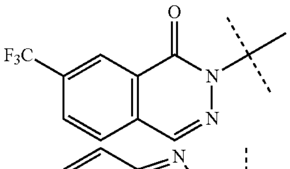

;

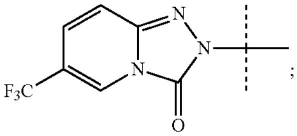

;

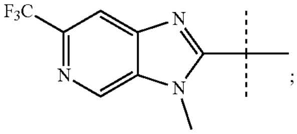

;

-continued

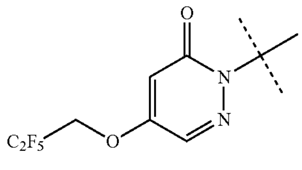

.

The present invention further concerns a compound of formula (I) as herein disclosed and/or claimed, wherein the compound is selected from the group consisting of:

1

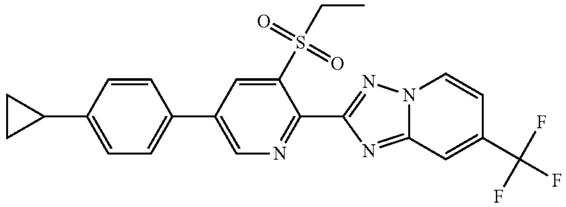

2

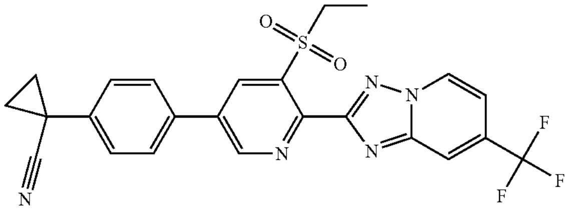

3

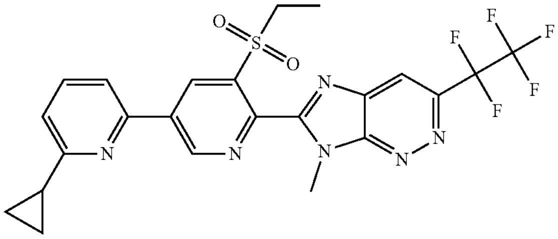

4

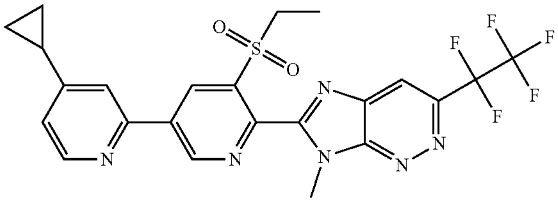

5

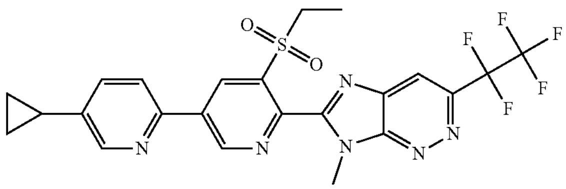

-continued
6
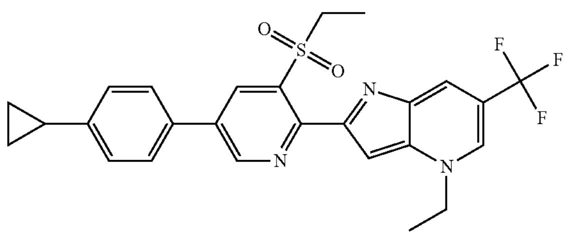
7
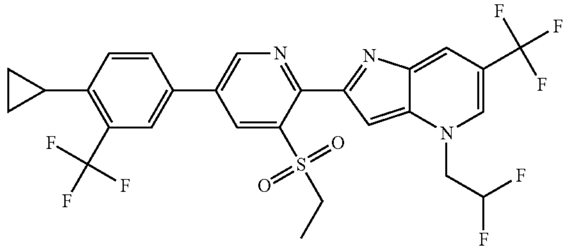
8
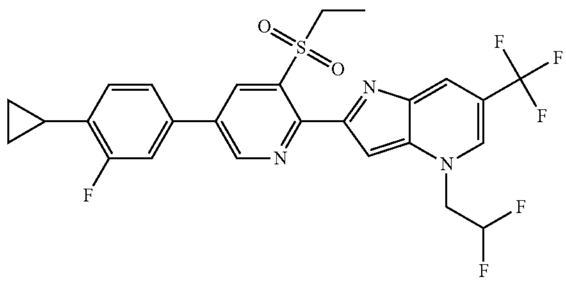
9
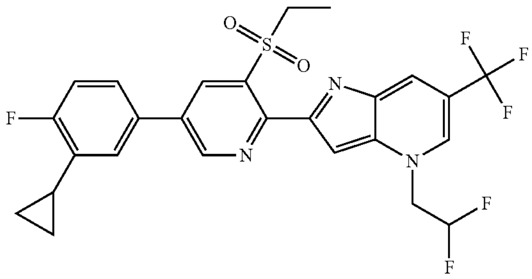
10
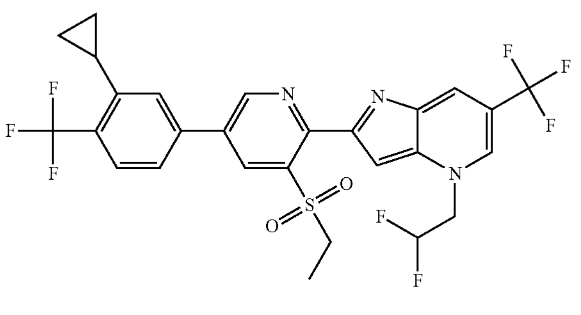
-continued
11
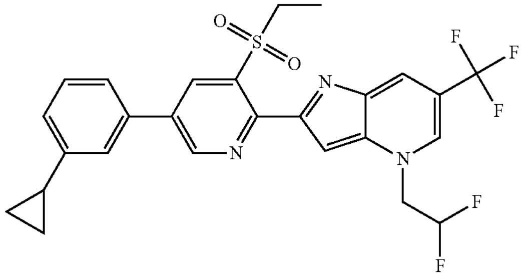
12
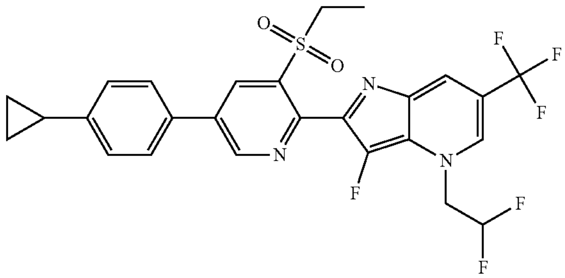
13
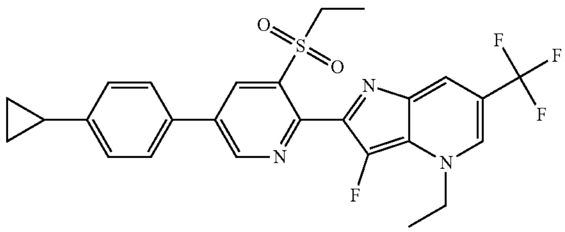
14
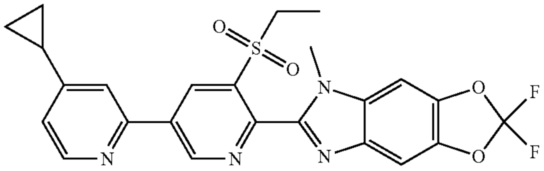
15
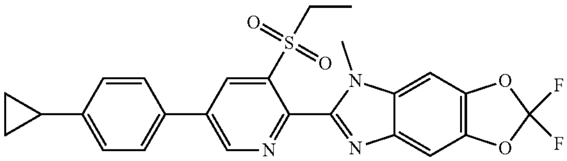
16
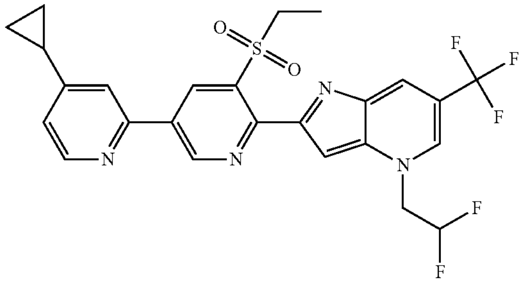

-continued
17
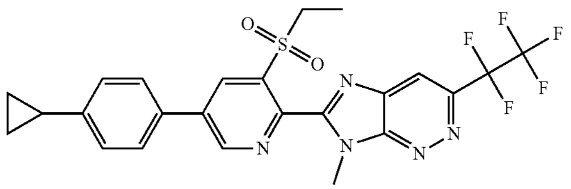
18
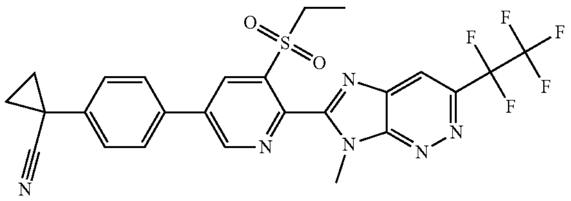
19
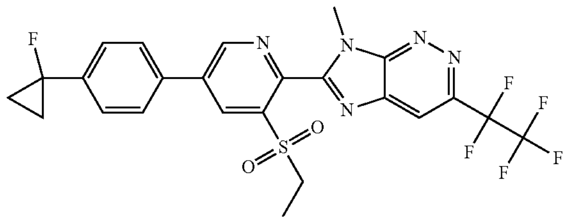
20
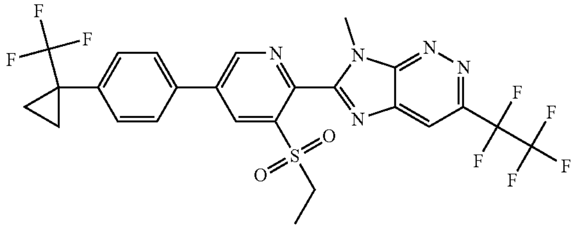
21
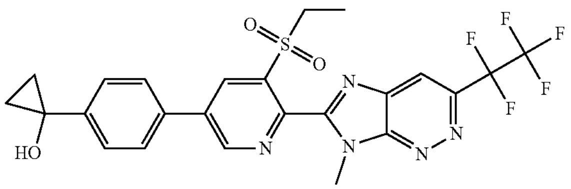
22
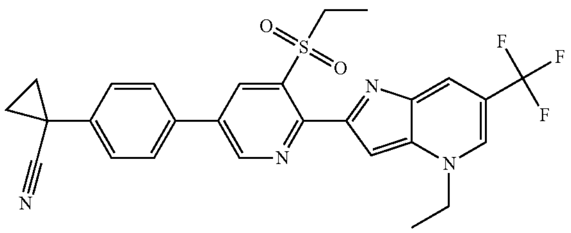
-continued
23
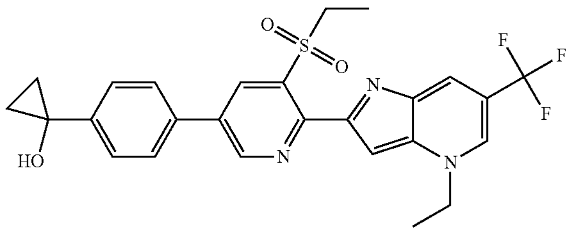
24
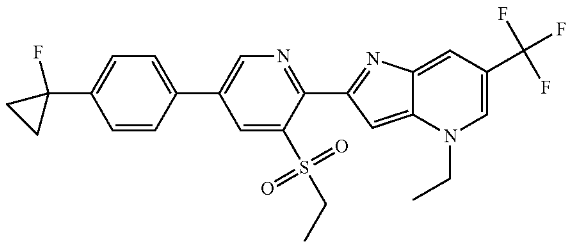
25
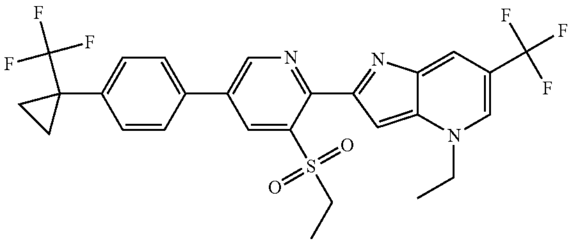
26
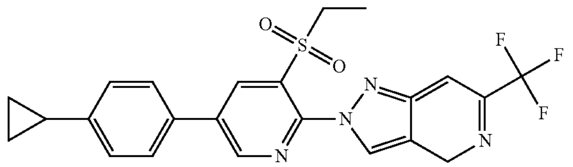
27
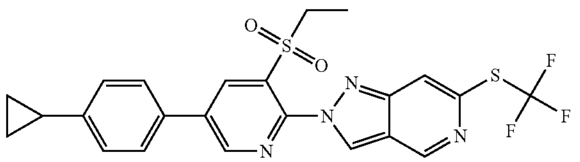
28
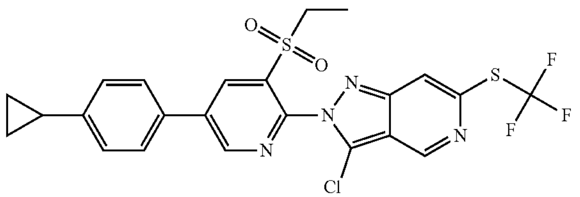

-continued
29
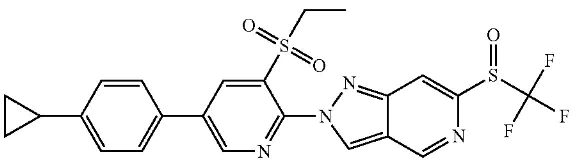
30
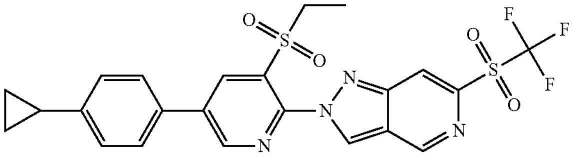
31
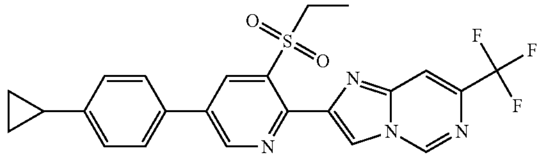
32
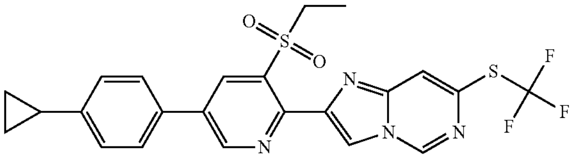
33
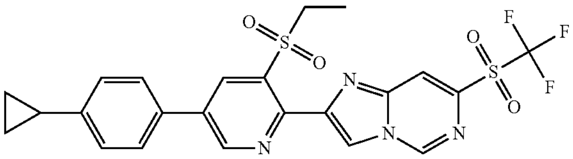
34
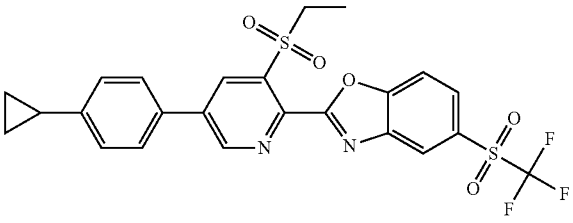
35
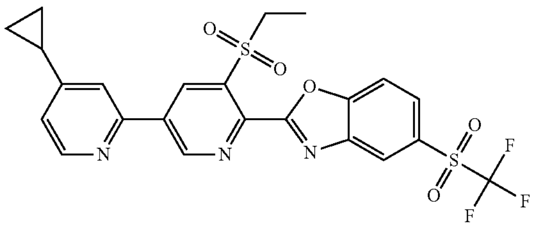
-continued
36
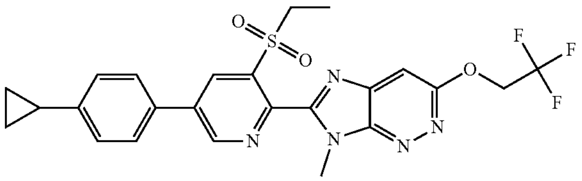
37
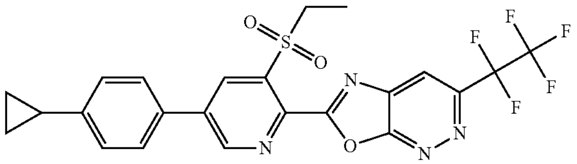
38
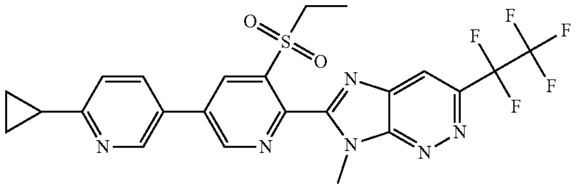
39
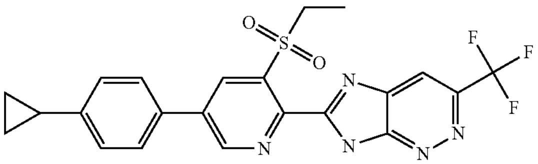
40
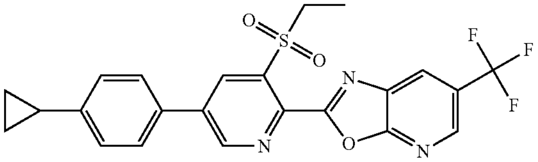
41
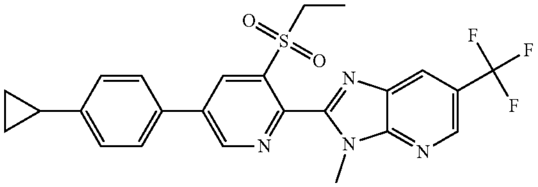
42
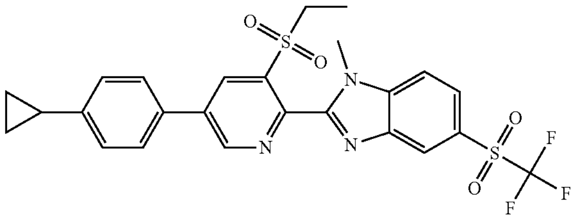
43
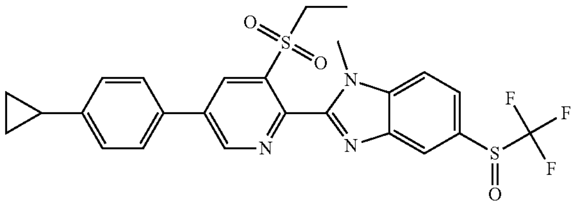

-continued
44
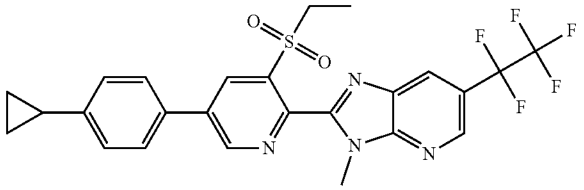
45
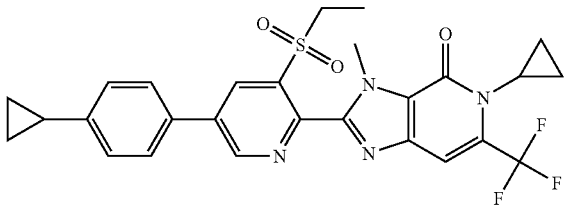
46
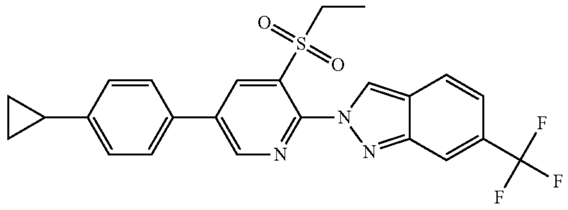
47
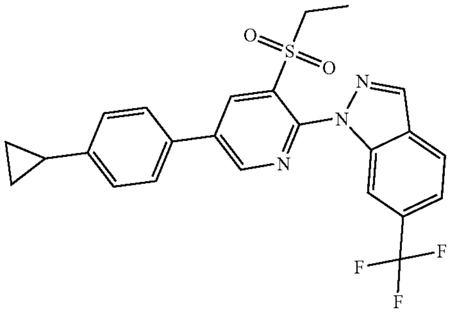
48
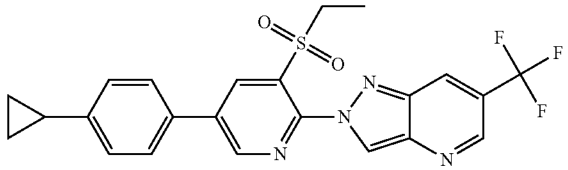
49
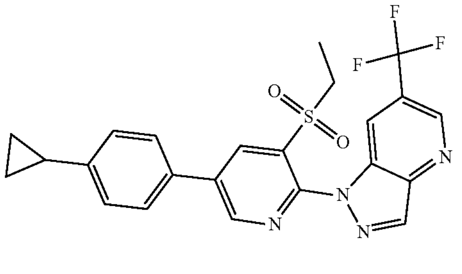
-continued
50
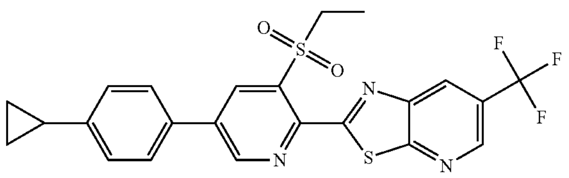
51
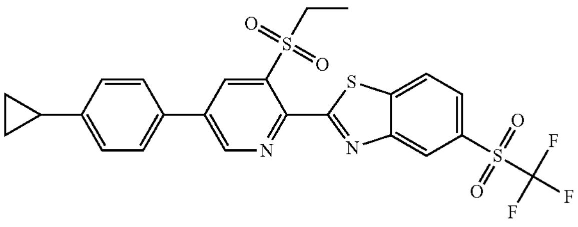
52
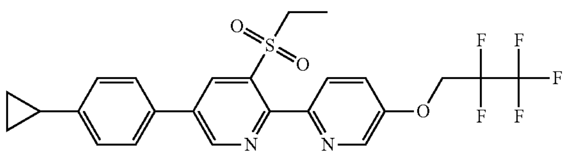
53
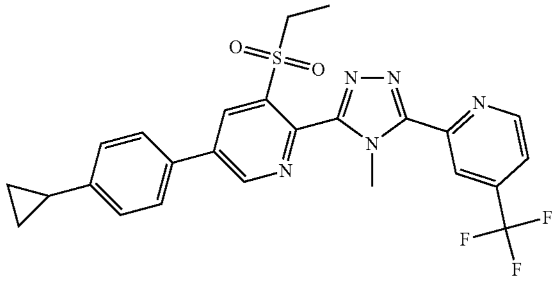
54
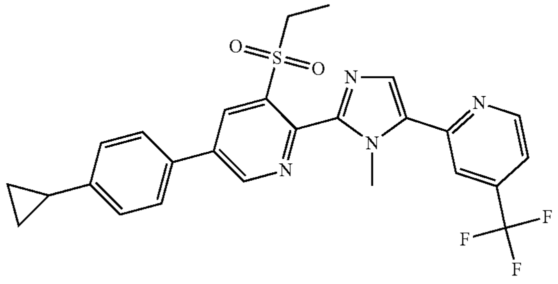
55
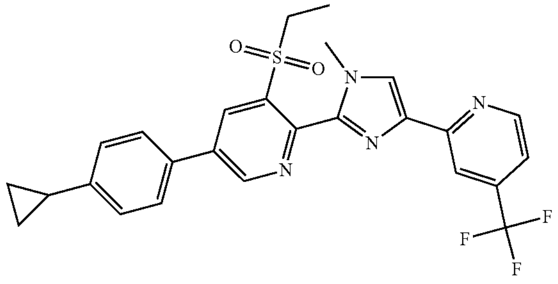

-continued
56
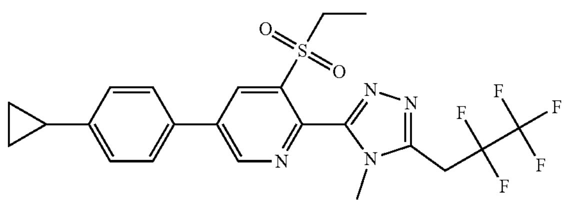
57
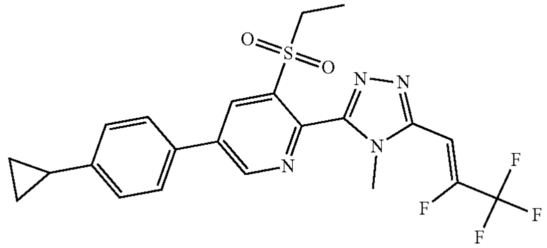
58
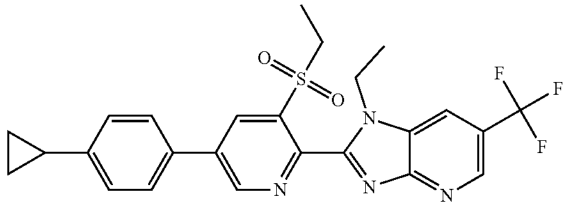
59
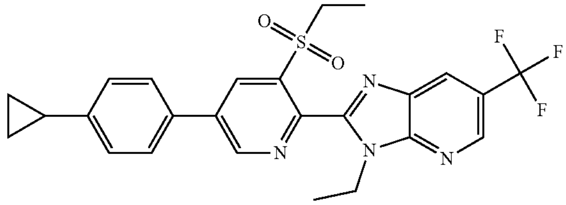
60
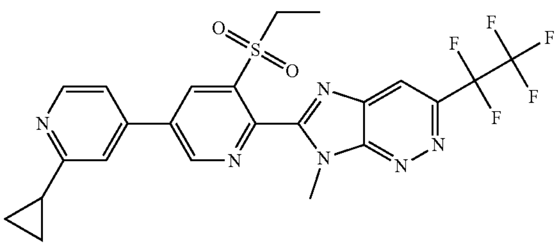
61
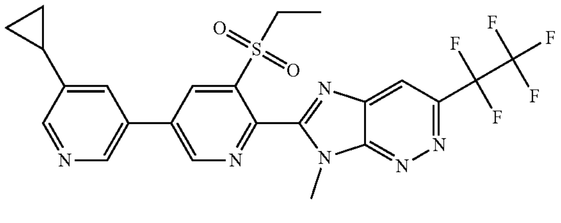
-continued
62
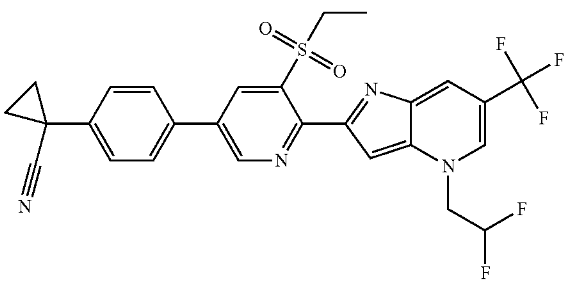
63
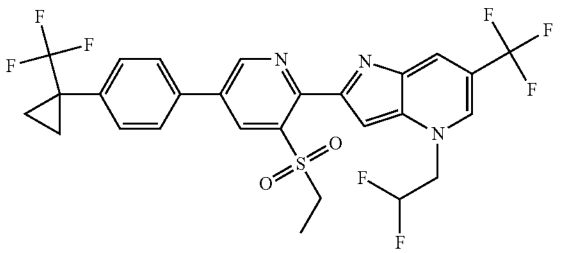
64
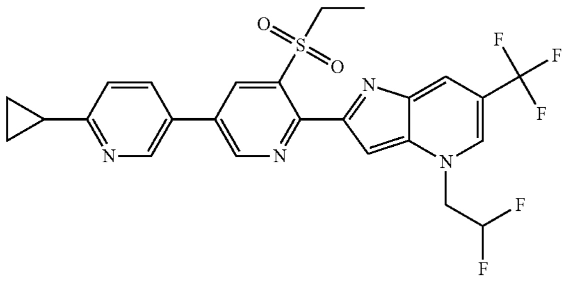
65
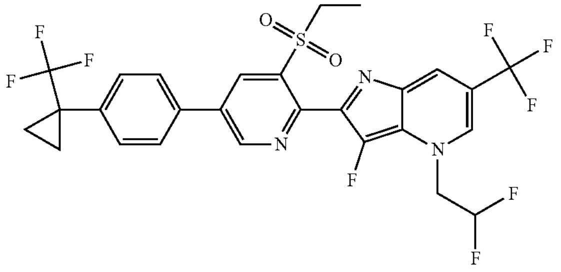
66
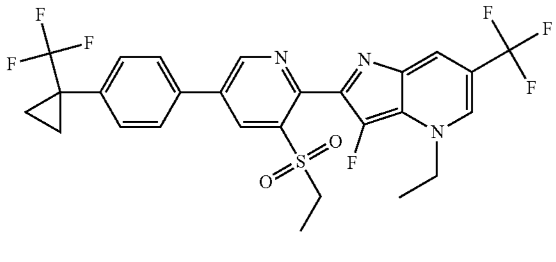

-continued
67
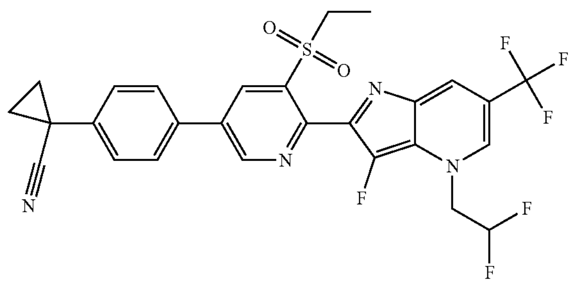
68
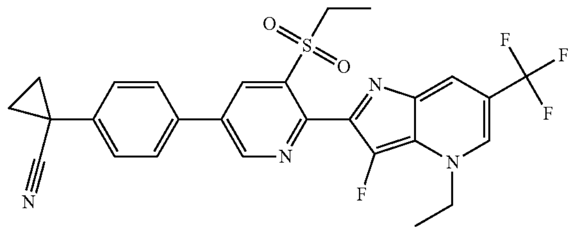
69
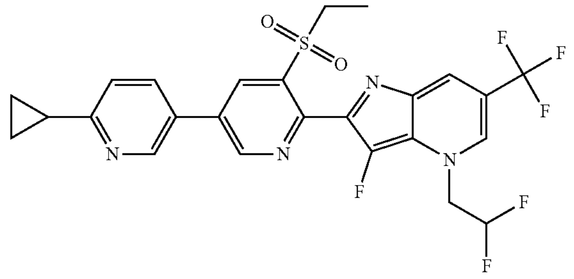
70
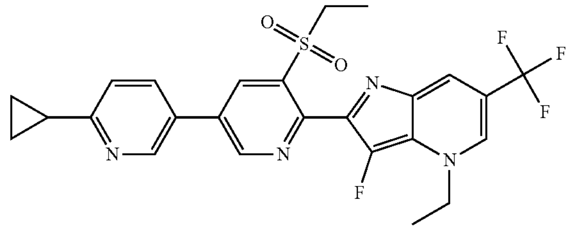
71
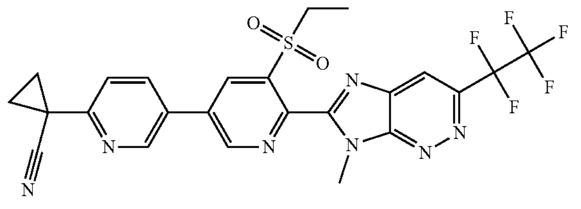
72
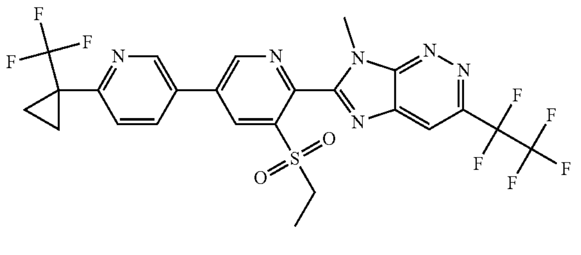
-continued
73
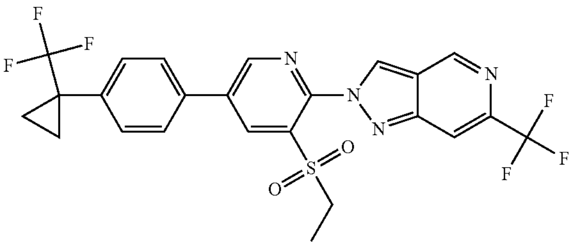
74
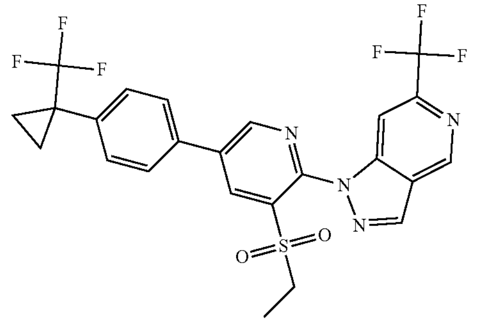
75
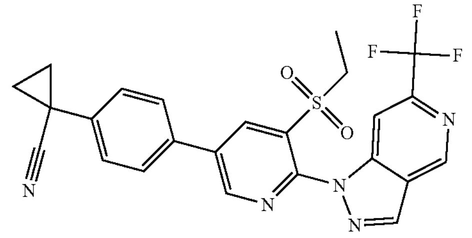
76
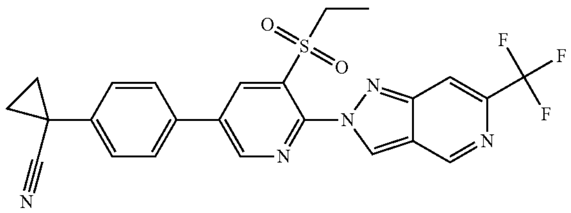
77
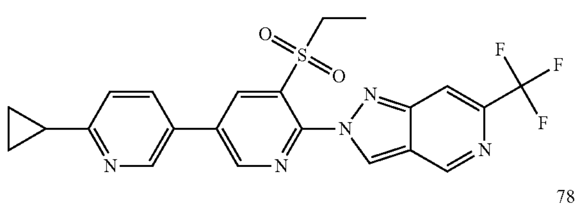
78
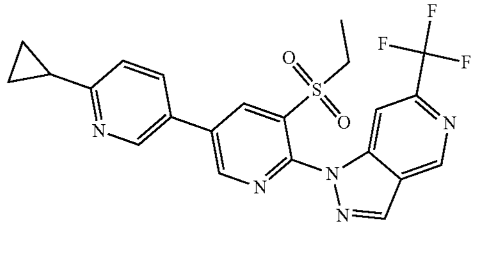

-continued
79
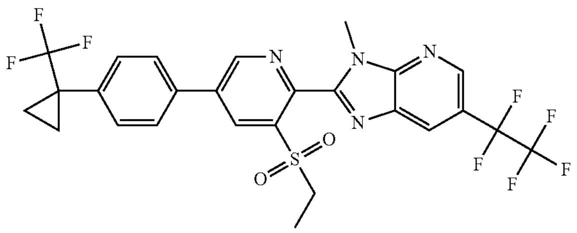
80
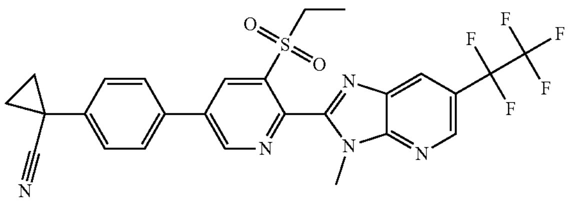
81
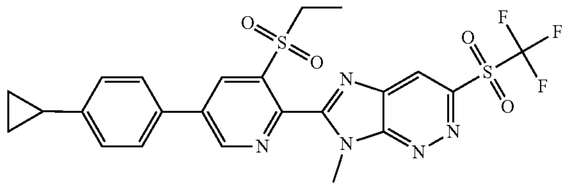
82
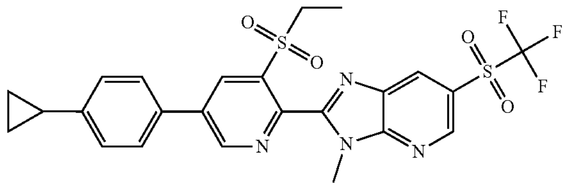
83
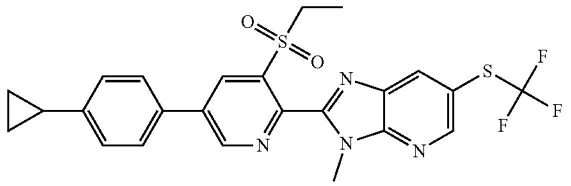
84
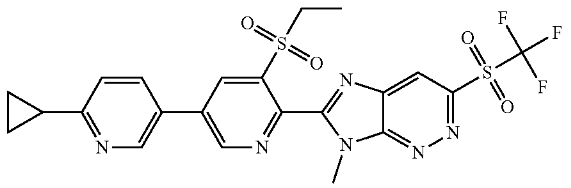
85
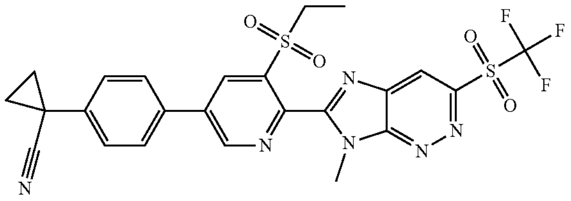
-continued
86
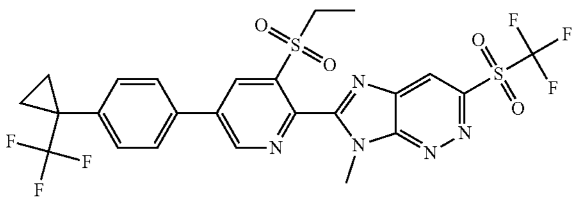
87
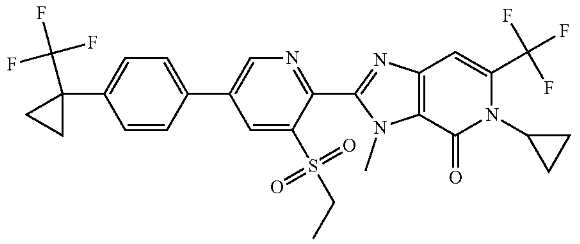
88
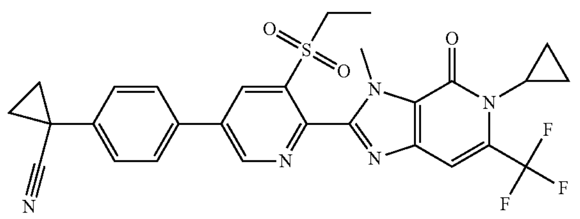
89
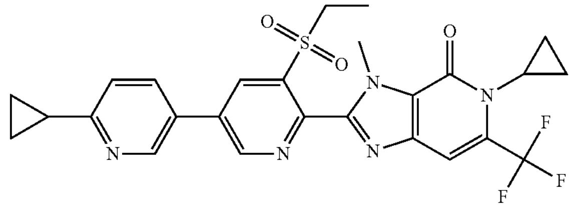
90
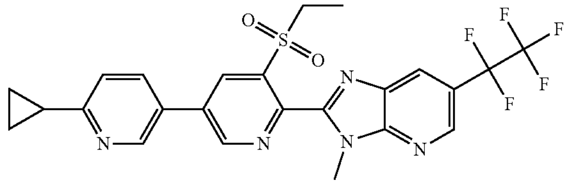
91
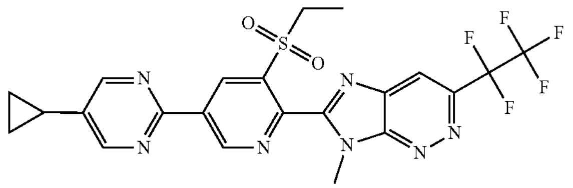

-continued
92
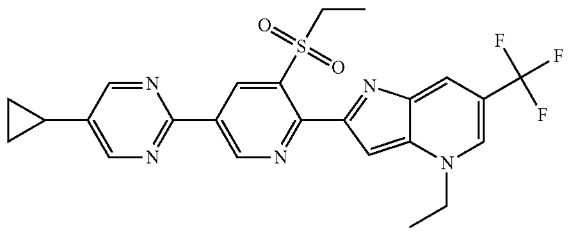
93
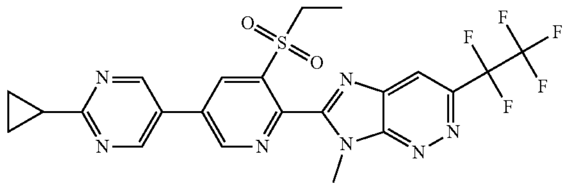
94
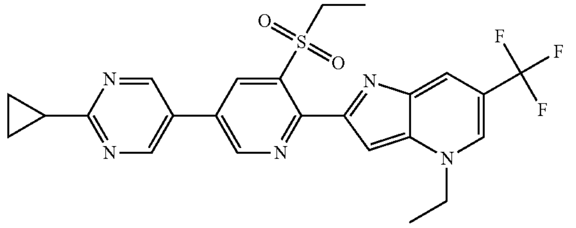
95
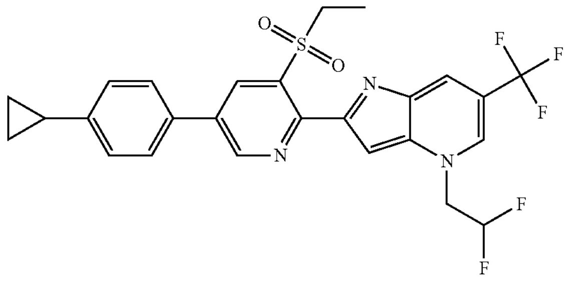
96
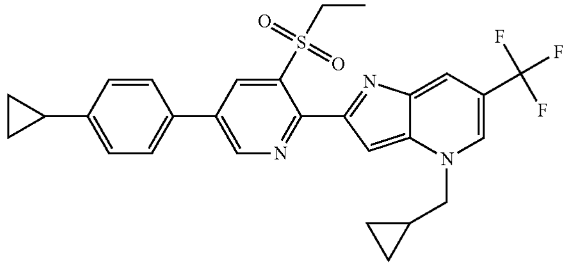
97
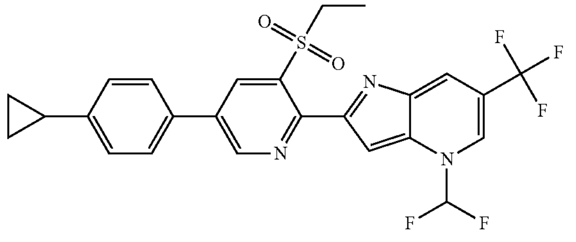
-continued
98
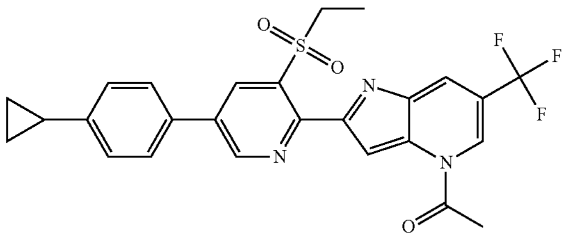
99
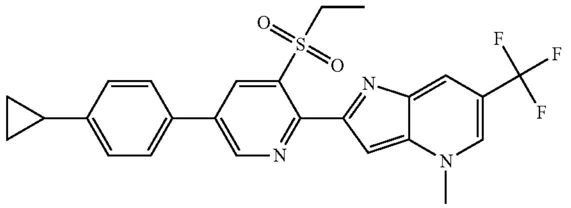
100
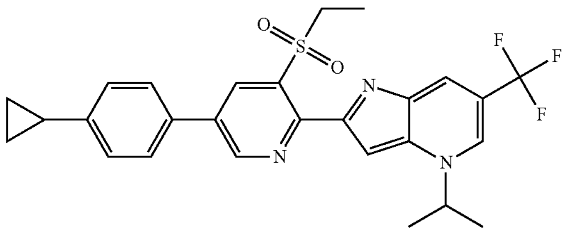
101
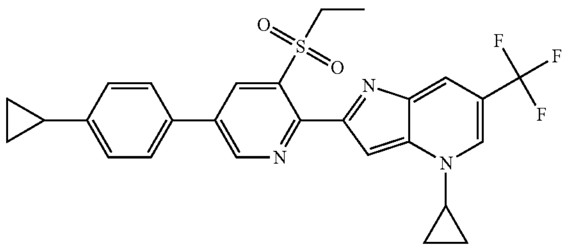
102
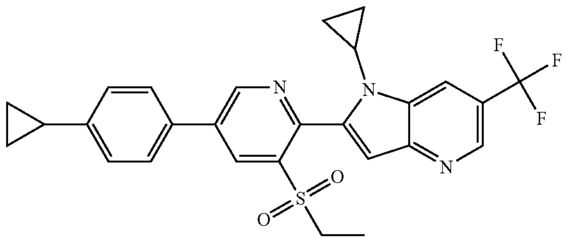
103
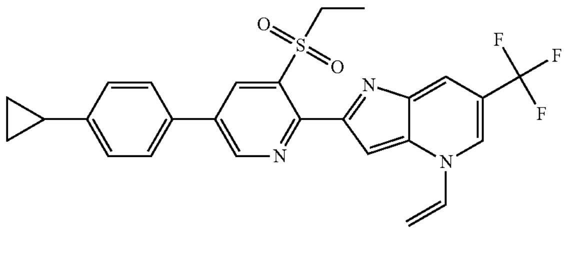

-continued
104
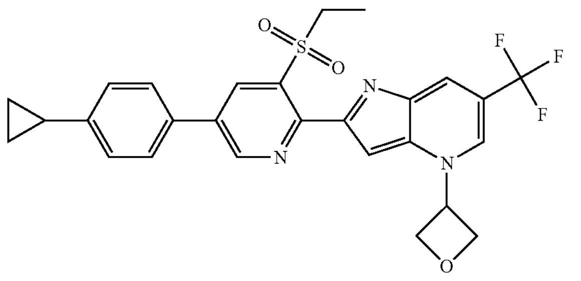
105
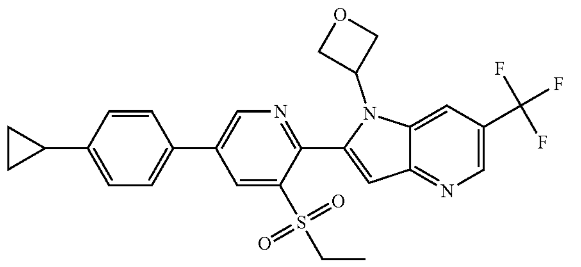
106
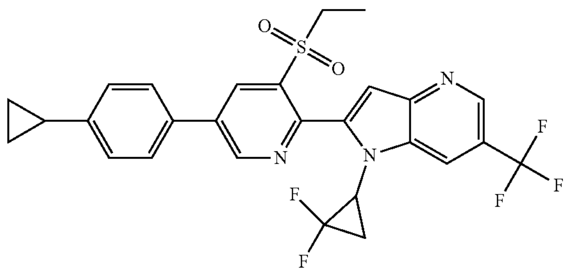
107
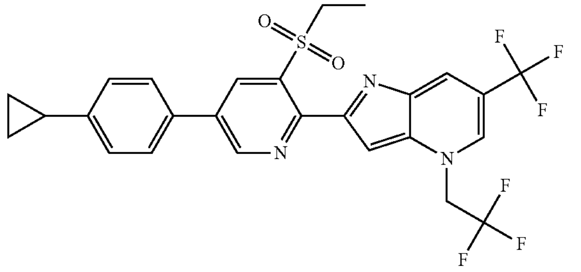
108
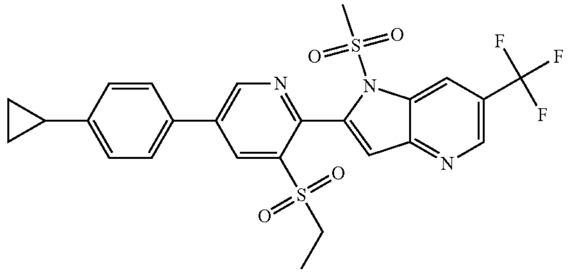
-continued
109
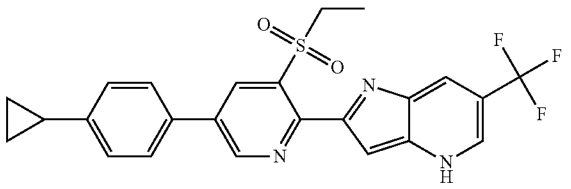
110
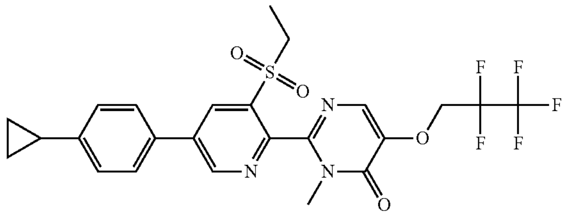
111
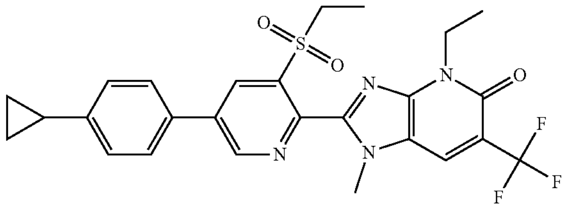
112
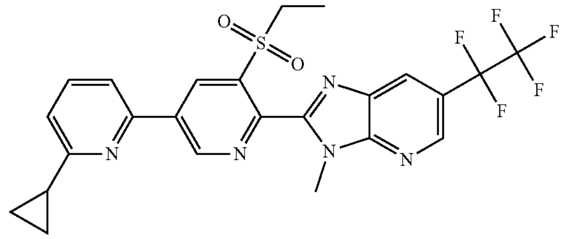
113
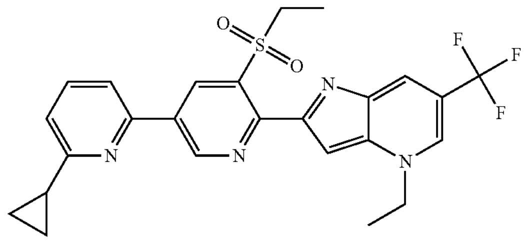
114
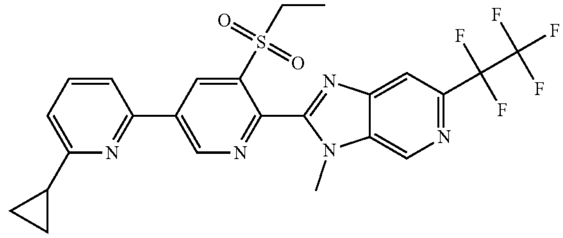

-continued
115
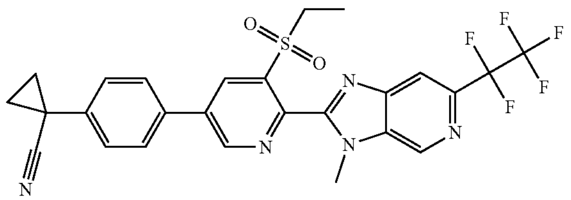
116
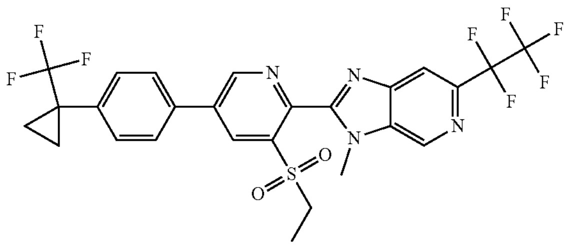
117
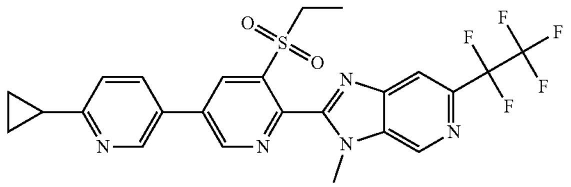
118
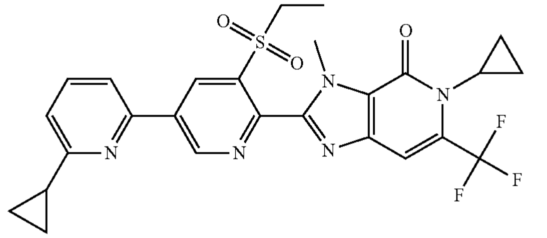
119
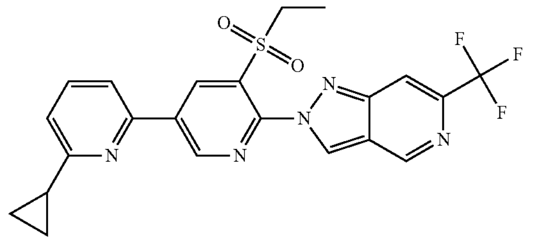
120
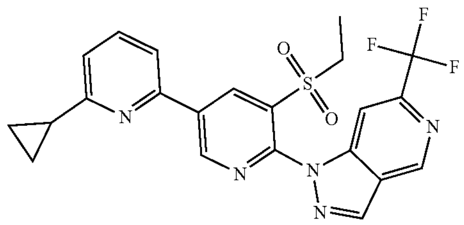
-continued
121
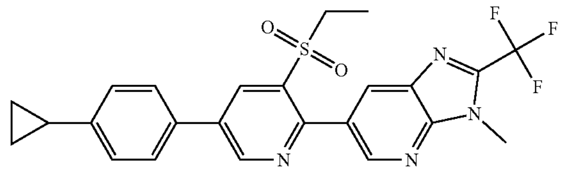
122
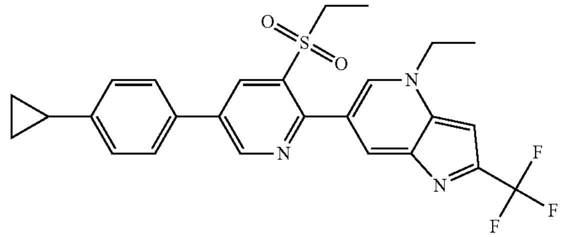
123
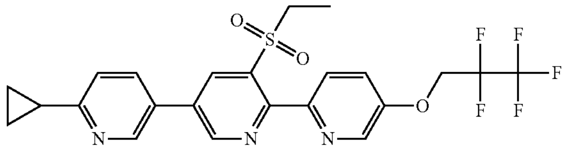
124
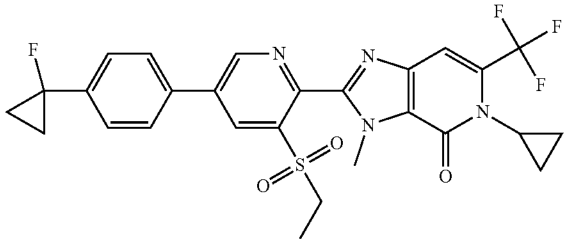
125
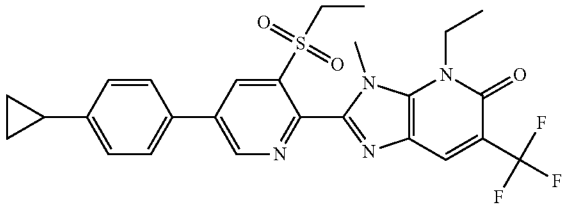
126
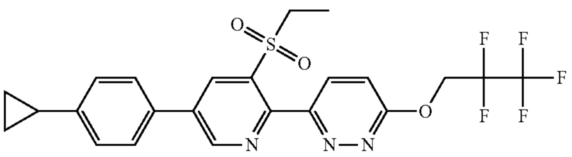

-continued
127
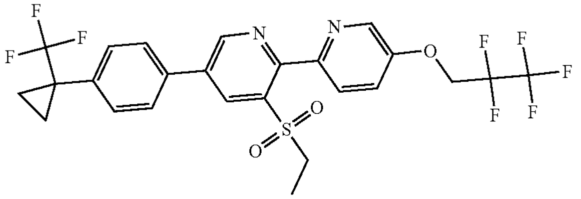
128
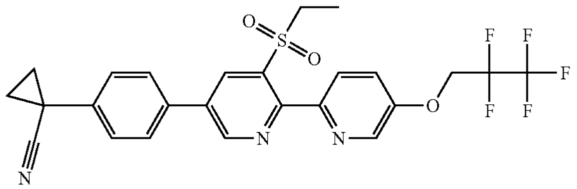
129
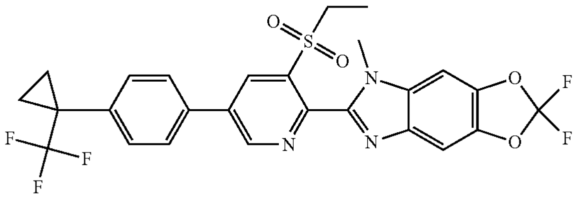
130
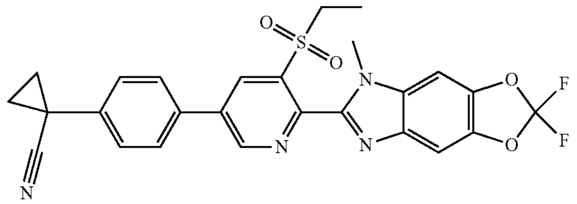
131
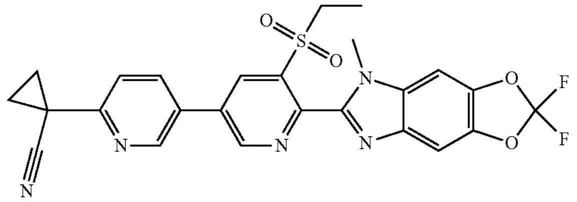
132
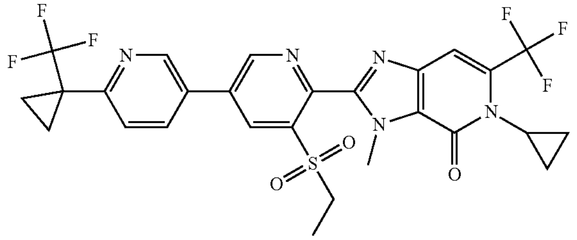
133
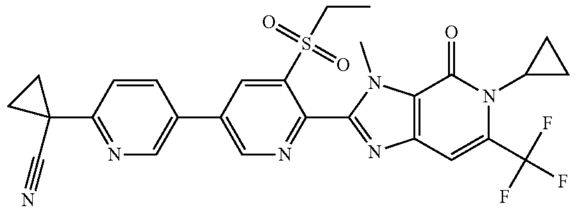
-continued
134
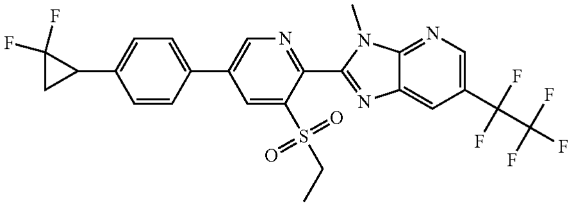
135
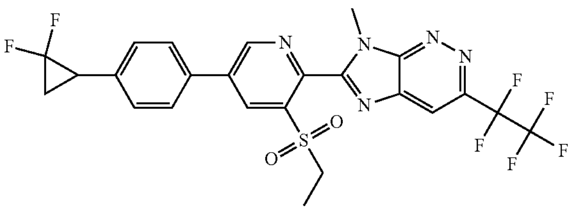
136
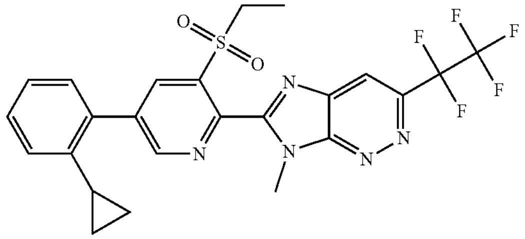
137
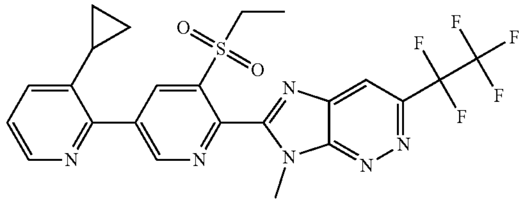
138
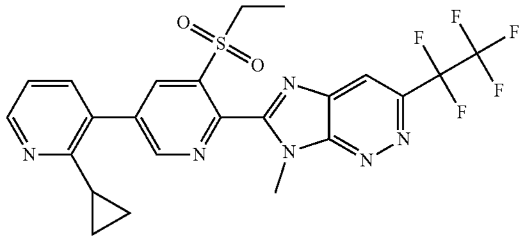
139
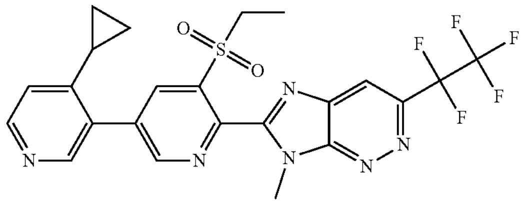

-continued
140
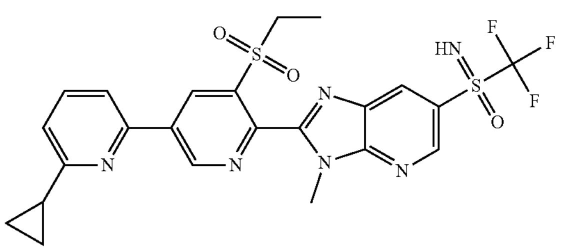
141
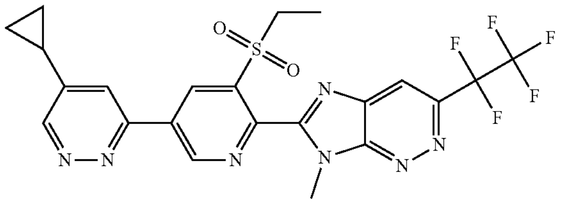
142
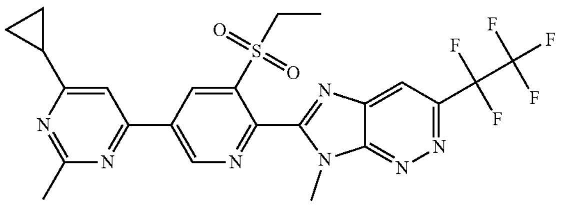
143
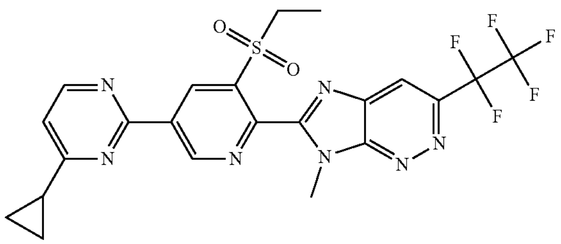
144
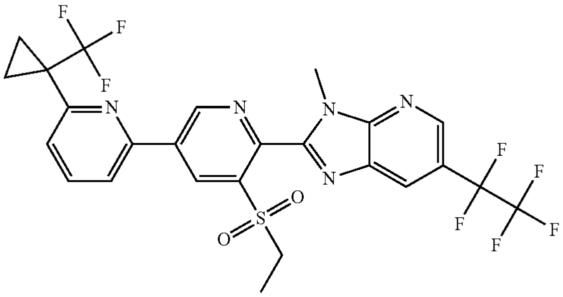
145
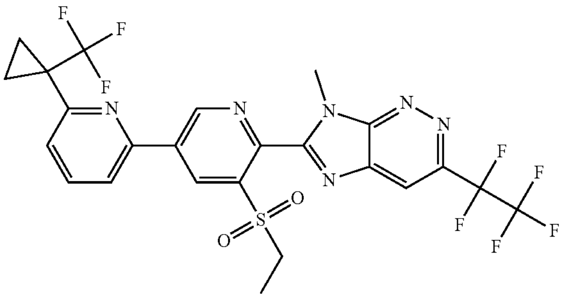
-continued
146
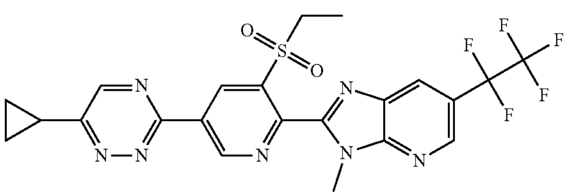
147
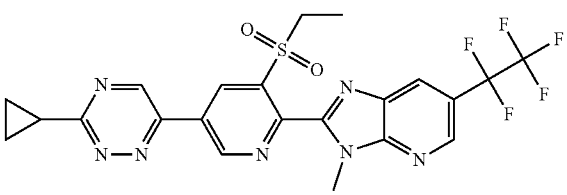
148
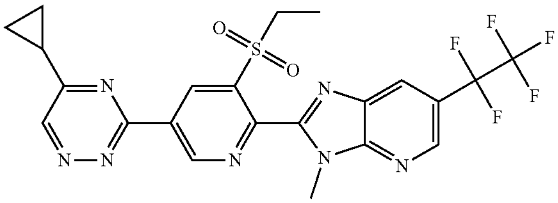
149
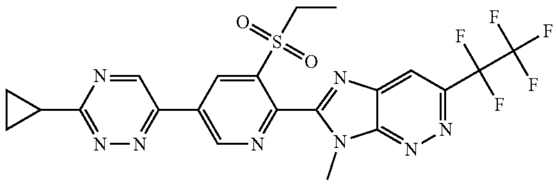
150
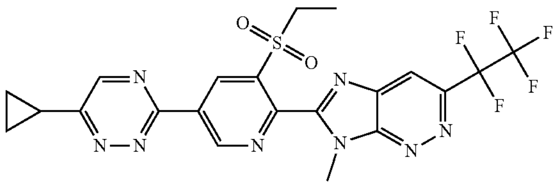
151
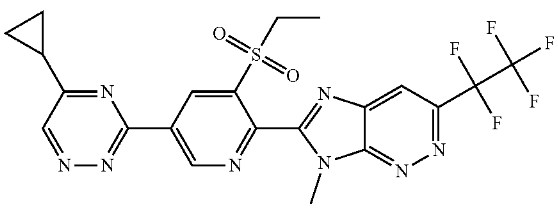
152
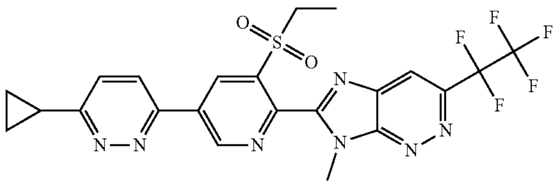

-continued
153
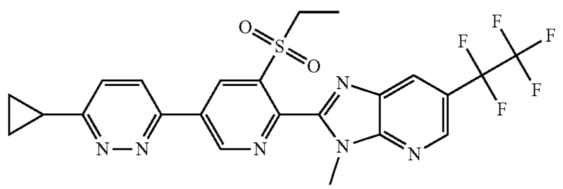
154
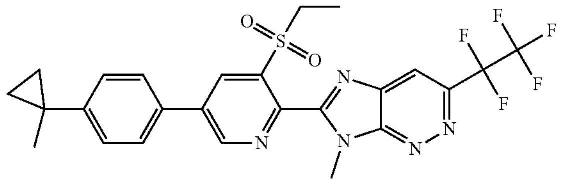
155
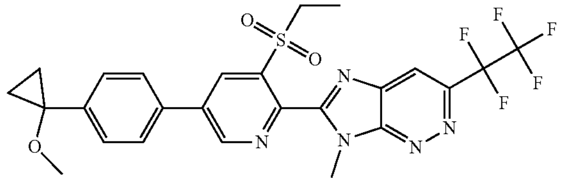
156
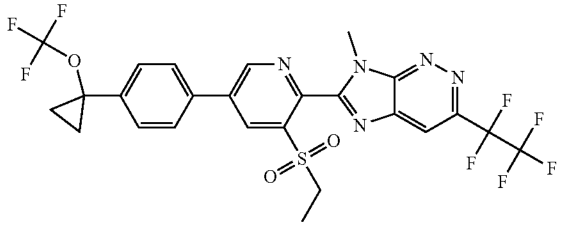
157
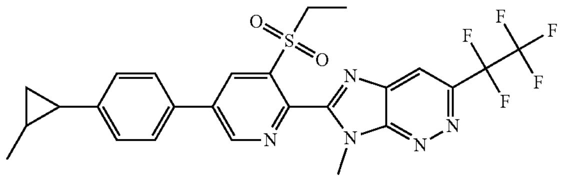
158
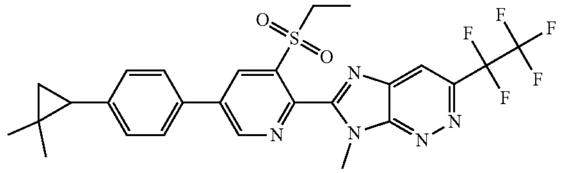
159
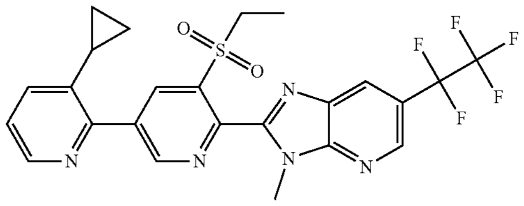
-continued
160
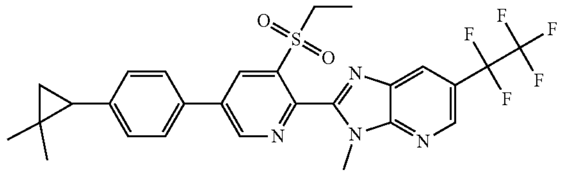
161
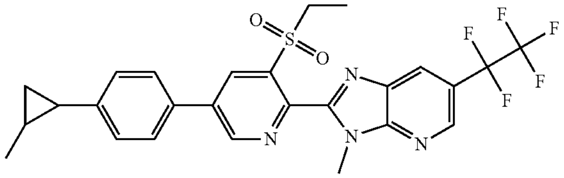
162
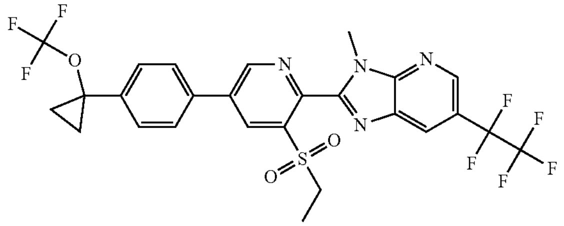
163
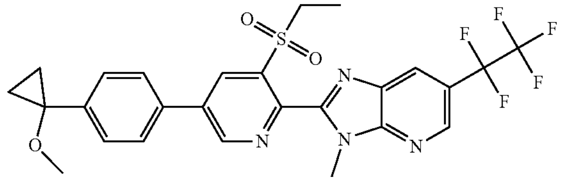
164
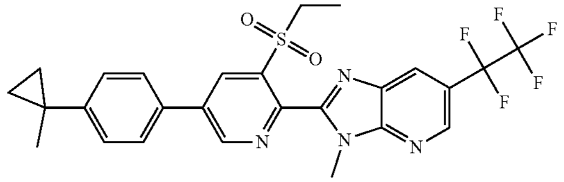
165
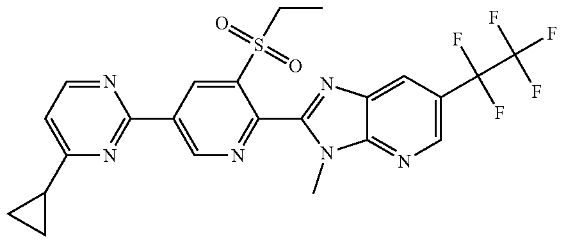
166
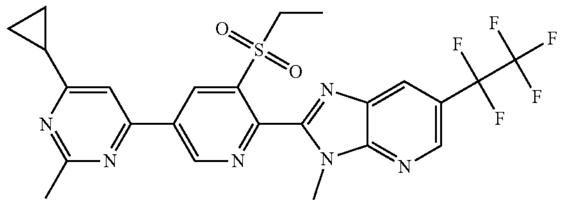

-continued
167
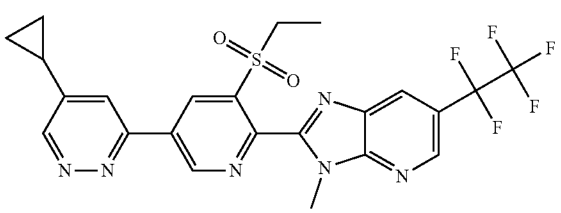
168
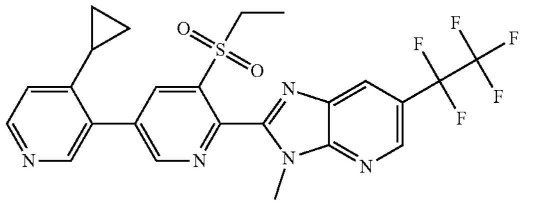
169
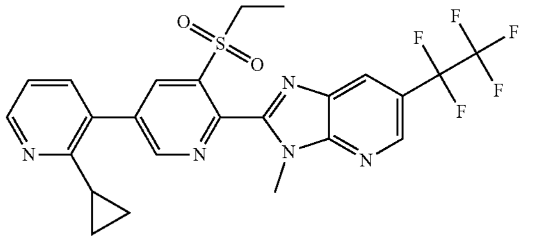
170
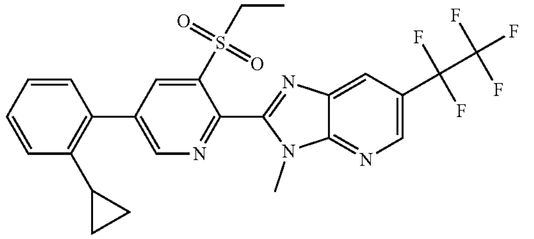
171
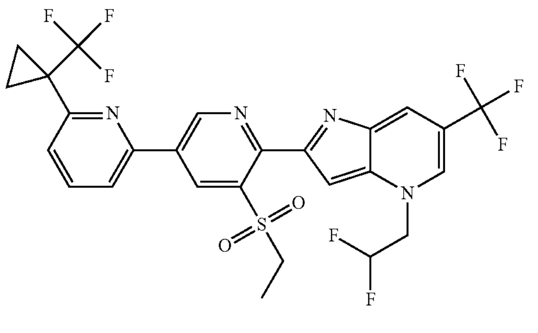
172
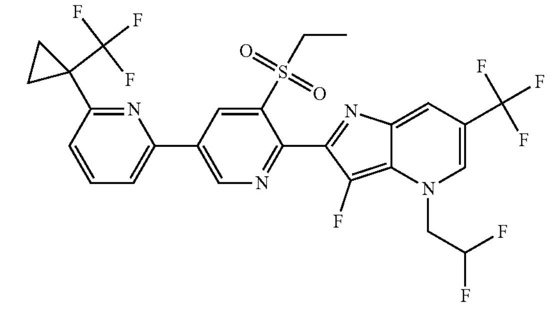
173
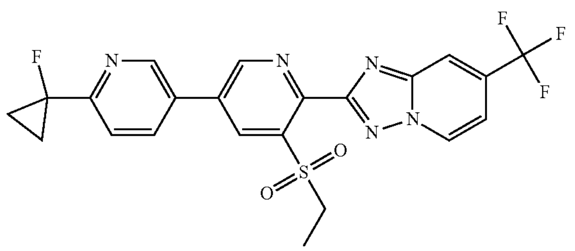
174
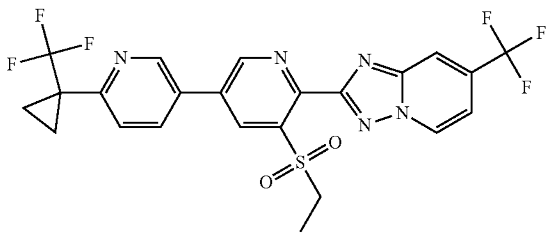
175
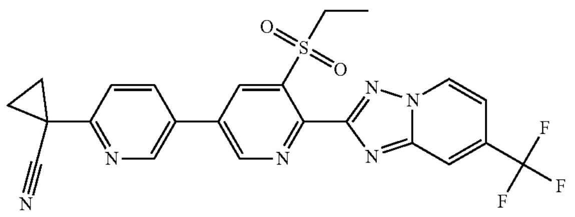
176
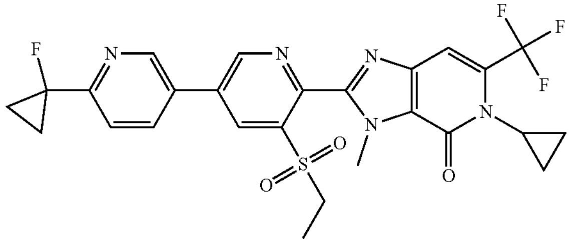
177
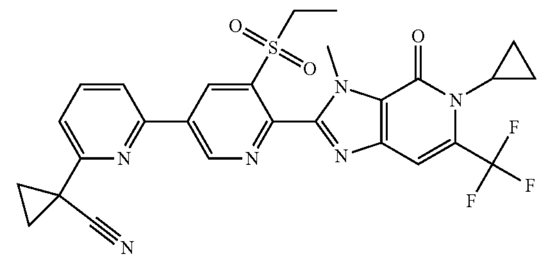

-continued
178
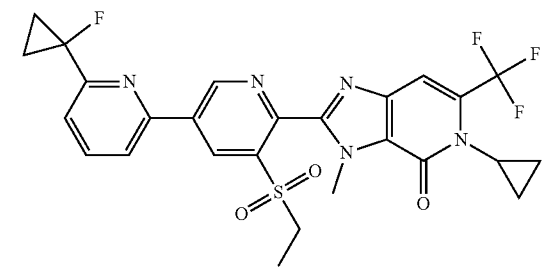
179
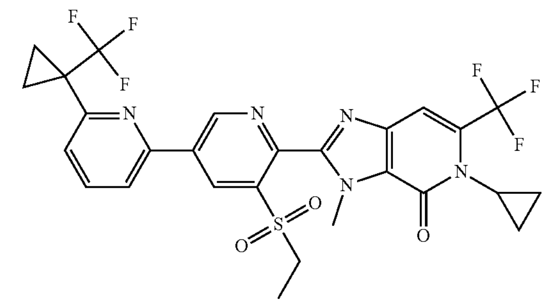
180
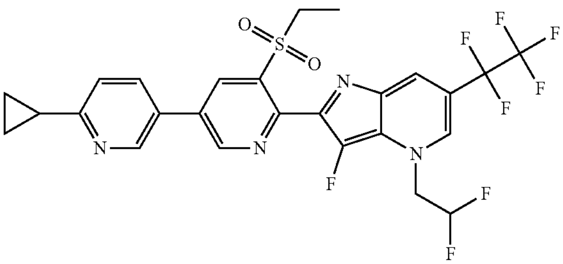
181
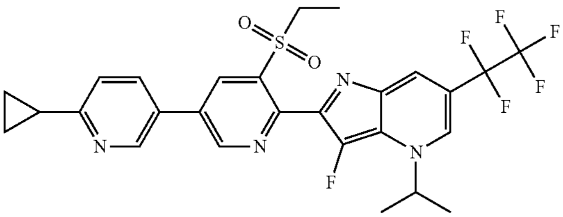
182
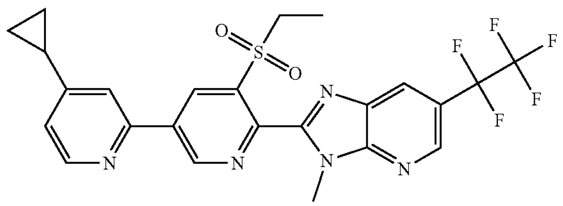
183
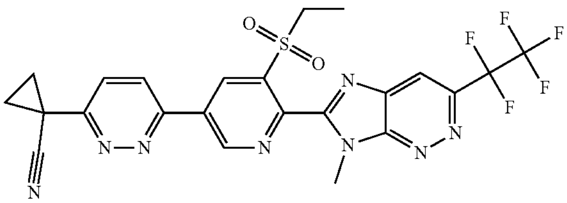
-continued
184
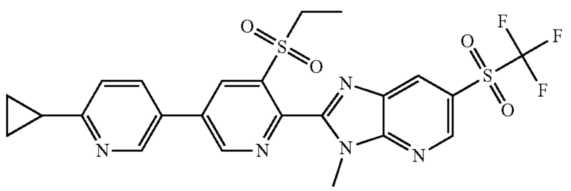
185
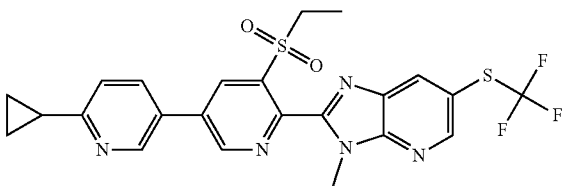
186
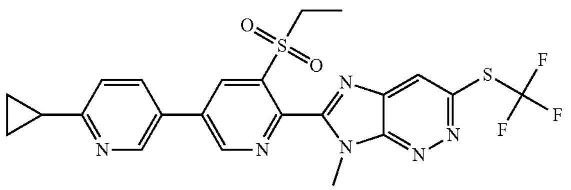
187
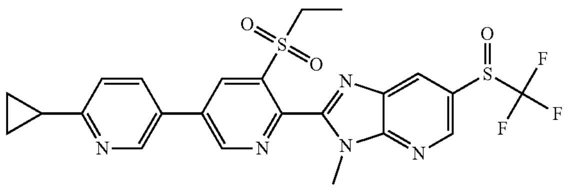
188
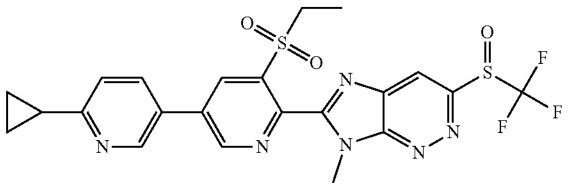
189
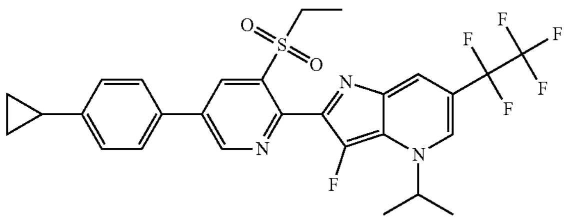
190
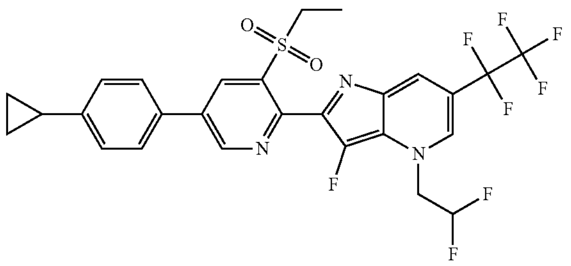

-continued
191
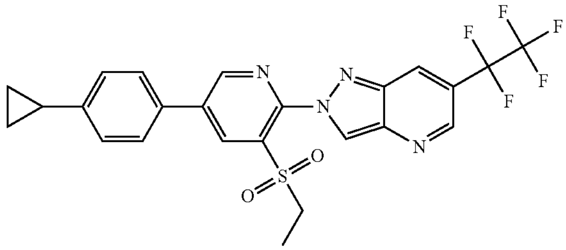
192
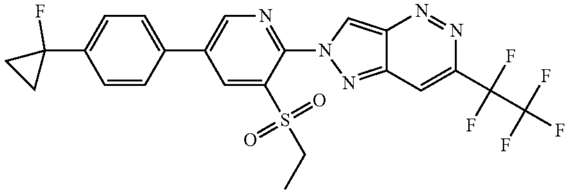
193
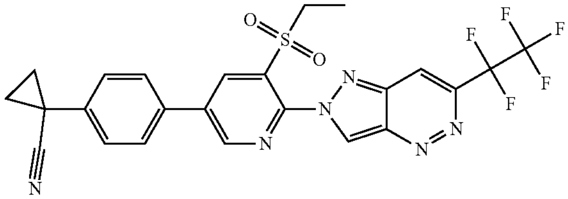
194
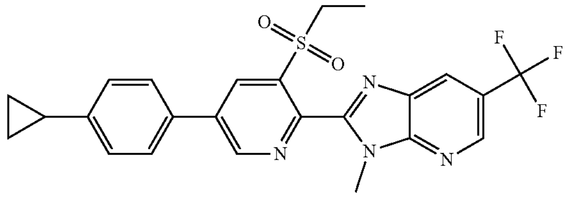
195
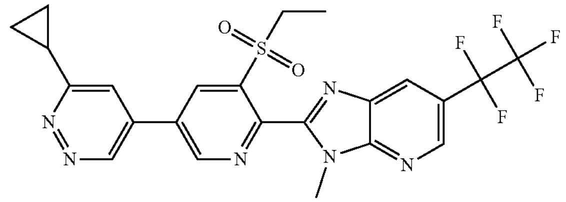
196
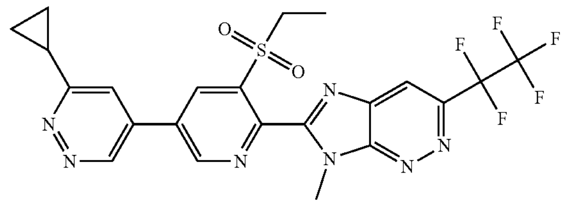
-continued
197
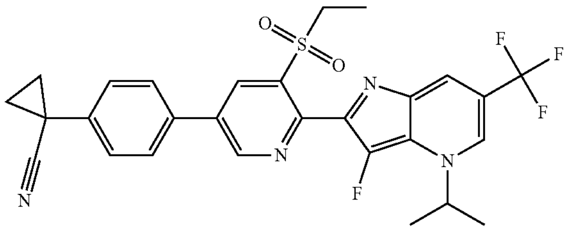
198
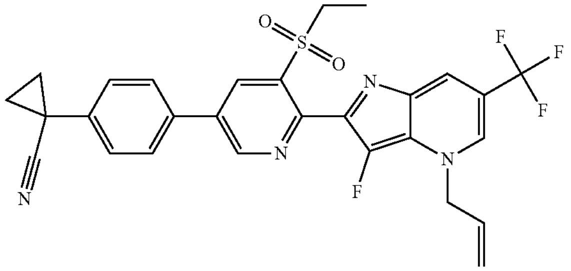
199
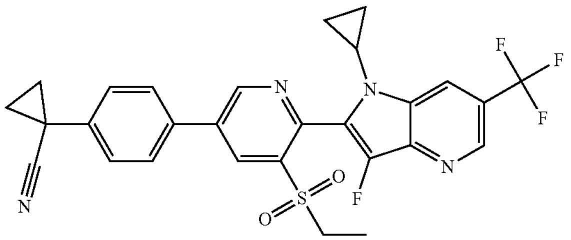
200
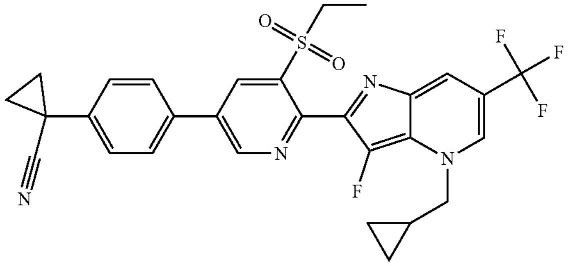
201
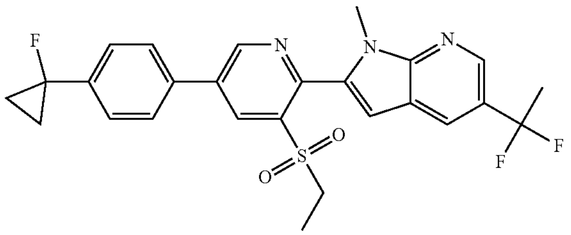
202
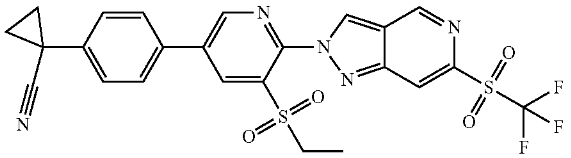

-continued

203

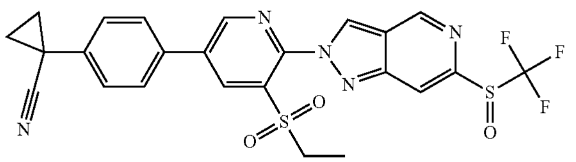

204

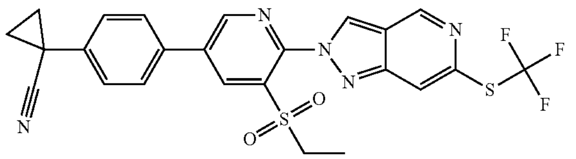

205

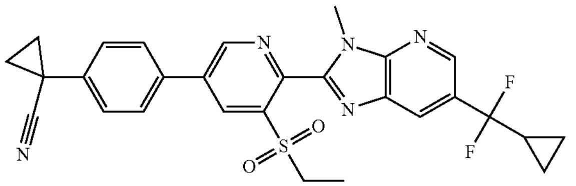

206

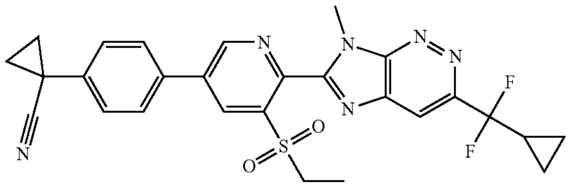

207

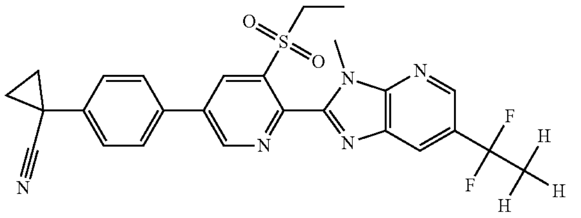

208

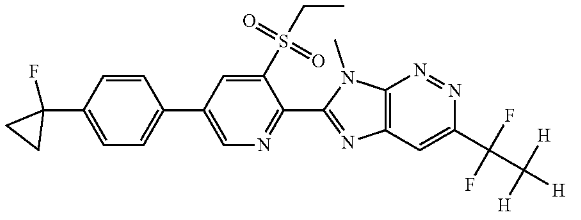

209

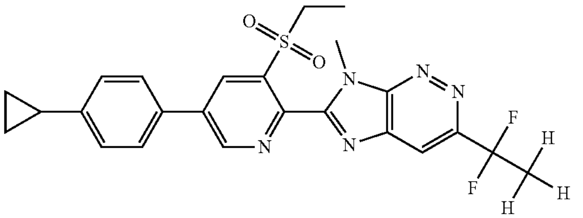

-continued

210

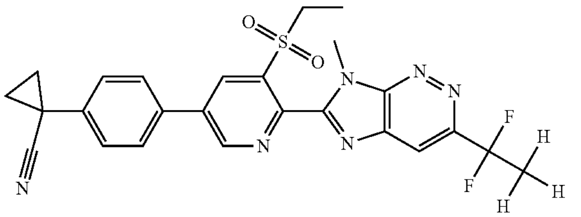

211

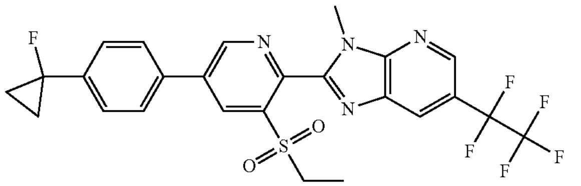

212

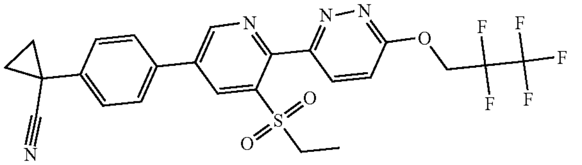

213

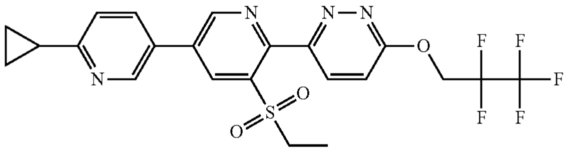

214

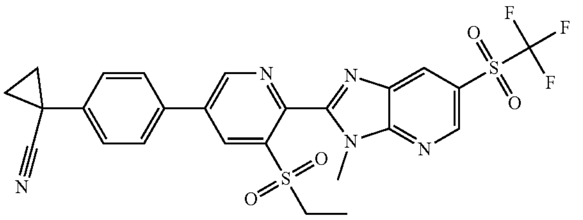

or a pharmaceutically acceptable salt thereof.

The present invention also concerns a compound of formula (I) as herein disclosed and/or claimed, wherein:

W1, W2, W3, W4, W5 are independently C or C—H;

or

W1 is an N atom, and

W2, W3, W4, W5 are independently C or C—H;

or

W2 is an N atom, and

W1, W3, W4, W5 are independently C or C—H;

or

W1, W2 are independently an N atom, and

W3, W4, W5 are independently C or C—H;

or

W1, W3 are independently an N atom, and

W2, W4, W5 are independently C or C—H;

and

R3 is as defined as herein disclosed and/or claimed, such as R3 is “methyl”;

and

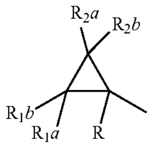

is attached to W1, wherein W1 is a C atom, wherein R, R1a, R1b, R2a, R2b are as defined as herein disclosed and/or claimed, such as R is "hydrogen" or "F" or "CN" and R1a, R1b, R2a, R2b are independently "hydrogen" or "F";

or

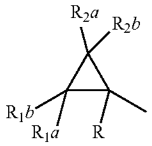

is attached to W2, wherein W2 is a C atom, wherein R, R1a, R1b, R2a, R2b are as defined as herein disclosed and/or claimed, such as R is "hydrogen" or "F" or "CN" and Ria, R1b, R2a, R2b are independently "hydrogen" or "F";

or

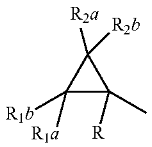

is attached to W3, wherein W3 is a C atom, wherein R, R1a, R1b, R2a, R2b are as defined as herein disclosed and/or claimed, such as R is "hydrogen" or "F" or "CN" and R1a, R1b, R2a, R2b are independently "hydrogen" or "F";

or

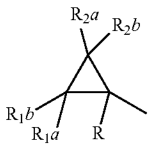

is attached to W4, wherein W4 is a C atom, wherein R, R1a, R1b, R2a, R2b are as defined as herein disclosed and/or claimed, such as R is "hydrogen" or "F" or "CN" and R1a, R1b, R2a, R2b are independently "hydrogen" or "F";

and n is 0or 1;

and

Q1, Q2, Q3 independently are selected from the group consisting of:

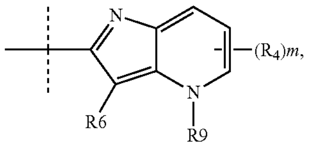

wherein R4, R6, R9, m are as defined as herein disclosed and/or claimed, such as R6 is "hydrogen" or "F", R9 is "$CHF_2$" or "$CH_2$—$CHF_2$" or "ethyl" or "$CH_2$-cyclopropyl", m is 1 and R4 is "$CF_3$";

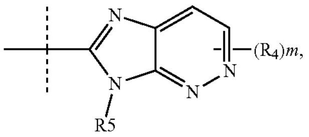

wherein R4, R5, m are as defined as herein disclosed and/or claimed, such as R5 is "methyl", m is 1 and R4 is "$CF_2$-cyclopropyl" or "$CF_2$—$CF_3$" or "S—$CF_3$" or "$S(O)_2$—$CF_3$";

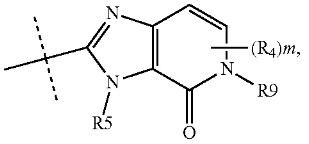

wherein R4, R5, R9, m are as defined as herein disclosed and/or claimed, such as R5 is "methyl", R9 is "cyclopropyl", m is 1 and R4 is "$CF_3$";

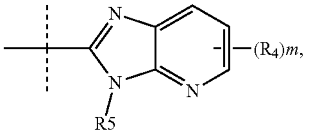

wherein R4, R5, m are as defined as herein disclosed and/or claimed, such as R5 is "methyl", m is 1 and R4 is "$CF_2$—$CF_3$" or "$CF_2$-cyclopropyl" or "$S(O)_2$—$CF_3$";

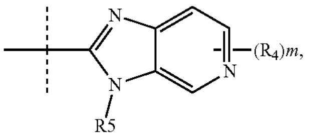

wherein R4, R5, m are as defined as herein disclosed and/or claimed, such as R5 is "methyl", m is 1 and R4 is "$CF_2$—$CF_3$";

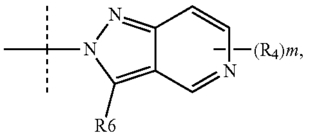

wherein R4, R6, m are as defined as herein disclosed and/or claimed, such as R6 is "hydrogen" or "F", m is 1 and R4 is "$CF_3$" or "$CF_2$—$CF_3$" or "S—$CF_3$" or "S(O)—$CF_3$" or "$S(O)_2$—$CF_3$";

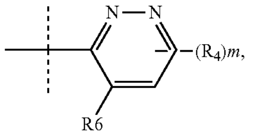
wherein R4, R6, m are as defined as herein disclosed and/or claimed, such as R6 is "hydrogen", m is 1 and R4 is "—O—$CF_2$—$CF_3$";
or a pharmaceutically acceptable salt thereof.
The present invention further concerns a compound of formula (I) as herein disclosed and/or claimed, wherein the compound is selected from the group consisting of:
12
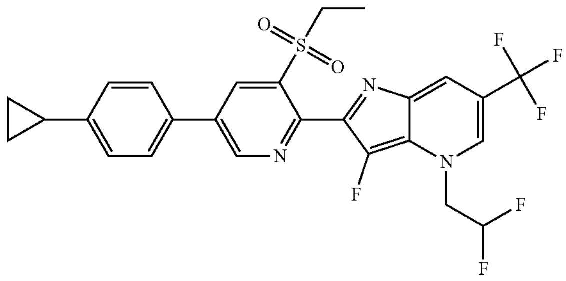
19
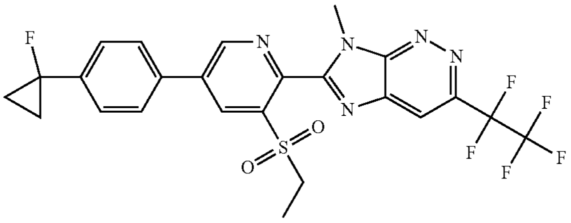
44
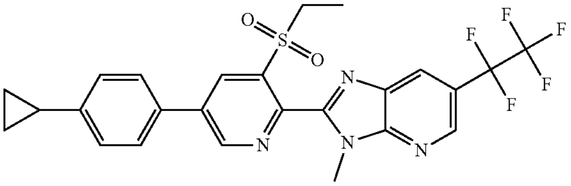
45
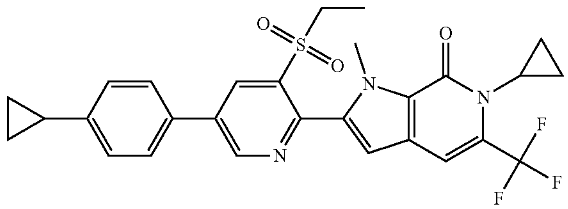
46
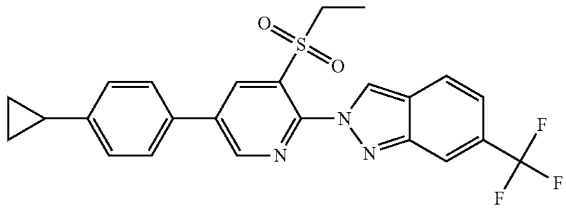
-continued
67
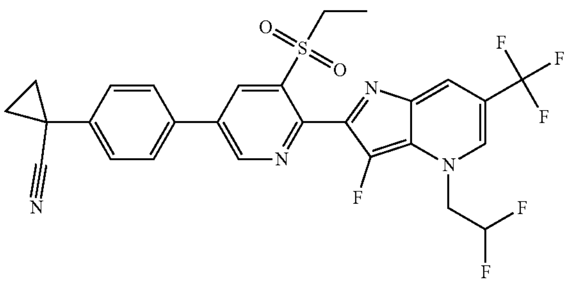
76
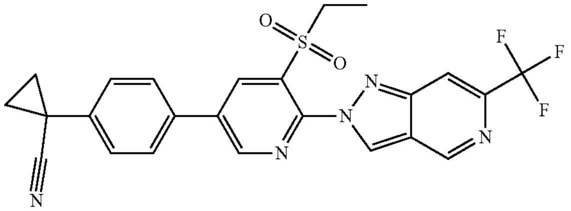
80
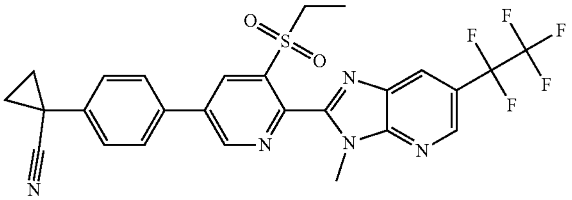
88
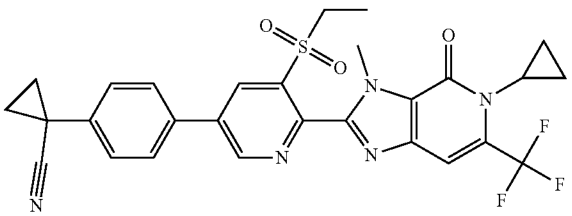
89
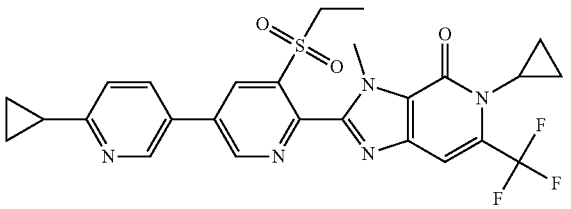
96
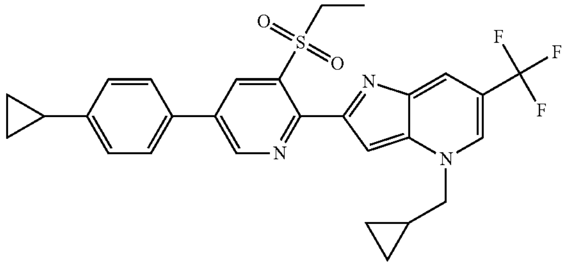

-continued
97
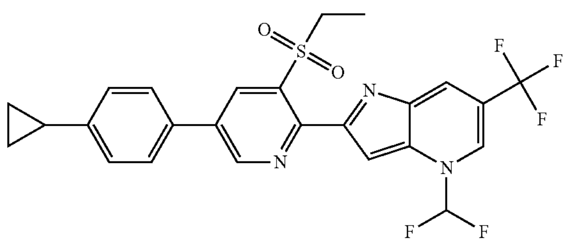
112
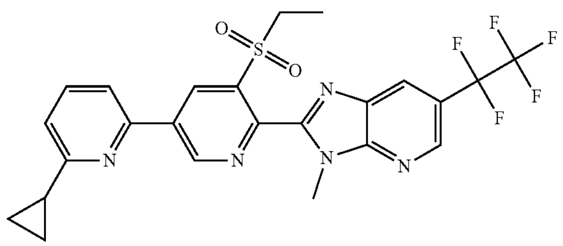
115
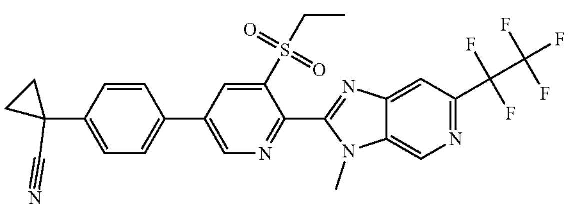
124
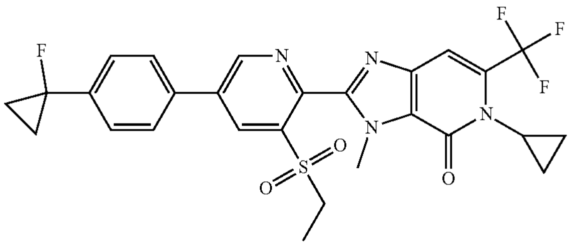
133
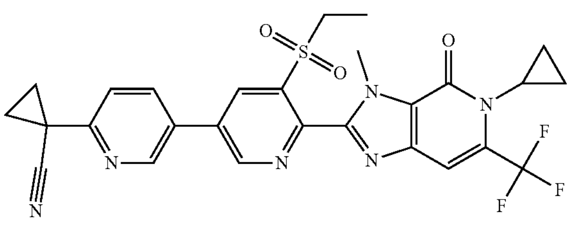
134
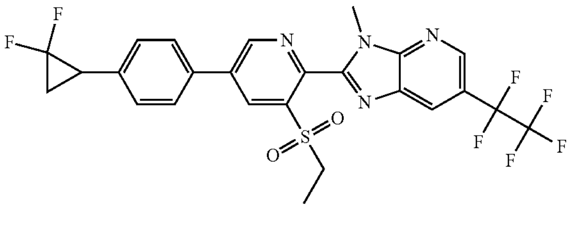
-continued
135
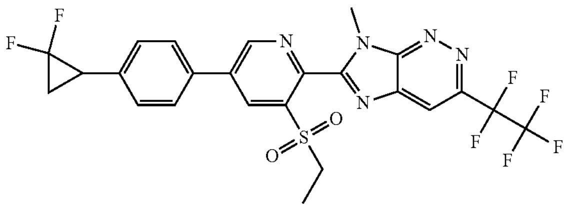
142
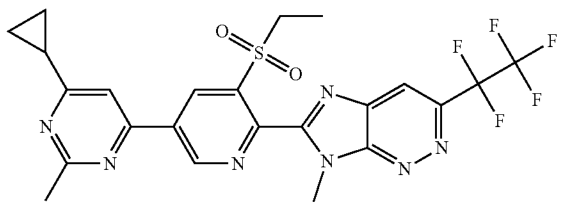
153
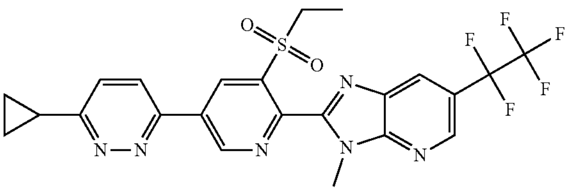
166
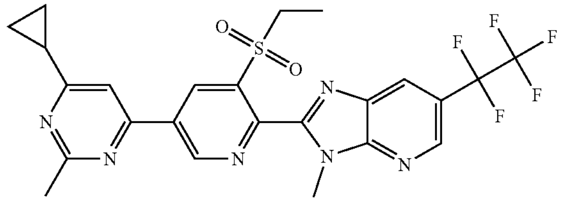
169
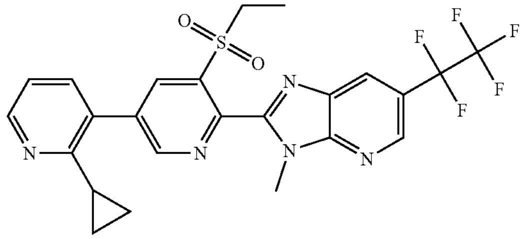
186
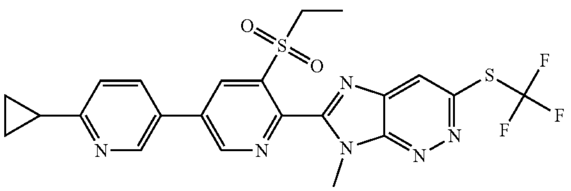
197
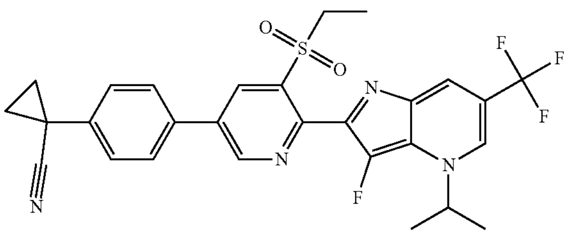

-continued
200
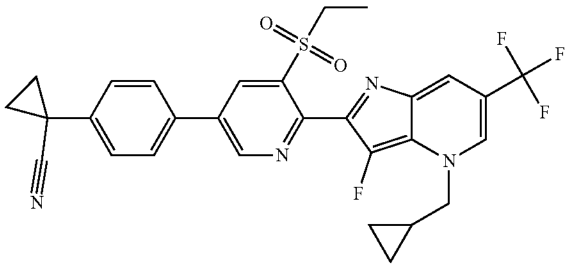
202
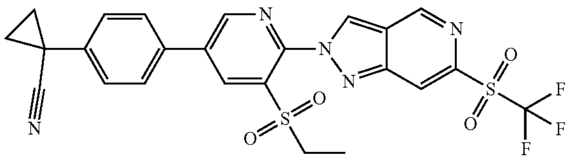
203
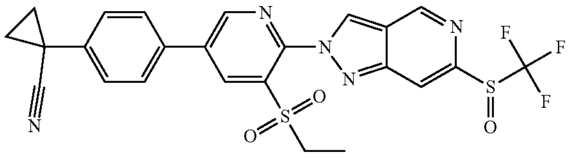
204
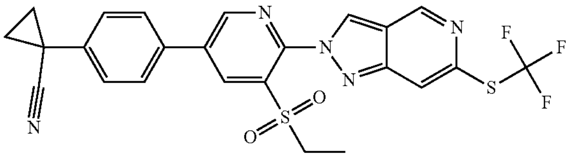
205
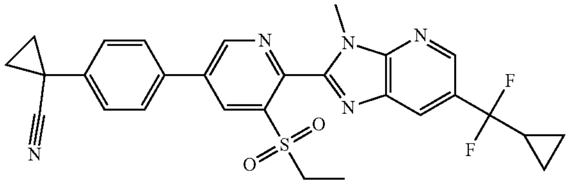
206
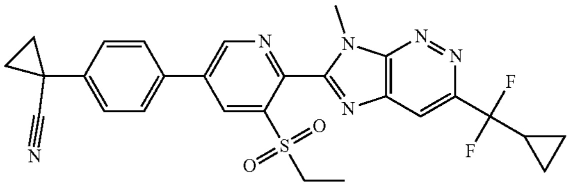
207
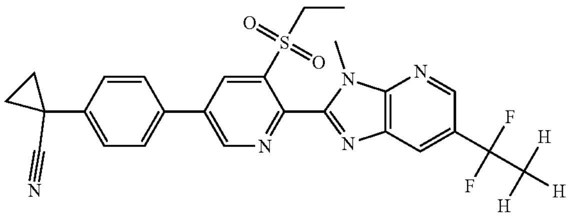
-continued
208
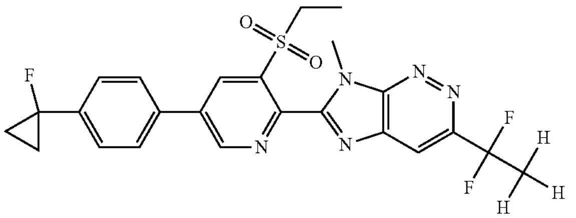
209
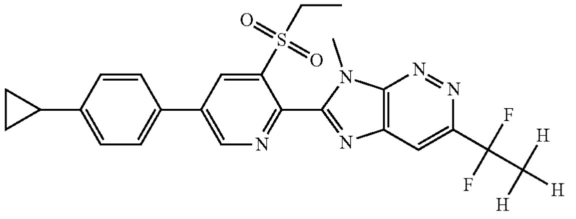
210
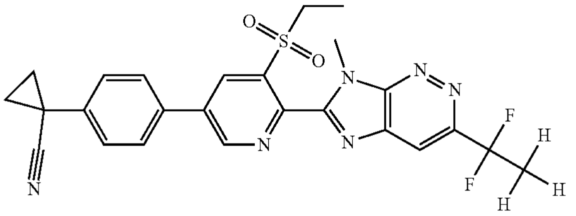
211
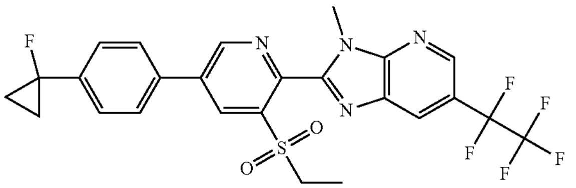
212
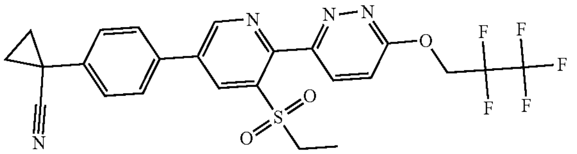
213
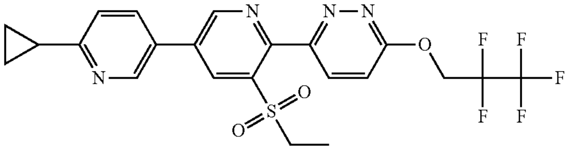
214
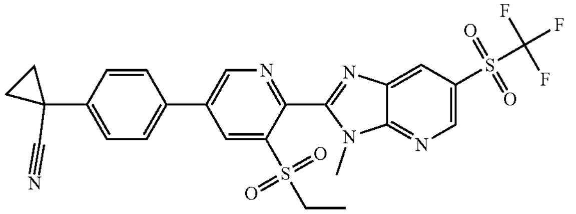
or a pharmaceutically acceptable salt thereof.
The present invention further concerns a compound selected from the group consisting of:

-continued
12
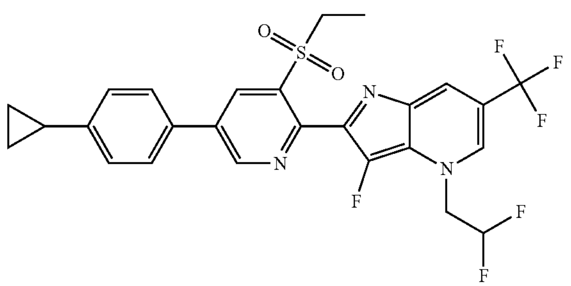
19
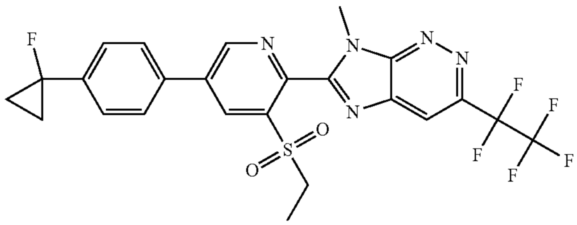
44
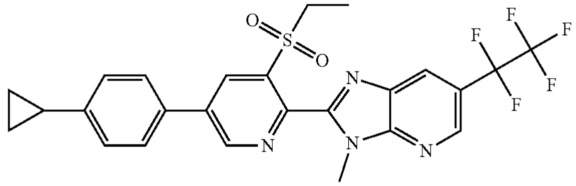
45
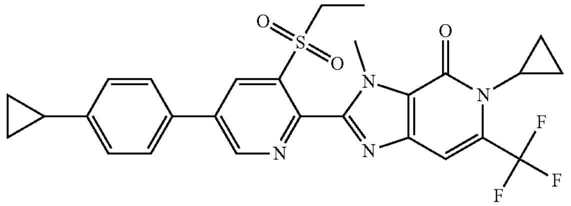
46
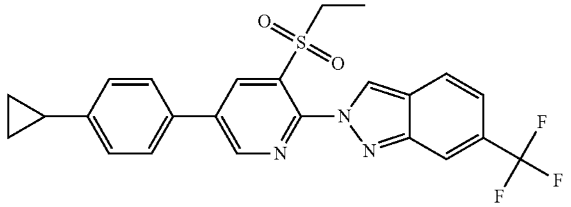
67
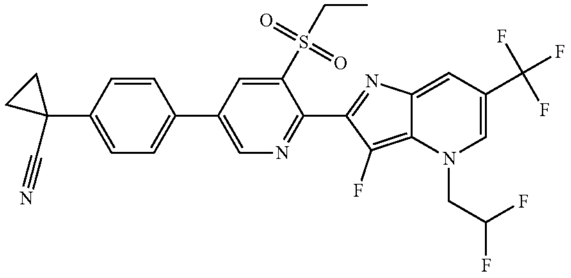
76
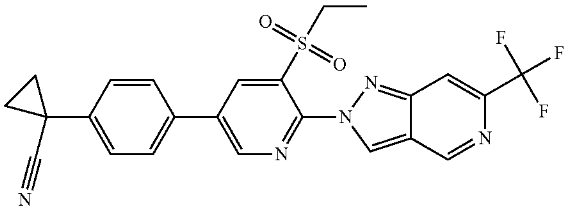
80
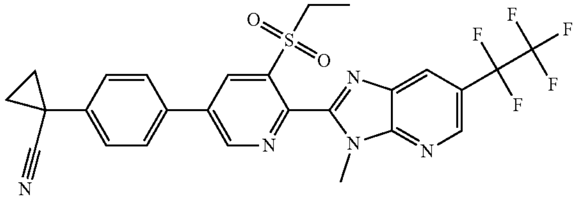
88
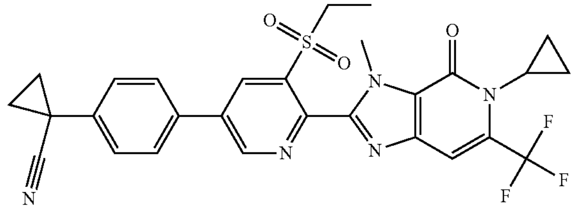
89
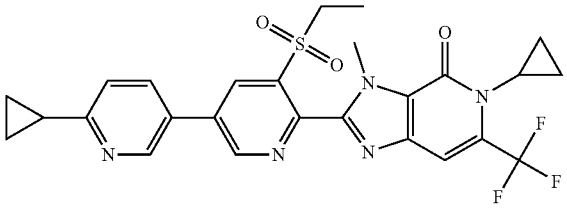
96
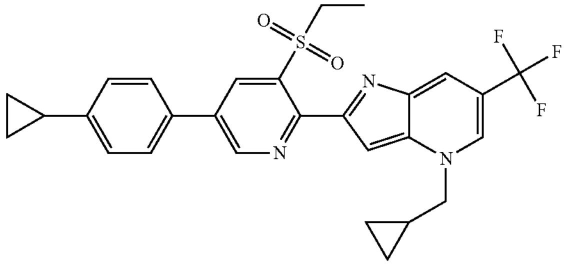
97
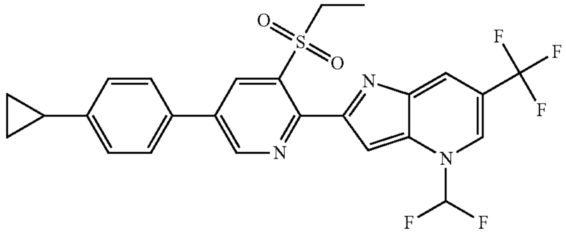

-continued
112
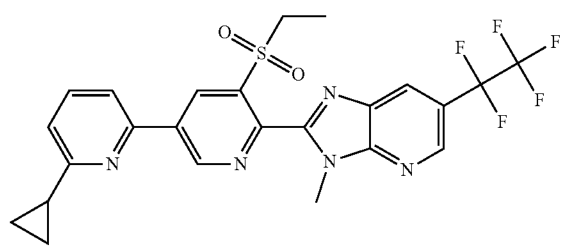
115
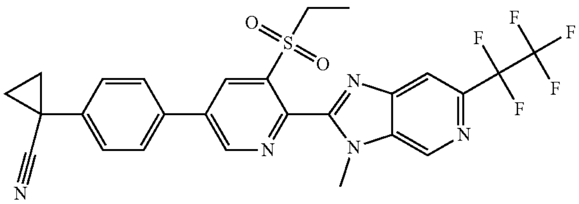
124
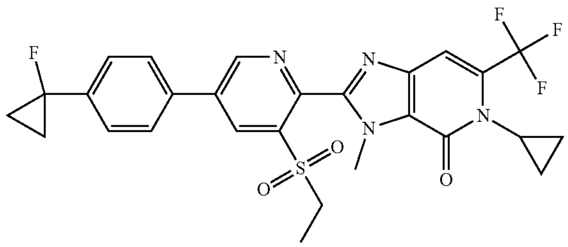
133
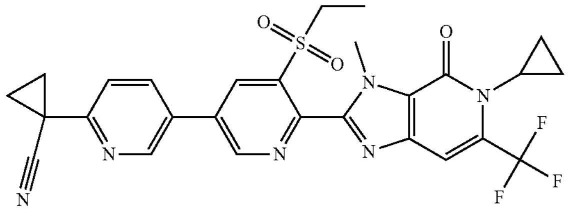
134
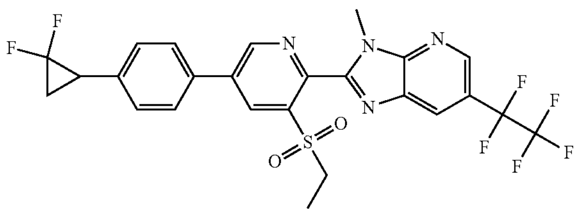
135
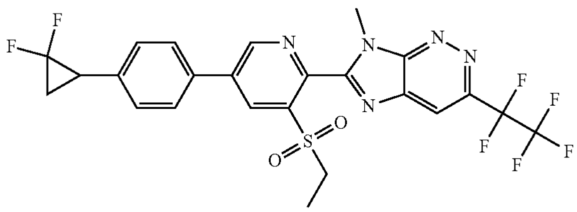
-continued
142
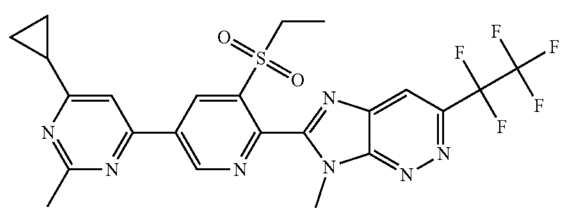
153
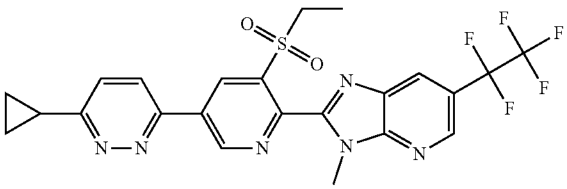
166
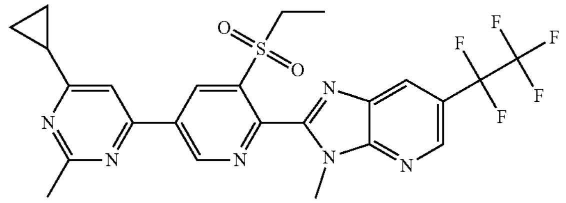
169
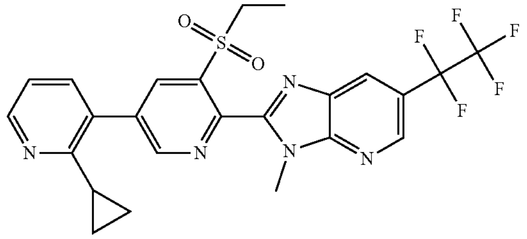
186
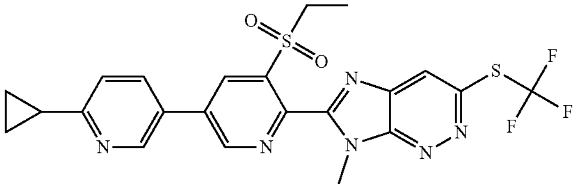
197
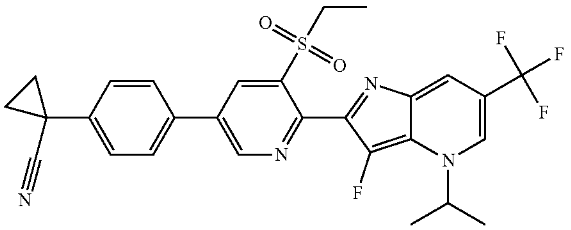

-continued
200
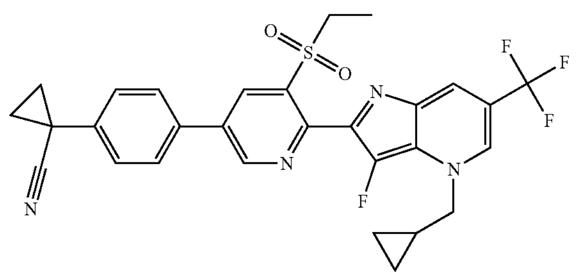
202
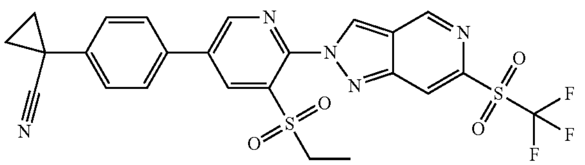
203
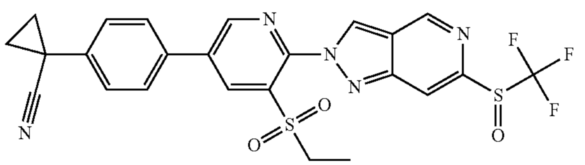
204
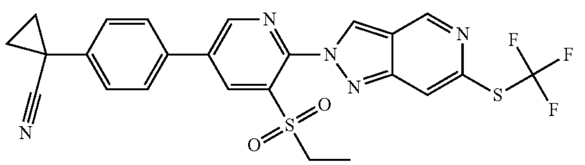
205
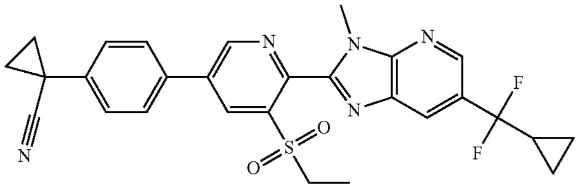
206
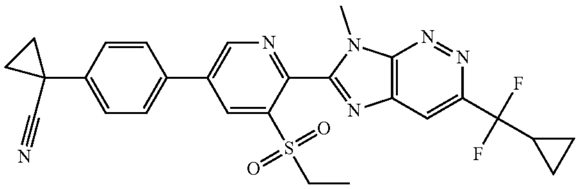
207
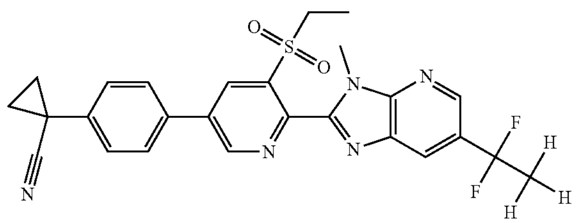
-continued
208
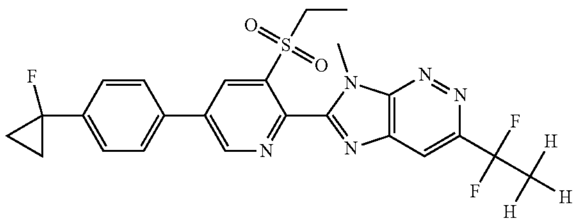
209
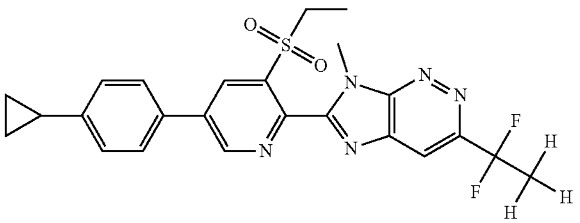
210
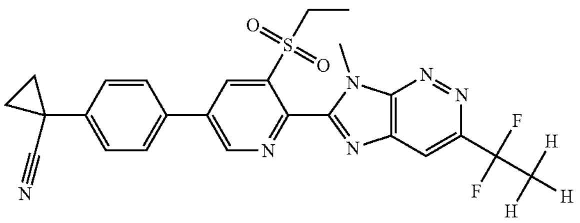
211
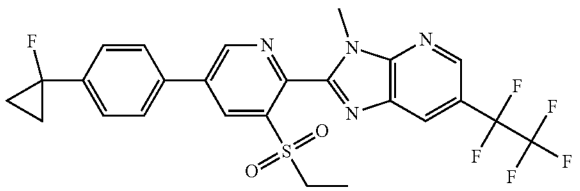
212
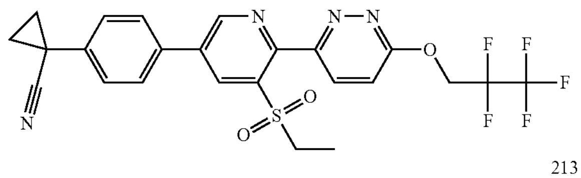
213
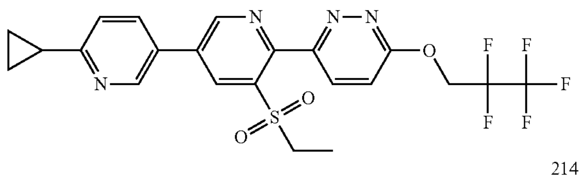
214
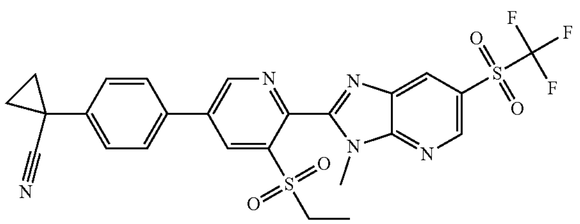
or a pharmaceutically acceptable salt thereof.
The present invention further concerns a pharmaceutical composition comprising one or more compound(s) of formula (I) as herein disclosed and/or claimed or a pharmaceutically acceptable salt thereof and one or more pharmaceutically acceptable excipient(s).

The present invention further concerns a pharmaceutical composition consisting essentially of one or more compound(s) of formula (I) as herein disclosed and/or claimed or a pharmaceutically acceptable salt thereof and one or more pharmaceutically acceptable excipient(s).

The present invention further concerns a pharmaceutical composition consisting of one or more compound(s) of formula (I) as herein disclosed and/or claimed or a pharmaceutically acceptable salt thereof and one or more pharmaceutically acceptable excipient(s).

The present invention further concerns a pharmaceutical composition comprising one or more compound(s) of formula (I) as herein disclosed and/or claimed or a pharmaceutically acceptable salt thereof, one or more additional pharmaceutically active agent(s), and one or more pharmaceutically acceptable excipient(s).

The present invention further concerns a pharmaceutical composition consisting essentially of one or more compound(s) of formula (I) as herein disclosed and/or claimed or a pharmaceutically acceptable salt thereof, one or more additional pharmaceutically active agent(s), and one or more pharmaceutically acceptable excipient(s).

The present invention further concerns a pharmaceutical composition consisting of one or more compound(s) of formula (I) as herein disclosed and/or claimed or a pharmaceutically acceptable salt thereof, one or more additional pharmaceutically active agent(s), and one or more pharmaceutically acceptable excipient(s).

The present invention further concerns a compound of formula (I) as herein disclosed and/or claimed or a pharmaceutically acceptable salt thereof or a pharmaceutical composition as herein disclosed and/or claimed for use as a medicament, preferably for use as an antiparasitic medicament. A corresponding use of a compound of formula (I) as herein disclosed and/or claimed or a pharmaceutically acceptable salt thereof or a pharmaceutical composition as herein disclosed and/or claimed for the preparation of a medicament, preferably an antiparasitic medicament, are also intended to be comprised by the present invention.

The present invention further concerns a compound of formula (I) as herein disclosed and/or claimed or a pharmaceutically acceptable salt thereof or a pharmaceutical composition as herein disclosed and/or claimed for use in a method of treatment, prevention and/or control of a parasitic infection and/or infestation in an animal, preferably of an ectoparasitic infection and/or infestation in an animal, more preferably of an infection and/or infestation of fleas and/or ticks in an animal. A corresponding method of treatment, prevention and/or control of a parasitic infection and/or infestation in an animal, comprising administering an effective amount of compound of formula (I) as herein disclosed and/or claimed or a pharmaceutically acceptable salt thereof or a pharmaceutical composition as herein disclosed and/or claimed to such animals, as well as the corresponding use of compound of formula (I) as herein disclosed and/or claimed or a pharmaceutically acceptable salt thereof or a pharmaceutical composition as herein disclosed and/or claimed for the preparation of a medicament for the treatment, prevention and/or control of a parasitic infection and/or infestation in an animal, are also intended to be comprised by the present invention.

The present invention further concerns an intermediate compound selected from the group consisting of formula (II) or formula (III):

(II)

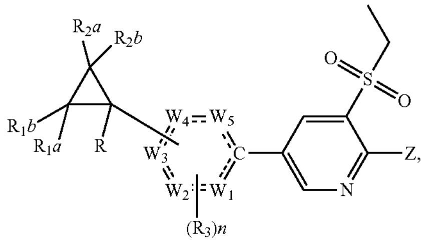

or (III)

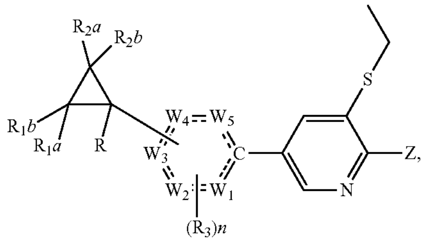

wherein independently from each other "Z" is a halogen, such as F, Cl, Br, I, C(O)—OH, C(O)-halogen, such as C(O)—Cl, or C(O)—O—$C_1$-$C_6$-alkyl, such as C(O)—O-methyl and C(O)—O-ethyl; and wherein the other variables W1, W2, W3, W4, W5, R, R1a, R1b, R2a, R2b, R3, n are as defined as herein disclosed and/or claimed.

The present invention further concerns an intermediate compound according to formula (IV):

(IV)

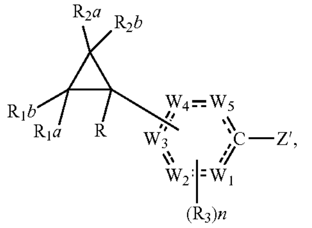

wherein independently from each other "Z'" is $B(OH)_2$, $Sn(CH_3)3$, halogen, such as F, Cl, Br, I, or

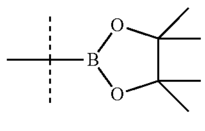

;

and wherein the other variables W1, W2, W3, W4, W5, R, R1a, R1b, R2a, R2b, R3, n are as defined as herein disclosed and/or claimed.

The compounds of formula (I) as herein disclosed and/or claimed or a pharmaceutically acceptable salt thereof are advantageously more potent/efficacious against the ectoparasites fleas and/or ticks, as compared to the four structurally closest prior art compounds (A), (B), (C) and (D) and as evidenced by the comparative experimental data in Example 9 in in vitro assays regarding flea membrane feeding (ingestion, blood feeding) activity against *Ctenocephalides felis* and/or contact activity against *Rhipicephalus sanguineus*: the results of these in vitro assays demonstrate their superior potency/efficacy vis-á-vis such four structurally closest prior art compounds.

DETAILED DESCRIPTION OF THE INVENTION

Generally, the present invention provides a compound of formula (I) or a pharmaceutically acceptable salt thereof as herein disclosed and/or claimed as well as their corresponding pharmaceutical compositions, combinations and uses.

In a specific aspect, a compound of formula (I) as herein disclosed and/or claimed is provided, wherein W1, W2, W3, W4, W5 are independently C or C—H; or a pharmaceutically acceptable salt thereof.

In another specific aspect, a compound of formula (I) as herein disclosed and/or claimed is provided, wherein W1 is an N atom, and W2, W3, W4, W5 are independently C or C—H; or a pharmaceutically acceptable salt thereof.

In yet another specific aspect, a compound of formula (I) as herein disclosed and/or claimed is provided, wherein W2 is an N atom, and W1, W3, W4, W5 are independently C or C—H; or a pharmaceutically acceptable salt thereof.

In yet another specific aspect, a compound of formula (I) as herein disclosed and/or claimed is provided, wherein W3 is an N atom, and W1, W2, W4, W5 are independently C or C—H; or a pharmaceutically acceptable salt thereof.

In yet another specific aspect, a compound of formula (I) as herein disclosed and/or claimed is provided, wherein W1, W3 are both N atoms, and W2, W4, W5 are independently C or C—H; or a pharmaceutically acceptable salt thereof.

In yet another specific aspect, a compound of formula (I) as herein disclosed and/or claimed is provided, wherein W1, W5 are both N atoms, and W2, W3, W4 are independently C or C—H; or a pharmaceutically acceptable salt thereof.

In yet another specific aspect, a compound of formula (I) as herein disclosed and/or claimed is provided, wherein W2, W3 are both N atoms, and W1, W4, W5 are independently C or C—H; or a pharmaceutically acceptable salt thereof.

In yet another specific aspect, a compound of formula (I) as herein disclosed and/or claimed is provided, wherein W2, W4 are both N atoms, and W1, W3, W5 are independently C or C—H; or a pharmaceutically acceptable salt thereof.

In yet another specific aspect, a compound of formula (I) as herein disclosed and/or claimed is provided, wherein W1, W2 are both N atoms, and W3, W4, W5 are independently C or C—H; or a pharmaceutically acceptable salt thereof.

In yet another specific aspect, a compound of formula (I) as herein disclosed and/or claimed is provided, wherein W1, W2, W4 are all N atoms, and W3, W5 are independently C or C—H; or a pharmaceutically acceptable salt thereof.

In yet another specific aspect, a compound of formula (I) as herein disclosed and/or claimed is provided, wherein W1, W2, W5 are all N atoms, and W3, W4 are independently C or C—H; or a pharmaceutically acceptable salt thereof.

In yet another specific aspect, a compound of formula (I) as herein disclosed and/or claimed is provided, wherein

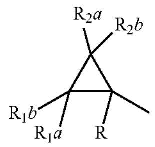

is attached to W3, wherein W3 is a C atom, wherein R, R1a, R1b, R2a, R2b are as defined as herein disclosed and/or claimed; or a pharmaceutically acceptable salt thereof.

In yet another specific aspect, a compound of formula (I) as herein disclosed and/or claimed is provided, wherein

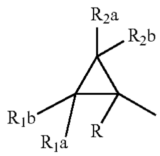

is attached to W2, wherein W2 is a C atom, wherein R, R1a, R1b, R2a, R2b are as defined as herein disclosed and/or claimed; or a pharmaceutically acceptable salt thereof.

In yet another specific aspect, a compound of formula (I) as herein disclosed and/or claimed is provided, wherein

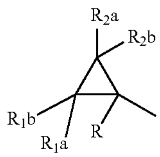

is attached to W4, wherein W4 is a C atom, wherein R, R1a, R1b, R2a, R2b are as defined as herein disclosed and/or claimed; or a pharmaceutically acceptable salt thereof.

In yet another specific aspect, a compound of formula (I) as herein disclosed and/or claimed is provided, wherein

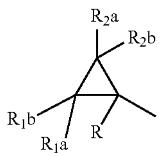

is attached to W1, wherein W1 is a C atom, wherein R, R1a, R1b, R2a, R2b are as defined as herein disclosed and/or claimed; or a pharmaceutically acceptable salt thereof.

In yet another specific aspect, a compound of formula (I) as herein disclosed and/or claimed is provided, wherein

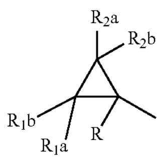

is attached to W5, wherein W5 is a C atom, wherein R, R1a, R1b, R2a, R2b are as defined as herein disclosed and/or claimed; or a pharmaceutically acceptable salt thereof.

In yet another specific aspect, a compound of formula (I) as herein disclosed and/or claimed is provided, wherein n is 0 or 1; or a pharmaceutically acceptable salt thereof.

In yet another specific aspect, a compound of formula (I) as herein disclosed and/or claimed is 10 provided, wherein m is 1 or 2; or a pharmaceutically acceptable salt thereof.

In yet another specific aspect, a compound of formula (I) as herein disclosed and/or claimed is provided, wherein Q1, Q2, Q3 independently are selected from the group consisting of:

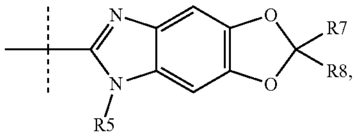

wherein R5, R7, R8 are as defined as herein disclosed and/or claimed, such as R5 is “methyl” and R7 and R8 are both “F”;

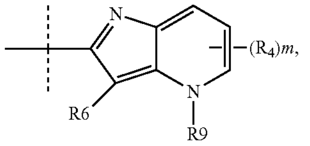

wherein R4, R6, R9, m are as defined as herein disclosed and/or claimed, such as R6 is “hydrogen” or “F”, R9 is “$CHF_2$” or “$CH_2$—$CHF_2$” or “ethyl” or “$CH_2$-cyclopropyl”, m is 1 and R4 is “$CF_3$”;

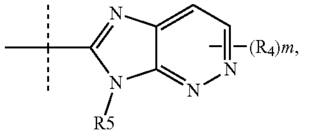

wherein R4, R5, m are as defined as herein disclosed and/or claimed, such as R5 is “methyl”, m is 1 and R4 is “$CF_2$-cyclopropyl” or “$CF_2$—$CF_3$” or “S—$CF_3$” or “$S(O)_2$—$CF_3$”;

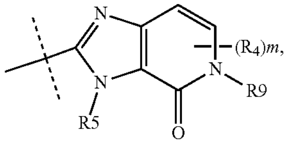

wherein R4, R5, R9, m are as defined as herein disclosed and/or claimed, such as R5 is “methyl”, R9 is “cyclopropyl”, m is 1 and R4 is “$CF_3$”;

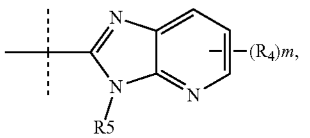

wherein R4, R5, m are as defined as herein disclosed and/or claimed, such as R5 is “methyl”, m is 1 and R4 is “$CF_2$—$CF_3$” or “$CF_2$-cyclopropyl” or “$S(O)_2$—$CF_3$”;

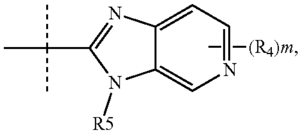

wherein R4, R5, m are as defined as herein disclosed and/or claimed, such as R5 is “methyl”, m is 1 and R4 is “$CF_2$—$CF_3$”;

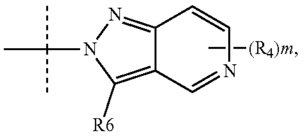

wherein R4, R6, m are as defined as herein disclosed and/or claimed, such as R6 is “hydrogen” or “F”, m is 1 and R4 is “$CF_3$” or “$CF_2$—$CF_3$” or “S—$CF_3$” or “S(O)—$CF_3$” or “$S(O)_2$—$CF_3$”;

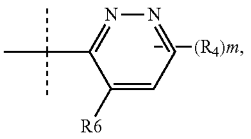

wherein R4, R6, m are as defined as herein disclosed and/or claimed, such as R6 is “hydrogen”, m is 1 and R4 is “—O—$CF_2$—$CF_3$”;

or a pharmaceutically acceptable salt thereof.

Definitions

Unless defined otherwise, all technical and scientific terms used herein have the same meaning as is commonly understood by one of skill in the art to which this invention belongs at the time of filing. Terms not specifically defined herein should be given the meanings that would be given to them by one of skill in the art in light of the disclosure and the context. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of “or” means “and/or” unless stated otherwise. Furthermore, the use of the term “including”, as well as other forms such as “includes” and “included” is not limiting. As used in the specification, however, unless specified to the contrary, the following terms have the meaning indicated and the following conventions are adhered to.

In the groups, radicals, or moieties defined herein, the number of carbon atoms is often specified preceding the group, for example, $C_1$-$C_6$-alkyl means an alkyl group or radical having 1 to 6 carbon atoms. In general in groups like HO, $H_2N$, (O)S, $(O)_2S$, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent “aryl-$C_{1-3}$-alkylene” means an aryl group which is bound to a $C_3$-alkyl-group, the latter of which is bound to the core or to the group to which the substituent is attached.

In case a compound of the present invention is depicted in the form of a chemical name and as a formula, in case of any discrepancy the formula shall prevail. An asterisk may be used in sub-formulas to indicate the bond which is connected to the core molecule as defined.

The numeration of the atoms of a substituent starts with the atom which is closest to the core or to the group to which the substituent is attached. For example, the term "3-carboxypropyl-group" represents the following substituent:

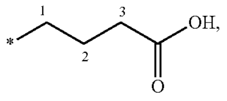

wherein the carboxy group is attached to the third carbon atom of the propyl group. The terms "1-methylpropyl-", "2,2-dimethylpropyl-" or "cyclopropylmethyl-" group represent the following groups:

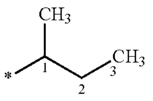
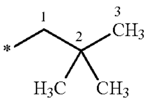
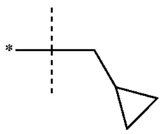

The asterisk or

" 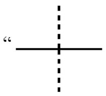 "

may be used in sub-formulas to indicate the bond which is connected to the core molecule as fined.

The term "substituted" as used herein, means that one or more hydrogens on the designated atom are replaced by a group selected from a defined group of substituents, provided that the designated atom's normal valence is not exceeded, and that the substitution results in a stable compound. Likewise, the term "substituted" may be used in connection with a chemical moiety instead of a single atom, e.g. "substituted alkyl", "substituted aryl" or the like.

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as solvates thereof such as for instance hydrates.

Unless specifically indicated, also "pharmaceutically acceptable salts" as defined in more detail below shall encompass solvates thereof such as for instance hydrates.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The phrase "pharmaceutically acceptable" is employed herein to refer to those compounds, materials, compositions, and/or dosage forms which are, within the scope of sound medical judgment, suitable for use in contact with the tissues of animals without excessive toxicity, irritation, allergic response, or other problem or complication, and commensurate with a reasonable benefit/risk ratio.

As used herein, "pharmaceutically acceptable salt" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid. Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent such as ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

The term "halogen" denotes fluorine, chlorine, bromine and iodine.

The term "$C_{1-a}$-alkyl", wherein n is an integer selected from 2, 3, 4, 5 or 6, preferably 4, 5, or 6, either alone or in combination with another radical, denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—CH($CH_3$)—, $H_3C$—$CH_2$—$CH_2$—$CH_2$—, $H_3C$—$CH_2$—CH($CH_3$)—, $H_3C$—CH($CH_3$)—$CH_2$—, $H_3C$—C($CH_3$)—, $H_3C$—$CH_2$—CH—$CH_2$—CH—, $H_3C$—$CH_2$—$CH_2$—CH($CH_3$)—, $H_3C$—$CH_2$—CH($CH_3$)—$CH_2$—, $H_3C$—CH($CH_3$)—$CH_2$—$CH_2$-, $H_3C$—$CH_2$—C($CH_3$)$_2$—, $H_3C$—C($CH_3$)$_2$—$CH_2$—, $H_3C$—CH($CH_3$)—CH($CH_3$)—and $H_3C$—$CH_2$—CH($CH_2CH_3$)—.

The term "$C_{1-m}$-alkylene", wherein n is an integer selected from 2, 3, 4, 5 or 6, preferably 4, 5 or 6, either alone or in combination with another radical, denotes an acyclic, saturated, branched or linear chain divalent alkyl radical containing from 1 to n carbon atoms. For example, the term $C_{1-4}$-alkylene includes —$CH_2$—, —$CH_2$—$CH_2$—, —CH($CH_3$)—, —$CH_2$—$CH_2$—$CH_2$—, —C($CH_3$)$_2$—, —CH($CH_2CH_3$)—, —CH($CH_3$)—$CH_2$—, —CH—C H($CH_3$)—, —$CH_2$—$CH_2$—$CH_2$—$CH_2$—, —$CH_2$—$CH_2$—CH($CH_3$)—, —CH($CH_3$)—$CH_2$—$CH_2$—, —$CH_2$—CH($CH_3$)—$CH_2$—, —$CH_2$—C(CH $_3$)2, —C($CH_3$)$_2$—CH—, —CH($CH_3$)—CH($CH_3$)—, —$CH_2$—CH($CH_2CH_3$)—, —CH($CH_2CH_3$)—CH—, —CH($CH_2CH_2CH_3$)—, —C H(CH($CH_3$))$_2$—and —C($CH_3$)($CH_2CH_3$)—.

The term "$C_{2-m}$-alkenyl" is used for a group "$C_{2-m}$-alkyl", wherein m is an integer selected from 3, 4, 5 or 6, preferably 4, 5 or 6, if at least two carbon atoms of said group are bonded to each other by a double bond.

The term "$C_{2-m}$-alkenylene" is used for a group "$C_{2-m}$-alkylene", wherein m is an integer selected from 3, 4, 5 or 6, preferably 4, 5 or 6, if at least two carbon atoms of said group are bonded to each other by a double bond.

The term "$C_{2-m}$-alkynyl" is used for a group "$C_{2-m}$-alkyl", wherein m is an integer selected from 3, 4, 5 or 6, preferably 4, 5 or 6, if at least two carbon atoms of said group are bonded to each other by a triple bond.

The term "$C_{2-m}$-alkynylene" is used for a group "$C_{2-m}$-alkylene", wherein m is an integer selected from 3, 4, 5 or 6, preferably 4, 5 or 6, if at least two of those carbon atoms of said group are bonded to each other by a triple bond.

The term "$C_{3-k}$-cycloalkyl", wherein k is an integer selected from 4, 5, 6, 7 or 8, preferably 4, 5 or 6, either alone or in combination with another radical, denotes a cyclic, saturated, unbranched hydrocarbon radical with 3 to k C atoms. For example the term $C_{3-7}$-cycloalkyl includes cyclopropyl, cyclobutyl, cyclopentyl, cyclohexyl and cycloheptyl.

The term "$C_{3-k}$-cycloalkenyl", wherein k is an integer selected from 4, 5, 6, 7 or 8, preferably 4, 5 or 6, either alone or in combination with another radical, denotes a cyclic, unsaturated, but non-aromatic, unbranched hydrocarbon radical with 3 to k C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl, cycloheptadienyl and cycloheptatrienyl.

The term "halo" added to an "alkyl", "alkylene", "alkenyl", "alkenylene", "alkynyl", "alkynylene", "cycloalkyl", "cycloalkenyl" or "alkoxy" group defines an alkyl, alkylene, alkenyl, alkenylene, alkynyl, alkynylene, cycloalkyl, cycloalkenyl or alkoxy group, wherein one or more hydrogen atoms are replaced by a halogen atom selected from among fluorine, chlorine, bromine or iodine, preferably fluorine and chlorine, particularly preferred is fluorine. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "fluoroalkyl" as used herein refers to an alkyl in which one or more of the hydrogen atoms is replaced with fluorine atoms, for example difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "alkoxy" refers to an alkyl-O—, wherein alkyl is as defined above. Similarly, the terms "alkenyloxy", "alkynyloxy", "haloalkoxy", "haloalkenyloxy", "haloalkynyloxy", "cycloalkoxy", "cycloalkenyloxy", "halocycloalkoxy", and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined herein. Examples of $C_1$-$C_6$-alkoxy include, but are not limited to, methoxy, ethoxy, $OCH_2$—$C_2H_5$, OCH($CH_3$)$_2$, n-butoxy, OCH($CH_3$)—$C_2$Hs, $OCH_2$—CH($CH_3$)$_2$, OC($CH_3$)$_3$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "carbocyclyl" or "carbocycle", either alone or in combination with another radical, means a mono-, bi- or tricyclic ring structure consisting of 3 to 14 carbon atoms. The term "carbocyclyl" or "carbocycle" refers to fully saturated, partially saturated and aromatic ring systems. The term "carbocyclyl" or "carbocycle" encompasses fused, bridged and spirocyclic systems. Examples include:

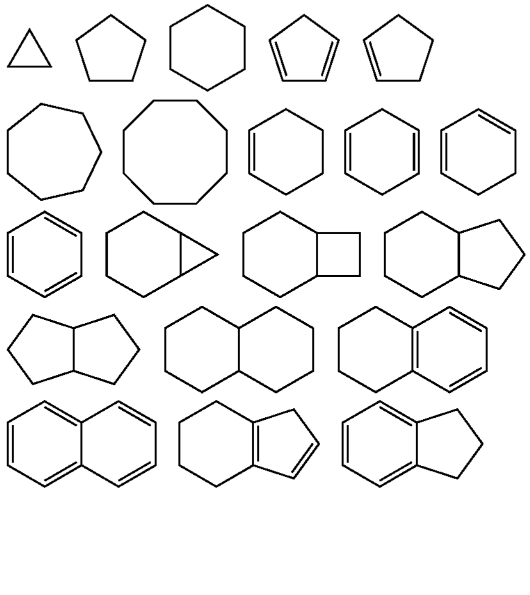

-continued

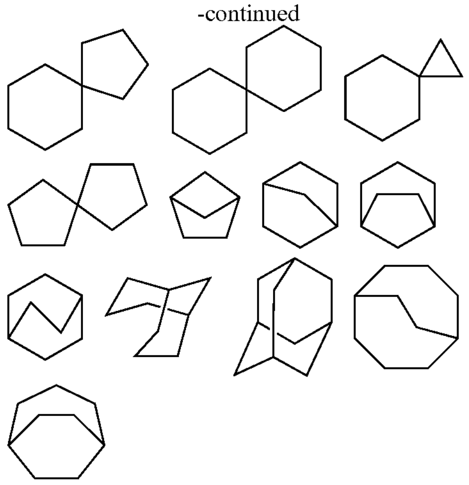

The term "aryl", either alone or in combination with another radical, denotes a carbocyclic aromatic monocyclic group containing 6 carbon atoms, which is optionally further fused to a second five- or six-membered, carbocyclic group which is aromatic, fully saturated or partially saturated. The term "aryl" includes, but is not limited to, phenyl, indanyl, indenyl, naphthyl, anthracenyl, phenanthrenyl, tetrahydronaphthyl and dihydronaphthyl.

The term "aralkyl" refers to an aryl group that is bonded to the parent compound through a diradical alkylene bridge, $(-CH_2-)_n$, where n is 1-6 and where "aryl" is as defined herein.

The term "heterocyclyl" or "heterocycle" means a saturated or unsaturated mono- or polycyclic ring system optionally comprising aromatic rings, containing one or more heteroatoms selected from N, O, S, S(O) or $S(O)_2$ consisting of 3 to 14 ring atoms, wherein none of the heteroatoms is part of the aromatic ring. The term "heterocyclyl" or "heterocycle" is intended to include all possible isomeric forms. Thus, the term "heterocyclyl" or "heterocycle" includes the following exemplary structures (not depicted as radicals as each form is optionally attached through a covalent bond to any atom so long as appropriate valences are maintained):

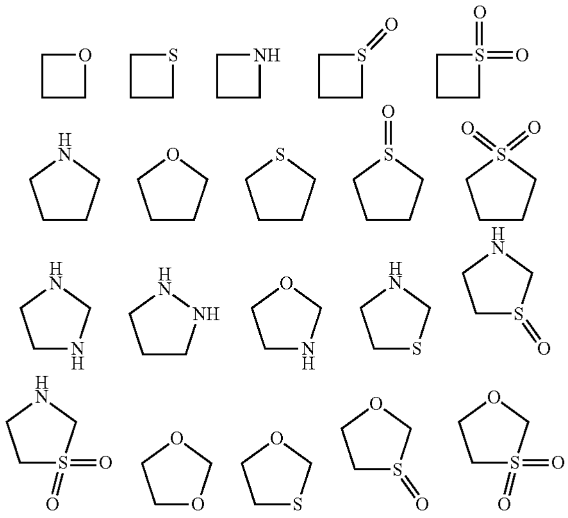

-continued

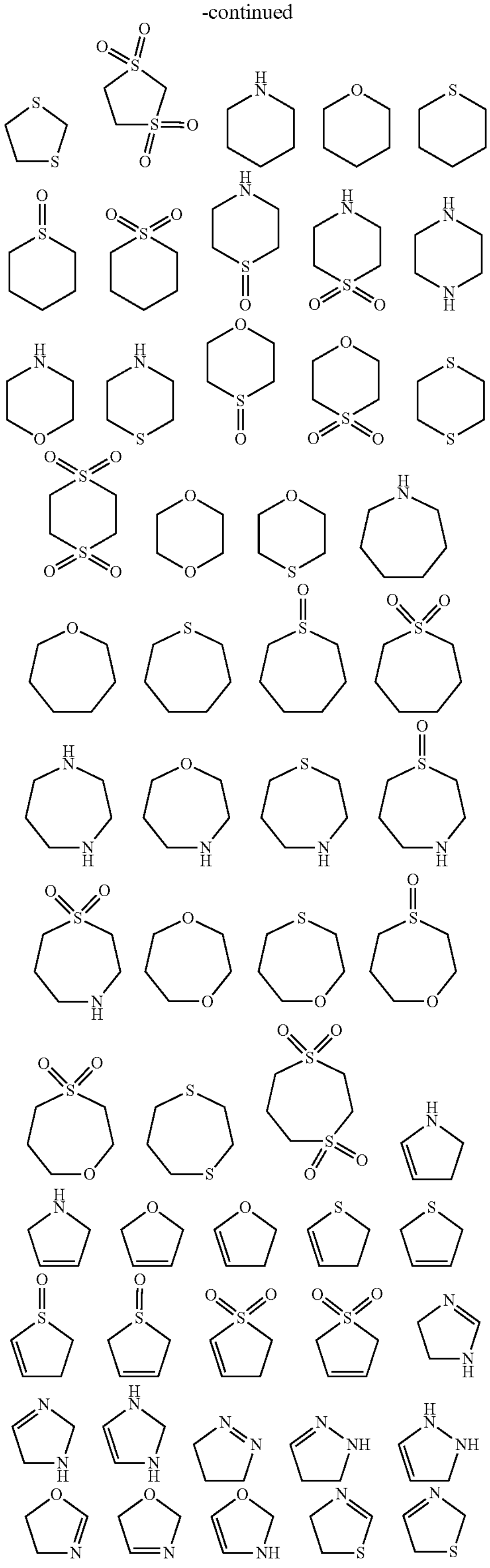

-continued

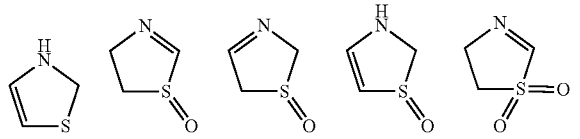
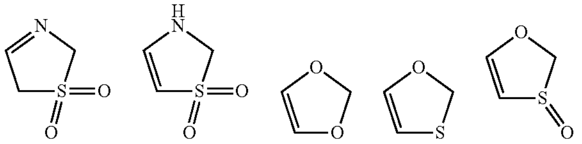
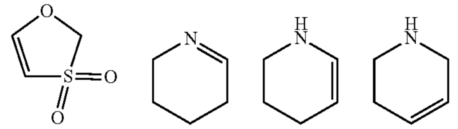
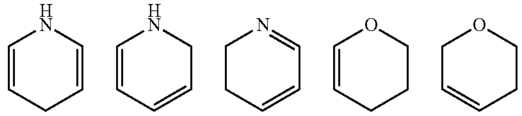
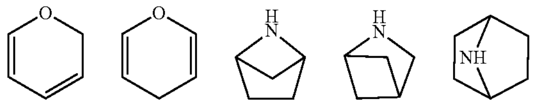
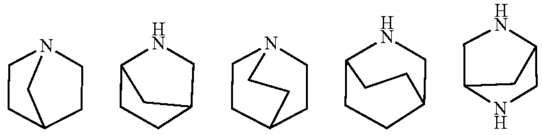
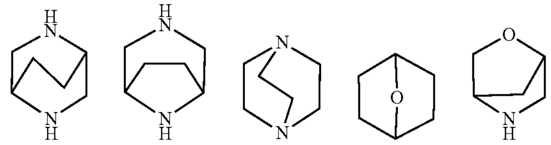
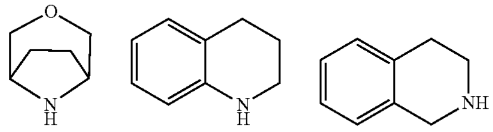
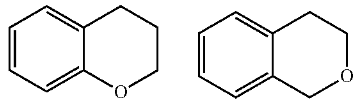
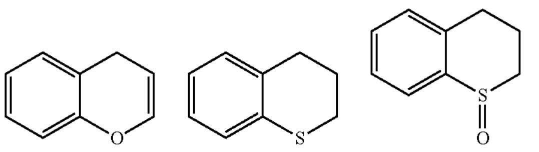
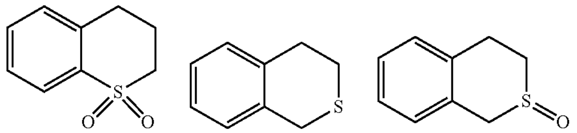
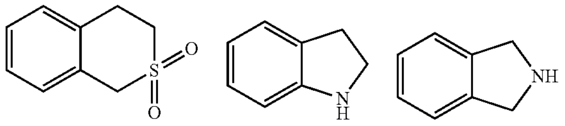
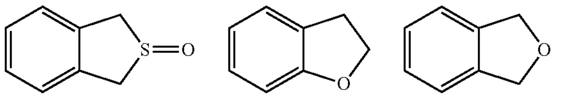

-continued

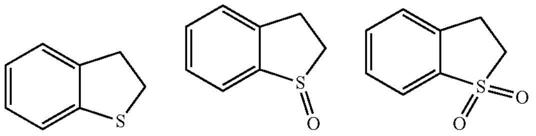
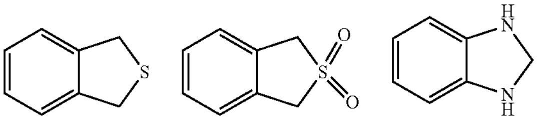
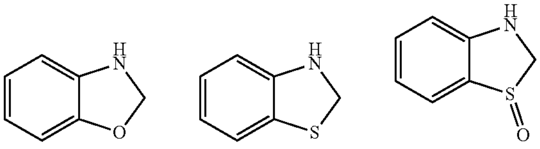
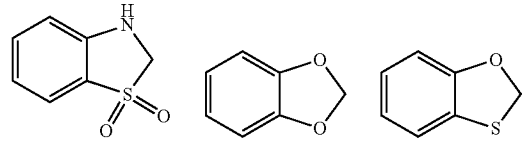
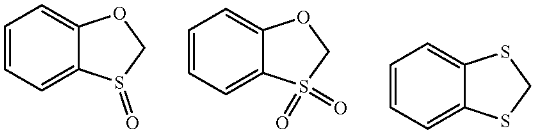
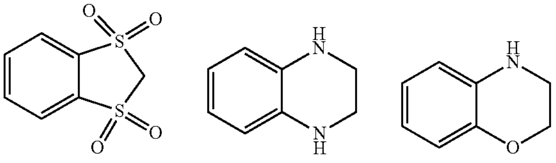
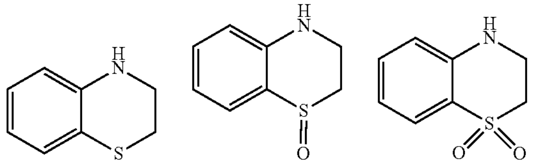
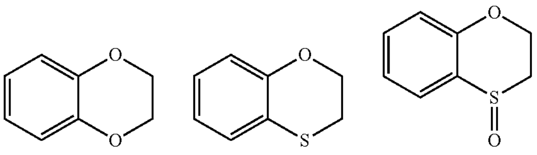
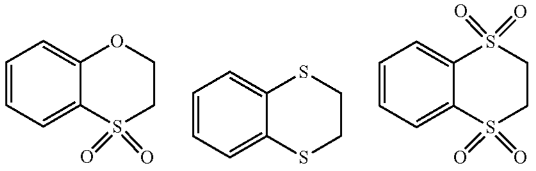
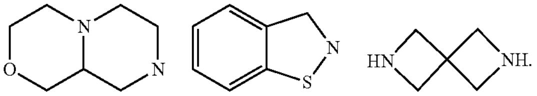

The term “heteroaryl” means a mono- or polycyclic ring system, comprising at least one aromatic ring, containing one or more heteroatoms selected from N, O, S, S(O) or $S(O)_2$, consisting of 5 to 14 ring atoms, wherein at least one of the heteroatoms is part of an aromatic ring. The term “heteroaryl” is intended to include all the possible isomeric forms. Thus, the term “heteroaryl” includes the following exemplary structures (not depicted as radicals as each form is optionally attached through a covalent bond to any atom so long as appropriate valences are maintained):

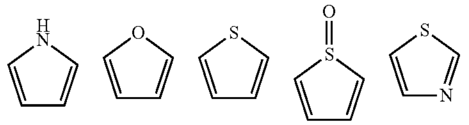

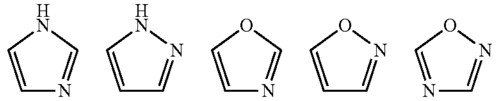

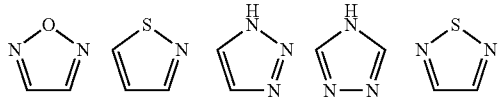

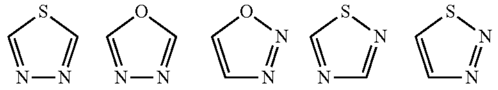

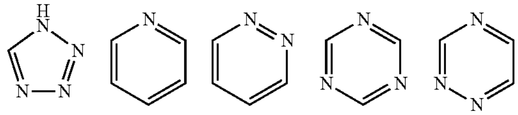

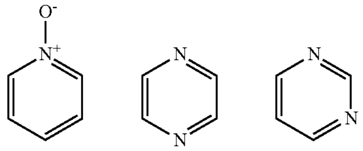

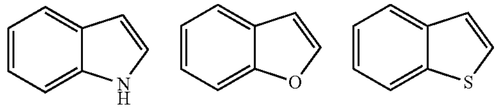

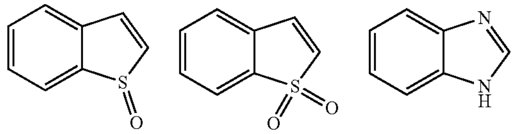

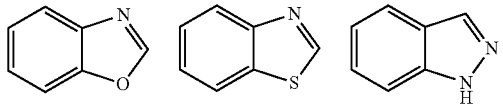

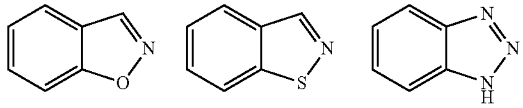

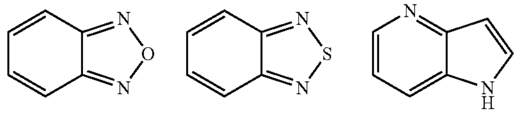

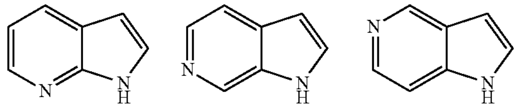

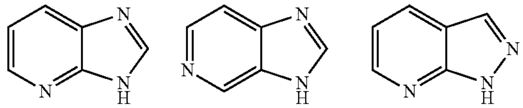

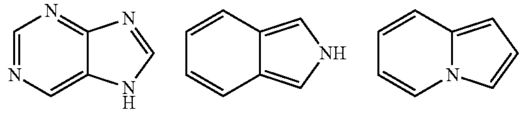

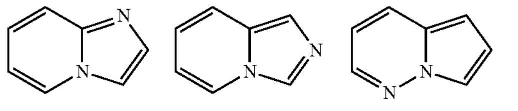

-continued

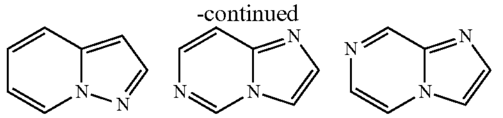

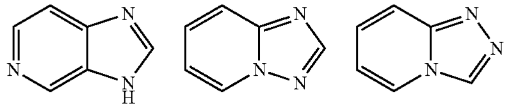

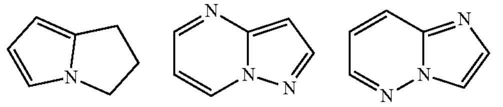

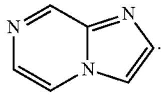

Many of the terms given herein may be used repeatedly in the definition of a formula or group and in each case have one of the meanings given herein, independently of one another.

The term bicyclic ring systems" means groups consisting of 2 joined cyclic substructures including spirocyclic, fused, and bridged ring systems.

The term tricyclic ring systems" means groups consisting of 3 joined cyclic substructures including spirocyclic, fused, and bridged ring systems.

As used herein, the term "control" in connection with "parasitic infections and/or infestations in animals" means that the parasitic infection and/or infestation is ameliorated or improved, sustainedly reduced in incidence and/or prevented from worsening as regards the animal.

METHODS OF TREATMENT

The present invention is directed to compounds of formula (I) which are useful in the treatment, prevention and/or control of parasitic infections and/or infestations in animals, preferably of ectoparasitic infections and/or infestations in animals, more preferably of infections and/or infestations of fleas and/or ticks in animals.

Accordingly, the present invention relates to a compound of formula (I) for use as a medicament, including but not limited to for use as an antiparasitic medicament.

Furthermore, the present invention relates to the use of a compound of formula (I) for the treatment, prevention and/or control of parasitic infections and/or infestations in animals, preferably of ectoparasite infections and/or infestations in animals, more preferably of infections and/or infestations of fleas and/or ticks in animals.

In a further aspect the present invention relates to a compound of formula (I) for use in the treatment, prevention and/or control of parasitic infections and/or infestations in animals, preferably of ectoparasitic infections and/or infestations in animals, more preferably of infections and/or infestations of fleas and/or ticks in animals.

In a further aspect the present invention relates to the use of a compound of formula (I) for the preparation of a medicament for the treatment, prevention and/or control of parasitic infections and/or infestations in animals, preferably of ectoparasitic infections and/or infestations in animals, more preferably of infections and/or infestations of fleas and/or ticks in animals.

In a further aspect of the present invention the present invention relates to methods for the treatment, prevention and/or control of parasitic infections and/or infestations in animals, preferably of ectoparasite infections and/or infestations in animals, more preferably of infections and/or infestations of fleas and/or ticks in animals, which methods comprise the administration of an effective amount of a compound of formula (I) to an animal/animal patient in need thereof.

The compounds of the present invention are highly effective for the treatment, prevention and/or control of external and/or internal parasites in animals, mammals, fish and birds, and in particular, cats, dogs, horses, chicken, pigs, sheep and cattle, but also humans with the aim of substantially ridding these hosts of ectoparasites and/or endoparasites. Mammals which can be treated, include but are not limited to, humans, cats, dogs, cattle, chicken, cows, bison, deer, goats, horses, llamas, camels, pigs, sheep and yaks. In one embodiment of the present invention, the mammals treated are humans, cats or dogs.

The dose range of the compounds of formula (I) applicable per day is usually from 0.001 mg to 1,000 mg for animals.

The actual pharmaceutically effective amount or therapeutic dosage will usually depend on factors known by those skilled in the art such as age and weight of the animal patient, route of administration and severity of disease. In any case the compounds will be administered at dosages and in a manner which allows a pharmaceutically effective amount to be delivered based upon animal patient's unique condition.

As depicted in detail in Example 9 herein, the four structurally closest prior art compounds (A), (B), (C) and (D) specifically excluded from the scope of formula (I) were characterized vis-á-vis selected compounds of formula (I) with regard to their potency in in vitro screening assays against fleas (*Ctenocehalides felis*) and ticks (*Rhipicephalus sanguineus*).

It is important to note that compounds that show better activity versus ticks are more desirable in the animal health field, as ticks are more difficult to control than fleas. Noteworthy, in particular with regard to fleas the illustrated comparative data are based on a flea membrane feeding (ingestion, blood feeding) assay. Membrane feeding assays differ to primary screening laboratory contact assays in that the latter only measure the effect of the direct contact of selected compounds on the parasite, such as the flea or the tick. The information derived from laboratory contact assays is strictly limited to the ability of the compound to be absorbed through the parasite surface and to reach its molecular target, and no information can be gleaned from these contact assays as to whether the compound would also be active when presented orally to the ectoparasite itself in a blood meal, such as with the membrane feeding assay, and certainly not when administered orally to an animal host (e.g. "in vivo") with subsequent exposure to the ectoparasite.

Profiling of the four structurally closest prior art compounds (A), (B), (C) and (D) specifically excluded from the scope of formula (I) in the flea membrane feeding (ingestion, blood feeding) assay as well as the flea and tick contact assays show some activity of these compounds against fleas, but no activity against ticks. However, as explained above, spectrum of action against this range of species (i.e. fleas and ticks) is a desirable property of ectoparasiticides for veterinary use. In table 1 of Example 9 herein comparative experimental data of the in vitro assays are shown regarding flea membrane feeding (ingestion, blood feeding) activity against *Ctenocephalides felis* and contact activity against *Rhipicephalus sanguineus*. The results of these two in vitro assays demonstrate the superior potency/efficacy of selected compounds of formula (1) over the four structurally closest prior art compounds (A), (B), (C) and (D) specifically excluded from the scope of formula (I): on the one hand, these results suggest the unsuitability of such structurally closest prior art compounds for administration methods that require the direct absorption through the parasite surface for efficacy (e.g. topical). On the other hand, the selected compounds of formula (I) show increased activity and potency against the desired spectrum of fleas and ticks while exhibiting better suitability for administration methods that require either ingestion of the compound in the blood meal, e.g. oral or other systemic route, or its direct absorption through the parasite surface by residue contact, e.g. topical.

The agricultural and horticultural insecticidal and acaricidal agent comprising the compounds of formula (I) of the present invention or a salt thereof as an active ingredient has a remarkable control effect on pests which damage lowland crops, field crops, fruit trees, vegetables, other crops, ornamental flowering plants, etc. The desired effect can be obtained when the agricultural and horticultural insecticidal and acaricidal agent is applied to nursery facilities for seedlings, paddy fields, fields, fruit trees, vegetables, other crops, ornamental flowering plants, etc. and their seeds, paddy water, foliage, cultivation media such as soil, or the like around the expected time of pest infestation, i.e., before the infestation or upon the confirmation of the infestation. In particularly preferable embodiments, the application of the agricultural and horticultural insecticidal and acaricidal agent utilizes so-called penetration and translocation. That is, nursery soil, soil in transplanting holes, plant foot, irrigation water, cultivation water in hydroponics. or the like is treated with the agricultural and horticultural insecticidal and acaricidal agent to allow crops, ornamental flowering plants, etc. to absorb the compound of the present invention through the roots via soil or otherwise.

Examples of useful plants to which the agricultural and horticultural insecticidal and acaricidal agent of the present invention can be applied include, but are not particularly limited to, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives and Welsh onions), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, sorghum, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., *chrysanthemum*, rose, carnation, orchid, tulip, lily, etc.), garden trees (e.g., ginkgo trees, cherry trees, Japanese *aucuba*, etc.) and forest trees (e.g., *Abies sachalinensis, Picea jezoensis*, pine, yellow cedar, Japanese cedar, hinoki cypress, *eucalyptus*, etc.).

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural and horticultural insecticidal and acaricidal agent of the present invention can be applied to these plants as well.

Further, exemplary toxins expressed in genetically modified plants include insecticidal proteins of *Bacillus cereus* or *Bacillus popilliae; Bacillus thuringiensis* S-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural and horticultural insecticidal and acaricidal agent of the present invention can be used in combination or used systematically.

In order to control target pests, the agricultural and horticultural insecticidal and acaricidal agent of the present invention, with or without appropriate dilution or suspension in water etc., is applied to plants potentially infested with the target insect pests or nematodes in an amount effective for the control of the insect pests or nematodes. For example, in order to control insect pests and nematodes that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed. Further, the agricultural and horticultural insecticidal and acaricidal agent of the present invention, with or without appropriate dilution or suspension in water etc., can be applied to sites potentially infested with pests in an amount effective for the control of the pests. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of an agrochemical and an adhesive carrier such as resins and polymers; and application of a solid or liquid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "cultivation medium" in the method of the present invention for using an agricultural and horticultural insecticide refers to a support medium for crop cultivation, in particular a support medium which allows crop plants to spread their roots therein, and the materials are not particularly limited as long as they allow plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage or to stored grain pests, house pests, sanitary pests, forest pests, etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application timing, in other words, depending on the cultivation stage such as seeding time, greening period and planting time. A formulation such as a dust, a water-dispersible granule and a granule may be mixed with nursery soil. For example, such a formulation is incorporated into bed soil, covering soil or the whole soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer, may be applied onto soil or injected into soil. In addition, an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of their plants, or the like may be treated in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The amount of the active ingredient compound in the agricultural and horticultural insecticidal and acaricidal agent of the present invention can be adjusted as needed, and basically, the amount of the active ingredient compound is appropriately selected from the range of 0.01 to 90 parts by weight in 100 parts by weight of the agricultural and horticultural insecticide. For example, in the case where the agricultural and horticultural insecticide is a dust, a granule, an emulsifiable concentrate or a wettable powder, it is suitable that the amount of the active ingredient compound is 0.01 to 50 parts by weight (0.01 to 50% by weight relative to the total weight of the agricultural and horticultural insecticidal and acaricidal agent).

The application rate of the agricultural and horticultural insecticidal and acaricidal agent of the present invention may vary with various factors, for example, the purpose, the target pest, the growing conditions of crops, the tendency of pest infestation, the weather, the environmental conditions, the dosage form, the application method, the application site, the application timing, etc., but basically, the application rate of the active ingredient compound is appropriately selected from the range of 0.001 g to 10 kg, and preferably 0.01 g to 1 kg per 10 ares depending on the purpose.

Veterinary Parasites

In one embodiment for the treatment, prevention and/or control of/against ectoparasites, the ectoparasite is one or more insect or arachnid including those of the genera *Ctenocephalides, Rhipicephalus, Dermacentor, Ixodes, Boophilus, Ambylomma, Haemaphysalis, Hyalomma, Sarcoptes, Psoroptes*, Otodectes, Chorioptes, *Hypoderma, Gasterophilus, Lucilia, Dermatobia, Cochliomyia, Chrysomyia, Damalinia, Linognathus, Haematopinus, Solenopotes, Trichodectes*, and Felicola.

In another embodiment for the treatment, prevention and/or control of/against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include, but are not limited to, cat and dog fleas (*Ctenocephalides felis, Ctenocephalides* sp. and the like), ticks (*Rhipicephalus* sp., *Ixodes* sp., *Dermacentor* sp., *Amblyomma* sp., *Haemaphysalis* sp., and the like), and mites (*Demodex* sp., *Sarcoptes* sp., Otodectes sp., *Cheyletiella* sp., and the like), lice (*Trichodectes* sp., Felicola sp., *Linognathus* sp., and the like), mosquitoes (*Aedes* sp., *Culex* sp., *Anopheles* sp., and the like) and flies (Hematobia sp. including *Haematobia irritans, Musca* sp., *Stomoxys* sp. including *Stomoxys calcitrans, Dermatobia* sp., *Cochliomyia* sp., and the like).

Additional examples of ectoparasites include but are not limited to the tick genus *Boophilus*, especially those of the species *microplus* (cattle tick), *decoloratus* and *annulatus*; myiases such as *Dermatobia hominis* (known as Berne in Brazil) and *Cochliomyia* honinivorax (greenbottle); sheep myiases such as *Lucilia sericata, Lucilia cuprina* (known as blowfly strike in Australia, New Zealand and South Africa) and Gasterophilus in horses. Flies proper, namely those whose adult constitutes the parasite, such as *Haematobia irritans* (horn fly) and *Stomoxys calcitrans* (stable fly); lice such as *Linognathus vituli*, etc.; and mites such as *Sarcoptes scabiei* and *Psoroptes ovis*. The herein disclosed list is not exhaustive and other ectoparasites are well known in the art to be harmful to animals and humans. These include, for example migrating dipteran larvae.

In some embodiments of the invention, the composition can also be used to treat and/or prevent animals for endoparasite infestations such as those comprised of helminths selected from the group consisting of Anaplocephala, Ancylostonia, Anecator, *Ascaris, Capillaria, Cooperia, Cyathostonmum, Dipylidium, Dirofilaria, Echinococcus, Enterobius, Fasciola, Haemonchus, Oesophagostumum, Ostertagia, Parascaris, Toxocara, Strongylus, Strongyloides, Toxascaris, Trichinella, Trichuris* and *Trichostrongylus*, among others.

In one embodiment, the invention provides uses and methods for the treatment, prevention and/or control of/against parasitic infections and infestations of animals (either wild or domesticated), including livestock and companion animals such as cats, dogs, horses, birds including chicken, sheep, goats, pigs, turkeys and cattle, with the aim of ridding these hosts of parasites commonly encountered by such animals.

In another embodiment, the invention provides uses and methods for the treatment, prevention and/or control of/against parasitic infections and infestations in companion animals including, but not limited to, cats and dogs. Some methods and compositions of the invention that comprise active agents of the invention are particularly effective for preventing, treating and/or controlling parasitic infestations of cats and dogs with fleas and ticks or other ectoparasites.

In another embodiment, the uses, methods and compositions of the invention are used for the treatment, prevention and/or control of/against parasitic infections and infestations in cattle or sheep. When treating livestock animals such as cattle or sheep, the methods and compositions of the invention are particularly effective against *Rhipicephalus* (*Boophilus*) *microplus, Haematobia irritans* (horn fly), *Stomoxys calcitrans* (stable fly), and sheep myiases such as *Lucilia sericata, Lucilia cuprina* (known as blowfly strike in Australia, New Zealand and South Africa).

The uses and methods of the invention for the treatment, prevention and/or control of/against of endoparasites are effective against parasitic nematodes (including roundworm, hookworm, whipworm and others), and/or *Dirofilaria immitis* (heartworm).

In some embodiments, the combination of certain additional active agents with at least one compound of formula (I) will expand the scope of coverage of the method depending on the biological activity of the additional active agent. For example, it is contemplated that combinations of the at least one compound of formula (I) with one or more additional active agents that are active against internal parasites such as parasitic nematodes (including roundworm, hookworm, whipworm and others), and/or *Dirofilaria immitis* (heartworm) will provide treatment, prevention and/or control of/against internal parasites as well as external parasites (e.g. fleas and ticks, etc.).

In one embodiment, the invention provides uses and methods for the treatment, prevention and/or control of/against a parasitic infestation and/or infection in an animal that comprises administering to the animal a soft chewable veterinary composition comprising an effective amount of at least one compound of formula (I) in combination with an effective amount of at least a second active agent in a pharmaceutically acceptable carrier. Any of the additional active agents described herein may be combined with the at least one compound according to formula (I) in the soft chewable veterinary compositions. Thus, the invention provides uses and methods for the treatment, prevention and/or control of/against an ectoparasitic infestation and an endoparasites infection, comprising administering to the animal in need a soft chewable veterinary composition comprising at least one compound according to formula (I) in combination with at least one compound that is active against internal parasites.

Agricultural and Horticultural Pests and Nematodes

The agricultural and horticultural insecticidal and acaricidal agent comprising the compound of formula (I) of the present invention or a salt thereof as an active ingredient is suitable for controlling a variety of pests which may damage paddy rice, fruit trees, vegetables, other crops and ornamental flowering plants. The target pests are, for example, agricultural and forest pests, horticultural pests, stored grain pests, sanitary pests, other pests such as nematodes, or mites, etc.

Examples of the above pests or nematodes include the following.

Examples of the species of the order Lepidoptera include Parasa consocia, Anomis mesogona, Papilio xuthus, Matsumuraeses azukivora, *Ostrinia* scapulalis, *Spodoptera exempta, Hyphantria cunea, Ostrinia furnacalis, Pseudaletia separata, Tinea translucens*, Bactra furfurana, Parnara guttata, Marasmia *exigua*, Parnara guttata, Sesamia inferens, Brachmia triannulella, Monema *flavescens, Trichoplusia ni*, Pleuroptya ruralis, Cystidia couaggaria, Lampides boeticus, Cephonodes hylas, *Helicoverpa armigera*, Phalerodonta manleyi, Eumeta *japonica, Pieris brassicae, Malacosoma neustria* testacea, Stathmopoda masinissa, Cuphodes diospyrosella, *Archips* xylosteanus, *Agrotis segetum*, Tetramoera schistaceana, Papilio machaon hippocrates, Endoclyta *sinensis, Lyonetia* prunifoliella, Phyllonorycter ringoneella, *Cydia* kurokoi, Eucoenogenes aestuosa, *Lobesia botrana, Latoia sinica*, Euzophera batangensis, Phalonidia mesotypa, Spilosoma imparilis, Glyphodes pyloalis, Olethreutes mori, Tineola bisselliella, Endoclyta excrescens, Nemapogon granellus, Synanthedon hector, *Cydia pomonella, Plutella xylostella, Cnaphalocrocis medinalis*, Sesamia calamistis, Scirpophaga incertulas, Pediasia *teterrellus, Phthorimaea operculella*, Stauropus fagi *persimilis, Etiella zinckenella, Spodoptera exigua, Palpifer sexnotata, Spodoptera mauritia*, Scirpophaga innotata, Xestia c-*nigrum, Spodoptera depravata*, Ephestia kuehniella, Angerona prunaria, Clostera anastomosis, *Pseudoplusia includens, Matsumuraeses falcana, Helicoverpa assulta, Autographa nigrisigna, Agrotis ipsilon, Euproctis pseudoconspersa, Adoxophyes orana*, Caloptilia theivora, Homona magnanima, Ephestia elutella, Eumeta minuscula, Clostera anachoreta, *Heliothis maritima, Sparganothis pilleriana, Busseola fusca, Euproctis* subflava, Biston *robustum, Heliothis zea*, Aedia leucomelas, Narosoideus flavidorsalis, Viminia rumicis, *Bucculatrix* pyrivorella, *Grapholita molesta*, Spulerina astaurota, Ectomyelois pyrivorella, *Chilo suppressalis*, Acrolepiopsis sapporensis, Plodia interpunctella, *Hellula undalis, Sitotroga cerealella, Spodoptera litura*, a species of the family Tortricidae (Eucosma aporema), Acleris comariana, Scopelodes contractus, *Orgyia* thyellina, *Spodoptera frugiperda, Ostrinia* zaguliaevi, Naranga aenescens, Andraca bipunctata, Paranthrene *regalis, Acosmeryx castanea, Phyllocnistis toparcha, Endopiza viteana, Eupoecillia ambiguella, Anticarsia gemmatalis, Cnephasia cinereipalpana, Lymantria dispar, Dendrolimus spectabilis*, Leguminivora glycinivorella, Maruca testulalis, Matsumuraeses *phaseoli, Caloptilia soyella, Phyllocnistis citrella, Omiodes indicata, Archips* fuscocupreanus, Acanthoplusia agnata, Bambalina sp., Carposina niponensis, Conogethes punctiferalis, Synanthedon sp., *Lyonetia clerkella*, Papilio helenus, Colias erate poliographus, *Phalera flavescens*, the species of the family Pieridae such as *Pieris rapae* crucivora and *Pieris rapae, Euproctis similis, Acrolepiopsis suzukiella, Ostrinia nubilalis, Mamestra brassicae*, Ascotis selenaria, Phtheochroides *clandestina*, Hoshinoa adumbratana, Odonestis *pruni* japonensis, Triaena *intermedia, Adoxophyes orana fasciata, Grapholita inopinata*, Spilonota ocellana, Spilonota lechriaspis, Illiberis *pruni, Argyresthia conjugella, Caloptilia zachrysa, Archips* breviplicanus, Anomis *flava, Pectinophora gossypiella, Notarcha derogata, Diaphania indica, Heliothis virescens* and *Earias* cupreoviridis.

Examples of the species of the order Hemiptera include *Nezara antennata, Stenotus rubrovittatus, Graphosoma rubrolineatum*, Trigonotylus coelestialium, Aeschynteles *maculatus, Creontiades pallidifer, Dysdercus cingulatus, Chrysomphalus ficus, Aonidiella aurantii, Graptopsaltria nigrofuscata, Blissus leucopterus, Icerya purchasi, Piezodorus hybneri, Lagynotomus elongatus, Thaia subrufa, Scotinophara lurida, Sitobion* ibarae, Stariodes iwasakii, Aspidiotus destructor, Taylorilygus *pallidulus, Myzus* mumecola, Pseudaulacaspis *prunicola, Acyrthosiphon pisum*, Anacanthocoris striicornis, Ectometopterus micantulus, *Eysarcoris lewisi, Molipteryx fuliginosa, Cicadella viridis*, Rhopalosophum rufiabdominalis, Saissetia *oleae, Trialeurodes vaporariorum, Aguriahana quercus, Lygus* spp., Euceraphis

*punctipennis*, Andaspis kashicola, Coccus pseudomagnoliarum, Cavelerius saccharivorus, Galeatus spinifrons, Macrosiphoniella sanborni, Aonidiella citrina, *Halyomorpha mista, Stephanitis fasciicarina, Trioza* camphorae, Leptocorisa *chinensis, Trioza* quercicola, Uhlerites latius, Erythroneura comes, Paromius *exiguus, Duplaspidiotus claviger, Nephotettix nigropictus, Halticiellus insularis, Perkinsiella saccharicida, Psylla* malivorella, Anomomeura mori, Pseudococcus longispinis, Pseudaulacaspis pentagona, Pulvinaria kuwacola, Apolygus *lucorum, Togo hemipterus, Toxoptera aurantii, Saccharicoccus sacchari*, Geoica lucifuga, Numata muiri, Comstockaspis perniciosa, Unaspis *citri, Aulacorthum solani, Eysarcoris ventralis, Bemisia argentifolii*, Cicadella spectra, Aspidiotus hederae, Liorhyssus hyalinus, Calophya nigridorsalis, *Sogatella furcifera, Megoura crassicauda. Brevicoryne brassicae, Aphis glycines, Leptocorisa oratorius, Nephotettix virescens, Uroeucon formosanum, Cyrtopeltis tennuis, Bemisia tabaci, Lecanium persicae*, Parlatoria theae, Pseudaonidia paeoniae, *Empoasca* onukii, *Plautia stali, Dysaphis tulipae, Macrosiphum euphorbiae*, Stephanitis pyrioides, Ceroplastes ceriferus, Parlatoria *camelliae, Apolygus spinolai, Nephotettix cincticeps, Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla* tobirae, Eurydema *rugosum, Schizaphis piricola, Psylla pyricola*, Parlatoreopsis pyri, Stephanitis nashi, Dysmicoccus wistariae, Lepholeucaspis *japonica, Sappaphis piri, Lipaphis erysimi, Neotoxoptera formosana*, Rhopalosophum nymphaeae, Edwardsiana *rosae, Pinnaspis aspidistrae, Psylla alni*, Speusotettix subfusculus, Alnetoidia alneti, *Sogatella* panicicola, Adelphocoris lineolatus, *Dysdercus poecilus*, Parlatoria ziziphi, Uhlerites debile, *Laodelphax striatellus, Eurydema pulchrum*, Cletus trigonus, Clovia *punctata, Empoasca* sp., Coccus *hesperidum, Pachybrachius luridus, Planococcus* kraunhiae, Stenotus binotatus, Arboridia *apicalis*, Macrosteles fascifrons, Dolycoris baccarum, Adelphocoris *triannulatus, Viteus vitifolii, Acanthocoris sordidus, Leptocorisa acuta*, Macropes obnubilus, Cletus punctiger, Riptortus *clavatus*, Paratrioza cockerelli, Aphrophora costalis, *Lygus* disponsi, *Lygus saundersi, Crisicoccus pini, Empoasca abietis, Crisicoccus matsumotoi, Aphis craccivora, Megacopta punctatissimum, Eysarcoris* guttiger, Lepidosaphes *beckii, Diaphorina citri, Toxoptera citricidus, Planococcus citri, Dialeurodes citri*, Aleurocanthus spiniferus, Pseudococcus citriculus, Zyginella *citri, Pulvinaria citricola*, Coccus discrepans, Pseudaonidia duplex, Pulvinaria *aurantii, Lecanium corni, Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopterus pruni, Aphis* farinose yanagicola, Metasalis *populi*, Unaspis yanonensis, Mesohomotoma camphorae, *Aphis spiraecola, Aphis pomi, Lepidosaphes ulmi, Psylla mali, Heterocordylus flavipes, Myzus* malisuctus, Aphidonuguis *mali, Orientus ishidai, Ovatus malicolens, Eriosoma lanigerum, Ceroplastes rubens* and *Aphis gossypii.*

Examples of the species of the order Coleoptera include Xystrocera *globosa, Paederus fuscipes*, Eucetonia roelofsi, Callosobruchus *chinensis, Cylas formicarius, Hypera postica, Echinocnemus squameus, Oulema oryzae, Donacia provosti, Lissorhoptrus oryzophilus*, Colasposoma dauricum, Euscepes postfasciatus, *Epilachna varivestis, Acanthoscelides obtectus, Diabrotica virgifera virgifera*, Involvulus cupreus, Aulacophora *femoralis, Bruchus pisorum, Epilachna vigintioctomaculata, Carpophilus dimidiatus, Cassida nebulosa, Luperomorpha tunebrosa, Phyllotreta striolata, Psacothea hilaris*, Aeolesthes chrysothrix, Curculio *sikkimensis, Carpophilus hemipterus, Oxycetonia jucunda, Diabrotica* spp., Mimela *splendens, Sitophilus* zeamais, Tribolium castaneum, *Sitophilus oryzae, Palorus subdepressus, Melolontha japonica, Anoplophora* malasiaca, Neatus picipes, *Leptinotarsa decemlineata, Diabrotica* undecimpunctata howardi, Sphenophorus venatus, *Crioceris* quatuordecimpunctata, Conotrachelus nenuphar, Ceuthorhynchidius albosuturalis, *Phaedon brassicae, Lasioderma serricorne, Sitona japonicus, Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes* spp., Attagenus unicolor *japonicus, Pagria signata, Anomala* rufocuprea, Palorus ratzeburgii, Alphitobius *laevigatus, Anthrenus verbasci, Lyctus brunneus, Tribolium confusum*, Medythia nigrobilineata, Xylotrechus pyrrhoderus, *Epitrix cucumeris*, Tomicus piniperda, Monochamus alternatus, *Popillia japonica, Epicauta gorhami, Sitophilus* zeamais, Rhynchites *heros*, Listroderes costirostris, Callosobruchus *maculatus, Phyllobius armatus, Anthonomus pomorum*, Linaeidea aenea and *Anthonomus grandis.*

Examples of the species of the order Diptera include *Culex pipiens pallens, Pegomya hyoscyami, Liriomyza huidobrensis, Musca domestica, Chlorops oryzae*, Hydrellia sasakii, Agromyza *oryzae*, Hydrellia griseola, Hydrellia griseola, Ophiomyia *phaseoli, Dacus cucurbitae, Drosophila* suzukii, Rhacochlaena *japonica, Muscina stabulans*, the species of the family Phoridae such as Megaselia spiracularis, Clogmia albipunctata, *Tipula* aino, Phormia regina, *Culex tritaeniorhynchus, Anopheles sinensis, Hylemya brassicae*, Asphondylia sp., *Delia platura, Delia antiqua, Rhagoletis cerasi, Culex pipiens* molestus Forskal, *Ceratitis capitata, Bradysia agrestis, Pegomya cunicularia, Liriomyza sativae, Liriomyza* bryoniae, Chromatomyia *horticola, Liriomyza chinensis, Culex quinquefasciatus, Aedes aegypti, Aedes albopictus, Liriomyza trifolii, Liriomyza sativae, Dacus dorsalis*, Dacus tsuneonis, Sitodiplosis mosellana, Meromuza nigriventris, Anastrepha ludens and *Rhagoletis pomonella.*

Examples of the species of the order Hymenoptera include Pristomyrmex *pungens*, the species of the family Bethylidae, *Monomorium pharaonis, Pheidole noda, Athalia rosae*, Dryocosmus kuriphilus, Formica *fusca japonica*, the species of the subfamily Vespinae, *Athalia* infumata infumata, Arge pagana, *Athalia japonica*, Acromyrmex spp., *Solenopsis* spp., Arge *mali* and Ochetellus glaber.

Examples of the species of the order Orthoptera include Homorocoryphus lineosus, *Gryllotalpa* sp., Oxya *hyla intricata, Oxya yezoensis, Locusta migratoria, Oxya japonica*, Homorocoryphus jezoensis and Teleogryllus emma.

Examples of the species of the order Thysanoptera include Selenothrips rubrocinctus, Stenchaetothrips *biformis, Haplothrips aculeatus, Ponticulothrips diospyrosi, Thrips flavus, Anaphothrips obscurus, Liothrips floridensis, Thrips simplex, Thrips nigropilosus, Heliothrips haemorrhoidalis*, Pseudodendrothrips mori, Microcephalothrips *abdominalis*, Leeuwenia pasanii, Litotetothrips pasaniae, *Scirtothrips citri, Haplothrips chinensis, Mycterothrips glycines, Thrips setosus, Scirtothrips dorsalis*, Dendrothrips minowai, Haplothrips *niger, Thrips tabaci, Thrips alliorum, Thrips hawaiiensis*, Haplothrips kurdjumovi, Chirothrips manicatus, *Frankliniella intonsa, Thrips coloratus,*

*Franklinella occidentalis, Thrips palmi, Frankliniella* lilivora and Liothrips vaneeckei.

Examples of the species of the order Acari include Leptotrombidium akamushi, *Tetranychus* ludeni, *Dermacentor variabilis, Tetranychus truncatus, Ornithonyssus bacoti, Demodex canis, Tetranychus viennensis, Tetranychus kanzawai*, the species of the family Ixodidae such as *Rhipicephalus sanguineus, Cheyletus malaccensis, Tyrophagus putrescentiae, Dermatophagoides farinae, Latrodectus hasseltii, Dermacentor taiwanensis, Acaphylla theavagrans, Polyphagotarsonemus latus, Aculops lycopersici, Ornithonyssus sylvairum, Tetranychus urticae, Eriophyes chibaensis, Sarcoptes scabiei, Haemaphysalis longicornis, Ixodes scapularis, Tyrophagus similis, Cheyletus eruditus, Panonychus citri, Cheyletus moorei, Brevipalpus phoenicis, Octodectes cynotis, Dermatophagoides ptrenyssnus, Haemaphysalis flava, Ixodes ovatus, Phyllocoptruta citri, Aculus schlechtendali, Panonychus ulmi, Amblyomma americanum, Dermanyssus gallinae*, Rhyzoglyphus robini and Sancassania sp.

Examples of the species of the order Isoptera include *Reticulitermes* miyatakei, *Incisitermes minor, Coptotermes formosanus, Hodotermopsis japonica, Reticulitermes* sp., *Reticulitermes flaviceps* amamianus, Glyptotermes kushimensis, *Coptotermes* guangzhoensis, Neotermes koshunensis, Glyptotermes kodamai, Glyptotermes satsumensis, Cryptotermes *domesticus, Odontotermes formosanus*, Glyptotermes nakajimai, Pericapritermes nitobei and *Reticulitermes speratus.*

Examples of the species of the order Blattodea include *Periplaneta fuliginosa, Blattella germanica, Blatta orientalis, Periplaneta brunnea, Blattella lituricollis, Periplaneta japonica* and *Periplaneta americana.*

Examples of the species of the phylum Nematoda include Nothotylenchus *acris, Aphelenchoides besseyi, Pratylenchus penetrans, Meloidogyne hapla, Meloidogyne incognita, Globodera rostochiensis, Meloidogyne javanica, Heterodera glycines, Pratylenchus coffeae, Pratylenchus neglectus* and Tylenchus *semipenetrans.*

Examples of the species of the phylum Mollusca include such as *Pomacea canaliculata, Achatina fulica*, Meghimatium bilineatum, Lehmannina valentiana, Limax *flavus* and Acusta despecta *sieboldiana.*

Pharmaceutical Compositions

Suitable preparations for administering the compounds of formula (I) will be apparent to those with ordinary skill in the art and include for example tablets, pills, capsules, suppositories, lozenges, troches, solutions, syrups, elixirs, sachets, injectables, topical pour-on or spot-on formulations, inhalables and powders etc., in particular soft chewable tablets.

Suitable tablets may be obtained, for example, by mixing one or more compounds of formula (I) with known excipients, for example inert diluents, carriers, disintegrants, adjuvants, surfactants, binders and/or lubricants.

In one embodiment of the invention, a soft chewable veterinary composition is provided comprising an effective amount of at least one compound of formula (I), optionally in combination with an effective amount of at least one second active agent in a pharmaceutically acceptable carrier. Any of the additional active agents described herein may be combined with the at least one compound of formula (I) in the soft chewable veterinary compositions.

The agricultural and horticultural insecticidal and acaricidal agent of the present invention is commonly used as a formulation convenient for application, which is prepared by the usual method for preparing agrochemical formulations. That is, the compound of the formula (I) of the present invention or a salt thereof and an appropriate inactive carrier, and if needed an adjuvant, are blended in an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

Combination Therapies

In one embodiment of the invention, arylpyrazole compounds such as phenylpyrazoles, known in the art may be combined with the compounds of formula (I) in the compositions of the invention.

In another embodiment of the invention, one or more macrocyclic lactones, which act as an acaricide, anthelmintic agent and/or insecticide, can be added to the compositions of the invention.

In another embodiment of the invention, the invention comprises a topical composition comprising a compound of formula (I) in combination with a class of acaricides or insecticides known as insect growth regulators (IGRs). Compounds belonging to this group are well known to the practitioner and represent a wide range of different chemical classes. These compounds all act by interfering with the development or growth of the insect pests.

In one embodiment, the IGR is a compound that mimics juvenile hormone.

In another embodiment, the IGR compound is a chitin synthesis inhibitor.

In yet another embodiment of the invention, adulticide insecticides and acaricides can also be added to the composition of the invention. In some embodiments, the compositions of the invention may include one or more antinematodal agents.

In other embodiments, the compositions of the invention may include antitrematodal agents.

Anticestodal compounds may also be advantageously used in the compositions of the invention.

In yet other embodiments, the compositions of the invention may include other active agents that are effective against arthropod parasites.

An antiparasitic agent that can be combined with the compound of the invention to form a composition can be a biologically active peptide or protein including, but not limited to, depsipeptides, which act at the neuromuscular junction by stimulating presynaptic receptors belonging to the secretin receptor family resulting in the paralysis and death of parasites.

In another embodiment, the compositions of the invention may comprise an active agent from the neonicotinoid class of pesticides. The neonicotinoids bind and inhibit insect specific nicotinic acetylcholine receptors.

In another embodiment, the compositions of the invention may advantageously include one or more isoxazoline active agents known in the art.

In another embodiment of the invention, nodulisporic acid and its derivatives (a class of known acaricidal, anthelmintic, anti-parasitic and insecticidal agents) may be added to the compositions of the invention.

In another embodiment, anthelmintic compounds of the amino acetonitrile class (AAD) of compounds may be added to the compositions of the invention.

The compositions of the invention may also be combined with paraherquamide compounds and derivatives of these compounds. The paraherquamide family of compounds is a known class of compounds that include a spirodioxepino indole core with activity against certain parasites. In addition, the structurally related marcfortine family of compounds are also known and may be combined with the formulations of the invention.

In another embodiment of the invention, the compositions may include a spinosyn active agent produced by the soil actinomycete *Saccharopolyspora spinosa* or a semi-synthetic spinosoid active agent. The spinosyns are typically referred to as factors or components A, B, C, D, E, F, G, H, J, K, L, M, N, O, P, Q, R, S, T, U, V, W, or Y, and any of these components, or a combination thereof, may be used in the compositions of the invention.

Furthermore, for the expansion of the range of target pests and the appropriate time for pest control, or for dose reduction, the agricultural and horticultural insecticidal and acaricidal agent of the present invention can be used after mixed with other agricultural and horticultural insecticidal and acaricidal agent, acaricides, nematicides, microbicides, biopesticides and/or the like. Further, the agricultural and horticultural insecticidal and acaricidal agent can be used after mixed with herbicides, plant growth regulators, fertilizers and/or the like depending on the situation.

In one embodiment of the invention, the compositions of the invention may also include the agricultural and horticultural insecticidal and acaricidal agent of the present invention combined with one or more compounds selected from th group consisting of: acetylcholinesterase (ACHE) inhibitors, baculoviruses, calcium-activated potassium-channel (KCA2) modulators, chordotonal organ modulators (undefined target size), chordotonal organ TRPV channel modulators, ecdysone receptor agonists, GABA-gated chloride channel allosteric modulators, GABA-gated chloride channel blockers, glutamate-gated chlorine channel (GLUCL) allosteric modulators, inhibitors of acetyl CoA carboxylase, inhibitors of chitin biosynthesis affecting CHSI, inhibitors of chitin biosynthesis type 1, inhibitors of mitochondrial ATP synthase, juvenile hormone mimics, microbial disruptors of insect midgut membranes, mite growth inhibitors affecting CHS 1, mitochondrial complex I electron transport inhibitors, mitochondrial complex II electron transport inhibitors, mitochondrial complex III electron transport inhibitors QI site, mitochondrial complex III electron transport inhibitors QO site, mitochondrial complex IV electron transport inhibitors, moulting disruptor, nicotinic acetylcholine receptor (NACHR) allosteric modulators—site I, nicotinic acetylcholine receptor (NACHR) allosteric modulators—site II, nicotinic acetylcholine receptor (NACHR) channel blockers, nicotinic acetylcholine receptor (NACHR) competitive modulators, octopamine receptor agonists, ryanodine receptor modulators, sodium channel modulators, uncouplers of oxidative phosphorylation via disruption of the proton gradient, voltage-dependent sodium channel blockers.

Chemical Synthesis

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used.

The general processes for preparing the compounds according to the invention will become apparent to the one skilled in the art studying the following schemes. Starting materials may be prepared by methods that are described in the literature or herein, or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

The Examples that follow are intended to illustrate the present invention without restricting it. The terms "ambient temperature" and "room temperature" are used interchangeably and designate a temperature of about 20° C. The compounds of formula (I) or pharmaceutically acceptable salts thereof may be prepared by adopting one of the following reaction schemes. The starting materials for their preparation can be prepared by methods known per se and as described in the literature or are an intermediate of any of the other schemes detailed herein. Although the following subject matter is described in some detail by way of illustration and example for purposes of clarity of understanding, it will be understood by those skilled in the art that certain changes and modifications can be practiced within the scope of the Examples.

Abbreviations

| | |
|---|---|
| ACN | acetonitrile |
| Alox | aluminium oxide |
| Aq. | aqueous |
| ° C. | degree Celsius |
| CyH/CH | cyclohexane |
| conc. | concentrated |
| DCC | N,N'-dicyclohexylmethanediimine |
| DCM | dichloro methane |
| 1,2-DCE | 1,2-dichloro ethane |
| DEE | diethyl ether |
| DIPE | diisopropylether |
| DIPEA | N,N-diisopropylethylamine |
| 1,2-DME | 1,2-dimethyl ether |
| DMF | N,N-dimethylformamide |
| DMSO | dimethyl sulfoxide |
| ESI-MS | electrospray ionisation mass spectrometry |
| $Et_2O$ | diethylether |
| EtOAc/EE/EA | ethyl acetate |
| ex | example |
| eq | equivalent |
| h | hour |
| HAc | acetic acid |
| HATU | N,N,N',N'-tetramethyl-O-(7-azabenzotriazol-1-yl) uranium hexafluorophosphate |
| HCl | hydrochlorid acid |
| $HNO_3$ | nitric acid |
| HOAc | acetic acid |
| HPLC | high performance liquid chromatography |
| $K_3PO_4$ | tripotassium phosphate |
| LED | light emitting diode |
| LiHMDS | lithium-bis(trimethylsilyl)amide |
| LiOH | lithium hydroxide |
| LR | Lawesson's reagent |
| MeOH | methanol |
| NaH | sodium hydride |
| $NaHCO_3$ | sodium bicarbonate |
| $Na_2SO_4$ | sodium sulfate |
| NBS | N-bromosuccinimide |
| NClS | N-chlorosuccinimide |
| $NH_3$ | ammonia |
| $NH_4Cl$ | ammonium chloride |
| NIS | N-iodosuccinimide |
| NMP | N-methyl-2-pyrrolidone |
| min | minute |
| mL | milliliter |
| Pd/C | palladium on activated carbon |
| Pd(dppf)Cl2 | [1,1'-bis(diphenylphosphino)ferrocene] |

-continued

| | |
|---|---|
| | dichloropalladium(II) |
| PE | petroleum ether |
| $PtO_2$ | platinum dioxide |
| RT | room temperature (about 20° C.) |
| $R_t$ | retention time |
| sat. | saturated |
| TEA | triethylamine |
| TFA | trifluoroacetic acid |
| THF | tetrahydrofuran |
| TLC | thin-layer chromatography on $SiO_2$ |

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Chemical Syntheses

Synthesis of 5-bromo-3-(ethanesulfonyl)-2-[7-methyl-3-(1,1,2,2,2-pentafluoroethyl)-7H-imidazo[4,5-c]pyridazin-6-yl]pyridine

Synthesis of N-methyl-6-(1,1,2,2,2-pentafluoroethyl)pyridazin-3-amine

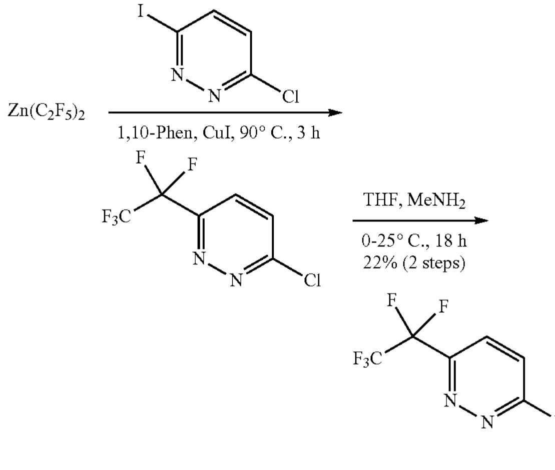

Into a 5-L3-necked round-bottom flask purged and maintained with an inert atmosphere of nitrogen, was placed a solution of bis(1,1,2,2,2-pentafluoroethyl)zinc (60.0 g, 197.7 mmol, 1.0 equiv) in NMP (2 mL), CuI (18.83 g, 98.9 mmol, 0.5 equiv), 1,10-phenanthroline (17.82 g, 98.9 mmol, 0.5 equiv), 3-chloro-6-iodopyridazine (47.6 g, 197.75 mmol, 1 equiv). The resulting solution was stirred for 3 hr at 90 degrees C. The mixture was used in the next step without any other purification.

Into a 5-L3-necked round-bottom flask, was placed a solution of 3-chloro-6-(1,1,2,2,2-pentafluoroethyl)

pyridazine (60.0 g, 258.0 mmol, 1.0 equiv) in NMP (2 L), THF (80.0 mL). This was followed by the addition of $MeNH_2$ in EtOH (200 mL, 10 equiv, 35%) at 0 degrees C. The resulting solution was stirred for 18 hr at 25 degrees C. The solids were filtered out. The resulting solution was extracted with 3×800 mL of ethyl acetate. The organic layer was washed with 5×800 mL of brine. The resulting mixture was concentrated. The residue was applied onto a silica gel column with ethyl acetate/petroleum ether (1:1). This resulted in 13 g (22%) of N-methyl-6-(1,1,2,2,2-pentafluoroethyl)pyridazin-3-amine as a yellow solid.

Synthesis of 4-bromo-N-methyl-6-(1,1,2,2,2-pentafluoroethyl)pyridazin-3-amine

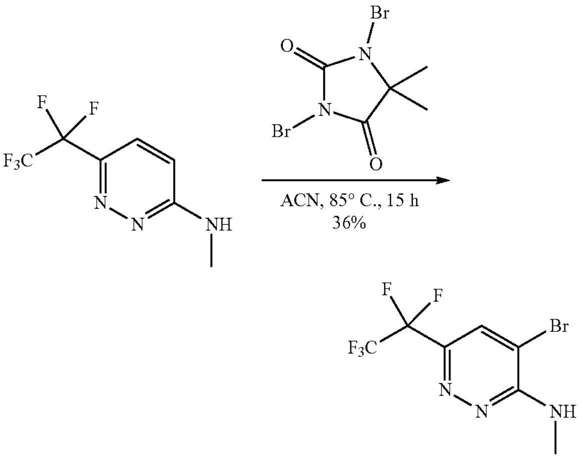

Into a 1-L round-bottom flask, was placed a solution of N-methyl-6-(1,1,2,2,2-pentafluoroethyl)pyridazin-3-amine (29.0 g, 127.7 mmol, 1.0 equiv) in ACN (400 mL), 1,3-Dibromo-5,5-dimethylhydantoin (80.31 g, 280.9 mmol, 2.2 equiv). The resulting solution was stirred for 15 hr at 85 degrees C. The reaction was then quenched by the addition of 500 mL of 10% $NaHSO_3$. The resulting solution was extracted with 2×500 mL of ethyl acetate. The resulting mixture was washed with 2×500 mL of brine. The resulting mixture was concentrated. The residue was applied onto a silica gel column with ethyl acetate/petroleum ether (1:5-1:1). This resulted in 14 g (36%) of 4-bromo-N-methyl-6-(1,1,2,2,2-pentafluoroethyl)pyridazin-3-amine as a light yellow solid.

Synthesis of N3-methyl-6-(1,1,2,2,2-pentafluoroethyl)pyridazine-3,4-diamine

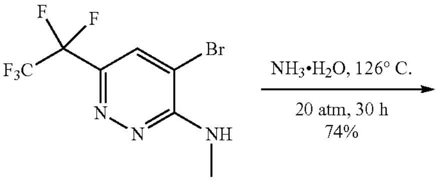

-continued

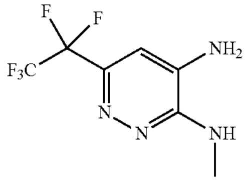

Into a 1-L pressure tank reactor purged and maintained with an inert atmosphere of nitrogen, was placed 4-bromo-N-methyl-6-(1,1,2,2,2-pentafluoroethyl)pyridazin-3-amine (17.0 g, 55.5 mmol, 1.0 equiv), $NH_3 \cdot H_2O$ (300.0 mL). The resulting solution was stirred for 30 hr at 126 degrees C. under 20 atm $N_2$ atmosphere. The resulting mixture was concentrated. The residue was applied onto a silica gel column with ethyl acetate/petroleum ether (1:0). This resulted in 10 g (74%) of N3-methyl-6-(1,1,2,2,2-pentafluoroethyl)pyridazine-3,4-diamine as a yellow solid.

Synthesis of 5-bromo-3-(ethylsulfanyl)-N-[3-(methylamino)-6-(1,1,2,2,2-pentafluoroethyl)pyridazin-4-yl]pyridine-2-carboxamide

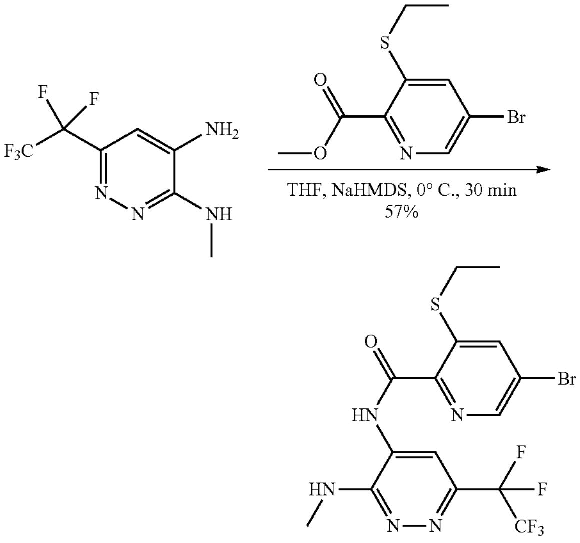

Into a 250-mL round-bottom flask purged and maintained with an inert atmosphere of nitrogen, was placed a solution of methyl 5-bromo-3-(ethylsulfanyl)pyridine-2-carboxylate (9 g, 32.6 mmol, 1.0 equiv) in THF (150 mL), N3-methyl-6-(1,1,2,2,2-pentafluoroethyl)pyridazine-3,4-diamine (8.29 g, 34.2 mmol, 1.05 equiv). This was followed by the addition of NaHMDS (29.3 mL, 58.6 mmol, 1.8 equiv, 2M) dropwise with stirring at 0 degrees C. The resulting solution was stirred for 30 min at 0 degrees C. The reaction was then quenched by the addition of 500 mL of 10% $NH_4Cl$. The resulting solution was extracted with 2×250 mL of ethyl acetate. The organic layer was concentrated, applied onto a silica gel column with ethyl acetate/petroleum ether (1:10-1:3). This resulted in 9 g (57%) of 5-bromo-3-(ethylsulfanyl)-N-[3-(methylamino)-6-(1,1,2,2,2-pentafluoroethyl) pyridazin-4-yl]pyridine-2-carboxamide as a yellow solid.

Synthesis of 5-bromo-3-(ethylsulfanyl)-2-[7-methyl-3-(1,1,2,2,2-pentafluoroethyl)-7H-imidazo[4,5-c] pyridazin-6-yl]pyridine

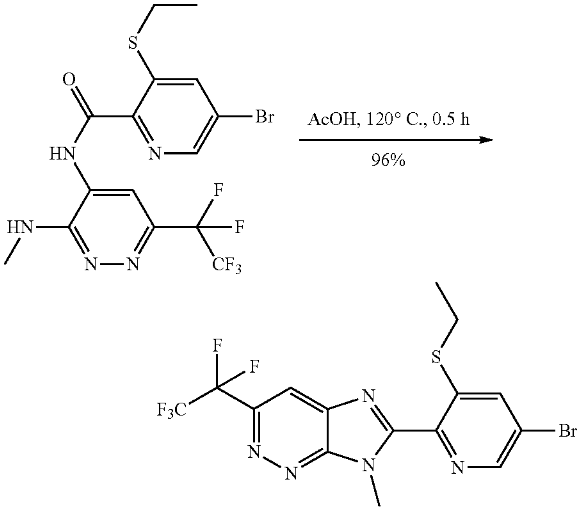

Into a 250-mL round-bottom flask, was placed 5-bromo-3-(ethylsulfanyl)-N-[3-(methylamino)-6-(1,1,2,2,2-pentafluoroethyl)pyridazin-4-yl]pyridine-2-carboxamide (6.5 g, 13.36 mmol, 1.0 equiv), AcOH (100.0 mL). The resulting solution was stirred for 0.5 hr at 120 degrees C. The resulting mixture was concentrated. The resulting solution was diluted with 200 mL of EA. The resulting mixture was washed with 2×50 mL of 10% $NaHCO_3$. The resulting mixture was washed with 2×50 mL of brine. The resulting mixture was concentrated. The residue was applied onto a silica gel column with ethyl acetate/petroleum ether (1:10-1:3). This resulted in 6 g (96%) of 5-bromo-3-(ethylsulfanyl)-2-[7-methyl-3-(1,1,2,2,2-pentafluoroethyl)imidazo[4,5-c]pyridazin-6-yl]pyridine as a light yellow solid.

Synthesis of 5-bromo-3-(ethanesulfonyl)-2-[7-methyl-3-(1,1,2,2,2-pentafluoroethyl)-7H-imidazo[4,5-c]pyridazin-6-yl]pyridine

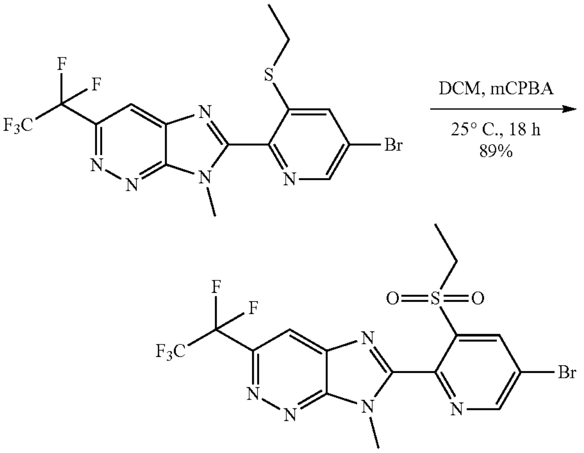

Into a 250-mL round-bottom flask, was placed a solution of 5-bromo-3-(ethylsulfanyl)-2-[7-methyl-3-(1,1,2,2,2-pentafluoroethyl)imidazo[4,5-c]pyridazin-6-yl]pyridine (8.0 g, 17.1 mmol, 1.0 equiv) in DCM (180 mL). This was followed by the addition of mCPBA (11.8 g, 68.3 mmol, 4.0 equiv) at 0 degrees C. The resulting solution was stirred for 10 hr at 0-25 degrees C. The resulting mixture was concentrated. The residue was applied onto a silica gel column with ethyl acetate/petroleum ether (1:4). This resulted in 7.6 g (89%) of 5-bromo-3-(ethanesulfonyl)-2-[7-methyl-3-(1,1,2,2,2-pentafluoroethyl) imidazo[4,5-c]pyridazin-6-yl]pyridine as a yellow solid.

Synthesis of 5-bromo-3-(ethanesulfonyl)-2-[3-methyl-6-(1,1,2,2,2-pentafluoroethyl)imidazo[4,5-b]pyridin-2-yl]pyridine Synthesis of 2-chloro-5-(1,1,2,2,2-pentafluoroethyl)pyridine

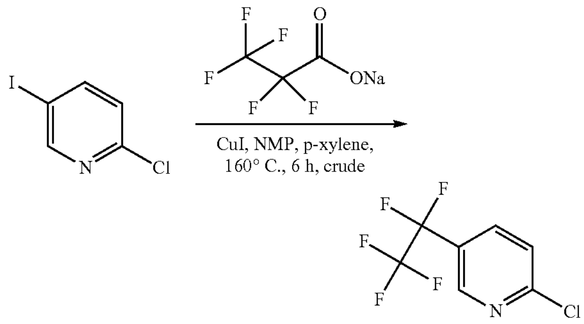

Into a 500-mL 3-necked round-bottom flask purged and maintained with an inert atmosphere of nitrogen, was placed 2-chloro-5-iodopyridine (20.0 g, 83.5 mmol, 1.00 equiv), sodium pentafluoropropanoate (77.7 g, 417.6 mmol, 5.00 equiv), CuI (47.7 g, 250.5 mmol, 3.00 equiv), NMP (84.00 mL), p-Xylene (84.00 mL). The resulting solution was stirred for 6 hr at 160 degrees C. The reaction mixture was cooled to room temperature. The reaction was then quenched by the addition of 200 mL of water. The resulting solution was extracted with 5×300 mL of MTBE. The resulting mixture was washed with 1×500 ml of brine. The mixture was dried over anhydrous sodium sulfate and concentrated. This resulted in 35 g (crude) of 2-chloro-5-(1,1,2,2,2-pentafluoroethyl)pyridine as a brown liquid.

Synthesis of N-methyl-5-(1,1,2,2,2-pentafluoroethyl)pyridin-2-amine

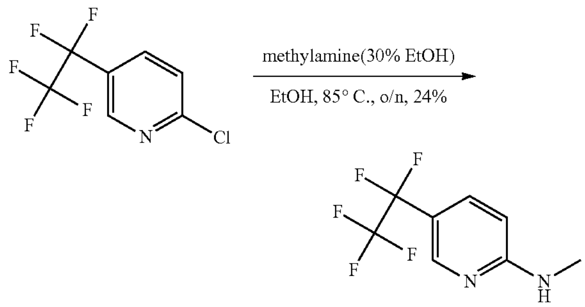

Into a 1000-mL pressure tank reactor, was placed 2-chloro-5-(1,1,2,2,2-pentafluoroethyl)pyridine (24 g, 1.00 equiv, crude), Methylamine ethanol solution (50 mL), EtOH (300 mL). The resulting solution was stirred overnight at 85 degrees C. The reaction mixture was cooled to room temperature. The resulting mixture was concentrated. The residue was applied onto a silica gel column with ethyl acetate/petroleum ether (1:10-1:4). This resulted in 3.8 g of N-methyl-5-(1,1,2,2,2-pentafluoroethyl)pyridin-2-amine as an off-white solid.

Synthesis of N-methyl-3-nitro-5-(1,1,2,2,2-pentafluoroethyl)pyridin-2-amine

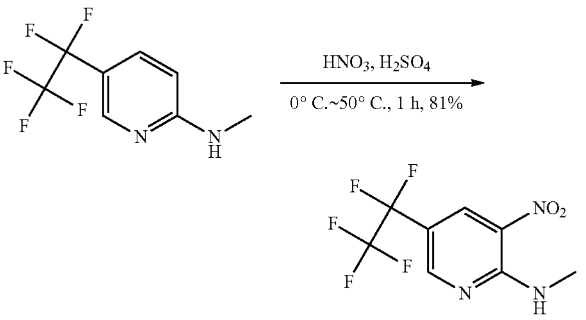

Into a 250-mL 3-necked round-bottom flask purged and maintained with an inert atmosphere of nitrogen, was placed N-methyl-5-(1,1,2,2,2-pentafluoroethyl)pyridin-2-amine (3.80 g, 16.8 mmol, 1.00 equiv), $H_2SO_4$ (80 mL). This was followed by the addition of $HNO_3$ (2.44 g, 25.1 mmol, 1.50 equiv, 65%) dropwise with stirring at 0 degrees C. The resulting solution was stirred for 1 hr at 50 degrees C. The reaction mixture was cooled to room temperature. The reaction was then quenched by the addition of 300 mL of water/ice. The pH value of the solution was adjusted to 8-9 with $Na_2CO_3$. The resulting solution was extracted with 3×100 mL of ethyl acetate. The resulting mixture was washed with 1×100 ml of brine. The mixture was dried over anhydrous sodium sulfate and concentrated. The residue was applied onto a silica gel column with ethyl acetate/petroleum ether (1:10-1:5). This resulted in 3.7 g (81%) of N-methyl-3-nitro-5-(1,1,2,2,2-pentafluoroethyl)pyridin-2-amine as a yellow solid.

Synthesis of N2-methyl-5-(1,1,2,2,2-pentafluoroethyl)pyridine-2,3-diamine

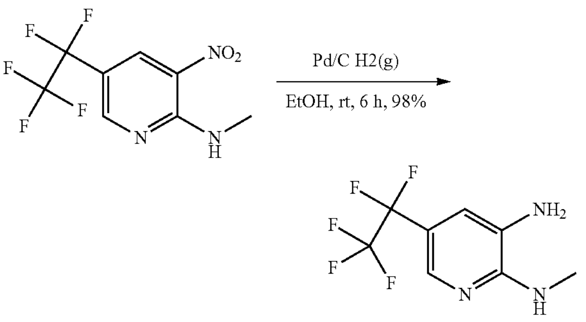

Into a 250-mL round-bottom flask, was placed N-methyl-3-nitro-5-(1,1,2,2,2-pentafluoroethyl)pyridin-2-amine (3.20 g, 11.8 mmol, 1.00 equiv), EtOH (70 mL), Pd/C (640. mg). The flask was evacuated and flushed three times with nitrogen, followed by flushing with hydrogen. The resulting mixture was stirred 6 h at room temperature under an atmosphere of hydrogen. The solids were filtered out. The resulting mixture was concentrated. This resulted in 2.8 g (98%) of N2-methyl-5-(1,1,2,2,2-pentafluoroethyl)pyridine-2,3-diamine as an off-white solid.

Synthesis of 5-bromo-3-(ethylsulfanyl)-N-[2-(methylamino)-5-(1,1,2,2,2-pentafluoroethyl)pyridin-3-yl] pyridine-2-carboxamide

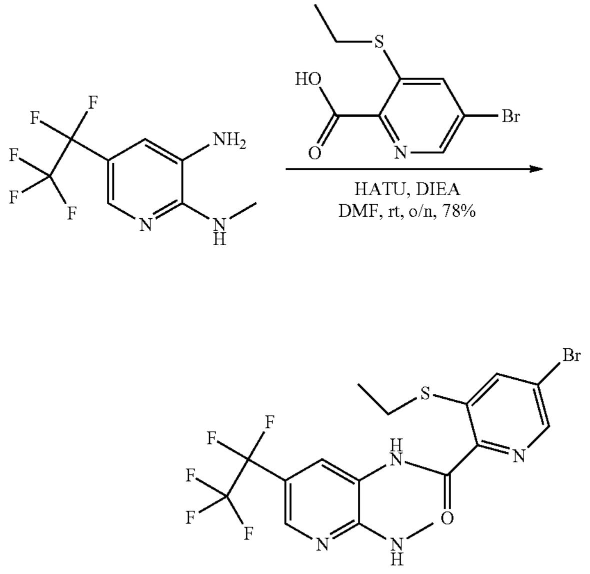

Into a 250-mL 3-necked round-bottom flask purged and maintained with an inert atmosphere of nitrogen, was placed N2-methyl-5-(1,1,2,2,2-pentafluoroethyl)pyridine-2,3-diamine (3.20 g, 13.2 mmol, 1.0 equiv), 5-bromo-3-(ethylsulfanyl)pyridine-2-carboxylic acid (3.83 g, 14.6 mmol, 1.1 equiv), HATU (7.57 g, 19.9 mmol, 1.5 equiv), DMF (70 mL), DIEA (5.1 g, 39.8 mmol, 3.0 equiv). The resulting solution was stirred for overnight at room temperature. The reaction was then quenched by the addition of 200 mL of water. The resulting solution was extracted with 3×100 mL of ethyl acetate The resulting mixture was washed with 1×100 ml of brine. The mixture was dried over anhydrous sodium sulfate and concentrated. The residue was applied onto a silica gel column with ethyl acetate/petroleum ether (1:10-1:3). This resulted in 5 g (78%) of 5-bromo-3-(ethylsulfanyl)-N-[2-(methylamino)-5-(1,1,2,2,2-pentafluoroethyl)pyridin-3-yl]pyridine-2-carboxamide as an off-white solid.

Synthesis of 5-bromo-3-(ethylsulfanyl)-2-[3-methyl-6-(1,1,2,2,2-pentafluoroethyl)imidazo[4,5-b]pyridin-2-yl]pyridine

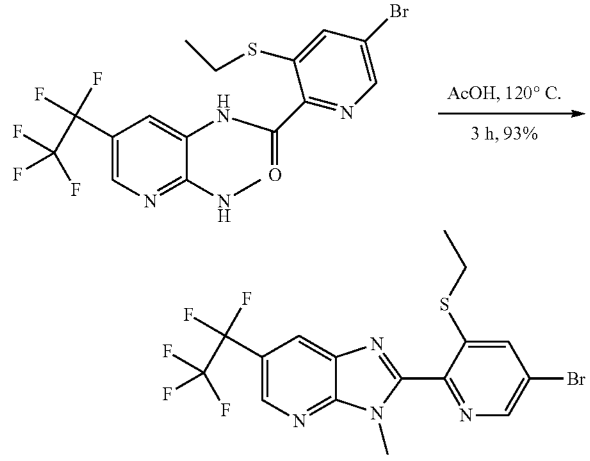

Into a 250-mL round-bottom flask purged and maintained with an inert atmosphere of nitrogen, was placed 5-bromo-3-(ethylsulfanyl)-N-[2-(methylamino)-5-(1,1,2,2,2-pentafluoroethyl)pyridin-3-yl]pyridine-2-carboxamide (5.0 g, 10.3 mmol, 1.00 equiv), AcOH (100 mL). The resulting solution was stirred for 3 h at 120 degrees C. The reaction mixture was cooled to room temperature. The resulting mixture was concentrated. The residue was applied onto a silica gel column with ethyl acetate/petroleum ether (1:10-1:3). This resulted in 4.5 g (93%) of 5-bromo-3-(ethylsulfanyl)-2-[3-methyl-6-(1,1,2,2,2-pentafluoroethyl)imidazo [4,5-b]pyridin-2-yl]pyridine as an off-white solid.

Synthesis of 5-bromo-3-(ethanesulfonyl)-2-[3-methyl-6-(1,1,2,2,2-pentafluoroethyl)imidazo[4,5-b] pyridin-2-yl]pyridine

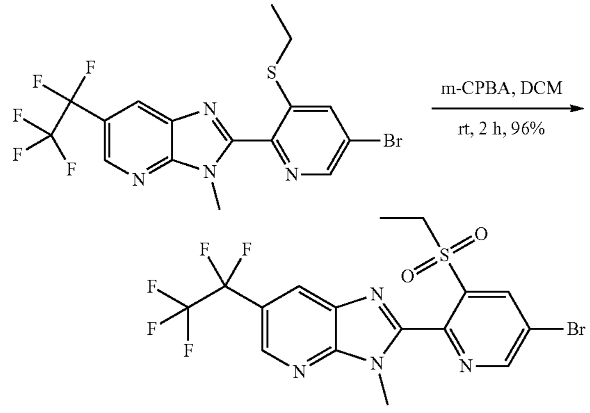

Into a 250-mL 3-necked round-bottom flask purged and maintained with an inert atmosphere of nitrogen, was placed 5-bromo-3-(ethylsulfanyl)-2-[3-methyl-6-(1,1,2,2,2-pentafluoroethyl)imidazo(4,5-b)pyridin-2-yl]pyridine (4.5 g, 9.6 mmol, 1.00 equiv), DCM (90 mL). This was followed by the addition of mCPBA (4.30 g, 21.1 mmol, 2.20 equiv, 85%), in portions at room temperature. The resulting solution was stirred for 2 hr at room temperature. The resulting mixture was washed with 1×50 ml of 10% $Na_2SO_3$ and 1×50 mL of 10% $NaHCO_3$, then 1×50 mL of brine. The organic phase was collected and dried over anhydrous sodium sulfate and concentrated. The residue was applied onto a silica gel column with ethyl acetate/petroleum ether (1:10-1:3). This resulted in 4.6 g (96%) of 5-bromo-3-(ethanesulfonyl)-2-[3-methyl-6-(1,1,2,2,2-pentafluoroethyl)imidazo[4,5-b]pyridin-2-yl]pyridine as an off-white solid.

Synthesis of 2-[5-bromo-3-(ethanesulfonyl)pyridin-2-yl]-5-trifluoromethanesulfonyl-1,3-benzoxazole core

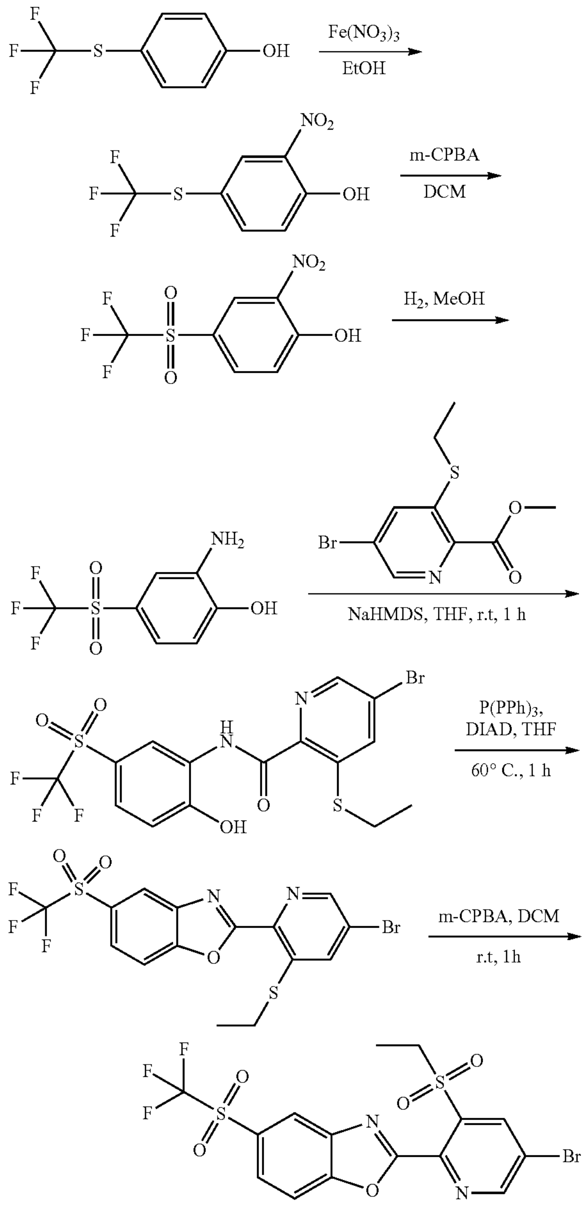

Synthesis of 2-nitro-4-[(trifluoromethyl)sulfanyl]phenol

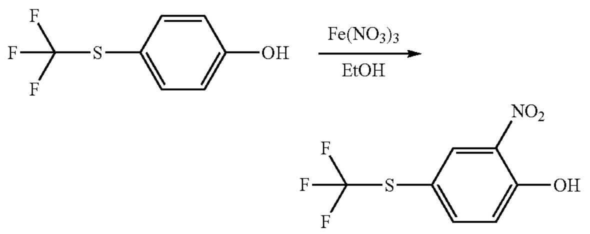

Into a 1000-mL round-bottom flask, was placed EtOH (500 mL, 10.9 mol, 55.7 equiv), 4-[(trifluoromethyl)sulfanyl]phenol (30 g, 154 mmol, 1.00 equiv), $Fe(NO_3)_4$(29.9 g, 123 mmol, 0.8 equiv). The resulting solution was stirred overnight at 80 degrees C. The resulting mixture was concentrated under vacuum. The residue was applied onto a silica gel column with ethyl acetate/petroleum ether (1:5). This resulted in 30 g (81%) of 2-nitro-4-[(trifluoromethyl)sulfanyl]phenol as a yellow solid.

Synthesis of 2-nitro-4-trifluoromethanesulfonylphenol

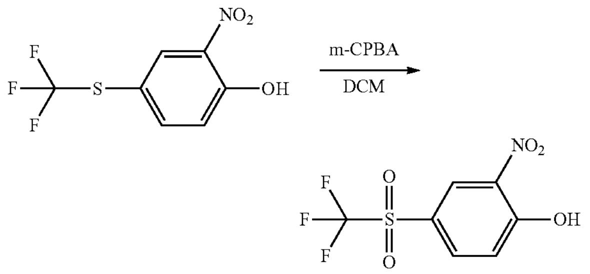

Into a 1000-mL round-bottom flask, was placed DCM (600 mL, 9.4 mol, 75.24 equiv), 2-nitro-4-[(trifluoromethyl)sulfanyl]phenol (30 g, 125 mmol, 1.00 equiv), m-CPBA (110 g, 637 mmol, 5.0 equiv). The resulting solution was stirred overnight at 50 degrees C. The solids were filtered out. The resulting mixture was concentrated under vacuum. The crude product was purified by Flash-Prep-HPLC with the following conditions (IntelFlash-1): Column, C18 silica gel; mobile phase, $H_2O$:ACN=70:30 increasing to $H_2O$:ACN=30:70 within 20 min; Detector, 254 nm. This resulted in 30 g (88%) of 2-nitro-4-trifluoromethanesulfonylphenol as light-yellow oil.

Synthesis of 2-amino-4-trifluoromethanesulfonylphenol

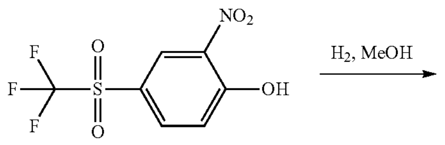

-continued

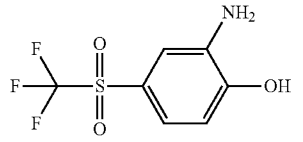

Into a 500-mL round-bottom flask, was placed MeOH (200 mL, 4.9 mol, 53.6 equiv), 2-nitro-4-trifluoromethanesulfonylphenol (25 g, 92.193 mmol, 1.00 equiv), Pd/C (20. g, 188 mmol, 2.0 equiv). To the above $H_2$(g) was introduced in. The resulting solution was stirred overnight at room temperature. The solids were filtered out. The filtrate was concentrated under vacuum. This resulted in 16 g (72%) of 2-amino-4-trifluoromethanesulfonylphenol as a yellow solid.

Synthesis of 5-bromo-3-(ethylsulfanyl)-N-(2-hydroxy-5-trifluoromethanesulfonylphenyl)pyridine-2-carboxamide

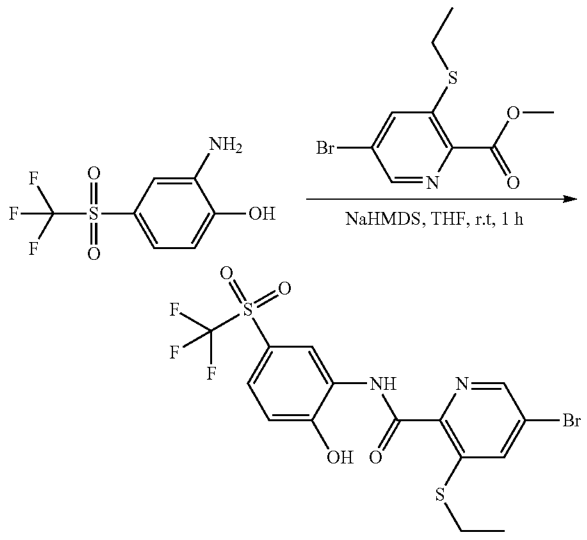

Into a 500-mL 3-necked round-bottom flask purged and maintained with an inert atmosphere of nitrogen, was placed methyl 5-bromo-3-(ethylsulfanyl)pyridine-2-carboxylate (10 g, 0.04 mmol, 1.00 equiv), THF (200.00 mL), 2-amino-4-trifluoromethanesulfonylphenol (8.7 g, 0.0 mmol, 1.00 equiv). This was followed by the addition of NaHMDS (36 mL) dropwise with stirring at 0 degrees C. The resulting solution was stirred for 1 hr at room temperature. The resulting solution was diluted with 40 mL of 2M HCl. The resulting solution was extracted with 2×200 mL of ethyl acetate and the organic layers combined and dried over anhydrous sodium sulfate and concentrated. The crude product was purified by Prep-Flash with the following conditions: Column, C18 silica gel; mobile phase, 0.1% FA in water and ACN (40% ACN increasing to 70% within 14 min). Detector, UV 254 nm, 220 nm. This resulted in 5.3 g (27%) of 5-bromo-3-(ethylsulfanyl)-N-(2-hydroxy-5-trifluoromethanesulfonylphenyl)pyridine-2-carboxamide as a brown solid.

Synthesis of 2-[5-bromo-3-(ethylsulfanyl)pyridin-2-yl]-5-trifluoromethanesulfonyl-1,3-benzoxazole

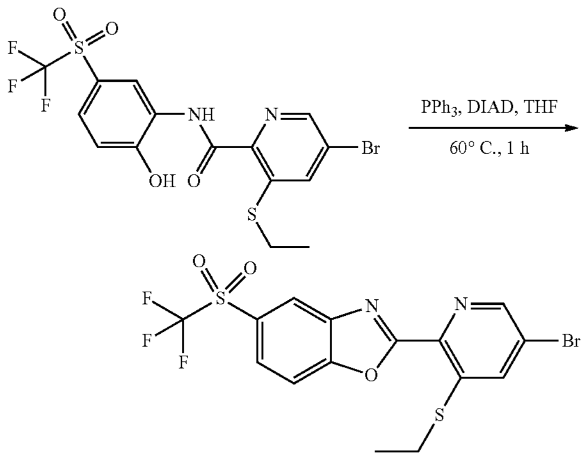

Into a 250-mL 3-necked round-bottom flask purged and maintained with an inert atmosphere of nitrogen, was placed 5-bromo-3-(ethylsulfanyl)-N-(2-hydroxy-5-trifluoromethanesulfonylphenyl)pyridine-2-carboxamide (4.80 g, 9.8 mmol, 1.0 equiv), THE (96.00 mL), $PPh_3$ (10.4 g, 39 mmol, 4 equiv), DIAD (8.0 g, 40 mmol, 4.0 equiv). The resulting solution was stirred for 1 hr at 60 degrees C. The crude product was purified by Prep-Flash with the following conditions: Column, C18 silica gel; mobile phase, 0.1% TFA in water and ACN (60% ACN increasing to 95% within 15 min). Detector, UV 254 nm, 220 nm. This resulted in 4 g (74%) of 2-[5-bromo-3-(ethylsulfanyl)pyridin-2-yl]-5-trifluoromethanesulfonyl-1,3-benzoxazole as a yellow solid.

Synthesis of 2-[5-bromo-3-(ethanesulfonyl)pyridin-2-yl]-5-trifluoromethanesulfonyl-1,3-benzoxazole

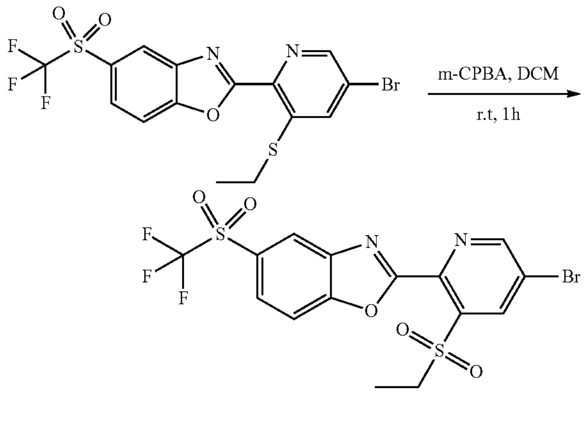

Into a 250-mL 3-necked round-bottom flask, was placed 2-[5-bromo-3-(ethylsulfanyl)pyridin-2-yl]-5-trifluoromethanesulfonyl-1,3-benzoxazole (4.0 g, 8.6 mmol, 1.00 equiv), DCM (80 mL). This was followed by the addition of m-CPBA (5.9 g, 34 mmol, 4 equiv) in several batches at 0 degrees C. The resulting solution was stirred for 1 hr at room temperature. The resulting solution was diluted with 100 mL of water. The resulting solution was extracted with 200 mL of dichloromethane and the organic layers combined. The resulting mixture was washed with 2×200 ml of $NaHCO_3$. The mixture was dried over anhydrous magnesium sulfate and concentrated. The residue was applied onto a silica gel column with ethyl acetate/petroleum ether (0-20%). This resulted in 3.7 g (85%) of 2-[5-bromo-3-(ethanesulfonyl) pyridin-2-yl]-5-trifluoromethanesulfonyl-1,3-benzoxazole as a white solid.

Synthesis of 5-bromo-3-(ethanesulfonyl)-2-[7-methyl-3-trifluoromethanesulfonylimidazo[4,5-c] pyridazin-6-yl]pyridine Synthesis of 3-chloro-6-[(trifluoromethyl)sulfanyl] pyridazine

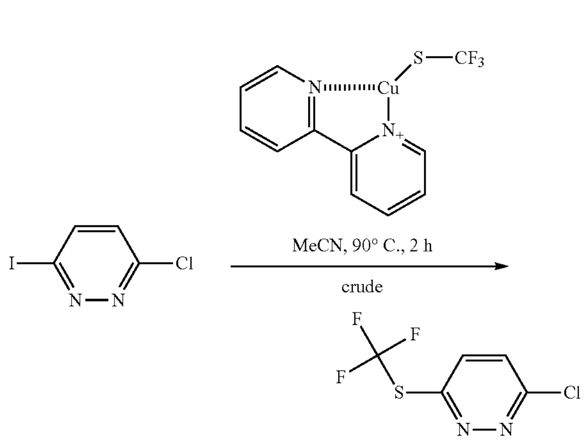

Into a 500 mL round-bottom flask, was placed 3-chloro-6-iodopyridazine (21 g, 87 mmol, 1.00 equiv), 8-[(trifluoromethyl)sulfanyl]-7lambda5,9lambda4-diaza-8-cupratricyclo[7.4.0.0/\{2,7}]trideca-1(9),2,4,6,10,12-hexaen-7-ylium (56. g, 175 mmol, 2.0 equiv), MeCN (200 mL). The reaction mixture was stirred at 90 degrees C. for 2 h. The mixture was allowed to cool down to rt. The resulting mixture was diluted with EA (1.0 L). The resulting mixture was washed with 3×300 mL of water. The resulting solution was dried by $Na_2SO_4$. The resulting mixture was concentrated under reduced pressure. The residue was purified by silica gel column chromatography, eluted with PE/EA (4/1) to afford 3-chloro-6-[(trifluoromethyl)sulfanyl]pyridazine (21 g, crude) as a yellow solid.

Synthesis of N-methyl-6-[(trifluoromethyl)sulfanyl] pyridazin-3-amine

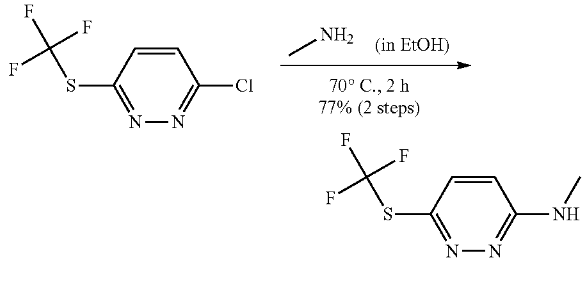

Into a 500 round-bottom flask, was placed 3-chloro-6-[(trifluoromethyl)sulfanyl]pyridazine (20 g, 93 mmol, 1.0 equiv), THF (200 mL), methylamine (29 g, 0.9 mol, 10 equiv). The reaction mixture was stirred at 70 degrees C. for 2 h. The mixture was allowed to cool down to rt. The resulting mixture was concentrated under reduced pressure. The crude product was re-crystallized from PE/EA (5/1) to afford N-methyl-6-[(trifluoromethyl)sulfanyl]pyridazin-3-amine (15 g, 77%) as a yellow solid.

Synthesis of 4-bromo-N-methyl-6-[(trifluoromethyl) sulfanyl]pyridazin-3-amine

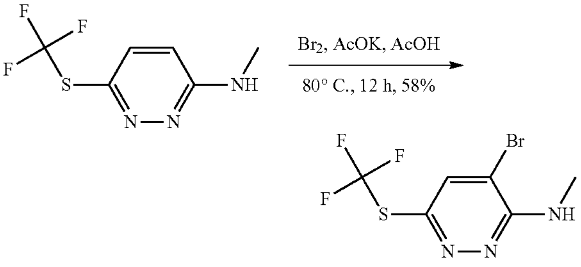

Into a 50-mL round-bottom flask, was placed N-methyl-6-[(trifluoromethyl)sulfanyl]pyridazin-3-amine (300. mg, 1.4 mmol, 1.0 equiv), AcOH (10.00 mL), $Br_2$ (687 mg, 4.3 mmol, 3.0 equiv), AcOK (141 mg, 1.4 mmol, 1.0 equiv). The resulting solution was stirred for 12 hr at 80 degrees C. in an oil bath. The reaction mixture was cooled. The resulting mixture was concentrated. The resulting solution was diluted with 200 mL of EA. The resulting mixture was washed 3× with 100 mL of $Na_2CO_3$ (aq. 2M). The mixture was dried over anhydrous sodium sulfate and concentrated. The residue was applied onto a silica gel column with ethyl acetate/petroleum ether (1/3). The collected fractions were combined and concentrated. This resulted in 240 mg (58.09%) of 4-bromo-N-methyl-6-[(trifluoromethyl)sulfanyl]pyridazin-3-amine as a light yellow solid.

Synthesis of N3-methyl-6-[(trifluoromethyl)sulfanyl]pyridazine-3,4-diamine

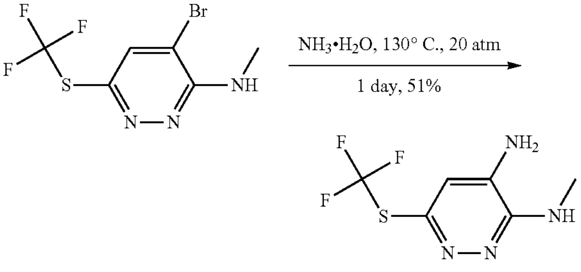

Into a 250-mL pressure tank reactor purged and maintained with an inert atmosphere of nitrogen, was placed 4-bromo-N-methyl-6-[(trifluoromethyl)sulfanyl]pyridazin-3-amine (800 mg, 2.7 mmol, 1.0 equiv), $NH_3 \cdot H_2O$ (200 mL). The resulting solution was stirred for 1 day at 130 degrees C., 20 atm. The reaction mixture was cooled. The resulting mixture was concentrated. The crude product was purified by Flash-Prep-HPLC with the following conditions (IntelFlash-1): Column, C18 silica gel; mobile phase, MeCN/H2O=0/100 increasing to MeCN/$H_2O$=40/60. The product was obtained and concentrated. This resulted in 320 mg (51%) of N3-methyl-6-[(trifluoromethyl)sulfanyl] pyridazine-3,4-diamine a yellow solid.

Synthesis of 5-bromo-3-(ethylsulfanyl)-N-[3-(methylamino)-6-[(trifluoromethyl)sulfanyl]pyridazin-4-yl]pyridine-2-carboxamide

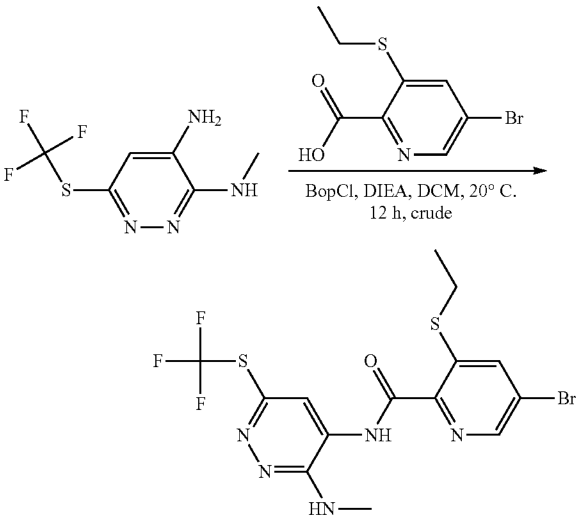

Into a 50-mL round-bottom flask, was placed N3-methyl-6-[(trifluoromethyl)sulfanyl]pyridazine-3,4-diamine (380 mg, 1.7 mmol, 1.0 equiv), 5-bromo-3-(ethylsulfanyl)pyridine-2-carboxylic acid (533 mg, 2.0 mmol, 1.2 equiv), DCM (20 mL), DIEA (657 mg, 5.1 mmol, 3.0 equiv), BOPCI (646 mg, 2.5 mmol, 1.5 equiv). The resulting solution was stirred for 12 hr at 20 degrees C. The resulting solution was diluted with 100 mL of DCM. The resulting mixture was washed with 3×50 mL of $H_2O$. The mixture was dried over anhydrous sodium sulfate and concentrated. This resulted in 870 mg crude of 5-bromo-3-(ethylsulfanyl)-N-[3-(methylamino)-6-[(trifluoromethyl)sulfanyl]pyridazin-4-yl]pyridine-2-carboxamide as yellow oil.

Synthesis of 5-bromo-3-(ethylsulfanyl)-2-[7-methyl-3-[(trifluoromethyl)sulfanyl]imidazo[4,5-c] pyridazin-6-yl]pyridine

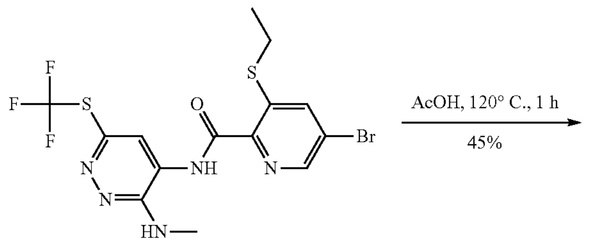

-continued

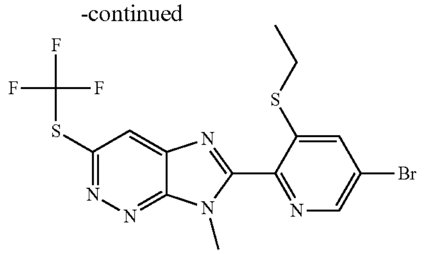

Into a 50-mL round-bottom flask, was placed 5-bromo-3-(ethylsulfanyl)-N-[3-(methylamino)-6-[(trifluoromethyl) sulfanyl]pyridazin-4-yl]pyridine-2-carboxamide (870 mg, 1.8 mmol, 1.0 equiv), AcOH (10 mL). The resulting solution was stirred for 1 hr at 120 degrees C. in an oil bath. The reaction mixture was cooled. The resulting mixture was concentrated. The resulting solution was diluted with 200 mL of EA. The resulting mixture was washed with 3×50 mL of $Na_2CO_3$ (2M, aq). The mixture was dried over anhydrous sodium sulfate and concentrated. The residue was applied onto a silica gel column with ethyl acetate/petroleum ether (1/4). The collected fractions were combined and concentrated. This resulted in 380 mg (45%) of 5-bromo-3-(ethylsulfanyl)-2-[7-methyl-3-[(trifluoromethyl)sulfanyl]imidazo [4,5-c]pyridazin-6-yl]pyridine as a light yellow solid.

Synthesis of 5-bromo-3-(ethanesulfonyl)-2-[7-methyl-3-[(trifluoromethyl)sulfanyl]imidazo[4,5-c] pyridazin-6-yl]pyridine

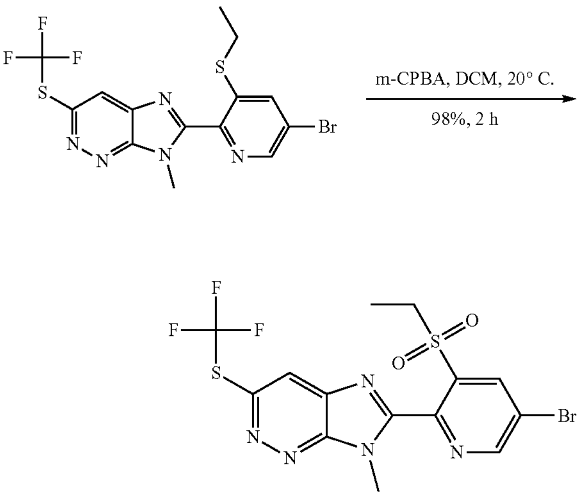

Into a 50-mL round-bottom flask, was placed 5-bromo-3-(ethylsulfanyl)-2-[7-methyl-3-[(trifluoromethyl)sulfanyl] imidazo[4,5-c]pyridazin-6-yl]pyridine (370 mg, 0.8 mmol, 1.0 equiv), DCM (10 mL), m-CPBA (354 mg, 2.1 mmol, 2.5 equiv). The resulting solution was stirred for 2 hr at 20 degrees C. The resulting mixture was concentrated. The residue was applied onto a silica gel column with ethyl acetate/petroleum ether (1/1). The collected fractions were combined and concentrated. This resulted in 390 mg (98%) of 5-bromo-3-(ethanesulfonyl)-2-[7-methyl-3-[(trifluoromethyl)sulfanyl]imidazo[4,5-c]pyridazin-6-yl]pyridine as a light yellow solid.

Synthesis of 5-bromo-3-(ethanesulfonyl)-2-[7-methyl-3-trifluoromethanesulfonylimidazo[4,5-c]pyridazin-6-yl]pyridine

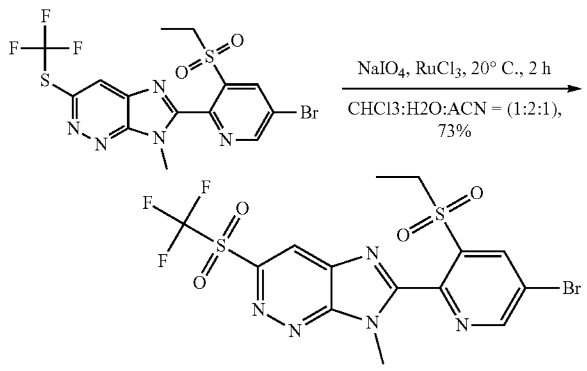

Into a 25-mL round-bottom flask, was placed 5-bromo-3-(ethanesulfonyl)-2-[7-methyl-3-[(trifluoromethyl)sulfanyl]imidazo[4,5-c]pyridazin-6-yl]pyridine (410 mg, 0.85 mmol, 1.0 equiv), $H_2O$ (4 mL), $CHCl_3$ (2 mL), MeCN (2 mL), $NaIO_4$ (545 mg, 2.6 mmol, 3.0 equiv), $RuCl_3 \cdot H_2O$ (38 mg, 0.17 mmol, 0.2 equiv). The resulting solution was stirred for 2 hr at 20 degrees C. The resulting solution was diluted with 50 mL of EA and washed with 3×50 mL of water and 1×50 mL of brine. The mixture was dried over anhydrous sodium sulfate and concentrated. The residue was applied onto a silica gel column with ethyl acetate/petroleum ether (1/1). The collected fractions were combined and concentrated. This resulted in 320 mg (73%) of 5-bromo-3-(ethanesulfonyl)-2-[7-methyl-3-trifluoromethanesulfonylimidazo[4,5-c]pyridazin-6-yl]pyridine as a white solid.

Synthesis of 5-bromo-3-(ethanesulfonyl)-2-[6-(trifluoro methyl)-1H-pyrrolo[3,2-b]pyridin-2-yl]pyridine Synthesis of 2-methyl-1-phenylpropan-2-yl 3-[5-bromo-3-(ethylsulfanyl)pyridin-2-yl]-3-oxopropanoate

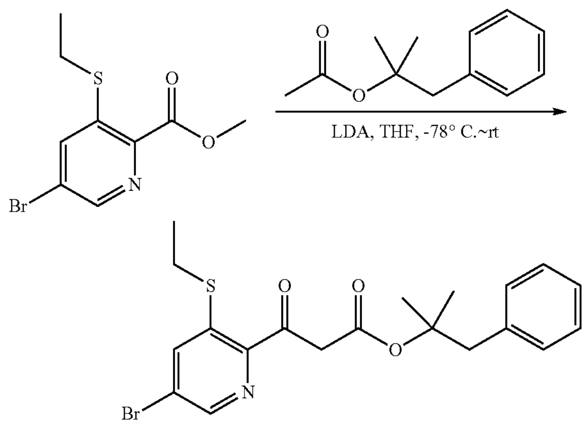

Into a 1-L3-necked round-bottom flask purged and maintained with an inert atmosphere of nitrogen, was placed dimethylbenzyl carbonyl acetate (29 g, 152 mmol, 1.2 equiv), THF (400 mL). This was followed by the addition of LDA (178 mL,2 M, 2.8 equiv) dropwise with stirring at −78 degrees C. The reaction was stirred for 30 min. To this was added methyl 5-bromo-3-(ethylsulfanyl)pyridine-2-carboxylate (35 g, 127 mmol, 1.0 equiv) dropwise with stirring at −78 degrees C. The resulting solution was stirred for 2 hr at room temperature. The reaction was then quenched by the addition of HCl (2 M). The resulting solution was extracted with 2×1 L of ethyl acetate and the organic layers combined and dried over anhydrous sodium sulfate and concentrated under vacuum. The residue was applied onto a silica gel column with ethyl acetate/petroleum ether (1/10). This resulted in 30.5 g (55%) of 2-methyl-1-phenylpropan-2-yl 3-[5-bromo-3-(ethylsulfanyl)pyridin-2-yl]-3-oxopropanoate as brown oil.

Synthesis of 2-methyl-1-phenylpropan-2-yl 3-[5-bromo-3-(ethylsulfanyl)pyridin-2-yl]-2-[3-nitro-5-(trifluoromethyl)pyridin-2-yl]-3-oxopropanoate

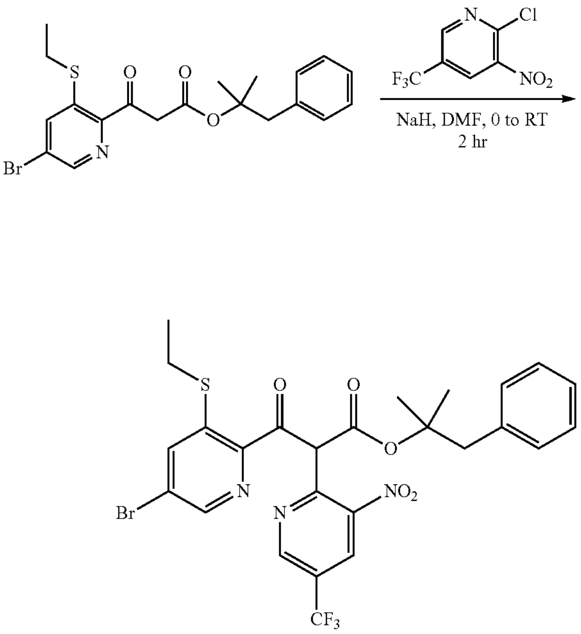 [SMILES: CCSc1cc(Br)cnc1C(=O)CC(=O)OC(C)(C)Cc1ccccc1 ; O=[N+]([O-])c1cc(C(F)(F)F)cnc1Cl ; CCSc1cc(Br)cnc1C(=O)C(C(=O)OC(C)(C)Cc1ccccc1)c1ncc(C(F)(F)F)cc1[N+](=O)[O-]]

Into a 500-mL 3-necked round-bottom flask purged and maintained with an inert atmosphere of nitrogen, was placed 2-methyl-1-phenylpropan-2-yl 3-[5-bromo-3-(ethylsulfanyl)pyridin-2-yl]-3-oxopropanoate (14.5 g, 33 mmol, 1.0 equiv), DMF (150 mL). This was followed by the addition of NaH (2.93 g, 60%, 2.2 equiv) in portions at 0 degrees C. The reaction was stirred for 30 min. To this was added 2-chloro-3-nitro-5-(trifluoromethyl)pyridine (9.8 g, 43 mmol, 1.3 equiv) dropwise with stirring at 0 degrees C. The resulting solution was stirred for 2 hr at room temperature. The reaction was then quenched by the addition of HCl (2 mol/L). The resulting solution was extracted with 2×500 mL of ethyl acetate. The organic layers were wished with 2×300 mL of $H_2O$ and combined concentrated under vacuum. This resulted in 26.5 g (crude) of 2-methyl-1-phenylpropan-2-yl 3-[5-bromo-3-(ethylsulfanyl)pyridin-2-yl]-2-[3-nitro-5-(trifluoromethyl)pyridin-2-yl]-3-oxopropanoate as brown oil.

Synthesis of 1-[5-bromo-3-(ethylsulfanyl)pyridin-2-yl]-2-[3-nitro-5-(trifluoromethyl)pyridin-2-yl]ethan-1-one

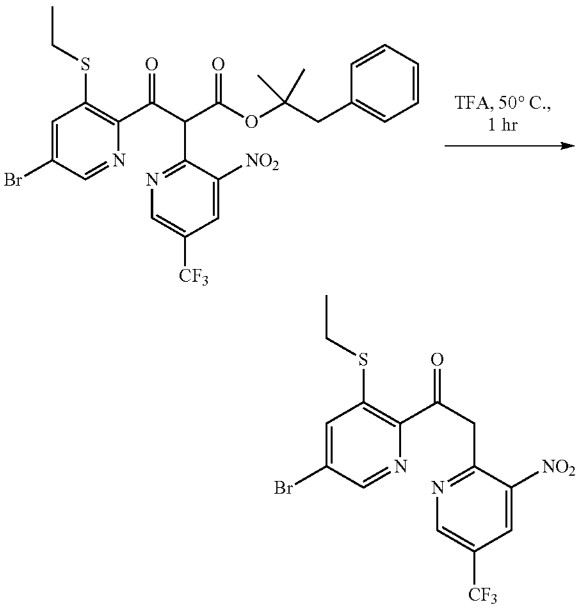

Into a 500-mL 3-necked round-bottom flask purged and maintained with an inert atmosphere of nitrogen, was placed 2-methyl-1-phenylpropan-2-yl 3-[5-bromo-3-(ethylsulfanyl)pyridin-2-yl]-2-[3-nitro-5-(trifluoromethyl)pyridin-2-yl]-3-oxopropanoate (26.5 g, 42 mmol, 1.0 equiv), TFA (150 mL, 1.3 mmol, 0.03 equiv). The resulting solution was stirred for 1 hr at 50 degrees C. The reaction mixture was used for next step directly without any further purification.

Synthesis of 5-bromo-3-(ethylsulfanyl)-2-[6-(trifluoromethyl)-1H-pyrrolo[3,2-b]pyridin-2-yl]pyridine

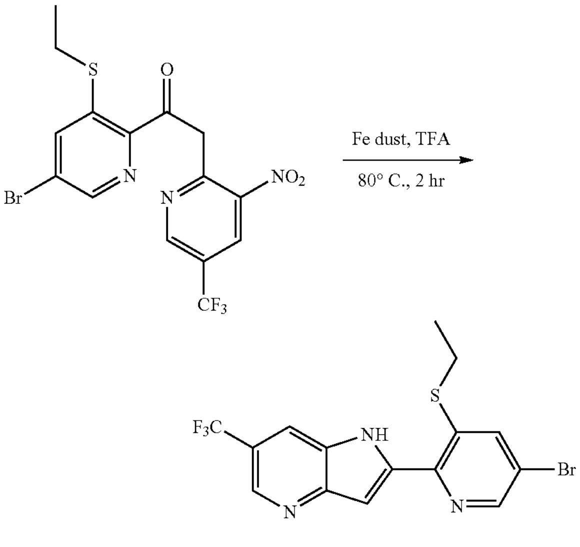

Into a 500-mL 3-necked round-bottom flask purged and maintained with an inert atmosphere of nitrogen, was placed 1-[5-bromo-3-(ethylsulfanyl)pyridin-2-yl]-2-[3-nitro-5-(trifluoromethyl)pyridin-2-yl]ethanone (26.5 g, 59 mmol, 1.0 equiv), TFA (150 mL). This was followed by the addition of Fe dust (13 g, 233 mmol, 4.0 equiv), in portions at room temperature. The resulting solution was stirred for 2 hr at 80 degrees C. The solids were filtered out. The filtrate was concentrated. The resulting mixture was washed with 2×300 ml of $NaHCO_3$ aqueous solution. The resulting solution was extracted with 2×500 mL of ethyl acetate. This resulted in 8.8 g(crude) of 5-bromo-3-(ethylsulfanyl)-2-[6-(trifluoromethyl)-1H-pyrrolo[3,2-b]pyridin-2-yl]pyridine as a black solid.

Synthesis of tert-butyl 2-[5-bromo-3-(ethylsulfanyl)pyridin-2-yl]-6-(trifluoro methyl)pyrrolo[3,2-b]pyridine-1-carboxylate

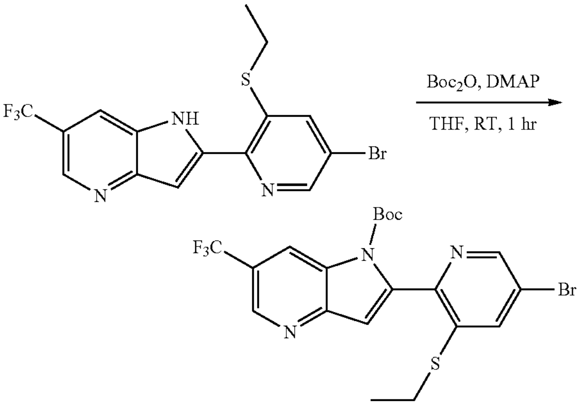

Into a 250-mL round-bottom flask, was placed 5-bromo-3-(ethylsulfanyl)-2-[6-(trifluoromethyl)-1H-pyrrolo[3,2-b]pyridin-2-yl]pyridine (8.8 g, 22 mmol, 1.0 equiv), THF (100 mg), $Boc_2O$ (5.73 g, 26 mmol, 1.2 equiv), DMAP (267 mg, 2.2 mmol, 0.1 equiv). The resulting solution was stirred for 1 hr at room temperature. The residue was applied onto a silica gel column with ethyl acetate/petroleum ether (1/10). This resulted in 9 g (82%) of tert-butyl 2-[5-bromo-3-(ethylsulfanyl)pyridin-2-yl]-6-(trifluoro methyl)pyrrolo[3,2-b]pyridine-1-carboxylate as a light yellow solid.

Synthesis of tert-butyl 2-[5-bromo-3-(ethanesulfonyl)pyridin-2-yl]-6-(trifluoromethyl)pyrrolo[3,2-b]pyridine-1-carboxylate

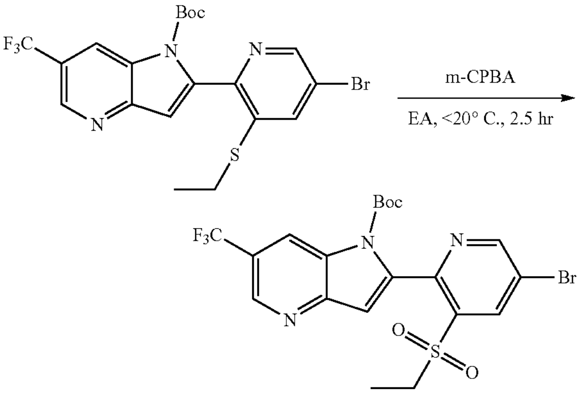

Into a 50-mL 3-necked round-bottom flask, was placed tert-butyl 2-[5-bromo-3-(ethylsulfanyl)pyridin-2-yl]-6-(trifluoromethyl)pyrrolo[3,2-b]pyridine-1-carboxylate (1.0 g, 2.0 mmol, 1.0 equiv), EA (20 mL, 204 mmol, 102 equiv). This was followed by the addition of m-CPBA (1.0 g, 4.9 mmol, 2.5 equiv, 85%) in several batches at 15 degrees C. The resulting solution was stirred for 2.5 hr below 20 degrees C. The resulting solution was diluted with 20 mL of water. The pH value of the solution was adjusted to 8 with sat. $NaHCO_3$(aq). The resulting solution was extracted with 3×20 mL of ethyl acetate and the organic layers combined. The resulting mixture was washed with 1×20 mL of brine. The mixture was dried over anhydrous sodium sulfate and concentrated under vacuum. The residue was applied onto a silica gel column with THF/PE (1:3). This resulted in 0.77 g (72%) of tert-butyl 2-[5-bromo-3-(ethanesulfonyl)pyridin-2-yl]-6-(trifluoromethyl)pyrrolo[3,2-b]pyridine-1-carboxylate as a yellow solid.

Synthesis of 5-bromo-3-(ethanesulfonyl)-2-[6-(trifluoromethyl)-1H-pyrrolo[3,2-b]pyridin-2-yl]pyridine

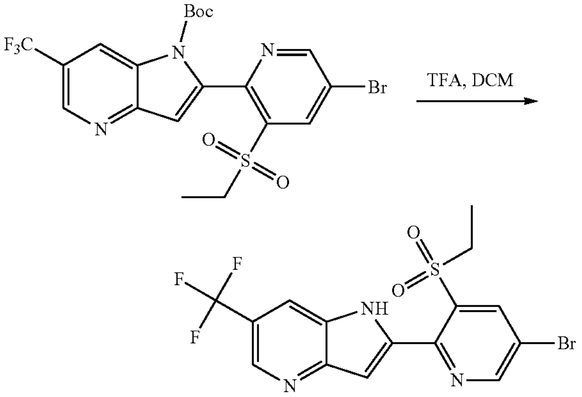

Into a 250-mL round-bottom flask purged and maintained with an inert atmosphere of nitrogen, was placed tert-butyl 2-[5-bromo-3-(ethanesulfonyl)pyridin-2-yl]-6-(trifluoromethyl)pyrrolo[3,2-b]pyridine-I-carboxylate (5.0 g, 9.4 mmol, 1.0 equiv), DCM (20 mL), TFA (20 mL). The resulting solution was stirred for 3 hr at room temperature. The resulting mixture was concentrated under vacuum. The resulting solution was diluted with 200 mL of EA. The pH value of the solution was adjusted to 8 with $NaHCO_3$ aqueous solution. The resulting solution was extracted with 2×500 mL of ethyl acetate and the organic layers combined and concentrated under vacuum. This resulted in 3.4 g (84%) of 5-bromo-3-(ethanesulfonyl)-2-[6-(trifluoromethyl)-1H-pyrrolo[3,2-b]pyridin-2-yl]pyridine as a light yellow solid.

Synthesis of 5-bromo-3-(ethanesulfonyl)-2-[4-ethyl-6-(trifluoromethyl)pyrrolo[3,2-b]pyridin-2-yl]pyridine

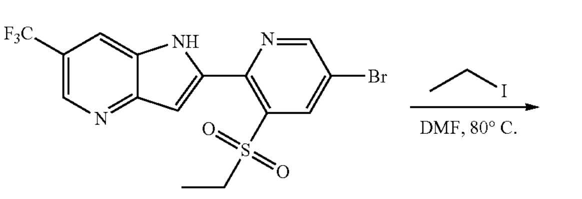

-continued

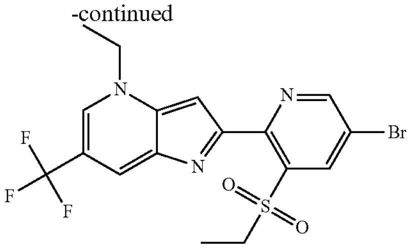

Into a 100-mL round-bottom flask purged and maintained with an inert atmosphere of nitrogen, was placed 5-bromo-3-(ethanesulfonyl)-2-[6-(trifluoromethyl)-1H-pyrrolo[3,2-b]pyridin-2-yl]pyridine (1.0 g, 2.3 mmol, 1.0 equiv), DMF (10 mL), ethyl iodide (11 g, 0.071 mmol, 0.03 equiv). The resulting solution was stirred for 2 hr at 80 degrees C. The resulting mixture was concentrated. The resulting solution was diluted with 200 ml of EA. The resulting mixture was washed with 2×100 ml of $H_2O$. The organic layer was combined and concentrated. The residue was applied onto a silica gel column with THF/PE (1/4). This resulted in 900 mg (85%) of 5-bromo-3-(ethanesulfonyl)-2-[4-ethyl-6-(trifluoromethyl)pyrrolo[3,2-b]pyridin-2-yl]pyridine as a yellow solid.

Synthesis of 5-bromo-3-(ethanesulfonyl)-2-[3-fluoro-6-(trifluoromethyl)-1H-pyrrolo[3,2-b]pyridin-2-yl]pyridine Synthesis of 5-bromo-2-[3-chloro-6-(trifluoromethyl)-1H-pyrrolo[3,2-b]pyridin-2-yl]-3-(ethanesulfonyl)pyridine

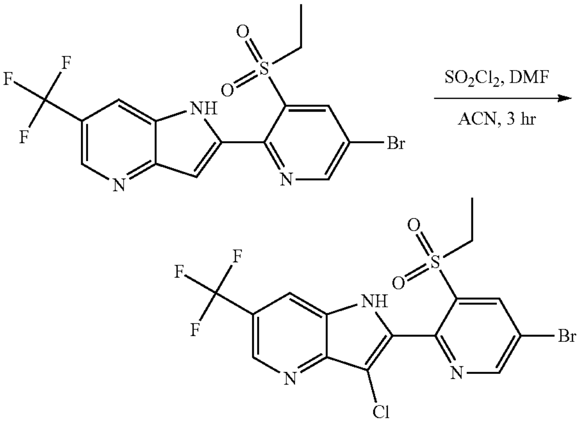

Into a 250-mL 3-necked round-bottom flask, was placed 5-bromo-3-(ethanesulfonyl)-2-[6-(trifluoromethyl)-1H-pyrrolo[3,2-b]pyridin-2-yl]pyridine (2.0 g, 4.6 mmol, 1.0 equiv), ACN (40 mL), DMF (0.01 mL). This was followed by the addition of $SO_2Cl_2$ (2.0 mL, 15 mmol, 5.4 equiv) dropwise with stirring at 0 degrees C. The resulting solution was stirred for 5 hr at room temperature. The resulting mixture was concentrated under vacuum. The resulting solution was diluted with 200 mL of EA. This was followed by the addition of 200 mL saturated solution of $NaHCO_3$ and $Na_2S_2O_3$. The mixture solution was stirred for 1 hr. The resulting solution was extracted with 2×300 mL of ethyl acetate. The residue was applied onto a silica gel column with THF/PE (1/4). This resulted in 1.3 g (60%) of 5-bromo-2-[3-chloro-6-(trifluoromethyl)-1H-pyrrolo[3,2-b]pyridin-2-yl]-3-(ethanesulfonyl)pyridine as a light yellow solid.

Synthesis of 5-bromo-3-(ethanesulfonyl)-2-[3-fluoro-6-(trifluoromethyl)-1H-pyrrolo[3,2-b]pyridin-2-yl]

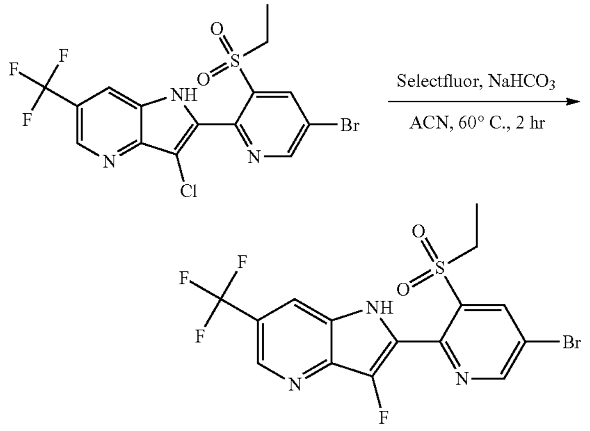

Into a 250-mL 3-necked round-bottom flask, was placed 5-bromo-2-[3-chloro-6-(trifluoromethyl)-1H-pyrrolo[3,2-b]pyridin-2-yl]-3-(ethanesulfonyl)pyridine (1.0 g, 2.1 mmol, 1.0 equiv), ACN (20 mL), $NaHCO_3$ (573 mg, 6.8 mmol, 3.2 equiv), Selectfluor®(2.26 g, 6.4 mmol, 3.0 equiv). The resulting solution was stirred for 2 hr at 60 degrees C. This was followed by the addition of $Na_2S_2O_3$ saturated solution (20 ml). This mixture solution was stirred for 1 hr at 60 degrees C. The resulting solution was extracted with 2×100 mL of ethyl acetate and the organic layers combined concentrated. The residue was applied onto a silica gel column with THF/PE (1/4). This resulted in 800 mg (83%) of 5-bromo-3-(ethanesulfonyl)-2-[3-fluoro-6-(trifluoromethyl)-1H-pyrrolo[3,2-b]pyridin-2-yl]pyridine as a pink solid.

Synthesis of 5-bromo-3-(ethanesulfonyl)-2-[4-ethyl-3-fluoro-6-(trifluoromethyl)-4H-pyrrolo[3,2-b]pyridin-2-yl]pyridine

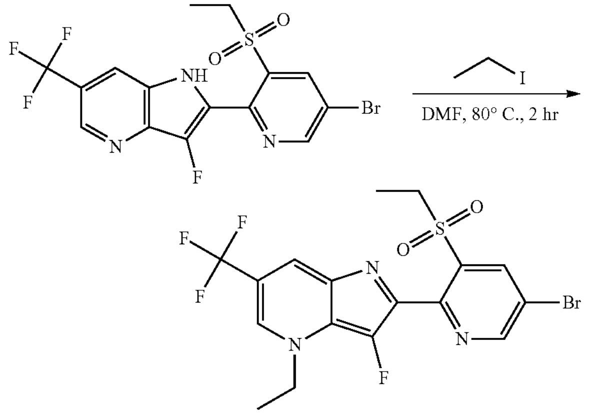

Into a 100-mL round-bottom flask purged and maintained with an inert atmosphere of nitrogen, was placed 5-bromo-3-(ethanesulfonyl)-2-[6-(trifluoromethyl)-1H-pyrrolo[3,2-b]pyridin-2-yl]pyridine (1.0 g, 2.3 mmol, 1.0 equiv), DMF (10 mL), ethyl iodide (11 g, 0.07 mmol, 0.03 equiv). The resulting solution was stirred for 2 hr at 80 degrees C. The resulting mixture was concentrated. The resulting solution was diluted with 200 ml of EA. The resulting mixture was washed with 2×100 ml of $H_2O$. The organic layer was combined and concentrated. The residue was applied onto a silica gel column with THF/PE (1/4). This resulted in 900 mg (85%) of 5-bromo-3-(ethanesulfonyl)-2-[4-ethyl-3-fluoro-6-(trifluoromethyl)-4H-pyrrolo[3,2-b]pyridin-2-yl]pyridine as a yellow solid.

Synthesis of 5-bromo-2-[4-(2,2-difluoroethyl)-6-(trifluoromethyl)pyrrolo[3,2-b]pyridin-2-yl]-3-(ethanesulfonyl)pyridine

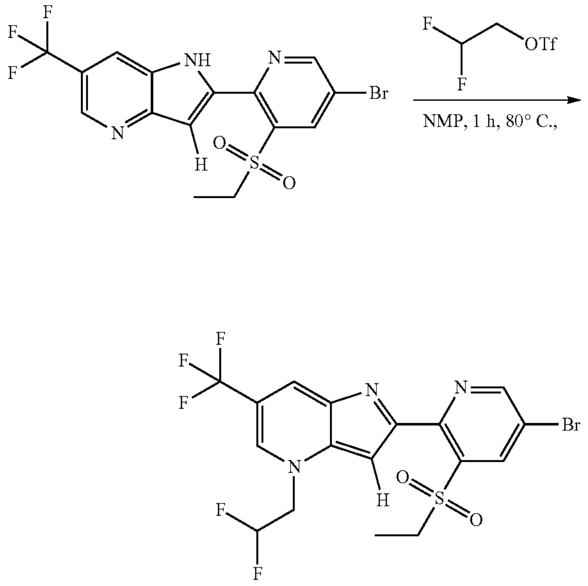 [SMILES: CCS(=O)(=O)c1cc(Br)cnc1-c1cc2ncc(C(F)(F)F)cc2[nH]1 ; O=S(=O)(OCC(F)F)C(F)(F)F ; CCS(=O)(=O)c1cc(Br)cnc1-c1cc2n(CC(F)F)cc(C(F)(F)F)cc-2n1]

Into a 8-mL round-bottom flask purged and maintained with an inert atmosphere of nitrogen, was placed 5-bromo-3-(ethanesulfonyl)-2-[6-(trifluoromethyl)-1H-pyrrolo[3,2-b]pyridin-2-yl]pyridine (100 mg, 0.2 mmol, 1.0 equiv), NMP (1 mL), 2,2-difluoroethyl trifluoromethanesulfonate (0.5 mL). The resulting solution was stirred for 1 hr at 80 degrees C. The reaction mixture was cooled to room temperature. The crude product was purified by Flash-Prep-HPLC with the following conditions (IntelFlash-1): Column, C18 silica gel; mobile phase, $CH_3CN:H_2O=0\%$ increasing to $CH_3CN:H_2O=40\%$ within 20 min. This resulted in 100 mg (87%) of 5-bromo-2-[4-(2,2-difluoroethyl)-6-(trifluoromethyl)pyrrolo[3,2-b]pyridin-2-yl]-3-(ethanesulfonyl)pyridine as a yellow solid.

Synthesis of 5-bromo-3-(ethanesulfonyl)-2-[1-ethyl-6-(trifluoromethyl)imidazo[4,5-b]pyridin-2-yl]pyridine Synthesis of 5-bromo-3-(ethanesulfinyl)-2-[1-ethyl-6-(trifluoromethyl)imidazo[4,5-b]pyridin-2-yl]pyridine

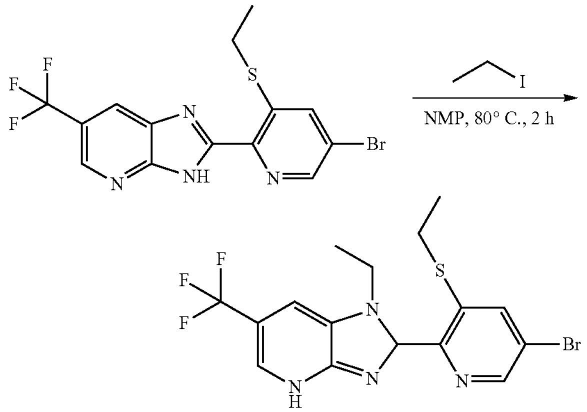

To a stirred solution/mixture of 5-bromo-3-(ethylsulfanyl)-2-[6-(trifluoromethyl)-3H-imidazo[4,5-b]pyridin-2-yl] pyridine (400 mg, 1.0 mmol, 1.00 equiv) in NMP was added ethyl iodide (773 mg, 5.0 mmol, 5 equiv). The resulting mixture was stirred for 2 h at 80 degrees C. The resulting mixture was diluted with water (20 mL). The resulting mixture was extracted with EtOAc (3×50 mL). The combined organic layers were washed with brine (3×20 mL), dried over anhydrous $Na_2SO_4$. After filtration, the filtrate was concentrated under reduced pressure. The crude product was purified by Prep-HPLC with the following conditions (Prep-HPLC-003): Sunfire Prep C18 OBD Column, 50*250 mm 5 μm 10 nm; mobile phase, Water (0.05% TFA) and ACN (20% Phase B up to 70% in 7 min); Detector, UV 254 nm. This resulted in 100 mg (23%) of 5-bromo-3-(ethanesulfinyl)-2-[1-ethyl-6-(trifluoromethyl)imidazo[4,5-b]pyridin-2-yl]pyridine as yellow oil.

Synthesis of 5-bromo-3-(ethanesulfonyl)-2-[1-ethyl-6-(trifluoromethyl)imidazo[4,5-b]pyridin-2-yl]pyridine

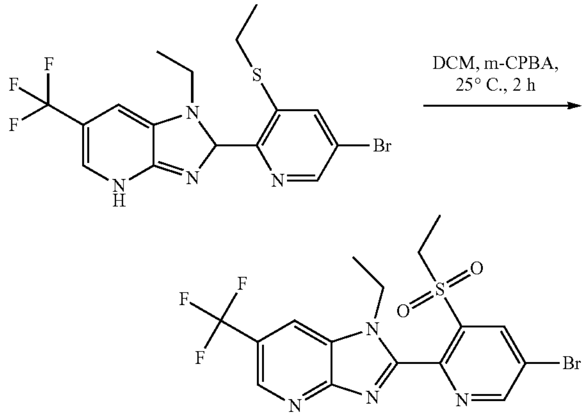

Into a 50 mL round-bottom flask were added 5-bromo-2-[L I-ethyl-6-(trifluoromethyl)imidazo[4,5-b]pyridin-2-yl]-3-(ethylsulfanyl)pyridine (90 mg, 0.2 mmol, 1.0 equiv) in DCM (5 mL) and m-CPBA (90 mg, 0.5 mmol, 2.5 equiv) at 25 degree C. The resulting mixture was stirred for 2 h at 25 degree C. The resulting mixture was diluted with water (5 mL). The resulting mixture was extracted with DCM (3×20 mL). The combined organic layers were washed with brine (3×10 mL), dried over anhydrous $Na_2SO_4$. After filtration, the filtrate was concentrated under reduced pressure. The residue was purified by silica gel column chromatography, eluted with PE/EA (4:1) to afford 5-bromo-3-(ethanesulfonyl)-2-[1-ethyl-6-(trifluoromethyl)imidazo[4,5-b]pyridin-2-yl]pyridine (50 mg, 52%) as a white solid.

Synthesis of 5-bromo-3-(ethanesulfonyl)-2-[3-ethyl-6-(trifluoromethyl)imidazo[4,5-b]pyridin-2-yl]pyridine Synthesis of 5-bromo-3-(ethanesulfinyl)-2-[1-ethyl-6-(trifluoromethyl)imidazo[4,5-b]pyridin-2-yl]pyridine

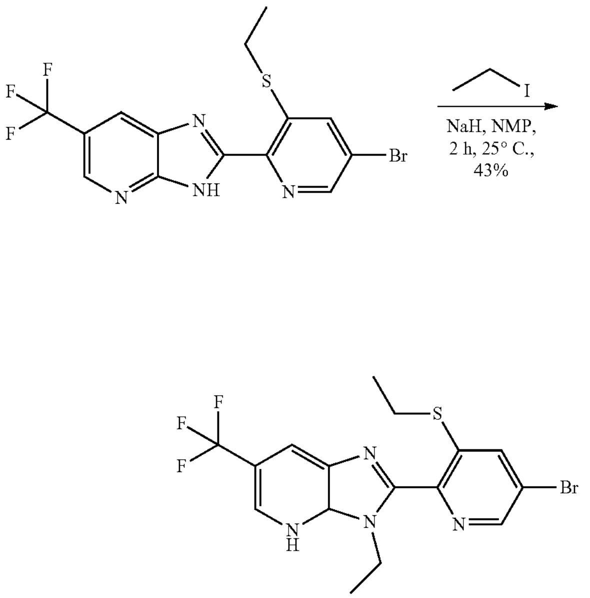

Into a 50-mL round-bottom flask, was placed 5-bromo-3-(ethylsulfanyl)-2-[6-(trifluoromethyl)-3H-imidazo[4,5-b] pyridin-2-yl]pyridine (50 mg, 0.1 mmol, 1.0 equiv), NMP (2 mL), NaH (8.9 mg, 0.4 mmol, 3.0 equiv). The resulting solution was stirred for 30 min at 25 degrees C. Then ethyl iodide (0.3 mL, 0.002 mmol, 0.02 equiv) was added. The resulting solution was further stirred for 2 h at 25 degrees C. The reaction was then quenched by the addition of 1 mL of water. The resulting mixture was concentrated. The crude product was purified by Prep-HPLC with the following conditions (Prep-HPLC-003): Sunfire Prep C18 OBD Column, 50*250 mm 5 μm 10 nm; mobile phase, Water (0.05% TFA) and ACN (20% Phase B up to 70% in 7 min); Detector, UV 254 nm. This resulted in 50 mg (45%) of 5-bromo-3-(ethanesulfinyl)-2-[1-ethyl-6-(trifluoromethyl)imidazo[4,5-b]pyridin-2-yl]pyridine as yellow oil.

Synthesis of 5-bromo-3-(ethanesulfonyl)-2-[3-ethyl-6-(trifluoromethyl)imidazo[4,5-b]pyridin-2-yl]pyridine

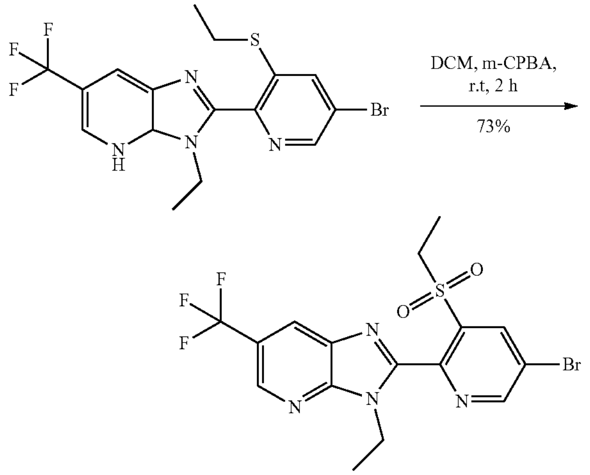

Into a 50-mL round-bottom flask, was placed 5-bromo-2-[3-ethyl-6-(trifluoromethyl)imidazo[4,5-b]pyridin-2-yl]-3-(ethylsulfanyl)pyridine (23 mg, 0.05 mmol, 1.00 equiv), DCM (2 mL), m-CPBA (26 mg, 0.15 mmol, 2.8 equiv). The resulting solution was stirred for 2 hr at 25 degrees C. The resulting mixture was concentrated. The residue was applied onto a silica gel column with ethyl acetate/petroleum ether (1:2). This resulted in 18 mg (73%) of 5-bromo-3-(ethanesulfonyl)-2-[3-ethyl-6-(trifluoromethyl)imidazo[4,5-b]pyridin-2-yl]pyridine as a white solid.

Synthesis of 11-[5-bromo-3-(ethanesulfonyl)pyridin-2-yl]-5,5-difluoro-12-methyl-4,6-dioxa-10,12-diazatricyclo[7.3.0.0/\[3,7]]dodeca-1,3(7),8,10-tetraene Synthesis of 2,2-difluoro-1,3-benzodioxol-5-amine

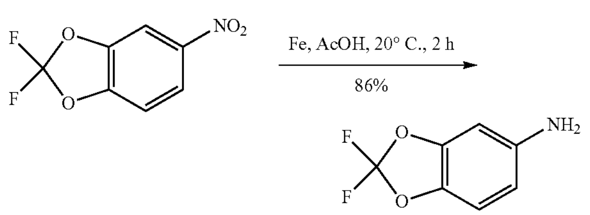

Into a 250-mL round-bottom flask, was placed 2,2-difluoro-5-nitro-1,3-benzodioxole (10.0 g, 49 mmol, 1.0 equiv), AcOH (100 mL), Fe (8.3 g, 148 mmol, 3.0 equiv). The resulting solution was stirred for 2 hr at 20 degrees C. The resulting mixture was concentrated. The resulting solution was diluted with 200 mL of $H_2O$. The pH value of the solution was adjusted to 9 with $Na_2CO_3$ (Sat.). The resulting solution was extracted with 3×100 mL of ethyl acetate. The organic phase dried over anhydrous sodium sulfate and concentrated. The residue was applied onto a silica gel column with ethyl acetate/petroleum ether (1/1). The collected fractions were combined and concentrated. This resulted in 8.1 g (86%) of 2,2-difluoro-1,3-benzodioxol-5-amine as yellow oil.

Synthesis of N-(2,2-difluoro-1,3-benzodioxol-5-yl)acetamide

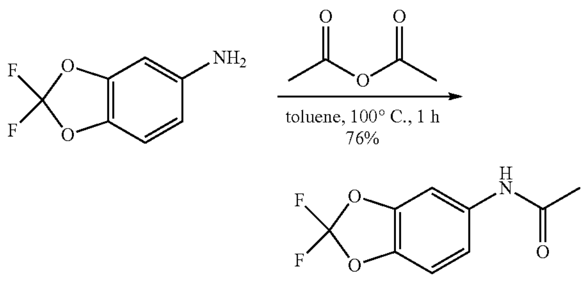

Into a 250-mL round-bottom flask, was placed 2,2-difluoro-1,3-benzodioxol-5-amine (7.6 g, 44 mmol, 1.0 equiv), Toluene (80 mL), acetic anhydride (6.7 g, 66 mmol, 1.5 equiv). The resulting solution was stirred for 1 hr at 100 degrees C. in an oil bath. The resulting mixture was concentrated. The crude product was purified by re-crystallization from PE. This resulted in 8.23 g (76%) of N-(2,2-difluoro-1,3-benzodioxol-5-yl)acetamide as a white solid.

Synthesis of N-(2,2-difluoro-6-nitro-1,3-benzodioxol-5-yl)acetamide

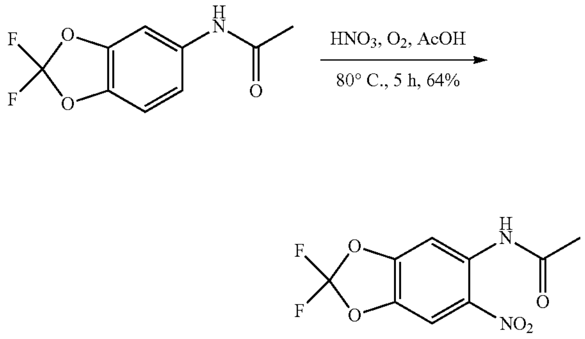

Into a 50-mL round-bottom flask, purged and maintained with an inert atmosphere of oxygen, placed N-(2,2-difluoro-1,3-benzodioxol-5-yl)acetamide (7.0 g, 33 mmol, 1.0 equiv), AcOH (70 mL), $HNO_3$ (7.2 g, 114 mmol, 3.5 equiv). The resulting solution was stirred for 5 hr at 80 degrees C. in an oil bath. The reaction mixture was cooled. The resulting mixture was concentrated. The resulting solution was diluted with 500 mL of EA. The resulting mixture was washed with 3×250 mL of $Na_2CO_3$ (aq, 2M). The organic phase was dried over anhydrous sodium sulfate and concentrated. The residue was applied onto a silica gel column with ethyl acetate/petroleum ether (1/5). The collected fractions were combined and concentrated. This resulted in 5.4 g (64%) of N-(2,2-difluoro-6-nitro-1,3-benzodioxol-5-yl) acetamide as a yellow solid.

Synthesis of N-(2,2-difluoro-6-nitro-1,3-benzodioxol-5-yl)-N-methylacetamide

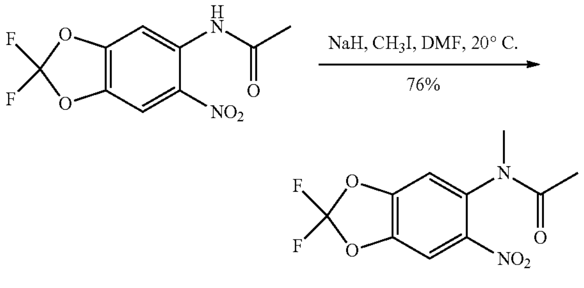

Into a 50-mL 3-necked round-bottom flask, was placed N-(2,2-difluoro-6-nitro-1,3-benzodioxol-5-yl)acetamide (5.00 g, 19.219 mmol, 1.00 equiv), DMF (20.00 mL), 0 degrees C. was added NaH (1.15 g, 29 mmol, 1.5 equiv, 60%). The resulting solution was stirred for 10 min at 20 degrees C. Then methyl iodide (4.1 g, 29 mmol, 1.5 equiv) was added at 0 degrees C. The resulting solution was stirred for 1 hr at 20 degrees C. The reaction was then quenched by the addition of 30 mL of water and diluted with 600 mL of EA. The resulting mixture was washed with 3×300 mL of water. The organic phase was dried over anhydrous sodium sulfate and concentrated. The residue was applied onto a silica gel column with ethyl acetate/petroleum ether (1/2). The collected fractions were combined and concentrated. This resulted in 4.0 g (76%) of N-(2,2-difluoro-6-nitro-1,3-benzodioxol-5-yl)-N-methylacetamide as a yellow solid.

Synthesis of 2,2-difluoro-N-methyl-6-nitro-1,3-benzodioxol-5-amine

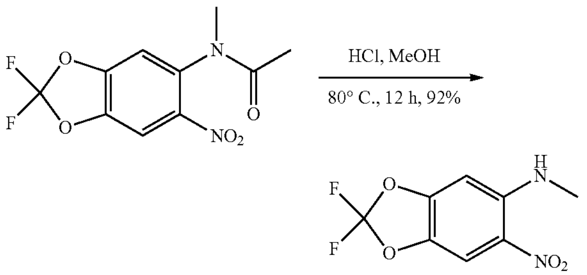

Into a 50-mL round-bottom flask, was placed N-(2,2-difluoro-6-nitro-1,3-benzodioxol-5-yl)-N-methylacetamide (3.6 g, 13 mmol, 1.0 equiv), MeOH (30 mL), HCl (10 mL). The resulting solution was stirred for 12 hr at 80 degrees C. in an oil bath. The reaction mixture was cooled. The resulting mixture was concentrated. The resulting solution was diluted with 500 mL of EA. The resulting mixture was washed with 3×250 mL of $Na_2CO_3$ (aq, 2M). The organic phase was dried over anhydrous sodium sulfate and concentrated. The residue was applied onto a silica gel column with ethyl acetate/petroleum ether (1/4). The collected fractions were combined and concentrated. This resulted in 2.8 g (92%) of 2,2-difluoro-N-methyl-6-nitro-1,3-benzodioxol-5-amine as a yellow solid.

Synthesis of 2,2-difluoro-N5-methyl-1,3-benzodioxole-5,6-diamine

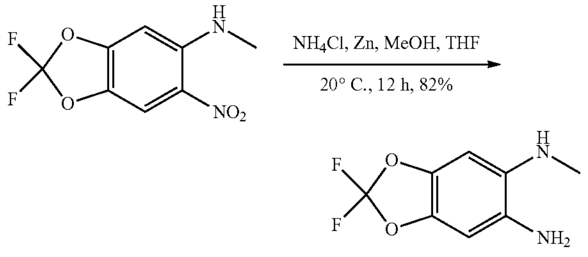

Into a 250-mL round-bottom flask, was placed 2,2-difluoro-N-methyl-6-nitro-1,3-benzodioxol-5-amine (2.8 g, 12. mmol, 1.0 equiv), THF (60 mL), MeOH (60 mL), Zn (5.5 g, 84 mmol, 7.0 equiv), $NH_4Cl$ (6.5 g, 120 mmol, 10 equiv). The resulting solution was stirred for 12 hr at 20 degrees C. The solids were filtered out. The filtrate was concentrated. The residue was applied onto a silica gel column with ethyl acetate/petroleum ether (1/2). The collected fractions were combined and concentrated. This resulted in 2.0 g (82%) of 2,2-difluoro-N5-methyl-1,3-benzodioxole-5,6-diamine as a brown solid.

Synthesis of 5-bromo-N-[2,2-difluoro-6-(methylamino)-1,3-benzodioxol-5-yl]-3-(ethylsulfanyl)pyridine-2-carboxamide

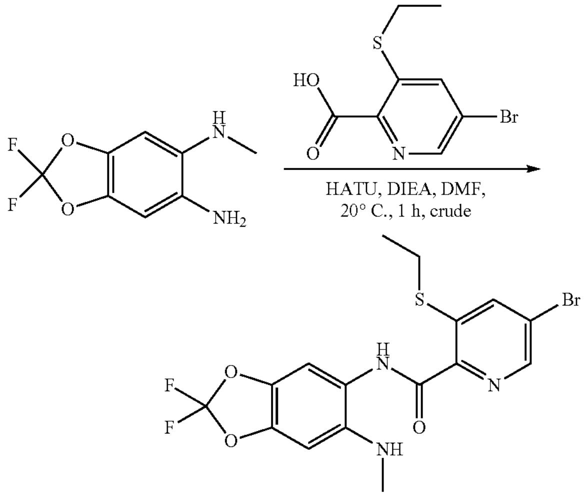

Into a 50-mL round-bottom flask, was placed 2,2-difluoro-N5-methyl-1,3-benzodioxole-5,6-diamine (350 mg, 1.7 mmol, 1.0 equiv), 5-bromo-3-(ethylsulfanyl)pyridine-2-carboxylic acid (454 mg, 1.7 mmol, 1.0 equiv), DCM (10 mL), DIEA (448 mg, 3.5 mmol, 2.0 equiv), HATU (790 mg, 2.1 mmol, 1.2 equiv). The resulting solution was stirred for 1 hr at 20 degrees C. The resulting solution was diluted with 50 mL of EA. The resulting mixture was washed with 3×20 mL of $H_2O$ and 1×20 mL of brine. The organic phase was dried over anhydrous sodium sulfate and concentrated. This resulted in 1.75 g of 5-bromo-N-[2,2-difluoro-6-(methylamino)-1,3-benzodioxol-5-yl]-3-(ethylsulfanyl)pyridine-2-carboxamide as black oil.

Synthesis of 11-[5-bromo-3-(ethylsulfanyl)pyridin-2-yl]-5,5-difluoro-12-methyl-4,6-dioxa-10,12-diazatricyclo[7.3.0.0/\[3,71]dodeca-1,3(7),8,10-tetraene

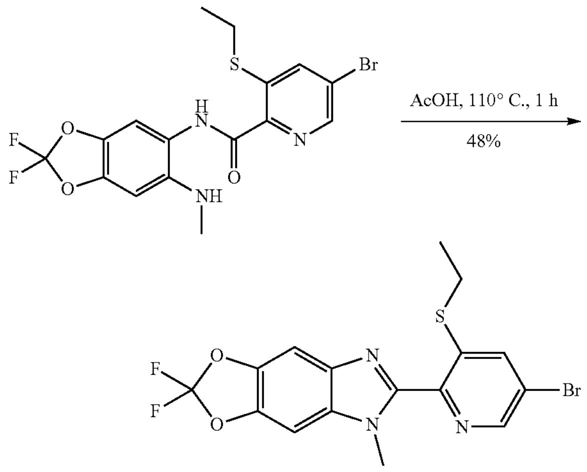

Into a 50-mL round-bottom flask, was placed 5-bromo-N-[2,2-difluoro-6-(methylamino)-1,3-benzodioxol-5-yl]-3-(ethylsulfanyl)pyridine-2-carboxamide (1.75 g, 3.9 mmol, 1.00 equiv), AcOH (20 mL). The resulting solution was stirred for 1 hr at 110 degrees C. The mixture was concentrated. The residue was applied onto a silica gel column with ethyl acetate/petroleum ether (1/4). The collected fractions were combined and concentrated. This resulted in 810 mg (48%) of 11-[5-bromo-3-(ethylsulfanyl)pyridin-2-yl]-5,5-difluoro-12-methyl-4,6-dioxa-10,12-diazatricyclo[7.3.0.0/\[3,7]]dodeca-1,3(7),8,10-tetraene as light yellow oil.

Synthesis of 11-[5-bromo-3-(ethanesulfonyl)pyridin-2-yl]-5,5-difluoro-12-methyl-4,6-dioxa-10,12-diazatricyclo[7.3.0.0/\[3,7]]dodeca-1,3(7),8,10-tetraene

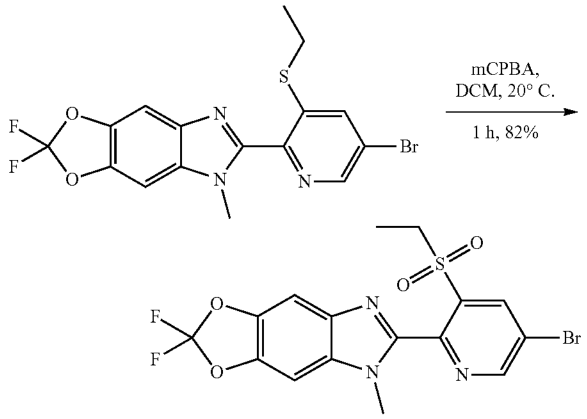

Into a 50-mL round-bottom flask, was placed 11-[5-bromo-3-(ethylsulfanyl)pyridin-2-yl]-5,5-difluoro-12-methyl-4,6-dioxa-10,12-diazatricyclo[7.3.0.0/\[3,7]]dodeca-1,3(7),8,10-tetraene (700 mg, 1.6 mmol, 1.0 equiv), DCM (14 mL), m-CPBA (564 mg, 3.3 mmol, 2.0 equiv). The resulting solution was stirred for 1 hr at 20 degrees C. The resulting mixture was concentrated. The residue was applied onto a silica gel column with ethyl acetate/petroleum ether (1/3). The collected fractions were combined and concentrated. This resulted in 705 mg (82%) of 11-[5-bromo-3-(ethanesulfonyl)pyridin-2-yl]-5,5-difluoro-12-methyl-4,6-dioxa-10,12-diazatricyclo[7.3.0.0/\[3,7]]dodeca-1,3(7),8,10-tetraene as a white solid.

Synthesis of 2-[5-bromo-3-(ethanesulfonyl)pyridin-2-yl]-5-cyclopropyl-3-methyl-6-(trifluoromethyl) imidazo[4,5-c]pyridin-4-one Synthesis of N-[2-oxo-6-(trifluoromethyl)pyran-3-yl]benzamide

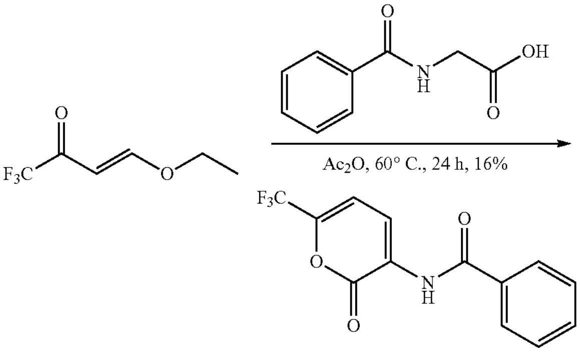

Into a 1000-mL round-bottom flask, was placed (3E)-4-ethoxy-1,1,1-trifluorobut-3-en-2-one (94 g, 559.1 mmol, 1.0 equiv), hippuric acid (100 g, 559 mmol, 1.0 equiv), $Ac_2O$ (50 mL). The resulting solution was stirred for 24 hr at 60 degrees C. The resulting mixture was concentrated. The crude product was re-crystallized from PE:EA in the ratio of 3:1. This resulted in 25 g (16%) of N-[2-oxo-6-(trifluoromethyl)pyran-3-yl]benzamide as a red solid.

Synthesis of N-[1-cyclopropyl-6-hydroxy-2-oxo-6-(trifluoromethyl)-5H-pyridin-3-yl]benzamide

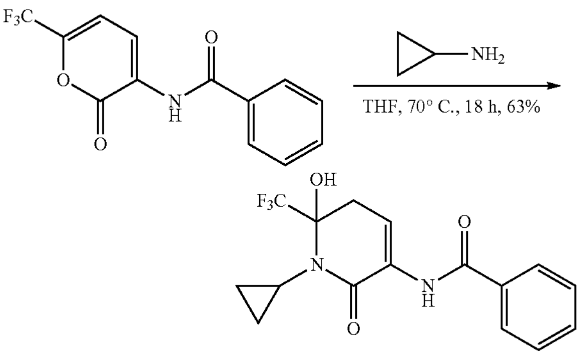

Into a 250-mL pressure tank reactor, was placed N-[2-oxo-6-(trifluoromethyl)pyran-3-yl]benzamide (21 g, 74 mmol, 1.0 equiv), aminocyclopropane (5.08 g, 89 mmol, 1.2 equiv), THE (200 mL). The resulting solution was stirred for 18 hr at 70 degrees C. The resulting mixture was concentrated. The residue was applied onto a silica gel column with ethyl acetate/petroleum ether (1:2). This resulted in 16 g (63%) of N-[1-cyclopropyl-6-hydroxy-2-oxo-6-(trifluoromethyl)-5H-pyridin-3-yl]benzamide as a yellow solid.

Synthesis of 3-amino-1-cyclopropyl-6-(trifluoromethyl)pyridin-2-one

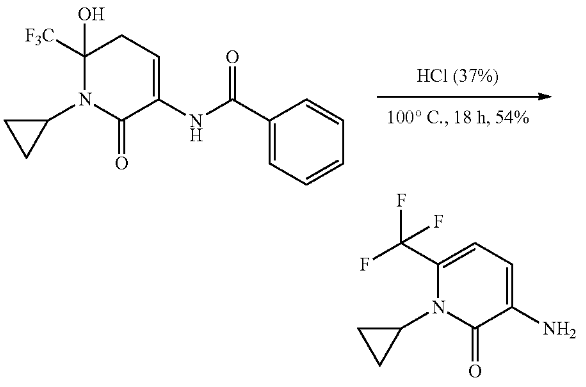

Into a 250-mL round-bottom flask, was placed N-[1-cyclopropyl-6-hydroxy-2-oxo-6-(trifluoromethyl)-5H-pyridin-3-yl]benzamide (14 g, 41 mmol, 1.0 equiv), HCl (140 mL, 37%). The resulting solution was stirred for 18 hr at 100 degrees C. The resulting solution was diluted with 150 mL of $H_2O$. The solids were filtered out. The resulting solution was extracted with 3×200 mL of ethyl acetate and the organic layers combined. The resulting mixture was washed with 2×200 mL of brine. The mixture was dried over anhydrous sodium sulfate and concentrated. This resulted in 4.8 g (53%) of 3-amino-1-cyclopropyl-6-(trifluoromethyl)pyridin-2-one as a grey solid.

Synthesis of 1-cyclopropyl-N-methyl-2-methylidene-6-(trifluoromethyl)pyridin-3-amine

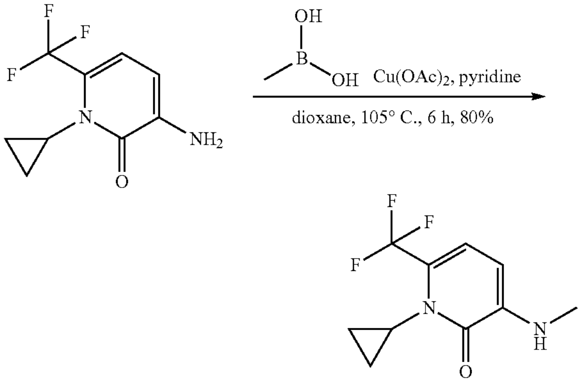

Into a 250-mL 3-necked round-bottom flask, was placed 1-cyclopropyl-2-methylidene-6-(trifluoromethyl)pyridin-3-amine (3.5 g, 16 mmol, 1.0 equiv), $Cu(OAc)_2$ (7.3 g, 40 mmol, 2.5 equiv), pyridine (4.4 g, 56 mmol, 3.5 equiv), dioxane (200 mL), methylboronic acid (2.4 g, 40 mmol, 2.5 equiv). The resulting solution was stirred for 20 min at room temperature. The resulting solution was allowed to react, with stirring, for an additional 6 hr at 105 degrees C. The solids were filtered out. The filtrate was concentrated. The residue was applied onto a silica gel column with ethyl acetate/petroleum ether (1:2). This resulted in 3.0 g (80%) of 1-cyclopropyl-N-methyl-2-methylidene-6-(trifluoromethyl)pyridin-3-amine as a yellow solid.

Synthesis of 1-cyclopropyl-3-(methylamino)-4-nitro-6-(trifluoromethyl)pyridin-2-one

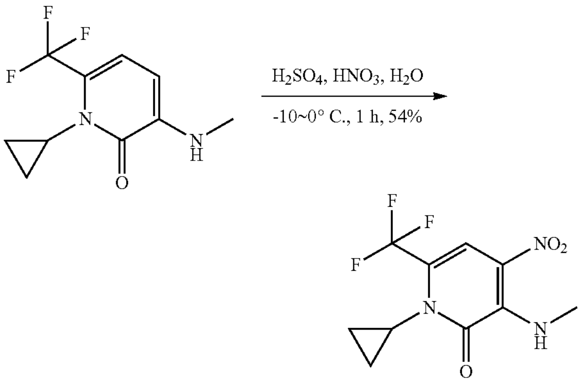

Into a 100-mL 3-necked round-bottom flask, was placed 1-cyclopropyl-3-(methylamino)-6-(trifluoromethyl)pyridin-2-one (1.85 g, 8.0 mmol, 1.0 equiv), $H_2SO_4$ (15.4 mL). This was followed by the addition of $H_2O$ (6.0 mL) dropwise with stirring at 0 degrees. To this was added $HNO_3$ (0.4 mL,) dropwise with stirring at −10 degrees C. The resulting solution was stirred for 1 hr at −10-0 degrees C. The reaction was then quenched by the addition of 150 mL of water/ice. The solids were collected by filtration. The solid was dried in an oven under reduced pressure. This resulted in 1.2 g (54%) of 1-cyclopropyl-3-(methylamino)-4-nitro-6-(trifluoromethyl)pyridin-2-one as a yellow solid.

Synthesis of 4-amino-1-cyclopropyl-3-(methylamino)-6-(trifluoromethyl)pyridin-2-one

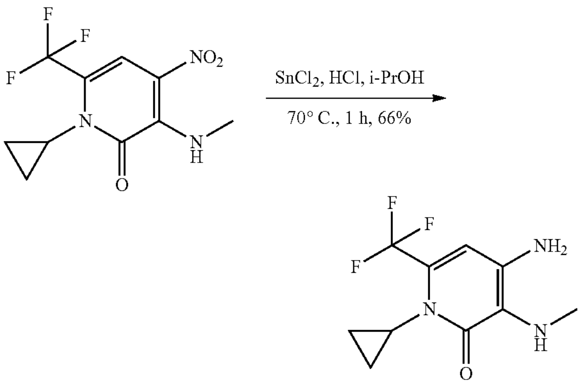

Into a 250-mL round-bottom flask. was placed 1-cyclopropyl-3-(methylamino)-4-nitro-6-(trifluoromethyl)pyridin-2-one (1.7 g. 6.1 mmol, 1.0 equiv). isopropyl alcohol (50 mL), $SnCl_2$ (4.2 g. 22.2 mmol, 3.6 equiv), HCl (5 mL, 37%). The resulting solution was stirred for 1 hr at 70 degrees C. The reaction was then quenched by the addition of 200 mL of water/ice. The pH value of the solution was adjusted to 12 with NaOH (6 mol/L). The resulting solution was extracted with 3×100 mL of ethyl acetate and the organic layers combined. The resulting mixture was washed with 2×100 mL of brine. The mixture was dried over anhydrous sodium sulfate. This resulted in 1 g (66%) of 4-amino-1-cyclopropyl-3-(methylamino)-6-(trifluoromethyl)pyridin-2-one as a yellow solid.

Synthesis of 5-bromo-N-[l-cyclopropyl-3-(methylamino)-2-oxo-6-(trifluoromethyl)pyridin-4-yl]-3-(ethylsulfanyl)pyridine-2-carboxamide

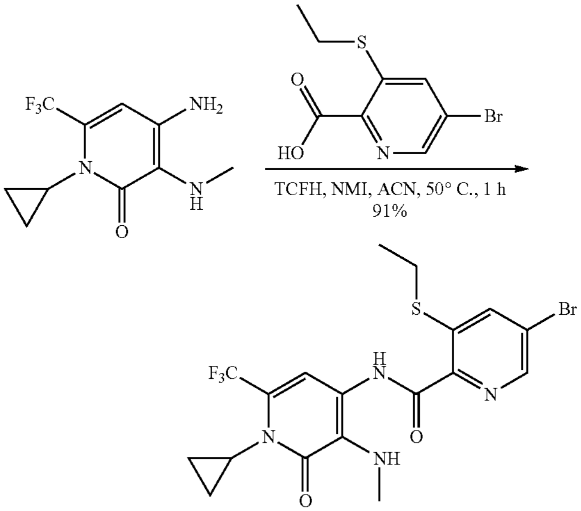

Into a 250-mL round-bottom flask, was placed 5-bromo-3-(ethylsulfanyl)pyridine-2-carboxylic acid (424 mg, 1.6 mmol, 1.0 equiv), ACN (40 ml), TCFH (500 mg, 1.8 mmol, 1.1 equiv). NMI (465 mg, 5.7 mmol, 3.5 equiv), 4-amino-1-cyclopropyl-3-(methylamino)-6-(trifluoromethyl)pyridin-2-one (400 mg, 1.6 mmol, 1.0 equiv). The resulting solution was stirred for 1 hr at 50 degrees C. The resulting mixture was concentrated. The residue was solvent with 50 ml of EA. The organic phase was washed with 3×20 mL of water and 1×20 mL of brine. The organic phase was dried over anhydrous sodium sulfate and concentrated. This resulted in 0.72 g (91%) of 5-bromo-N-[1-cyclopropyl-3-(methylamino)-2-oxo-6-(trifluoromethyl)pyridin-4-yl]-3-(ethylsulfanyl)pyridine-2-carboxamide as a yellow solid.

Synthesis of 2-[5-bromo-3-(ethylsulfanyl)pyridin-2-yl]-5-cyclopropyl-3-methyl-6-(trifluoromethyl)imidazo[4,5-c]pyridin-4-one

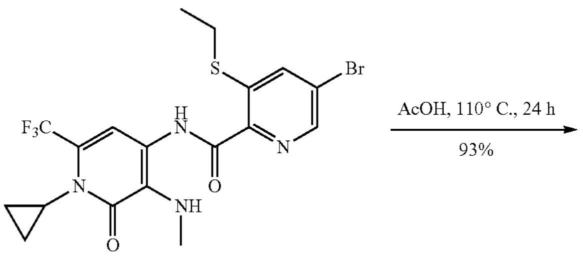

-continued

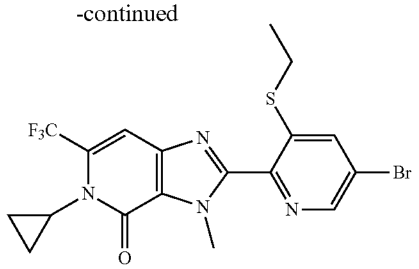

Into a 250-mL round-bottom flask, was placed 5-bromo-N-[1-cyclopropyl-3-(methylamino)-2-oxo-6-(trifluoromethyl)pyridin-4-yl]-3-(ethylsulfanyl)pyridine-2-carboxamide (0.67 g, 1.4 mmol, 1.0 equiv), AcOH (35.00 mL). The resulting solution was stirred for 24 hr at 110 degrees C. The reaction mixture was cooled to room temperature with a water/ice bath. The reaction was poured onto 200 mL of saturated aqueous $NaHCO_3$. The resulting solution was extracted with 3×50 mL of ethyl acetate and the organic layers combined. The organic layer was washed with 1×50 ml of brine. The organic phase was dried over anhydrous sodium sulfate and concentrated. The residue was applied onto a silica gel column with ethyl acetate/petroleum ether (1:4). This resulted in 0.60 g (93%) of 2-[5-bromo-3-(ethylsulfanyl)pyridin-2-yl]-5-cyclopropyl-3-methyl-6-(trifluoromethyl)imidazo[4,5-c]pyridin-4-one as a light yellow solid.

Synthesis of 2-[5-bromo-3-(ethanesulfonyl)pyridin-2-yl]-5-cyclopropyl-3-methyl-6-(trifluoromethyl)imidazo[4,5-c]pyridin-4-one

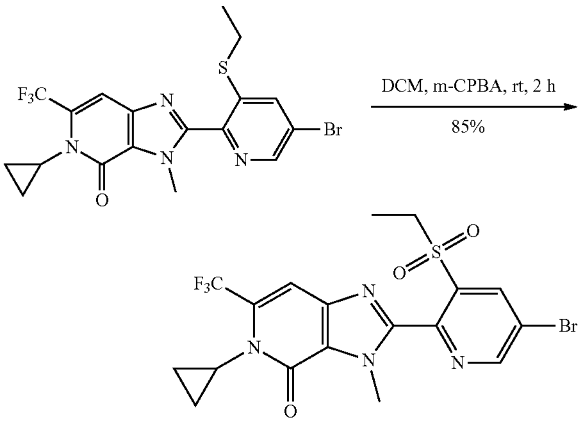

Into a 50-mL round-bottom flask, was placed 2-[5-bromo-3-(ethylsulfanyl)pyridin-2-yl]-5-cyclopropyl-3-methyl-6-(trifluoromethyl)imidazo[4,5-c]pyridin-4-one (0.55 g, 1.2 mmol, 1.0 equiv), DCM (11.00 mL), m-CPBA (0.4 g, 2.3 mmol, 2.0 equiv). The resulting solution was stirred for 2 hr at room temperature. The resulting mixture was washed with 1×20 ml of $NaHCO_3$ (sat.) and 1×20 mL of brine. The organic layer was dried over anhydrous sodium sulfate and concentrated. The residue was applied onto a silica gel column with ethyl acetate/petroleum ether (1:1). This resulted in 0.5 g (85%) of 2-[5-bromo-3-(ethanesulfonyl)pyridin-2-yl]-5-cyclopropyl-3-methyl-6-(trifluoromethyl)imidazo[4,5-c]pyridin-4-one as a white solid.

Synthesis of 6-(trifluoromethyl)-2H-pyrazolo[4,3-b]pyridine

Synthesis of 2-methyl-3-nitro-5-(trifluoromethyl)pyridine

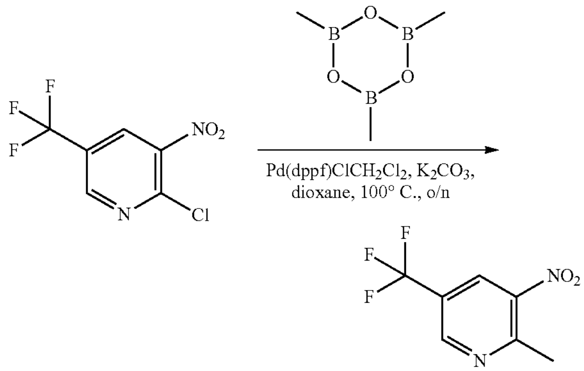

To a stirred solution/mixture of 2-chloro-3-nitro-5-(trifluoromethyl)pyridine (5 g, 22 mmol, 1.0 equiv) and trimethyl-1,3,5,2,4,6-trioxatriborinane (8.3 g, 66 mmol, 3 equiv) in dioxane was added Pd(dppf)$Cl_2$·$CH_2Cl_2$ (1.8 g, 2.2 mmol, 0.1 equiv) and $K_2CO_3$ (6.1 g, 44 mmol, 2 equiv).The resulting mixture was stirred for overnight at 100 degrees C. under nitrogen atmosphere. The resulting mixture was filtered, the filter cake was washed with ethyl acetate (2×50 mL). The filtrate was concentrated under reduced pressure. The residue was purified by silica gel column chromatography, eluted with PE/EA (10:1) to afford 2-methyl-3-nitro-5-(trifluoromethyl)pyridine (2.3 g, 51%) as a red oil.

Synthesis of 2-methyl-5-(trifluoromethyl)pyridin-3-amine

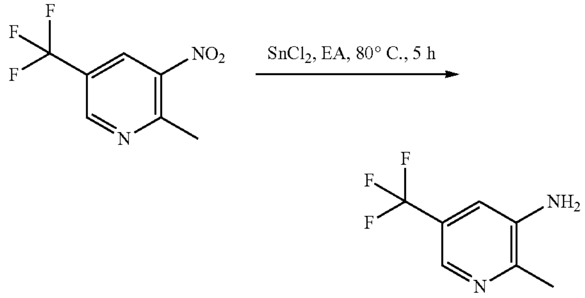

To a stirred solution/mixture of 2-methyl-3-nitro-5-(trifluoromethyl)pyridine (2 g, 9.7 mmol, 1.0 equiv) in EtOAc was added $SnCl_2$ (18.4 g, 97 mmol, 10 equiv). The resulting mixture was stirred for 5 h at 80 degrees C. The reaction was quenched by the addition of sat. $NaHCO_3$ (aq.) (50 mL). The resulting mixture was extracted with EtOAc (3×100 mL). The combined organic layers were washed with brine (2×100 mL), dried over anhydrous $Na_2SO_4$. After filtration, the filtrate was concentrated under reduced pressure. The residue was purified by silica gel column chromatography, eluted with PE/EA (1:1). The residue was purified by reverse flash chromatography with the following conditions: column, silica gel; mobile phase, MeCN in water, 40% to 50% gradient in 10 min; detector, UV 254 nm. to afford 2-methyl-5-(trifluoromethyl)pyridin-3-amine (960 mg, 56%) as a yellow solid.

Synthesis of 6-(trifluoromethyl)-2H-pyrazolo[4,3-b]pyridine

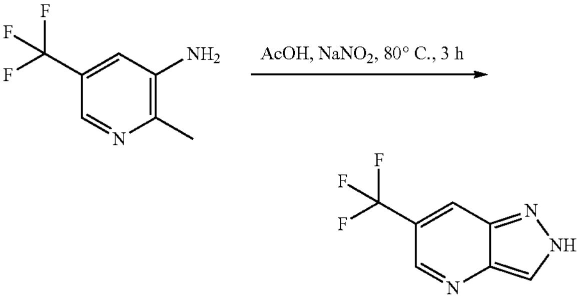

To a stirred solution/mixture of 2-methyl-5-(trifluoromethyl)pyridin-3-amine (910 mg, 5.2 mmol, 1.0 equiv) in AcOH was added $NaNO_2$ (428 mg, 6.2 mmol, 1.2 equiv) dropwise. The resulting mixture was stirred for 2 h at 80 degrees C. The resulting mixture was diluted with DCM (50 mL). The resulting mixture was washed with 2×20 mL of aq·$NaHCO_3$. The organic phase was collected and concentrated under reduced pressure. The crude product was purified by Flash-Prep-HPLC with the following conditions (IntelFlash-1): Column C18, silica gel; mobile phase, ACN/$H_2O$=20%-70%; Detector 254 nm. This resulted in 450 mg (47%) of 6-(trifluoromethyl)-2H-pyrazolo[4,3-b]pyridine as a brown solid.

Synthesis of 5-bromo-3-(ethanesulfonyl)-2-[6-(trifluoromethyl)pyrazolo[4,3-c]pyridin-2-yl]pyridine Synthesis of 4-chloro-6-(trifluoromethyl)pyridine-3-carboxylic acid

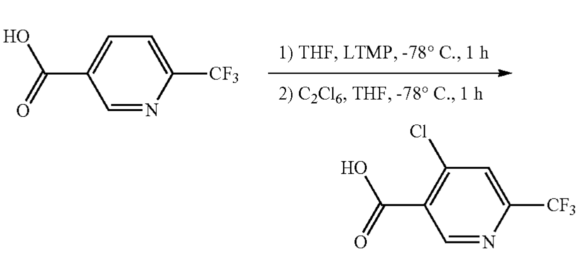

Into a 1000-mL 3-necked round-bottom flask, was placed lithium tetramethylpiperidide (58 g, 392 mmol, 2.5 equiv), cooled to −78 degrees C. To the solution was added for dropwise 6-(trifluoromethyl)pyridine-3-carboxylic acid (30 g, 157 mmol, 1.0 equiv) in THF (150 mL) at −78 degrees C. The resulting solution was stirred for 1 hr at −78 degrees C. To the solution was added for dropwise $C_2Cl_6$ (56 g, 235 mmol, 1.5 equiv) in THF (150 mL) at −78 degrees C. The resulting solution was stirred for 1 hr at −78 degrees C. The mixture was wormed to room temperature. The pH value of the solution was adjusted to 3 with HCl (1 mol/L). The resulting solution was extracted with 2×200 mL of ethyl acetate and the organic layers combined. The resulting mixture was washed with 1×300 mL of brine. The resulting EA mixture was concentrated. The residue was applied onto a silica gel column with ethyl acetate/petroleum ether (1; 1). This resulted in 17.8 g (37%) of 4-chloro-6-(trifluoromethyl)pyridine-3-carboxylic acid as a light brown solid.

Synthesis of 2,5-dibromopyridin-3-amine

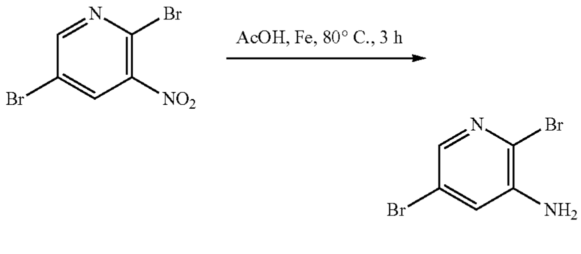

Into a 1000-mL 3-necked round-bottom flask, was placed 2,5-dibromo-3-nitropyridine (100.00 g, 354.747 mmol, 1.00 equiv), AcOH (500 mL), Fe (99 g, 1.7 mol, 5.0 equiv). The resulting solution was stirred for 1 hr at 80 degrees C. The solids were filtered out. The cake was washed with 100 mL EtOH. The resulting mixture was concentrated. This resulted in 75 g (84%) of 2,5-dibromopyridin-3-amine as a dark brown solid.

Synthesis of 2,5-dibromo-3-(ethylsulfanyl)pyridine

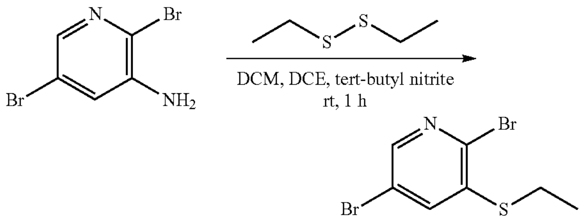

Into a 2000-mL 3-necked round-bottom flask, was placed 2,5-dibromopyridin-3-amine (45 g, 179 mmol, 1.0 equiv), DCM (225 mL), DCE (450 mL), diethyl disulfide (43.7 g, 357 mmol, 2.0 equiv), t-BuONO (36.8 g, 357 mmol, 2.0 equiv). The resulting solution was stirred for 1 hr at room temperature. The resulting mixture was washed with 1×500 mL of $H_2O$ and 1×500 mL of brine. The mixture was dried over anhydrous sodium sulfate and concentrated. The residue was applied onto a silica gel column with ethyl acetate/petroleum ether (1:15). This resulted in 38 g (72%) of 2,5-dibromo-3-(ethylsulfanyl)pyridine as yellow oil.

Synthesis of 2,5-dibromo-3-(ethanesulfonyl)pyridine

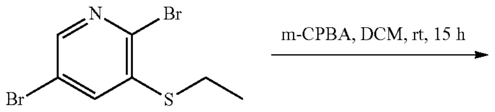

-continued

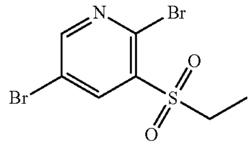

Into a 1000-mL 3-necked round-bottom flask, was placed 2,5-dibromo-3-(ethylsulfanyl)pyridine (38 g, 128 mmol, 1.0 equiv), DCM (760 mL), m-CPBA (55 g, 320 mmol, 2.5 equiv). The resulting solution was stirred for 15 hr at room temperature. The resulting mixture was washed with 3×500 mL of $NaHCO_3$ and 1×500 mL of brine. The mixture was dried over anhydrous sodium sulfate and concentrated. The resulting solution was diluted with 500 mL of PE. The solids were collected by filtration. This resulted in 33 g (78%) of 2,5-dibromo-3-(ethanesulfonyl)pyridine as a light yellow solid.

Synthesis of 5-bromo-3-(ethanesulfonyl)-2-hydrazinylpyridine

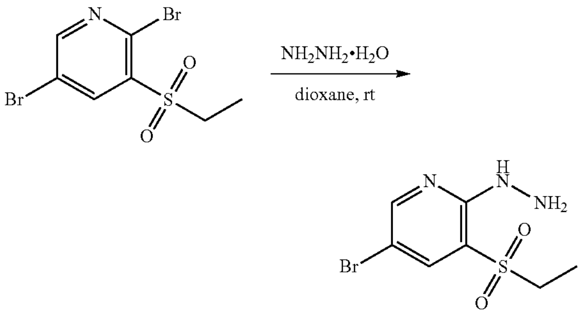

Into a 1000-mL 3-necked round-bottom flask, was placed 2,5-dibromo-3-(ethanesulfonyl)pyridine (49 g, 149 mmol, 1.0 equiv), dioxane (490 mL), $NH_2NH_2{\cdot}H_2O$ (42 g, 833 mmol, 5.6 equiv). The resulting solution was stirred for 1 hr at room temperature. The resulting mixture was concentrated. The resulting solution was diluted with 300 mL of PE. The solids were collected by filtration. This resulted in 36 g (86%) of 5-bromo-3-(ethanesulfonyl)-2-hydrazinylpyridine as a light yellow solid.

Synthesis of 4-[2-[5-bromo-3-(ethanesulfonyl)pyridin-2-yl]hydrazin-1-yl]-6-(trifluoromethyl)pyridine-3-carboxylic acid

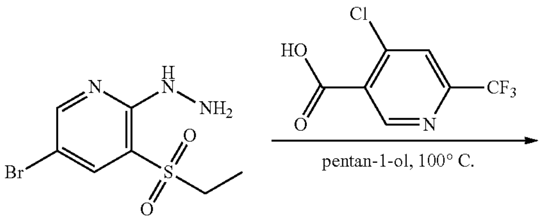

-continued

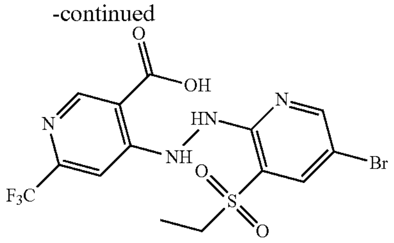

Into a 20-mL vial, was placed 5-bromo-3-(ethanesulfonyl)-2-hydrazinylpyridine (807 mg, 2.9 mmol, 1.3 equiv), 4-chloro-6-(trifluoromethyl)pyridine-3-carboxylic acid (500 mg, 2.2 mmol, 1.0 equiv), pentan-1-ol (5 mL). The resulting solution was stirred overnight at 100 degrees C. The reaction mixture was cooled. The reaction was then quenched by the addition of 30 mL of PE. The solids were collected by filtration. The resulting solution was diluted with of MeOH. The crude product was purified by Flash-Prep-HPLC 0.1% HCOOH:MeCN=30% increasing to 0.I % HCOOH: MeCN=70% within 9 min. This resulted in 100 mg (9.6%) of 4-[2-[5-bromo-3-(ethanesulfonyl)pyridin-2-yl]hydrazin-1-yl]-6-(trifluoromethyl)pyridine-3-carboxylic acid as a brown solid.

Synthesis of 5-bromo-2-[3-chloro-6-(trifluoromethyl) pyrazolo[4,3-c]pyridin-2-yl]-3-(ethanesulfonyl)pyridine

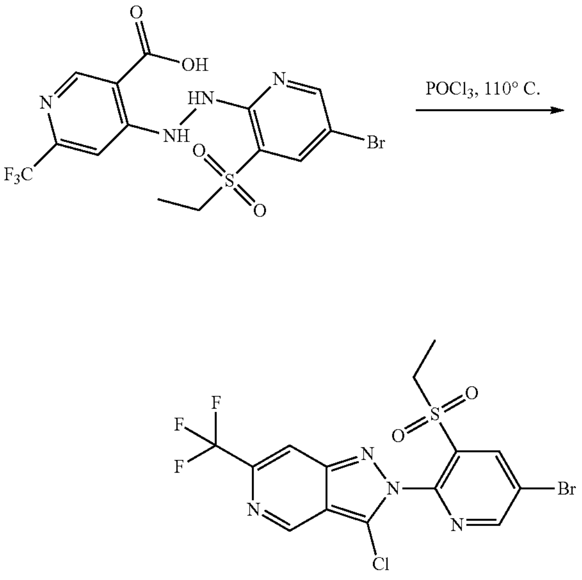

Into a 8-mL vial, was placed 4-[2-[5-bromo-3-(ethanesulfonyl)pyridin-2-yl]hydrazin-1-yl]-6-(trifluoromethyl) pyridine-3-carboxylic acid (160 mg, 0.34 mmol, 1.0 equiv), $POCl_3$ (3.0 mL). The resulting solution was stirred for 2 hr at 110 degrees C. The reaction mixture was cooled to room temperature. The resulting mixture was concentrated under vacuum. The residue was applied onto a silica gel column with ethyl acetate/petroleum ether (1:3). This resulted in 110 mg (69%) of 5-bromo-2-[3-chloro-6-(trifluoromethyl) pyrazolo[4,3-clpyridin-2-yl]-3-(ethanesulfonyl)pyridine as a white solid.

Synthesis of 5-bromo-3-(ethanesulfonyl)-2-[6-(trifluoromethyl)pyrazolo[4,3-clpyridin-2-yl]pyridine

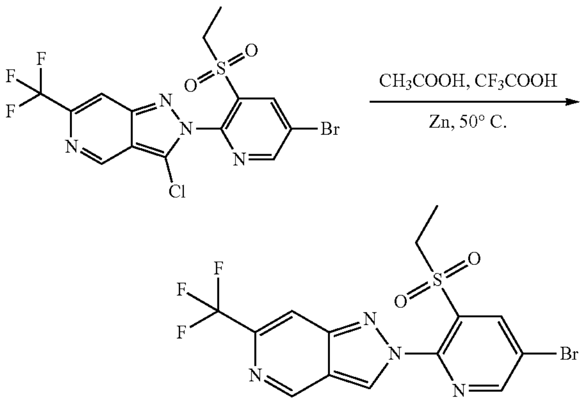

Into a 20-mL vial, was placed 5-bromo-2-[3-chloro-6-(trifluoromethyl)pyrazolo[4,3-c]pyridin-2-yl]-3-(ethanesulfonyl)pyridine (100 mg, 0.2 mmol, 1.0 equiv), AcOH (5 mL), $CF_3COOH$ (0.5 mL), Zn (70 mg, 1.1 mmol, 5 equiv). The resulting solution was stirred for 1.5 hr at 50 degrees C. The reaction mixture was cooled to room temperature. The resulting mixture was concentrated under vacuum. The residue was applied onto a silica gel column with ethyl acetate/petroleum ether (1:3). This resulted in 60 mg (65%) of 5-bromo-3-(ethanesulfonyl)-2-[6-(trifluoromethyl)pyrazolo[4,3-c]pyridin-2-yl]pyridine as a white solid.

Synthesis of 5-bromo-3-(ethanesulfonyl)-2-[7-[(trifluoromethyl)sulfanyl]imidazo[1,2-c]pyrimidin-2-yl] pyridine

Synthesis of 2-bromo-1-[5-bromo-3-(ethylsulfanyl) pyridin-2-yl]ethanone

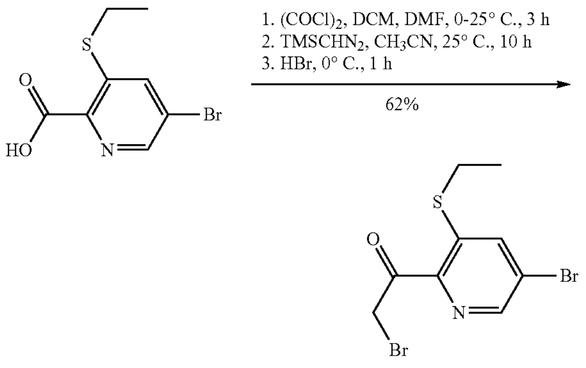

Into a 250-mL round-bottom flask, was placed a solution of 5-bromo-3-(ethylsulfanyl)pyridine-2-carboxylic 20 acid (10 g, 38 mmol, 1.0 equiv) in DCM (120 mL), $(COCl)_2$ (7.75 g, 61 mmol, 1.6 equiv) and DMF (140 mg, 1.9 mmol, 0.05 equiv) was added in at 0 degrees C. The resulting solution was stirred for 3 hr at 0-25 degrees C. The mixture was concentrated under vacuum followed by the addition of ACN (130.0 mL). Then $TMSCHN_2$ (76 mL) was added in at 0 degrees C. dropwise. The resulting solution was allowed to react, with stirring, for an additional 10 hr at 25 degrees C. Then HBr (20.0 mL) was added at 0 degrees C. The resulting solution was allowed to react, with stirring, for an additional 1 hr at 0 degrees C. The reaction was poured into 300 mL of water/ice. The pH value of the solution was adjusted to 6 with 500 mL $Na_2CO_3$ (10%). The resulting solution was extracted with 2x 200 mL of ethyl acetate. The organic layer was washed with 2×200 mL of brine. The resulting mixture was concentrated. The residue was applied onto a silica gel column with ethyl acetate/petroleum ether (1:12-1:6). This resulted in 8 g (62%) of 2-bromo-1-[5-bromo-3-(ethylsulfanyl)pyridin-2-yl]ethanone as a light yellow solid.

Synthesis of 5-bromo-3-(ethanesulfonyl)pyridine-2-carboxylic acid

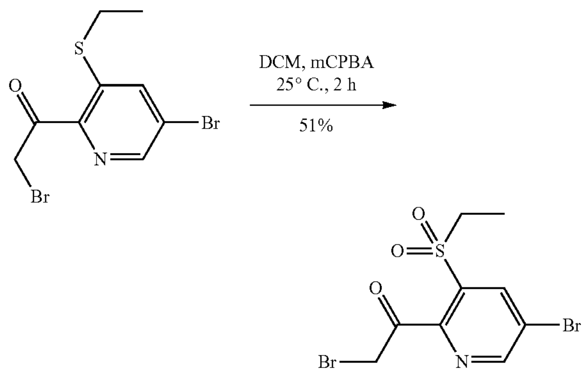

Into a 250-mL round-bottom flask, was placed a solution of 5-bromo-3-(ethylsulfanyl)pyridine-2-carboxylic acid (7.0 g, 27 mmol, 1.0 equiv) in DCM (100 mL), mCPBA (14 g, 80 mmol, 3 equiv). The resulting solution was stirred for 2 hr at 25 degrees C. The resulting mixture was concentrated. The residue was applied onto a silica gel column with dichloromethane/methanol (20:1-8:1). This resulted in 4 g (51%) of 5-bromo-3-(ethanesulfonyl)pyridine-2-carboxylic acid as a yellow solid.

Synthesis of 5-bromo-3-(ethanesulfonyl)-2-[7-[(trifluoromethyl)sulfanyl]imidazo[1,2-c]pyrimidin-2-yl] pyridine

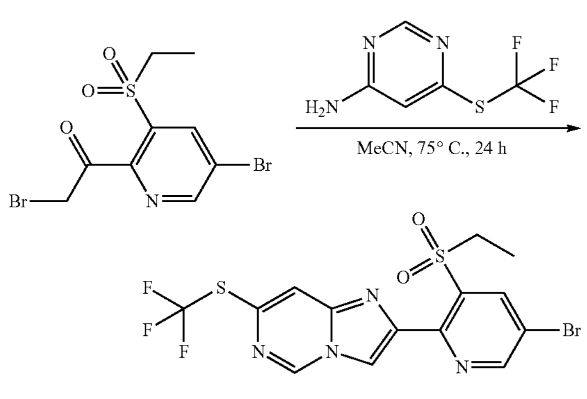

Into a 500-mL round-bottom flask, was placed 6-[(trifluoromethyl)sulfanyl]pyrimidin-4-amine (1.0 g, 5.1 mmol, 1.0 equiv), 2-bromo-1-[5-bromo-3-(ethanesulfonyl)pyridin-2-yl]ethanone (1.9 g, 5.1 mmol, 1.0 equiv), MeCN (100 mL, 2.4 mmol, 0.5 equiv). The resulting solution was stirred for 24 hr at 75 degrees C. The resulting mixture was concentrated. The residue was applied onto a silica gel column with ethyl acetate/petroleum ether (1:5). This resulted in 500 mg (21%) of 5-bromo-3-(ethanesulfonyl)-2-[7-[(trifluoromethyl)sulfanyl]imidazo[1,2-c]pyrimidin-2-yl]pyridine as a yellow solid.

Synthesis of 5-bromo-3-(ethanesulfonyl)-2-[6-(trifluoromethyl) pyrazolo[4,3-c]pyridin-1-yl]pyridine Synthesis of 5-bromo-2-chloro-3-(ethanesulfonyl)pyridine

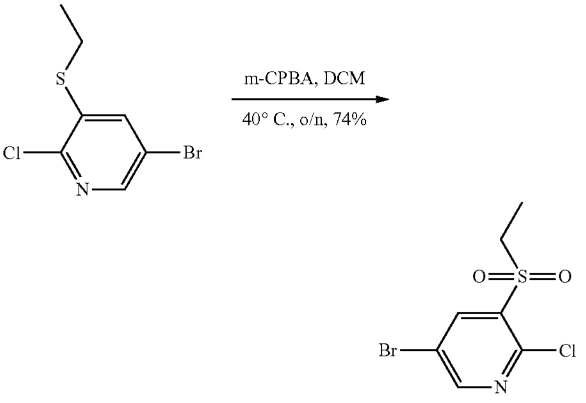

Into a 100-mL round-bottom flask, was placed 5-bromo-2-chloro-3-(ethylsulfanyl)pyridine (600 mg, 2.4 mmol, 1.0 equiv), DCM (30 mL), m-CPBA (2050 mg, 11.9 mmol, 5.0 equiv). The resulting solution was stirred overnight at 40 degrees C. The resulting solution was diluted with 20 mL water and extracted with 3×50 mL of dichloromethane. Then solution was concentrated. The residue was applied onto a silica gel column with ethyl acetate/petroleum ether (1:1). This resulted in 500 mg (74%) of 5-bromo-2-chloro-3-(ethanesulfonyl)pyridine as a white solid.

Synthesis of 5-bromo-3-(ethanesulfonyl)-2-[6-(trifluoromethyl) pyrazolo[4,3-c]pyridin-1-yl]pyridine

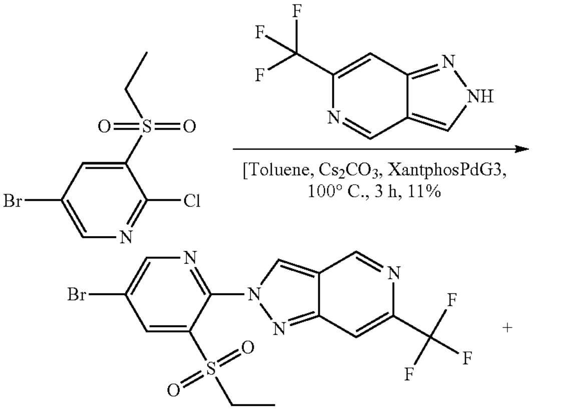

-continued

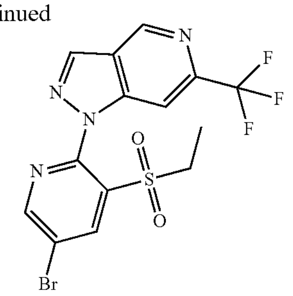

Into a 40-mL vial purged and maintained with an inert atmosphere of nitrogen, was placed 5-bromo-2-chloro-3-(ethanesulfonyl)pyridine (300 mg, 1.1 mmol, 1.0 equiv), toluene (30 mL), 6-(trifluoromethyl)-2H-pyrazolo[4,3-c] pyridine (217 mg, 1.2 mmol, 1.1 equiv), $Cs_2CO_3$ (690 mg, 2.1 mmol, 2 equiv), XANTPHOS Pd G3 (100 mg, 0.1 mmol, 0.1 equiv). The resulting solution was stirred for 3 h at 100 degrees C. The residue was applied onto a silica gel column with ethyl acetate/petroleum ether (1:2). The crude product was further purified by Prep-HPLC with the following conditions: Column, XBridge Shield RP18 OBD Column, 5 um,19*150 mm; mobile phase, Water(0.05% TFA) and ACN (60% Phase B up to 75% in 7 min); Detector, UV. This resulted in 64 mg (14%) of 5-bromo-3-(ethanesulfonyl)-2-[6-(trifluoromethyl)pyrazolo[4,3-c]pyridin-2-yl]pyridine as a white solid and 50 mg (11%) of 5-bromo-3-(ethanesulfonyl)-2-[6-(trifluoromethyl)pyrazolo[4,3-c]pyridin-1-yl] pyridine as a white solid.

Synthesis of 5-bromo-3-(ethanesulfonyl)-2-[6-(1,1,2,2,2-pentafluoroethyl)-2H-pyrazolo[4,3-c]pyridazin-2-yl]pyridine

Synthesis of 5-bromo-2-chloro-3-(ethylsulfanyl)pyridine

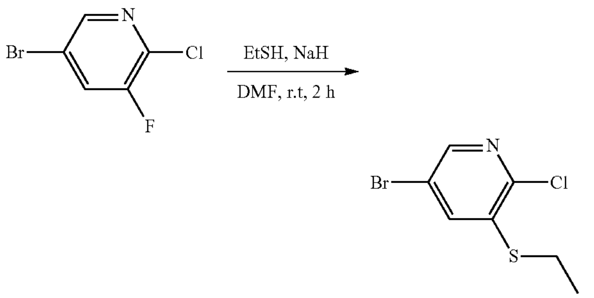

Into a 250 mL 3-necked round-bottom flask were added 5-bromo-2-chloro-3-fluoropyridine (10 g, 48 mmol, 1 equiv) and DMF (100 mL), ethanethiol (3.5 g, 57 mmol, 1.2 equiv) at room temperature. To the above mixture was added NaH (2.9 g, 71 mmol, 1.5 equiv, 60%) in portions at 0° C. The resulting mixture was stirred for additional 2h at room temperature. The reaction was quenched with sat. NH4CL (aq.) at room temperature. The resulting mixture was extracted with EtOAc (2×200 mL). The combined organic layers were washed with brine (2×200 mL), dried over anhydrous Na2SO4. After filtration, the filtrate was concentrated under reduced pressure. The residue was purified by silica gel column chromatography, eluted with PE/EA (10:1) to afford 5-bromo-2-chloro-3-(ethylsulfanyl)pyridine (12 g, 88%) as a yellow oil.

Synthesis of 5-bromo-3-(ethylsulfanyl)-2-hydrazinylpyridine

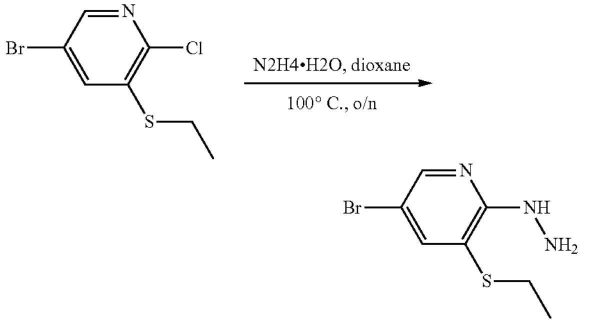

Into a 250 mL 3-necked round-bottom flask were added 5-bromo-2-chloro-3-(ethylsulfanyl)pyridine (7 g, 27 mmol, 1 equiv) and EtOH (70 mL), hydrazinium hydroxide (28 g, 554 mmol, 20 equiv, 98%) at room temperature. The resulting mixture was stirred for overnight at 100° C. The mixture was allowed to cool down to room temperature. The resulting mixture was diluted with water (100 mL). The resulting mixture was extracted with EtOAc (2×200 mL), dried over anhydrous Na2SO4. After filtration, the filtrate was concentrated under reduced pressure. This resulted in 5-bromo-3-(ethylsulfanyl)-2-hydrazinylpyridine (7.8 g, 88%) as a brown solid.

Synthesis of bis(1,1,2,2,2-pentafluoroethyl)zinc

C2F5I
Zn, NMP
0° C.~r.t, 1 h
$Zn(C_2F_5)_2$

Into a 500 mL 3-necked round-bottom flask were added Zn (2.0 g, 30 mmol, 0.5 equiv) and NMP (250 mL) at room temperature. To the above mixture was added 1,1,1,1,1-pentafluoro-2-iodoethyne (15 g, 61 mmol, 1 equiv) and NMP(50 mL) dropwise at 0° C. The resulting mixture was stirred for additional 1 h at room temperature. The resulting mixture was used in the next step directly without further purification.

Synthesis of 3-chloro-6-(1,1,2,2,2-pentafluoroethyl)pyridazine

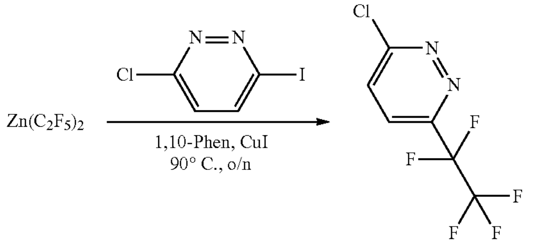 [SMILES: "Zn(C2F5)2" ; Clc1ccc(I)nn1 ; FC(F)(F)C(F)(F)c1ccc(Cl)nn1]

Into a 500 mL 3-necked round-bottom flask were added 3-chloro-6-iodopyridazine (7.0 g, 29 mmol, 1 equiv) and bis(1,1,2,2,2-pentafluoroethyl)zinc (8.8 g, 29 mmol, 1 equiv) in NMP (300 mL), 1,10-Phen (2.6 g, 15 mmol, 0.5 equiv), CuI (2.8 g, 15 mmol, 0.5 equiv) at room temperature. The resulting mixture was stirred for overnight at 90° C. under nitrogen atmosphere. The mixture was allowed to cool down to room temperature. The resulting mixture was diluted with water (500 mL). The resulting mixture was filtered. The resulting mixture was extracted with EtOAc (2×500 mL), dried over anhydrous Na2SO4. After filtration, the filtrate was concentrated under reduced pressure. The residue was purified by silica gel column chromatography, eluted with PE/EA (10:1) to afford 3-chloro-6-(1,1,2,2,2-pentafluoroethyl)pyridazine (7.9 g) as a yellow solid.

Synthesis of methyl 6-(1,1,2,2,2-pentafluoroethyl) pyridazine-3-carboxylate

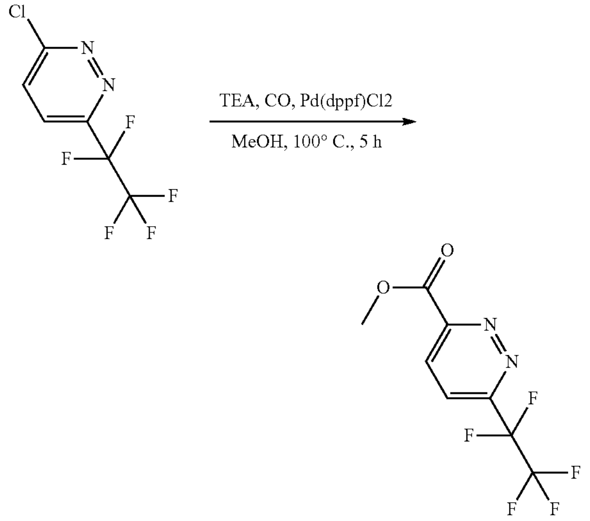

Into a 1L pressure tank reactor were added 3-chloro-6-(1,1,2,2,2-pentafluoroethyl)pyridazine (7 g, 30 mmol, 1 equiv) and MeOH (600 mL), TEA (9.1 g, 90 mmol, 3.00 equiv), Pd(dppf)Cl2. $CH_2$Cl2 (490 mg, 0.6 mmol, 0.02 equiv) at room temperature. The resulting mixture was stirred for 5 h at 100° C. under CO (20 atm) atmosphere. The mixture was allowed to cool down to room temperature. The resulting mixture was concentrated under vacuum. The residue was purified by silica gel column chromatography, eluted with PE/EA (6:1) to afford methyl 6-(1,1,2,2,2-pentafluoroethyl)pyridazine-3-carboxylate (8.1 g, 93%) as a white solid.

Synthesis of methyl 4-iodo-6-(1,1,2,2,2-pentafluoroethyl)pyridazine-3-carboxylate

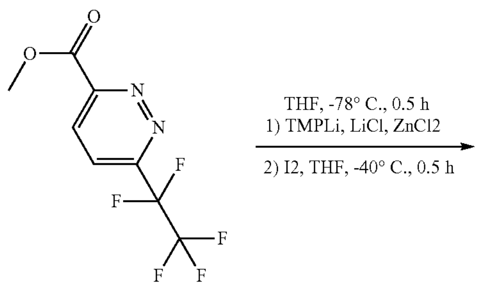

-continued

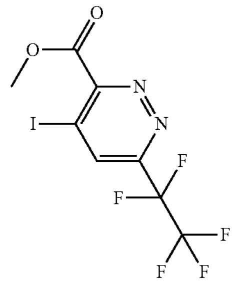

TMPLi/THF (0.63 M): Into a 250 mL 3-necked round-bottom flask were added 2,2,6,6-tetramethylpiperidine (10 g) and THF (100 mL) at room temperature. To the above mixture was added n-BuLi (43 mL) dropwise at −40° C. The resulting mixture was stirred for additional 1 h at −40° C. Into another 1 L 4-necked round-bottom flask were added methyl 6-(1,1,2,2,2-pentafluoroethyl)pyridazine-3-carboxylate (6.9 g, 27 mmol, 1 equiv) and THF (150 mL), LiCl in THF (85 mL, 60 mmol, 2.2 equiv), ZnCl2 in THF (42 mL, 30 mmol, 1.1 equiv) at room temperature. To the above mixture was added TMPLi/THF (94 mL, 60 mmol, 2.2 equiv) dropwise at −40° C. The resulting mixture was stirred for additional 1 h at −40° C. To the above mixture was added 12 (8.2 g, 32 mmol, 1.2 equiv) and THF (50 mL) dropwise at −40° C. The resulting mixture was stirred for additional 1 h at −40° C. The reaction was quenched with 200 mL sat. NH4Cl (aq.) at −40° C. The resulting mixture was extracted with EtOAc (2×200 mL), dried over anhydrous Na2SO4. After filtration, the filtrate was concentrated under reduced pressure. The residue was purified by silica gel column chromatography, eluted with PE/EA (10:1) to afford methyl 4-iodo-6-(1,1,2,2,2-pentafluoroethyl)pyridazine-3-carboxylate (3.8 g, 36%) as a yellow solid.

Synthesis of 4-iodo-6-(1,1,2,2,2-pentafluoroethyl) pyridazine-3-carbaldehyde

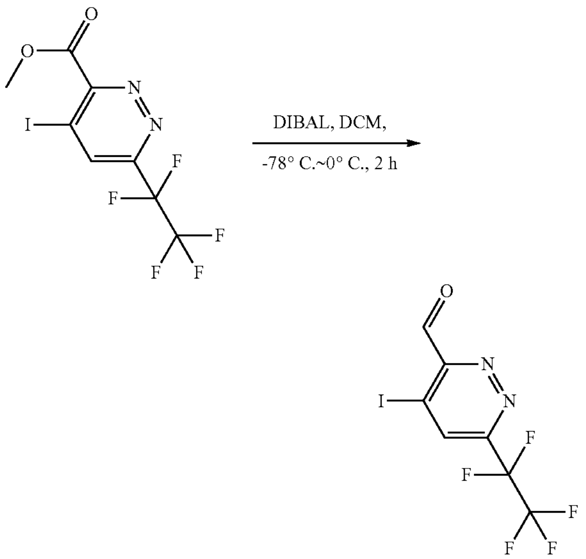

Into a 100 mL 3-necked round-bottom flask were added methyl 4-iodo-6-(1,1,2,2,2-pentafluoroethyl)-pyridazine-3-carboxylate (3.2 g, 8.4 mmol, 1 equiv) and DCM (65 mL) at room temperature. To the above mixture was added DIBALH (13 mL, 13 mmol, 1.5 equiv) dropwise at −78° C. The resulting mixture was stirred for additional 2h at −78° C.~0° C. The reaction was quenched with sat. NH4Cl (aq.) (50 mL) at 0° C. The residue was acidified to pH 4 with HCl (aq.). The resulting mixture was extracted with $CH_2Cl2$ (2×100 mL), dried over anhydrous MgSO4. After filtration, the filtrate was concentrated under reduced pressure. The residue was purified by silica gel column chromatography, eluted with PE/EA (4:1) to afford 4-iodo-6-(1,1,2,2,2-pentafluoroethyl)pyridazine-3-carbaldehyde (1.8 g, 50%) as a brown solid.

Synthesis of 5-bromo-3-(ethylsulfanyl)-2-[6-(1,1,2,2,2-pentafluoroethyl)-2H-pyrazolo[4,3-c]pyridazin-2-yl]pyridine

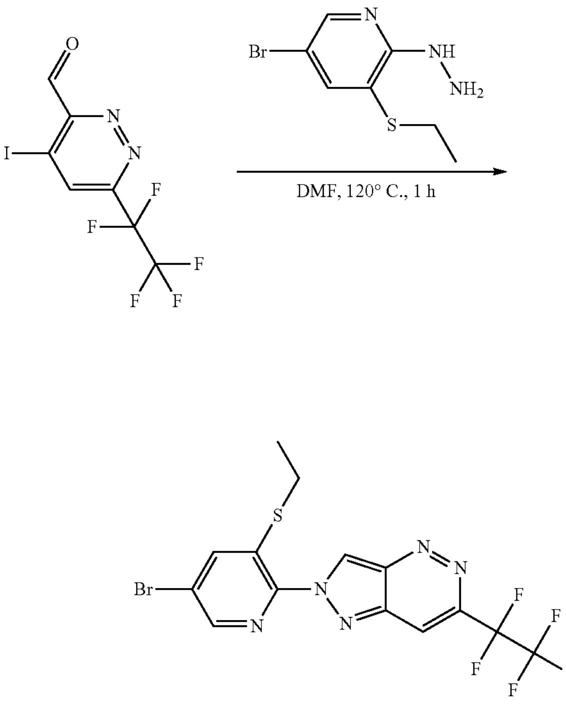

Into a 100 mL 3-necked round-bottom flask were added 4-iodo-6-(1,1,2,2,2-pentafluoroethyl)pyridazine-3-carbaldehyde (1.8 g, 5.1 mmol, 1 equiv) and 5-bromo-3-(ethylsulfanyl)-2-hydrazinylpyridine (2.5 g, 10 mmol, 2 equiv), DMF (18 mL) at room temperature. The resulting mixture was stirred for 3 h at 120° C. The mixture was allowed to cool down to room temperature. The residue was purified by reverse flash chromatography with the following conditions: column, C18 silica gel; mobile phase, MeCN in Water (0.1% FA), 20% to 95% gradient in 20 min; detector, UV 254 nm. This resulted in 5-bromo-3-(ethylsulfanyl)-2-[6-(1,1,2,2,2-pentafluoroethyl)pyrazolo[4,3-c]pyridazin-2-yl]pyridine (1.8 g, 66%) as a brown solid.

Synthesis of 5-bromo-3-(ethanesulfonyl)-2-[6-(1,1,2,2,2-pentafluoroethyl)-2H-pyrazolo[4,3-c]pyridazin-2-yl]pyridine

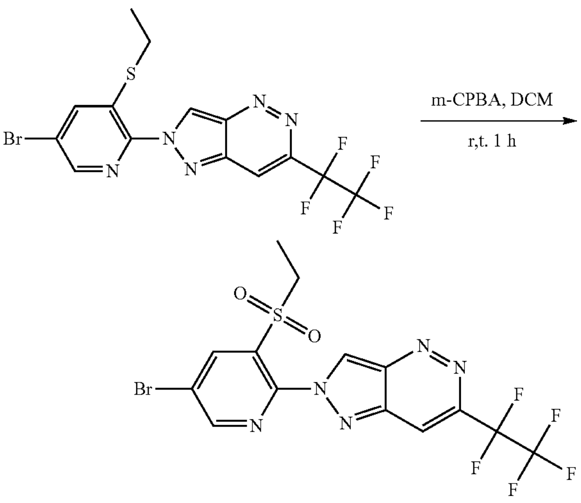

Into a 50 mL 3-necked round-bottom flask were added 5-bromo-3-(ethylsulfanyl)-2-[6-(1,1,2,2,2-pentafluoroethyl)pyrazolo[4,3-c]pyridazin-2-yl]pyridine (1.7 g, 3.7 mmol, 1 equiv) and DCM (17 mL) at room temperature. To the above mixture was added m-CPBA (1.9 g, 11 mmol, 3.0 equiv) in portions at 0° C. The resulting mixture was stirred for additional 1 h at room temperature. The resulting mixture was concentrated under vacuum. The residue was purified by reverse flash chromatography with the following conditions: column, C18 silica gel; mobile phase, MeCN in Water (0.1% NH3·$H_2O$), 30% to 95% gradient in 15 min; detector, UV 254 nm. This resulted in 5-bromo-3-(ethanesulfonyl)-2-[6-(1,1,2,2,2-pentafluoroethyl)pyrazolo[4,3-c]pyridazin-2-yl]pyridine (1.6 g, 57%) as a yellow solid.

Synthesis of 2-cyclopropyl-6-(trimethylstannyl)pyridine

Specifically, the following examples can be synthesized by adopting the subsequent scheme of 2-cyclopropyl-6-(trimethylstannyl)pyridine by someone who is skilled in the art: 4-bromo-2-cyclopropylpyridine, 3-bromo-5-cyclopropylpyridine, 5-bromo-2-cyclopropylpyridine.

Synthesis of 2-bromo-6-cyclopropylpyridine

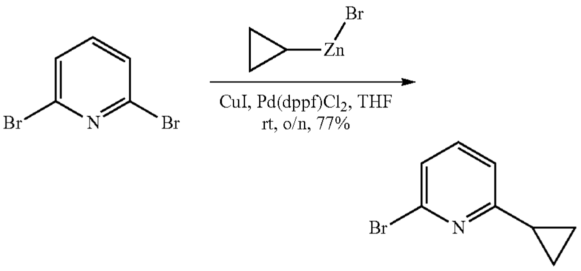

Into a 250-mL 3-necked round-bottom flask, was placed pyridine, 2,6-dibromo-(2.5 g, 11 mmol, 1.0 equiv), CuI (0.5 g, 2.6 mmol, 0.25 equiv), Pd(dppf)$Cl_2$ (0.77 g, 1.0 mmol, 0.1 equiv), THF (25 mL), bromo(cyclopropyl)zinc (25 mL, 13 mmol, 1.2 equiv, 0.5 M). The resulting solution was stirred for 1 overnight at room temperature. The reaction was then quenched by the addition of 200 mL of $H_2O$. The resulting solution was extracted with 3×200 mL of ethyl acetate and the organic layers combined. The resulting mixture was washed with 3×200 mL of brine. The mixture was dried over anhydrous sodium sulfate and concentrated. The residue was applied onto a silica gel column with ethyl acetate/petroleum ether (1:5). This resulted in 1.6 g (77%) of 2-bromo-6-cyclopropylpyridine as a yellow solid.

Synthesis of 2-cyclopropyl-6-(trimethylstannyl)pyridine

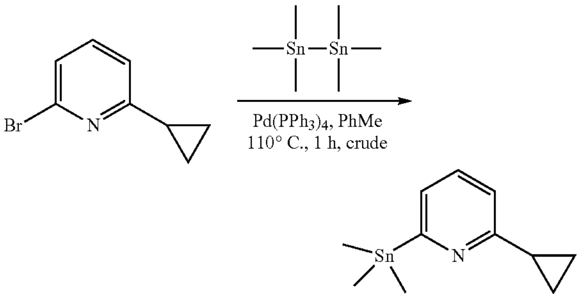

Into a 40-mL vial purged and maintained with an inert atmosphere of nitrogen, was placed 2-bromo-6-cyclopropylpyridine (800 mg, 4.0 mmol, 1.0 equiv), hexamethyldistannane (1.32 g, 4.0 mmol, 1.0 equiv), Toluene (10 mL), $Pd(PPh_3)_4$(467 mg, 0.4 mmol, 0.1 equiv). The resulting solution was stirred for 1 hr at 110 degrees C. The reaction mixture was cooled to 25 degrees C. The resulting mixture was concentrated. This resulted in 1.2 g (crude) of 2-cyclopropyl-6-(trimethylstannyl)pyridine as yellow oil.

Synthesis of 4-cyclopropyl-2-(trimethylstannyl)pyridine

Specifically, the following examples can be synthesized by adopting the subsequent scheme of 4-cyclopropyl-2-(trimethylstannyl)pyridine by someone who is skilled in the art: 5-cyclopropyl-2-(trimethylstannyl)pyridine.

Synthesis of 2-chloro-4-cyclopropylpyridine

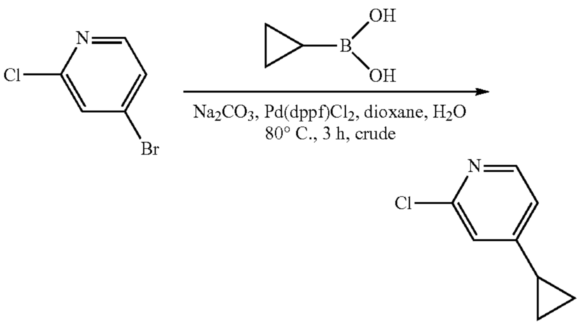

Into a 250-mL 3-necked round-bottom flask purged and maintained with an inert atmosphere of nitrogen, was placed 4-bromo-2-chloropyridine (1.0 g, 0.005 mol, 1.0 equiv), cyclopropylboronic acid (0.54 g, 0.006 mol, 1.2 equiv), dioxane (30 mL), $H_2O$ (13 mL), $Na_2CO_3$ (1.27 g, 0.012 mol, 2.3 equiv), Pd(dppf)$Cl_2CH_2Cl_2$ (0.08 g, 0.02 equiv). The resulting solution was stirred for 1 overnight at 80 degrees C. The reaction mixture was cooled to 25 degrees C. The reaction was then quenched by the addition of 200 mL of water/ice. The resulting solution was extracted with 3×200 mL of ethyl acetate and the organic layers combined. The resulting mixture was washed with 3×200 mL of brine. The mixture was dried over anhydrous sodium sulfate and concentrated. The residue was applied onto a silica gel column with ethyl acetate/petroleum ether (1:3). This resulted in 650 mg (crude) of 2-chloro-4-cyclopropylpyridine as yellow oil.

Synthesis of 4-cyclopropyl-2-(trimethylstannyl)pyridine

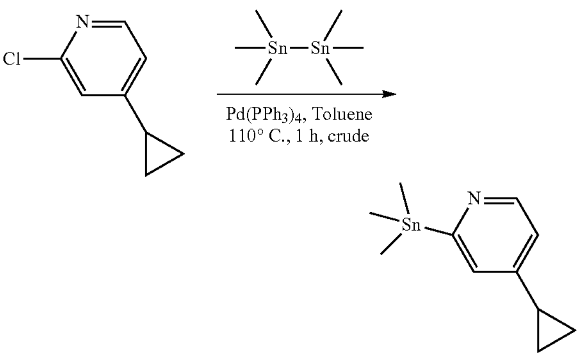

Into a 40-mL vial purged and maintained with an inert atmosphere of nitrogen, was placed 2-chloro-4-cyclopropylpyridine (200 mg, 1.3 mmol, 1.0 equiv), Toluene (5 mL), hexamethyldistannane (427 mg, 1.3 mmol, 1.0 equiv), $Pd(PPh_3)_4$ (150 mg, 0.13 mmol, 0.1 equiv). The resulting solution was stirred for 1 hr at 110 degrees C. The mixture was directly used to next step.

Synthesis of 3-cyclopropyl-6-(trimethylstannyl)pyridazine

Synthesis of 3-chloro-6-cyclopropylpyridazine

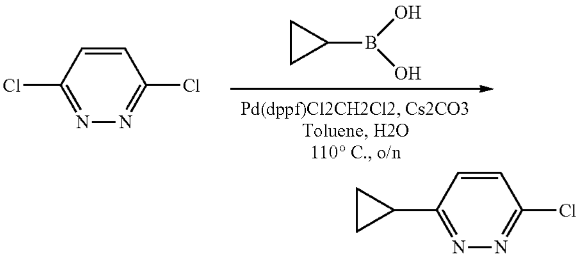

Into a 40-mL vial purged and maintained with an inert atmosphere of nitrogen, was placed 3,6-dichloro pyridazine (1.0 g, 6.7 mmol, 1 equiv), cyclopropylboronic acid (0.7 g, 8.0 mmol, 1.2 equiv), Cs2CO3 (4.4 g, 13 mmol, 2 equiv), Pd(dppf)C12·CH2Cl2 (0.55 g, 0.7 mmol, 0.1 equiv), toluene (15 mL) and $H_2O$ (3 mL). The 20 resulting solution was stirred ovenight at 110 degrees C. The resulting mixture was concentrated. The residue was applied onto a silica gel column with ethyl acetate/petroleum ether (1:3). This resulted in 3-chloro-6-cyclopropylpyridazine (530 mg, 51%) as a light-yellow solid.

Synthesis of 3-cyclopropyl-6-(trimethylstannyl)pyridazine

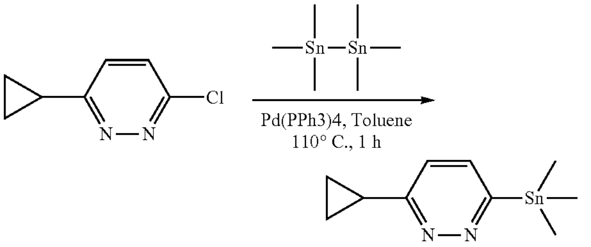

Into a 40-mL round-bottom flask purged and maintained with an inert atmosphere of nitrogen, was placed 3-chloro-6-cyclopropylpyridazine (200 mg, 1.3 mmol, 1 equiv), 1,1,1,2,2,2-hexamethyldistannane (506 mg, 1.4 mmol, 1.1 equiv), toluene (4 mL) and Pd(PPh3)4 (149 mg, 0.13 mmol, 0.1 equiv). The resulting solution was stirred for 1 h at 110 degrees C. The resulting mixture was concentrated. This resulted in 3-cyclopropyl-6-(trimethylstannyl)pyridazine (crude) as a black solid. It was used directly in next step without further purification.

Synthesis of 4-cyclopropyl-2-(trimethylstannyl)pyrimidine

Synthesis of 2-chloro-4-cyclopropylpyrimidine

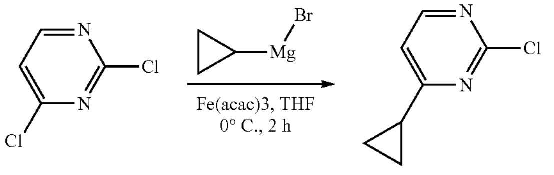

To a stirred mixture of 2,4-dichloropyrimidine (10 g, 67.128 mmol, 1 equiv) and Fe(acac)3 (2.4 g, 6.7 mmol, 0.1 equiv) in THF (100 mL) was added 1M bromo(cyclopropyl) magnesium (135 mL, 2.0 equiv) dropwise at 0° C. under nitrogen atmosphere. The mixture was stirred for 2 h at 0° C. The reaction was quenched with saturated NH4C1 (aq.) at 0° C. The aqueous layer was extracted with EtOAc (1×500 mL) and dried over anhydrous Na2SO4. The organic layer was concentrated under vacuum. The residue was purified by reverse flash chromatography with the following conditions: column, silica gel; mobile phase, MeCN in water (FA 0.1%), 0% to 60% gradient in 10 min; detector, UV 254 nm. This resulted in 2-chloro-4-cyclopropylpyrimidine (5.0 g, 48%) as a light yellow oil.

Synthesis of 4-cyclopropyl-2-(trimethylstannyl)pyrimidine

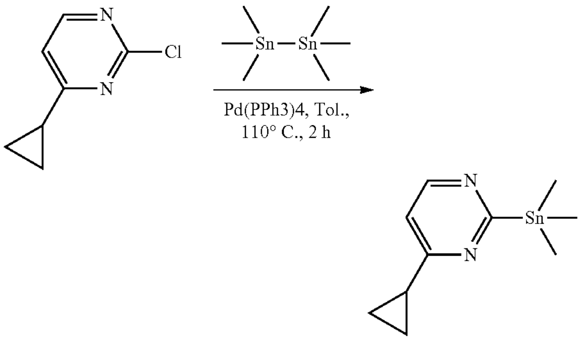

Into an 8 mL round-bottom flask were added 2-chloro-4-cyclopropylpyrimidine (350 mg, 2.3 mmol, 1 equiv), toluene (3.5 mL), hexamethyldistannane (890 mg, 2.7 mmol, 1.2 equiv) and Pd(PPh3)4 (262 mg, 0.2 mmol, 0.10 equiv) at room temperature. The resulting mixture was stirred for 2 h at 110° C. under nitrogen atmosphere. The resulting mixture was concentrated under vacuum. This resulted in 4-cyclopropyl-2-(trimethylstannyl)pyrimidine (400 mg, crude) as a brown oil.

Synthesis of 6-cyclopropyl-3-(trimethylstannyl)-1,2,4-triazine

Synthesis of 6-cyclopropyl-1,2,4-triazin-3-amine

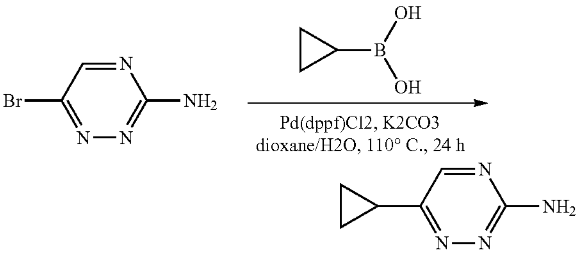

Into a 250-ml round-bottom flask was place 6-bromo-1,2,4-triazin-3-amine (4.0 g, 23 mmol, 1 equiv), cyclopropylboronic acid (7.8 g, 91 mmol, 4 equiv), K2CO3 (9.5 g, 69 mmol, 3 equiv), Pd(dppf)Cl2$CH_2$Cl2 (3.7 g, 4.6 mmol, 0.2 equiv) and dioxane (80 mL), $H_2O$ (8 mL) at room temperature under N2 atmosphere. The mixture was stirring for 24 h at 100° C. The mixture was allowed to cool down to room temperature and concentrated under reduced pressure. The residue was purified by silica gel column chromatography, eluted with PE/EA (7/3) to afford 6-cyclopropyl-1,2,4-triazin-3-amine (1.0 g, 29%) as a yellow oil.

Synthesis of 3-bromo-6-cyclopropyl-1,2,4-triazine

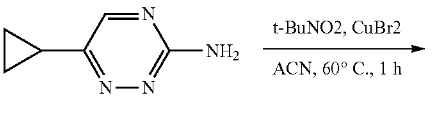

-continued

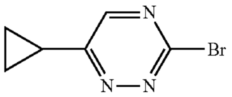

Into a 100-ml round-bottom flask was place 6-cyclopropyl-1,2,4-triazin-3-amine (500 mg, 3.7 mmol, 1 equiv), tBuNO2 (454 mg, 4.4 mmol, 1.2 equiv), CuBr2 (984 mg, 4.4 mmol, 1.2 equiv) and ACN (25 mL) at room temperature under N2 atmosphere. The mixture was stirring for 1 h at 60° C. The mixture was allowed to cool down to room temperature and concentrated under reduced pressure. The residue was dissolved in EA (20 ml), washed with 2*15 ml of water. The organic layer was dried over anhydrous Na2SO4 and concentrated under reduced pressure. The residue was purified by silica gel column chromatography, eluted with PE/EA (85/15) to afford 3-bromo-6-cyclopropyl-1,2,4-triazine (210 mg, 27%) as a yellow oil.

Synthesis of 6-cyclopropyl-3-(trimethylstannyl)-1,2,4-triazine

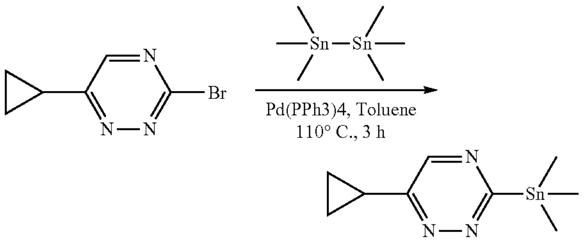

Into a 40 ml vial, was place 3-bromo-6-cyclopropyl-1,2,4-triazine (200 mg, 1.0 mmol, 1 equiv), hexamethyldistannane (491 mg, 1.5 mmol, 1.5 equiv), Pd(PPh3)4 (116 mg, 0.1 mmol, 0.1 equiv) and toluene (10 mL) at room temperature under N2 atmosphere. The mixture was stirring for 3 h at 110° C. The mixture was concentrated under reduced pressure. The crude product 6-cyclopropyl-3-(trimethylstannyl)-1,2,4-triazine (400 mg, crude) was used in the next step directly without further purification.

Synthesis of 5-cyclopropyl-3-(trimethylstannyl)-1,2,4-triazine

Synthesis of 2-cyclopropyl-2-oxoacetaldehyde

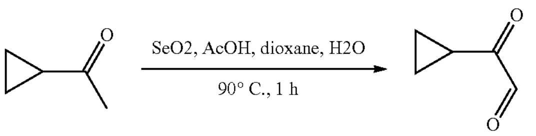

Into a 250 mL round-bottom flask were added SeO2 (9.2 g, 83 mmol, 1.4 equiv) and AcOH (2.5 g, 42 mmol, 0.7 equiv), $H_2O$ (1.7 g), dioxane (90 mL). The resulting mixture was stirred for 1 h at 90° C. under nitrogen atmosphere. To the above mixture was added cyclopropyl methyl ketone (5 g, 60 mmol, 1 equiv) dropwise. The resulting mixture was stirred for additional overnight at 90° C. The mixture was allowed to cool down to room temperature. The resulting mixture was concentrated under reduced pressure. The residue was purified by silica gel column chromatography, eluted with PE/THF (3:1) to afford 2-cyclopropyl-2-oxoacetaldehyde (7 g, crude) as a yellow oil.

Synthesis of 5-cyclopropyl-1,2,4-triazin-3-amine

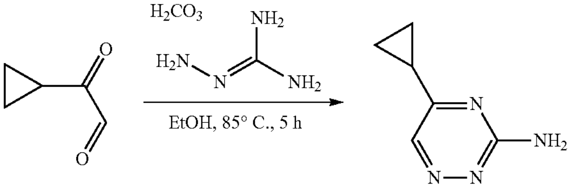

Into a 250 mL round-bottom flask were added 2-cyclopropyl-2-oxoacetaldehyde (7 g, 71 mmol, 1 equiv) and aminoguanidine; carbonic acid (11.7 g, 86 mmol, 1.2 equiv) and EtOH (70 mL). The resulting mixture was stirred for 5 h at 85° C. The mixture was allowed to cool down to room temperature. The resulting mixture was concentrated under reduced pressure. The residue was purified by silica gel column chromatography, eluted with PE/THF (1:1) to afford 5-cyclopropyl-1,2,4-triazin-3-amine (1.2 g, 12%) as a yellow solid.

Synthesis of 3-bromo-5-cyclopropyl-1,2,4-triazine

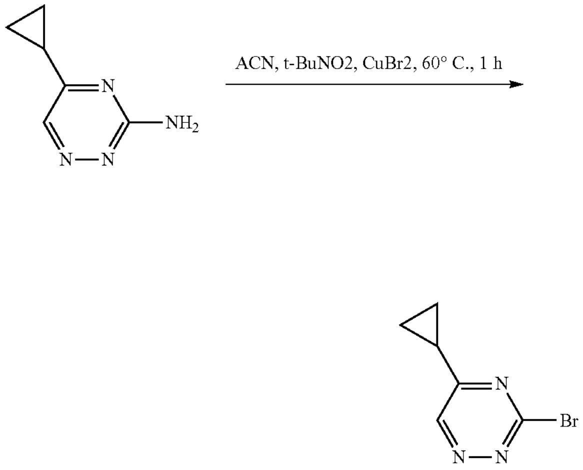

Into a 250 mL round-bottom flask were added 5-cyclopropyl-1,2,4-triazin-3-amine (1.2 g, 8.8 mmol, 1 equiv) and ACN (50 mL) and t-BuNO2 (1.1 g, 11 mmol, 1.2 equiv), CuBr2 (2.4 g, 11 mmol, 1.2 equiv). The resulting mixture was stirred for 1 h at 60° C. under nitrogen atmosphere. The mixture was allowed to cool down to room temperature. The resulting mixture was concentrated under reduced pressure. The residue was purified by silica gel column chromatography, eluted with PE/THF (1:1) to afford 3-bromo-5-cyclopropyl-1,2,4-triazine (600 mg, 34%) as a yellow solid.

Synthesis of 5-cyclopropyl-3-(trimethylstannyl)-1,2,4-triazine

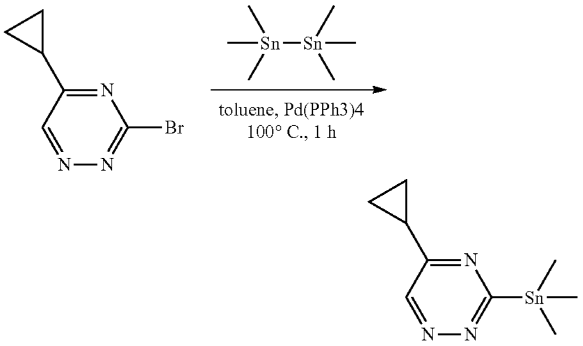

Into a 40 mL vial were added 3-bromo-5-cyclopropyl-1,2,4-triazine (600 mg, 3.0 mmol, 1 equiv) and hexamethyldistannane (1.5 g, 4.5 mmol, 1.5 equiv), toluene (10 mL), Pd(PPh3)4 (350 mg, 0.3 mmol, 0.1 equiv). The resulting mixture was stirred for 1 h at 100° C. under nitrogen atmosphere. The mixture was allowed to cool down to room temperature. The resulting mixture was concentrated under reduced pressure. The residue was purified by silica gel column chromatography, eluted with PE/EA (2:1) to afford 5-cyclopropyl-3-(trimethylstannyl)-1,2,4-triazine (500 mg, 59%) as a white solid.

Synthesis of 4-cyclopropyl-2-methyl-6-(trimethylstannyl)pyrimidine Synthesis of 4-chloro-6-cyclopropyl-2-methylpyrimidine

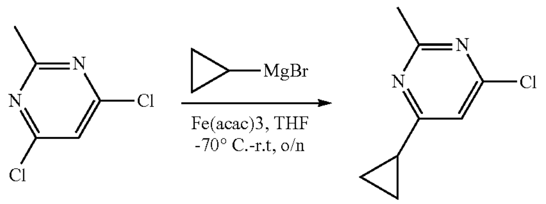

Into a 100 mL 3-necked round-bottom flask were added 4,6-dichloro-2-methylpyrimidine (500 mg, 3.0 mmol, 1 equiv), THE (20 mL) and Fe(acac)3 (54 mg, 0.2 mmol, 0.1 equiv) at room temperature. To the above mixture was added bromo(cyclopropyl)magnesium (6.1 mL, 42 mmol, 14 equiv) dropwise at −70° C. The resulting mixture was stirred overnight at room temperature. The reaction was quenched with saturated NH4Cl (aq.) at room temperature. The resulting mixture was extracted with EtOAc (3×100 mL). The combined organic layers were concentrated under reduced pressure. The residue was purified by silica gel column chromatography, eluted with 100% PE to afford the product. The product was further purified by reverse flash chromatography with the following conditions: column, C18 silica gel; mobile phase, 0.05% HCOOH in water, 100% gradient in 10 min; detector, UV 254 nm. This resulted in 4-chloro-6-cyclopropyl-2-methylpyrimidine (300 mg, 58%) as a yellow oil.

Synthesis of 4-cyclopropyl-2-methyl-6-(trimethylstannyl)pyrimidine

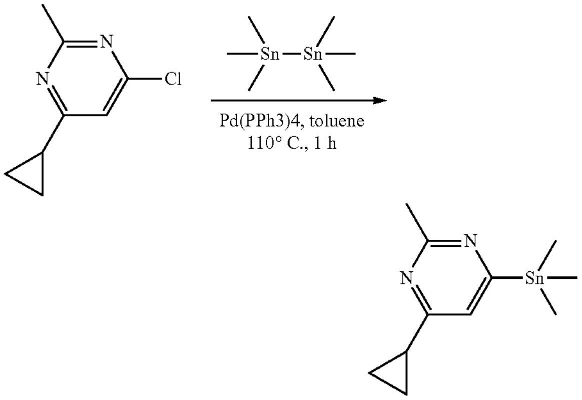

Into a 8 mL vial were added 4-chloro-6-cyclopropyl-2-methylpyrimidine (100 mg, 0.6 mmol, 1 equiv), toluene (1 mL), Sn2Me6 (194 mg, 0.6 mmol, 1 equiv) and Pd(PPh3)4 (68 mg, 0.06 mmol, 0.10 equiv) at room temperature. The resulting mixture was stirred for 1 h at 110° C. under nitrogen atmosphere. The mixture was allowed to cool down to room temperature. The resulting mixture was concentrated under vacuum. The crude product was used in the next step directly without further purification.

Synthesis of 2-[1-(trifluoromethyl)cyclopropyl]-6-(trimethylstannyl)pyridine

Synthesis of 2-bromo-6-[1-(trifluoromethyl)cyclopropyl]pyridine

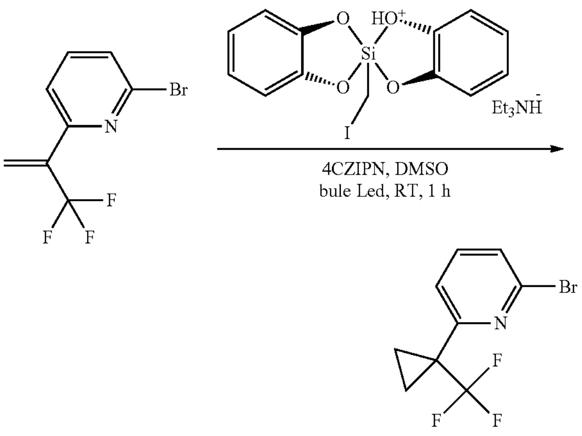

To a solution of 2-bromo-6-(3,3,3-trifluoroprop-1-en-2-yl)pyridine (300 mg, 1.2 mmol, 1 equiv) and 2-(iodomethyl)-1H-2lambda5-2,2'-spirobi[[1,3,2]benzodioxasilol]-1-ium; butane; ethanaminide (696 mg, 1.4 mmol, 1.2 equiv) in DMSO (18 mL) were added 4CZIPN (8 mg, 0.01 mmol, 0.05 equiv). After stirring for 1 h at room temperature under Blue LEDs under a nitrogen atmosphere. The aqueous layer was extracted with PE (4×15 mL). The resulting mixture was washed with 3×15 mL of water. The combined organic layers were dried over anhydrous Na2SO4. After filtration, the filtrate was concentrated under reduced pressure. This resulted in 2-bromo-6-[l-(trifluoromethyl)cyclopropyl]pyridine (160 mg, 512%) as a yellow oil.

Synthesis of 2-[1-(trifluoromethyl)cyclopropyl]-6-(trimethylstannyl)pyridine

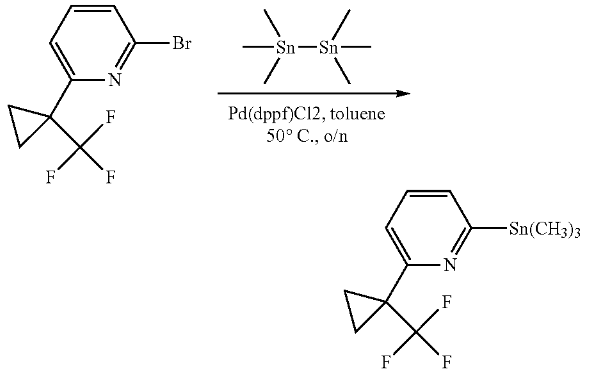

Into a 20 mL vial were added 2-bromo-6-[1-(trifluoromethyl)cyclopropyl]pyridine (160 mg, 0.6 mmol, 1 equiv) and hexamethyldistannane (296 mg, 0.9 mmol, 1.5 equiv). To the above mixture was added toluene (4.8 mL) and Pd(dppf) Cl2·$CH_2$Cl2 (25 mg, 0.03 mmol, 0.05 equiv). The resulting mixture was stirred overnight at 50° C. under nitrogen atmosphere. The mixture was allowed to cool down to room temperature. The resulting mixture was concentrated under reduced pressure. This resulted in 2-[1-(trifluoromethyl) cyclopropyl]-6-(trimethylstannyl)pyridine (310 mg, crude) as a yellow oil.

Synthesis of 3-cyclopropyl-5-(4,4,5,5-tetramethyl-1,3,2-dioxaborolan-2-yl)pyridine Synthesis of 3-bromo-5-cyclopropylpyridine

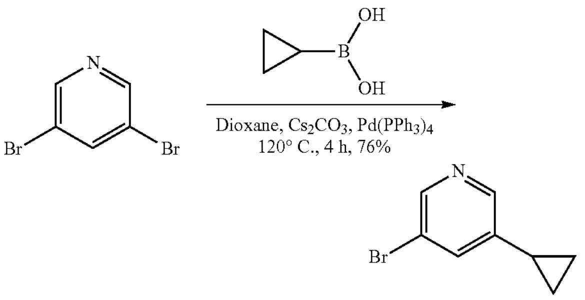

Into a 40-mL round-bottom flask purged and maintained with an inert atmosphere of nitrogen, was placed 3,5-dibromopyridine (235 mg, 1.0 mmol, 1.0 equiv), cyclopropylboronic acid (128 mg, 1.5 mmol, 1.5 equiv), $Cs_2CO_3$ (646 mg, 2.0 mmol, 2.0 equiv), dioxane (10 mL), $Pd(PPh_3)_4$(115 mg, 0.1 mmol, 0.1 equiv). The resulting solution was stirred for 4 hr at 120 degrees C. The resulting mixture was concentrated. The residue was 25 applied onto a silica gel column with ethyl acetate/petroleum ether (1:5). This resulted in 150 mg (76%) of 3-bromo-5-cyclopropylpyridine as an off-white solid.

Synthesis of 3-cyclopropyl-5-(4,4,5,5-tetramethyl-1,3,2-dioxaborolan-2-yl)pyridine

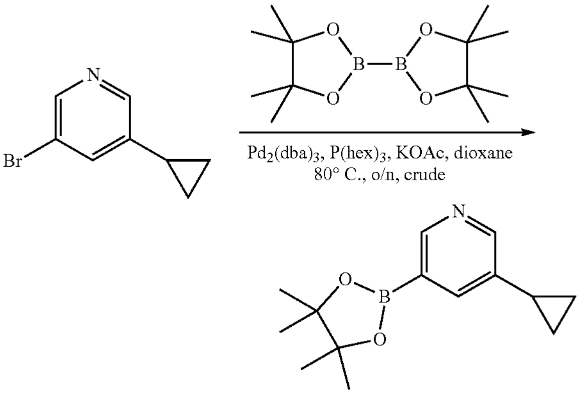

Into a 40-mL round-bottom flask purged and maintained with an inert atmosphere of nitrogen, was placed 3-bromo-5-cyclopropylpyridine (150 mg, 0.8 mmol, 1.0 equiv), bis (pinacolato)diboron (231 mg, 0.9 mmol, 1.2 equiv), KOAc (149 mg, 1.5 mmol, 2.0 equiv), dioxane (15 mL), $Pd_2(dba)_3$ (44 mg, 0.08 mmol, 0.1 equiv), $P(hex)_3$ (32 mg, 0.1 mmol, 0.15 equiv). The resulting solution was stirred for 1 overnight at 80 degrees C. The product can be used directly as a crude compound in a subsequent reaction vide infra.

Synthesis of 4,4,5,5-tetramethyl-2-[4-[1-(trifluoromethyl)cyclopropyl]phenyl]-1,3,2-dioxaborolane Specifically, the following examples can be synthesized by adopting the subsequent scheme of 4,4,5,5-tetramethyl-2-[4-[l-(trifluoromethyl)cyclopropyl]phenyl]-1,3,2-dioxaborolane by someone who is skilled in the art: 5-(4,4,5,5-tetramethyl-1,3,2-dioxaborolan-2-yl)-2-[1-(trifluoromethyl)cyclopropyl]pyridine Synthesis of 1-bromo-4-[1-(trifluoromethyl)cyclopropyl]benzene

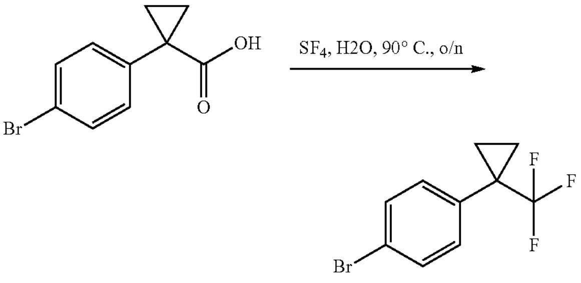

Into a 50-mL pressure tank reactor, was placed SF4 (20 g). This was followed by the addition of 1-(4-bromophenyl) cyclopropane-1-carboxylic acid (5.0 g, 20.740 mmol, 1.00 equiv), in portions at −78 degrees C. To this was added $H_2O$ (400 μL) dropwise with stirring at −78 degrees C. The resulting solution was stirred overnight at 90 degrees C. The resulting solution was diluted with 50 mL of EA. The resulting mixture was washed with 2×50 ml of Saturated $NaHCO_3$ solution. The mixture was dried over anhydrous sodium sulfate and concentrated. The residue was applied onto a silica gel column with ethyl petroleum. This resulted in 4.5 g (75%) of 1-bromo-4-[l-(trifluoromethyl)cyclopropyl]benzene as colorless oil.

Synthesis of 4,4,5,5-tetramethyl-2-[4-[1-(trifluoromethyl)cyclopropyl]phenyl]-1,3,2-dioxaborolane

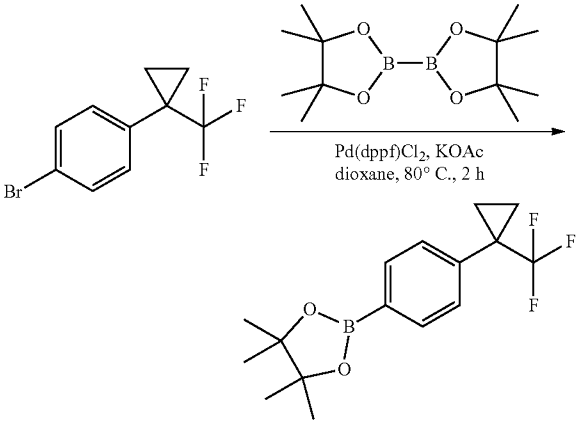

Into a 25-mL 3-necked round-bottom flask purged and maintained with an inert atmosphere of nitrogen, was placed 1-bromo-4-[1-(trifluoromethyl)cyclopropyl]benzene (500 mg, 1.9 mmol, 1.0 equiv), dioxane (10 mL), bis(pinacolato) diboron (1.2 g, 4.7 mmol, 2.5 equiv), KOAc (370 mg, 3.8 mmol, 2.0 equiv), $Pd(dppf)Cl_2$ (138 mg, 0.19 mmol, 0.1 equiv). The resulting solution was stirred for 2 hr at 80 degrees C. The reaction mixture was cooled to room temperature. The resulting mixture was concentrated. The residue was applied onto a silica gel column with petroleum. This resulted in 500 mg (81%) of 4,4,5,5-tetramethyl-2-[4-[l-(trifluoromethyl)cyclopropyl]phenyl]-1,3,2-dioxaborolane as a white solid.

Synthesis of 2-[4-(1-fluorocyclopropyl)phenyl]-4,4,5,5-tetramethyl-1,3,2-dioxaborolane Synthesis of 1-bromo-4-(2-bromo-1-fluoroethyl)benzene

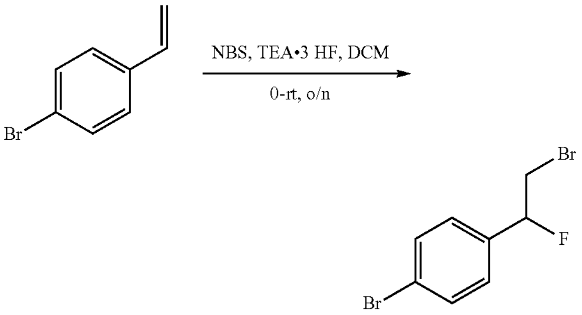

Into a 250-mL round-bottom flask, was placed 4-bromostyrene (10 g, 55 mmol, 1.0 equiv), DCM (100 mL), TEA·3HF (26 g, 0.16 mol, 3 equiv), the NBS (24 g, 0.14 mol, 2.50 equiv) was added at 0 degrees C. The resulting solution was stirred for 1 overnight at room temperature. The resulting mixture was washed with 2×50 ml of aq. $NaHCO_3$ and 2×50 mL of aq. HCl. The resulting mixture was concentrated. The residue was applied onto a silica gel column with ethyl acetate/petroleum ether (0:100). This resulted in 8 g (52%) of 1-bromo-4-(2-bromo-1-fluoroethyl) benzene as yellow oil.

Synthesis of 1-bromo-4-(1-fluoroethenyl)benzene

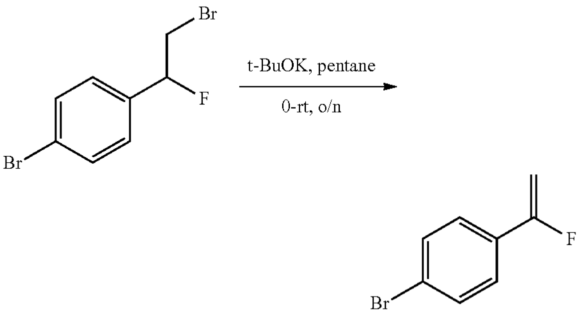

Into a 250-mL round-bottom flask, was placed 1-bromo-4-(2-bromo-1-fluoroethyl)benzene (8.00 g, 28 mmol, 1.0 equiv), pentane (80 mL), t-BuOK (19 g, 0.17 mol, 6 equiv). The resulting solution was stirred overnight at 25 degrees C. The solids were filtered out. The filtrate was concentrated. The residue was applied onto a silica gel column with ethyl acetate/petroleum ether (0:100). This resulted in 3 g (53%) of 1-bromo-4-(1-fluoroethenyl)benzene as yellow oil.

Synthesis of 1-bromo-4-(1-fluorocyclopropyl)benzene

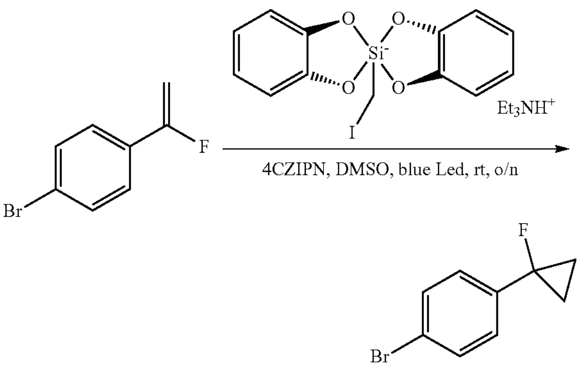

Into a 40 mL vial were added 1-bromo-4-(1-fluoroethenyl)benzene (500 mg, 2.5 mmol, 1.0 equiv), DMSO (12 mL), 2-(iodomethyl)-1H-2lambda5-2,2'-spirobi[[1,3,2]benzodioxasilol]-1-ium (1.45 g, 3.8 mmol, 1.5 equiv) and 4CZIPN (98 mg, 0.12 mmol, 0.05 equiv). The resulting mixture was stirred overnight at room temperature under nitrogen atmosphere and blue LEDs. The resulting mixture was diluted with ethyl acetate (200 mL). The resulting mixture was filtered through a celite pad. The filtrate was diluted with brine (200 mL). The resulting mixture was extracted with EtOAc (3×200 mL). The combined organic layers were washed with brine (3×500 mL). The combined organic layers were concentrated under reduced pressure. The residue was purified by silica gel column chromatography, eluted with 100% PE to afford 1-bromo-4-(1-fluorocyclopropyl)benzene (460 mg, 43%) as a light-yellow oil.

Synthesis of 2-[4-(1-fluorocyclopropyl)phenyl]-4,4,5,5-tetramethyl-1,3,2-dioxaborolane

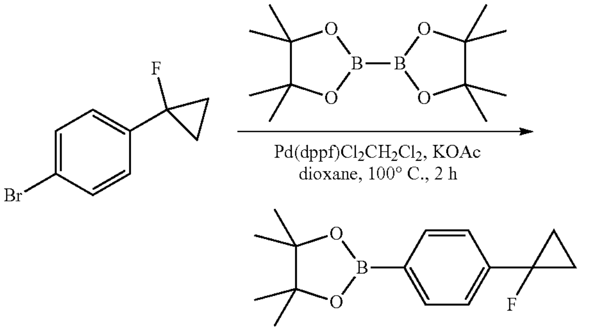

Into a 40 mL vial were added 1-bromo-4-(1-fluorocyclopropyl)benzene (460 mg, 2.1 mmol, 1.0 equiv), dioxane (5 mL), bis(pinacolato)diboron (708 mg, 2.8 mmol, 2.0 equiv), $Pd(dppf)Cl_2 \cdot CH_2Cl_2$ (114 mg, 0.14 mmol, 0.1 equiv) and KOAc (420 mg, 4.3 mmol, 2.0 equiv). The resulting mixture was stirred for 2 h at 100° C. under nitrogen atmosphere. The mixture was allowed to cool down to room temperature. The resulting mixture was concentrated under reduced pressure. The residue was purified by silica gel column chromatography, eluted with 100% PE to afford 2-[4-(1-fluorocyclopropyl)phenyl]-4,4,5,5-tetramethyl-1,3,2-dioxaborolane (300 mg) as a light yellow solid.

Synthesis of 1-[4-(4,4,5,5-tetramethyl-1,3,2-dioxaborolan-2-yl)phenyl]cyclopropane-1-carbonitrile

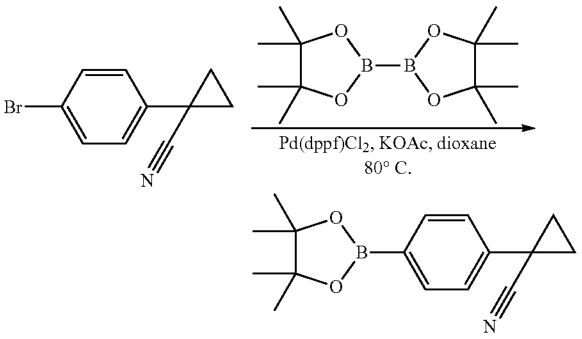

Into a 50-mL round-bottom flask purged and maintained with an inert atmosphere of nitrogen, was placed 1-(4-bromophenyl)cyclopropane-1-carbonitrile (1.0 g, 4.5 mmol, 1.0 equiv), dioxane (10 mL), bis(pinacolato)diboron (2.3 g, 9.1 mmol, 2.0 equiv), KOAc (890 mg, 9.0 mmol, 2.0 equiv), $Pd(dppf)Cl_2$ (165 mg, 0.23 mmol, 0.05 equiv). The resulting solution was stirred for 2 hr at 80 degrees C. The resulting mixture was concentrated under vacuum. The residue was applied onto a silica gel column with ethyl acetate/petroleum ether (1/4). This resulted in 1.2 g (79%) of 1-[4-(4,4,5,5-tetramethyl-1,3,2-dioxaborolan-2-yl)phenyl]cyclopropane-1-carbonitrile as a white solid.

Synthesis of 1-[4-(4,4,5,5-tetramethyl-1,3,2-dioxaborolan-2-yl)phenyl]cyclopropane-1-carbonitrile

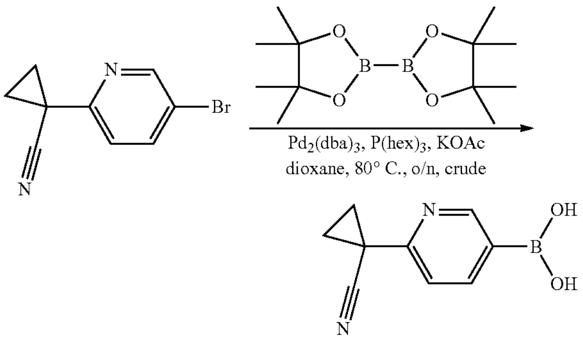

Into a 40-mL vial purged and maintained with an inert atmosphere of nitrogen, was placed 1-(5-bromopyridin-2-yl)cyclopropane-1-carbonitrile (500 mg, 2.2 mmol, 1.0 equiv), bis(pinacolato)diboron (683 mg, 2.7 mmol, 1.2 equiv), KOAc (550 mg, 5.6 mmol, 2.5 equiv), dioxane (10 mL), $P(hex)_3$ (94 mg, 0.3 mmol, 0.15 equiv), $Pd_2(dba)_3$ (205 mg, 0.2 mmol, 0.1 equiv). The resulting solution was stirred overnight at 80 degrees C. in an oil bath. The product was used in the next step directly without further purification.

Synthesis of 5-(4,4,5,5-tetramethyl-1,3,2-dioxaborolan-2-yl)-2-[1-(trifluoromethyl)cyclopropyl]pyridine

Synthesis of 1-(5-bromopyridin-2-yl)cyclopropane-1-carboxylic acid

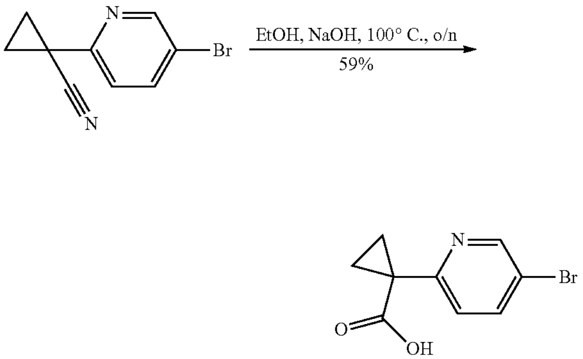

Into a 40-mL round-bottom flask, was placed 1-(5-bromopyridin-2-yl)cyclopropane-1-carbonitrile (500 mg, 2.2 mmol, 1.0 equiv), EtOH (20 mL), a solution of NaOH (6 mL, 25%) in $H_2O$. The resulting solution was stirred overnight at 100 degrees C. The resulting mixture was concentrated. The pH value of the solution was adjusted to 3-4 with (1 mol/L). The resulting solution was extracted with 3×50 mL of ethyl acetate and the organic layers combined and dried over anhydrous $Na_2SO_4$ and concentrated. This resulted in 320 mg (59%) of 1-(5-bromopyridin-2-yl)cyclopropane-1-carboxylic acid as a light yellow solid.

Synthesis of 5-bromo-2-[1-(trifluoromethyl)cyclopropyl]pyridine

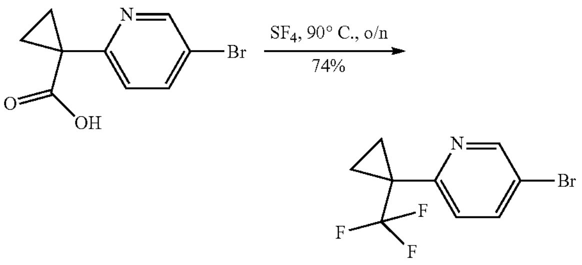

Into a 30-mL pressure tank reactor, was placed 1-(5-bromopyridin-2-yl)cyclopropane-1-carboxylic acid (320 mg, 1.3 mmol, 1.0 equiv). This was followed by the addition of tetrafluoro-lambda4-sulfane (5 mL) at −180 degrees C. To this was added $H_2O$ (47 mg, 2.6 mmol, 2 equiv) at −180 degrees C. The resulting solution was stirred overnight at 90 degrees C. in an oil bath. The resulting mixture was concentrated. The residue was applied onto a silica gel column with ethyl acetate/petroleum ether (1:8). This resulted in 260 mg (74%) of 5-bromo-2-[1-(trifluoromethyl)cyclopropyl]pyridine as light-yellow oil.

Synthesis of 5-(4,4,5,5-tetramethyl-1,3,2-dioxaborolan-2-yl)-2-[1-(trifluoromethyl)cyclopropyl]pyridine

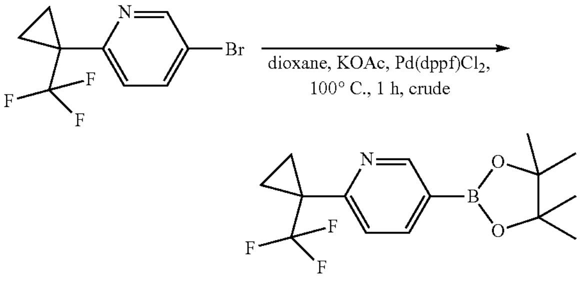

Into a 40-mL round-bottom flask purged and maintained with an inert atmosphere of nitrogen, was placed 5-bromo-2-[1-(trifluoromethyl)cyclopropyl]pyridine (260 mg, 1.0 mmol, 1.0 equiv), bis(pinacolato)diboron (372 mg, 1.5 mmol, 1.5 equiv), dioxane (20 mL), KOAc (240 mg, 2.4 mmol, 2.5 equiv), $Pd(dppf)Cl_2$ (72 mg, 0.1 mmol, 0.1 equiv). The resulting solution was stirred for 1 hr at 100 degrees C. The product can be used directly as a crude compound in a subsequent reaction vide infra.

Synthesis of 2-[4-cyclopropyl-3-(trifluoromethyl)phenyl]-4,4,5,5-tetramethyl-1,3,2-dioxaborolane Synthesis of tert-butyl N-[4-bromo-3-(trifluoromethyl)phenyl]carbamate

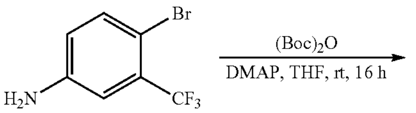

-continued

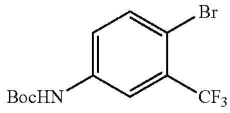

Into a 500-mL round-bottom flask, was placed 4-bromo-3-(trifluoromethyl)aniline (2.7 g, 11 mmol, 1.0 equiv), THF (45 mL), di-tert-butyl dicarbonate (3.7 g, 17 mmol, 1.5 equiv), DMAP (1.37 g, 11 mmol, 1.0 equiv). The resulting solution was stirred for 3 hr at room temperature. The reaction was then quenched by the addition of 100 mL of water. The resulting solution was extracted with 2×200 mL of ethyl acetate dried over anhydrous sodium sulfate and concentrated. The residue was applied onto a silica gel column with ethyl acetate/petroleum ether (1:20). This resulted in 2.9 g (80%) of tert-butyl N-[4-bromo-3-(trifluoromethyl)phenyl]carbamate as yellow oil.

Synthesis of tert-butyl N-[4-cyclopropyl-3-(trifluoromethyl)phenyl]carbamate

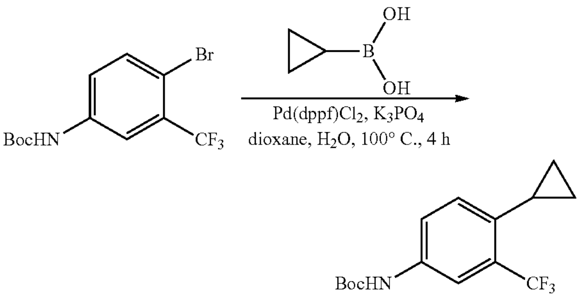

Into a 500-mL round-bottom flask purged and maintained with an inert atmosphere of nitrogen, was placed tert-butyl N-[4-bromo-3-(trifluoromethyl)phenyl]carbamate (2.9 g, 8.5 mmol, 1.0 equiv), cyclopropylboronic acid (1.5 g, 17 mmol, 2.0 equiv), $Pd(dppf)Cl_2$ (0.6 g, 0.9 mmol, 0.10 equiv), $K_3PO_4$ (3.6 g, 17 mmol, 2.0 equiv), dioxane (29 mL), $H_2O$ (2.9 mL). The resulting solution was stirred for 4 hr at 100 degrees C. The resulting mixture was concentrated. The residue was applied onto a silica gel column with ethyl acetate/petroleum ether (1:10). This resulted in 2.3 g (90%) of tert-butyl N-[4-cyclopropyl-3-(trifluoromethyl)phenyl]carbamate as yellow oil.

Synthesis of 4-cyclopropyl-3-(trifluoromethyl)aniline

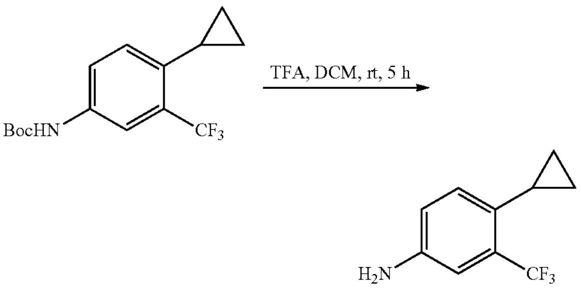

Into a 500-mL round-bottom flask, was placed tert-butyl N-[4-cyclopropyl-3-(trifluoromethyl)phenyl]carbamate (2.1 g, 7.0 mmol, 1.0 equiv), DCM (100 mL), TFA (20 mL). The resulting solution was stirred for 5 hr at room temperature. The pH value of the solution was adjusted to 8 with $NaHCO_3$ (1 mol/L). The resulting solution was extracted with 4×200 mL of dichloromethane concentrated. This resulted in 0.95 g (68%) of 4-cyclopropyl-3-(trifluoromethyl)aniline as yellow oil.

Synthesis of 2-[4-cyclopropyl-3-(trifluoromethyl) phenyl]-4,4,5,5-tetramethyl-1,3,2-dioxaborolane

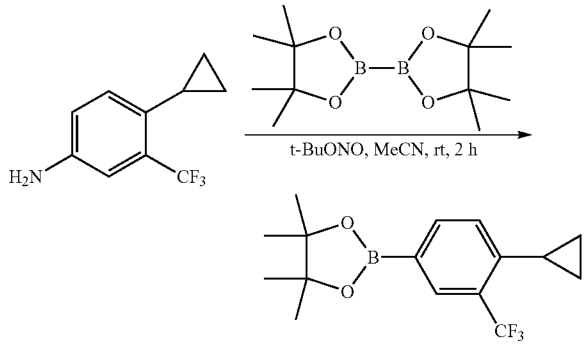

Into a 250-mL round-bottom flask, was placed 4-cyclopropyl-3-(trifluoromethyl)aniline (1.0 g, 5.0 mmol, 1.0 equiv), MeCN (50 mL), bis(pinacolato)diboron (1.9 g, 7.5 mmol, 1.5 equiv), 2-methyl-2-propylnitrit (1.0 g, 9.9 mmol, 2.0 equiv). The resulting solution was stirred for 2 hr at room temperature. The resulting mixture was concentrated. The residue was applied onto a silica gel column with ethyl acetate/petroleum ether (1:100). This resulted in 400 mg (26%) of 2-[4-cyclopropyl-3-(trifluoromethyl)phenyl]-4,4,5,5-tetramethyl-1,3,2-dioxaborolane as yellow oil.

Synthesis of tert-butyldimethyl[1-[4-(4,4,5,5-tetramethyl-1,3,2-dioxaborolan-2-yl)phenyl]cyclopropoxy] silane Synthesis of [[1-(4-bromophenyl)ethenyl]oxy](tert-butyl)dimethylsilane

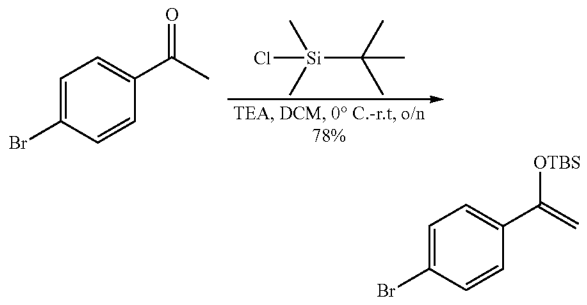

Into a 250-mL 3-necked round-bottom flask, was placed p-bromoacetophenone (5.0 g, 25 mmol, 1.0 equiv), DCM (50 mL). This was followed by the addition of TEA (3.8 g, 38 mmol, 1.5 equiv) dropwise with stirring at 0° C. To this was added a solution of tert-butyldimethylsilyl trifluoromethanesulfonate (8.6 g, 33 mmol, 1.3 equiv) in DCM (5 mL) dropwise with stirring at 0° C. The resulting solution was stirred for 2 hr at 0° C. in an ice/salt bath. The resulting solution was stirred for 15 hr at room temperature. The reaction was then quenched by the addition of 200 mL of saturated aqueous $NaHCO_3$. The resulting solution was extracted with 3x 150 mL of dichloromethane and the organic layers combined and concentrated. The residue was applied onto a silica gel column with PE (100%). This resulted in 6.1 g (78%) of [[l-(4-bromophenyl)ethenyl]oxy] (tert-butyl)dimethylsilane as light yellow oil.

Synthesis of [1-(4-bromophenyl)cyclopropoxy](tert-butyl)dimethylsilane

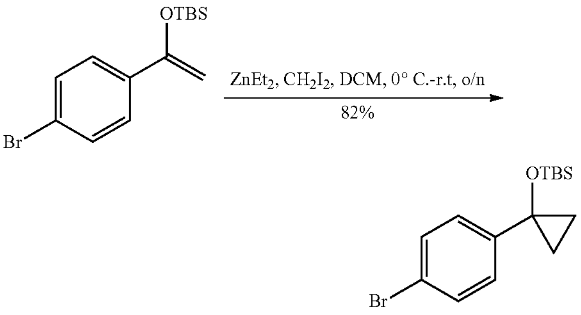

Into a 250-mL 3-necked round-bottom flask purged and maintained with an inert atmosphere of nitrogen, was placed [[1-(4-bromophenyl)ethenyl]oxy](tert-butyl)dimethylsilane (1 g, 3.2 mmol, 1.0 equiv), DCM (50 mL). This was followed by the addition of $CH_2I_2$(4.3 g, 16 mmol, 5.0 equiv) dropwise with stirring at 0° C. To this was added ZnEt2 in hexanes (8.0 mL, 8.0 mmol, 2.5 equiv) dropwise with stirring at 0° C. The resulting solution was stirred for 1 hr at 0° C. in an ice/salt bath. The resulting solution was stirred for 15 hr at room temperature. The resulting solution was diluted with 100 mL of saturated aqueous $NaHCO_3$. The solids were filtered out. The resulting solution was extracted with 3×150 mL of dichloromethane and the organic layers combined and concentrated. The residue was applied onto a silica gel column with ethyl acetate/petroleum ether (100% PE). This resulted in 860 mg (82%) of [1-(4-bromophenyl) cyclopropoxy](tert-butyl)dimethylsilane as light-yellow oil.

Synthesis of tert-butyldimethyl[1-[4-(4,4,5,5-tetramethyl-1,3,2-dioxaborolan-2-yl)phenyl]cyclopropoxy] silane

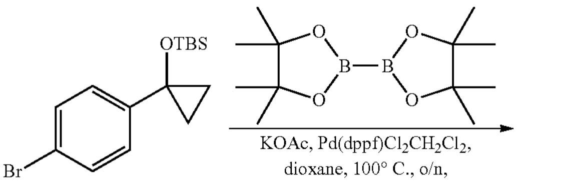

-continued

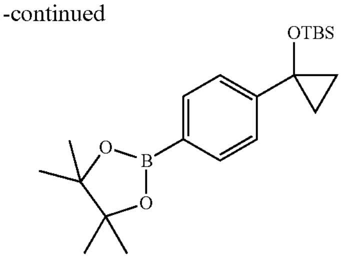

Into a 100-mL round-bottom flask purged and maintained with an inert atmosphere of nitrogen, was placed [1-(4-bromophenyl)cyclopropoxy](tert-butyl)dimethylsilane (800 mg, 2.4 mmol, 1.0 equiv), dioxane (25 mL), bis(pinacolato) diboron (750 mg, 2.9 mmol, 1.2 equiv), KOAc (481 mg, 4.9 mmol, 2.0 equiv), $Pd(dppf)C1_2CH_2Cl_2$ (100 mg, 0.12 mmol, 0.05 equiv). The resulting solution was stirred for 15 hr at 100° C. in an oil bath. The reaction mixture was cooled to room temperature. The resulting mixture was concentrated. The residue was applied onto a silica gel column with ethyl acetate/petroleum ether (100% PE). This resulted in 900 mg (crude) of tert-butyldimethyl[1-[4-(4,4,5,5-tetramethyl-1,3,2-dioxaborolan-2-yl)phenyl]cyclopropoxy]silane as light-yellow oil.

Synthesis of 2-[3-cyclopropyl-4-(trifluoromethyl) phenyl]-4,4,5,5-tetramethyl-1,3,2-dioxaborolane

Synthesis of tert-butyl N-[3-bromo-4-(trifluoromethyl)phenyl]carbamate

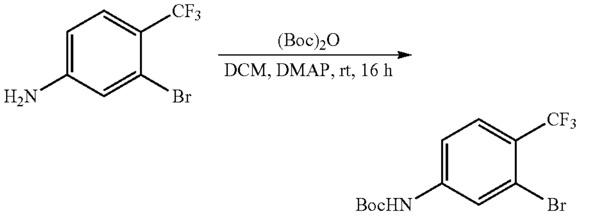

Into a 500-mL round-bottom flask, was placed 3-bromo-4-(trifluoromethyl)aniline (10 g, 42 mmol, 1.0 equiv), DCM (100 mL), DMAP (2.5 g, 21 mmol, 0.5 equiv), di-tert-butyl dicarbonate (11 g, 50 mmol, 1.2 equiv). The resulting solution was stirred for 16 hr at room temperature. The reaction was then quenched by the addition of water. The resulting solution was extracted with 2×300 mL of dichloromethane dried over anhydrous sodium sulfate and concentrated. The residue was applied onto a silica gel column with ethyl acetate/petroleum ether (1:20). This resulted in 8 g (56%) of tert-butyl N-[3-bromo-4-(trifluoromethyl)phenyl]carbamate as a yellow solid.

Synthesis of tert-butyl N-[3-cyclopropyl-4-(trifluoromethyl)phenyl]carbamate

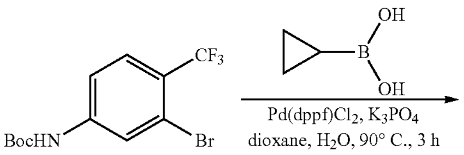

-continued

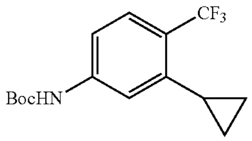

Into a 500-mL round-bottom flask purged and maintained with an inert atmosphere of nitrogen, was placed tert-butyl N-[3-bromo-4-(trifluoromethyl)phenyl]carbamate (6.0 g, 17 mmol, 1.0 equiv), cyclopropylboronic acid (3.0 g, 35 mmol, 2.0 equiv), $Pd(dppf)Cl_2$ (1.3 g, 1.8 mmol, 0.1 equiv), $K_3PO_4$ (9.4 g, 44 mmol, 2.5 equiv), dioxane (60 mL), $H_2O$ (6 mL). The resulting solution was stirred for 3 hr at 90 degrees C. The resulting mixture was concentrated. The residue was applied onto a silica gel column with ethyl acetate/petroleum ether (1:20). This resulted in 5 g (94%) of tert-butyl N-[3-cyclopropyl-4-(trifluoromethyl)phenyl]carbamate as yellow oil.

Synthesis of 3-cyclopropyl-4-(trifluoromethyl)aniline

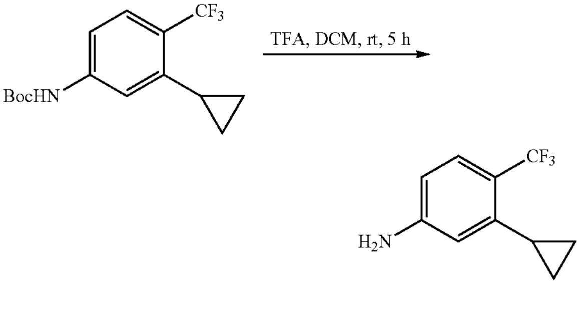

Into a 1000-mL round-bottom flask, was placed tert-butyl N-[3-cyclopropyl-4-(trifluoromethyl)phenyl]carbamate (5.0 g, 16 mmol, 1.0 equiv), DCM (500 mL), TFA (50 mL). The resulting solution was stirred for 5 hr at room temperature. The pH value of the solution was adjusted to 8 with $NaHCO_3$ (1 mol/L). The resulting solution was extracted with 2×300 mL of dichloromethane and dried over anhydrous sodium sulfate and concentrated. This resulted in 2.8 g (84%) of 3-cyclopropyl-4-(trifluoromethyl)aniline as yellow oil.

Synthesis of 2-[3-cyclopropyl-4-(trifluoromethyl) phenyl]-4,4,5,5-tetramethyl-1,3,2-dioxaborolane

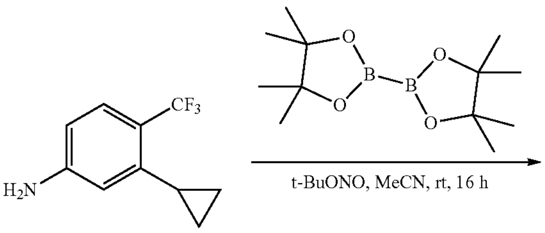

-continued

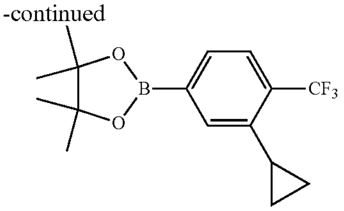

Into a 250-mL round-bottom flask, was placed 3-cyclopropyl-4-(trifluoromethyl)aniline (500 mg, 2.5 mmol, 1.0 equiv), MeCN (25 mL), bis(pinacolato)diboron (950 mg, 3.7 mmol, 1.5 equiv), 2-methyl-2-propylnitrit (513 mg, 5.0 mmol, 2.00 equiv). The resulting solution was stirred for 16 hr at room temperature. The resulting mixture was concentrated. The residue was applied onto a silica gel column with ethyl acetate/petroleum ether (1:100). This resulted in 160 mg (21%) of 2-[3-cyclopropyl-4-(trifluoromethyl)phenyl]-4,4,5,5-tetramethyl-1,3,2-dioxaborolane as yellow oil.

Synthesis of 2-(4-cyclopropyl-3-fluorophenyl)-4,4,5,5-tetramethyl-1,3,2-dioxaborolane Synthesis of 1-cyclopropyl-2-fluoro-4-nitrobenzene

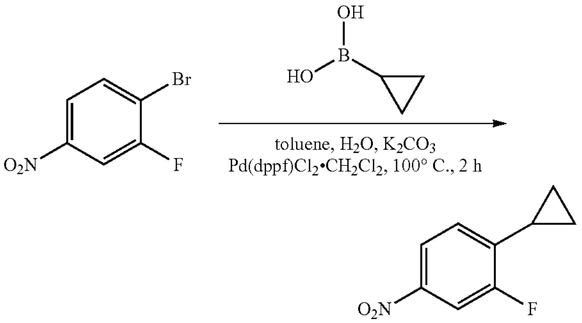

Into a 250-mL round-bottom flask purged and maintained with an inert atmosphere of nitrogen, was placed 1-bromo-2-fluoro-4-nitrobenzene (5.0 g, 23 mmol, 1.0 equiv), cyclopropylboronic acid (3.0 g, 35 mmol, 1.5 equiv), toluene (50 mL), $H_2O$ (10 mL), $K_2CO_3$ (6.3 g, 46 mmol, 2.0 equiv). $Pd(dppf)Cl_2·CH_2Cl_2$ (1.8 g, 2.2 mmol, 0.1 equiv). The resulting solution was stirred for 2 hr at 100 degrees C. The reaction mixture was cooled to room temperature. The reaction was then quenched by the addition of 100 mL of water. The resulting solution was extracted with 3×100 mL of ethyl acetate and the organic layers combined and dried over anhydrous sodium sulfate and concentrated under vacuum. The residue was applied onto a silica gel column with ethyl acetate/petroleum ether (1:5). This resulted in 3.4 g (83%) of 1-cyclopropyl-2-fluoro-4-nitrobenzene as yellow oil.

Synthesis of 4-cyclopropyl-3-fluoroaniline

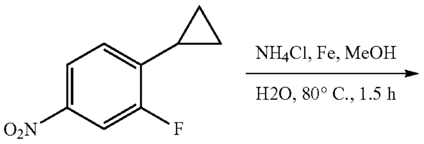

-continued

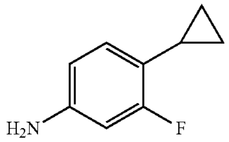

Into a 250-mL round-bottom flask purged and maintained with an inert atmosphere of nitrogen, was placed 1-cyclopropyl-2-fluoro-4-nitrobenzene (3.0 g, 17 mmol, 1.0 equiv), MeOH (45.00 mL), $NH_4Cl$ (8.8 g, 164 mmol, 9.9 equiv), $H_2O$ (45 mL), Fe (4.6 g, 82 mmol, 5.0 equiv). The resulting solution was stirred for 1.5 hr at 80 degrees C. The reaction mixture was cooled to room temperature. The solids were filtered out. The reaction was then quenched by the addition of 100 mL. of NaCl (100.00 mL). The resulting solution was extracted with 2×100 mL of ethyl acetate and the organic layers combined and dried over anhydrous sodium sulfate and concentrated under vacuum. This resulted in 2.4 g (96%) of 4-cyclopropyl-3-fluoroaniline as yellow oil.

Synthesis of 2-(4-cyclopropyl-3-fluorophenyl)-4,4,5,5-tetramethyl-1,3,2-dioxaborolane

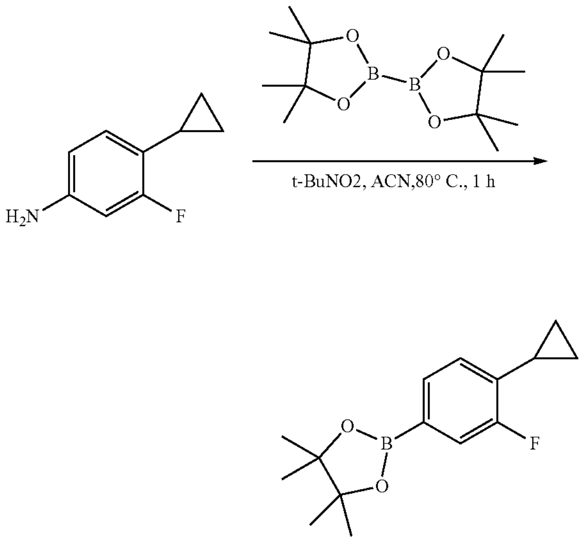

Into a 500-mL round-bottom flask purged and maintained with an inert atmosphere of nitrogen, was placed 4-cyclopropyl-3-fluoroaniline (2.4 g, 16 mmol, 1.0 equiv), ACN (30 mL), bis(pinacolato)diboron (6 g, 24 mmol, 1.5 equiv), t-$BuONO_2$ (3.7 g, 31 mmol, 2.0 equiv). The resulting solution was stirred for 1 hr at 80 degrees C. The reaction mixture was cooled to room temperature. The resulting mixture was concentrated under vacuum. The residue was applied onto a silica gel column with ethyl acetate/petroleum ether (1:4). This resulted in 2 g (48%) of 2-(4-cyclopropyl-3-fluorophenyl)-4,4,5,5-tetramethyl-1,3,2-dioxaborolane as yellow oil.

Synthesis of 5-bromo-3-ethylsulfonyl-2-[6-trifluoromethyl-triazolo[1,5-a]pyridine-2-yl]pyridine

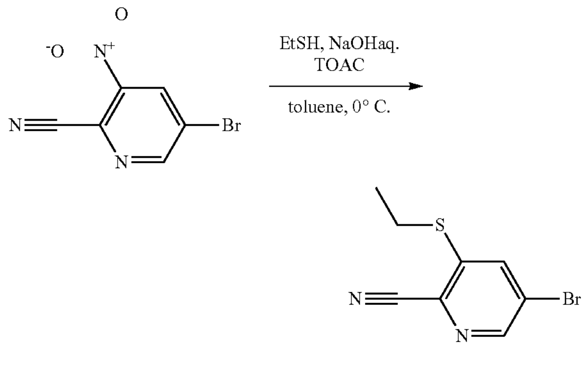

5-bromo-2-cyano-3-nitro-pyridine (5 g, 21.9 mmol, 1.0 equiv.) and tetraoctylammonium bromide (360 mg, 0.658 mmol, 3 mol %) in toluene (40 ml) were cooled to 0 degrees C. and added a solution of sodium hydroxide (1.08 g, 27 mmol, 1.23 equiv.) and ethanethiol (1.95 ml, 27 mmol, 1.23 equiv.) in ice water (20 ml). After 15 stirring for 1 hr at 0 degrees C. The reaction was then quenched by the addition of 100 mL of water. The resulting solution was extracted with 2×200 mL of ethyl acetate dried over anhydrous sodium sulfate and concentrated. The residue was applied onto a silica gel column with ethyl acetate/hexane (1:5). This resulted in 3.6 g (67.72%) of 5-bromo-2-cyano-3-ethylsulfanyl-pyridine as a yellow solid.

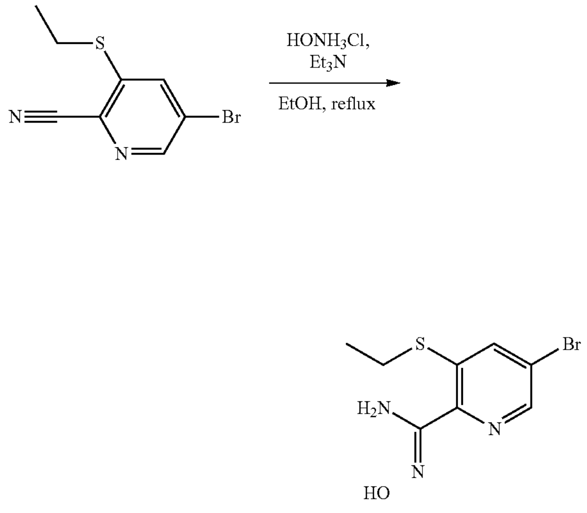

5-bromo-2-cyano-3-ethylsulfanyl-pyridine (3.6 g, 14.8 mmol, 1.0 equiv.) and hydroxylamine hydrochloride (3.1 g, 44.6 mmol, 3.0 equiv.) in ethanol (20 ml) was added triethylamine (5 ml) and heated to reflux. The mixture was stirred for 4 hr. After cooled to room temperature, the mixture was added water (20 ml) and stirred for 30 min. The precipitate was filtered and washed with ethanol and water. The residue was dried by vacuo. This resulted in 3.2 g (78.33%) of 5-bromo-3-ethylsulfanyl-2-pyridine carboximidamide as a white solid.

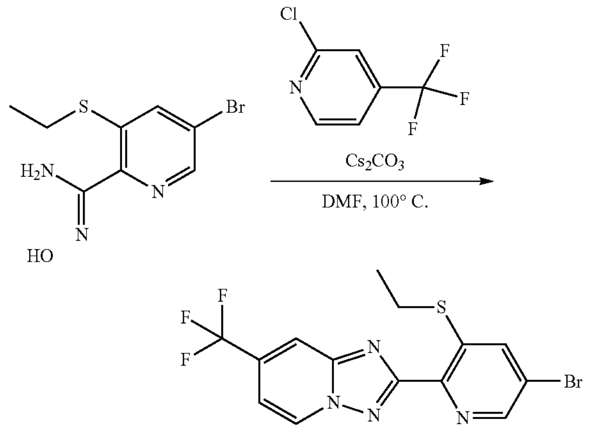

5-bromo-3-ethylsulfanyl-2-pyridine carboximidamide (276 mg, 1 mmol, 1.0 equiv.) and cesium bicarbonate (1.3 g, 4.0 mmol, 4.0 equiv.) in dimethylformamide (2 ml) was added 2-chloro-4-trifluoromethylpyridine (567 mg, 3.0 mmol, 3 equiv.) and heated to 120 degrees C. The mixture was stirred for 1 hr. After cooled to room temperature, the mixture was added water (5 ml) and ethylacetate (5 ml). The resulting solution was extracted with 2×5 mL of ethyl acetate dried over anhydrous sodium sulfate and concentrated. The residue was applied onto a silica gel column with ethyl acetate/hexane (1:2). This resulted in 195 mg (48.39%) of 5-bromo-3-ethylsulfanyl-2-[6-trifluoromethyl-triazolo[1,5-a]pyridine-2-yl]pyridine as a yellow solid.

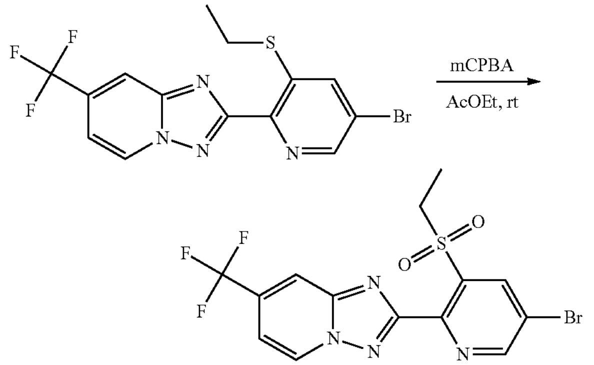

5-bromo-3-ethylsulfanyl-2-[6-trifluoromethyl-triazolo[1,5-a]pyridine-2-yl]pyridine (195 mg, 0.49 mmol, 1.0 equiv.) in ethyl acetate was added 65% m-chloroperbenzoic acid (287 mg, 1.07 mmol, 2.2 equiv.) and stirred for 2 hr at room temperature. The mixture was added water (5 ml) and ethylacetate (5 ml). The resulting solution was extracted with 2×5 mL of ethyl acetate dried over anhydrous sodium sulfate and concentrated. The residue was applied onto a silica gel column with ethyl acetate/hexane (1:2). This resulted in 178 mg (83.51%) of 5-bromo-3-ethylsulfonyl-2-[6-trifluoromethyl-triazolo[1,5-a]pyridine-2-yl]pyridine as a white solid.

Synthesis of Compound 1

Specifically, the following compounds of formula (I) can be synthesized by adopting the subsequent scheme of Compound 1 by someone who is skilled in the art and employing the starting material described vide supra: 173, 174, 175.

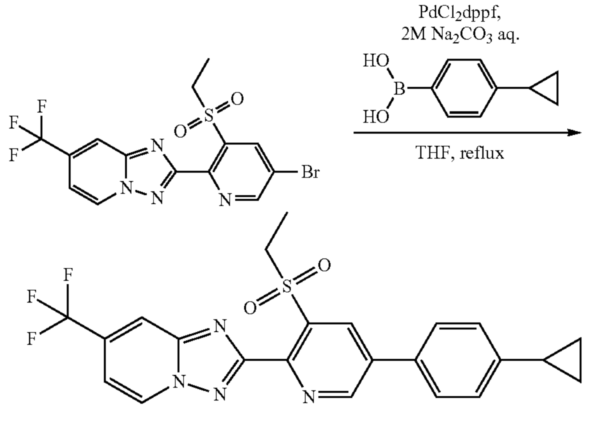

1

5-bromo-3-ethylsulfonyl-2-[6-trifluoromethyl-triazolo[1,5-a]pyridine-2-yl]pyridine (40.00 mg, 0.092 mmol, 1.00 equiv), tetrahydrofuran (2.00 mL), 4-cyclopropylphenylboronic acid (30.00 mg, 0.184 mmol, 2.00 equiv), 2M Na2CO3 aq. (0.2 ml, 0.4 mmol, 4.35 equiv), $PdCl_2dppf$ (7.00 mg, 0.009 mmol, 0.1 equiv). The resulting solution was stirred for 1 hr at 80 degrees C. The resulting mixture was concentrated and applied onto a silica gel column with ethyl acetate/hexane (1:2). This resulted in 41 mg (93.75%) of 5-(4-cyclopropylphenyl)-3-ethylsulfonyl-2-[6-trifluoromethyl-triazolo[1,5-a]pyridine-2-yl]pyridine as a white solid.

Synthesis of Compound 2

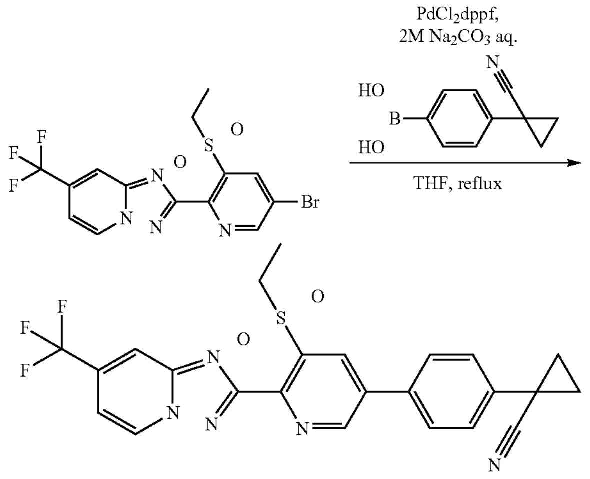

2

5-bromo-3-ethylsulfonyl-2-[6-trifluoromethyl-triazolo[1,5-a]pyridine-2-yl]pyridine (78.00 mg, 0.179 mmol, 1.00 equiv), tetrahydrofuran (2.00 mL), 4-cyclopropylphenylboronic acid (67.00 mg, 0.184 mmol, 2.00 equiv), 2M Na2CO3 aq. (0.5 ml, 1.0 mmol, 5.6 equiv), $PdCl_2dppf$ (14.00 mg, 0.018 mmol, 0.1 equiv). The resulting solution was stirred for 1 hr at 80 degrees C. The resulting mixture was concentrated and applied onto a silica gel column with ethyl acetate/hexane (1:2). This resulted in 41 mg (93.75%) of 1-[4-[5-(ethylsulfonyl)-6-[[6-trifluoromethyl-triazolo[1,5-a]pyridine-2-yl]pyridine]pyridin-3-yl]phenyl]cyclopropane-1-carbonitrile as a white solid.

Synthesis of Compound 3

Specifically, the following compounds of formula (I) can be synthesized by adopting the subsequent scheme of Compound 3 by someone who is skilled in the art and employing the starting material described vide supra: 4, 5, 16, 35, 112, 113, 118, 119, 120, 142, 143, 144, 145, 146, 148, 150, 151, 152, 153, 177, 180, 183:

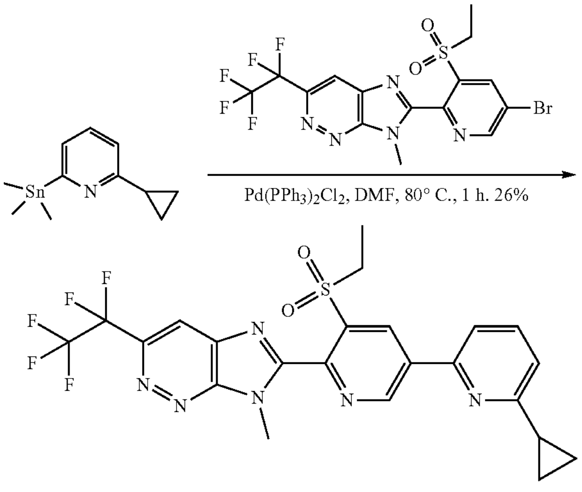

3

Into a 40-mL vial purged and maintained with an inert atmosphere of nitrogen, was placed 5-bromo-3-(ethanesulfonyl)-2-[7-methyl-3-(1,1,2,2,2-pentafluoroethyl)imidazo[4,5-clpyridazin-6-yl]pyridine (100 mg, 0.2 mmol, 1.0 equiv), 2-cyclopropyl-6-(trimethylstannyl)pyridine (684 mg, 0.2 mmol, 1.2 equiv), DMF (3 mL), $Pd(PPh_3)_2Cl_2$ (14 mg, 0.02 mmol, 0.1 equiv). The resulting solution was stirred for 1 hr at 80 degrees C. The reaction mixture was cooled to 25 degrees C. The reaction was then quenched by the addition of 50 mL of water/ice. The resulting solution was extracted with 3×50 mL of ethyl acetate and the organic layers combined. The resulting mixture was washed with 3×50 mL of brine. The mixture was dried over anhydrous sodium sulfate and concentrated. The crude product was purified by Flash-Prep-HPLC with the following conditions (CombiFlash-1): Column, Cl18 silica gel; mobile phase, $CH_3CN:H_2O$=32:68 increasing to $CH_3CN:H_2O$=84:16 within 8 min; Detector, 220 nm. This resulted in 27.5 mg (26%) of 6-cyclopropyl-5'-(ethanesulfonyl)-6'-[7-methyl-3-(1,1,2,2,2-pentafluoroethyl)imidazo[4,5-c]pyridazin-6-yl]-2,3'-bipyridine as a white solid Synthesis of Compound 6

Specifically, the following compounds of formula (I) can be synthesized by adopting the subsequent scheme of Compound 6 by someone who is skilled in the art and employing the starting material described vide supra: 13, 15, 17, 18, 19, 20, 22, 24, 25, 26, 32, 34, 44, 58, 59, 66, 68, 70, 71, 73, 74, 77, 78, 79, 80, 81, 84, 85, 86, 87, 88, 89, 90, 94, 109, 124, 129, 130, 131, 132, 133, 134, 135, 136, 137, 138, 139, 140, 141, 154, 155, 156, 157, 158, 159, 160, 161, 162, 163, 164, 165, 166, 167, 168, 169, 170, 184, 185, 186, 187, 188, 192, 193, 201, 211, 213:

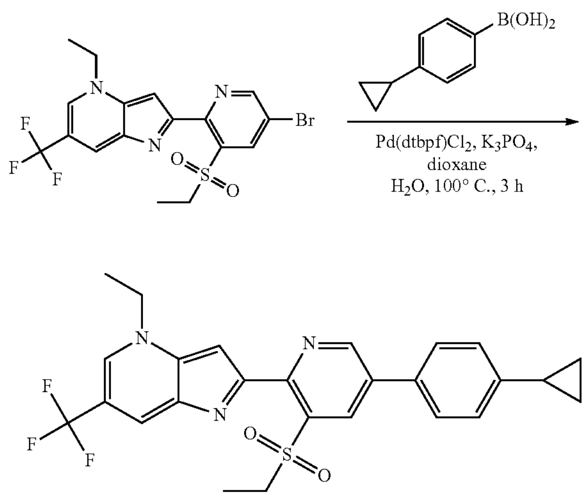

6

Into a 8-mL round-bottom flask purged and maintained with an inert atmosphere of nitrogen, was placed 5-bromo-3-(ethanesulfonyl)-2-[4-ethyl-6-(trifluoromethyl)pyrrolo[3,2-b]pyridin-2-yl]pyridine (50 mg, 0.1 mmol, 1.0 equiv), dioxane/$H_2O$=10/1 (2.00 mL), 4-cyclopropylphenylboronic acid (35 mg, 0.22 mmol, 2.0 equiv), $K_3PO_4 \cdot 3H_2O$ (58 mg, 0.22 mmol, 2.0 equiv), Pd(DtBPF)$Cl_2$ (7.0 mg, 0.01 mmol, 0.1 equiv). The resulting solution was stirred for 3 hr at 100 degrees C. The resulting mixture was concentrated. The crude product was purified by Flash-Prep-HPLC. This resulted in 30 mg (56%) of 5-(4-cyclopropylphenyl)-3-(ethanesulfonyl)-2-[4-ethyl-6-(trifluoromethyl)pyrrolo[3,2-b]pyridine-2-yl]pyridine as a yellow solid.

Synthesis of Compound 60

Specifically, the following compounds of formula (I) can be synthesized by adopting the subsequent scheme of Compound 60 by someone who is skilled in the art and employing the starting material described vide supra: 91

Into a 8-mL vial purged and maintained with an inert atmosphere of nitrogen, was placed 5-bromo-3-(ethanesulfonyl)-2-[7-methyl-3-(1,1,2,2,2-pentafluoroethyl)imidazo[4,5-c]pyridazin-6-yl]pyridine (55 mg, 0.11 mmol, 1.0 equiv), 4-bromo-2-cyclopropylpyridine (26 mg, 0.13 mmol, 1.2 equiv), bis(pinacolato)diboron (84 mg, 0.33 mmol, 3.0 equiv), $K_3PO_4$ (70 mg, 0.33 mmol, 3.0 equiv), THF (2 mL), $H_2O$ (0.5 mL), Pd(DtBPF)$C1_2$ (7.2 mg, 0.011 mmol, 0.1 equiv). The resulting solution was stirred for 2 hr at 70 degrees C. in an oil bath. The reaction mixture was cooled. The resulting solution was diluted with 100 mL of EA. The resulting mixture was washed with 3×50 mL of $H_2O$. The mixture was dried over anhydrous sodium sulfate and concentrated. The crude product was purified by Prep-HPLC with the following conditions (2 #SHIMADZU (HPLC-01)): Column, XBridge Shield RP18 OBD Column, 5 um,19*150 mm; mobile phase, Water (0.05% NH3$H_2O$) and ACN (44% Phase B up to 65% in 7 min). The product was obtained. This resulted in 24 mg (40%) of 2'-cyclopropyl-5-(ethanesulfonyl)-6-[7-methyl-3-(1,1,2,2,2-pentafluoroethyl)imidazo[4,5-c]pyridazin-6-yl]-3,4'-bipyridine as a white solid.

Synthesis of Compound 61

Specifically, the following compounds of formula (I) can be synthesized by adopting the subsequent scheme of Compound 61 by someone who is skilled in the art: 72 Synthesis of 5'-cyclopropyl-5-(ethylsulfanyl)-6-[7-methyl-3-(1,1,2,2,2-pentafluoroethyl)imidazo[4,5-c]pyridazin-6-yl]-3,3'-bipyridine

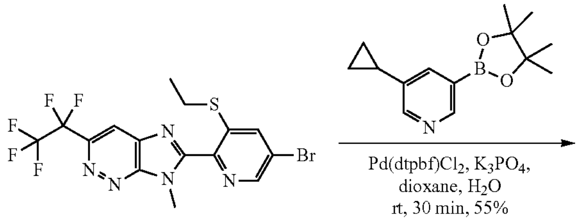

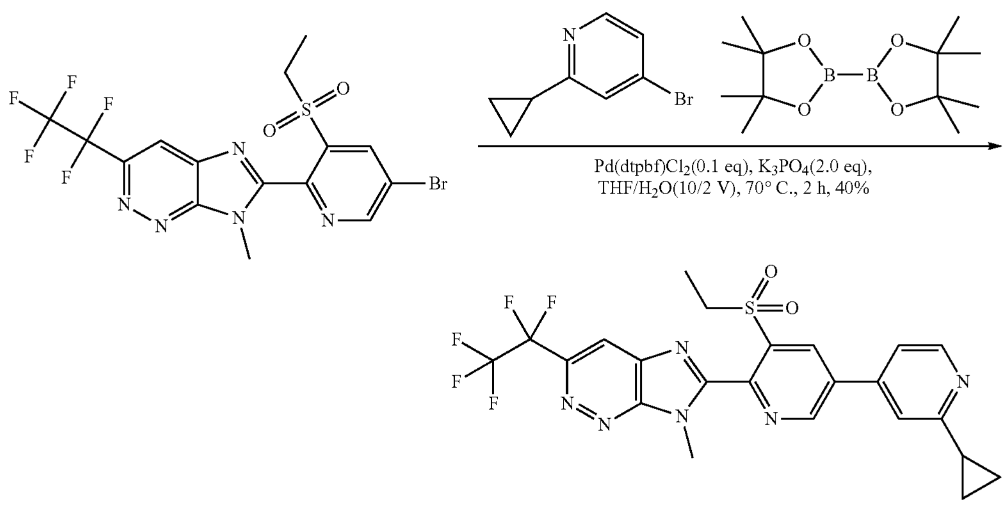

-continued

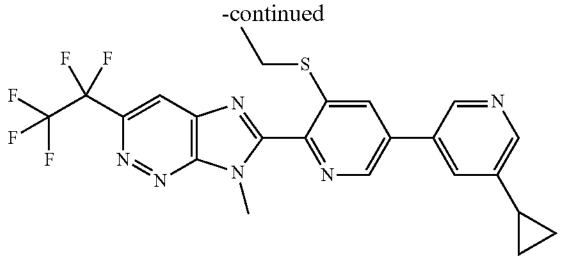

Into a 40-mL round-bottom flask purged and maintained with an inert atmosphere of nitrogen, was placed 5-bromo-3-(ethylsulfanyl)-2-[7-methyl-3-(1,1,2,2,2-pentafluoroethyl)imidazo[4,5-c]pyridazin-6-yl]pyridine (100 mg, 0.2 mmol, 1 equiv), 3-cyclopropyl-5-(4,4,5,5-tetramethyl-1,3,2-dioxaborolan-2-yl)pyridine (79 mg, 0.3 mmol, 1.5 equiv), Pd(dtbpf)$Cl_2$ (8.4 mg, 0.01 mmol, 0.06 equiv), $K_3PO_4$ (91 mg, 0.4 mmol, 2 equiv), dioxane (10 mL), $H_2O$ (2 mL). The resulting solution was stirred for 30 min at room temperature. The resulting solution was extracted with 3×50 mL of ethyl acetate and the organic layers combined and dried over anhydrous sodium sulfate and concentrated. The residue was applied onto a silica gel column with ethyl acetate/petroleum ether (1:2). This resulted in 60 mg (55%) of 5'-cyclopropyl-5-(ethylsulfanyl)-6-[7-methyl-3-(1,1,2,2,2-pentafluoroethyl)imidazo[4,5-c]pyridazin-6-yl]-3,3'-bipyridine as a brown solid.

Synthesis of 5'-cyclopropyl-5-(ethanesulfonyl)-6-[7-methyl-3-(1,1,2,2,2-pentafluoroethyl)imidazo[4,5-c]pyridazin-6-yl]-3,3'-bipyridine

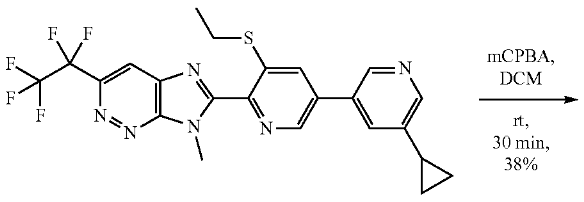

-continued

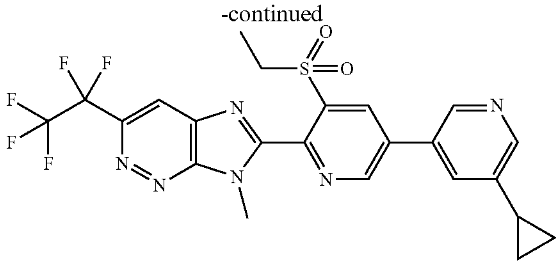

61

Into a 8-mL round-bottom flask purged and maintained with an inert atmosphere of nitrogen, was placed 5 (60 mg, 0.12 mmol, 1 equiv), DCM (5 mL), mCPBA (61 mg, 0.4 mmol, 3 equiv). The resulting solution was stirred for 30 min at room temperature. The crude product was purified by Prep-HPLC with the following conditions (2 #SHIMADZU (HPLC-01)): Column, XBridge Shield RP18 OBD Column, 5 um,19*150 mm; mobile phase, Water (0.05% NH3$H_2O$) and ACN (35% Phase B up to 58% in 7 min); This resulted in 24.3 mg (38%) of 5'-cyclopropyl-5-(ethanesulfonyl)-6-[7-methyl-3-(1,1,2,2,2-pentafluoroethyl)imidazo[4,5-c]pyridazin-6-yl]-3,3'-bipyridine as an off-white solid.

Synthesis of Compound 93

Synthesis of 2-cyclopropyl-5-[5-(ethylsulfanyl)-6-[7-methyl-3-(1,1,2,2,2-pentafluoroethyl)imidazo[4,5-c]pyridazin-6-yl]pyridin-3-yl]pyrimidine

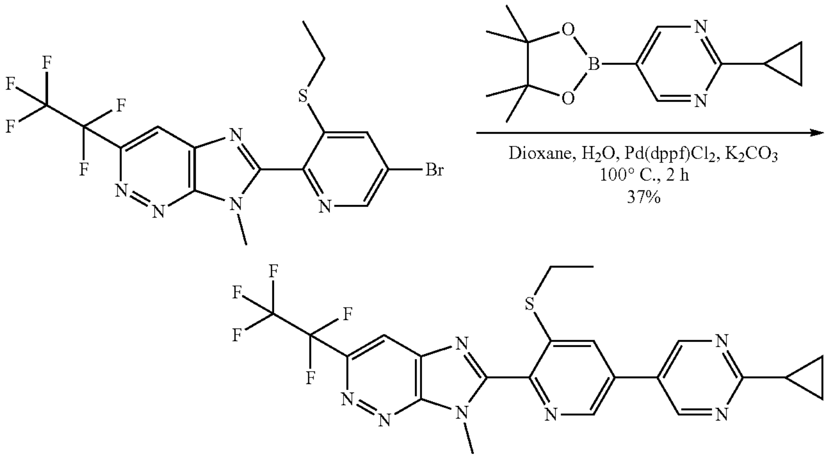

Into a 25-mL round-bottom flask purged and maintained with an inert atmosphere of nitrogen, was placed a solution of 5-bromo-3-(ethylsulfanyl)-2-[7-methyl-3-(1,1,2,2,2-pentafluoroethyl)imidazo[4,5-c]pyridazin-6-yl]pyridine (100 mg, 0.2 mmol, 1.0 equiv) in Dioxane (16 mL), a solution of $K_2CO_3$ (89 mg, 0.6 mmol, 3 equiv) in $H_2O$ (2 mL), Pd(dppf)$Cl_2$ (7.8 mg, 0.01 mmol, 0.05 equiv), 2-cyclopropyl-5-(4,4,5,5-tetramethyl-1,3,2-dioxaborolan-2-yl)pyrimidine (105 mg, 0.4 mmol, 2 equiv). The resulting solution was stirred for 2 hr at 100 degrees C. The mixture was dried over anhydrous sodium sulfate. The solids were filtered out. The filtrate was concentrated. The residue was applied onto a silica gel column with ethyl acetate/petroleum ether (1:3). This resulted in 40 mg (37%) of 2-cyclopropyl-5-[5-(ethylsulfanyl)-6-[7-methyl-3-(1,1,2,2,2-pentafluoroethyl)imidazo[4,5-c]pyridazin-6-yl]pyridin-3-yl]pyrimidine as yellow oil.

Synthesis of 2-cyclopropyl-5-[5-(ethanesulfonyl)-6-[7-methyl-3-(1,1,2,2,2-pentafluoroethyl)imidazo[4,5-c]pyridazin-6-yl]pyridin-3-yl]pyrimidine

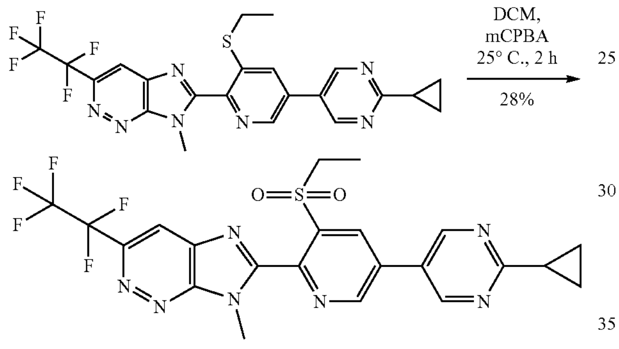

93

Into a 25-mL round-bottom flask, was placed a solution of 2-cyclopropyl-5-[5-(ethylsulfanyl)-6-[7-methyl-3-(1,1,2,2,2-pentafluoroethyl)imidazo[4,5-c]pyridazin-6-yl]pyridin-3-yl]pyrimidine (30 mg, 0.06 mmol, 1.0 equiv) in DCM (10 mL), mCPBA (31 mg, 0.18 mmol, 3 equiv). The resulting solution was stirred for 3 hr at 25 degrees C. The mixture was concentrated. The residue was purified by Prep-HPLC with the following conditions: Column, X-Bridge Column C18, 19*150 um, 20 ml/min; mobile phase, A: $H_2O$ (0.05% $NH_3H_2O$), B: ACN, 50-80% B, 9 min; Detector, 254 nm. This resulted in 9 mg (28%) of 2-cyclopropyl-5-[5-(ethanesulfonyl)-6-[7-methyl-3-(1,1,2,2,2-pentafluoroethyl)imidazo[4,5-c]pyridazin-6-yl]pyridin-3-yl]pyrimidine as a light yellow solid.

Synthesis of Compound 115

Specifically, the following compounds of formula (I) can be synthesized by adopting the subsequent scheme of Compound 115 by someone who is skilled in the art: 114, 116, 117

Synthesis of bis(pentafluoroethyl)zinc

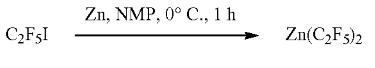

Into a 1-L 3-necked round-bottom flask purged and maintained with an inert atmosphere of nitrogen, was placed Zn (3.43 g, 52.457 mmol, 0.5 equiv), NMP (350.00 mL). This was followed by the addition of 1,1,1,1,1-pentafluoro-2-iodoethyne (25.80 g, 104.913 mmol, 1.00 equiv) dropwise with stirring at 0 degrees C. in 1 min. The resulting solution was stirred for 1 hr at room temperature. which was used in the next step without further purification.

Synthesis of 5-chloro-2-(1,1,2,2,2-pentafluoroethyl)pyridine

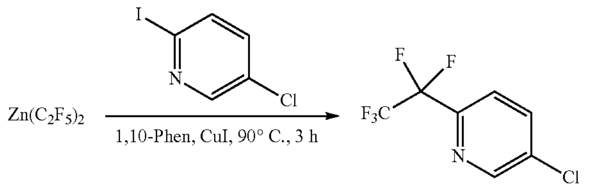 [SMILES: "Zn(C2F5)2" ; Clc1ccc(I)nc1 ; FC(F)(F)C(F)(F)c1ccc(Cl)cn1]

Into a 1000-mL 3-necked round-bottom flask purged and maintained with an inert atmosphere of nitrogen, was placed 5-chloro-2-iodopyridine (10 g, 41 mmol, 1. equiv), bis(1,1,2,2,2-pentafluoroethyl)zinc (16 g, 52 mol, 1.25 equiv), CuI (4.0 g, 21 mol, 0.5 equiv), 1,10-phenanthroline (3.8 g, 21 mol, 0.5 equiv), NMP (350 mL). The resulting solution was stirred for 3 hr at 90 degrees C. which was used in the next step without further purification.

Synthesis of N-methyl-6-(1,1,2,2,2-pentafluoroethyl)pyridin-3-amine

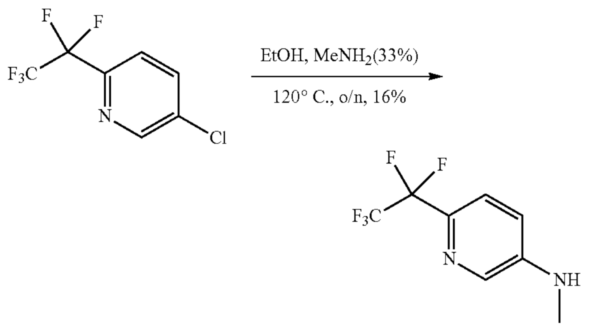

Into a 1-L pressure tank reactor purged and maintained with an inert atmosphere of nitrogen, was placed 5-chloro-2-(1,1,2,2,2-pentafluoroethyl)pyridine (10 g, 437 mmol, 1.0 equiv), EtOH (100 mL, 1.7 mol, 40 equiv), $CH_3NH_2$ (13 g, 0.4 mol, 10 equiv), NMP (300 mL), Cui (4.1 g, 22 mol, 0.5 equiv). The resulting solution was stirred overnight at 120 degrees C. The reaction was then quenched by the addition of 500 mL of water. The resulting solution was extracted with 3x500 mL of ethyl acetate and the organic layers combined and dried over anhydrous sodium sulfate and concentrated. The residue was applied onto a silica gel column with ethyl acetate/petroleum ether (1:1). This resulted in 1.6 g (16%) of N-methyl-6-(1,1,2,2,2-pentafluoroethyl)pyridin-3-amine as a light yellow solid.

Synthesis of tert-butyl N-methyl-N-[6-(1,1,2,2,2-pentafluoroethyl)pyridin-3-yl]carbamate

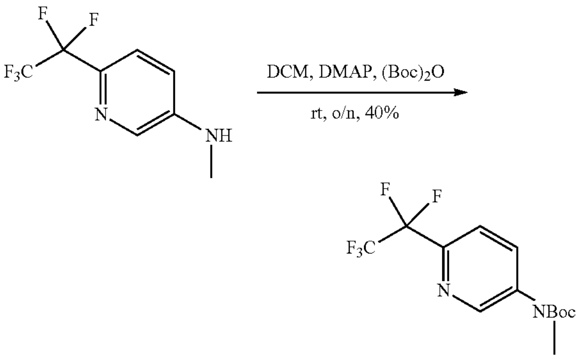

Into a 40-mL round-bottom flask purged and maintained with an inert atmosphere of nitrogen, was placed N-methyl-6-(1,1,2,2,2-pentafluoroethyl)pyridin-3-amine (226 mg, 1.0 mmol, 1.0 equiv), DCM (10 mL), DMAP (244 mg, 2.0 mmol, 2 equiv), $Boc_2O$(327 mg, 1.5 mmol, 1.5 equiv). The resulting solution was stirred overnight at room temperature. The resulting mixture was concentrated. The residue was applied onto a silica gel column with ethyl acetate/petroleum ether (1:6). This resulted in 130 mg (40%) of tert-butyl N-methyl-N-[6-(1,1,2,2,2-pentafluoroethyl)pyridin-3-yl] carbamate as colorless oil.

Synthesis of tert-butyl N-[4-bromo-6-(1,1,2,2,2-pentafluoroethyl)pyridin-3-yl]-N-methylcarbamate

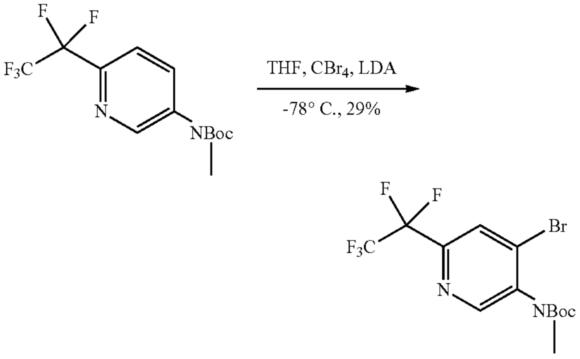

Into a 25-mL 3-necked round-bottom flask purged and maintained with an inert atmosphere of nitrogen, was placed tert-butyl N-methyl-N-[6-(1,1,2,2,2-pentafluoroethyl)pyridin-3-yl]carbamate (100 mg, 0.3 mmol, 1.0 equiv), THE (5 mL). This was followed by the addition of LDA (0.2 mL, 1.5 mmol, 5.0 equiv) dropwise with stirring at −78 degrees C. in 1 hr. To this was added a solution of CBr4 (508 mg, 1.5 mmol, 5 equiv) in THF (2 mL) dropwise with stirring at −78 degrees C. in 5 min. The resulting solution was stirred for 30 min at −78 degrees C. in a liquid nitrogen bath. The reaction was then quenched by the addition of 20 mL of water/ice. The resulting solution was extracted with 3×20 mL of ethyl acetate and the organic layers combined and dried over anhydrous sodium sulfate and concentrated. The residue was applied onto a silica gel column with ethyl acetate/petroleum ether (1:10). This resulted in 36 mg (29%) of tert-butyl N-[4-bromo-6-(1,1,2,2,2-pentafluoroethyl)pyridin-3-yl]-N-methylcarbamate as light-yellow oil.

Synthesis of 4-bromo-N-methyl-6-(1,1,2,2,2-pentafluoroethyl)pyridin-3-amine

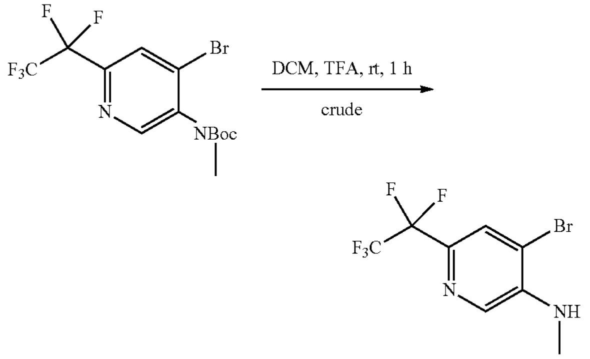

Into a 20-mL round-bottom flask purged and maintained with an inert atmosphere of nitrogen, was placed tert-butyl N-[4-bromo-6-(1,1,2,2,2-pentafluoroethyl)pyridin-3-yl]-N-methylcarbamate (36 mg, 0.9 mmol, 1.0 equiv), DCM (5 mL), TFA (1.0 mL, 13 mmol, 150 equiv). The resulting solution was stirred for 1 hr at room temperature. The resulting mixture was concentrated. This resulted in 28 mg (crude) of 4-bromo-N-methyl-6-(1,1,2,2,2-pentafluoroethyl) pyridin-3-amine as a light yellow solid.

Synthesis of N3-methyl-6-(1,1,2,2,2-pentafluoroethyl)pyridine-3,4-diamine

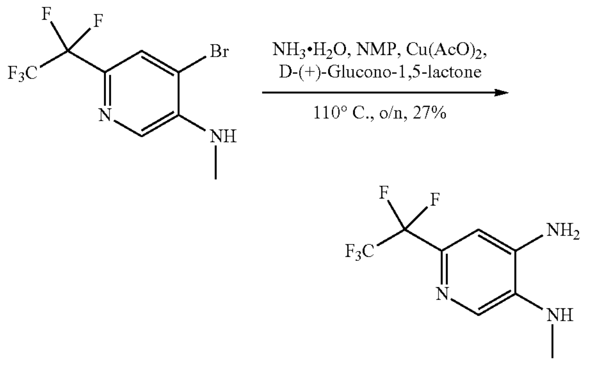

Into a 50-mL round-bottom flask purged and maintained with an inert atmosphere of nitrogen, was placed 4-bromo-N-methyl-6-(1,1,2,2,2-pentafluoroethyl)pyridin-3-amine (100 mg, 0.3 mmol, 1.0 equiv), NMP (5 mL), $Cu(OAc)_2$ (178 mg, 0.98 mmol, 3 equiv), d-glucuronolactone (173 mg, 0.9 mmol, 3 equiv), $NH_3 \cdot H_2O$ (15 mL). The resulting solution was stirred overnight at 110 degrees C. in an oil bath. The resulting solution was extracted with 3×100 mL of ethyl acetate and the organic layers combined and dried over anhydrous sodium sulfate and concentrated. The crude product was purified by Flash-Prep-HPLC with the following conditions (IntelFlash-1): Column, C18 silica gel; mobile phase, ACN:H2O=30% increasing to ACN:H2O=35% within 7 min; Detector, 220 nm. This resulted in 21 mg (27%) of N3-methyl-6-(1,1,2,2,2-pentafluoroethyl)pyridine-3,4-diamine as a brown solid.

Synthesis of 1-[4-[5-(ethylsulfanyl)-6-[3-methyl-6-(1,1,2,2,2-pentafluoroethyl)imidazo[4,5-c]pyridin-2-yl]pyridin-3-yl]phenyl]cyclopropane-1-carbonitrile

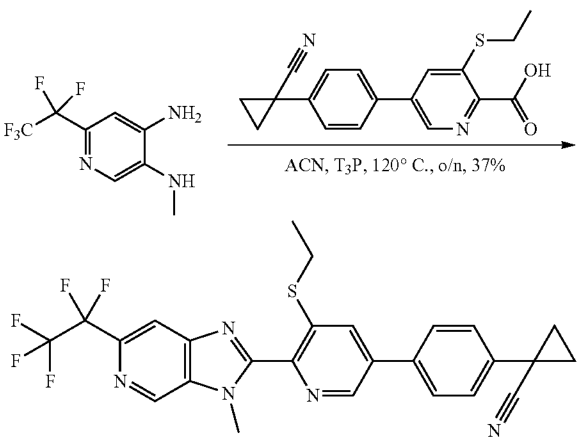

Into a 40-mL round-bottom flask purged and maintained with an inert atmosphere of nitrogen, was placed 5-[4-(1-cyanocyclopropyl)phenyl]-3-(ethylsulfanyl)pyridine-2-carboxylic acid (50 mg, 0.15 mmol, 1.0 equiv), N3-methyl-6-(1,1,2,2,2-pentafluoroethyl)pyridine-3,4-diamine (37 mg, 0.15 mmol, 1 equiv), ACN (5 mL), $T_3P$ (980 mg, 1.5 mmol, 10 equiv, 50%). The resulting solution was stirred overnight at 120 degrees C. The crude product was purified by Flash-Prep-HPLC with the following conditions (IntelFlash-1): Column, C18 silica gel; mobile phase, ACN:H2O=55 increasing to ACN:H2O=80 within 9 min; Detector, 254 nm. This resulted in 30 mg (37%) of 1-[4-[5-(ethylsulfanyl)-6-[3-methyl-6-(1,1,2,2,2-pentafluoroethyl)imidazo[4,5-c]pyridin-2-yl]pyridin-3-yl]phenyl]cyclopropane-1-carbonitrile as an off-white solid.

Synthesis of methyl 5-[4-(1-cyanocyclopropyl)phenyl]-3-(ethylsulfanyl)pyridine-2-carboxylate

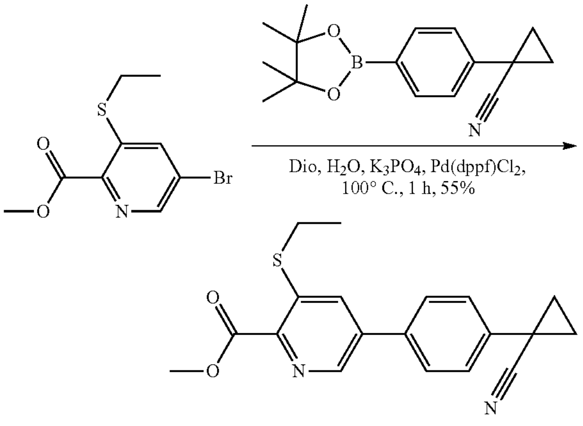

Into a 40-mL round-bottom flask purged and maintained with an inert atmosphere of nitrogen, was placed 1-(4-(4,4,5,5-tetramethyl-1,3,2-dioxaborolan-2-yl)phenyl)cyclopropane-1-carbonitrile (144 mg, 0.5 mmol, 1.0 equiv), methyl 5-bromo-3-(ethylsulfanyl)pyridine-2-carboxylate (148 mg, 0.5 mmol, 1.0 equiv), dioxane (10.00 mL), $H_2O$ (2.00 mL), $K_3PO_4$ (340 mg, 1.6 mmol, 3.0 equiv), Pd(dppf)$Cl_2$ (39 mg, 0.05 mmol, 0.1 equiv). The resulting solution was stirred for 1 hr at 100 degrees C. The resulting mixture was concentrated. The residue was applied onto a silica gel column with ethyl acetate/petroleum ether (1:1). This resulted in 100 mg (55%) of methyl 5-[4-(1-cyanocyclopropyl)phenyl1-3-(ethylsulfanyl)pyridine-2-carboxylate as a light yellow solid.

Synthesis of 5-[4-(1-cyanocyclopropyl)phenyl]-3-(ethylsulfanyl)pyridine-2-carboxylic acid

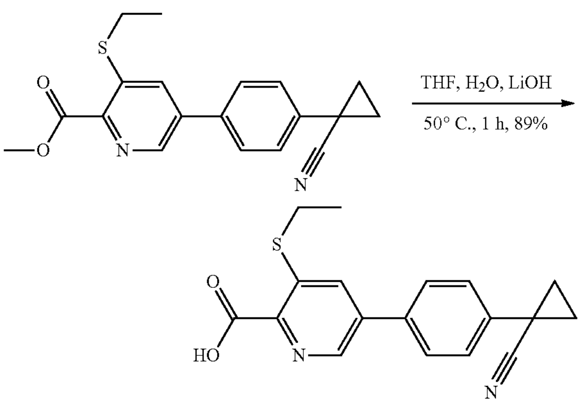

Into a 40-mL round-bottom flask, was placed methyl 5-[4-(1-cyanocyclopropyl)phenyl]-3-(ethylsulfanyl)pyridine-2-carboxylate (100 mg, 0.3 mmol, 1.0 equiv), THF (15 mL), $H_2O$ (5 mL), LiOH (35 mg, 1.5 mmol, 5 equiv). The resulting solution was stirred for 1 hr at 50 degrees C. The pH value of the solution was adjusted to 3-4 with HCl (2 mol/L). The resulting solution was extracted with 3×20 mL of ethyl acetate and the organic layers combined and dried over anhydrous sodium sulfate. This resulted in 85 mg (89%) of 5-[4-(1-cyanocyclopropyl)phenyl]-3-(ethylsulfanyl)pyridine-2-carboxylic acid as an off-white solid.

Synthesis of 1-[4-[5-(ethanesulfonyl)-6-[3-methyl-6-(1,1,2,2,2-pentafluoroethyl)imidazo[4,5-c]pyridin-2-yl]pyridin-3-yl]phenyl]cyclopropane-1-carbonitrile

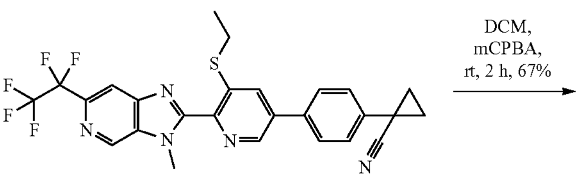

-continued

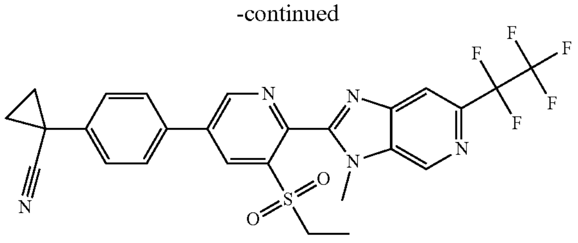

115

Into a 8-mL round-bottom flask purged and maintained with an inert atmosphere of nitrogen, was placed 1-[4-[5-(ethylsulfanyl)-6-[3-methyl-6-(1,1,2,2,2-pentafluoroethyl) imidazo[4,5-c]pyridin-2-yl]pyridin-3-yl]phenyl]cyclopropane-1-carbonitrile (30 mg, 0.06 mmol, 1.0 equiv), DCM (5 mL), mCPBA (29 mg, 0.2 mmol, 3 equiv). The resulting solution was stirred for 2 hr at room temperature. The resulting mixture was concentrated. The crude product was purified by Prep-HPLC with the following conditions (2 #SHIMADZU (HPLC-01)): Column, XBridge Shield RP18 OBD Column, 5 um,19*150 mm; mobile phase, Water (0.05% $NH3H_2O$) and ACN (40% ACN up to 75% in 7 min); Detector, 254 nm. This resulted in 21 mg (67%) of 1-[4-[5-(ethanesulfonyl)-6-[3-methyl-6-(1,1,2,2,2-pentafluoroethyl) imidazo[4,5-clpyridin-2-yl]pyridin-3-yl]phenyl]cyclopropane-1-carbonitrile as an off-white solid.

Synthesis of Compound 210

Specifically, the following compounds of formula (I) can be synthesized by adopting the subsequent scheme of Compound 210 by someone who is skilled in the art: 208, 209

Synthesis of N-[6-chloro-3-(methylamino)pyridazin-4-yl]-5-[4-(1-cyanocyclopropyl)phenyl]-3-(ethylsulfanyl)pyridine-2-carboxamide

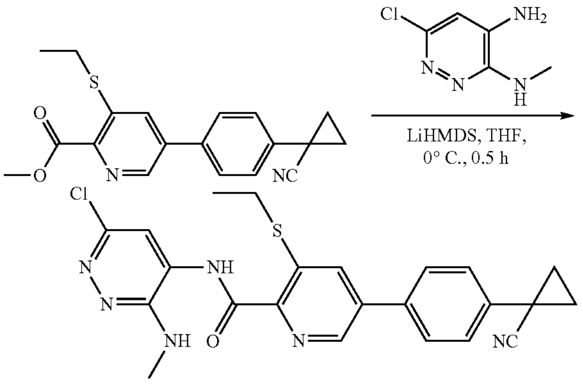

Into a 100 mL 3-necked round-bottom flask were added methyl 5-[4-(1-cyanocyclopropyl)phenyl]-3-(ethylsulfanyl) pyridine-2-carboxylate(2 g, 5.9 mmol, 1 equiv), THF(50 mL) and 6-chloro-N3-methylpyridazine-3,4-diamine (1.22 g, 7.7 mmol, 1.3 equiv) at room temperature. To the above mixture was added LiHMDS (3.0 mL, 6.0 mmol, 1.0 equiv) dropwise at 0° C. The resulting mixture was stirred for additional 0.5h at 0° C. The resulting mixture was diluted with water (200 mL). The resulting mixture was extracted with EtOAc (3×150 mL). The combined organic layers were dried over anhydrous Na2SO4. After filtration, the filtrate was concentrated under reduced pressure. The residue was purified by silica gel column chromatography, eluted with THF/PE (1:1) to afford N-[6-chloro-3-(methylamino) pyridazin-4-yl]-5-[4-(I-cyanocyclopropyl)phenyl]-3-(ethylsulfanyl)pyridine-2-carboxamide (900 mg, 33%) as a yellow solid.

Synthesis of 1-[4-(6-{3-chloro-7-methyl-7H-imidazo[4,5-c]pyridazin-6-yl}-5-(ethylsulfanyl)pyridin-3-yl)phenyl]cyclopropane-1-carbonitrile

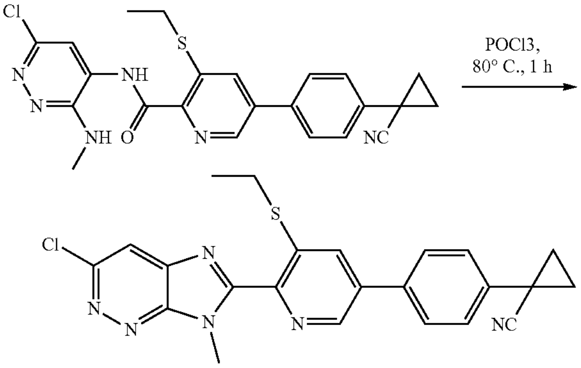

Into a 50 mL round-bottom flask were added N-[6-chloro-3-(methylamino)pyridazin-4-yl]-5-[4-(1-cyanocyclopropyl) phenyl]-3-(ethylsulfanyl)pyridine-2-carboxamide (900 mg, 1.9 mmol, 1 equiv) and POCl3 (10 mL) at room temperature. The resulting mixture was stirred for 1 h at 80° C. The mixture was allowed to cool down to room temperature. The resulting mixture was concentrated under reduced pressure. The residue was purified by reversed-phase flash chromatography with the following conditions: column, Cl18 silica gel; mobile phase, MeCN in Water (0.1% FA), 85% gradient in 10 min; detector, UV 254 nm. This resulted in 1-[4-(6-{3-chloro-7-methylimidazo[4,5-c]pyridazin-6-yl)-5-(ethylsulfanyl)pyridin-3-yl)phenyl]cyclopropane-1-carbonitrile (540 mg, 62%) as a yellow solid.

Synthesis of 1-[4-(6-{3-chloro-7-methyl-7H-imidazo[4,5-c]pyridazin-6-yl}-5-(ethanesulfonyl)pyridin-3-yl)phenyl]cyclopropane-1-carbonitrile

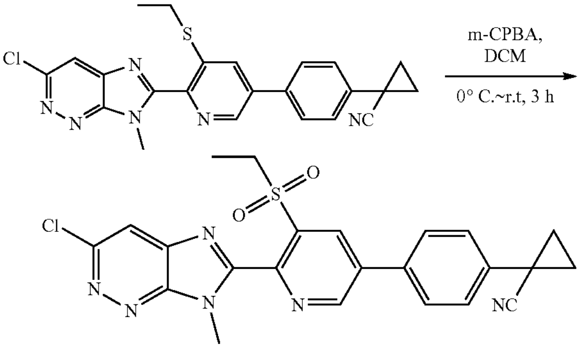

Into a 250 mL round-bottom flask were added 1-[4-(6-{3-chloro-7-methylimidazo[4,5-c]pyridazin-6-yl-5-(ethylsulfanyl)pyridin-3-yl)phenyl]cyclopropane-1-carbonitrile (630 mg, 1.4 mmol, 1 equiv) and DCM (100 mL) at room temperature. To the above mixture was added m-CPBA (715 mg, 3.5 mmol, 2.5 equiv, 85%) in portions at 0° C. The resulting mixture was stirred for additional 3h at room temperature. The resulting mixture was diluted with saturated $NaHCO_3$(aq.) (150 mL). The resulting mixture was stirred for additional 15 min at room temperature. The resulting mixture was extracted with $CH_2Cl2$ (3×100 mL). The combined organic layers were concentrated under reduced pressure. The residue was purified by silica gel column chromatography, eluted with THF/PE (1:1) to afford 1-[4-(6-f(3-chloro-7-methylimidazo[4,5-c]pyridazin-6-yl}-5-(ethanesulfonyl)pyridin-3-yl)phenyl]cyclopropane-1-carbonitrile (600 mg, 89%) as a yellow solid.

Synthesis of 1-[4-(6-{3-bromo-7-methyl-7H-imidazo[4,5-c]pyridazin-6-yl}-5-(ethanesulfonyl)pyridin-3-yl)phenyl]cyclopropane-1-carbonitrile

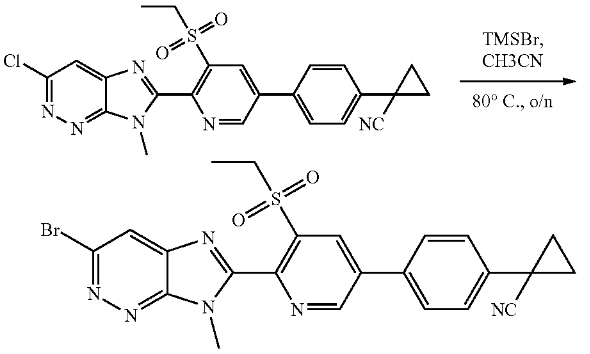

Into a 40 mL vial were added 1-[4-(6-[3-chloro-7-methylimidazo[4,5-c]pyridazin-6-yl}-5-(ethanesulfonyl)pyridin-3-yl)phenyl]cyclopropane-1-carbonitrile (300 mg, 0.6 mmol, 1 equiv), $CH_3CN$ (6 mL) and bromotrimethylsilane (6 mL) at room temperature. The resulting mixture was stirred for overnight at 80° C. The mixture was allowed to cool down to room temperature. The reaction was quenched with sat. $NaHCO_3$(aq.) (250 mL) at 0° C. The resulting mixture was extracted with $CH_2Cl2$ (3×100 mL). The combined organic layers were concentrated under reduced pressure. The residue was purified by silica gel column chromatography, eluted with THF/PE (1:1) to afford 1-[4-(6-{3-bromo-7-methylimidazo[4,5-c]pyridazin-6-yl}-5-(ethanesulfonyl)pyridin-3-yl)phenyl]cyclopropane-1-carbonitrile (500 mg, 76%) as a yellow solid.

Synthesis of 1-{4-[5-(ethanesulfonyl)-6-[3-(1-ethoxyethenyl)-7-methyl-7H-imidazo[4,5-c]pyridazin-6-yl]pyridin-3-yl]phenyl}cyclopropane-1-carbonitrile

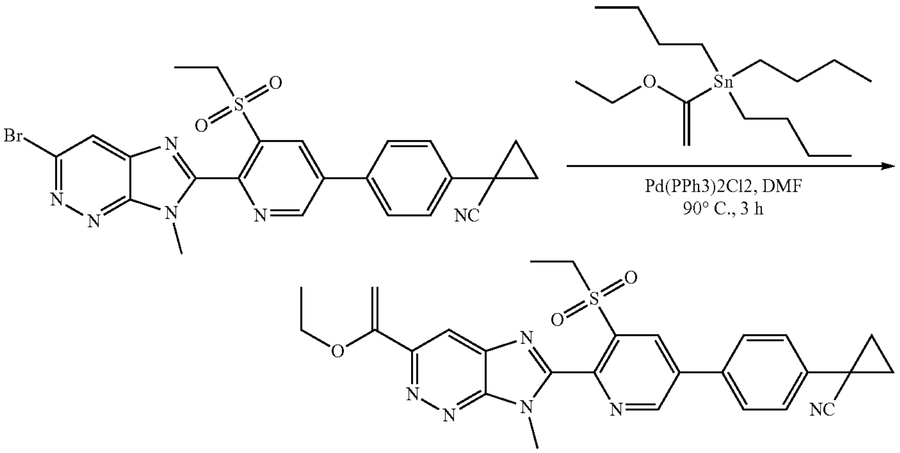

Into a 50 mL round-bottom flask were added 1-[4-(6-{3-bromo-7-methylimidazo[4,5-c]pyridazin-6-yl}-5-(ethanesulfonyl)pyridin-3-yl)phenyl]cyclopropane-1-carbonitrile (500 mg, 1.0 mmol, 1 equiv), DMF (10 mL), tributyl(1-ethoxyethenyl)stannane (1.0 g, 2.9 mmol, 3 equiv) and Pd(PPh3)2C12 (67 mg, 0.1 mmol, 0.1 equiv) at room temperature. The resulting mixture was stirred for 3 h at 90° C. under nitrogen atmosphere. The mixture was allowed to cool down to room temperature. The resulting mixture was diluted with water (100 mL). The resulting mixture was extracted with EtOAc (3×100 mL). The combined organic layers were washed with brine (3×250 mL), dried over anhydrous Na2SO4. After filtration, the filtrate was concentrated under reduced pressure. The residue was purified by silica gel column chromatography, eluted with THF/PE (1:1) to afford 1-{4-[5-(ethanesulfonyl)-6-[3-(1-ethoxyethenyl)-7-methylimidazo[4,5-c]pyridazin-6-yl]pyridin-3-yl]phenyl}cyclopropane-1-carbonitrile (300 mg, 61%) as a yellow solid.

Synthesis of 1-[4-(6-{3-acetyl-7-methyl-7H-imidazo [4,5-c]pyridazin-6-yl}-5-(ethanesulfonyl)pyridin-3-yl)phenyl]cyclopropane-1-carbonitrile

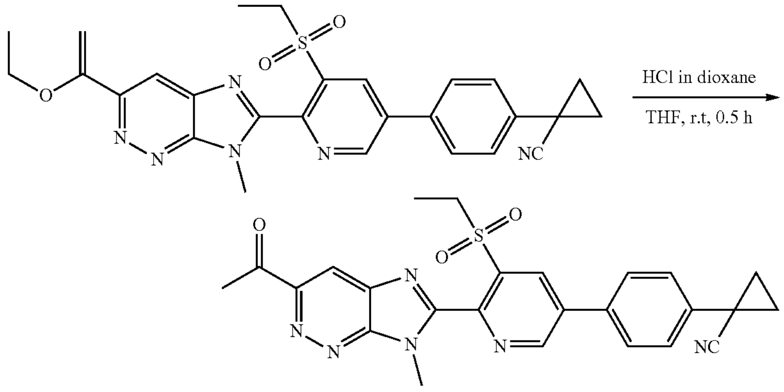

Into a 50 mL round-bottom flask were added 1-{4-[5-(ethanesulfonyl)-6-[3-(I-ethoxyethenyl)-7-methylimidazo [4,5-c]pyridazin-6-yl]pyridin-3-yl]phenyl)cyclopropane-1-carbonitrile (300 mg, 0.6 mmol, 1 equiv), THF (3 mL) and HCl(gas) in 1,4-dioxane (3 mL) at room temperature. The resulting mixture was stirred for 0.5h at room temperature. The resulting mixture was concentrated under reduced pressure. The residue was purified by reversed-phase flash chromatography with the following conditions: column, C18 silica gel; mobile phase, MeCN in Water (0.1% NH3·$H_2O$), 80% gradient in 10 min; detector, UV 254 nm. This resulted in 1-[4-(6-{3-acetyl-7-methylimidazo[4,5-c]pyridazin-6-yl}-5-(ethanesulfonyl)pyridin-3-yl)phenyl]cyclopropane-1-carbonitrile (270 mg, 95%) as a yellow solid.

Synthesis of 1-(4-{6-[3-(1,1-difluoroethyl)-7-methyl-7H-imidazo[4,5-c]pyridazin-6-yl]-5-(ethanesulfonyl)pyridin-3-yl}phenyl)cyclopropane-1-carbonitrile

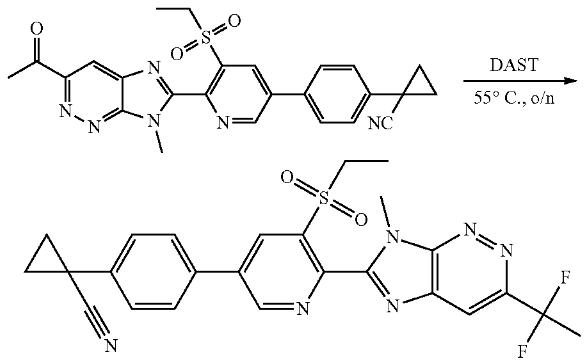

210

Into a 50 mL round-bottom flask were added 1-[4-(6-{3-acetyl-7-methylimidazo[4,5-c]pyridazin-6-yl}-5-(ethanesulfonyl)pyridin-3-yl)phenyl)cyclopropane-1-carbonitrile (270 mg, 0.6 mmol, 1 equiv) and DAST (6 mL) at room temperature. The resulting mixture was stirred for overnight at 55° C. The mixture was allowed to cool down to room temperature. The reaction was quenched by the addition of sat. $NaHCO_3$(aq.) (150 mL) at 0° C. The resulting mixture was extracted with EtOAc (3×100 mL). The combined organic layers were concentrated under reduced pressure. The residue was purified by reversed-phase flash chromatography with the following conditions: column, C18 silica gel; mobile phase, MeCN in Water (0.1% NH3·$H_2O$), 60% gradient in 10 min; detector, UV 254 nm. This resulted in 1-(4-{6-[3-(1,1-difluoroethyl)-7-methylimidazo[4,5-c] pyridazin-6-yl]-5-(ethanesulfonyl)pyridin-3-yl}phenyl)cyclopropane-1-carbonitrile (25 mg, 9%) as a light yellow solid.

Synthesis of Compound 206

Synthesis of 6-chloro-N-methoxy-N—methylpyridazine-3-carboxamide

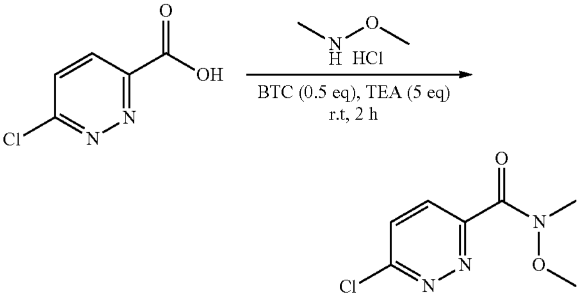

To a stirred solution of 6-chloropyridazine-3-carboxylic acid (100 g, 630 mmol) in DCM (640 mL) at 0° C. were added triphosgene (93 g, 315 mmol), Et3N (440 mL, 3150 mmol), and N,O-dimethylhydroxylamine hydrochloride (60.8 g, 630 mmol). The reaction mixture was stirred at room temperature for 2 h. The salt was filtered, after removal of the solvent in vacuo. The residue was purified by silica gel column chromatography, eluted with PE/THF (1:1) to afford 6-chloro-N-methoxy-N—methylpyridazine-3-carboxamide (80 g, 63%) as a yellow oil.

Synthesis of 3-chloro-6-cyclopropanecarbonylpyridazine

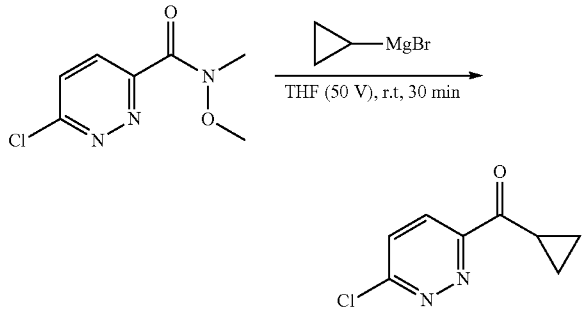

To a stirred solution of 6-chloro-N-methoxy-N-methylpyridazine-3-carboxamide (70 g, 350 mmol, 1 equiv) in THF (3.5 L) were added bromo(cyclopropyl)magnesium (695 mL, 695 mmol, 2.00 equiv) dropwise at −30° C. under nitrogen atmosphere. The resulting mixture was stirred for additional 30 min at −30° C. The reaction was quenched by the addition of sat. NH4Cl (aq.) (500 mL). The resulting mixture was extracted with EtOAc (3×500 mL). The combined organic layers were washed with brine (3×500 mL), dried over anhydrous Na2SO4. After filtration, the filtrate was concentrated under reduced pressure. The residue was purified by silica gel column chromatography, eluted with PE/EA (65:35) to afford 3-chloro-6-cyclopropanecarbonylpyridazine (29 g, 46%) as a yellow solid.

Synthesis of 3-chloro-6-(cyclopropyldifluoromethyl)pyridazine

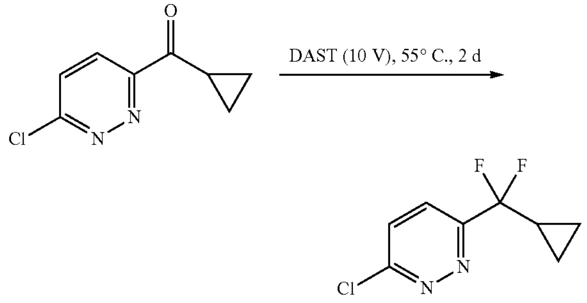

Into a 50 mL round-bottom flask were added 3-chloro-6-cyclopropanecarbonylpyridazine (29 g, 160 mmol, 1 equiv) and DAST (290 mL) was stirred for 2d at 55° C. The mixture was allowed to cool down to room temperature. The reaction was quenched by the addition of sat. $NaHCO_3$(aq.) (1 L) at 0° C. The resulting mixture was extracted with EtOAc (3×500 mL). The combined organic layers were washed with brine (3×500 mL), dried over anhydrous Na2SO4. After filtration, the filtrate was concentrated under reduced pressure. The residue was purified by silica gel column chromatography, eluted with PE/EA (65:35) to afford 3-chloro-6-(cyclopropyldifluoromethyl)pyridazine (7.1 g, 22%) as a yellow solid.

Synthesis of tert-butyl N-[6-(cyclopropyldifluoromethyl)pyridazin-3-yl]carbamate

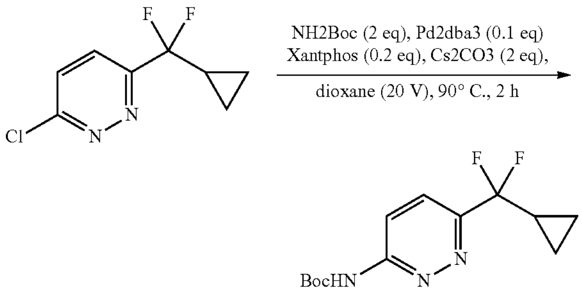

To a solution of 3-chloro-6-(cyclopropyldifluoromethyl)pyridazine (7.1 g, 35 mmol, 1 equiv), Cs2CO3 (23 g, 704 mmol, 2 equiv) and BocNH2 (8.1 g, 70 mmol, 2 equiv) in dioxane (150 mL) were added Pd2(dba)3 (3.2 g, 3.5 mmol, 0.1 equiv) and XantPhos (4.0 g, 7.0 mmol, 0.2 equiv) After stirring for 2 h at 90° C. under a nitrogen atmosphere, the resulting mixture was concentrated under reduced pressure. The residue was purified by silica gel column chromatography, eluted with PE/EA (75:25) to afford tert-butyl N-[6-(cyclopropyldifluoromethyl)pyridazin-3-yl]carbamate (6.5 g, 66%) as a white solid.

Synthesis of N-[6-(cyclopropyldifluoromethyl) pyridazin-3-yl]-N-methyl-carbamate

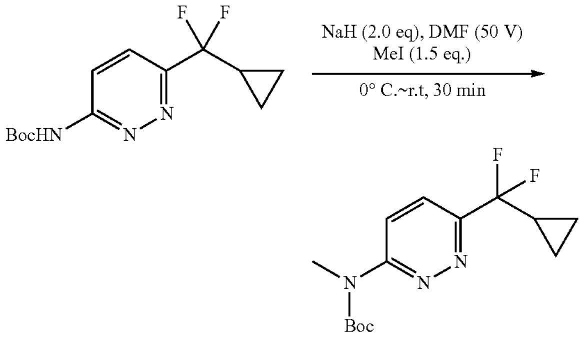

To a solution of tert-butyl N-[6-(cyclopropyldifluoromethyl)pyridazin-3-yl]carbamate (6.5 g, 21 mmol, 1 equiv) in DMF (300 mL) was added NaH (1.0 g, 42 mmol, 2 equiv, 60%) at 0° C. The mixture was stirred for 30 min at 0° C. Then methyl iodide (4.5 g, 32 mmol, 1.5 equiv) was added and the mixture was allowed to warm to RT and stirred for 30 min. The reaction was quenched by the addition of sat. NH4Cl (aq.) (300 mL). The resulting mixture was extracted with EtOAc (3×500 mL). The combined organic layers were washed with brine (3×500 mL), dried over anhydrous Na2SO4. After filtration, the filtrate was concentrated under reduced pressure. The residue was purified by silica gel column chromatography, eluted with PE/EA (70:30) to afford tert-butyl N-[6-(cyclopropyldifluoromethyl) pyridazin-3-yl]-N-methyl-carbamate (6 g, 88%) as a yellow solid.

Synthesis of 6-(cyclopropyldifluoromethyl)-N-methyl pyridazin-3-amine

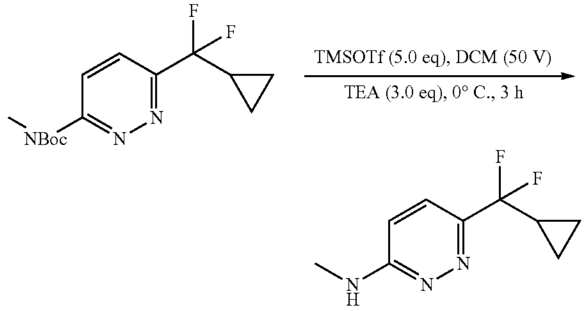

Into a 500 mL round-bottom flask were added tert-butyl N-[6-(cyclopropyldifluoromethyl)pyridazin-3-yl]-N-methylcarbamate (6 g, 20 mmol, 1 equiv), TEA (6 g, 60 mmol, 3 equiv) and DCM (300 mL) at 0° C. To the above mixture was added TMSOTf (22 g, 100 mmol, 5 equiv) dropwise at 0° C. The resulting mixture was stirred for additional 3 h at 0° C. The reaction was quenched by the addition of sat. $NaHCO_3$(aq.) (500 mL). The resulting mixture was extracted with DCM (3×500 mL). The combined organic layers were washed with brine (2×500 mL), dried over anhydrous Na2SO4. After filtration, the filtrate was concentrated under reduced pressure. The residue was purified by reverse flash chromatography with the following conditions: column, silica gel; mobile phase, MeCN in water (0.1% TFA), 15% to 70% gradient in 9 min; detector, UV 254 nm. This resulted in 6-(cyclopropyldifluoromethyl)-N-methyl pyridazin-3-amine (3.5 g, 88%) as a yellow oil.

Synthesis of 4-bromo-6-(cyclopropyldifluoromethyl)-N-methylpyridazin-3-amine

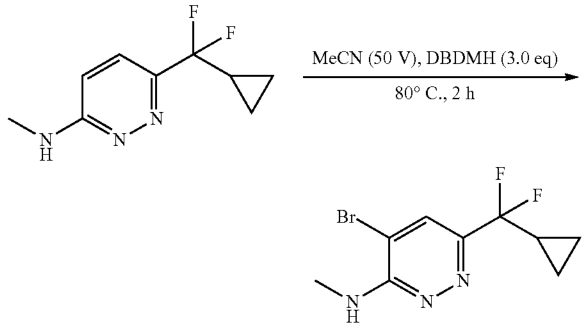

Into a 100 mL round-bottom flask were added 6-(cyclopropyldifluoromethyl)-N-methylpyridazin-3-amine (3.5 g, 18 mmol, 1 equiv), 1,3-dibromo-5,5-dimethylimidazolidine-2,4-dione (10 g, 35 mmol, 3 equiv) and MeCN (175 mL) was stirred for 2 h at 80° C. The mixture was allowed to cool down to room temperature. The resulting mixture was concentrated under reduced pressure. The residue was purified by silica gel column chromatography, eluted with PE/THE (80:20). The residue was purified by reverse flash chromatography with the following conditions: column, silica gel; mobile phase, MeCN in water (0.1% TFA), 15% to 75% gradient in 9 min; detector, UV 254 nm. This resulted in 4-bromo-6-(cyclopropyldifluoromethyl)-N-methylpyridazin-3-amine (1 g, 22%) as a yellow solid.

Synthesis of 6-(cyclopropyldifluoromethyl)-N4-(diphenylmethylidene)-N3-methylpyridazine-3,4-diamine

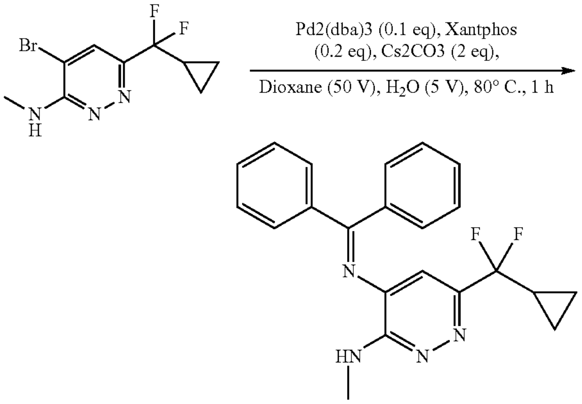

To a solution of 4-bromo-6-(cyclopropyldifluoromethyl)-N-methylpyridazin-3-amine (1 g, 3.6 mmol, 1 equiv), diphenylmethanimine (1.3 g, 7.2 mmol, 2.00 equiv), Cs2CO3 (2.3 g, 7.2 mmol, 2.00 equiv) in dioxane (3 mL) were added Pd2(dba)3 (0.3 g, 0.4 mmol, 0.1 equiv) and XantPhos (0.4 g, 0.7 mmol, 0.2 equiv). After stirring for 1 h at 80° C. under a nitrogen atmosphere. The mixture was allowed to cool down to room temperature. The resulting mixture was concentrated under reduced pressure. The residue was purified by silica gel column chromatography, eluted with PE/THF (80:20). The residue was purified by reverse flash chromatography with the following conditions: column, silica gel; mobile phase, MeCN in water (0.1% TFA), 20% to 80% gradient in 9 min; detector, UV 254 nm. This resulted in 6-(cyclopropyldifluoromethyl)-N4-(diphenylmethylidene)-N3-methylpyridazine-3,4-diamine (1 g, 73%) as a white solid.

Synthesis of 6-(cyclopropyldifluoromethyl)-N3-methyl-pyridazine-3,4-diamine

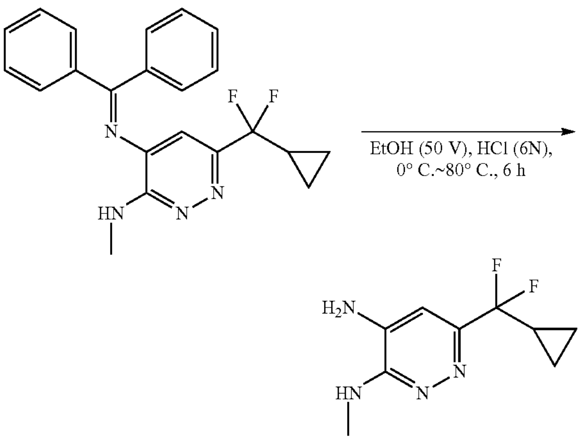

Into a 250 mL round-bottom flask were added 6-(cyclopropyldifluoromethyl)-N4-(diphenylmethylidene)-N3-methylpyridazine-3,4-diamine (1 g, 2.6 mmol, 1 equiv), EtOH (50 mL) and HCl (10 mL). The mixture was stirred for 6 h at 80° C. The mixture was allowed to cool down to room temperature. The reaction was quenched by the addition of ice water (300 mL). The resulting mixture was extracted with EtOAc (2×500 mL). The combined organic layers were washed with brine (2×400 mL), dried over anhydrous Na2SO4. After filtration, the filtrate was concentrated under reduced pressure. The residue was purified by silica gel column chromatography, eluted with PE/THF (80:20) to afford 6-(cyclopropyldifluoromethyl)-N3-methyl-pyridazine-3,4-diamine (300 mg, 53%) as a light yellow solid.

Synthesis of 5-[4-(1-cyanocyclopropyl)phenyl]-N-[6-(cyclopropyldifluoromethyl)-3-(methylamino) pyridazin-4-yl]-3-(ethylsulfanyl)pyridine-2-carboxamide

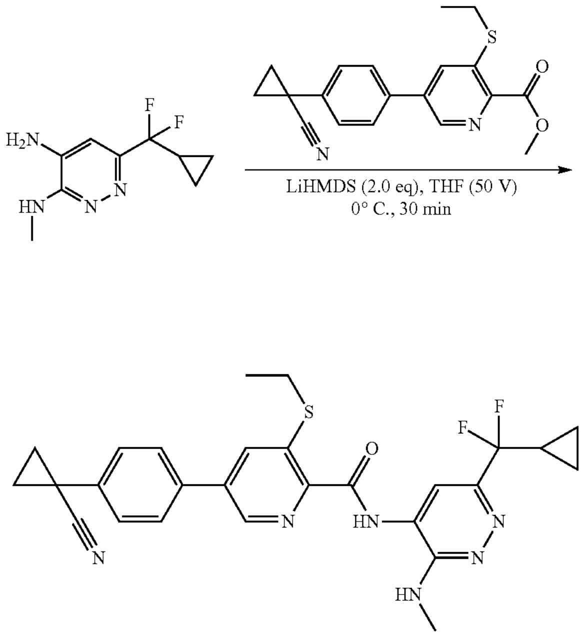

To a stirred solution of 6-(cyclopropyldifluoromethyl)-N3-methylpyridazine-3,4-diamine (90 mg, 0.4 mmol, 1 equiv) and methyl 5-[4-(1-cyanocyclopropyl)phenyl]-3-(ethylsulfanyl)pyridine-2-carboxylate (142 mg, 0.4 mmol, 1 equiv) in THE (3.5 mL) was added LiHMDS (0.4 mL, 0.8 mmol, 2.00 equiv) dropwise at 0° C. under nitrogen atmosphere. The resulting mixture was stirred for additional 30 min at 0° C. The reaction was quenched by the addition of ice water (50 mL). The resulting mixture was extracted with EtOAc (2×50 mL). The combined organic layers were washed with brine (2×40 mL), dried over anhydrous Na2SO4. After filtration, the filtrate was concentrated under reduced pressure. The residue was purified by silica gel column chromatography, eluted with PE/THE (1:1) to afford 5-[4-(I-cyanocyclopropyl)phenyl]-N-[6-(cyclopropyldifluoromethyl)-3-(methylamino)pyridazin-4-yl]-3-(ethylsulfanyl)pyridine-2-carboxamide (50 mg, 23%) as a yellow solid.

Synthesis of 1-(4-{16-[3-(cyclopropyldifluoromethyl)-7-methyl-7H-imidazo[4,5-c]pyridazin-6-yl]-5-(ethylsulfanyl)pyridin-3-yl}phenyl)cyclopropane-1-carbonitrile

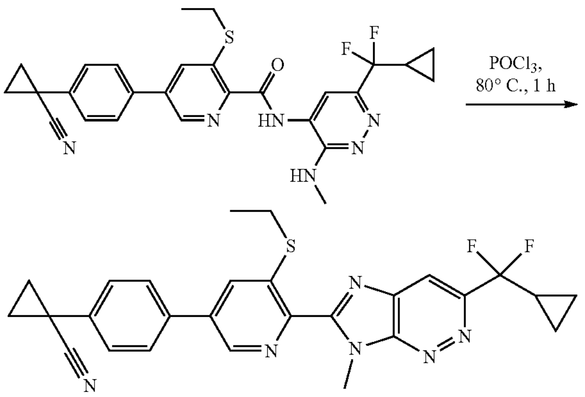

Into a 50 mL round-bottom flask were added 5-[4-(1-cyanocyclopropyl)phenyl]-N-[6-(cyclopropyldifluoromethyl)-3-(methylamino)pyridazin-4-yl]-3-(ethylsulfanyl) pyridine-2-carboxamide (40 mg, 0.08 mmol, 1 equiv) and POCl3 (1 mL) at room temperature. The resulting mixture was stirred for 1 h at 80° C. The mixture was allowed to cool down to room temperature. The resulting mixture was concentrated under reduced pressure. The residue was purified by reversed-phase flash chromatography with the following conditions: column, C18 silica gel; mobile phase, MeCN in Water (0.1% FA), 85% gradient in 10 min; detector, UV 254 nm. This resulted in 1-[4-(6-{3-chloro-7-methylimidazo[4,5-c]pyridazin-6-yl}-5-(ethylsulfanyl)pyridin-3-yl)phenyl]cyclopropane-1-carbonitrile (30 mg, 75%) as a yellow solid.

Synthesis of 1-(4-{6-[3-(cyclopropyldifluoromethyl)-7-methyl-7H-imidazo[4,5-c]pyridazin-6-yl]-5-(ethanesulfonyl)pyridin-3-yl)phenyl)cyclopropane-1-carbonitrile

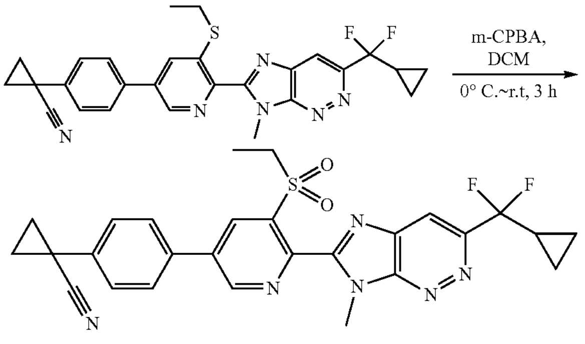

206

Into a 250 mL round-bottom flask were added 1-(4-{6-[3-(cyclopropyldifluoromethyl)-7-methyl-7H-imidazo[4,5-c]pyridazin-6-yl]-5-(ethylsulfanyl)pyridin-3-yl}phenyl)cyclopropane-1-carbonitrile (22 mg, 0.04 mmol, 1 equiv) and DCM (5 mL) at room temperature. To the above mixture was added m-CPBA (22 mg, 0.1 mmol, 2.5 equiv, 85%) in portions at 0° C. The resulting mixture was stirred for additional 3h at room temperature. The resulting mixture was diluted with saturated $NaHCO_3$(aq.) (10 mL). The resulting mixture was stirred for additional 15 min at room temperature. The resulting mixture was extracted with $CH_2$Cl2 (3×5 mL). The combined organic layers were concentrated under reduced pressure. The residue was purified by silica gel column chromatography, eluted with THF/PE (1:1) to afford 1-(4-{6-{13-(cyclopropyldifluoromethyl)-7-methyl-7H-imidazo[4,5-c]pyridazin-6-yl]-5-(ethanesulfonyl)pyridin-3-yl}phenyl)cyclopropane-I-carbonitrile (19 mg, 82%) as a yellow solid.

Synthesis of Compound 14

Specifically, the following compounds of formula (I) can be synthesized by adopting the subsequent scheme of Compound 14 by someone who is skilled in the art: 38

Synthesis of (6-{5,5-dfluoro-12-methyl-4,6-dioxa-10,12-diazatricyclo[7.3.0.0$^{3,7}$]dodeca-1(9),2,7,10-tetraen-11-yl}-5-(ethanesulfonyl)pyridine-3-yl)boronic acid

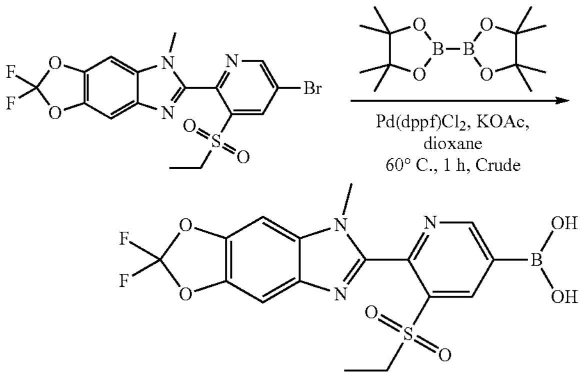

Into a 20-mL vial purged and maintained with an inert atmosphere of nitrogen, was placed 6-(5-bromo-3-(ethylsulfonyl)pyridin-2-yl)-2,2-difluoro-5-methyl-5H-[1,3]dioxolo[4',5':4,5]benzo [1,2-d]imidazole (60 mg, 0.13 mmol, 1.0 equiv), dioxane (5 mL), bis(pinacolato)diboron (83 mg, 0.3 mmol, 2.5 equiv), KOAc (25 mg, 0.26 mmol, 2 equiv) and Pd(dppf)$Cl_2$ (9.5 mg, 0.01 mmol, 0.1 equiv). The resulting solution was stirred for 1 h at 60 degrees C. The reaction mixture was used by directly in the next step.

Synthesis of 6-(4-cyclopropyl-5'-(ethylsulfonyl)-[2,3'-bipyridin]-6'-yl)-2,2-difluoro-5-methyl-5H-[1,3]dioxolo[4',5':4,5]benzo[1,2-d]imidazole

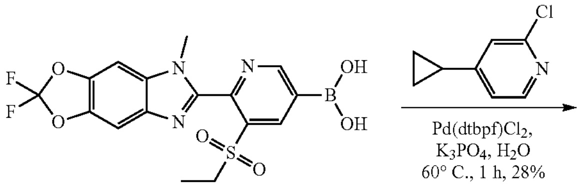

-continued

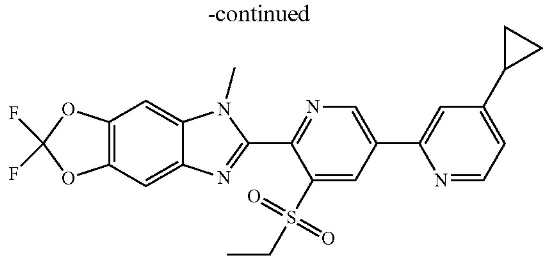

14

Into a 20-mL vial purged and maintained with an inert atmosphere of nitrogen, was placed the mixture of the previous step, $H_2O$ (0.50 mL), 2-chloro-4-cyclopropylpyridine (27 mg, 0.18 mmol, 1.5 equiv), $K_3PO_4$ (50 mg, 0.2 mmol, 2 equiv) and Pd(dtbpf)$Cl_2$ (7.7 mg, 0.01 mmol, 0.1 equiv). The resulting solution was stirred for 1 h at 60 degrees C. The resulting mixture was concentrated. The residue was applied onto a silica gel column with ethyl acetate/petroleum ether (1:1). The crude product was further purified by Prep-HPLC with the following conditions (2 #SHIMADZU (HPLC-01)): Column, XBridge Prep C18 OBD Column, 5 um,19*1 50 mm; mobile phase, Water (0.05% $NH_3H_2O$) and ACN (50% Phase B up to 70% in 7 min); Detector, UV. product was obtained. This resulted in 16 mg (28%) of 6-(4-cyclopropyl-5'-(ethylsulfonyl)-[2,3'-bipyridin]-6'-yl)-2,2-difluoro-5-methyl-5H-[1,3]dioxolo[4',5':4,5]benzo[1,2-d]imidazole as a white solid.

Synthesis of Compound 182

Synthesis of 2-chloro-4-cyclopropylpyridine

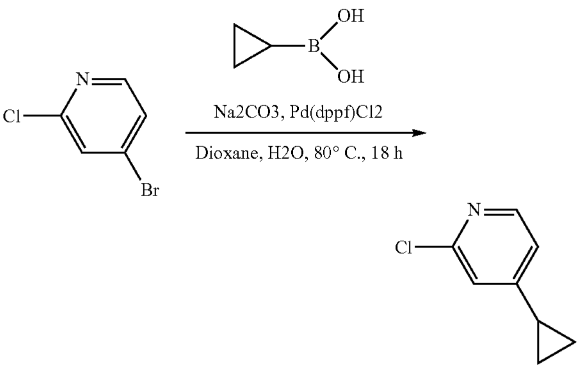

Into a 100 mL round-bottom flask were added 4-bromo-2-chloropyridine (I g, 5.2 mmol, 1 equiv) in Dioxane (50 mL, 590 mmol, 114 equiv) and cyclopropylboronic acid (536 mg, 6.2 mmol, 1.2 equiv). To the above mixture was added Na2CO3 (1.1 g, 10 mmol, 2 equiv) in water (5 mL) and Pd(dppf)C12 (190 mg, 0.26 mmol, 0.05 equiv) at 25° C. The resulting mixture was stirred for 18 h at 80° C. under N2 atmosphere. The resulting mixture was dried with Na2SO4. The resulting mixture was filtered, the filter cake was washed with EA (1×50 mL). The filtrate was concentrated under reduced pressure. The residue was purified by silica gel column chromatography, eluted with PE/EA (8:1) to afford 2-chloro-4-cyclopropylpyridine (300 mg, 38%) as a light yellow oil.

Synthesis of 3-(ethanesulfonyl)-2-[3-methyl-6-(1,1,2,2,2-pentafluoroethyl)-3H-imidazo[4,5-b]pyridin-2-yl]-5-(trimethylstannyl)pyridine

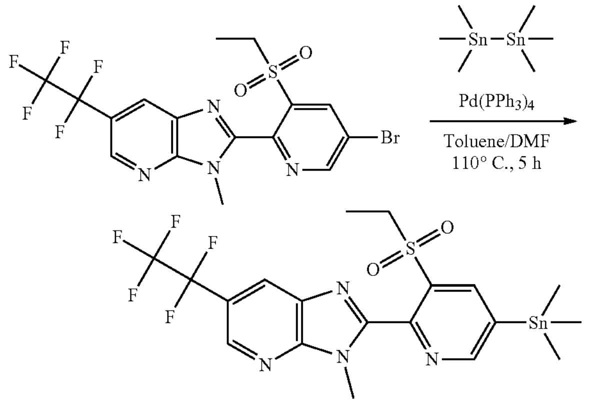

Into a 8 mL vial were added 5-bromo-3-(ethanesulfonyl)-2-[3-methyl-6-(1,1,2,2,2-pentafluoroethyl)imidazo[4,5-b]pyridin-2-yl]pyridine (80 mg, 0.16 mmol, 1 equiv) in toluene (2 mL) and hexamethyldistannane (58 mg, 0.18 mmol, 1.1 equiv) in DMF (1.5 mL). To the above mixture was added Pd(PPh3)4 (9.3 mg, 0.01 mmol, 0.05 equiv) at 25° C. The resulting mixture was stirred for 5 h at 110° C. under N2 atmosphere. The mixture was used in the next step directly without further purification.

Synthesis of 4-cyclopropyl-5'-(ethanesulfonyl)-6'-[3-methyl-6-(1,1,2,2,2-pentafluoroethyl)-3H-imidazo[4,5-b]pyridin-2-yl]-2,3'-bipyridine

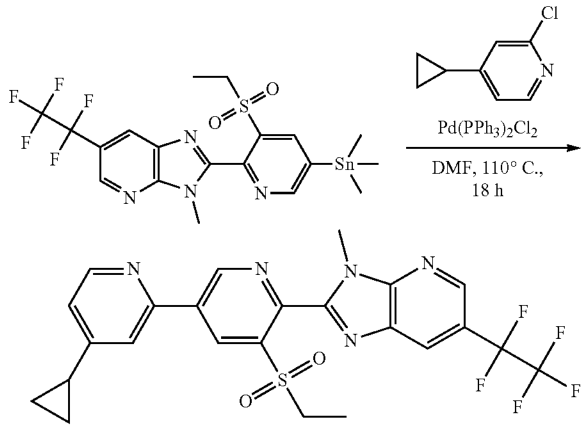

Into the above solution of 3-(ethanesulfonyl)-2-[3-methyl-6-(1,1,2,2,2-pentafluoroethyl)imidazo[4,5-b]pyridin-2-yl]-5-(trimethylstannyl)pyridine was added 2-chloro-4-cyclopropylpyridine (25 mg, 0.16 mmol, 1 equiv). To the above mixture was added palladium chloride; bis(triphenylphosphine) (4.8 mg, 0.01 mmol, 0.05 equiv) at 25° C. The resulting mixture was stirred for 18 h at 110° C. under N2 atmosphere. The reaction mixture was purified by Prep-HPLC with the following conditions (Column: Xbridge, 19*150 mm, 5 pm; Mobile Phase, A: Water/0.05% NH3*H2O+10 mM NH4HCO3; B: ACN; 30-75% B in 10 min, Flow Rate: 20 mL/min; Detection: 220/254 nm.) to afford 4-cyclopropyl-5'-(ethanesulfonyl)-6'-[3-methyl-6-(1,1,2,2,2-pentafluoroethyl)imidazo[4,5-b]pyridin-2-yl]-2,3-bipyridine (13 mg, 18%) as a white solid.

Synthesis of Compound 194

Specifically, the following compounds of formula (I) can be synthesized by adopting the subsequent scheme of Compound 194 by someone who is skilled in the art: 201

Synthesis of N-(3-amino-5-bromopyridin-2-yl)-5-(4-cyclopropylphenyl)-3-(ethylsulfanyl)-N-methylpyridine-2-carboxamide

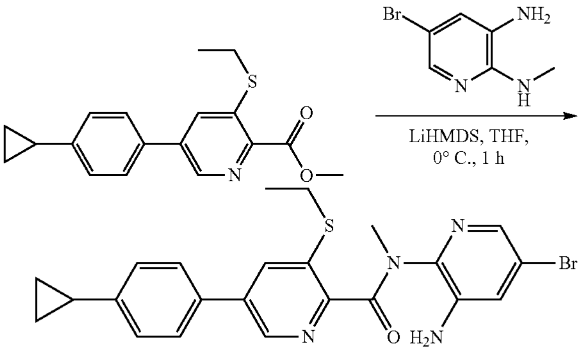

Into a 50 mL 3-necked round-bottom flask were added methyl 5-(4-cyclopropylphenyl)-3-(ethylsulfanyl)pyridine-2-carboxylate (1.15 g, 3.7 mmol, 1 equiv) and 5-bromo-N2-methylpyridine-2,3-diamine (734 mg, 3.7 mmol, 1 equiv), THF (23 mL) at room temperature. A solution of LiHMDS (7.34 mL, 7.3 mmol, 2 equiv) was added by dropwise at 0° C. under nitrogen atmosphere. The resulting mixture was stirred for 1 h at 0° C. under nitrogen atmosphere. The reaction was quenched by the addition of Water (30 mL) at room temperature. The resulting mixture was extracted with EtOAc (3x30 mL). The combined organic layers were washed with brine (3x30 mL), dried over anhydrous Na2SO4. After filtration, the filtrate was concentrated under reduced pressure. The residue was purified by silica gel column chromatography, eluted with PE/EA (1:1) to afford N-(3-amino-5-bromopyridin-2-yl)-5-(4-cyclopropylphenyl)-3-(ethylsulfanyl)-N-methylpyridine-2-carboxamide (1.3 g, 51) as a yellow solid.

Synthesis of 2-{6-bromo-3-methyl-3H-imidazo[4,5-b]pyridin-2-yl}-5-(4-cyclopropylphenyl)-3-(ethylsulfanyl)pyridine

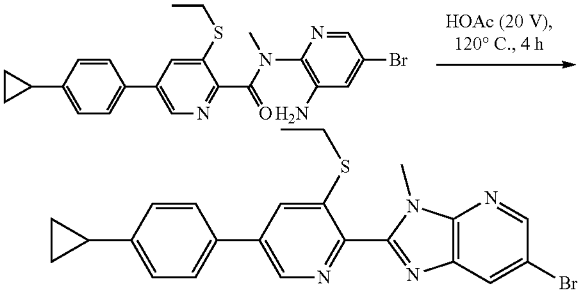

Into a 40 mL vial were added N-(3-amino-5-bromopyridin-2-yl)-5-(4-cyclopropylphenyl)-3-(ethylsulfanyl)-N-methylpyridine-2-carboxamide (1.3 g, 2.7 mmol, 1 equiv) and HOAc (26 mL) at room temperature. The resulting mixture was stirred for 2 h at 120° C. The mixture was allowed to cool down to room temperature. The resulting mixture was diluted with water (30 mL). The resulting mixture was extracted with EtOAc (3×30 mL). The combined organic layers were washed with brine (3×30 mL), dried over anhydrous Na2SO4. After filtration, the filtrate was concentrated under reduced pressure. This resulted in 2-{6-bromo-3-methylimidazo[4,5-b]pyridin-2-yl}-5-(4-cyclopropylphenyl)-3-(ethylsulfanyl)pyridine (1.25 g, 65%) as a purple solid.

Synthesis of 2-{6-bromo-3-methyl-3H-imidazo[4,5-b]pyridin-2-yl}-5-(4-cyclopropylphenyl)-3-(ethanesulfonyl)pyridine

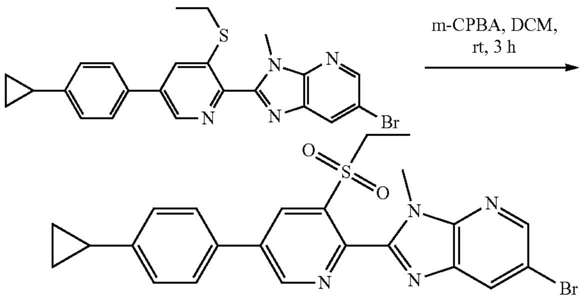

Into a 100 mL round-bottom flask were added 2-{6-bromo-3-methylimidazo[4,5-b]pyridin-2-yl)-5-(4-cyclopropylphenyl)-3-(ethylsulfanyl)pyridine (1.24 g, 2.7 mmol, 1 equiv), DCM (37 mL) and m-CPBA (1.38 g, 8.0 mmol, 3 equiv) at room temperature. The resulting mixture was stirred for 1 h at room temperature. The resulting mixture was diluted with DCM (30 mL). The reaction was quenched by the addition of sat. K2CO3 (aq.) (30 mL) at room temperature. The resulting mixture was extracted with $CH_2Cl2$ (3×30 mL). The combined organic layers were washed with brine (3×30 mL), dried over anhydrous Na2SO4. After filtration, the filtrate was concentrated under reduced pressure. The residue was purified by silica gel column chromatography, eluted with PE/EA (3:1) to afford 2-{6-bromo-3-methylimidazo[4,5-b]pyridin-2-yl}-5-(4-cyclopropylphenyl)-3-(ethanesulfonyl)pyridine (1.08 g, 65%) as a yellow solid.

Synthesis of 5-(4-cyclopropylphenyl)-3-(ethanesulfonyl)-2-[6-(1-ethoxyethenyl)-3-methyl-3H-imidazo[4,5-b]pyridin-2-yl]pyridine

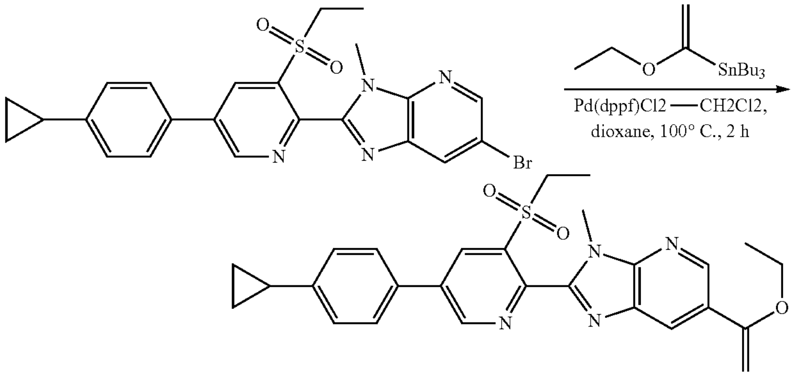

Into a 40 mL vial were added 2-{6-bromo-3-methylimidazo[4,5-b]pyridin-2-yl}-5-(4-cyclopropylphenyl)-3-(ethanesulfonyl)pyridine (870 mg, 1.75 mmol, 1 equiv), dioxane (26 mL), tributyl(1-ethoxyethenyl)stannane (3.1 g, 8.75 mmol, 5.0 equiv) and Pd(dppf)Cl2·$CH_2$Cl2 (285 mg, 0.35 mmol, 0.2 equiv) at room temperature. The resulting mixture was stirred for 1 h at 100° C. under nitrogen atmosphere. The mixture was allowed to cool down to room temperature. The reaction solution was used directly in next step without further purification.

Synthesis of 1-{2-[5-(4-cyclopropylphenyl)-3-(ethanesulfonyl)pyridin-2-yl]-3-methyl-3H-imidazo[4,5-b]pyridin-6-yl}ethan-1-one

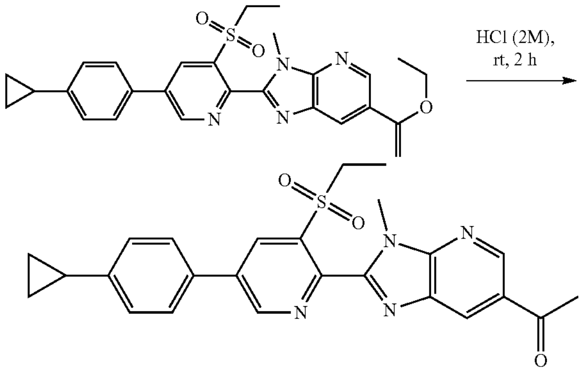

Into above reaction solution HCl (2M, 26 mL) was added at room temperature. The resulting mixture was stirred for 30 min at room temperature. The resulting mixture was diluted with water (30 mL). The resulting mixture was extracted with EtOAc (3×30 mL). The combined organic layers were washed with brine (3×30 mL), dried over anhydrous Na2SO4. After filtration, the filtrate was concentrated under reduced pressure. The residue was purified by silica gel column chromatography, eluted with PE/EA (1:2)

to afford 1-(2-[5-(4-cyclopropylphenyl)-3-(ethanesulfonyl)pyridin-2-yl]-3-methylimidazo[4,5-b]pyridin-6-yl}ethanone (583 mg, 66%) as a yellow solid.

Synthesis of 1-{2-[5-(4-cyclopropylphenyl)-3-(ethanesulfonyl)pyridin-2-yl]-3-methyl-3H-imidazo[4,5-b]pyridin-6-yl}ethan-1-one

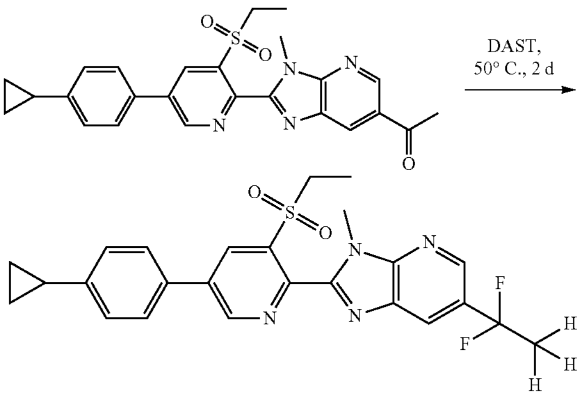

194

Into a 40 mL vial were added 1-{2-[5-(4-cyclopropylphenyl)-3-(ethanesulfonyl)pyridin-2-yl]-3-methylimidazo[4,5-b]pyridin-6-yl}ethanone (400 mg, 0.87 mmol, 1 equiv) and DAST (20 mL) at room temperature. The resulting mixture was stirred for 2 days at 50° C. The mixture was allowed to cool down to room temperature. The resulting mixture were slowly added by dropwise into the mixture Ice/sat. $NaHCO_3$ (aq.). The resulting mixture was extracted with EtOAc (3x50 mL). The combined organic layers were washed with brine (3x50 mL), dried over anhydrous Na2SO4. After filtration, the filtrate was concentrated under reduced pressure. The residue was purified by reverse flash chromatography with the following conditions: column, C18 silica gel; mobile phase, MeCN in Water (0.05% NH3·$H_2O$), 30% to 100% gradient in 10 min; detector, UV 254 nm. This resulted in 5-(4-cyclopropylphenyl)-2-[6-(1,1-difluoroethyl)-3-methylimidazo[4,5-b]pyridin-2-yl]-3-(ethanesulfonyl)pyridine (157 mg, 37%) as a yellow solid.

Synthesis of Compound 195

Specifically, the following compounds of formula (I) can be synthesized by adopting the subsequent scheme of Compound 194 by someone who is skilled in the art: 196

1. Synthesis of 3-chloro-5-[5-(ethanesulfonyl)-6-[3-methyl-6-(1,1,2,2,2-pentafluoroethyl)-3H-imidazo[4,5-b]pyridin-2-yl]pyridin-3-yl]pyridazine

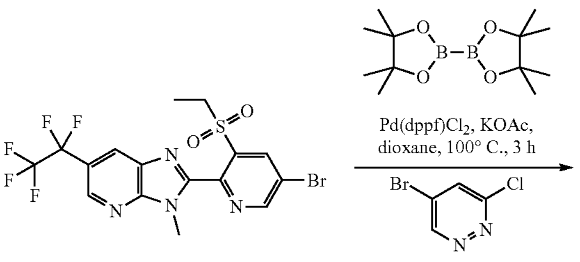

-continued

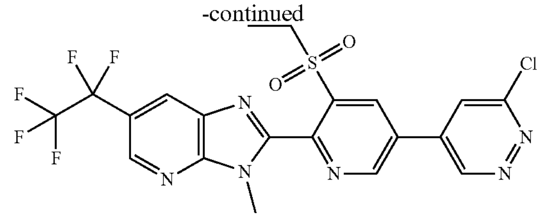

To a stirred mixture of 5-bromo-3-(ethanesulfonyl)-2-[3-methyl-6-(1,1,2,2,2-pentafluoroethyl)imidazo[4,5-b]pyridin-2-yl]pyridine (300 mg, 0.6 mmol, 1 equiv) and bis(pinacolato)diboron (229 mg, 0.9 mmol, 1.5 equiv) in dioxane (8 mL) were added KOAc (177 mg, 1.8 mmol, 3 equiv) and Pd(dppf)Cl2·$CH_2$Cl2 (98 mg, 0.1 mmol, 0.2 equiv) at room temperature under nitrogen atmosphere. The resulting mixture was stirred for 1 h at 100° C. under nitrogen atmosphere. To the above mixture was added 5-bromo-3-chloropyridazine (232 mg, 1.2 mmol, 2 equiv) at 100° C. The resulting mixture was stirred for additional 2 h at 100° C. The mixture was allowed to cool down to room temperature. The resulting mixture was concentrated under vacuum. The residue was purified by Prep-TLC (PE/EA 3:1) to afford 3-chloro-5-[5-(ethanesulfonyl)-6-[3-methyl-6-(1,1,2,2,2-pentafluoroethyl)imidazo[4,5-b]pyridin-2-yl]pyridin-3-yl]pyridazine (170 mg, 53%) as yellow oil.

2. Synthesis of 3-cyclopropyl-5-[5-(ethanesulfonyl)-6-[3-methyl-6-(1,1,2,2,2-pentafluoroethyl)-3H-imidazo[4,5-b]pyridin-2-yl]pyridin-3-yl]pyridazine

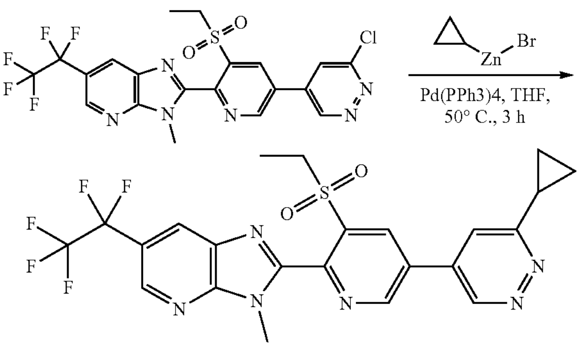

195

To a stirred mixture of 3-chloro-5-[5-(ethanesulfonyl)-6-[3-methyl-6-(1,1,2,2,2-pentafluoroethyl)imidazo[4,5-b]pyridin-2-yl]pyridin-3-yl]pyridazine (130 mg, 0.24 mmol, 1 equiv) and Pd(PPh3)4 (28 mg, 0.02 mmol, 0.1 equiv) in THF (3 mL) was added bromo(cyclopropyl)zinc (0.73 mL, 0.73 mmol, 3 equiv) at room temperature under nitrogen atmosphere. The resulting mixture was stirred for 3 h at 50° C. under nitrogen atmosphere. The mixture was allowed to cool down to room temperature. The reaction was quenched with Water at room temperature. The resulting mixture was extracted with EtOAc (2x20 mL). The combined organic layers were washed with brine (2x5 mL), dried over anhydrous Na2SO4. After filtration, the filtrate was concentrated under reduced pressure. The residue was purified by reverse flash chromatography with the following conditions: column, C18 silica gel; mobile phase, MeCN in Water (0.1% NH3·$H_2O$), 30% to 90% gradient in 15 min; detector, UV 254 nm to afford 3-cyclopropyl-5-[5-(ethanesulfonyl)-6-[3-methyl-6-(1,1,2,2,2-pentafluoroethyl)imidazo[4,5-b]pyridin-2-yl]pyridin-3-yl]pyridazine (30 mg, 23%) as an off-white solid.

Synthesis of Compound 96

Specifically, the following compounds of formula (I) can be synthesized by adopting the subsequent scheme of Compound 96 by someone who is skilled in the art: 99, 200

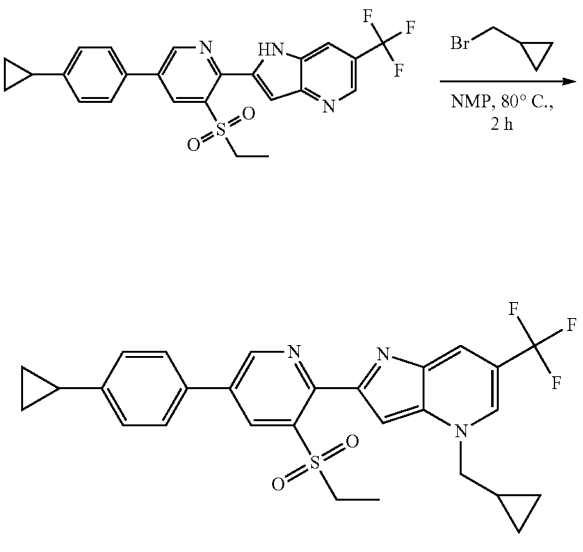

96

Into a 8-mL round-bottom flask, was placed 5-(4-cyclopropylphenyl)-3-(ethanesulfonyl)-2-[6-(trifluoromethyl)-1H-pyrrolo[3,2-b]pyridin-2-yl]pyridine (50 mg, 0.1 mmol, 1.0 equiv), NMP (2 mL), (bromo methyl)cyclopropane (71 mg, 0.5 mmol, 5.0 equiv). The resulting solution was stirred for 2 hr at 80 degrees C. The resulting mixture was concentrated under vacuum. The crude product was purified by Flash-Prep-HPLC. This resulted in 32 mg (57%) of 2-[4-(cyclopropylmethyl)-6-(trifluoromethyl)pyrrolo[3,2-b]pyridin-2-yl]-5-(4-cyclopropylphenyl)-3-(ethanesulfonyl)pyridine as a yellow solid.

Synthesis of Compound 104 and Compound 105

Specifically, the following compounds of formula (I) can be synthesized by adopting the subsequent scheme of Compound 104 by someone who is skilled in the art: 101, and by adopting the subsequent scheme of Compound 105 by someone who is skilled in the art: 102

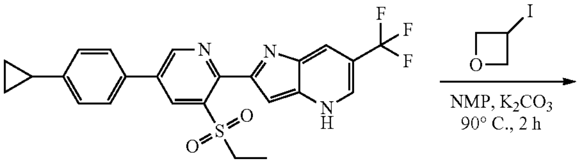

-continued

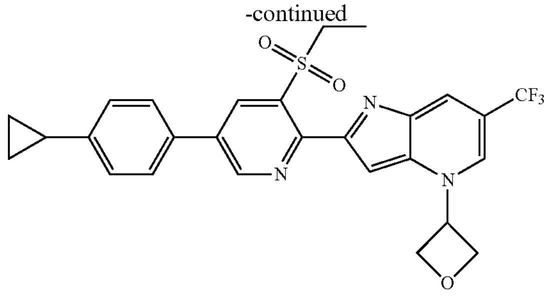

+

104

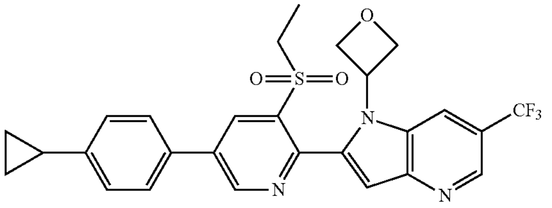

105

Into a 8-ml vial, was placed 5-(4-cyclopropylphenyl)-3-(ethanesulfonyl)-2-[6-(trifluoromethyl)-1H-pyrrolo[3,2-b]pyridin-2-yl]pyridine (100 mg, 1.0 equiv), 3-iodooxetane (0.1 mL), NMP (1 mL), $K_2CO_3$ (88 mg, 3.0 equiv). The resulting solution was stirred for 2 hr at 90 degrees C. The resulting solution was diluted with 4 mL of ACN. The solids were filtered out. The crude product was purified by Flash-Prep-HPLC with the following conditions (IntelFlash-1): Column, C18 silica gel; mobile phase, ACN=30% increasing to ACN=80% within 8 min; Detector, 254 nm. This resulted in 14 mg of 5-(4-cyclopropylphenyl)-3-(ethanesulfonyl)-2-[1-(oxetan-3-yl)-6-(trifluoromethyl)-3aH,4H-pyrrolo[3,2-b]pyridin-2-yl]pyridine as a yellow solid and 6.5 mg of 5-(4-cyclopropylphenyl)-3-(ethanesulfonyl)-2-[1-(oxetan-3-yl)-6-(trifluoromethyl)-3aH,4H-pyrrolo[3,2-b]pyridin-2-yl]pyridine as a white solid.

Synthesis of Compound 108

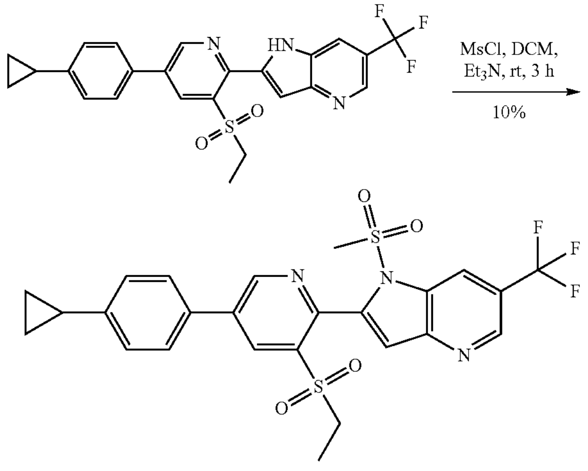

108

Into a 40-mL vial, was placed 5-(4-cyclopropylphenyl)-3-(ethanesulfonyl)-2-[6-(trifluoromethyl)-1H-pyrrolo[3,2-b]pyridin-2-yl]pyridine (150 mg, 0.3 mmol, 1.0 equiv), $Et_3N$ (161 mg, 1.6 mmol, 5.0 equiv), DCM (10 mL), methanesulfonyl chloride (110 mg, 1.0 mmol, 3.0 equiv). The resulting solution was stirred for 3 hr at room temperature. The resulting solution was diluted with 30 mL of DCM. The resulting mixture was washed with 3×30 ml of $H_2O$ and 1×30 mL of brine. The organic phase was dried over anhydrous sodium sulfate and concentrated. The residue was applied onto a silica gel column with ethyl acetate/petroleum ether (1:3). This resulted in 17 mg (10%) of 2-[5-(4-cyclopropylphenyl)-3-(ethanesulfonyl)pyridin-2-yl]-6-(trifluoromethyl)pyrrolo[3,2-b]pyridine-4-sulfonyl chloride as a light yellow solid.

Synthesis of Compound 107

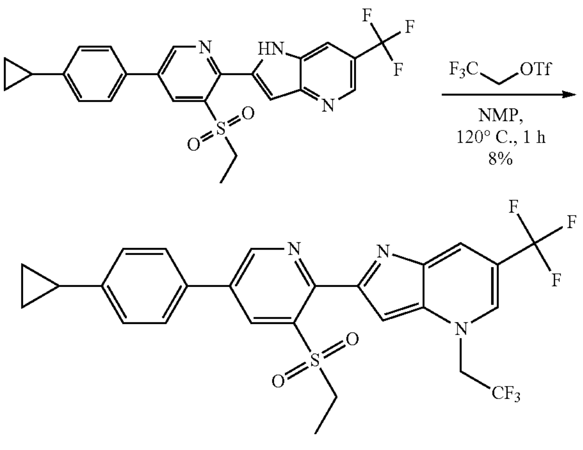

107

Into a 40-mL round-bottom flask, was placed 5-(4-cyclopropylphenyl)-3-(ethanesulfonyl)-2-[6-(trifluoromethyl)-1H-pyrrolo[3,2-b]pyridin-2-yl]pyridine (50 mg, 0.1 mmol, 1.0 equiv), NMP (5 mL), 2,2,2-trifluoroethyl trifluoromethanesulfonate (0.98 g, 4.2 mmol, 40 equiv). The resulting solution was stirred for 1 hr at 120 degrees C. The reaction mixture was purified by Prep-HPLC with the following conditions: Column, X-Bridge Column C18, 19*150 um, 20 ml/min; mobile phase, A: $H_2O$ (0.05% $NH3H_2O$), B:ACN, 50-80% B, 9 min; Detector, 254 nm. This resulted in 4.4 mg (8%) of 5-(4-cyclopropylphenyl)-3-(ethanesulfonyl)-2-[4-(2,2,2-trifluoroethyl)-6-(trifluoromethyl) pyrrolo[3,2-b]pyridin-2-yl]pyridine as a yellow solid.

Synthesis of Compound 97

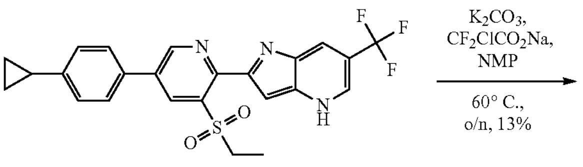

-continued

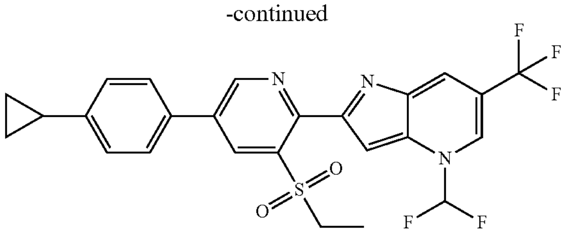

97

Into a 40-mL round-bottom flask purged and maintained with an inert atmosphere of nitrogen, was placed 5-(4-cyclopropylphenyl)-3-(ethanesulfonyl)-2-[6-(trifluoromethyl)-4H-pyrrolo[3,2-b]pyridin-2-yl]pyridine (100 mg, 0.2 mmol, 1.0 equiv), ACN (10 mL), $K_2CO_3$ (88 mg, 0.6 mmol, 3 equiv), $CF_2C1CO_2Na$ (96 mg, 0.6 mmol, 3 equiv). The resulting solution was stirred overnight at 60 degrees C. in an oil bath. The crude product was purified by Prep-HPLC with the following conditions (Prep-HPLC-003): Column, XBridge Prep C18 OBD Column, 19*150 mm Sum; mobile phase, Water (0.05% $NH_3H_2O$) and ACN (45% ACN up to 85% in 7 min); Detector, 254 nm. This resulted in 18 mg (13%) of 2-[5-(4-cyclopropylphenyl)-3-(ethanesulfonyl) pyridin-2-yl]-4-(difluoromethyl)-1-methyl-6-(trifluoromethyl)pyrrolo[3,2-b]pyridin-1-ium as a yellow solid.

Synthesis of Compound 98

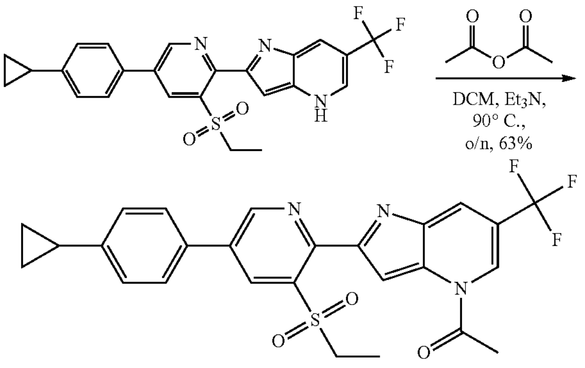

98

Into a 8-mL round-bottom flask purged and maintained with an inert atmosphere of nitrogen, was placed 5-(4-cyclopropylphenyl)-3-(ethanesulfonyl)-2-[6-(trifluoromethyl)-4H-pyrrolo[3,2-b]pyridin-2-yl]pyridine (50 mg, 0.1 mmol, 1.0 equiv), NMP (3 mL), acetic anhydride (32 mg, 0.3 mmol, 3 equiv). The resulting solution was stirred for overnight at 90 degrees C. The crude product was purified by Prep-HPLC with the following conditions (Prep-HPLC-003): Column, XBridge Prep C18 OBD Column, 19*150 mm 5 um; mobile phase, Water (0.05% $NH3H_2O$) and ACN (45% ACN up to 85% in 7 min); Detector, 254 nm. This resulted in 35 mg (62%) of 1-[2-[5-(4-cyclopropylphenyl)-3-(ethanesulfonyl)pyridin-2-yl]-6-(trifluoromethyl)pyrrolo [3,2-b]pyridin-4-yl]ethanone as an off-white solid.

Synthesis of Compound 100

Specifically, the following compounds of formula (I) can be synthesized by adopting the subsequent scheme of Compound 100 by someone who is skilled in the art: 189, 197

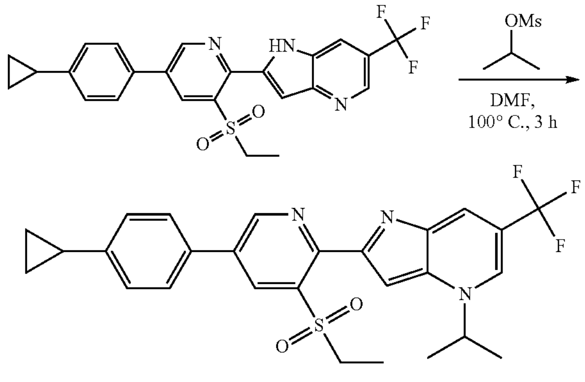

100

Into a 8-mL vial purged and maintained with an inert atmosphere of nitrogen, was placed 5-(4-cyclopropylphenyl)-3-(ethanesulfonyl)-2-[6-(trifluoromethyl)-1H-pyrrolo[3,2-b]pyridin-2-yl]pyridine(100 mg, 0.2 mmol, 1.0 equiv), DMF (2 mL), isopropyl methanesulfonate (1 mL). The resulting solution was stirred for 3 hr at 100 degrees C. The resulting mixture was concentrated under vacuum. The crude product was purified by Flash-Prep-HPLC. This resulted in 11 mg (10%) of 5-(4-cyclopropylphen yl)-3-(ethanesulfonyl)-2-[4-isopropyl-6-(trifluoromethyl)pyrrolo[3,2-b]pyridin-2yl]pyridine as a yellow solid.

Synthesis of Compound 103

Synthesis of 2-[4-(2-chloroethyl)-6-(trifluoromethyl)pyrrolo[3,2-b]pyridin-2-yl]-5-(4-cyclopropylphenyl)-3-(ethanesulfonyl)pyridine

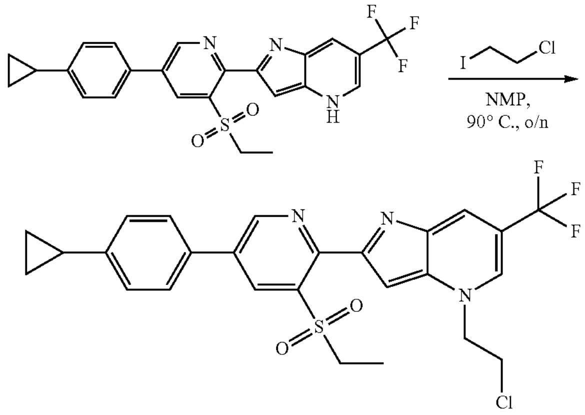

Into a 8-mL sealed tube purged and maintained with an inert atmosphere of nitrogen, was placed 5-(4-cyclopropylphenyl)-3-(ethanesulfonyl)-2-[6-(trifluoromethyl)-4H-pyrrolo[3,2-b]pyridin-2-yl]pyridine (100 mg, 0.2 mmol, 1.0 equiv), NMP (2 mL), 1-chloro-2-iodoethane (1 mL). The resulting solution was stirred for overnight at 90 degrees C. The crude product was purified by Flash-Prep-HPLC with the following conditions (IntelFlash-1): Column, C18 silica gel; mobile phase, ACN:$H_2O$(TFA 0.05%)=45% increasing to ACN:$H_2O$(TFA 0.05%)=60% within 12 min; Detector, 254 nm. This resulted in 105 mg (93%) of 2-[4-(2-chloroethyl)-6-(trifluoromethyl)pyrrolo[3,2-b]pyridin-2-yl]-5-(4-cyclopropylphenyl)-3-(ethanesulfonyl)pyridine as a brown solid.

Synthesis of 5-(4-cyclopropylphenyl)-3-(ethanesulfonyl)-2-[4-ethenyl-6-(trifluoromethyl)pyrrolo[3,2-b]pyridin-2-yl]pyridine

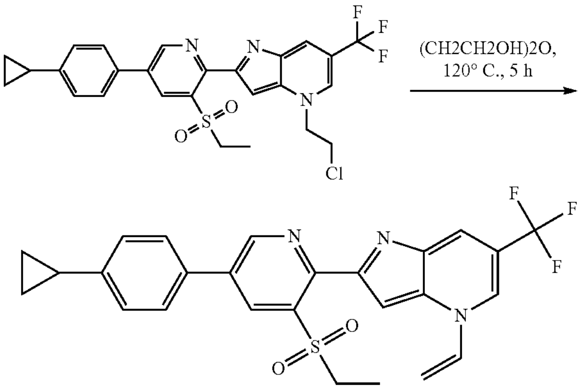

103

Into a 20-mL round-bottom flask purged and maintained with an inert atmosphere of nitrogen, was placed 2-[4-(2-chloroethyl)-6-(trifluoromethyl)pyrrolo[3,2-b]pyridin-2-yl]-5-(4-cyclopropylphenyl)-3-(ethanesulfonyl)pyridine (50 mg, 0.09 mmol, 1.00 equiv), diethylene glycol (5 mL). The resulting solution was stirred for 5 hr at 120 degrees C. in an oil bath. The crude product was purified by Prep-HPLC with the following conditions (Prep-HPLC-003): Column, SunFire Prep C18 OBD Column, 19*150 mm 5 um 10 nm; mobile phase, Water (0.1% FA) and ACN (35% ACN up to 68% in 7 min); Detector, 254 nm. This resulted in 6.1 mg (13%) of 5-(4-cyclopropylphenyl)-3-(ethanesulfonyl)-2-[4-ethenyl-6-(trifluoromethyl)pyrrolo[3,2-b]pyridin-2-yl]pyridine as a yellow solid.

Synthesis of Compound 198

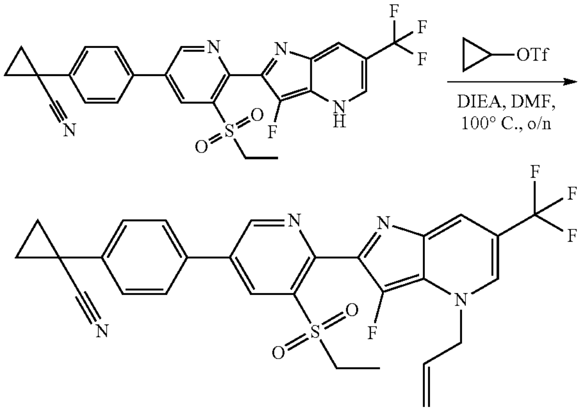

198

To a stirred solution of 1-{4-[5-(ethanesulfonyl)-6-[3-fluoro-6-(trifluoromethyl)-4H-pyrrolo[3,2-b]pyridin-2-yl]

pyridin-3-yl]phenyl}cyclopropane-1-carbonitrile (250 mg, 0.5 mmol, 1 equiv) and cyclopropyltrifluoromethanesulfonate (1848 mg, 9.7 mmol, 20 equiv) in DMF (2.5 mL) was added DIEA (628 mg, 4.9 mmol, 10.00 equiv) at room temperature. The resulting mixture was stirred for overnight at 100° C. The mixture was purified by Prep-HPLC with the following conditions (column, C18 silica gel; mobile phase, MeCN in water (0.1% $NH_3 \cdot H_2O$), 60% to 80% gradient in 10 min; detector, UV 254 nm. to afford 1-{4-[5-(ethanesulfonyl)-6-[3-fluoro-4-(prop-2-en-1-yl)-6-(trifluoromethyl)pyrrolo[3,2-b]pyridin-2-yl]pyridin-3-yl]phenyl}cyclopropane-1-carbonitrile (24 mg, 9%) as a white solid.

Synthesis of Compound 199

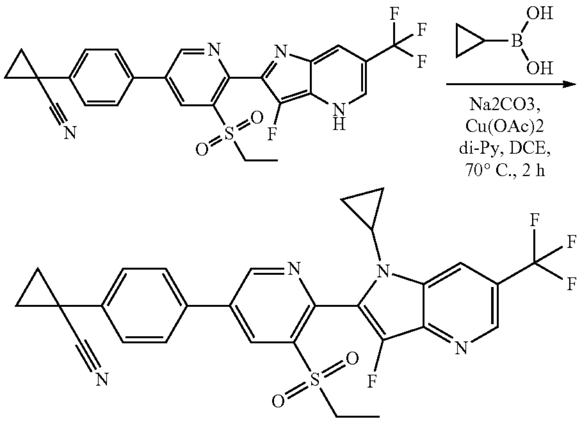

199

To a stirred solution of 1-{4-[5-(ethanesulfonyl)-6-[3-fluoro-6-(trifluoromethyl)-4H-pyrrolo[3,2-b]pyridine-2-yl]pyridin-3-yl]phenyl}cyclopropane-1-carbonitrile (50 mg, 0.1 mmol, 1 equiv) and cyclopropylboronic acid (25 mg, 0.3 mmol, 3 equiv) in DCE (I mL) were added Cu(OAc)2 (19 mg, 0.3 mmol, 3 equiv), 2,2-bipyridine (18 mg, 0.1 mmol, 1.2 equiv) and Na2CO3 (31 mg, 0.3 mmol, 3 equiv) at room temperature. The resulting mixture was stirred for 2 h at 70° C. under oxygen atmosphere. The resulting mixture was concentrated under vacuum. The crude product was purified by Prep-HPLC with the following conditions: column, C18 silica gel; mobile phase, MeCN in Water (0.1% $NH_3 \cdot H_2O$), 50% to 80% gradient in 10 min; detector, UV 254 nm to afford 1-(4-{6-[1-cyclopropyl-3-fluoro-6-(trifluoromethyl)pyrrolo[3,2-b]pyridin-2-yl]-5-(ethanesulfonyl)pyridin-3-yl}phenyl)cyclopropane-1-carbonitrile (19 mg, 36%) as an off-white solid.

Synthesis of Compound 106

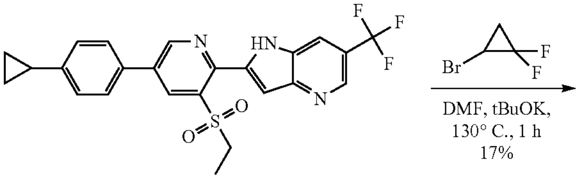

-continued

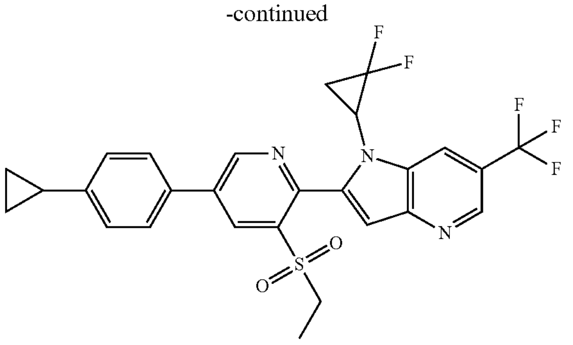

106

Into a 40-mL round-bottom flask, was placed a solution of 5-(4-cyclopropylphenyl)-3-(ethanesulfonyl)-2-[6-(trifluoromethyl)-1H-pyrrolo[3,2-b]pyridin-2-yl]pyridine (85 mg, 0.2 mmol, 1.0 equiv) in DMF (20 mL), tBuOK (85 mg, 0.8 mmol, 4.2 equiv). This was followed by the addition of a solution of 2-bromo-1,1-difluorocyclopropane (141 mg, 0.9 mmol, 5.0 equiv) in DMF (10 mL) dropwise with stirring at 130 degrees C. The resulting solution was stirred for 1 hr at 130 degrees C. The mixture was purified by Prep-HPLC with the following conditions: Column, X-Bridge Column 19*150 um, 20 ml/min; mobile phase, A: $H_2O$ (0.05% $NH_3H_2O$) B: ACN, 50-80% B, 9 min; Detector, 254 nm. This resulted in 17 mg (17%) of 5-(4-cyclopropylphenyl)-2-[1-(2,2-difluorocyclopropyl)-6-(trifluoromethyl)pyrrolo[3,2-b]pyridin-2-yl]-3-(ethanesulfonyl)pyridine as a yellow solid.

Synthesis of Compound 7

Specifically, the following compounds of formula (I) can be synthesized by adopting the subsequent scheme of Compound 7 by someone who is skilled in the art: 8, 9, 10, 11, 12, 62, 63, 64, 65, 67, 69, 95, 180, 190

Synthesis of 5-[4-cyclopropyl-3-(trifluoromethyl)phenyl]-3-(ethanesulfonyl)-2-[6-(trifluoromethyl)-1H-pyrrolo[3,2-b]pyridin-2-yl]pyridine

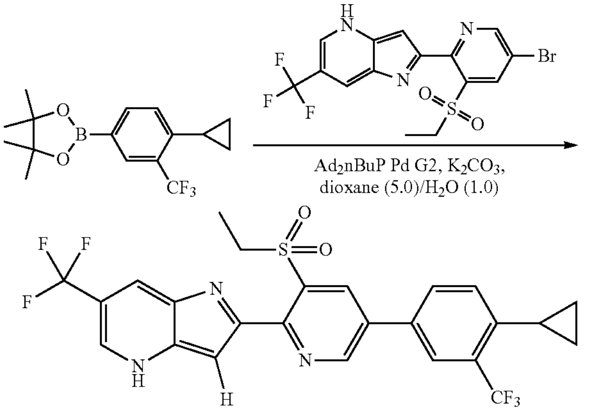

Into a 50-mL round-bottom flask purged and maintained with an inert atmosphere of nitrogen, was placed 5-bromo-3-(ethanesulfonyl)-2-[6-(trifluoromethyl)-1H-pyrrolo[3,2-b]pyridin-2-yl]pyridine (150 mg, 0.3 mmol, 1.0 equiv), 2-[4-cyclopropyl-3-(trifluoromethyl)phenyl]-4,4,5,5-tetramet hyl-1,3,2-dioxaborolane (216 mg, 0.7 mmol, 2.0 equiv), $Ad_2$(n-BuP)Pd-$G_2$ (69 mg, 0.1 mmol, 0.3 equiv), $K_2CO_3$ (119 mg, 0.9 mmol, 2.5 equiv), dioxane (15 mL), $H_2O$ (3 mL). The resulting solution was stirred for 16 hr at 80 degrees C. The resulting mixture was concentrated. The residue was applied onto a silica gel column with ethyl acetate/petroleum ether (1:50). This resulted in 132 mg (71%) of 5-[4-cyclopropyl-3-(trifluoromethyl)phenyl]-3-(ethanesulfonyl)-2-[6-(trifluoromethyl)-1H-pyrrolo[3,2-b]pyridin-2-yl]pyridine as yellow oil.

Synthesis of 5-[4-cyclopropyl-3-(trifluoromethyl)phenyl]-2-[4-(2,2-difluoroethyl)-6-(trifluoromethyl)pyrrolo[3,2-b]pyridin-2-yl]-3-(ethanesulfonyl)pyridine

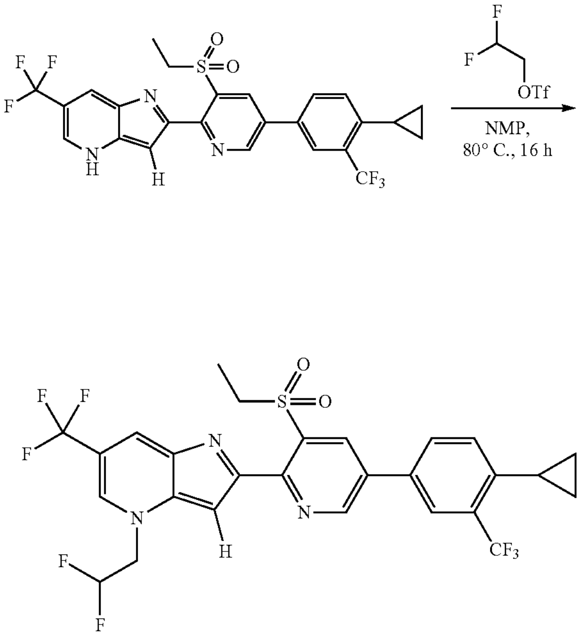

7

Into a 50-mL round-bottom flask, was placed 5-[4-cyclopropyl-3-(trifluoromethyl)phenyl]-3-(ethanesulfonyl)-2-[6-(trifluoromethyl)-1H-pyrrolo[3,2-b]pyridin-2-yl]pyridine (130 mg, 0.2 mmol, 1.0 equiv), NMP (13 mL), 2,2-difluoroethyl trifluoromethanesulfonate (1.3 mL). The resulting solution was stirred for 16 hr at 80 degrees C. The crude product was purified by Flash-Prep-HPLC with the following conditions (IntelFlash-1): Column, C18 silica gel; mobile phase, $CH_3CN$/0.05% $NH_3 \cdot H_2O$=60 increasing to $CH_3CN$/0.05% $NH_3 \cdot H_2O$=95 within 12 min; Detector, 254 nm. product was obtained. This resulted in 22 mg (15%) of 5-[4-cyclopropyl-3-(trifluoromethyl)phenyl]-2-[4-(2,2-difluoroethyl)-6-(trifluoromethyl) pyrrolo[3,2-b]pyridin-2-yl]-3-(ethanesulfonyl)pyridine as a yellow solid.

Synthesis of Compound 171

Specifically, the following compounds of formula (I) can be synthesized by adopting the subsequent scheme of 25 Compound 171 by someone who is skilled in the art: 172

Synthesis of 5'-(ethanesulfonyl)-6'-[6-(trifluoromethyl)-4H-pyrrolo[3,2-b]pyridin-2-yl]-6-[1-(trifluoromethyl)cyclopropyl]-2,3'-bipyridine

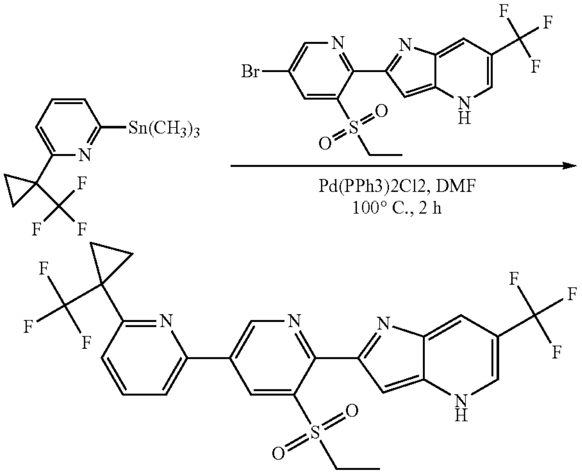

Into a 8 mL vial were added 5-bromo-3-(ethanesulfonyl)-2-[6-(trifluoromethyl)-1H-pyrrolo[3,2-b]pyridin-2-yl]pyridine (147 mg, 0.34 mmol, 1 equiv) and 2-[1-(trifluoromethyl)cyclopropyl]-6-(trimethyl stannyl)pyridine (178 mg, crude), DMF (3 mL), Pd(PPh3)2C12 (24 mg, 0.03 mmol, 0.1 equiv). The resulting mixture was stirred for 2 h at 100° C. under nitrogen atmosphere. The mixture was allowed to cool down to room temperature. The residue was purified by reverse flash chromatography with the following conditions: column, C18 silica gel; mobile phase, MeCN in water, 0% to 80% gradient in 20 min; detector, UV 254 nm to afford 5'-(ethanesulfonyl)-6'-[6-(trifluoromethyl)-4H-pyrrolo[3,2-b]pyridin-2-yl]-6-[1-(trifluoromethyl)cyclopropyl]-2,3'-bipyridine (70 mg, 38%) as a white solid.

Synthesis of 5'-(ethanesulfonyl)-6'-[6-(trifluoromethyl)-4H-pyrrolo[3,2-b]pyridin-2-yl]-6-[1-(trifluoromethyl)cyclopropyl]-2,3'-bipyridine

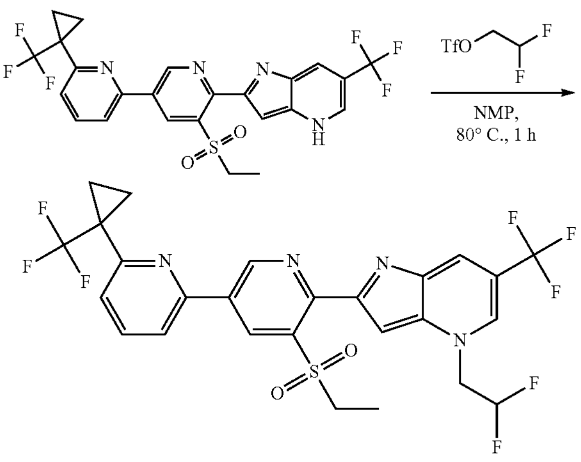

171

A solution of 5'-(ethanesulfonyl)-6'-[6-(trifluoromethyl)-4H-pyrrolo[3,2-b]pyridin-2-yl]-6-[1-(trifluoro methyl)cyclopropyl]-2,3'-bipyridine (50 mg, 0.09 mmol, 1 equiv) and 2,2-difluoroethyl trifluoromethanesulfonate (0.5 mL) in NMP (1 mL) was stirred for 1 h at 80° C. under nitrogen atmosphere. The mixture was allowed to cool down to room temperature. The mixture was purified by reverse flash chromatography with the following conditions: column, C18 silica gel; mobile phase, MeCN in water, 40% to 80% gradient in 10 min; detector, UV 254 nm to afford 6'-[4-(2,2-difluoroethyl)-6-(trifluoromethyl) pyrrolo[3,2-b]pyridin-2-yl]-5'-(ethanesulfonyl)-6-[I-(trifluoromethyl)cyclopropyl]-2,3'-bipyridine (27 mg, 49%) as a yellow solid.

Synthesis of Compound 23

Specifically, the following compounds of formula (I) can be synthesized by adopting the subsequent scheme of Compound 23 by someone who is skilled in the art: 21, 181

Synthesis of 5-(4-[1-[(tert-butyldimethylsilyl)oxy] cyclopropyl]phenyl)-3-(ethanesulfonyl)-2-[4-ethyl-6-(trifluoromethyl)pyrrolo[3,2-b]pyridin-2-yl]pyridine

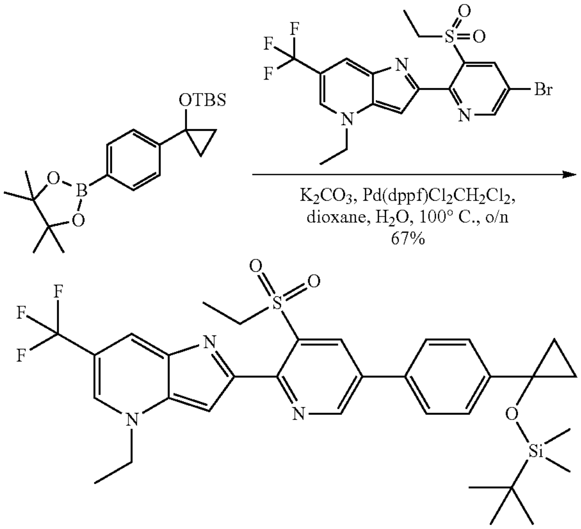

Into a 40-mL vial purged and maintained with an inert atmosphere of nitrogen, was placed 5-bromo-3-(ethanesulfonyl)-2-[4-ethyl-6-(trifluoromethyl)pyrrolo[3,2-b]pyridin-2-yl]pyridine (60 mg, 0.1 mmol, 1.0 equiv), dioxane (5 mL), tert-butyldimethyl[1-[4-(4,4,5,5-tetramethyl-1,3,2-dioxaborolan-2-yl)phenyl]cyclopropoxy]silane (97 mg, 0.26 mmol, 2.0 equiv), $K_2CO_3$ (36 mg, 0.26 mmol, 2.0 equiv), Pd(dppf)$Cl_2CH_2Cl_2$ (11 mg, 0.01 mmol, 0.1 equiv), $H_2O$(I mL). The resulting solution was stirred overnight at 100° C. in an oil bath. The reaction mixture was cooled to room temperature. The crude product was purified by Flash-Prep-HPLC with the following conditions (IntelFlash-1): Column, C18 silica gel; mobile phase, $CH_3CN$/0.05% NH3·$H_2O$=100%; Detector, 254&220 nm. This resulted in 55 mg (67%) of 5-(4-[l-[(tert-butyldimethylsilyl)oxy]cyclopropyl]phenyl)-3-(ethanesulfonyl)-2-[4-ethyl-6-(trifluoromethyl)pyrrolo[3,2-b]pyridin-2-yl]pyridine as a yellow solid.

Synthesis of 1-[4-[5-(ethanesulfonyl)-6-[4-ethyl-6-(trifluoro methyl)pyrrolo[3,2-b]pyridin-2-yl]pyridin-3-yl]phenyl]cyclopropan-1-ol

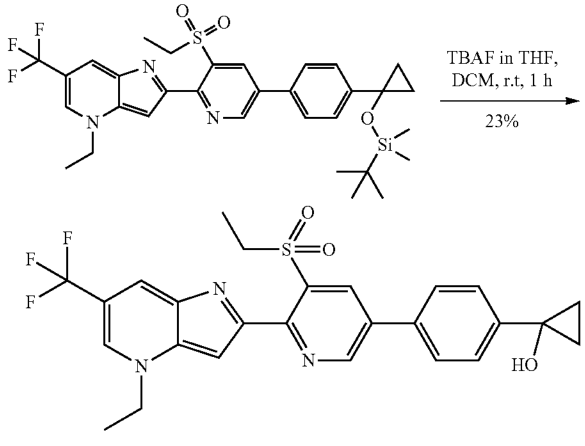

23

Into a 8-mL vial, was placed 5-(4-[1-l(tert-butyldimethylsilyl)oxy]cyclopropyl]phenyl)-3-(ethanesulfonyl)-2-[4-ethyl-6-(trifluoromethyl)pyrrolo[3,2-b]pyridin-2-yl]pyridine (50 mg, 0.08 mmol, 1.0 equiv), DCM (6 mL), TBAF in THF (0.24 mL, 0.24 mmol, 3.0 equiv). The resulting solution was stirred for 1 hr at room temperature. The pH value of the solution was adjusted to 7-8 with HCl (0.25M). The resulting solution was extracted with 3×15 mL of dichloromethane and the organic layers combined and concentrated. The crude product was purified by Flash-Prep-HPLC with the following conditions (IntelFlash-1): Column, C18 silica gel; mobile phase, $CH_3CN$/0.05% $NH_3$·$H_2O$=65% increasing to $CH_3CN$/0.05% $NH_3$·$H_2O$=70%; Detector, 254&220 nm. This resulted in 9.3 mg (23%) of]-[4-[5-(ethanesulfonyl)-6-[4-ethyl-6-(trifluoro methyl)pyrrolo[3,2-b]pyridin-2-yl]pyridin-3-yl]phenyl]cyclopropan-1-ol as a yellow solid.

Synthesis of Compound 45

Synthesis of 5-bromo-3-(ethylsulfanyl)pyridine-2-carbonitrile

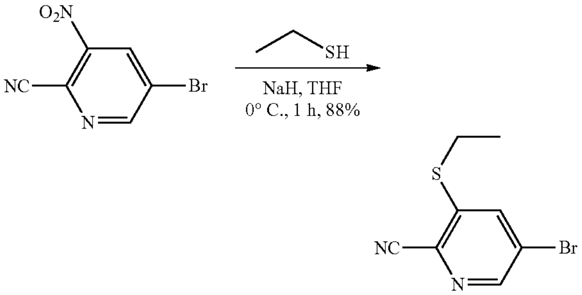

Into a 3.0-L 3-necked round-bottom flask, was placed 5-bromo-3-nitropyridine-2-carbonitrile (150 g, 0.6 mol, 1.0 equiv), THF (1.5 L), ethanethiol (38 g, 0.6 mol, 0.95 equiv), 0 degrees C. was added NaH (32 g, 0.8 mol, 1.2 equiv, 60%).

The resulting solution was stirred for 1 hr at 0 degrees C. The reaction was then quenched by the addition of 2.0 L of water. The resulting solution was extracted with 3×1.0 L of ethyl acetate dried over anhydrous sodium sulfate and concentrated. This resulted in 141 g (88%) of 5-bromo-3-(ethylsulfanyl)pyridine-2-carbonitrile as a black solid.

Synthesis of 5-bromo-3-(ethylsulfanyl)pyridine-2-carboxylic acid

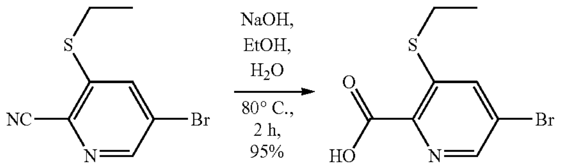

Into a 3000-mL round-bottom flask, was placed 5-bromo-3-(ethylsulfanyl)pyridine-2-carbonitrile (160 g, 660 mmol, 1.0 equiv), EtOH (1.6 L), $H_2O$ (0.8 L), NaOH (131 g, 3.2 mol, 5.0 equiv). The resulting solution was stirred for 2 hr at 80 degrees C. in an oil bath. The pH value of the solution was adjusted to 2 with HCl (3 mol/L). The solids were collected by filtration. The solid was dried by infrared lamp. This resulted in 163 g (94%) of 5-bromo-3-(ethylsulfanyl) pyridine-2-carboxylic acid as a light yellow solid.

Synthesis of methyl 5-bromo-3-(ethylsulfanyl)pyridine-2-carboxylate

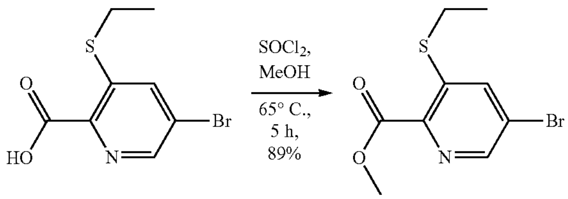

Into a 2000-mL round-bottom flask, was placed 5-bromo-3-(ethylsulfanyl)pyridine-2-carboxylic acid (100 g, 420 mmol, 1.0 equiv), MecOH (1.1 L), $SOCl_2$ (150 g, 1.3 mol, 3.0 equiv). The resulting solution was stirred for 5 hr at 65 degrees C. in an oil bath. The reaction was then quenched by the addition of 8.0 L of water. The solids were collected by filtration. The solid was washed three times with 500 mL of water. Then dried by infrared lamp. This resulted in 94 g (89%) of methyl 5-bromo-3-(ethylsulfanyl)pyridine-2-carboxylate as a yellow solid.

Synthesis of methyl 5-(4-cyclopropylphenyl)-3-(ethylsulfanyl)pyridine-2-carboxylate

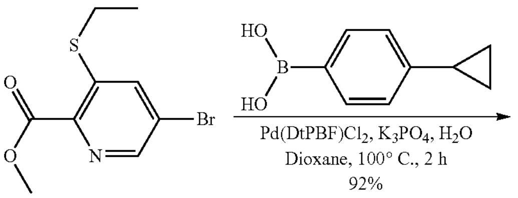

-continued

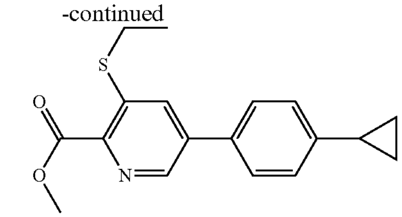

Into a 50-mL round-bottom flask purged and maintained with an inert atmosphere of nitrogen, was placed methyl 5-bromo-3-(ethylsulfanyl)pyridine-2-carboxylate (500 mg, 1.8 mmol, 1.0 equiv), 4-cyclopropylphenylboronic acid (440 mg, 2.7 mmol, 1.5 equiv), $K_3PO_4$ (769 mg, 3.6 mmol, 2.0 equiv), dioxane (10 mL), $H_2O$ (2 mL), $Pd(Dtbpf)Cl_2$ (118 mg, 0.18 mmol, 0.1 equiv). The resulting solution was stirred for 2 hr at 100 degrees C. in an oil bath. The reaction mixture was cooled. The resulting mixture was concentrated. The residue was applied onto a silica gel column with ethyl acetate/petroleum ether (1/4). The collected fractions were combined and concentrated. This resulted in 520 mg (92%) of methyl 5-(4-cyclopropylphenyl)-3-(ethylsulfanyl) pyridine-2-carboxylate as a yellow solid.

Synthesis of 5-(4-cyclopropylphenyl)-3-(ethanesulfonyl)pyridine-2-carboxylic acid

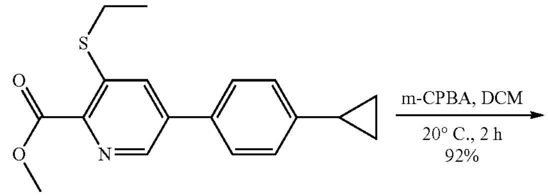

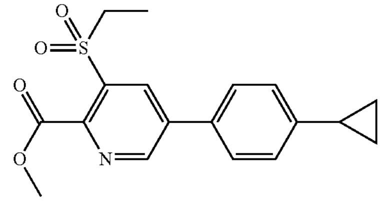

Into a 50-mL round-bottom flask purged and maintained with an inert atmosphere of nitrogen, was placed methyl 5-(4-cyclopropylphenyl)-3-(ethylsulfanyl)pyridine-2-carboxylate (500 mg, 1.5 mmol, 1.0 equiv), DCM (25 mL), mCPBA (780 mg, 4.5 mmol, 3 equiv). The resulting solution was stirred for 2 hr at room temperature. The resulting mixture was concentrated. The crude product was purified by Prep-HPLC with the following conditions (2 #SHIMADZU (HPLC-01)): Column, XBridge Shield RP18 OBD Column, 5 um,19*150 mm; mobile phase, Water (0.05% NH3H2O) and ACN (40% ACN up to 75% in 7 min); Detector, 254 nm. This resulted in 500 mg (92%) of. methyl 5-(4-cyclopropylphenyl)-3-(ethanesulfonyl)pyridine-2-carboxylate as a white solid.

Synthesis of 5-(4-cyclopropylphenyl)-3-(ethanesulfonyl)pyridine-2-carboxylic acid

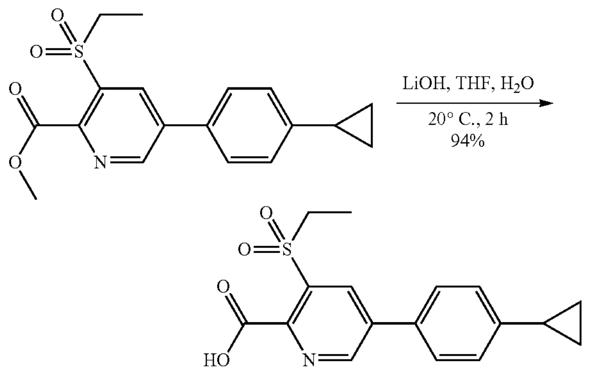

Into a 50-mL round-bottom flask, was placed methyl 5-(4-cyclopropylphenyl)-3-(ethanesulfonyl)pyridine-2-carboxylate (500 mg, 1.5 mmol, 1.0 equiv), THF (10 mL), $H_2O$ (2 mL), LiOH (139 mg, 5.8 mmol, 4.0 equiv). The resulting solution was stirred for 2 hr at 20 degrees C. The pH value of the solution was adjusted to 3 with HCl (2 N). The solids were collected by filtration. The solid was dried by infrared lamp. This resulted in 450 mg (94%) of 5-(4-cyclopropylphenyl)-3-(ethanesulfonyl)pyridine-2-carboxylic acid as a white solid.

Synthesis of N-[1-cyclopropyl-3-(methylamino)-2-oxo-6-(trifluoromethyl)pyridin-4-yl]-5-(4-cyclopropylphenyl)-3-(ethanesulfonyl)pyridine-2-carboxamide

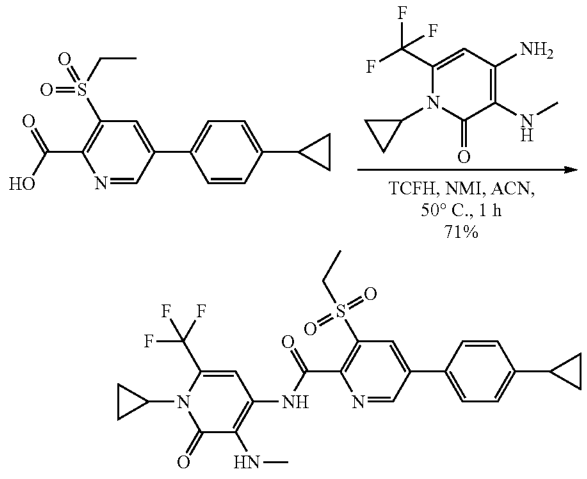

Into a 8-mL vial, was placed 4-amino-1-cyclopropyl-3-(methylamino)-6-(trifluoromethyl)pyridin-2-one (50 mg, 0.2 mmol, 1.0 equiv), 5-(4-cyclopropylphenyl)-3-(ethanesulfonyl)pyridine-2-carboxylic acid (67 mg, 0.2 mmol, 1.0 equiv), ACN (2 mL), NMI (58 mg, 0.7 mmol, 3.5 equiv), TCFH (62 mg, 0.2 mmol, 1.1 equiv). The resulting solution was stirred for 1 hr at 50 degrees C. The reaction mixture was cooled to 25 degrees C. The reaction was then quenched by the addition of 30 mL of water/ice. The resulting solution was extracted with 3×50 mL of ethyl acetate and the organic layers combined. The resulting mixture was washed with 3×50 mL of brine and dried over anhydrous sodium sulfate and concentrated. The residue was applied onto a silica gel column with ethyl acetate/petroleum ether (1.5:1). This resulted in 80 mg (71%) of N-[l-cyclopropyl-3-(methylamino)-2-oxo-6-(trifluoromethyl)pyridin-4-yl]-5-(4-cyclopropylphenyl)-3-(ehanesulfonyl)pyridine-2-carboxamide as a white solid.

Synthesis of 5-cyclopropyl-2-[5-(4-cyclopropylphenyl)-3-(ethanesulfonyl)pyridin-2-yl]-3-methyl-6-(trifluoromethyl)imidazo[4,5-c]pyridin-4-one

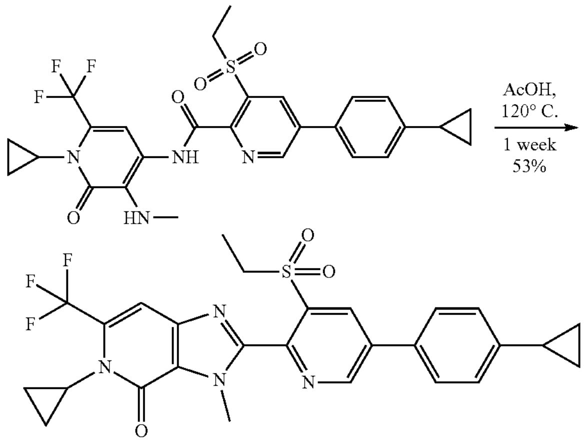

45

Into a 8-mL vial, was placed N—[I-cyclopropyl-3-(methylamino)-2-oxo-6-(trifluoromethyl)pyridin-4-yl]-5-(4-cyclopropylphenyl)-3-(ethanesulfonyl)pyridine-2-carboxamide; ethane (40 mg, 0.07 mmol, 1.0 equiv), AcOH (2 mL). The resulting solution was stirred for 7 days at 120 degrees C. The resulting mixture was concentrated. The crude product was purified by Prep-HPLC with the following conditions (2 #SHIMADZU (HPLC-01)): Column, XBridge Prep C18 OBD Column, 5 um,19*150 mm; mobile phase, Water (0.05% $NH_3H_2O$) and ACN (50% Phase B up to 81% in 7 min); Detector, 220 nm. This resulted in 19.4 mg (53%) of 5-cyclopropyl-2-[5-(4-cyclopropylphenyl)-3-(ethanesulfonyl)pyridin-2-yl]-3-methyl-6-(trifluoromethyl)imidazo[4,5-c]pyridin-4-one as a white solid.

Synthesis of Compound 111

Synthesis of 1-ethyl-5-nitro-3-(trifluoromethyl)pyridin-2-one

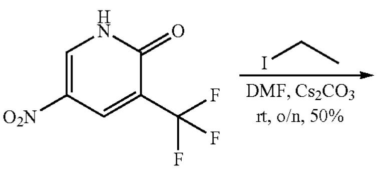

-continued

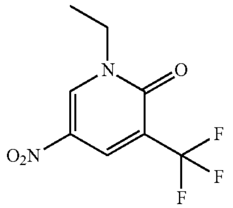

Into a 2000 mL 4-neck round-bottom flask were added 5-nitro-3-(trifluoromethyl)-1H-pyridin-2-one (20.8 g, 100 mmol, 1 equiv), DMF (1000 mL), $Cs_2CO_3$ (98 g, 300 mmol, 3 equiv) and ethyl iodide (23.4 g, 150 mmol, 1.5 equiv). The resulting mixture was stirred overnight at room temperature. The resulting mixture was diluted with water (2000 mL). The resulting mixture was extracted with EA (3×1000 mL). The combined organic layers were washed with water (3×1000 mL) and brine (1×1000 mL), dried over anhydrous Na2SO4. After filtration, the filtrate was concentrated under reduced pressure. The residue was purified by silica gel column chromatography, eluted with PE: EA (3:1) to afford 1-ethyl-5-nitro-3-(trifluoromethyl)pyridin-2-one (12 g, 50%) as a yellow solid.

Synthesis of PH-6-amino-1-ethyl-5-nitro-3-(trifluoromethyl)pyridin-2-one

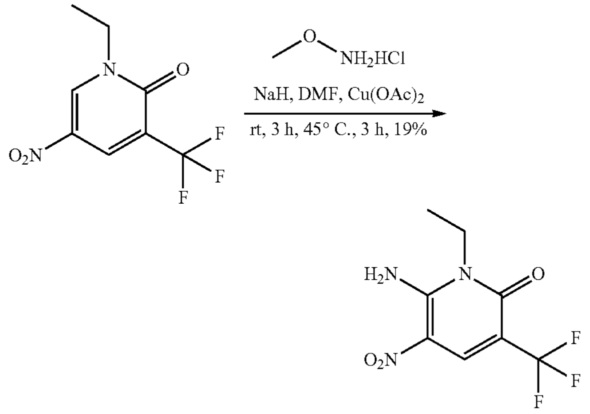

Into a 50 mL round-bottom flask were added 1-ethyl-5-nitro-3-(trifluoromethyl)pyridin-2-one (2 g, 8.5 mmol, 1 equiv), $Cu(OAc)_2$ (0.15 g, 0.85 mmol, 0.1 equiv) and DMF (40 mL) at room temperature. To the above mixture was added NaH (2.24 g, 56 mmol, 6.6 equiv, 60%) in portions at 0° C. The resulting mixture was stirred for additional 30 mins at room temperature. To this was added the solution of $CH_3ONH_2HCl$ (1.41 g, 16.938 mmol, 2.0 equiv) DMF (10 mL) with dropwise at room temperature. The resulting mixture was stirred for 3 h at room temperature and 3 h at 45° C. The reaction mixture was poured into 100 mL of $NH_4Cl$ (sat.), then extracted with EA (3×100 mL). The combined organic layers were washed with water (3×100 mL) and brine (1x 100 mL), dried over anhydrous $Na_2SO_4$. After filtration, the filtrate was concentrated under reduced pressure. The residue was purified by silica gel column chromatography, eluted with PE:EA (3:1) to afford 6-amino-1-ethyl-5-nitro-3-(trifluoromethyl)pyridin-2-one (400 mg, 19%) as a yellow solid.

Synthesis of 5-(4-cyclopropylphenyl)-3-(ethylthio)picolinoyl chloride

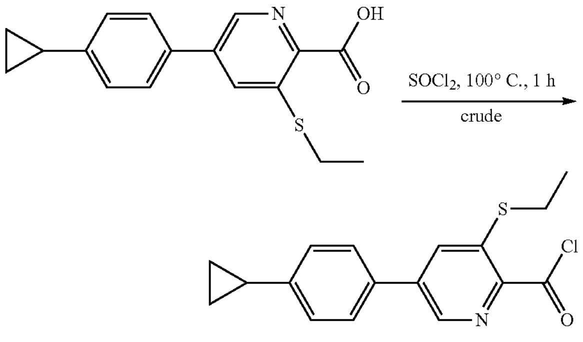

Into a 40 mL were added 5-(4-cyclopropylphenyl)-3-(ethylthio)picolinic acid (110 mg, 0.4 mmol, 1.0 equiv) and thionyl chloride (5 mL) at 100 degrees C. 1 h, The resulting mixture was concentrated under reduced pressure.

Synthesis of 5-(4-cyclopropylphenyl)-N-(1-ethyl-3-nitro-6-oxo-5-(trifluoromethyl)-1,6-dihydropyridin-2-yl)-3-(ethylthio)picolinamide

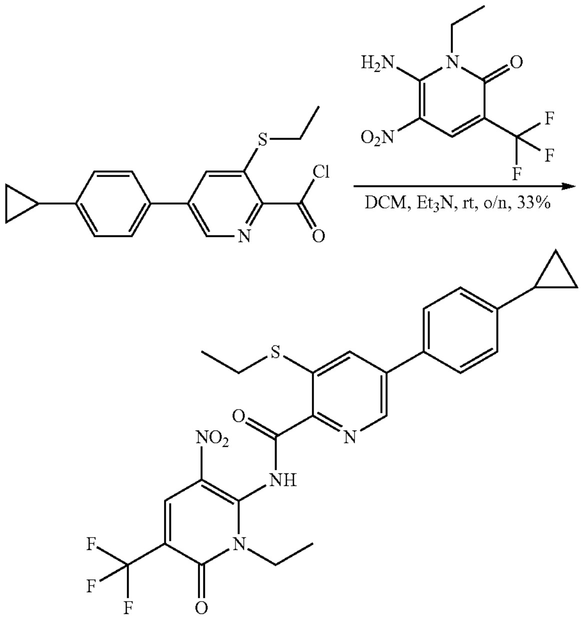

Into a 40-mL round-bottom flask purged and maintained with an inert atmosphere of nitrogen, was added 6-amino-1-ethyl-5-nitro-3-(trifluoromethyl)pyridin-2-one (60 mg, 0.24 mmol, 1.0 equiv), DCM (20 mL), triethylamine (242 mg, 2.4 mmol, 10 equiv) and 5-(4-cyclopropylphenyl)-3-(ethylthio)picolinoyl chloride (106 mg, 0.4 mmol, 1.5 equiv), the reaction was stirred overnight at room temperature. The resulting mixture was concentrated under reduced pressure. The residue was applied onto a silica gel column with ethyl acetate/petroleum ether (1:2). 5-(4-cyclopropylphenyl)-N-(1-ethyl-3-nitro-6-oxo-5-(trifluoromethyl)-1,6-dihydropyridin-2-yl)-3-(ethylthio)picolinamide (38 mg, 33%) as a light yellow solid.

Synthesis of 2-(5-(4-cyclopropylphenyl)-3-(ethylthio)pyridin-2-yl)-4-ethyl-6-(trifluoromethyl)-3,4-dihydro-5H-imidazo[4,5-b]pyridin-5-one

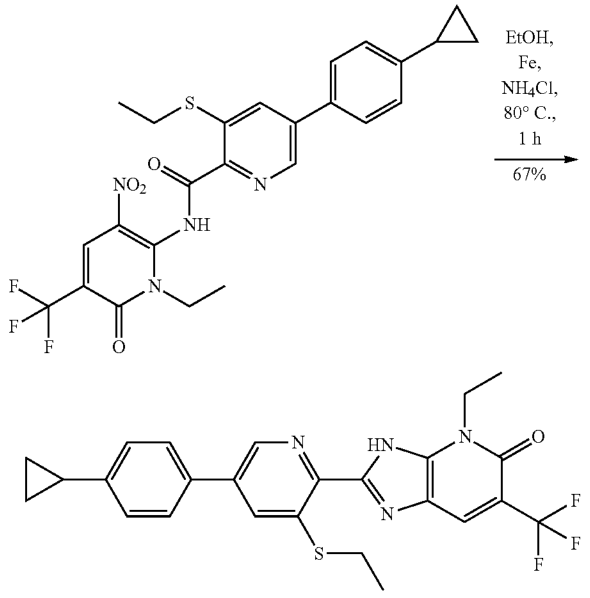 [SMILES: CCSc1cc(-c2ccc(C3CC3)cc2)cnc1C(=O)Nc1c([N+](=O)[O-])cc(C(F)(F)F)c(=O)n1CC ; CCSc1cc(-c2ccc(C3CC3)cc2)cnc1-c1nc2cc(C(F)(F)F)c(=O)n(CC)c2[nH]1]

Into a 40-mL sealed tube, was placed 5-(4-cyclopropylphenyl)-N-(1-ethyl-3-nitro-6-oxo-5-(trifluoromethyl)-1,6-dihydropyridin-2-yl)-3-(ethylthio)picolinamide (65 mg, 0.13 mmol, 1.0 equiv)ethyl alcohol (20 mL), iron dust (36 mg, 0.6 mmol, 5 equiv), $NH_4Cl$ (68 mg, 1.3 mmol, 10 equiv), the resulting mixture was stirred for 1 h at 80 degrees C. The reaction mixture was cooled to room temperature. The resulting mixture was filtered, the filtrate was concentrated under reduced pressure. The residue was applied onto a silica gel column with ethyl acetate/petroleum ether (1:2). 2-(5-(4-cyclopropylphenyl)-3-(ethylthio)pyridin-2-yl)-4-ethyl-6-(trifluoromethyl)-3,4-dihydro-5H-imidazo[4,5-b] pyridin-5-one (27 mg, 67%) as a light yellow solid.

Synthesis of 2-(5-(4-cyclopropylphenyl)-3-(ethylthio)pyridin-2-yl)-4-ethyl-1-methyl-6-(trifluoromethyl)-1,4-dihydro-5H-imidazo[4,5-b]pyridin-5-one

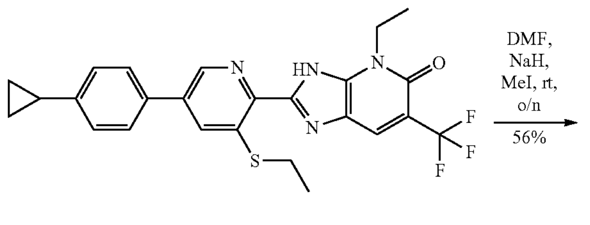

-continued

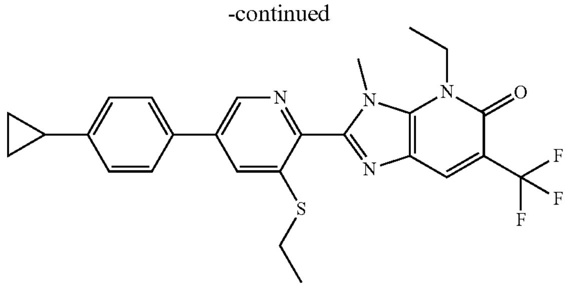

Into a 8-mL sealed tube, was placed 2-(5-(4-cyclopropylphenyl)-3-(ethylthio)pyridin-2-yl)-4-ethyl-6-(trifluoromethyl)-3,4-dihydro-5H-imidazo[4,5-b]pyridin-5-one (40 mg, 0.09 mmol, 1.0 equiv), dimethylformamide (5 mL), sodium hydride (39 mg, 0.26 mmol, 3 equiv), the reaction was stirred for 0.5 h at room temperature, to this was added methyl iodide (25 mg, 0.17 mmol, 2 equiv), and stirred overnight at room temperature. The reaction was quenched by the addition of $H_2O$ (25 mL). The aqueous layer was extracted with EA (3×50 mL). The mixture was dried over anhydrous sodium sulfate and concentrated. This was resulted in 16 mg (56%) of 2-(5-(4-cyclopropylphenyl)-3-(ethylthio)pyridin-2-yl)-4-ethyl-1-methyl-6-(trifluoromethyl)-1,4-dihydro-5H-imidazo[4,5-b]pyridin-5-one as a light yellow solid.

Synthesis of 2-[5-(4-cyclopropylphenyl)-3-(ethanesulfonyl)pyridin-2-yl]-4-ethyl-1-methyl-6-(trifluoromethyl)imidazo[4,5-b]pyridin-5-one

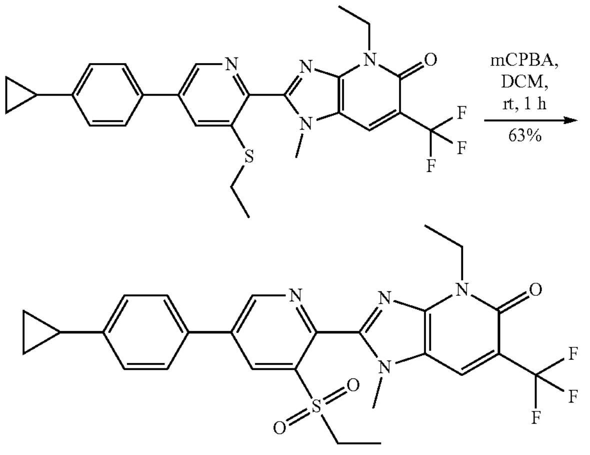

111

Into a 40 mL were added 2-[5-(4-cyclopropylphenyl)-3-(ethylsulfanyl)pyridin-2-yl]-4-ethyl-1-methyl-6-(trifluoromethyl)imidazo[4,5-b]pyridin-5-one (16 mg, 0.03 mmol, 1.0 equiv), DCM (5 mL) and m-CPBA (17 mg, 0.1 mmol, 3 equiv), The resulting mixture was stirred for 1 h, at rt under $N_2$ atmosphere. The resulting mixture was concentrated under reduced pressure. The crude product was purified by Flash-Prep-HPLC with the following conditions (IntelFlash-1): Column, C18 silica gel; mobile phase, $H_2O$ (0.05% $NH_3{\cdot}H_2O$) and $CH_3CN$: (55% $CH_3CN$ increasing to 85% within 9 min); Detector, UV 254 nm/220 nm to afford 2-[5-(4-cyclopropylphenyl)-3-(ethanesulfonyl)pyridin-2-yl]-4-ethyl-1-methyl-6-(trifluoromethyl)imidazo[4,5-b] pyridin-5-one (11 mg, 63%) as a light yellow solid.

Synthesis of Compound 176

Specifically, the following compounds of formula (I) can be synthesized by adopting the subsequent scheme of Compound 176 by someone who is skilled in the art: 178

Synthesis of 2-(1-fluoroethenyl)-5-(4,4,5,5-tetramethyl-1,3,2-dioxaborolan-2-yl)pyridine

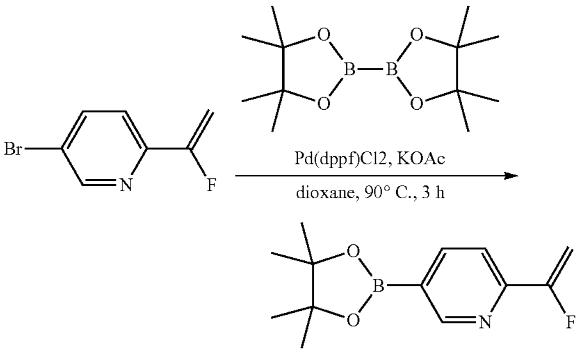

Into a 40 ml vial, was place 5-bromo-2-(I-fluoroethenyl) pyridine (20 mg, 0.1 mmol, 1 equiv), bis(pinacolato)diboron (38 mg, 0.15 mmol, 1.5 equiv), KOAc (19 mg, 0.2 mmol, 2 equiv), Pd(dppf)Cl2$CH_2$Cl2 (8 mg, 0.01 mmol, 0.1 equiv) and dioxane (2 mL) at room temperature under N2 atmosphere. The mixture was stirring for 2 h at 90° C. The mixture was concentrated under vacuum. The residue was purified by silica gel column chromatography, eluted with PE/EA (4/1) to afford 2-(1-fluoroethenyl)-5-(4,4,5,5-tetramethyl-1,3,2-dioxaborolan-2-yl)pyridine (105 mg, 85%) as off white solid.

Synthesis of 5-cyclopropyl-2-[5-(ethanesulfonyl)-6'-(1-fluoroethenyl)-[3,3'-bipyridin]-6-yl]-3-methyl-6-(trifluoromethyl)-3H,4H,5H-imidazo[4,5-c]pyridin-4-one

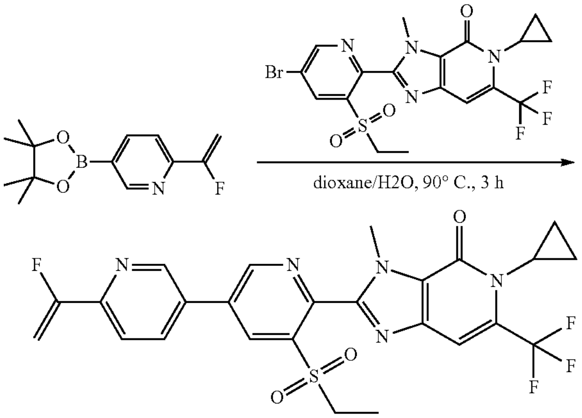

Into a 8 ml vial, was place 2-(I-fluoroethenyl)-5-(4,4,5,5-tetramethyl-1,3,2-dioxaborolan-2-yl)pyridine (105 mg, 0.38 mmol, 1 equiv, 90%), 2-[5-bromo-3-(ethanesulfonyl) pyridin-2-yl]-5-cyclopropyl-3-methyl-6-(trifluoromethyl) imidazo[4,5-c]pyridin-4-one (134 mg, 0.27 mmol, 0.7 equiv), K2C03 (105 mg, 0.76 mmol, 2 equiv), Pd(dppf) Cl2$CH_2$Cl2 (31 mg, 0.04 mmol, 0.1 equiv), dioxane (9 mL) and $H_2O$ (1 mL) at room temperature under N2 atmosphere. The mixture was stirring for 1 h at 90° C. The resulting mixture was concentrated under vacuum. The residue was purified by silica gel column chromatography, eluted with PE/EA (1/1) to afford 5-cyclopropyl-2-[5-(ethanesulfonyl)-6'-(l-fluoroethenyl)-[3,3'-bipyridin]-6-yl]-3-methyl-6-(trifluoromethyl)imidazo[4,5-c]pyridin-4-one (90 mg, 39%) as off white soild.

Synthesis of 5-cyclopropyl-2-[5-(ethanesulfonyl)-6'-(1-fluorocyclopropyl)-[3,3'-bipyridin]-6-y]-3-methyl-6-(trifluoromethyl)-3H,4H,5H-imidazo[4,5-c]pyridin-4-one

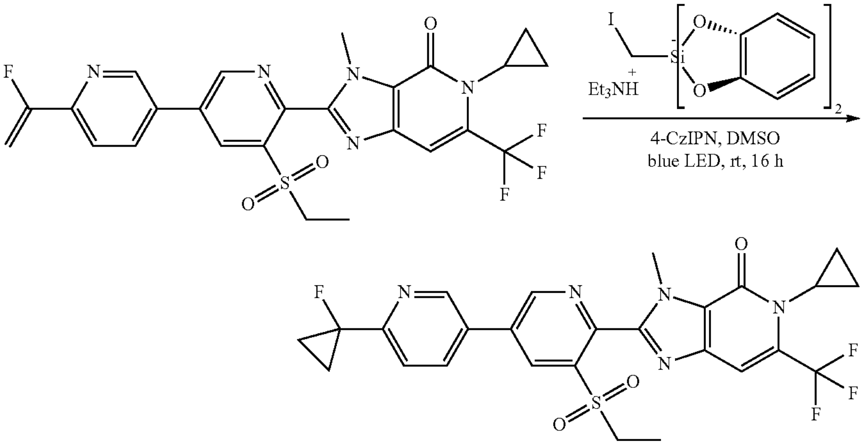

Into a 40 ml vial, was place 2-(iodomethyl)-2H-1,3,2-benzodioxasilol-2-ide; TEAH (88 mg, 0.23 mmol, 1.5 equiv), 4-CZIPN (12 mg, 0.02 mmol, 0.1 equiv) at room temperature under N2 atmosphere. To this was added a solution of 5-cyclopropyl-2-[5-(ethanesulfonyl)-6'-(1-fluoroethenyl)-[3,3'-bipyridin]-6-yl]-3-methyl-6-(trifluoromethyl)imidazo[4,5-c]pyridin-4-one (85 mg, 0.16 mmol, 1 equiv) in DMSO (8 mL) dropwise at room temperature under N2 atmosphere. The mixture was stirring for 3 h at blue LED and room temperature. The mixture was diluted with EA (50 ml) and washed with water (2×25 ml). The organic layer was dried over anhydrous sodium sulfate and concentrated under vacuum. The residue was purified by reverse flash chromatography with the following conditions: column, C18 silica gel; mobile phase, NH3$H_2$O in ACN, 60% to 90% gradient in 10 min; detector, UV 254 nm to afford 5-cyclopropyl-2-[5-(ethanesulfonyl)-6'-(1-fluoro cyclopropyl)-[3,3'-bipyridin]-6-yl]-3-methyl-6-(trifluoromethyl)imidazo[4,5-c]pyridin-4-one (9.6 mg, 11%) as white solid.

Synthesis of Compound 75 and Compound 76

Synthesis of 2-methyl-5-(trifluoromethyl)pyridine

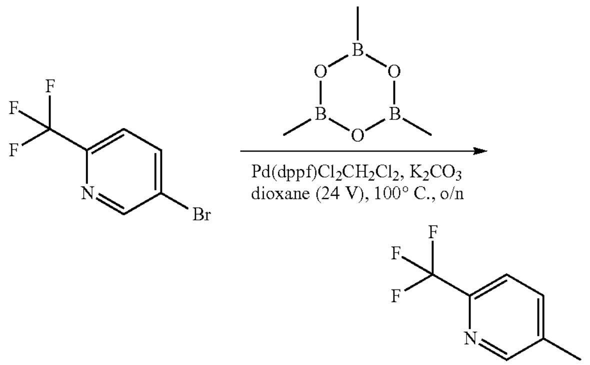

Into a 1-L round-bottom flask purged and maintained with an inert atmosphere of nitrogen, was placed 2-bromo-5-(trifluoromethyl)pyridine (34 g, 150 mmol, 1.0 equiv). This was followed by the addition of dioxane (800.00 mL), Pd(dppf)$Cl_2CH_2Cl_2$ (6.1 g, 7.5 mmol, 0.05 equiv), $K_2CO_3$ (62 g, 450 mmol, 3.0 equiv), trimethyl-1,3,5,2,4,6-trioxatri borinane (225 g, 1800 mmol, 12 equiv). The resulting solution was stirred overnight at 100 degrees C. The resulting solution was diluted with 1000 mL of EA. The resulting mixture was washed with 800 ml of brine. The resulting mixture was dried over anhydrous sodium sulfate and concentrated under vacuum. The residue was applied onto a silica gel column with ethyl acetate/petroleum ether (1/10). This resulted in 7.0 g (29%) of 2-methyl-5-(trifluoromethyl) pyridine as a solid.

Synthesis of 5-methyl-2-(trifluoromethyl)pyridin-1-ium-1-olate

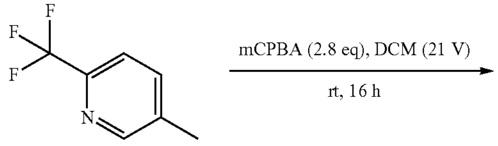

-continued

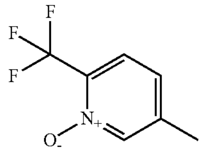

Into a 250-mL round-bottom flask, was placed 5-methyl-2-(trifluoromethyl)pyridine (7.0 g, 44 mmol, 1.0 equiv), DCM (150 mL), m-CPBA (21 g, 122 mmol, 2.8 equiv). The resulting solution was stirred for 16 hr at room temperature. The resulting mixture was washed with 1×200 ml of aq. $NaHCO_3$. The DCM mixture was dried over anhydrous sodium sulfate and concentrated. The residue was applied onto a silica gel column with ethyl acetate/petroleum ether (1:2). This resulted in 3.7 g (47%) of 5-methyl-2-(trifluoromethyl)pyridin-1-ium-1-olate as yellow oil.

Synthesis of 5-methyl-4-nitro-2-(trifluoromethyl) pyridin-1-ium-1-olate

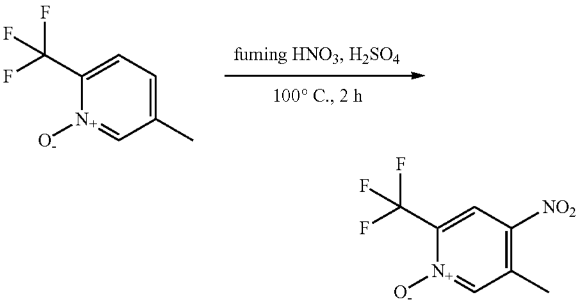

Into a 250-mL round-bottom flask, was placed 5-methyl-2-(trifluoromethyl)pyridin-1-ium-1-olate (3.67 g, 20.7 mmol, 1.0 equiv), $H_2SO_4$ (90 mL), fuming $HNO_3$ (30 mL). The resulting solution was stirred for 2 hr at 100 degrees C. The reaction was then quenched by the addition of 400 ml water. The pH value of the solution was adjusted to 9 with NaOH (4 mol/L). The resulting solution was extracted with 2×500 mL of ethyl acetate dried over anhydrous sodium sulfate and concentrated. The residue was applied onto a silica gel column with ethyl acetate/petroleum ether (1:1). This resulted in 2.3 g (50%) of 5-methyl-4-nitro-2-(trifluoromethyl)pyridin-1-ium-1-olate as yellow oil.

Synthesis of 5-methyl-2-(trifluoromethyl)pyridin-4-amine

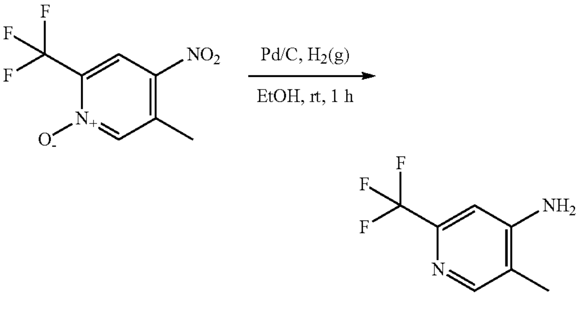

Into a 250-mL round-bottom flask, was placed 5-methyl-4-nitro-2-(trifluoromethyl)pyridin-1-ium-1-olate (2.1 g, 9.5 mmol, 1.0 equiv), EtOH (60 mL), Pd/C (2.0 g). Enough $H_2$ (g) was introduced in. The resulting solution was stirred for 1 hr at room temperature. The solids were collected by filtration. The filtrate was concentrated under vacuum. This resulted in 1.6 g (97%) of 5-methyl-2-(trifluoromethyl) pyridin-4-amine as a yellow solid.

Synthesis of 6-(trifluoromethyl)-2H-pyrazolo[4,3-c] pyridine

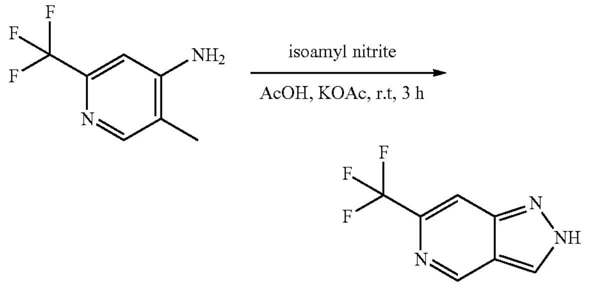

Into a 250-mL round-bottom flask, was placed 5-methyl-2-(trifluoromethyl)pyridin-4-amine (1.6 g, 9.1 mmol, 1.0 equiv), AcOH (50 mL), KOAc (1.8 g, 2.0 equiv), isoamyl nitrite (1.9 mL, 25 mmol, 2.7 equiv). The resulting solution was stirred for 3 hr at room temperature. The residue was dissolved in 50 of EA. The pH value of the solution was adjusted to 7 with NaOH (3 mol/L). The resulting solution was extracted with 2×500 mL of ethyl acetate. The resulting mixture was washed with 1×100 ml of aq. $NaHCO_3$. The EA mixture was dried over anhydrous sodium sulfate and concentrated under vacuum. The crude product was purified by Flash-Prep-HPLC with the following conditions (IntelFlash-1): Column, C18 silica gel; mobile phase, 0.05% NH3·$H_2O$ in $H_2O$ and MeCN (20% MeCN increasing to 60% within 10 min; Detector, 254 nm. This resulted in 0.8 g (48%) of 6-(trifluoromethyl)-2H-pyrazolo[4,3-c]pyridine as a yellow solid.

Synthesis of 1-{4-[6-chloro-5-(ethanesulfonyl)pyridin-3-yl]phenyl}cyclopropane-1-carbonitrile

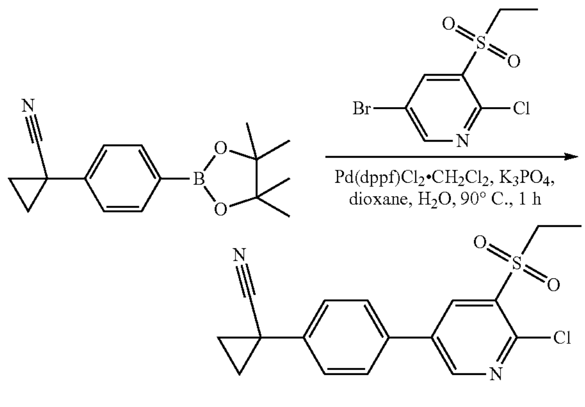

To a stirred mixture of 5-bromo-2-chloro-3-(ethanesulfonyl)pyridine (100 mg, 0.3 mmol, 1.0 equiv) and 1-[4-(4,4,5,5-tetramethyl-1,3,2-dioxaborolan-2-yl)phenyl]cyclopropane-1-carbonitrile (114 mg, 0.4 mmol, 1.2 equiv) in dioxane (5 mL, 59 mmol, 168 equiv) and $H_2O$ (1 mL, 55 mmol, 160 equiv) were added $K_3PO_4$ (150 mg, 0.7 mmol, 2 equiv) and $Pd(dppf)Cl_2CH_2Cl_2$ (29 mg, 0.04 mmol, 0.1 equiv) at room temperature. The resulting mixture was stirred for 1 h at 90 degrees C. under nitrogen atmosphere. The mixture was allowed to cool down to room temperature. The resulting mixture was concentrated under vacuum. The residue was purified by Prep-TLC (PE/EA 3:1) to afford 1-(4-[6-chloro-5-(ethanesulfonyl)pyridin-3-yl] phenyl}cyclopropane-1-carbonitrile (140 mg, 115%) as an off-white solid.

Synthesis of 1-[4-[5-(ethanesulfonyl)-6-[6-(trifluoromethyl)pyrazolo [4,3-c]pyridin-2-yl]pyridin-3-yl] phenyl]cyclopropane-1-carbonitrile and 1-[4-[5-(ethanesulfonyl)-6-[6-(trifluoromethyl) pyrazolo[4,3-c]pyridin-1-yl]pyridin-3-yl]phenyl]cyclopropane-1-carbonitrile

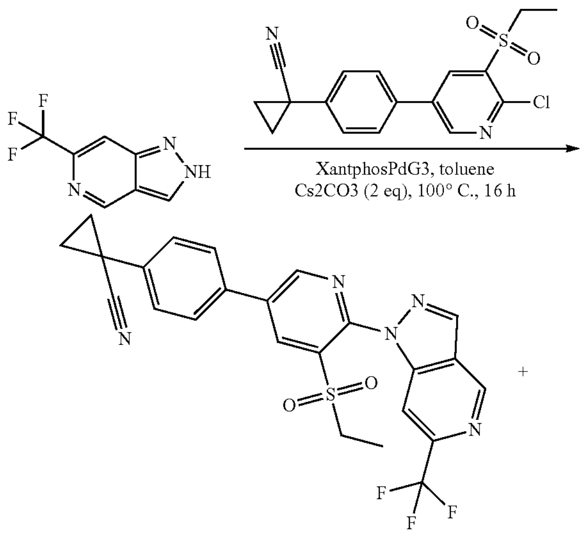

75

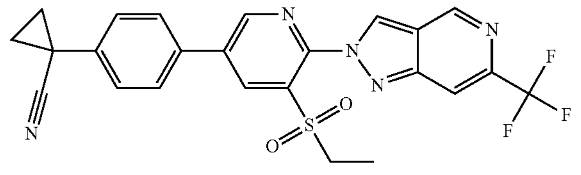

76

Into a 8-mL vial was placed 6-(trifluoromethyl)-2H-pyrazolo[4,3-c]pyridine (65 mg, 0.35 mmol, 3.0 equiv), 1-[4-[6-chloro-5-(ethanesulfonyl)pyridin-3-yl]phenyl]cyclopropane-1-carbo nitrile (40 mg, 0.12 mmol, 1.0 equiv), Xantphos Pd G3 (11 mg, 0.01 mmol, 0.1 equiv), $Cs_2CO_3$ (75 mg, 0.2 mmol, 2.0 equiv), toluene (1.6 mL). The resulting solution was stirred for 16 hr at 100 degrees C. The reaction mixture was cooled. The resulting solution was diluted with 5 mL of EA. The resulting mixture was concentrated under vacuum. The residue was applied onto a silica gel column with ethyl acetate/petroleum ether (1/2). This resulted in 7.9 mg (14%) of 1-[4-[5-(ethanesulfonyl)-6-[6-(trifluoromethyl)pyrazolo [4,3-c]pyridin-2-yl]pyridin-3-yl]phenyl]cyclopropane-1-carbonitrile as a solid and 1-[4-[5-(ethanesulfonyl)-6-[6-(trifluoromethyl) pyrazolo[4,3-clpyridin-1-yl]pyridin-3-yl]phenyl]cyclopropane-1-carbonitrile as a white solid.

Synthesis of Compound 27, Compound 28, and Compound 29

Specifically, the following compounds of formula (I) can be synthesized by adopting the subsequent scheme of Compound 27, 28 and 29 by someone who is skilled in the art: 202, 203, 204

Synthesis of 2-bromo-5-iodopyridin-4-amine

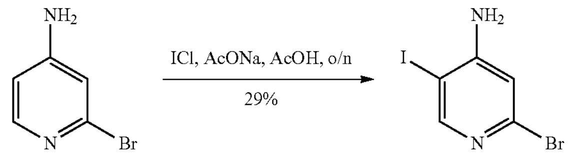 [SMILES: Nc1ccnc(Br)c1 ; Nc1cc(Br)ncc1I]

Into a 1-L 3-necked round-bottom flask purged and maintained with an inert atmosphere of nitrogen, was placed 2-bromopyridin-4-amine (100 g, 580 mmol, 1.0 equiv), AcOH (500 mL), AcONa (95 g, 1.2 mol, 2.0 equiv), ICI (94 g, 580 mmol, 1.0 equiv). The resulting solution was stirred overnight at 70 degrees C. The resulting mixture was concentrated. The resulting solution was diluted with 500 mL of $H_2O$. The resulting solution was extracted with 2×1 L of ethyl acetate. The organic solution was concentrated. The residue was applied onto a silica gel column with EA/DCM/PE (1/8/10). This resulted in 50 g (29%) of 2-bromo-5-iodopyridin-4-amine as a white solid.

Synthesis of 2-bromo-4-chloro-5-iodopyridine

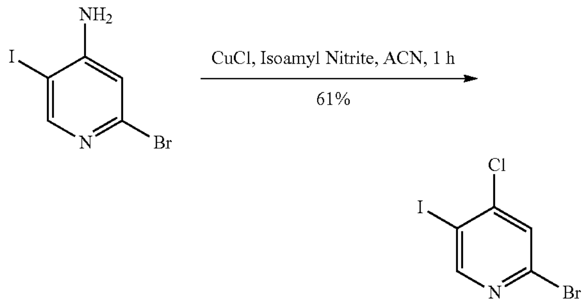

Into a 1-L round-bottom flask purged and maintained with an inert atmosphere of nitrogen, was placed 2-brom o-5-iodopyridin-4-amine (20 g, 67 mmol, 1.0 equiv), ACN (200 mL), CuCl (10 g, 101 mmol, 1.51 equiv). This was followed by the addition of Isoamyl Nitrite (16 g, 130 mmol, 2.0 equiv) dropwise with stirring at 50 degrees C. The resulting solution was stirred for 1 hr at 50 degrees C. The solids were filtered out. The resulting mixture was concentrated. The residue was applied onto a silica gel column with ethyl acetate/petroleum ether (1/10). This resulted in 13 g (61%) of 2-bromo-4-chloro-5-iodopyridine as a yellow oil.

Synthesis of methyl 6-bromo-4-chloropyridine-3-carboxylate

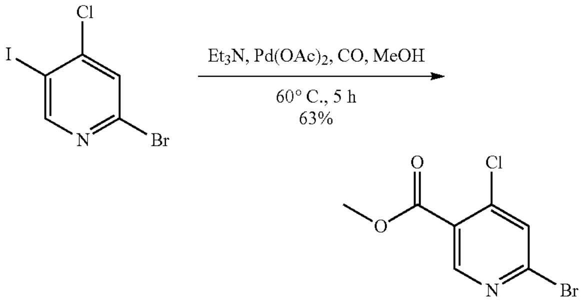

Into a 250-mL pressure tank reactor, was placed 2-bromo-4-chloro-5-iodopyridine (12.5 g, 39 mmol, 1.0 equiv), MeOH (200 mL), $Et_3N$ (11.9 g, 0.12 mmol, 3.0 equiv), $Pd(AcO)_2$ (880 mg, 3.9 mmol, 0.1 equiv). Followed by flushing with CO at ambient pressure. The resulting solution was stirred for 5 hr at 60 degrees C. The solids were filtered out. The filtrate was concentrated. The residue was applied onto a silica gel column with ethyl acetate/petroleum ether (1/20). This resulted in 6.9 g (63%) of methyl 6-bromo-4-chloropyridine-3-carboxylate as a white solid.

Synthesis of methyl 4-chloro-6-[(trifluoromethyl) sulfanyl]pyridine-3-carboxylate

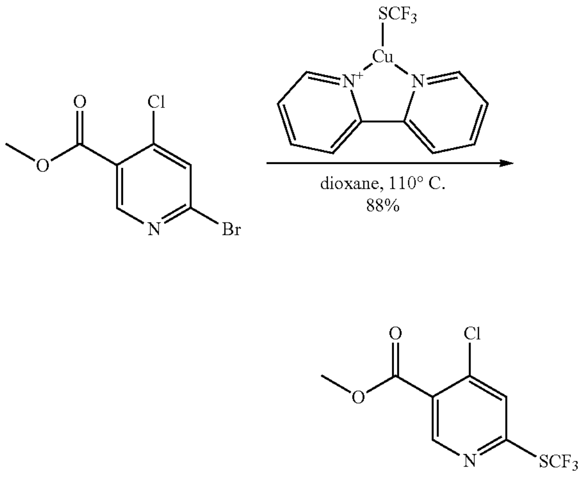

Into a 500-mL round-bottom flask purged and maintained with an inert atmosphere of nitrogen, was placed methyl 6-bromo-4-chloropyridine-3-carboxylate (6.9 g, 27.5 mmol, 1.0 equiv), 7lambda4,9lambda4-diaza-8-cupratricyclo [7.4.0.0/\[2,7]]trideca-1(13),2,4,6,9,11-hexaen-8-ylium-8-yl(trifluoromethyl)-lambda3-sulfanide (11.5 g, 50 mmol, 1.8 equiv), dioxane (200 mL). The resulting solution was stirred for 5 hr at 110 degrees C. The solids were filtered out. The residue was applied onto a silica gel column with ethyl acetate/petroleum ether (1/10). This resulted in 6.6 g (88%) of methyl 4-chloro-6-[(trifluoromethyl)sulfanyl]pyridine-3-carboxylate as yellow oil.

Synthesis of 4-chloro-6-[(trifluoromethyl)sulfanyl]pyridine-3-carboxylic acid

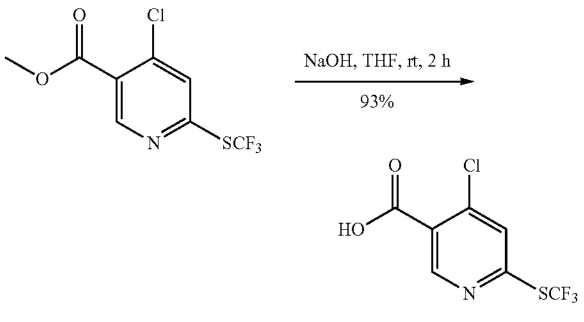

Into a 250-mL round-bottom flask purged and maintained with an inert atmosphere of nitrogen, was placed methyl 4-chloro-6-[(trifluoromethyl)sulfanyl]pyridine-3-carboxylate (6.9 g, 25.4 mmol, 1.0 equiv), NaOH (2.0 g, 51 mmol, 2.0 equiv), THF (30 mL), $H_2O$ (5 mL). The resulting solution was stirred for 2 hr at room temperature. The resulting mixture was concentrated. The resulting solution was diluted with 20 mL of $H_2O$. The pH value of the solution was adjusted to 4 with HCl(I mol/L) aqueous solution. The solids were collected by filtration. This resulted in 6.1 g (93%) of 4-chloro-6-[(trifluoromethyl)sulfanyl]pyridine-3-carboxylic acid as a white solid.

Synthesis of 2-chloro-5-(4-cyclopropylphenyl)-3-(ethylsulfanyl)pyridine

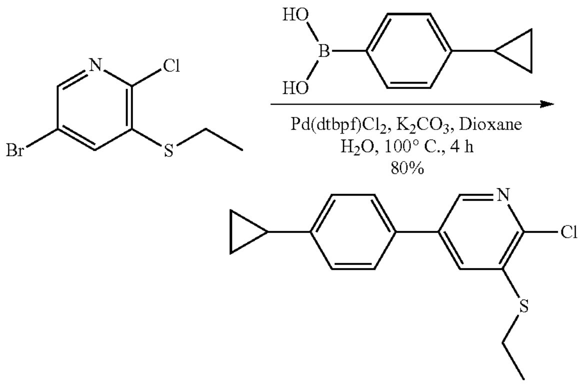

Into a 100-mL round-bottom flask purged and maintained with an inert atmosphere of nitrogen, was placed 5-bromo-2-chloro-3-(ethylsulfanyl)pyridine (690 mg, 2.7 mmol, 1.0 equiv), dioxane (25 mL), 4-cyclopropylphenylboronic acid (490 mg, 3.0 mmol, 1.1 equiv), Pd(dtbpf)$Cl_2$ (224 mg, 0.34 mmol, 0.13 equiv), $K_2CO_3$ (948 mg, 6.9 mmol, 2.5 equiv), $H_2O$ (5 mL). The resulting solution was stirred for 4 hr at 100° C. in an oil bath. The reaction mixture was cooled to room temperature. The resulting solution was diluted with 150 mL of $H_2O$. The resulting solution was extracted with 3×100 mL of ethyl acetate and the organic layers combined and concentrated. The residue was applied onto a silica gel column with ethyl acetate/petroleum ether (1/10). This resulted in 630 mg (80%) of 2-chloro-5-(4-cyclopropylphenyl)-3-(ethylsulfanyl)pyridine as yellow oil.

Synthesis of 2-chloro-5-(4-cyclopropylphenyl)-3-(ethanesulfonyl)pyridine

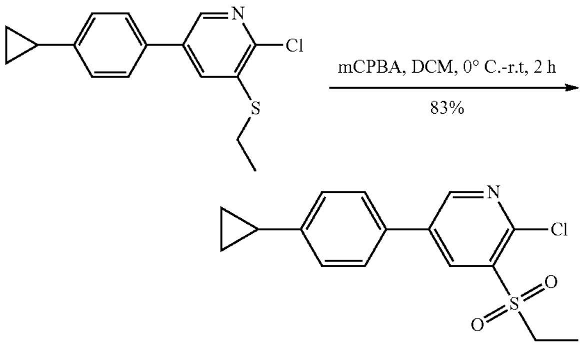

Into a 100-mL round-bottom flask, was placed 2-chloro-5-(4-cyclopropylphenyl)-3-(ethylsulfanyl)pyridine (630 mg, 2.2 mmol, 1.0 equiv), DCM (50 mL). This was followed by the addition of m-CPBA (1.2 g, 5.9 mmol, 2.7 equiv, 85%) at 0° C. The resulting solution was stirred for 2 hr at room temperature. The resulting solution was diluted with 150 mL of saturated aqueous $NaHCO_3$. The resulting solution was stirred for 15 min at room temperature. The resulting solution was extracted with 3×100 ml of dichloromethane and the organic layers combined and concentrated. The residue was applied onto a silica gel column with ethyl acetate/petroleum ether (1/3). This resulted in 580 mg (83%) of 2-chloro-5-(4-cyclopropylphenyl)-3-(ethanesulfonyl)pyridine as a yellow solid.

Synthesis of 5-(4-cyclopropylphenyl)-3-(ethanesulfonyl)-2-hydrazinylpyridine

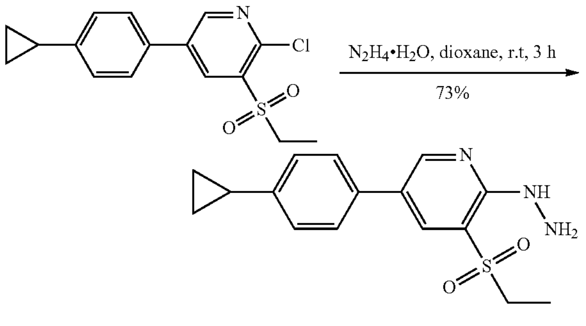

Into a 100-mL round-bottom flask, was placed 2-chloro-5-(4-cyclopropylphenyl)-3-(ethanesulfonyl)pyridine (580 mg, 1.8 mmol, 1.0 equiv), dioxane (25 mL), $N_2H_4{\cdot}H_2O$ (1.4 g, 27 mmol, 15 equiv, 98%). The resulting solution was stirred for 3 hr at room temperature. The resulting mixture was concentrated. The resulting solution was diluted with 80 mL of saturated aqueous $NaHCO_3$. The resulting solution was extracted with 6×50 mL of dichloromethane and the organic layers combined and dried over anhydrous sodium sulfate and concentrated. This resulted in 420 mg (73%) of 5-(4-cyclopropylphenyl)-3-(ethanesulfonyl)-2-hydrazinylpyridine as a yellow solid.

Synthesis of 4-[2-[5-(4-cyclopropylphenyl)-3-(ethanesulfonyl)pyridin-2-yl]hydrazin-1-yl]-6-[(trifluoromethyl)sulfanyl]pyridine-3-carboxylic acid

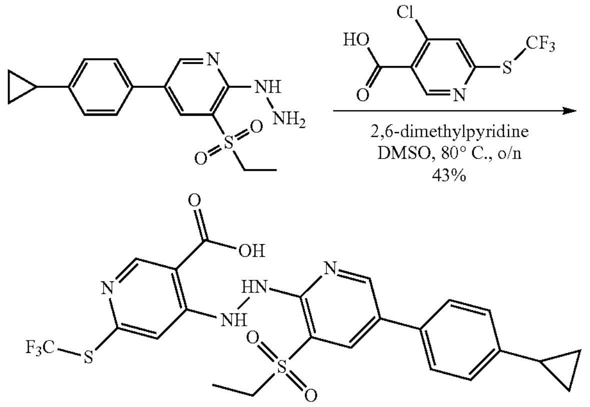

Into a 40-mL vial, was placed 4-chloro-6-[(trifluoromethyl)sulfanyl]pyridine-3-carboxylic acid (289 mg, 1.1 mmol, 0.99 equiv), DMSO (5.00 mL), 2,6-dimethylpyridine (180.00 mg, 1.7 mmol, 1.5 equiv), 5-(4-cyclopropylphenyl)-3-(ethanesulfonyl)-2-hydrazinylpyridine (360 mg, 1.1 mmol, 1.00 equiv). The resulting solution was stirred overnight at 80° C. in an oil bath. The reaction mixture was cooled to room temperature. The crude product was purified by Flash-Prep-HPLC with the following conditions (IntelFlash-1): Column, C18 silica gel; mobile phase, $CH_3CN$/0.05% HCOOH=85%; Detector, 254 & 220 nm. This resulted in 260 mg (43%) of 4-[2-[5-(4-cyclopropylphenyl)-3-(ethanesulfonyl)pyridin-2-yl]hydrazin-1-yl]-6-[(trifluoromethyl)sulfanyl]pyridine-3-carboxylic acid as a yellow solid.

Synthesis of 2-[3-chloro-6-[(trifluoromethyl)sulfanyl]pyrazolo[4,3-c]pyridin-2-yl]-5-(4-cyclopropylphenyl)-3-(ethanesulfonyl)pyridine

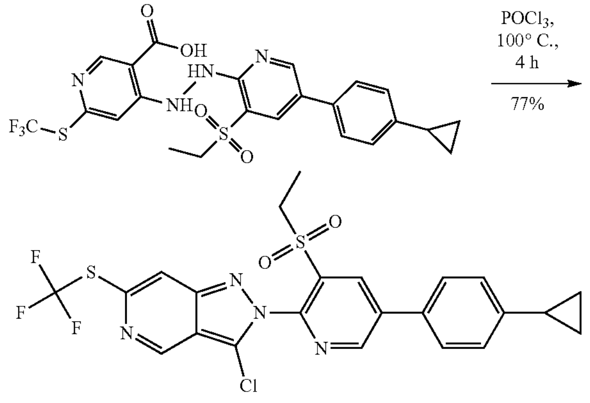

28

Into a 50-mL round-bottom flask, was placed 4-[2-[5-(4-cyclopropylphenyl)-3-(ethanesulfonyl)pyridine-2-yl]hydrazin-1-yl]-6-[(trifluoromethyl)sulfanyl]pyridine-3-carboxylic acid (260 mg, 0.5 mmol, 1.0 equiv), $POCl_3$ (4.0 mL). The resulting solution was stirred for 4 hr at 100° C. in an oil bath. The resulting solution was diluted with 50 mL of EA. The pH value of the solution was adjusted to 8 with saturated aqueous $NaHCO_3$. The resulting solution was extracted with 3×40 mL of ethyl acetate and the organic layers combined and concentrated. The residue was applied onto a silica gel column with ethyl acetate/petroleum ether (1/4). This resulted in 200 mg (77%) of 2-[3-chloro-6-[(trifluoromethyl)sulfanyl]pyrazolo[4,3-c]pyridin-2-yl]-5-(4-cyclopropylphenyl)-3-(ethanesulfonyl)pyridine as a yellow solid.

Synthesis of 5-(4-cyclopropylphenyl)-3-(ethanesulfonyl)-2-[6-[(trifluoromethyl)sulfanyl]pyrazolo[4,3-c]pyridin-2-yl]pyridine

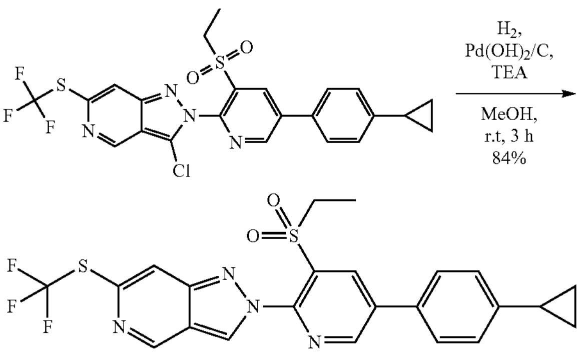

27

Into a 250-mL round-bottom flask, was placed 2-[3-chloro-6-[(trifluoromethyl)sulfanyl]pyrazolo[4,3-c]pyridin-2-yl]-5-(4-cyclopropylphenyl)-3-(ethanesulfonyl)pyridine (190 mg, 0.35 mmol, 1.0 equiv), MeOH (150 mL), TEA (36 mg, 0.35 mmol, 1.0 equiv), $Pd(OH)_2/C$ (190 mg, 1.35 mmol, 3.8 equiv). The flask was evacuated and flushed three times with nitrogen, followed by flushing with hydrogen. The mixture was stirred 3h at room temperature under an atmosphere of hydrogen (balloon). The solids were filtered out. The filtrate was concentrated. The residue was applied onto a silica gel column with THF/PE (1/4). This resulted in 150 mg (84%) of 5-(4-cyclopropylphenyl)-3-(ethanesulfonyl)-2-[6-[(trifluoromethyl)sulfanyl]pyrazolo[4,3-c]pyridin-2-yl]pyridine as a yellow solid.

Synthesis of 5-(4-cyclopropylphenyl)-3-(ethanesulfonyl)-2-[6-trifluoromethanesulfinylpyrazolo[4,3-c]pyridin-2-yl]pyridine

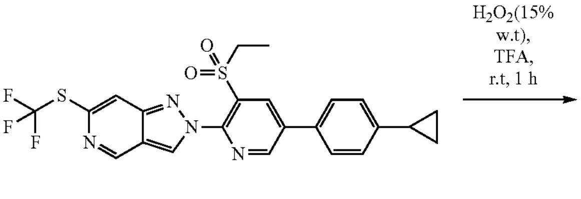

-continued

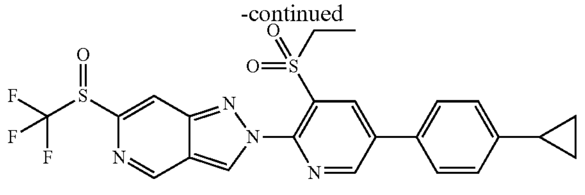

29

Into a 8-mL vial, was placed 5-(4-cyclopropylphenyl)-3-(ethanesulfonyl)-2-[6-[(trifluoromethyl)sulfanyl]pyrazolo[4,3-c]pyridin-2-yl]pyridine (70 mg, 0.14 mmol, 1.0 equiv), TFA (2 mL). This was followed by the addition of $H_2O_2$(0.4 mL, 33%) dropwise with stirring at room temperature. The resulting solution was stirred for 1 hr at room temperature. The reaction was then quenched by the addition of 50 mL of saturated aqueous $Na_2SO_3$. The resulting solution was stirred for 15 min at room temperature. The pH value of the solution was adjusted to 8 with $NaHCO_3$. The resulting solution was extracted with 3×30 mL of ethyl acetate and the organic layers combined and concentrated. The crude product was purified by Flash-Prep-HPLC with the following conditions (IntelFlash-1): Column. C18 silica gel; mobile phase, $CH_3CN$/0.05% $NH_4HCO_3$=65%; Detector, 254&220 nm. This resulted in 7.6 mg (11%) of 5-(4-cyclopropylphenyl)-3-(ethanesulfonyl)-2-[6-trifluoromethanesulfinylpyrazolo[4,3-c]pyridin-2-yl]pyridine as a light yellow solid.

Synthesis of Compound 30

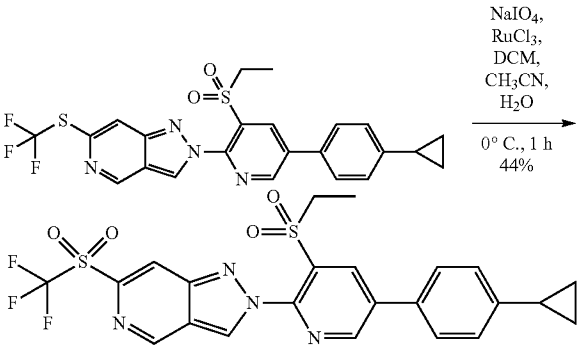

30

Into a 50-mL round-bottom flask, was placed 5-(4-cyclopropylphenyl)-3-(ethanesulfonyl)-2-[6-[(trifluoromethyl)sulfanyl]pyrazolo[4,3-c]pyridin-2-yl]pyridine (50 mg, 0.1 mmol, 1.0 equiv), DCM (0.5 mL), $CH_3CN$ (0.5 mL), $H_2O$ (1.0 mL), $RuCl_3 \cdot H_2O$ (2.2 mg, 0.01 mmol, 0.1 equiv). This was followed by the addition of $NaIO_4$ (106 mg, 0.5 mmol, 5.0 equiv) at 0° C. The resulting solution was stirred for 1 hr at 0° C. in an ice/salt bath. The resulting solution was diluted with 30 mL of $H_2O$. The resulting solution was extracted with 4×20 mL of dichloromethane and the organic layers combined and concentrated. The crude product was purified by Flash-Prep-HPLC with the following conditions (IntelFlash-1): Column, C18 silica gel; mobile phase, $CH_3CN$/0.05% $NH_3 \cdot H_2O$=70%; Detector, 254&220 nm. This resulted in 24 mg (44%) of 5-(4-cyclopropylphenyl)-3-(ethanesulfonyl)-2-[6-trifluoromethanesulfonylpyrazolo[4,3-c]pyridin-2-yl]pyridine as a light-yellow solid Synthesis of Compound 46 and Compound 47

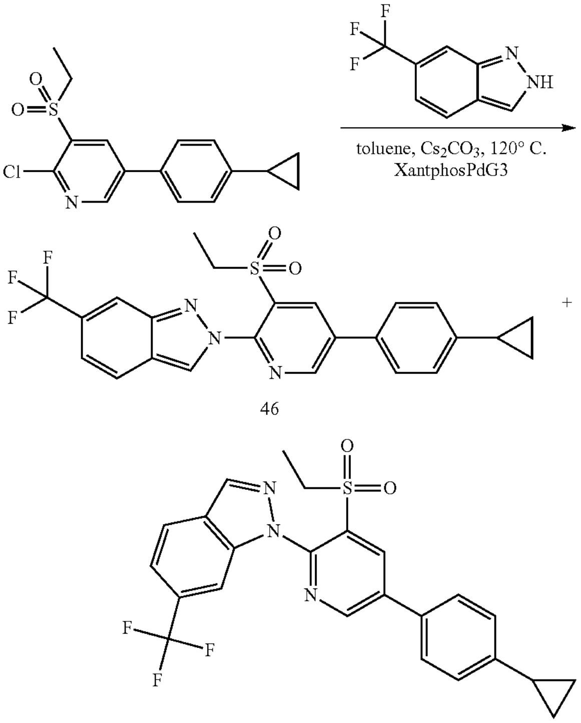

46

47

Into a 8-mL vial purged and maintained with an inert atmosphere of nitrogen, was placed 2-chloro-5-(4-cyclopropylphenyl)-3-(ethanesulfonyl)pyridine (100 mg, 0.3 mmol, 1.0 equiv), 6-(trifluoromethyl)-2H-indazole (174 mg, 0.9 mmol, 3.0 equiv), toluene (2 mL), $Cs_2CO_3$ (202 mg, 0.6 mmol, 2.0 equiv), Xantphos-Pd-G3 (30 mg, 0.03 mmol, 0.1 equiv). The resulting solution was stirred overnight at 120 degrees C. The reaction mixture was cooled to room temperature. The resulting mixture was concentrated under vacuum. The residue was applied onto a silica gel column with ethyl acetate/petroleum ether (1:10). This resulted in 14 mg of 2-[5-(4-cyclopropylphenyl)-3-(ethanesulfonyl)pyridin-2-yl]-6-(trifluoromethyl)indazole as an off-white solid.

Synthesis of Compound 48 and Compound 49

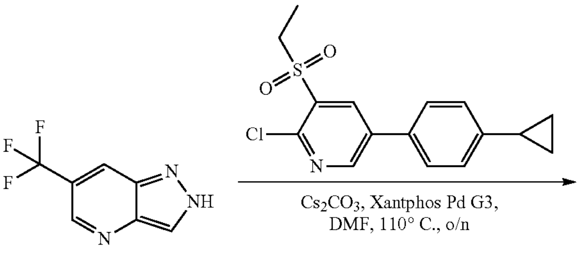

-continued

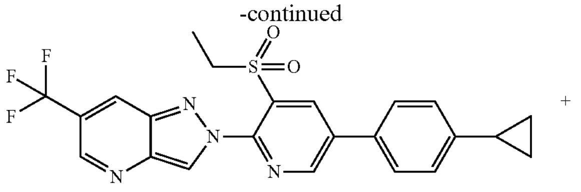

48

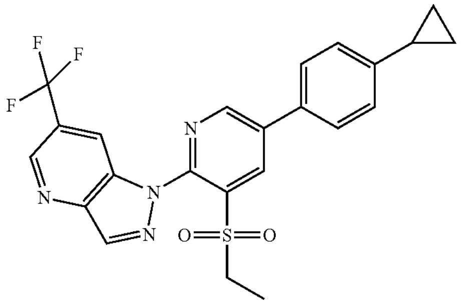

49

To a stirred solution/mixture of 6-(trifluoromethyl)-2H-pyrazolo[4,3-b]pyridine (72 mg, 0.4 mmol, 1.0 equiv) and 2-chloro-5-(4-cyclopropylphenyl)-3-(ethanesulfonyl)pyridine (124 mg, 0.4 mmol, 1 equiv) in toluene was added Xantphos Pd G3 (36 mg, 0.04 mmol, 0.1 equiv), $Cs_2CO_3$ (250 mg, 0.8 mmol, 2 equiv). The resulting mixture was stirred for 3 h at 100 degrees C. under nitrogen atmosphere. The resulting mixture was concentrated under reduced pressure. The crude product was purified by Prep-HPLC with the following conditions (Column, XBridge Shield RP18 OBD Column, 5 um, 19*150 mm; mobile phase, Water (0.05% $NH_3H_2O$) and ACN (40% Phase B up to 90% in 7 min) to afford 5-(4-cyclopropylphenyl)-3-(ethanesulfonyl)-2-[6-(trifluoromethyl)pyrazolo[4,3-b]pyridin-2-yl]pyrid-ine (13 mg, 7%) as a white solid.

Synthesis of Compound 191

Synthesis of 6-bromo-2-(oxan-2-yl)-2H-pyrazolo[4,3-b]pyridine

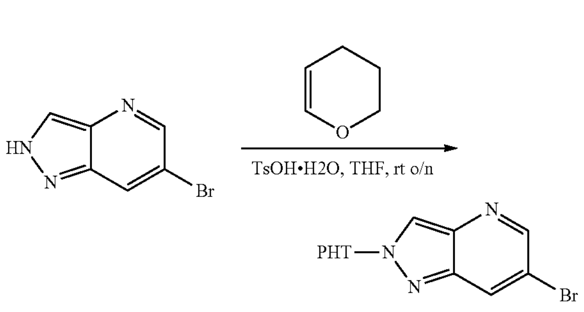

To a stirred mixture of 6-bromo-2H-pyrazolo[4,3-b]pyridine (5 g, 25 mmol, 1 equiv) and dihydropyran (4.3 g, 50 mmol, 2 equiv) in THF (50 mL) was added TsOH·$H_2O$ (0.96 g, 5 mmol, 0.2 equiv) at room temperature. The resulting mixture was stirred for overnight at room temperature. The resulting mixture was quenched with water (100 mL). The resulting mixture was extracted with EtOAc (2×100 mL). The combined organic layers were washed with brine (2×10 mL), dried over anhydrous Na2SO4. After filtration, the filtrate was concentrated under reduced pressure. The residue was purified by silica gel column chromatography, eluted with PE/EA (2:1) to afford 6-bromo-2-(oxan-2-yl)pyrazolo[4,3-b]pyridine (5.8 g, 81%) as an off-white solid.

Synthesis of 6-iodo-2-(oxan-2-yl)-2H-pyrazolo[4,3-b]pyridine

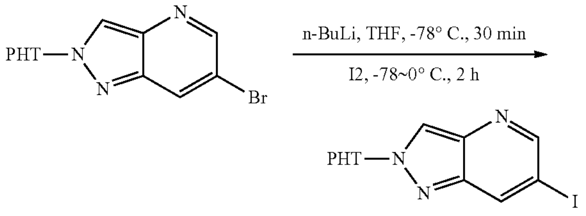

To a stirred mixture of 6-bromo-2-(oxan-2-yl)pyrazolo[4,3-b]pyridine (2 g, 7.1 mmol, 1 equiv) in THF (30 mL, 370 mmol, 52 equiv) was added n-BuLi (3.7 mL, 9.2 mmol, 1.3 equiv) dropwise at −78° C. under nitrogen atmosphere. The resulting mixture was stirred for 30 min at −78° C. under nitrogen atmosphere. To the above mixture was added 12 (2.3 g, 9.2 mmol, 1.3 equiv) in THF (10 mL) over 5 min at −78° C. The resulting mixture was stirred for additional 2 h at 0° C. The reaction was quenched with sat. NH4Cl (aq.) at room temperature. The resulting mixture was extracted with EtOAc (2×100 mL). The combined organic layers were washed with brine (2×10 mL), dried over anhydrous Na2SO4. After filtration, the filtrate was concentrated under reduced pressure. The residue was purified by silica gel column chromatography, eluted with PE/EA (2:1) to afford 6-iodo-2-(oxan-2-yl)pyrazolo[4,3-b]pyridine (700 mg, 30%) as a yellow oil.

Synthesis of 2-(oxan-2-yl)-6-(1,1,2,2,2-pentafluoroethyl)-2H-pyrazolo[4,3-b]pyridine

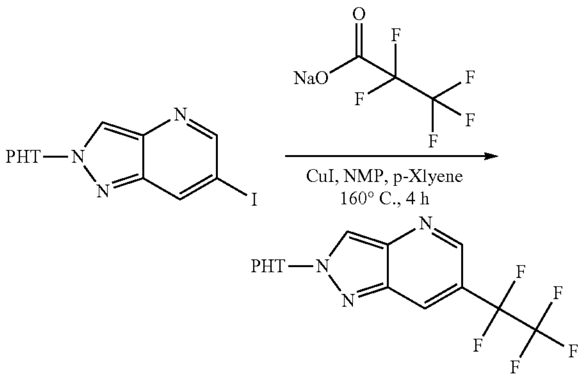

To a stirred mixture of 6-iodo-2-(oxan-2-yl)pyrazolo[4,3-b]pyridine (500 mg, 1.5 mmol, 1 equiv) and sodium 2,2,3,3,3-pentafluoropropanoate (1.4 g, 7.6 mmol, 5 equiv) in NMP (5 mL) and xylene (5 mL) was added CuI (434 mg, 2.3 mmol, 1.5 equiv) at room temperature under nitrogen atmosphere. The resulting mixture was stirred for 4 h at 160° C. under nitrogen atmosphere. The mixture was allowed to cool down to room temperature. The resulting mixture was diluted with water (50 mL). The resulting mixture was extracted with EtOAc (2×50 mL). The combined organic layers were washed with brine (2×10 mL), dried over anhydrous Na2SO4. After filtration, the filtrate was concentrated under reduced pressure. The residue was purified by silica gel column chromatography, eluted with PE/EA (3:1) to afford 2-(oxan-2-yl)-6-(1,1,2,2,2-pentafluoroethyl)pyrazolo[4,3-b]pyridine (290 mg, 59%) as a off-white solid.

Synthesis of 6-(1,1,2,2,2-pentafluoroethyl)-2H-pyrazolo[4,3-b]pyridine

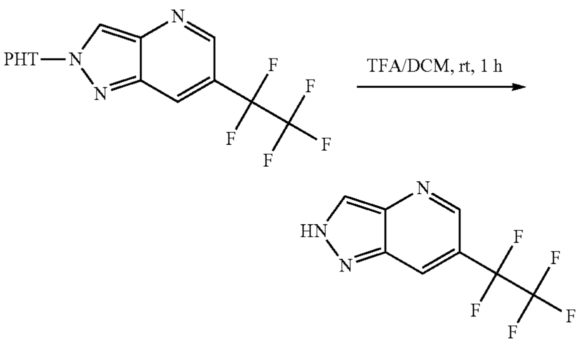

A mixture of 2-(oxan-2-yl)-6-(1,1,2,2,2-pentafluoroethyl) pyrazolo[4,3-b]pyridine (240 mg, 0.75 mmol, 1 equiv) 20 in DCM (6 mL) and TFA (2 mL) was stirred for 1 h at room temperature. The resulting mixture was concentrated under vacuum. The residue was purified by reverse flash chromatography with the following conditions: column, C18 silica gel; mobile phase, MeCN in Water (0.1% NH3·$H_2O$), 20% to 80% gradient in 15 min; detector, UV 254 nm. This resulted in 6-(1,1,2,2,2-pentafluoroethyl)-2H-pyrazolo[4,3-b]pyridine (110 mg, 62%) as an off-white solid.

Synthesis of 5-bromo-3-(ethanesulfonyl)-2-[6-(1,1,2,2,2-pentafluoroethyl)-1H-pyrazolo[4,3-b]pyridin-1-yl]pyridine

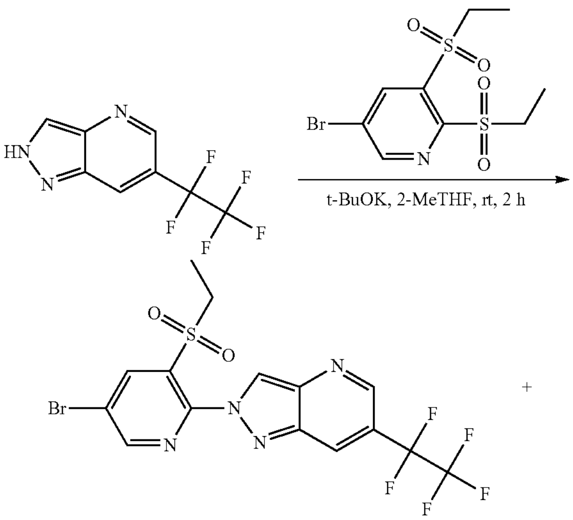

-continued

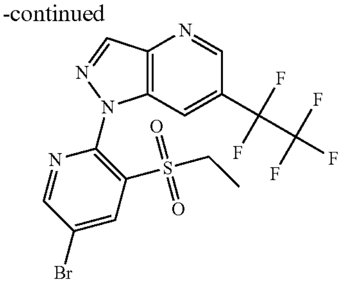

To a stirred mixture of 6-(1,1,2,2,2-pentafluoroethyl)-2H-pyrazolo[4,3-b]pyridine (100 mg, 0.4 mmol, 1 equiv) and 5-bromo-2,3-bis(ethanesulfonyl)pyridine (159 mg, 0.5 mmol, 1.1 equiv) in 2-methyltetrahydrofuran (5 mL) was added t-BuOK (62 mg, 0.5 mmol, 1.3 equiv) at room temperature under nitrogen atmosphere. The resulting mixture was stirred for 2 h at room temperature under nitrogen atmosphere. The reaction was quenched with Water at room temperature. The resulting mixture was extracted with EtOAc (2×20 mL). The combined organic layers were washed with brine (2×5 mL), dried over anhydrous Na2SO4. After filtration, the filtrate was concentrated under reduced pressure. The residue was purified by Prep-TLC (PE/EA 1:1) to afford mixture of 2-(5-bromo-3-(ethylsulfonyl)pyridin-2-yl)-6-(perfluoroethyl)-2H-pyrazolo[4,3-b]pyridine and 1-(5-bromo-3-(ethylsulfonyl)pyridin-2-yl)-6-(perfluoroethyl)-1H-pyrazolo[4,3-b]pyridine (120 mg) as a light yellow oil.

Synthesis of 5-(4-cyclopropylphenyl)-3-(ethanesulfonyl)-2-[6-(1,1,2,2,2-pentafluoroethyl)-1H-pyrazolo[4,3-b]pyridin-1-yl]pyridine

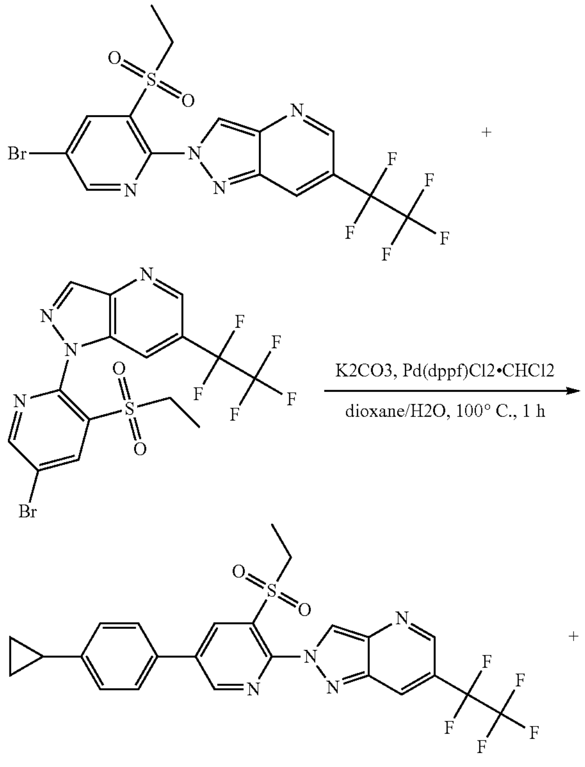

-continued

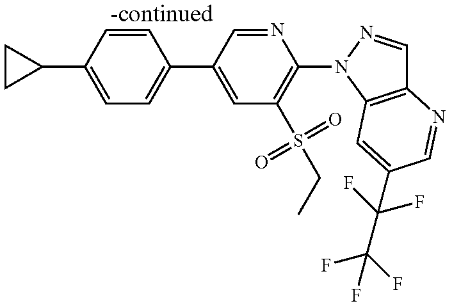

To a stirred mixture of 5-bromo-3-(ethanesulfonyl)-2-[6-(1,1,2,2,2-pentafluoroethyl)pyrazolo[4,3-b]pyridin-2-yl]pyridine (120 mg, 0.25 mmol, 1 equiv) and 4-cyclopropylphenylboronic acid (60 mg, 0.37 mmol, 1.5 equiv) in dioxane (2 mL) and $H_2O$ (0.5 mL) were added K2CO3 (102 mg, 0.74 mmol, 3 equiv) and Pd(dppf)Cl2·$CH_2Cl_2$ (20 mg, 0.03 mmol, 0.1 equiv) at room temperature under nitrogen atmosphere. The resulting mixture was stirred for 1 h at 100° C. under nitrogen atmosphere. The mixture was allowed to cool down to room temperature. The resulting mixture was concentrated under vacuum. The residue was purified by reverse flash chromatography with the following conditions: column, C18 silica gel; mobile phase, MeCN in Water (0.1% NH3·$H_2O$), 20% to 90% gradient in 10 min; detector, UV 254 nm. This resulted in 5-(4-cyclopropylphenyl)-3-(ethanesulfonyl)-2-[6-(1,1,2,2,2-pentafluoroethyl)pyrazolo[4,3-b]pyridin-2-yl]pyridine [0](39 mg, 30%) as an off-white solid and 5-(4-cyclopropylphenyl)-3-(ethanesulfonyl)-2-[6-(1,1,2,2,2-pentafluoroethyl)pyrazolo[4,3-b]pyridin-1-yl]pyridine [OA](47 mg, 36%) as an off-white solid.

Synthesis of Compound 33

Specifically, the following compounds of formula (I) can be synthesized by adopting the subsequent scheme of Compound 33 by someone who is skilled in the art: 31

Synthesis of 6-[(trifluoromethyl)sulfanyl]pyrimidin-4-amine

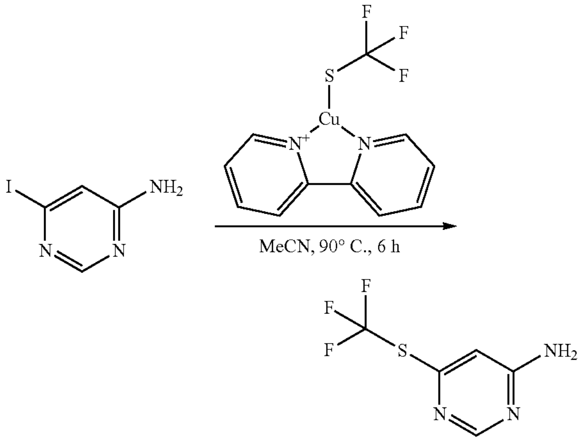

Into a 250 mL round-bottom flask were added 6-iodopyrimidin-4-amine (5 g, 23 mmol, 1.0 equiv), 8-[(trifluoromethyl)sulfanyl]-7lambda4,9lambda4-diaza-8-cupratricyclo [7.4.0.0/\{2,7}trideca-1(13),2,4,6,9,11-hexaen-8-ylium (22 g, 68 mmol, 3 equiv) and MeCN (100 mL).The final reaction mixture was irradiated with microwave radiation for 6 h at 90 degrees C. The resulting mixture was concentrated under reduced pressure. The residue was purified by silica gel column chromatography, eluted with PE/EA (1:1) to afford 6-[(trifluoromethyl)sulfanyl]pyrimidin-4-amine (1.7 g, 39%) as an off-white solid.

Synthesis of 6-trifluoromethanesulfonylpyrimidin-4-amine

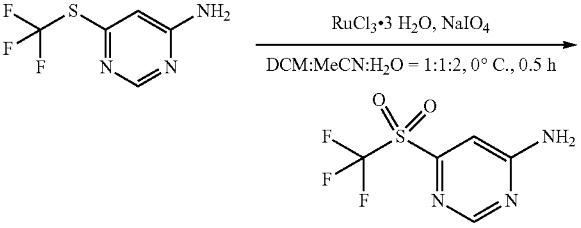

Into a 250 mL round-bottom flask were added to a stirred solution/mixture of 6-[(trifluoromethyl)sulfanyl]pyrimidin-4-amine (500 mg, 2.6 mmol, 1.0 equiv) and MeCN (40 mL) in DCM (40 mL), $H_2O$ (80 mL) was added $RuCl_3$·$H_2O$ (115 mg, 0.5 mmol, 0.2 equiv) and $NaIO_4$ (2.7 g, 13 mmol. 5 equiv) dropwise/in portions at 0 degrees C. at 0.5 h. The resulting mixture was extracted with $CH_2C2$ (3×100 mL). The combined organic layers were washed with dried over anhydrous $Na_2SO_4$. After filtration, the filtrate was concentrated under reduced pressure. The residue was purified by silica gel column chromatography, eluted with PE/EA (1:1) to afford 6-trifluoromethanesulfonylpyrimidin-4-amine (300 mg, 52%) as a white solid.

Synthesis of 2-bromo-1-[5-(4-cyclopropylphenyl)-3-(ethanesulfonyl)pyridin-2-yl]ethanone

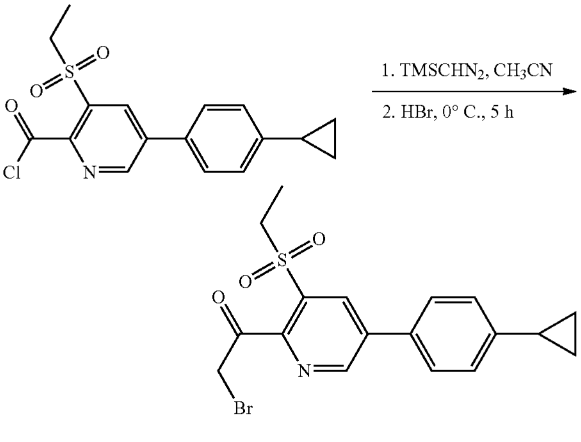

Into a 250-mL 3-necked round-bottom flask, was placed 5-(4-cyclopropylphenyl)-3-(ethanesulfonyl)pyridine-2-carbonyl chloride (1.3 g, 3.7 mmol, 1.0 equiv), $CH_3CN$ (52 mL), $TMSCHN_2$ (7.8 mL, 4 equiv), HBr (1.8 g, 22 mmol, 6.0 equiv). The resulting solution was stirred for 5 hr at 0 degrees C. The pH value of the solution was adjusted to 8 with $NaHCO_3$ (1 mol/L). The resulting solution was extracted with 2×200 mL of ethyl acetate and concentrated.

The residue was applied onto a silica gel column with ethyl acetate/petroleum ether (1:4). This resulted in 780 mg (51%) of 2-bromo-1-[5-(4-cyclopropylphenyl)-3-(ethanesulfonyl) pyridin-2-yl]ethanone as a yellow solid.

Synthesis of 5-(4-cyclopropylphenyl)-3-(ethanesulfonyl)-2-{17-trifluoromethane-sulfonylimidazo[1,2-c]pyrimidin-2-yl}pyridine

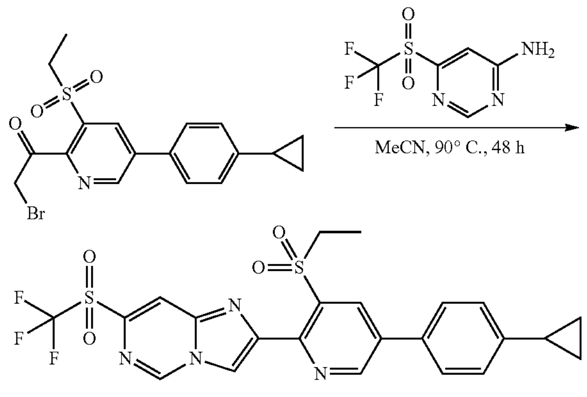

33

Into a 8 mL vial were added 2-bromo-1-[5-(4-cyclopropylphenyl)-3-(ethanesulfonyl)pyridin-2-yl]ethanone (50 mg, 0.1 mmol, 1.0 equiv) and 6-trifluoromethanesulfonylpyrimidin-4-amine (28 mg, 0.1 mmol, 1 equiv), MeCN (2 mL) at 90 degrees C. at 48 h. The resulting mixture was concentrated under reduced pressure. The residue was purified by reverse flash chromatography with the following conditions: column, silica gel; mobile phase, MeCN in 0.05% FA water, 25% to 65% gradient in 24 min; detector, UV 254 nm. The residue was purified to afford 5-(4-cyclopropylphenyl)-3-(ethanesulfonyl)-2-{7-trifluoromethane-sulfonylimidazo [1,2-c]pyrimidin-2-yl}pyridine (22 mg, 33%) as a light yellow solid.

Synthesis of Compound 41

Specifically, the following compounds of formula (1) can be synthesized by adopting the subsequent scheme of Compound 41 by someone who is skilled in the art: 39

Synthesis of 5-(4-cyclopropylphenyl)-3-(ethylsulfanyl)-N-[2-(methylamino)-5-(trifluoromethyl)pyridin-3-yl]pyridine-2-carboxamide

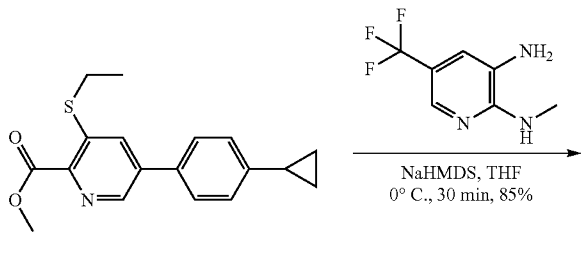

-continued

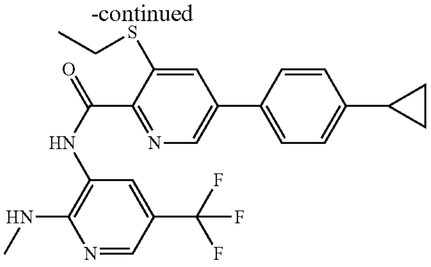

Into a 40-mL round-bottom flask purged and maintained with an inert atmosphere of nitrogen, was placed methyl 5-(4-cyclopropylphenyl)-3-(ethylsulfanyl)pyridine-2-carboxylate (100 mg, 0.32 mmol, 1.0 equiv), N2-methyl-5-(trifluoromethyl)pyridine-2,3-diamine (67 mg, 0.35 mmol, 1.1 equiv), THF (10 mL). This was followed by the addition of NaHMDS (0.32 mL, 0.64 mmol, 2.0 equiv) dropwise with stirring at 0 degrees C. in 5 min. The resulting solution was stirred for 30 min at 0 degrees C. The reaction was then quenched by the addition of 10 mL of water/ice. The resulting solution was extracted with 3×20 mL of ethyl acetate and the organic layers combined. The organic phase was dried over anhydrous sodium sulfate and concentrated. This resulted in 128 mg (85%) of 5-(4-cyclopropylphenyl)-3-(ethylsulfanyl)-N-[2-(methylamino)-5-(trifluoromethyl) pyridin-3-yl]pyridine-2-carboxamide as a brown solid.

Synthesis of 5-(4-cyclopropylphenyl)-3-(ethylsulfanyl)-2-[3-methyl-6-(trifluoromethyl)imidazo[4,5-b]pyridin-2-yl]pyridine

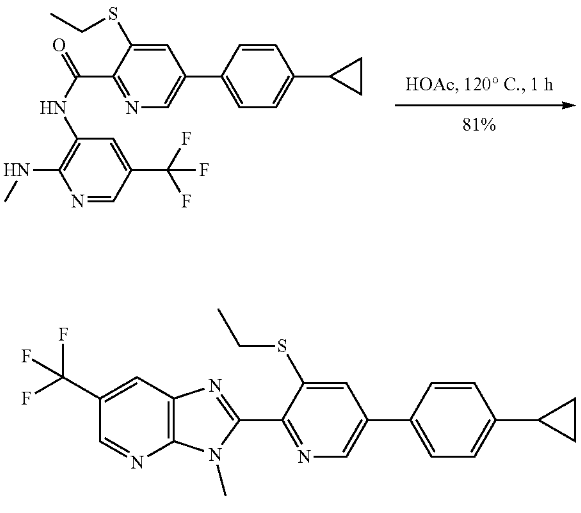 [SMILES: CCSc1cc(-c2ccc(C3CC3)cc2)cnc1C(=O)Nc1cc(C(F)(F)F)cnc1NC ; CCSc1cc(-c2ccc(C3CC3)cc2)cnc1-c1nc2cc(C(F)(F)F)cnc2n1C]

Into a 40-mL round-bottom flask purged and maintained with an inert atmosphere of nitrogen, was placed 5-(4-cyclopropylphenyl)-3-(ethylsulfanyl)-N-[2-(methylamino)-5-(trifluoromethyl)pyridin-3-yl]pyridine-2-carboxamide (128 mg, 0.271 mmol, 1.0 equiv), acetic acid (10 mL). The resulting solution was stirred for 1 hr at 120 degrees C. The resulting mixture was concentrated. The residue was applied onto a silica gel column with ethyl acetate/petroleum ether (1:2). This resulted in 100 mg (81%) of 5-(4-cyclopropylphenyl)-3-(ethylsulfanyl)-2-[3-methyl-6-(trifluoromethyl) imidazo[4,5-b]pyridin-2-yl]pyridine as a brown solid.

Synthesis of 5-(4-cyclopropylphenyl)-3-(ethanesulfonyl)-2-[3-methyl-6-(trifluoromethyl)imidazo[4,5-b]pyridin-2-yl]pyridine

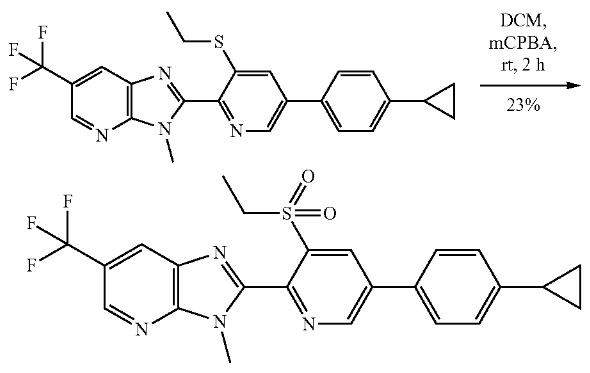

41

Into a 40-mL round-bottom flask purged and maintained with an inert atmosphere of nitrogen, was placed 5-(4-cyclopropylphenyl)-3-(ethylsulfanyl)-2-[3-methyl-6-(trifluoromethyl)imidazo[4,5-b]pyridin-2-yl]pyridine (100 mg, 0.2 mmol, 1.0 equiv), DCM (10 mL), m-CPBA (95 mg, 0.55 mmol, 2.5 equiv). The resulting solution was stirred for 2 hr at room temperature. The resulting mixture was concentrated. The residue was applied onto a silica gel column with ethyl acetate/petroleum ether (1:2). This resulted in 25 mg (24%) of 5-(4-cyclopropylphenyl)-3-(ethanesulfonyl)-2-[3-methyl-6-(trifluoromethyl)imidazo[4,5-b]pyridin-2-yl]pyridine as an off-white solid.

Synthesis of Compound 205

Synthesis of 5-bromo-N-methyl-3-nitropyridin-2-amine

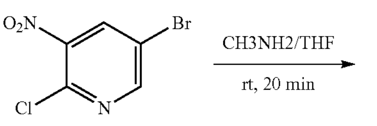

Into a 1 L 4-necked round-bottom flask were added 5-bromo-2-chloro-3-nitropyridine (30 g, 126 mmol, 1 equiv), THF (150 mL) and methanamine (177 mL, 354 mmol, 2.8 equiv) at room temperature. The resulting mixture was stirred for 20 min at room temperature. The resulting mixture was concentrated under reduced pressure. This resulted in 5-bromo-N-methyl-3-nitropyridin-2-amine (31 g, 99%) as a yellow solid.

Synthesis of 6-(methylamino)-5-nitropyridine-3-carbonitrile

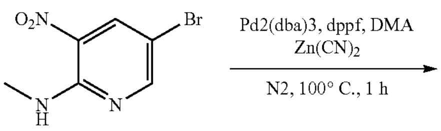

-continued

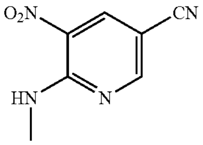

Into a 250 mL 3-necked round-bottom flask were added 5-bromo-N-methyl-3-nitropyridin-2-amine (5 g, 22 mmol, 1 equiv), DMA (100 mL), Zn(CN)2 (5.1 g, 43 mmol, 2 equiv), Dppf (3.6 g, 6.5 mmol, 0.3 equiv) and Pd2(dba)3 (2.9 g, 3.2 mmol, 0.15 equiv) at room temperature. The resulting mixture was stirred for 1 h at 100° C. under nitrogen atmosphere. The mixture was allowed to cool down to room temperature. The resulting mixture was diluted with water (100 mL). The resulting mixture was extracted with EtOAc (3×100 mL). The combined organic layers were washed with brine (3×100 mL), dried over anhydrous Na2SO4. After filtration, the filtrate was concentrated under reduced pressure. The residue was purified by silica gel column chromatography, eluted with PE/EA (3:1) to afford 6-(methylamino)-5-nitropyridine-3-carbonitrile (2.6 g, 66%) as a yellow solid.

Synthesis of 5-amino-6-(methylamino)pyridine-3-carbonitrile

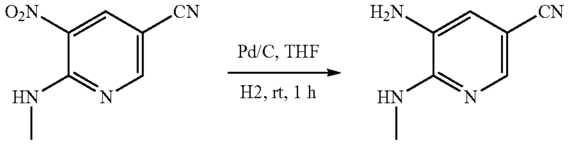

Into a 100 mL round-bottom flask were added 6-(methylamino)-5-nitropyridine-3-carbonitrile (2.6 g, 15 mmol, 1 equiv), THF (53 mL) and palladium (2.6 g, 9.8 mmol, 0.7 equiv, 40%) at room temperature. The resulting mixture was stirred for 1 h at room temperature under hydrogen atmosphere. The resulting mixture was filtered, the filter cake was washed with THF (3×50 mL). The filtrate was concentrated under reduced pressure. This resulted in 5-amino-6-(methylamino)pyridine-3-carbonitrile (2.4 g, 74%) as a black solid.

Synthesis of 5-bromo-N-[5-cyano-2-(methylamino)pyridin-3-yl]-3-(ethylsulfanyl)pyridine-2-carboxamide

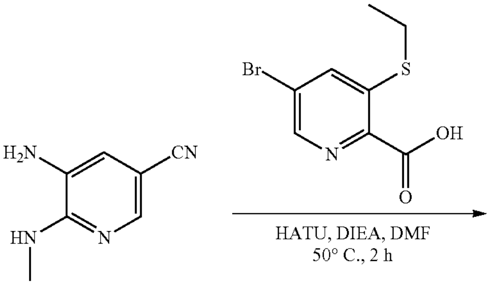

-continued

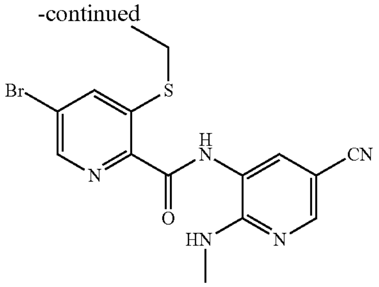

Into a 100 mL 3-necked round-bottom flask were added 5-amino-6-(methylamino)pyridine-3-carbonitrile (2.4 g, 16 mmol, 1 equiv), DMF (72 mL), 5-bromo-3-(ethylsulfanyl) pyridine-2-carboxylic acid (6.4 g, 24 mmol, 1.5 equiv), DIEA (6.3 g, 49 mmol, 3 equiv) and HATU (12 g, 32 mmol, 2 equiv) at room temperature. The resulting mixture was stirred for 2 h at 50° C. The mixture was allowed to cool down to room temperature. The resulting mixture was diluted with water (100 mL). The resulting mixture was extracted with EtOAc (3×100 mL). The combined organic layers were washed with brine (3×100 mL), dried over anhydrous Na2SO4. After filtration, the filtrate was concentrated under reduced pressure. This resulted in 5-bromo-N-[5-cyano-2-(methylamino)pyridin-3-yl]-3-(ethylsulfanyl) pyridine-2-carboxamide (5 g, 69%) as a black solid.

Synthesis of 2-[5-bromo-3-(ethylsulfanyl)pyridin-2-yl]-3-methylimidazo[4,5-b]pyridine-6-carbonitrile

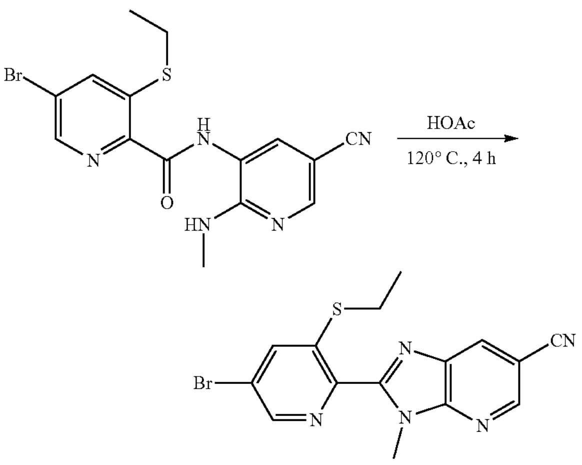

Into a 250 mL 3-necked round-bottom flask were added 5-bromo-N-[5-cyano-2-(methylamino)pyridin-3-yl]-3-(ethylsulfanyl)pyridine-2-carboxamide (5 g, 12 mmol, 1 equiv) and HOAc (100 mL) at room temperature. The resulting mixture was stirred for 4 h at 120° C. The mixture was allowed to cool down to room temperature. The resulting mixture was diluted with water (100 mL). The resulting mixture was extracted with EtOAc (3×100 mL). The combined organic layers were washed with brine (3×100 mL), dried over anhydrous Na2SO4. After filtration, the filtrate was concentrated under reduced pressure. The residue was purified by silica gel column chromatography, eluted with PE/EA (3:1) to afford 2-[5-bromo-3-(ethylsulfanyl)pyridin-2-yl]-3-methylimidazo[4,5-b]pyridine-6-carbonitrile (1.9 g, 39%) as a yellow solid.

Synthesis of afford 5-bromo-2-{6-cyclopropanecarbonyl-3-methylimidazo[4,5-b]pyridin-2-yl}-3-(ethylsulfanyl)pyridine

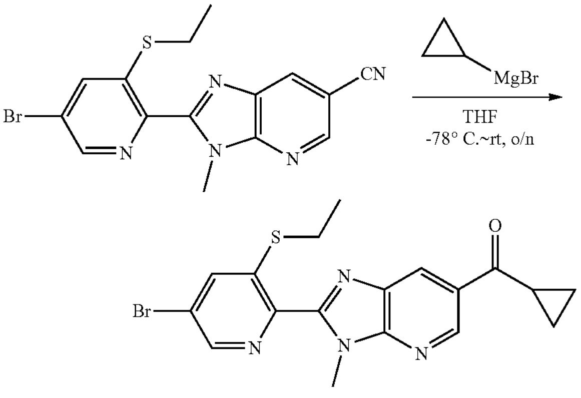

Into a 100 mL round-bottom flask were added 2-[5-bromo-3-(ethylsulfanyl)pyridin-2-yl]-3-methylimidazo[4,5-b]pyridine-6-carbonitrile (1 g, 2.7 mmol, 1 equiv), THF (20 mL) and bromo(cyclopropyl)magnesium (1 1 mL, 11 mmol, 4 equiv) at −78° C. The resulting mixture was stirred for 5 h at −78° C.-rt. The reaction was quenched by the addition of sat. NH4Cl (aq.) (30 mL) at room temperature. The resulting mixture was extracted with EtOAc (3×30 mL). The combined organic layers were washed with brine (3×30 mL), dried over anhydrous Na2SO4. After filtration, the filtrate was concentrated under reduced pressure. The residue was purified by silica gel column chromatography, eluted with PE/EA (5:1) to afford 5-bromo-2-{6-cyclopropanecarbonyl-3-methylimidazo[4,5-b]pyridin-2-yl}-3-(ethylsulfanyl)pyridine (314 mg, 27%) as a yellow solid.

Synthesis of afford 5-bromo-2-{6-cyclopropanecarbonyl-3-methylimidazo[4,5-b]pyridin-2-yl}-3-(ethanesulfonyl)pyridine

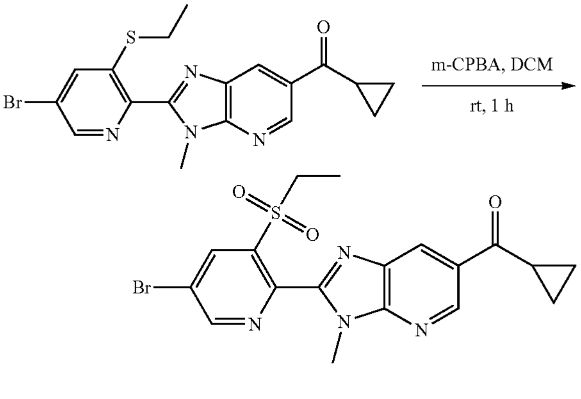

Into a 100 mL round-bottom flask were added 5-bromo-2-{6-cyclopropanecarbonyl-3-methylimidazo[4,5-b]pyridin-2-yl}-3-(ethylsulfanyl)pyridine (263 mg, 0.630 mmol, 1 equiv), DCM (8 mL) and m-CPBA (217 mg, 1.3 mmol, 2 equiv) at room temperature. The resulting mixture was stirred for 1 h at room temperature. The resulting mixture was diluted with DCM (20 mL). The resulting mixture were washed with sat. K2CO3 (aq.) (2×20 mL). The combined organic layers were washed with brine (3×20 mL), dried over anhydrous Na2SO4. After filtration, the filtrate was concentrated under reduced pressure. The residue was purified by silica gel column chromatography, eluted with PE/EA (1:1) to afford 5-bromo-2-{6-cyclopropanecarbonyl-3-methylimidazo[4,5-b]pyridin-2-yl}-3-(ethanesulfonyl) pyridine (230 mg, 77%) as a yellow solid.

Synthesis of afford 1-[4-(6-{6-cyclopropanecarbonyl-3-methylimidazo[4,5-b]pyridin-2-yl)-5-(ethanesulfonyl)pyridin-3-yl)phenyl]cyclopropane-1-carbonitrile

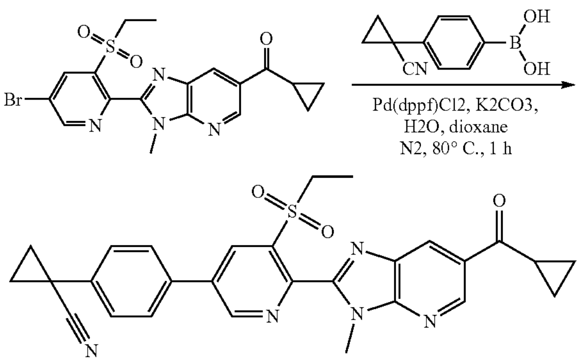

Into a 40 mL vial were added 5-bromo-2-(6-cyclopropanecarbonyl-3-methylimidazo[4,5-b]pyridin-2-yl}-3-(ethanesulfonyl)pyridine (120 mg, 0.3 mmol, 1 equiv), $H_2O$ (1.2 mL), dioxane (6 mL), 4-(1-cyanocyclopropyl)phenylboronic acid (75 mg, 0.4 mmol, 1.5 equiv), Pd(dppf) Cl2·$CH_2$Cl2 (22 mg, 0.03 mmol, 0.1 equiv) and K2CO3 (111 mg, 0.8 mmol, 3 equiv) at room temperature. The resulting mixture was stirred for 1 h at 80° C. under nitrogen atmosphere. The mixture was allowed to cool down to room temperature. The resulting mixture was concentrated under reduced pressure. The residue was purified by reversed-phase flash chromatography with the following conditions: column, C18 silica gel; mobile phase, MeCN in Water (0.05% NH3·$H_2O$), 40% to 100% gradient in 10 min; detector, UV 254 nm. This resulted in 1-[4-(6-{6-cyclopropanecarbonyl-3-methylimidazo[4,5-b]pyridin-2-yl}-5-(ethanesulfonyl)pyridin-3-yl)phenyl]cyclopropane-1-carbonitrile (114 mg, 83%) as a white solid.

Synthesis of afford 1-(4-{6-[6-(cyclopropyldifluoromethyl)-3-methylimidazo[4,5-b]pyridin-2-yl]-5-(ethanesulfonyl)pyridin-3-yl)phenyl)cyclopropane-1-carbonitrile

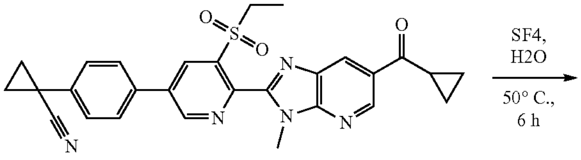

-continued

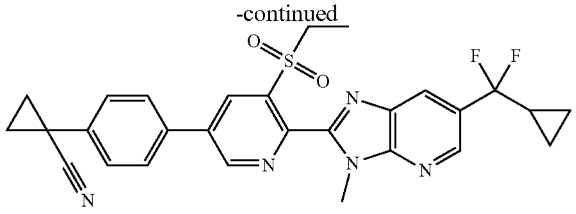

205

Into a 50 mL pressure tank reactor were added 1-[4-(6-(6-cyclopropanecarbonyl-3-methylimidazo[4,5-b]pyridin-2-yl)-5-(ethanesulfonyl)pyridin-3-yl)phenyl]cyclopropane-1-carbonitrile (100 mg, 0.2 mmol, 1 equiv), tetrafluoro-lambda4-sulfane (40 g, 370 mmol, 1894 equiv) and $H_2O$ (0.3 mL) at −78° C. The resulting mixture was stirred for 6 h at 50° C. The mixture was allowed to cool down to room temperature. The resulting mixture was cooled to rt. The residue was purified by reversed-phase flash chromatography with the following conditions: column, C18 silica gel; mobile phase, MeCN in Water (0.05% NH3·$H_2O$), 30% to 100% gradient in 10 min; detector, UV 254 nm. This resulted in 1-(4-{6-[6-(cyclopropyldifluoromethyl)-3-methylimidazo[4,5-b]pyridin-2-yl]-5-(ethanesulfonyl)pyridin-3-yl}phenyl)cyclopropane-1-carbonitrile (17 mg, 16%) as a yellow solid.

Synthesis of Compound 37

Synthesis of 6-(1,1,2,2,2-pentafluoroethyl)pyridazin-3-ol

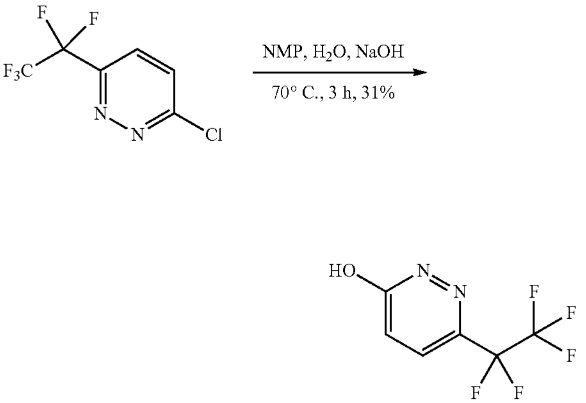 [SMILES: FC(F)(F)C(F)(F)c1ccc(Cl)nn1 ; Oc1ccc(C(F)(F)C(F)(F)F)nn1]

Into a 1-L round-bottom flask purged and maintained with an inert atmosphere of nitrogen, was placed 3-chloro-6-(1,1,2,2,2-pentafluoroethyl)pyridazine (10 g, 43 mmol, 1.0 equiv), NMP (200 mL), $H_2O$ (100 mL), NaOH (17 g, 430 mmol, 10 equiv). The resulting solution was stirred for 3 hr at 70 degrees C. The reaction was then quenched by the addition of 26 mL of HOAc. The resulting solution was extracted with 3×500 mL of ethyl acetate and the organic layers combined. The organic phase was dried over anhydrous sodium sulfate and concentrated. The residue was applied onto a silica gel column with ethyl acetate/petroleum ether (1:8). This resulted in 2.9 g (31%) of 6-(1,1,2,2,2-pentafluoroethyl)pyridazin-3-ol as an off-white solid.

Synthesis of 4-bromo-6-(1,1,2,2,2-pentafluoroethyl) pyridazin-3-ol

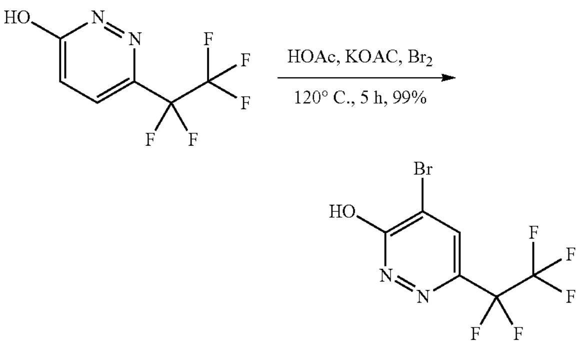

Into a 250-mL round-bottom flask purged and maintained with an inert atmosphere of nitrogen, was placed 6-(1,1,2,2,2-pentafluoroethyl)pyridazin-3-ol (2.85 g, 13 mmol, 1.0 equiv), HOAc (60 mL), KOAc (13 g, 133 mmol, 10 equiv), $Br_2$ (21 g, 133 mmol, 10 equiv). The resulting solution was stirred for 5 hr at 120 degrees C. in an oil bath. The resulting mixture was concentrated. The residue was applied onto a silica gel column with ethyl acetate/petroleum ether (1:5). This resulted in 3.85 g (99%) of 4-bromo-6-(1,1,2,2,2-pentafluoroethyl)pyridazin-3-ol as a white solid.

Synthesis of 4-amino-6-(1,1,2,2,2-pentafluoroethyl) pyridazin-3-ol

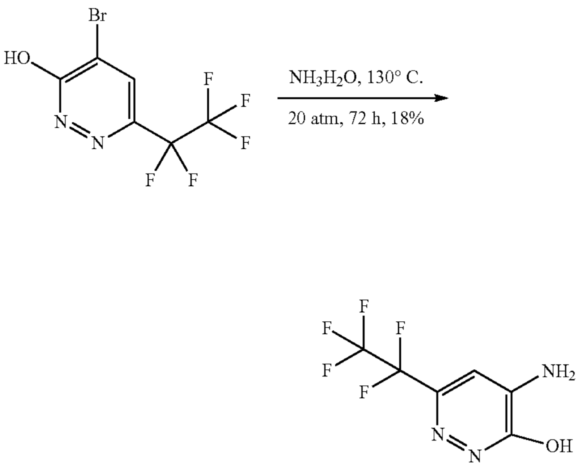

Into a 500-mL sealed tube purged and maintained with an inert atmosphere of nitrogen, was placed 4-bromo-6-(1,1,2,2,2-pentafluoroethyl)pyridazin-3-ol (2.5 g, 8.5 mmol, 1.0 equiv), $NH_3H_2O$ (300 mL). The resulting solution was stirred for 72 hr at 130 degrees C. in an oil bath. The resulting solution was extracted with 3×100 mL of ethyl acetate and the organic layers combined. The organic phase was dried over anhydrous sodium sulfate and concentrated. This resulted in 350 mg (18%) of 4-amino-6-(1,1,2,2,2-pentafluoroethyl)pyridazin-3-ol as a light yellow solid.

Synthesis of 5-(4-cyclopropylphenyl)-3-(ethylsulfanyl)-N-[3-hydroxy-6-(1,1,2,2,2-pentafluoroethyl) pyridazin-4-yl]pyridine-2-carboxamide

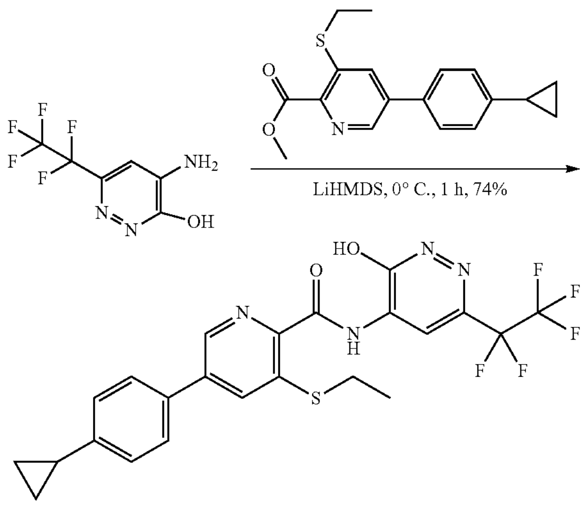

Into a 20-mL round-bottom flask purged and maintained with an inert atmosphere of nitrogen, was placed methyl 5-(4-cyclopropylphenyl)-3-(ethylsulfanyl)pyridine-2-carboxylate (100 mg, 0.32 mmol, 1.0 equiv), 4-amino-6-(1,1,2,2,2-pentafluoroethyl)pyridazin-3-ol (80 mg, 0.35 mmol, 1.10 equiv), LiHMDS (10 mL). The resulting solution was stirred for 1 hr at 0 degrees C. The reaction was then quenched by the addition of 20 mL of water/ice. The resulting solution was extracted with 3×20 mL of ethyl acetate and the organic layers combined. The organic phase was dried over anhydrous sodium sulfate and concentrated. This resulted in 120 mg (74%) of 5-(4-cyclopropylphenyl)-3-(ethylsulfanyl)-N-[3-hydroxy-6-(1,1,2,2,2-pentafluoroethyl)pyridazin-4-yl]pyridine-2-carboxamide as a grey solid.

Synthesis of 5-(4-cyclopropylphenyl)-3-(ethylsulfanyl)-2-[3-(1,1,2,2,2-pentafluoroethyl)-[1,3]oxazolo [5,4-c]pyridazin-6-yl]pyridine

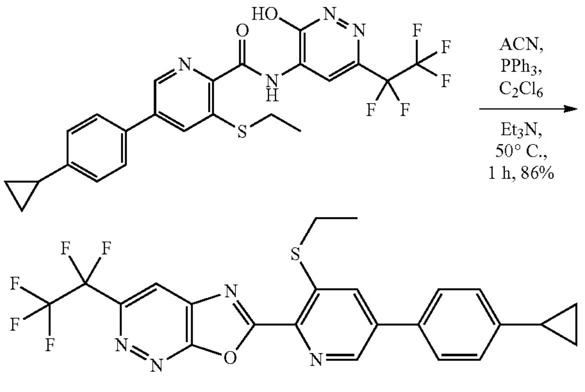

Into a 40-mL round-bottom flask purged and maintained with an inert atmosphere of nitrogen, was placed ACN (20 mL), $PPh_3$ (616 mg, 2.4 mmol, 10 equiv). This was followed by the addition of $(CCl_3)_2$(550 mg, 2.4 mmol, 10 equiv) at rt 15 min. To this was added $Et_3N$ (357 mg, 3.5 mmol, 15 equiv) at rt in 15 min. To the mixture was added 5-(4-cyclopropylphenyl)-3-(ethylsulfanyl)-N-[3-hydroxy-6-(1,1,2,2,2-pentafluoroethyl)pyridazin-4-yl]pyridine-2-carboxamide (120.00 mg, 0.235 mmol, 1.00 equiv) at rt. The resulting solution was stirred for 1 hr at 50 degrees C. The resulting mixture was concentrated. This resulted in 100 mg (86%) of 5-(4-cyclopropylphenyl)-3-(ethylsulfanyl)-2-[3-(1,1,2,2,2-pentafluoroethyl)-[1,3]oxazolo[5,4-c]pyridazin-6-yl]pyridine as a brown solid.

Synthesis of 5-(4-cyclopropylphenyl)-3-(ethanesulfonyl)-2-[3-(1,1,2,2,2-pentafluoroethyl)-[1,3]oxazolo[5,4-c]pyridazin-6-yl]pyridine

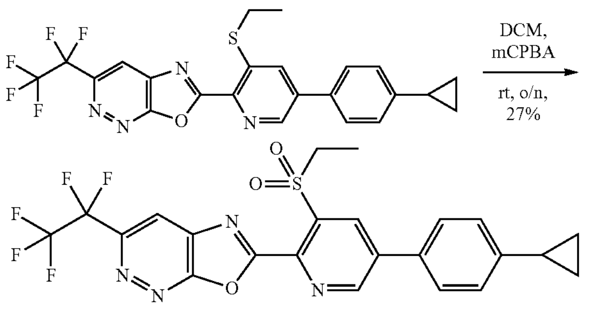

37

Into a 10-mL vial purged and maintained with an inert atmosphere of nitrogen, was placed 5-(4-cyclopropylphenyl)-3-(ethylsulfanyl)-2-[3-(1,1,2,2,2-pentafluoroethyl)-[1,3]oxazolo[5,4-c]pyridazin-6-yl]pyridine (30 mg, 0.06 mmol, 1.0 equiv), DCM (5.00 mL), mCPBA (26 mg, 0.15 mmol, 2.5 equiv). The resulting solution was stirred for 1 hr at room temperature. The resulting mixture was concentrated. The crude product was purified by Flash-Prep-HPLC with the following conditions (CombiFlash-2): Column, C18 silica gel; mobile phase, ACN:$H_2O$=45% increasing to ACN:$H_2O$=55% within 10 min; Detector, 254 nm. This resulted in 9 mg (27%) of 5-(4-cyclopropylphenyl)-3-(ethanesulfonyl)-2-[3-(1,1,2,2,2-pentafluoroethyl)-[1,3]oxazolo[5,4-c]pyridazin-6-yl]pyridine as a light yellow solid.

Synthesis of Compound 40

Synthesis of 3-amino-5-(trifluoromethyl)pyridin-2-ol

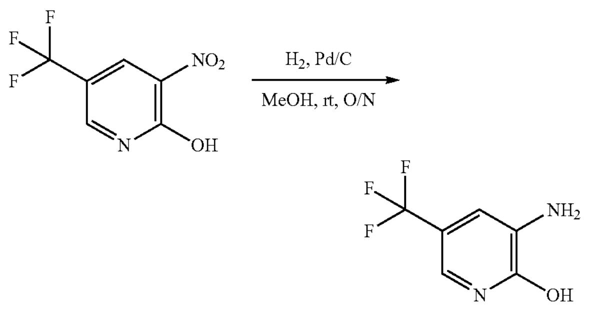

Into a 250-mL 3-necked round-bottom flask, was placed 3-nitro-5-(trifluoromethyl)pyridin-2-ol (5.0 g, 24 mmol, 1.0 equiv), MeOH (50 mL), Pd/C (1.5 g, 14 mmol, 0.6 equiv). To the above $H_2$ (g) was introduced in at room temperature. The resulting solution was stirred overnight at room temperature. The solids were filtered out. The filtrate was concentrated. This resulted in 4.2 g (98%) of 3-amino-5-(trifluoromethyl)pyridin-2-ol as a yellow solid.

Synthesis of 5-(4-cyclopropylphenyl)-3-(ethanesulfonyl)-N-[2-hydroxy-5-(trifluoromethyl)pyridin-3-yl]pyridine-2-carboxamide

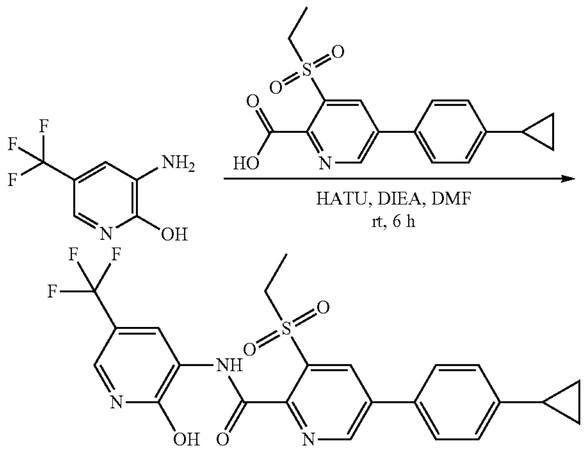

Into a 8-mL vial, was placed 5-(4-cyclopropylphenyl)-3-(ethanesulfonyl)pyridine-2-carboxylic acid (100 mg, 0.3 mmol, 1.0 equiv), DMF (1 mL), 3-amino-5-(trifluoromethyl)pyridin-2-ol (65 mg, 0.4 mmol, 1.2 equiv), DIEA (117 mg, 0.9 mmol, 3.0 equiv), HATU (172 mg, 0.5 mmol, 1.5 equiv). The resulting solution was stirred for 6 hr at room temperature. The residue was applied onto a C18 column with ($H_2O$ (0.1% TFA) and ACN: 75% ACN up to 85% within 6 min). This resulted in 40 mg (26%) of 5-(4-cyclopropylphenyl)-3-(ethanesulfonyl)-N-[2-hydroxy-5-(trifluoromethyl)pyridin-3-yl]pyridine-2-carboxamide as an off-white solid.

3. Synthesis of 5-(4-cyclopropylphenyl)-3-(ethanesulfonyl)-2-[6-(trifluoromethyl)-[1,3]oxazolo[5,4-b]pyridin-2-yl]pyridine

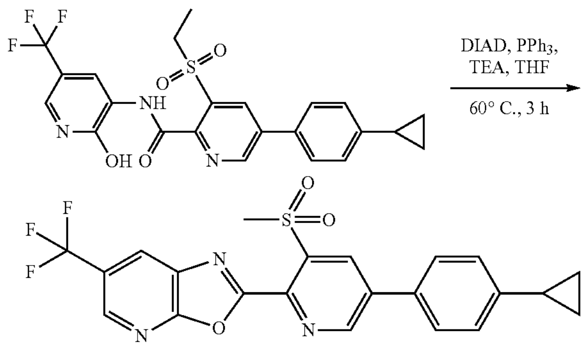

40

Into a 8-mL vial, was placed 5-(4-cyclopropylphenyl)-3-(ethanesulfonyl)-N-[2-hydroxy-5-(trifluoromethyl)pyridin-3-yl]pyridine-2-carboxamide (34 mg, 0.07 mmol, 1.0 equiv), THF (1 mL), TEA (28 mg, 0.28 mmol, 4 equiv), $Ph_3P$ (73 mg, 0.28 mmol, 4 equiv), DIAD (56 mg, 0.28 mmol, 4 equiv). The resulting solution was stirred for 3 hr at 60° C. The residue was applied onto a C18 column with ($H_2O$ (0.05% $NH3H_2O$) and ACN: 75% ACN up to 85% within 8 min). This resulted in 22 mg (67%) of 5-(4-cyclopropylphenyl)-3-(ethanesulfonyl)-2-[6-(trifluoromethyl)-[1,3]oxazolo[5,4-b]pyridin-2-yl]pyridine as an off-white solid.

Synthesis of Compound 42 and Compound 43

Synthesis of N-[4-[(trifluoromethyl)sulfanyl]phenyl] acetamide

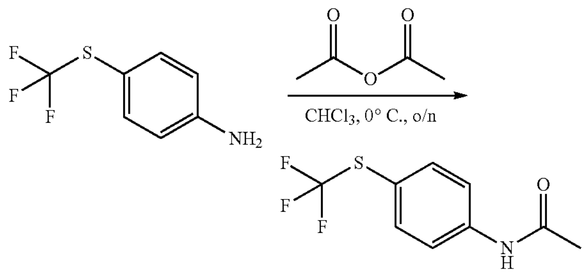

Into a 250-mL 3-necked round-bottom flask purged and maintained with an inert atmosphere of nitrogen, was placed 4-[(trifluoromethyl)sulfanyl]aniline (20 g, 104 mmol, 1.0 equiv), $CHCl_3$ (40 mL). This was followed by the addition of acetic anhydride (20 mL) dropwise with stirring at 0° C. The resulting solution was stirred overnight at room temperature. The resulting solution was diluted with 50 mL of PE. The solids were collected by filtration. This resulted in 23 g (92%) of N-[4-[(trifluoromethyl)sulfanyl]phenyl]acetamide as a white solid.

Synthesis of N-[2-nitro-4-[(trifluoromethyl)sulfanyl] phenyl]acetamide

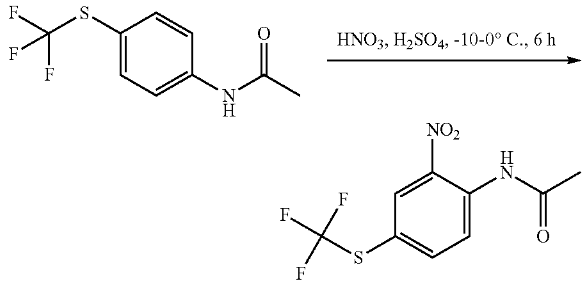

Into a 500-mL 3-necked round-bottom flask, was placed N-[4-[(trifluoromethyl)sulfanyl]phenyl]acetamide (22 g, 94 mmol, 1.0 equiv), $H_2SO_4$ (96 mL). This was followed by the addition of a solution of $HNO_3$ fuming (7.2 mL) in $H_2SO_4$ (24 mL) dropwise with stirring at −10° C. The resulting solution was stirred for 6 hr at 0° C. in an ice/water bath. The reaction was then quenched by the addition of 500 mL of water/ice. The resulting solution was extracted with 3×100 mL of ethyl acetate dried over anhydrous sodium sulfate and the organic layer was concentrated. The residue was applied onto a silica gel column with ethyl acetate/petroleum ether (1:3). This resulted in 5 g (19%) of N-[2-nitro-4-[(trifluoromethyl)sulfanyl]phenyl]acetamide as a yellow solid.

Synthesis of N-methyl-N-[2-nitro-4-[(trifluoromethyl)sulfanyl]phenyl]acetamide

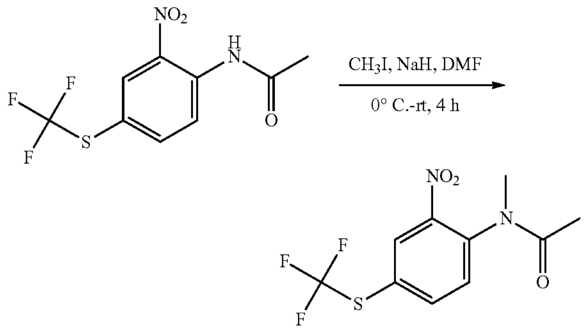

Into a 100-mL 3-necked round-bottom flask purged and maintained with an inert atmosphere of nitrogen, was placed N-[2-nitro-4-[(trifluoromethyl)sulfanyl]phenyl]acetamide (5 g, 18 mmol, 1.0 equiv), DMF (20 mL). This was followed by the addition of NaH (0.8 g, 33 mmol, 60%, 1.8 equiv) in several batches at 0 degrees C. The resulting solution was stirred for 10 min. To this was added a solution of $CH_3I$ (3.0 g, 21 mmol, 1.2 equiv) in DMF (2 mL) dropwise with stirring at 0 degrees C. The resulting solution was stirred for 4 hr at room temperature. The reaction was then quenched by the addition of 50 mL of $NH_4Cl$(aq.). The resulting solution was extracted with 3×50 mL of ethyl acetate, and the organic layer was dried over anhydrous sodium sulfate and concentrated. This resulted in 5 g (95%) of N-methyl-N-[2-nitro-4-[(trifluoromethyl)sulfanyl]phenyl]acetamide as a yellow solid.

Synthesis of N-methyl-2-nitro-4-[(trifluoromethyl) sulfanyl]aniline

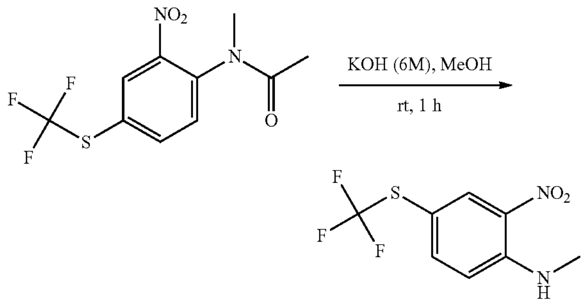

Into a 100-mL round-bottom flask, was placed N-methyl-N-[2-nitro-4-[(trifluoromethyl)sulfanyl]phenyl]acetamide (5.3 g, 0.02 mmol, 1.0 equiv), (10 mL), KOH (5 mL, 6M), MeOH 20 (10 mL). The resulting solution was stirred for 1 hr at room temperature. The resulting solution was diluted with 30 mL of water. The resulting solution was extracted with 3×100 mL of ethyl acetate, and the organic layer was dried over anhydrous sodium sulfate and concentrated. The residue was applied onto a silica gel column with ethyl acetate/petroleum ether (1:5). This resulted in 3.7 g (81%) of N-methyl-2-nitro-4-[(trifluoromethyl)sulfanyl]aniline as a yellow solid.

Synthesis of N1-methyl-4-[(trifluoromethyl)sulfanyl]benzene-1,2-diamine

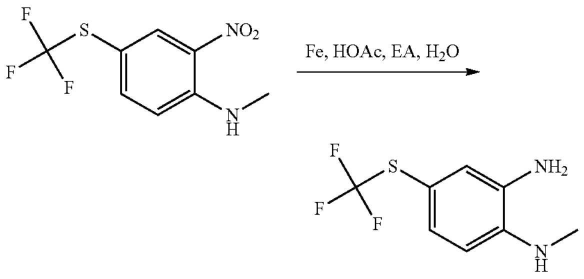

Into a 50-mL round-bottom flask, was placed N-methyl-2-nitro-4-[(trifluoromethyl)sulfanyl]aniline (3.6 g, 14.3 mmol, 1.0 equiv), EA (10 mL), Fe (3.6 g, 65 mmol, 4.5 equiv), $H_2O$ (5 mL), HOAc (5 mL). The resulting solution was stirred for 1 hr at 80 degrees C. in an oil bath. The resulting solution was diluted with 20 mL of water. The resulting solution was extracted with 3×20 mL of ethyl acetate, the organic layer was dried over anhydrous sodium sulfate and concentrated. The residue was applied onto a silica gel column with ethyl acetate/petroleum ether (1:3). This resulted in 2.5 g (79%) of N1-methyl-4-[(trifluoromethyl)sulfanyl]benzene-1,2-diamine as a dark blue solid.

Synthesis of 5-(4-cyclopropylphenyl)-3-(ethylsulfanyl)-N-[2-(methylamino)-5-[(trifluoromethyl) sulfanyl]phenyl]pyridine-2-carboxamide

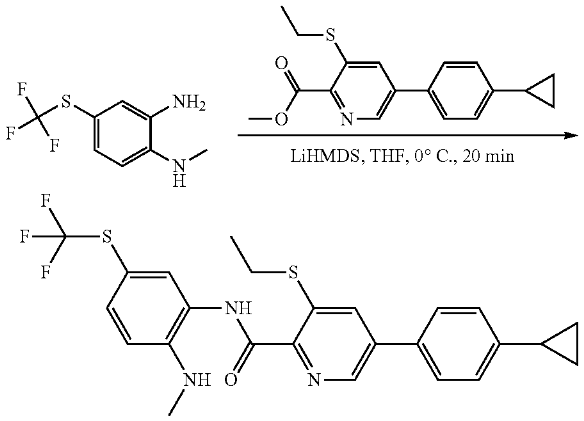

Into a 40-mL vial purged and maintained with an inert atmosphere of nitrogen, was placed methyl 5-(4-cyclopropylphenyl)-3-(ethylsulfanyl)pyridine-2-carboxylate (150 mg, 0.48 mmol, 1.0 equiv), N1-methyl-4-[(trifluoromethyl) sulfanyl]benzene-1,2-diamine (213 mg, 1.0 mmol, 2.0 equiv), THF (2 mL). This was followed by the addition of LiHMDS (0.95 mL, 0.950 mmol, 1.98 equiv) dropwise with stirring at 0 degrees C. The resulting solution was stirred for 20 min at room temperature. The reaction was then quenched by the addition of 10 mL of water. The resulting solution was extracted with 3×10 mL of ethyl acetate and the organic layers combined. The resulting mixture was washed with 10×10 mL of brine. The mixture was dried over anhydrous sodium sulfate and concentrated under vacuum. This resulted in 314 mg (crude) of 5-(4-cyclopropylphenyl)-3-(ethylsulfanyl)-N-[2-(methylamino)-5-[(trifluoromethyl) sulfanyl]phenyl]pyridine-2-carboxamide as light brown oil.

Synthesis of 2-[5-(4-cyclopropylphenyl)-3-(ethylsulfanyl)pyridin-2-yl]-1-methyl-5-[(trifluoromethyl) sulfanyl]-1,3-benzodiazole

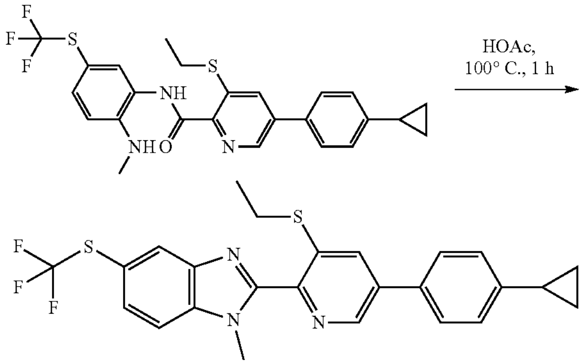

Into a 40-mL vial, was placed 5-(4-cyclopropylphenyl)-3-(ethylsulfanyl)-N-[2-(methylamino)-5-[(trifluoromethyl) sulfanyl]phenyl]pyridine-2-carboxamide (142 mg, 0.28 mmol, 1 equiv), acetic acid (3 mL). The resulting solution was stirred for 1 hr at 100 degrees C. in an oil bath. The reaction mixture was cooled to room temperature. The reaction was then quenched by the addition of 10 mL of water. The resulting solution was extracted with 3×10 mL of ethyl acetate and the organic layers combined. The resulting mixture was washed with 3×10 mL of brine. The mixture was dried over anhydrous sodium sulfate and concentrated. The residue was purified by silica gel column chromatography, eluted with PE/EtOAc (3:1) to afford 89 mg (65%) of 2-[5-(4-cyclopropylphenyl)-3-(ethylsulfanyl)pyridin-2-yl]-1-methyl-5-[(trifluoromethyl)sulfanyl]-1,3-benzodiazole as a solid.

Synthesis of 2-[5-(4-cyclopropylphenyl)-3-(ethanesulfonyl)pyridin-2-yl]-1-methyl-5-trifluoromethanesulfonyl-1,3-benzodiazole and 2-[5-(4-cyclopropylphenyl)-3-(ethanesulfonyl)pyridin-2-yl]-1-methyl-5-trifluoromethanesulfinyl-1,3-benzodiazole

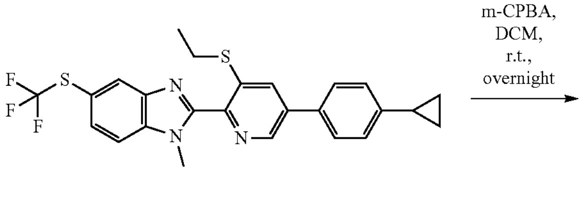

-continued

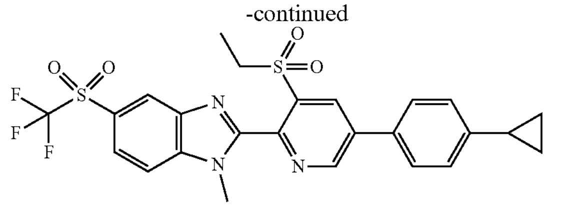

42

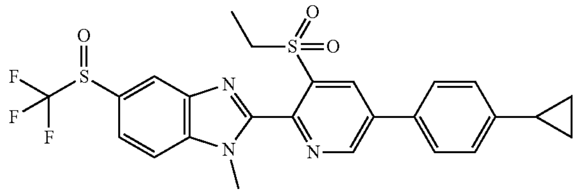

43

Into a 40-mL vial, was placed 2-[5-(4-cyclopropylphenyl)-3-(ethylsulfanyl)pyridin-2-yl]-1-methyl-5-[(trifluoromethyl)sulfanyl]-1,3-benzodiazole (84 mg, 0.2 mmol, 1.0 equiv), DCM (5 mL). This was followed by the addition of m-CPBA (180 mg, 1.0 mmol, 6.0 equiv) at room temperature. The resulting solution was stirred overnight at room temperature. The reaction was then quenched by the addition of 10 mL of $K_2CO_3$(aq). The resulting solution was extracted with 3x 10 mL of dichloromethane and the organic layers combined and concentrated. The crude product was purified by Prep-HPLC with the following conditions: Column: XBridge Prep C18 OBD Column, 5 um,19*150 mm; Mobile Phase A:Water (0.05% $NH3H_20$), Mobile Phase B:ACN; Flow rate: 20 mL/min; Gradient: 55 B to 80 B in 8 min; 220 nm. This resulted in 18.2 mg of 2-[5-(4-cyclopropylphenyl)-3-(ethanesulfonyl)pyridin-2-yl]-1-methyl-5-trifluoromethanesulfonyl-1,3-benzodiazole as a white solid and 5.7 mg of 2-[5-(4-cyclopropylphenyl)-3-(ethanesulfonyl) pyridin-2-yl]-1-methyl-5-trifluoromethanesulfinyl-1,3-benzodiazole as a white solid.

Synthesis of Compound 82

Synthesis of 5-(4-cyclopropylphenyl)-3-(ethylsulfanyl)-N-[2-(methylamino)-5-[(trifluoromethyl)sulfanyl]pyridin-3-yl]pyridine-2

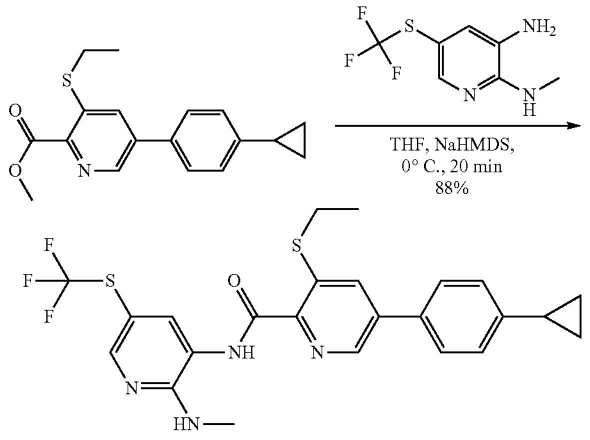

Into a 100-ml round-bottom flask purged and maintained with an inert atmosphere of nitrogen, was placed a solution of methyl 5-(4-cyclopropylphenyl)-3-(ethylsulfanyl)pyridine-2-carboxylate (120 mg, 0.4 mmol, 1.0 equiv) in THF (10 mL), N2-methyl-5-[(trifluoromethyl)sulfanyl]pyridine-2,3-diamine (85 mg, 0.4 mmol, 1 equiv). This was followed by the addition of NaHMDS (0.48 mL, 0.96 mmol, 2.5 equiv, 2M) at 0 degrees C. The resulting solution was stirred for 20 min at 0 degrees C. 100 mL of EA was added in. The organic phase was washed with 1×100 mL of 1% HCl and 2×50 mL of brine. The organic phase was dried over anhydrous sodium sulfate and concentrated. This resulted in 170 mg (88%) of 5-(4-cyclopropylphenyl)-3-(ethylsulfanyl)-N-[2-(methylamino)-5-[(trifluoromethyl)sulfanyl]pyridin-3-yl]pyridine-2-carboxamide as a yellow solid.

Synthesis of 5-(4-cyclopropylphenyl)-3-(ethylsulfanyl)-2-[3-methyl-6-[(trifluoromethyl)sulfanyl]imidazo[4,5-b]pyridin-2-yl]pyridine

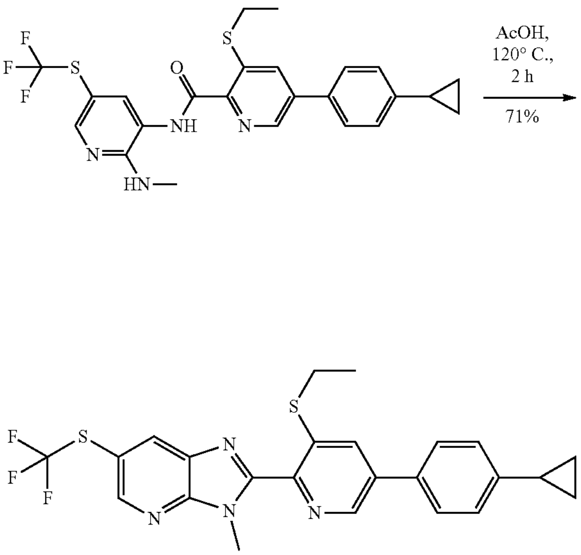

Into a 50-mL round-bottom flask, was placed 5-(4-cyclopropylphenyl)-3-(ethylsulfanyl)-N-[2-(methylamino)-5-[(trifluoromethyl)sulfanyl]pyridin-3-yl]pyridine-2-carboxamide (160 mg, 0.32 mmol, 1.0 equiv), AcOH (10 mL). The resulting solution was stirred for 2 hr at 120 degrees C. The resulting mixture was concentrated. 50 mL of EA was added in. The resulting mixture was washed with 1×50 mL of 10% $NaHCO_3$. The organic phase was dried over anhydrous sodium sulfate and concentrated. This resulted in 110 mg (71%) of 5-(4-cyclopropylphenyl)-3-(ethylsulfanyl)-2-[3-methyl-6-[(trifluoromethyl)sulfanyl]imidazo[4,5-b]pyridin-2-yl]pyridine as a yellow solid.

Synthesis of 5-(4-cyclopropylphenyl)-3-(ethanesulfonyl)-2-[3-methyl-6-trifluoromethane sulfonylimidazo[4,5-b]pyridin-2-yl]pyridine

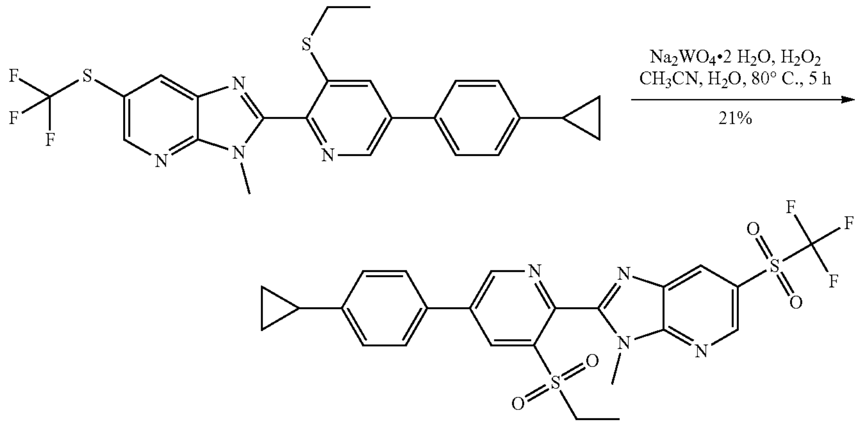

82

Into a 25-mL round-bottom flask, was placed 5-(4-cyclopropylphenyl)-3-(ethylsulfanyl)-2-[3-methyl-6-[(trifluoromethyl)sulfanyl]imidazo[4,5-b]pyridin-2-yl]pyridine (80 mg, 0.16 mmol, 1.0 equiv), ACN (3.0 mL), $H_2O$ (3.0 mL), $H_2$02(30%) (0.5 mL), $Na_2WO_4$ $2H_2O$ (0.62 mg, 0.002 mmol, 0.01 equiv) was added in at 0 degrees C. The resulting solution was stirred for 5 hr at 80 degrees C. The reaction was then quenched by the addition of 10 mL of 10% $Na_2S_2O_4$. The resulting solution was extracted with 2×40 mL of ethyl acetate. The organic phase was dried over anhydrous sodium sulfate and concentrated. The residue was purified by Prep-HPLC with the following conditions: Column, X-Bridge Column C18, 19*150 um, 20 ml/min; mobile phase, A: $H_2O$ (0.05% $NH_3H_2O$) B: ACN, 40-75% B, 8 min; Detector, 254 nm. This resulted in 19 mg (21%) of 5-(4-cyclopropylphenyl)-3-(ethanesulfonyl)-2-[3-methyl-6-trifluoromethane sulfonylimidazo[4,5-b]pyridin-2-yl]pyridine as a white solid.

Synthesis of Compound 83

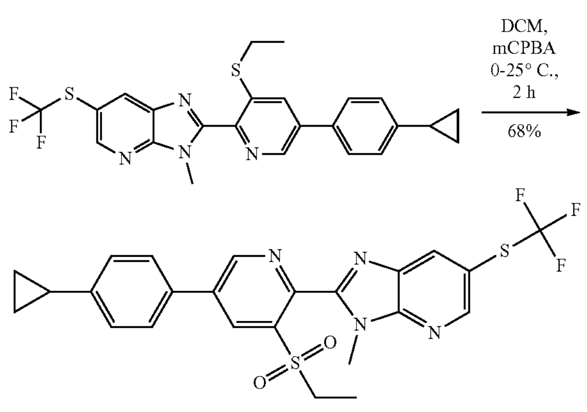

83

Into a 25-mL round-bottom flask, was placed a solution of 5-(4-cyclopropylphenyl)-3-(ethylsulfanyl)-2-[3-methyl-6-[(trifluoromethyl)sulfanyl]imidazo[4,5-b]pyridin-2-yl]pyridine (30 mg, 0.06 mmol, 1.0 equiv) in DCM (10 mL), mCPBA (53 mg, 0.3 mmol, 5 equiv). The resulting solution was stirred for 5 hr at 25 degrees C. The resulting mixture was concentrated. The crude product was purified by Prep-HPLC with the following conditions: Column, X-Bridge Column C18, 19*150 um, 20 ml/min; mobile phase, A: $H_2O$ (0.05% $NH_3H_2O$) B: ACN, 40% ACN up to 75% in 8 min; Detector, 254 nm. This resulted in 22 mg (68%) of 5-(4-cyclopropylphenyl)-3-(ethanesulfonyl)-2-[3-methyl-6-[(trifluoromethyl) sulfanyl]imidazo[4,5-b]pyridin-2-yl]pyridine as a light yellow solid.

Synthesis of Compound 147

Specifically, the following compounds of formula (I) can be synthesized by adopting the subsequent scheme of Compound 147 by someone who is skilled in the art: 149

Synthesis of methyl 3-(ethylsulfanyl)-5-(4,4,5,5-tetramethyl-1,3,2-dioxaborolan-2-yl)pyridine-2-carboxylate

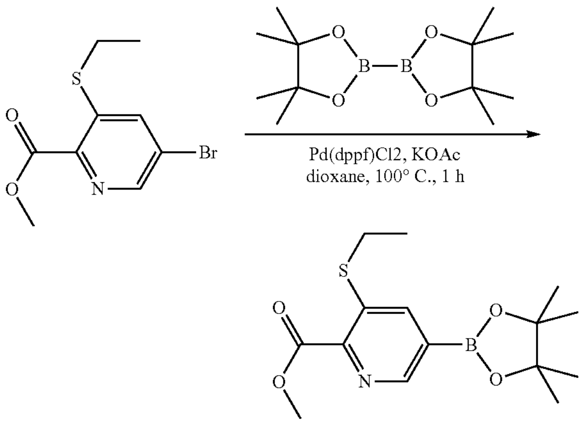

Into a 100-mL round-bottom flask purged and maintained with an inert atmosphere of nitrogen, was placed methyl 5-bromo-3-(ethylsulfanyl)pyridine-2-carboxylate (2 g, 7.2 mmol, 1 equiv), bis(pinacolato)diboron (2.76 g, 11 mmol, 1.5 equiv), Pd(dppf)Cl2·$CH_2$Cl2 (0.6 g, 0.7 mmol, 0.1 equiv), KOAc (2.1 g, 22 mmol, 3 equiv) and dioxane (40 mL). The resulting solution was stirred for 1 h at 100 degrees C. Desired product was detected by LCMS, This reaction mixture of methyl 3-(ethylsulfanyl)-5-(4,4,5,5-tetramethyl-1,3,2-dioxaborolan-2-yl)pyridine-2-carboxylate was used directly in the next step without further purification.

Synthesis of methyl 5-(3-amino-1,2,4-triazin-6-yl)-3-(ethylsulfanyl)pyridine-2-carboxylate

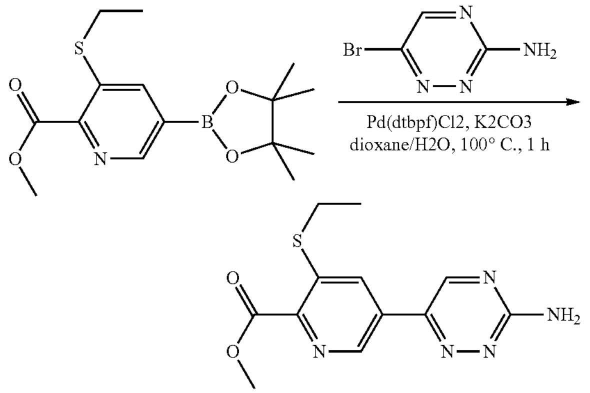

Into above mixture of 3-(ethylsulfanyl)-5-(4,4,5,5-tetramethyl-1,3,2-dioxaborolan-2-yl)pyridine-2-carboxylate, 6-bromo-1,2,4-triazin-3-amine (1.4 g, 8.2 mmol, 1 equiv), Pd(dtbpf)C12 (0.5 g, 0.8 mmol, 0.1 equiv), K2CO3 (2.8 g, 20 mmol, 2.5 equiv) and $H_2O$ (5 mL). The resulting solution was stirred for 1 h at 100 degrees C. The mixture was purified by Flash-Prep-HPLC with the following conditions (IntelFlash-1): Column, C18 silica gel; mobile phase, A0.05% TFA B:$CH_3$CN=25% increasing to A0.05% TFA B:$CH_3$CN=55% within 10 min; Detector, UV 254 nm/220 nm. This resulted in methyl 5-(3-amino-1,2,4-triazin-6-yl)-3-(ethylsulfanyl)pyridine-2-carboxylate (1.3 g, 66%) as a light yellow solid.

Synthesis of methyl 5-(3-bromo-1,2,4-triazin-6-yl)-3-(ethylsulfanyl)pyridine-2-carboxylate

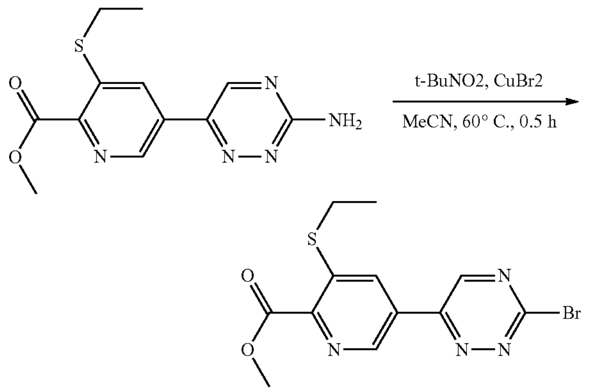

Into a 250-mL round-bottom flask purged and maintained with an inert atmosphere of nitrogen, was placed methyl 5-(3-amino-1,2,4-triazin-6-yl)-3-(ethylsulfanyl)pyridine-2-carboxylate (1.3 g, 4.5 mmol, 1 equiv) 2-methyl-2-nitropropane (0.55 g, 5.4 mmol, 1.2 equiv), CuBr2 (1.5 g, 6.7 mmol, 1.5 equiv) and MeCN (75 mL). The resulting solution was stirred for 0.5 h at 60 degrees C. The reaction was then quenched by the addition of 100 mL of $H_2O$. The resulting solution was extracted with 3×50 mL of ethyl acetate and the combined organic layers was dried over anhydrous sodium sulfate and concentrated. The residue was applied onto a silica gel column with ethyl acetate/petroleum ether (1:2). This resulted in methyl 5-(3-bromo-1,2,4-triazin-6-yl)-3-(ethylsulfanyl)pyridine-2-carboxylate (100 mg, 6%) as a light yellow solid.

Synthesis of methyl 5-(3-cyclopropyl-1,2,4-triazin-6-yl)-3-(ethylsulfanyl)pyridine-2-carboxylate

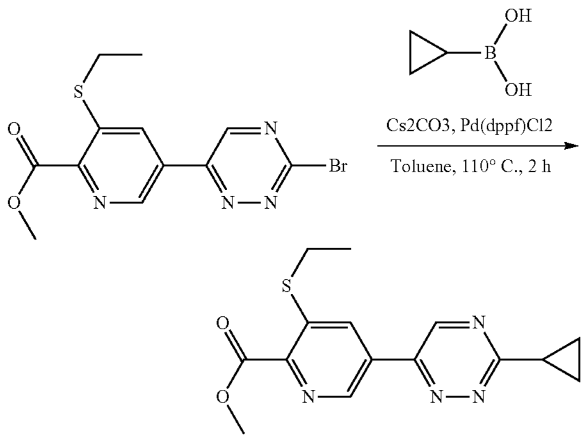

Into a 40-mL round-bottom flask purged and maintained with an inert atmosphere of nitrogen, was placed methyl 5-(3-bromo-1,2,4-triazin-6-yl)-3-(ethylsulfanyl)pyridine-2-carboxylate (100 mg, 0.28 mmol, 1 equiv)cyclopropylboronic acid (36 mg, 0.42 mmol, 1.5 equiv), toluene (15 mL), Cs2CO3 (275 mg, 0.85 mmol, 3 equiv), $H_2O$ (1 mL) and Pd(dppf)Cl2$CH_2$Cl2 (23 mg, 0.03 mmol, 0.1 equiv). The resulting solution was stirred for 2 h at 110 degrees C. The resulting mixture was concentrated. The residue was applied onto a silica gel column with ethyl acetate/petroleum ether (1:2). This resulted in methyl 5-(3-cyclopropyl-1,2,4-triazin-6-yl)-3-(ethylsulfanyl)pyridine-2-carboxylate (52 mg, 58) as a light yellow solid.

Synthesis of 5-(3-cyclopropyl-1,2,4-triazin-6-yl)-3-(ethylsulfanyl)pyridine-2-carboxylic acid

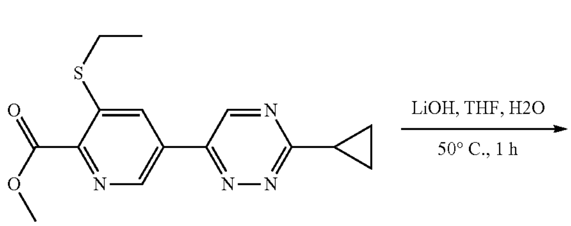

-continued

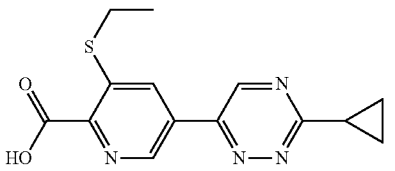

Into a 8-mL vial purged and maintained with an inert atmosphere of nitrogen. was placed methyl 5-(3-cyclopropyl-1,2,4-triazin-6-yl)-3-(ethylsulfanyl)pyridine-2-carboxylate (45 mg, 0.14 mmol, 1 equiv), THF (3 mL), $H_2O$ (2 mL) and LiOH (10 mg, 0.43 mmol, 3 equiv). The resulting solution was stirred for 1 h at 50 degrees C. The pH value of the solution was adjusted to 5-6 with HCl (1 M) at 0 degrees C. The resulting solution was extracted with 3×50 mL of ethyl acetate and the combined organic layers was dried over anhydrous sodium sulfate and concentrated. This resulted in 5-(3-cyclopropyl-1,2,4-triazin-6-yl)-3-(ethyl sulfanyl)pyridine-2-carboxylic acid (22 mg, 51%) as a light yellow solid.

Synthesis of 5-(3-cyclopropyl-1,2,4-triazin-6-yl)-3-(ethylsulfanyl)-N-[2-(methylamino)-5-(1,1,2,2,2-pentafluoroethyl)pyridin-3-yl]pyridine-2-carboxamide

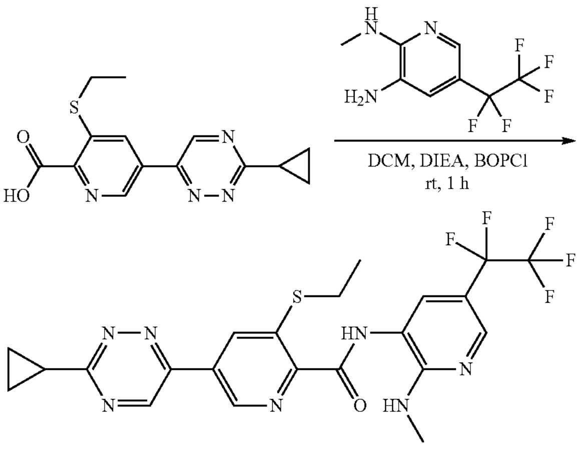

Into a 8-mL vial purged and maintained with an inert atmosphere of nitrogen, was placed 5-(3-cyclopropyl-1,2,4-triazin-6-yl)-3-(ethylsulfanyl)pyridine-2-carboxylic acid (22 mg, 0.07 mmol, 1 equiv) N2-methyl-5-(1,1,2,2,2-pentafluoroethyl)pyridine-2,3-diamine (19 mg, 0.08 mmol, 1.1 equiv), DCM (5 mL), DIEA (28 mg, 0.22 mmol, 3 equiv) and BOPCI (22 mg, 0.09 mmol, 1.2 equiv). The resulting solution was stirred for 1 h at room temperature. The reaction was then quenched by the addition of 20 mL of $H_2O$. The resulting solution was extracted with 3×20 mL of DCM and the combined organic layers was dried over anhydrous sodium sulfate and concentrated. This resulted in 5-(3-cyclopropyl-1,2,4-triazin-6-yl)-3-(ethylsulfanyl)-N-[2-(methylamino)-5-(1,1,2,2,2-pentafluoroethyl)pyridin-3-yl] pyridine-2-carboxamide (32 mg, 84%) as a light yellow solid.

Synthesis of 3-cyclopropyl-6-[5-(ethylsulfanyl)-6-[3-methyl-6-(1,1,2,2,2-pentafluoroethyl)-3H-imidazo[4,5-b]pyridin-2-yl]pyridin-3-yl]-1,2,4-triazine

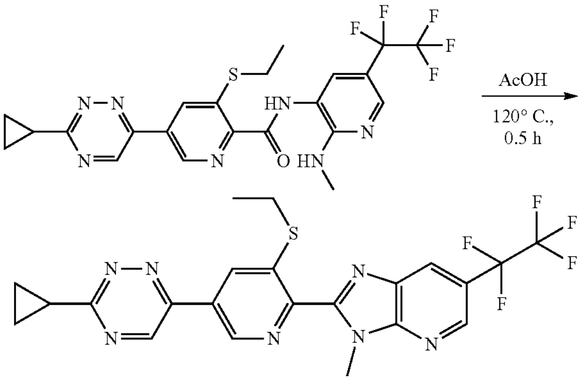

Into a 8-mL vial purged and maintained with an inert atmosphere of nitrogen, was placed 5-(3-cyclopropyl-1,2,4-triazin-6-yl)-3-(ethylsulfanyl)-N-[2-(methylamino)-5-(1,1,2,2,2-pentafluoroethyl)pyridin-3-yl]pyridine-2-carboxamide (32 mg, 0.01 mmol, 1 equiv) and AcOH (10 mL). The resulting solution was stirred for 0.5 h at 120 degrees C. The resulting mixture was concentrated. This resulted in 3-cyclopropyl-6-[5-(ethyl sulfanyl)-6-[3-methyl-6-(1,1,2,2,2-pentafluoroethyl)imidazo[4,5-b]pyridin-2-yl]pyridin-3-yl]-1,2,4-triazine (30 mg, 97%) as a brown solid.

Synthesis of 3-cyclopropyl-6-[5-(ethanesulfonyl)-6-[3-methyl-6-(1,1,2,2,2-pentafluoroethyl)-3H-imidazo[4,5-b]pyridin-2-yl]pyridin-3-yl]-1,2,4-triazine

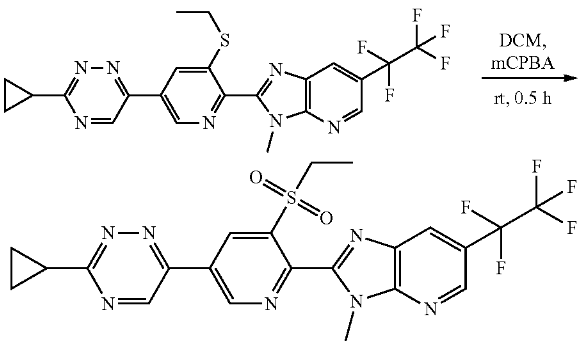

147

Into a 8-mL vial purged and maintained with an inert atmosphere of nitrogen, was placed 3-cyclopropyl-6-[5-(ethylsulfanyl)-6-[3-methyl-6-(1,1,2,2,2-pentafluoroethyl) imidazo[4,5-b]pyridin-2-yl]pyridin-3-yl]-1,2,4-triazine (30 mg, 0.01 mmol, 1 equiv), DCM (5 mL) and mCPBA (7 mg, 0.04 mmol, 3 equiv). The resulting solution was stirred for 1 h at room temperature. The reaction was then quenched by the addition of 10 mL of saturated Na2CO3. The resulting solution was extracted with 3×20 mL of DCM and the combined organic layers was dried over anhydrous sodium sulfate and concentrated. The residue was purified by Flash-Prep-HPLC with the following conditions (IntelFlash-1):

Column, C18 silica gel; mobile phase, Water(0.05% $NH3H_2O$) and ACN (35% ACN up to 70% in 7 min); Detector, UV 254 nm. This resulted in 3-cyclopropyl-6-[5-(ethanesulfonyl)-6-[3-methyl-6-(1,1,2,2,2-pentafluoroethyl)imidazo[4,5-b]pyridin-2-yl]pyridin-3-yl]-1,2,4-triazine (4.1 mg, 58%) as an off-white solid.

Synthesis of Compound 36

Synthesis of 3-chloro-6-(2,2,2-trifluoroethoxy)pyridazine

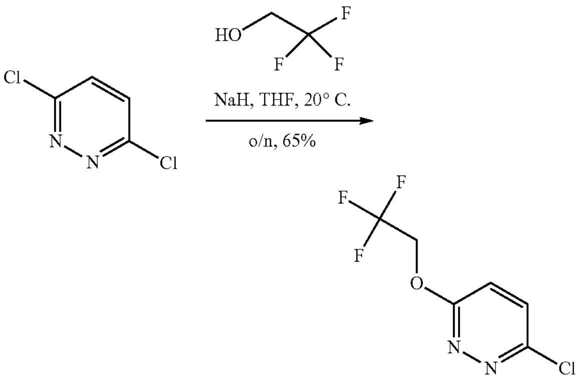

Into a 5.0-L 3-necked round-bottom flask, was placed pyridazine, 3,6-dichloro-(4000 g, 2700 mmol, 1.0 equiv), THF (4.0 L), trifluoroethanol (295 g, 3000 mmol, 1.1 equiv), 0 degrees C. was added NaH (215 g, 5400 mmol, 2.0 equiv, 60%). The resulting solution was stirred overnight at 20 degrees C. The reaction was then quenched by the addition of 2.0 mL of water. The resulting solution was extracted with 3×10 mL of ethyl acetate. The organic phase was dried over anhydrous sodium sulfate and concentrated. This resulted in 370 g (65%) of 3-chloro-6-(2,2,2-trifluoroethoxy)pyridazine as a white solid.

Synthesis of N-methyl-6-(2,2,2-trifluoroethoxy)pyridazin-3-amine

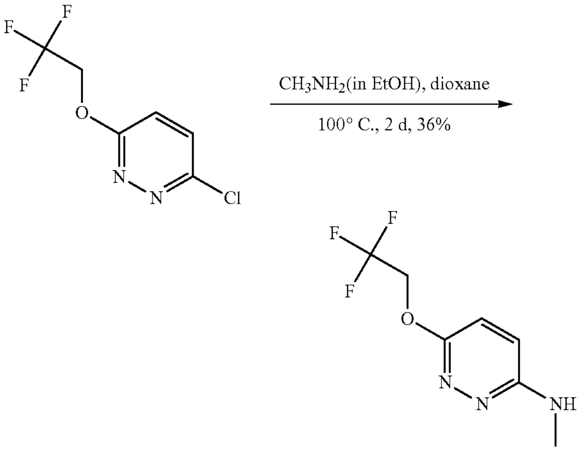

Into a 1000-mL round-bottom flask, was placed 3-chloro-6-(2,2,2-trifluoroethoxy)pyridazine (60 g, 280 mmol, 1.0 equiv), dioxane (600 mL), methylamine (221 mL, 1411 mmol, 5.0 equiv, 30-33 wt. % in EtOH). The resulting solution was stirred for 2 days at 100 degrees C. in an oil bath. The reaction mixture was cooled. The resulting mixture was concentrated. The residue was applied onto a silica gel column with ethyl acetate/petroleum ether (1/1). The collected fractions were combined and concentrated. This resulted in 21 g (35.91%) of N-methyl-6-(2,2,2-trifluoroethoxy)pyridazin-3-amine as an off-white solid.

Synthesis of 4-bromo-N-methyl-6-(2,2,2-trifluoroethoxy)pyridazin-3-amine

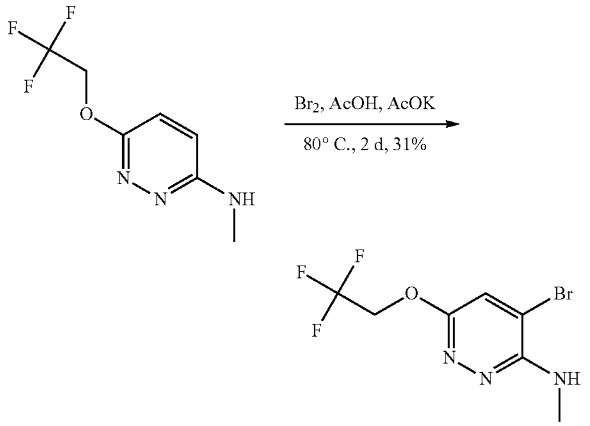

Into a 1000-mL round-bottom flask, was placed N-methyl-6-(2,2,2-trifluoroethoxy)pyridazin-3-amine (20 g, 97 mmol, 1.0 equiv), AcOH (400 mL), AcOK (28 g, 290 mmol, 3.0 equiv), $Br_2$ (154.29 g, 965.456 mmol, 10.00 equiv). The resulting solution was stirred for 2 days at 80 degrees C. in an oil bath. The resulting mixture was 10 concentrated. The resulting solution was diluted with 800 mL of EA. The resulting mixture was washed with 3×300 mL of $NaHCO_3$ (aq). The organic phase was dried over anhydrous sodium sulfate and concentrated. The residue was applied onto a silica gel column with ethyl acetate/petroleum ether (1/4). The collected fractions were combined and concentrated. This resulted in 8.2 g (31%) of 4-bromo-N-methyl-6-(2,2,2-trifluoroethoxy)pyridazin-3-amine as a yellow solid.

Synthesis of N3-methyl-6-(2,2,2-trifluoroethoxy)pyridazine-3,4-diamine

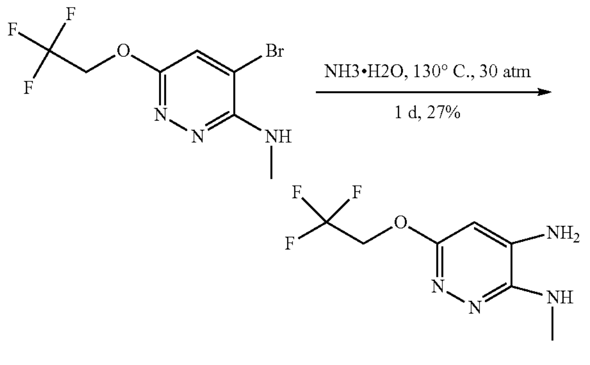

Into a 1000-mL pressure tank reactor, was placed 4-bromo-N-methyl-6-(2,2,2-trifluoroethoxy)pyridazin-3-amine (5.00 g, 17.479 mmol, 1.00 equiv), $NH_3 \cdot H_2O$ (800.00 mL). The resulting solution was stirred for 1 day at 130 degrees C., 30 atm. The reaction mixture was cooled and treated. The resulting mixture was concentrated. The residue was purified by Flash-Prep-HPLC with the following conditions (IntelFlash-1): Column, C18 silica gel; mobile phase, $MeCN/H_2O$=0/100 increasing to $MeCN/H_2O$=33/67. The product was obtained and concentrated. This resulted in 1.05 g (27.04%) of N3-methyl-6-(2,2,2-trifluoroethoxy) pyridazine-3,4-diamine as a light orange solid.

Synthesis of 5-(4-cyclopropylphenyl)-3-(ethylsulfanyl)-N-[3-(methylamino)-6-(2,2,2-trifluoroethoxy) pyridazin-4-yl]pyridine-2-carboxamide

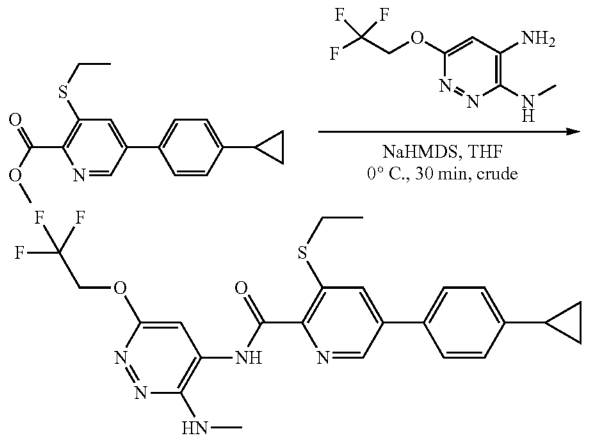

Into a 50-mL 3-necked round-bottom flask purged and maintained with an inert atmosphere of nitrogen, was placed N3-methyl-6-(2,2,2-trifluoroethoxy)pyridazine-3,4-diamine (100.00 mg, 0.450 mmol, 1.00 equiv), THF (10.00 mL), methyl 5-(4-cyclopropylphenyl)-3-(ethylsulfanyl)pyridine-2-carboxylate (155.18 mg, 0.495 mmol, 1.10 equiv), NaHMDS (123.81 mg, 0.675 mmol, 1.50 equiv) was added at 0 degrees C. The resulting solution was stirred for 30 min at 0 degrees C. The resulting solution was diluted with 50 mL of EA. The resulting mixture was washed with 3×50 mL of $H_2O$ and dried over anhydrous sodium sulfate and concentrated. This resulted in 200 mg (crude) of 5-(4-cyclopropylphenyl)-3-(ethylsulfanyl)-N-[3-(methylamino)-6-(2,2,2-trifluoroethoxy)pyridazin-4-yl]pyridine-2-carboxamide as a dark yellow solid.

Synthesis of 5-(4-cyclopropylphenyl)-3-(ethylsulfanyl)-2-[7-methyl-3-(2,2,2-trifluoroethoxy)imidazo[4,5-c]pyridazin-6-yl]pyridine

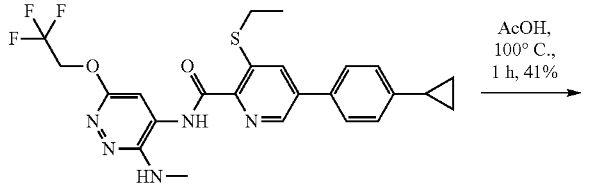

-continued

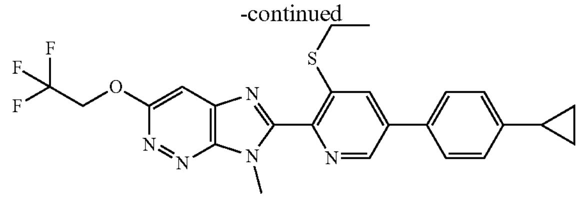

Into a 8-mL vial, was placed 5-(4-cyclopropylphenyl)-3-(ethylsulfanyl)-N-[3-(methylamino)-6-(2,2,2-trifluoroethoxy)pyridazin-4-yl]pyridine-2-carboxamide (150.00 mg, 0.298 mmol, 1.00 equiv), AcOH (3.00 mL). The resulting solution was stirred for 1 hr at 100 degrees C. in an oil bath. The reaction mixture was cooled. The resulting solution was diluted with 100 mL of EA. The resulting mixture was washed with 3×50 mL of $Na_2CO_3$ (aq, 2 M). The mixture was dried over anhydrous sodium sulfate and concentrated. The crude product was purified by re-crystallization from EA. This resulted in 60 mg (41%) of 5-(4-cyclopropylphenyl)-3-(ethylsulfanyl)-2-[7-methyl-3-(2,2,2-trifluoroethoxy) imidazo[4,5-c]pyridazin-6-yl]pyridine as a yellow solid.

Synthesis of 5-(4-cyclopropylphenyl)-3-(ethanesulfonyl)-2-[7-methyl-3-(2,2,2-trifluoroethoxy)imidazo[4,5-c]pyridazin-6-yl]pyridine

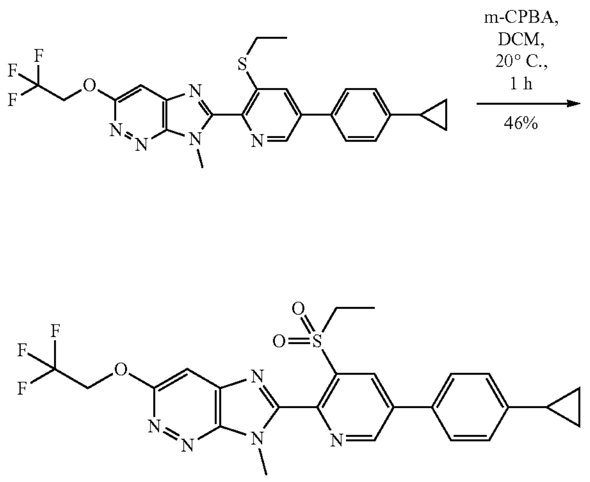

36

Into a 50-mL round-bottom flask, was placed 5-(4-cyclopropylphenyl)-3-(ethylsulfanyl)-2-[7-methyl-3-(2,2,2-trifluoroethoxy)imidazo[4,5-c]pyridazin-6-yl]pyridine (50 mg, 0.1 mmol, 1.0 equiv), DCM (10 mL), m-CPBA (53 mg, 0.3 mmol, 3.0 equiv). The resulting solution was stirred for 1 hr at 20 degrees C. The resulting mixture was concentrated. The residue was purified by Prep-HPLC with the following conditions (2 #SHIMADZU (HPLC-01)): Column, XBridge Prep C18 OBD Column, 5 um,19*150 mm; mobile phase, Water (0.05% $NH_3H_2O$) and ACN (52% ACN up to 74% in 7 min); Detector, UV. The product was obtained and concentrated. This resulted in 30 mg (46%) of 5-(4-cyclopropylphenyl)-3-(ethanesulfonyl)-2-[7-methyl-3-(2,2,2-trifluoroethoxy)imidazo[4,5-c]pyridazin-6-yl]pyridine as a white solid.

Synthesis of Compound 50

Synthesis of 3-nitro-5-(trifluoromethyl)-1H-pyridine-2-thione

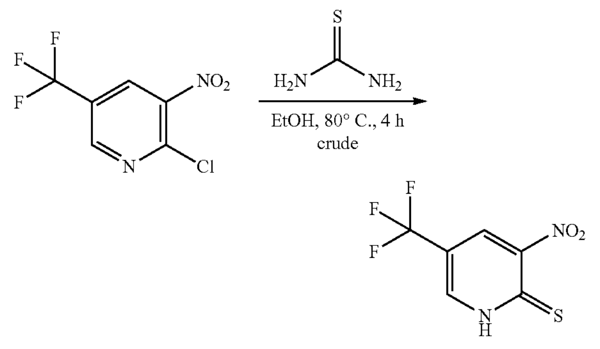

Into a 250-mL round-bottom flask, was placed 2-chloro-3-nitro-5-(trifluoromethyl)pyridine (2.0 g, 8.8 mmol, 1.0 equiv), EtOH (20 mL), thiourea (806 mg, 0.01 mmol, 1.2 equiv). The resulting solution was stirred for 4 hr at 80 degrees C. The reaction mixture was cooled to 25-degree C. The reaction was then quenched by the addition of 200 mL of water/ice. The resulting solution was extracted with 3×200 mL of ethyl acetate and the organic layers combined. The resulting mixture was washed with 3×200 mL of brine. The mixture was dried over anhydrous sodium sulfate and concentrated. The residue was applied onto a silica gel column with ethyl acetate/petroleum ether (1:1). This resulted in 2.5 g (crude) of 3-nitro-5-(trifluoromethyl)-1H-pyridine-2-thione as yellow oil.

Synthesis of 3-amino-5-tert-butylpyridine-2-thiol

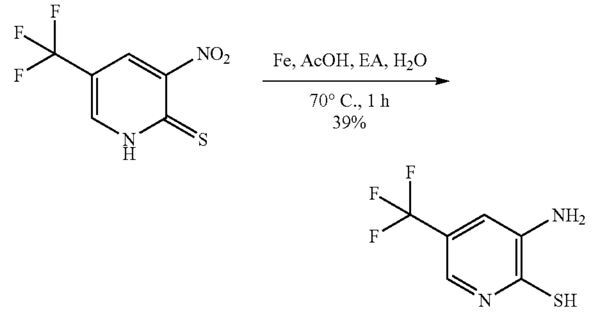

Into a 250-mL round-bottom flask, was placed 3-nitro-5-(trifluoromethyl)-1H-pyridine-2-thione (2.5 g, 11 mmol, 1.0 equiv), EA (10 mL), $H_2O$ (10 mL), AcOH (10 mL, 175 mmol, 16 equiv), Fe (1.50 g, 27 mmol, 2.4 equiv). The resulting solution was stirred for 1 hr at 70 degrees C. The reaction mixture was cooled to 25 degrees C. The reaction was then quenched by the addition of 200 mL of water/ice. The resulting solution was extracted with 3×200 mL of ethyl acetate and the organic layers combined. The resulting mixture was washed with 3×200 mL of brine. The mixture was dried over anhydrous sodium sulfate and concentrated. The residue was applied onto a silica gel column with ethyl acetate/petroleum ether (1:4). This resulted in 800 mg (39%) of 3-amino-5-tert-butylpyridine-2-thiol as a yellow solid.

Synthesis of 5-(4-cyclopropylphenyl)-3-(ethylsulfanyl)-N-[2-sulfanyl-5-(trifluoromethyl)pyridin-3-yl]pyridine-2-carboxamide

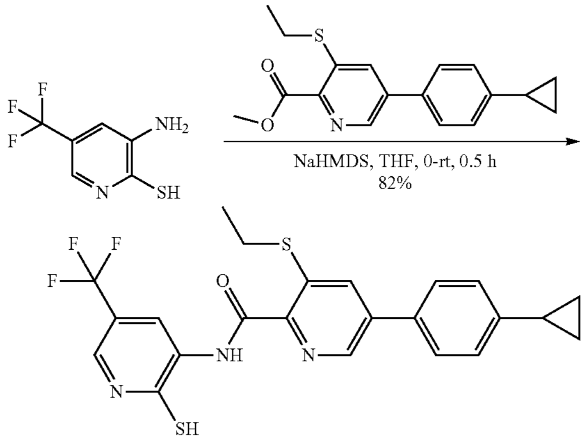

Into a 8-mL vial purged of nitrogen, was placed 3-amino-5-(trifluoromethyl)pyridine-2-thiol (100 mg, 0.5 mmol, 1.0 equiv), methyl 5-(4-cyclopropylphenyl)-3-(ethylsulfanyl)pyridine-2-carboxylate (161 mg, 0.5 mmol, 1.0 equiv), THF (2 mL), NaHMDS (189 mg, 1.0 mmol, 2.0 equiv). The resulting solution was stirred for 0.5 hr at 25 degrees C. The reaction was then quenched by the addition of 50 mL of water/ice. The resulting solution was extracted with 3×50 mL of ethyl acetate and the organic layers combined. The resulting mixture was washed with 3×50 mL of brine. The mixture was dried over anhydrous sodium sulfate and concentrated. The crude product was re-crystallized from PE: EA in the ratio of 4:1. This resulted in 200 mg (82%) of 5-(4-cyclopropylphenyl)-3-(ethylsulfanyl)-N-[2-sulfanyl-5-(trifluoromethyl)pyridin-3-yl]pyridine-2-carboxamide as a yellow solid.

Synthesis of 5-(4-cyclopropylphenyl)-3-(ethylsulfanyl)-2-[6-(trifluoromethyl)-[1,3]thiazolo[5,4-b]pyridin-2-yl]pyridine

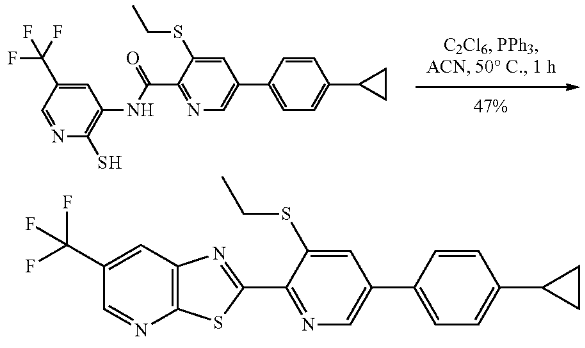

Into a 40-mL vial purged and maintained with an inert atmosphere of nitrogen, was placed $C_2C1_6$ (498 mg, 2.1 mmol, 10 equiv), $PPh_3$ (551 mg, 2.1 mmol, 10 equiv), ACN (5 mL).The mixture was stirred for 30 min at 25 degrees C. Then TEA (319 mg, 3.2 mmol, 15 equiv) was added to the mixture and stirred for 5 min at 25 degrees C. Then 5-(4-cyclopropylphenyl)-3-(ethylsulfanyl)-N-[2-sulfanyl-5-(trifluoromethyl)pyridin-3-yl]pyridine-2-carboxamide (100 mg, 0.2 mmol, 1.0 equiv) was added to the mixture. The resulting solution was stirred for 1 hr at 50 degrees C. The resulting mixture was concentrated. The residue was applied onto a silica gel column with ethyl acetate/petroleum ether (1:4). This resulted in 45 mg (47%) of 5-(4-cyclopropylphenyl)-3-(ethylsulfanyl)-2-[6-(trifluoromethyl)-[1,3]thiazolo[5,4-b]pyridin-2-yl]pyridine as a yellow solid.

Synthesis of 5-(4-cyclopropylphenyl)-3-(ethanesulfonyl)-2-[6-(trifluoromethyl)-[1,3]thiazolo[5,4-b]pyridin-2-yl]pyridine

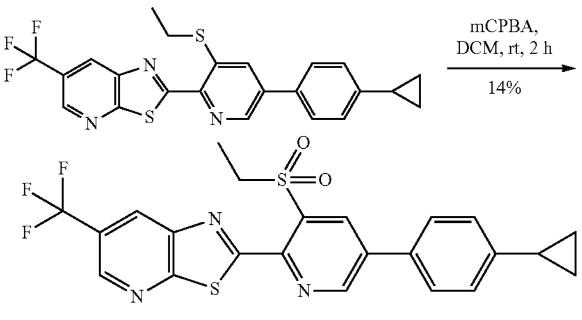

50

Into a 8-mL vial, was placed 5-(4-cyclopropylphenyl)-3-(ethylsulfanyl)-2-[6-(trifluoromethyl)-[1,3]thiazolo[5,4-b]pyridin-2-yl]pyridine (39 mg, 0.9 mmol, 1.0 equiv), DCM (2 mL), m-CPBA (29 mg, 0.2 mmol, 2.0 equiv). The resulting solution was stirred for 2 hr at 25 degrees C. The reaction was then quenched by the addition of 50 mL of water/ice. The resulting solution was extracted with 3×50 mL of ethyl acetate and the organic layers combined. The resulting mixture was washed with 3×50 mL of brine. The mixture was dried over anhydrous sodium sulfate and concentrated. The crude product was purified by Prep-HPLC with the following conditions (2 #SHIMADZU (HPLC-01)): Column, XBridge Prep C18 OBD Column, 5 um,19*150 mm; mobile phase, Water(0.05% $NH3H_2O$) and ACN (66% Phase B up to 85% in 7 min); Detector, 220 nm. This resulted in 6 mg (14%) of 5-(4-cyclopropylphenyl)-3-(ethanesulfonyl)-2-[6-(trifluoromethyl)-[1,3]thiazolo[5,4-b]pyridin-2-yl]pyridine as a white solid.

Synthesis of Compound 51

Synthesis of 2-nitro-4-[(trifluoromethyl)sulfanyl]phenol

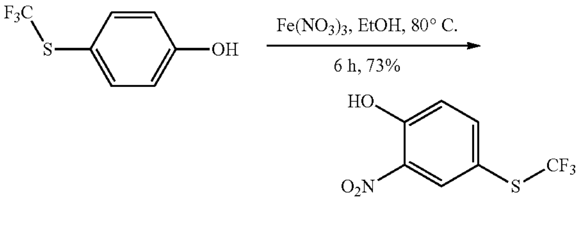

Into a 100-mL round-bottom flask, was placed 4-[(trifluoromethyl)sulfanyl]phenol (2.0 g, 10 mmol, 1.0 equiv), EtOH (40 mL), $Fe(NO_3)_3$(1.99 g, 8.2 mmol, 0.8 equiv). The resulting solution was stirred for 6 hr at 80 degrees C. in an oil bath. The reaction mixture was cooled. The resulting mixture was concentrated. The residue was applied onto a silica gel column with ethyl acetate/petroleum ether (1/4). The collected fractions were combined and concentrated. This resulted in 1.8 g (73%) of 2-nitro-4-[(trifluoromethyl)sulfanyl]phenol as yellow oil.

Synthesis of 1-methoxy-2-nitro-4-trifluoromethanesulfonylbenzene

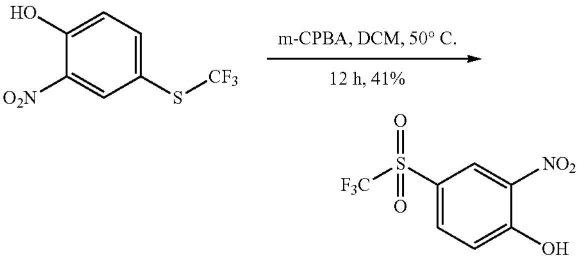

Into a 100-mL round-bottom flask, was placed 2-nitro-4-[(trifluoromethyl)sulfanyl]phenol (1.6 g, 6.7 mmol, 1.0 equiv), DCM (50 mL), m-CPBA (4.6 g, 26.8 mmol, 4.0 equiv). The resulting solution was stirred for 12 hr at 50 degrees C. in an oil bath. The reaction mixture was cooled. The resulting mixture was concentrated. The crude product was purified by Flash-Prep-HPLC with the following conditions (IntelFlash-1): Column, C18 silica gel; mobile phase, MeCN/H2O=0/100 increasing to MeCN/H2O=30/70. The product was obtained and concentrated. This resulted in 780 mg (41%) of 1-methoxy-2-nitro-4-trifluoromethanesulfonylbenzene as a yellow solid.

Synthesis of 1-chloro-2-nitro-4-trifluoromethanesulfonylbenzene

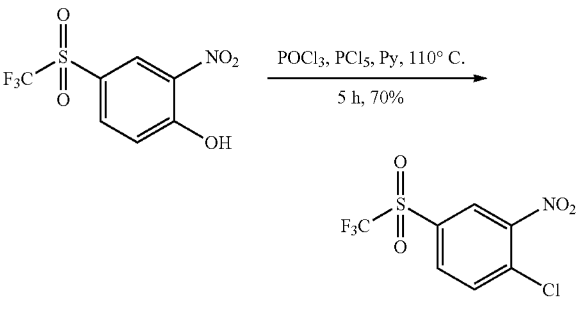

Into a 50-mL round-bottom flask, was placed 2-nitro-4-trifluoromethanesulfonylphenol (700 mg, 2.6 mmol, 1.0 equiv), $POCl_3$ (7.0 mL), pyridine (408 mg, 5.2 mmol, 2.0 equiv), $PCl_5$ (2.69 g, 12.9 mmol, 5.0 equiv). The resulting solution was stirred for 5 hr at 110 degrees C. in an oil bath. The reaction mixture was cooled. The resulting mixture was concentrated. The resulting solution was diluted with 100 mL of EA. The resulting mixture was washed with 3×100 mL of $Na_2CO_3$ (aq. 2M). The mixture was dried over anhydrous sodium sulfate. The residue was applied onto a silica gel column with ethyl acetate/petroleum ether (1/5).

This resulted in 520 mg (70%) of 1-chloro-2-nitro-4-trifluoromethanesulfonylbenzene as light-yellow oil.

Synthesis of 2-chloro-5-trifluoromethanesulfonylaniline

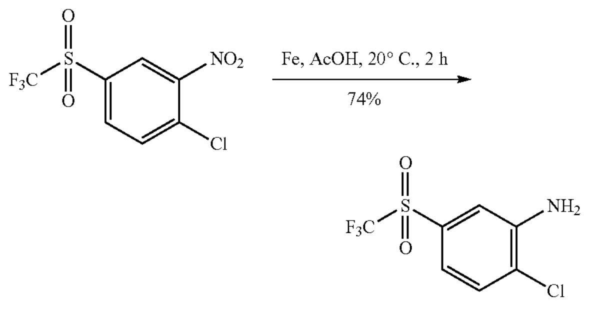

Into a 25-mL round-bottom flask, was placed 1-chloro-2-nitro-4-trifluoromethanesulfonylbenzene (200 mg, 0.69 mmol, 1.0 equiv), AcOH (5 mL), Fe dust (116 mg, 2.1 mmol, 3.0 equiv). The resulting solution was stirred for 2 hr at 20 degrees C. The resulting solution was diluted with 200 mL of EA. The resulting mixture was washed with 3×100 mL of $Na_2CO_3$ (aq. 2M). The mixture was dried over anhydrous sodium sulfate and concentrated. The residue was applied onto a silica gel column with ethyl acetate/petroleum ether (1/4). The collected fractions were combined and concentrated. This resulted in 160 mg (74%) of 2-chloro-5-trifluoromethanesulfonylaniline as a white solid.

Synthesis of N-(2-chloro-5-trifluoromethanesulfonylphenyl)-5-(4-cyclopropylphenyl)-3-(ethylsulfanyl)pyridine-2-carboxamide

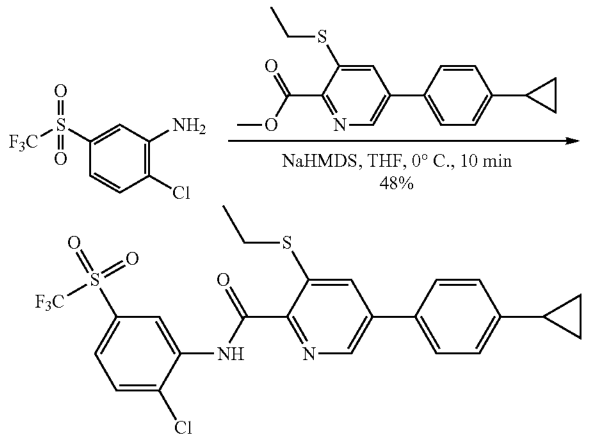

Into a 25-mL round-bottom flask purged and maintained with an inert atmosphere of nitrogen, was placed 2-chloro-5-trifluoromethanesulfonylaniline (100 mg, 0.4 mmol, 1.0 equiv), methyl 5-(4-cyclopropylphenyl)-3-(ethylsulfanyl)pyridine-2-carboxylate (121 mg, 0.4 mmol, 1.0 equiv), THF (5.0 mL), 0 degrees C. was added NaHMDS (212 mg, 1.2 mmol, 3.0 equiv). The resulting solution was stirred for 10 min at 0 degrees C. The resulting solution was diluted with 100 mL of EA. The resulting mixture was washed with 3×50 mL of $H_2O$. The solid was dried in an oven under reduced pressure. The residue was applied onto a silica gel column with ethyl acetate/petroleum ether (1/4). The collected fractions were combined and concentrated. This resulted in 100 mg (48%) of N-(2-chloro-5-trifluoromethanesulfonylphenyl)-5-(4-cyclopropylphenyl)-3-(ethylsulfanyl)pyridine-2-carboxamide as a white solid.

Synthesis of 2-[5-(4-cyclopropylphenyl)-3-(ethylsulfanyl)pyridin-2-yl]-5-trifluoromethanesulfonyl-1,3-benzothiazole

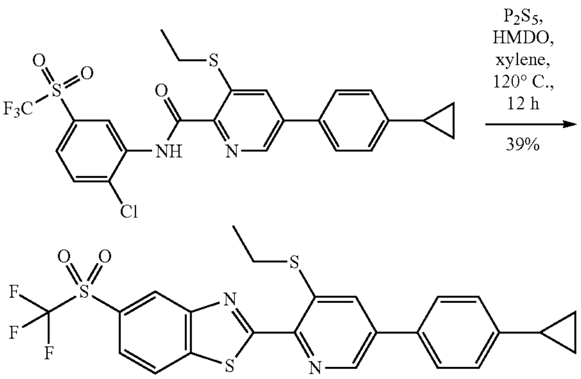

Into a 25-mL round-bottom flask, was placed N-(2-chloro-5-trifluoromethanesulfonylphenyl)-5-(4-cyclopropylphenyl)-3-(ethylsulfanyl)pyridine-2-carboxamide (80 mg, 0.15 mmol, 1.0 equiv), xylene (8.00 mL), $P_2S_5$(164 mg, 0.74 mmol, 5.0 equiv), HMDO (120 mg, 0.74 mmol, 5.0 equiv). The resulting solution was stirred for 12 hr at 120 degrees C. in an oil bath. The reaction mixture was cooled. The resulting solution was diluted with 50 mL of EA. The resulting mixture was washed with 3×20 mL of $H_2O$. The mixture was dried over anhydrous sodium sulfate and concentrated. The residue was applied onto a silica gel column with ethyl acetate/petroleum ether (1/4). The collected fractions were combined and concentrated. This resulted in 30 mg (39%) of 2-[5-(4-cyclopropylphenyl)-3-(ethylsulfanyl)pyridin-2-yl]-5-trifluoromethanesulfonyl-1,3-benzothiazole as yellow oil.

Synthesis of-[5-(4-cyclopropylphenyl)-3-(ethanesulfonyl)pyridin-2-yl]-5-trifluoromethanesulfonyl-1,3-benzothiazole

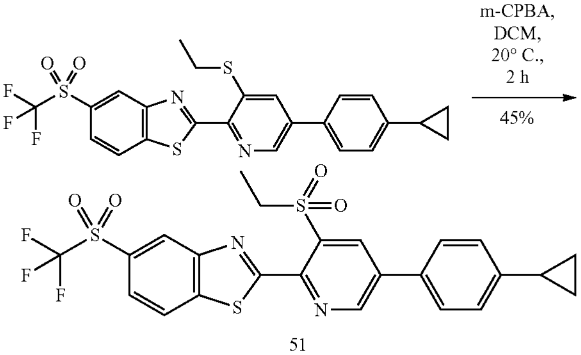

51

Into a 8-mL vial, was placed 2-[5-(4-cyclopropylphenyl)-3-(ethylsulfanyl)pyridin-2-yl]-5-trifluoromethanesulfonyl-1,3-benzothiazole (25 mg, 0.05 mmol, 1.00 equiv), DCM (2.5 mL), m-CPBA (17 mg, 0.1 mmol, 2.0 equiv). The resulting solution was stirred for 2 hr at 20 degrees C. The resulting mixture was concentrated. The resulting solution was diluted with 3 mL of DMF. The crude product was purified by Prep-HPLC with the following conditions (2 #SHIMADZU (HPLC-01)): Column, XBridge Prep C18 OBD Column, 5 um,19*150 mm; mobile phase, Water (0.05% $NH3H_2O$) and ACN (68% Phase B up to 83% in 7 min); Detector, UV 254 nm. The product was obtained and concentrated. This resulted in 12 mg (45%) of 2-[5-(4-cyclopropylphenyl)-3-(ethanesulfonyl)pyridin-2-yl]-5-trifluoromethanesulfonyl-1,3-benzothiazole as a white solid.

Synthesis of Compound 53

Synthesis of 4-(trifluoromethyl)pyridine-2-carbonyl chloride

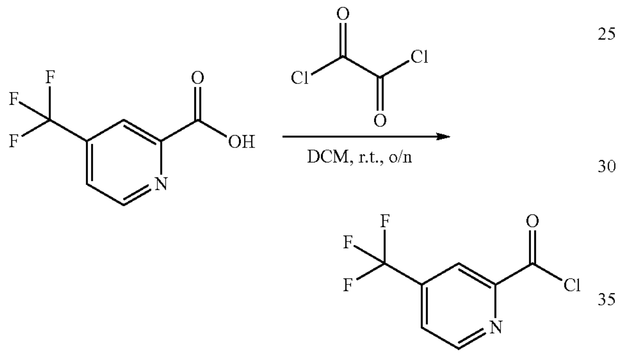

Into a 100-mL round-bottom flask, was placed 4-(trifluoromethyl)pyridine-2-carboxylic acid (1.0 g, 5.2 mmol, 1.0 equiv), DCM (30 mL), a drop DMF, oxalyl chloride (0.86 g, 6.8 mmol, 13 equiv). The resulting solution was stirred for 15 hr at room temperature. The resulting mixture was concentrated. This resulted in 1.1 g (crude) of 4-(trifluoromethyl)pyridine-2-carbonyl chloride as a yellow solid.

Synthesis of N-methyl-4-(trifluoromethyl)pyridine-2-carboxamide

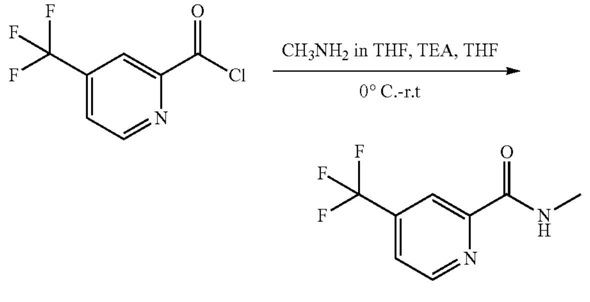

Into a 50-mL round-bottom flask, was placed $CH_3NH_2$ in THE (6.5 mL, 13 mmol, 2.5 equiv), THF (10 mL). This was followed by the addition of TEA (0.79 g, 7.8 mmol, 1.5 equiv) dropwise with stirring at 0° C. To this was added a solution of 4-(trifluoromethyl)pyridine-2-carbonyl chloride (1.1 g, 5.25 mmol, 1.0 equiv) in THF (10 mL) dropwise with stirring at 0° C. The resulting solution was stirred for 2 hr at room temperature. The resulting solution was diluted with 300 mL of saturated aqueous $NaHCO_3$. The resulting solution was extracted with 5×100 mL of ethyl acetate and the organic layers combined and concentrated. The residue was applied onto a silica gel column with ethyl acetate/petroleum ether (1/1). This resulted in 800 mg (75%) of N-methyl-4-(trifluoromethyl)pyridine-2-carboxamide as yellow oil.

Synthesis of N-methyl-4-(trifluoromethyl)pyridine-2-carbothioamide

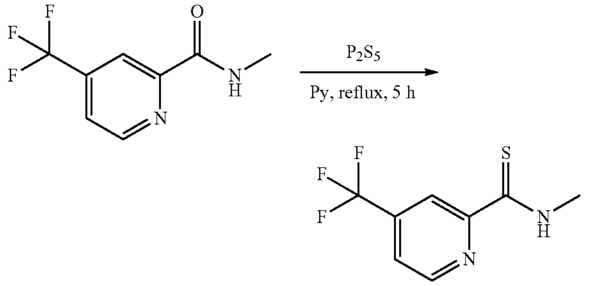

Into a 50-mL round-bottom flask, was placed N-methyl-4-(trifluoromethyl)pyridine-2-carboxamide (400 mg, 2.0 mmol, 1.0 equiv), Pyridine (10 mL), $P_2S_5$(260 mg, 1.2 mmol, 0.6 equiv). The resulting solution was heated to reflux for 5 hr in an oil bath. The reaction mixture was cooled to room temperature. The resulting solution was diluted with 200 mL of $H_2O$. The resulting solution was extracted with 3×150 mL of ethyl acetate and the organic layers combined. The resulting mixture was washed with 3×500 ml of brine. The resulting mixture was concentrated. The residue was applied onto a silica gel column with ethyl acetate/petroleum ether (1/1). This resulted in 200 mg (46%) of N-methyl-4-(trifluoromethyl)pyridine-2-carbothioamide as a yellow solid.

Synthesis of (Z)-[(ethylsulfanyl)[4-(trifluoromethyl) pyridin-2-yl]methylidene](methyl)amine

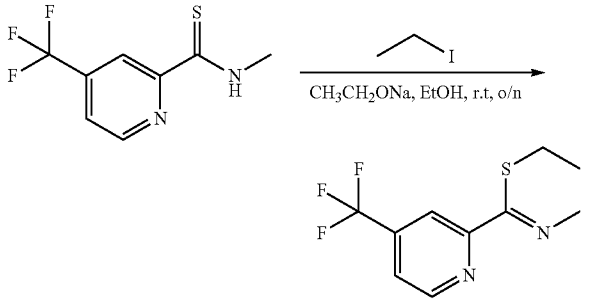

Into a 50-mL round-bottom flask, was placed N-methyl-4-(trifluoromethyl)pyridine-2-carbothioamide (190 mg, 0.9 mmol, 1.0 equiv), EtOH (5 mL), EtONa in EtOH (294 mg, 0.9 mmol, 1.0 equiv, 20%). The resulting solution was stirred for 0.5 hr at room temperature. This was followed by the addition of ethyl iodide (269 mg, 1.7 mmol, 2.0 equiv)

dropwise with stirring at room temperature. The resulting solution was stirred overnight at room temperature. The resulting mixture was concentrated. The resulting solution was diluted with 30 mL of saturated aqueous $NaHCO_3$. The resulting solution was extracted with 3×25 mL of ethyl acetate and the organic layers combined and concentrated. The residue was applied onto a silica gel column with ethyl acetate/petroleum ether (l/10). This resulted in 110 mg (51%) of (Z)-[(ethylsulfanyl)[4-(trifluoromethyl)pyridin-2-yl]methylidene](methyl)amine as yellow oil.

Synthesis of 5-(4-cyclopropylphenyl)-3-(ethylsulfanyl)pyridine-2-carbohydrazide

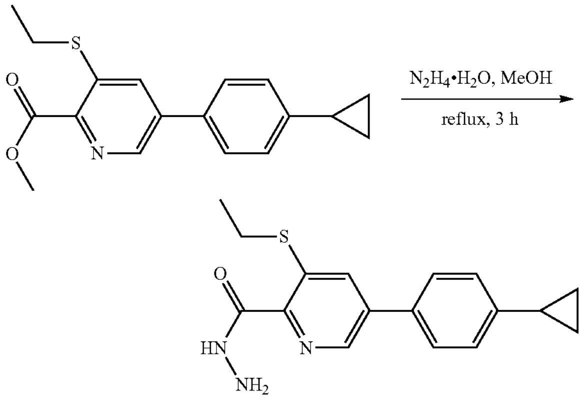

Into a 50-mL round-bottom flask, was placed methyl 5-(4-cyclopropylphenyl)-3-(ethylsulfanyl)pyridine-2-carboxylate (100 mg, 0.32 mmol, 1.0 equiv), MeOH (5.0 mg), hydrazine (164 mg, 3.2 mmol, 10 equiv, 98%). The resulting solution was heated to reflux for 3 hr in an oil bath. The reaction mixture was cooled to room temperature. The resulting mixture was concentrated. The crude product was purified by Flash-Prep-HPLC with the following conditions (IntelFlash-1): Column, C18 silica gel; mobile phase, $CH_3CN/H_2O$=85%; Detector, 254&220 nm. This resulted in 75 mg (75%) of 5-(4-cyclopropylphenyl)-3-(ethylsulfanyl) pyridine-2-carbohydrazide as a light brown solid.

Synthesis of 5-(4-cyclopropylphenyl)-3-(ethylsulfanyl)-2-[4-methyl-5-[4-(trifluoromethyl)pyridin-2-yl]-1,2,4-triazol-3-yl]pyridine

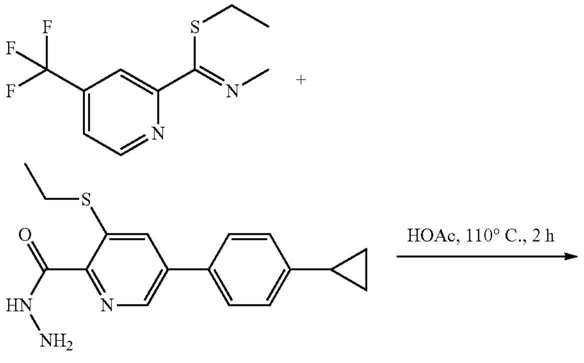

-continued

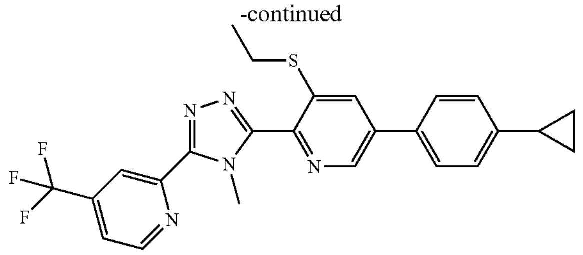

Into a 50-mL round-bottom flask, was placed 5-(4-cyclopropylphenyl)-3-(ethylsulfanyl)pyridine-2-carbohydrazide (60 mg, 0.2 mmol, 1.0 equiv), (Z)-[(ethylsulfanyl)[4-(trifluoromethyl)pyridin-2-yl]methylidene](methyl)amine (71 mg, 0.29 mmol, 1.5 equiv), HOAc (2.0 mL). The resulting solution was stirred for 2 hr at 110° C. in an oil bath. The reaction mixture was cooled to room temperature. The pH value of the solution was adjusted to 8 with saturated aqueous $NaHCO_3$. The resulting solution was extracted with 3×50 mL of ethyl acetate and the organic layers combined and concentrated. The residue was applied onto a silica gel column with ethyl acetate/petroleum ether (1/1). This resulted in 50 mg (54%) of 5-(4-cyclopropylphenyl)-3-(ethylsulfanyl)-2-[4-methyl-5-[4-(trifluoromethyl)pyridin-2-yl]-1,2,4-triazol-3-yl]pyridine as a yellow solid.

Synthesis of 5-(4-cyclopropylphenyl)-3-(ethanesulfonyl)-2-[4-methyl-5-[4-(trifluoromethyl)pyridin-2-yl]-1,2,4-triazol-3-yl]pyridine

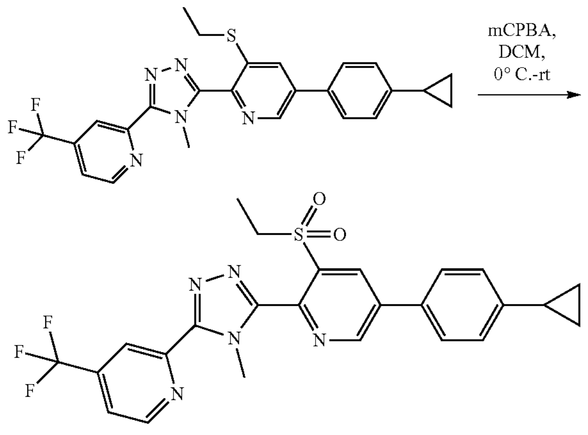

53

Into a 50-mL round-bottom flask, was placed 5-(4-cyclopropylphenyl)-3-(ethylsulfanyl)-2-[4-methyl-5-[4-(trifluoromethyl)pyridin-2-yl]-1,2,4-triazol-3-yl]pyridine (74 mg, 0.15 mmol, 1.0 equiv), DCM (15 mL). This was followed by the addition of m-CPBA (95 mg, 0.47 mmol, 3.0 equiv, 85%) at 0° C. The resulting solution was stirred for 1 hr at room temperature. The reaction was then quenched by the addition of 100 mL of saturated aqueous $NaHCO_3$. The resulting solution was extracted with 3×50 mL of dichloromethane and the organic layers combined and concentrated. The crude product was purified by Flash-Prep-HPLC with the following conditions (IntelFlash-1): Column, C18 silica gel; mobile phase, $CH_3CN$/0.05% $NH_3 \cdot H_2O$=65% increasing to $CH_3CN$/0.05% $NH_3 \cdot H_2O$=70%; Detector, 254&220 nm. This resulted in 31 mg (39%) of 5-(4-cyclopropylphenyl)-3-(ethanesulfonyl)-2-[4-methyl-5-[4-(trifluoromethyl)pyridin-2-yl]-1,2,4-triazol-3-yl]pyridine as an off-white solid.

Synthesis of Compound 54

Synthesis of 1-[4-(trifluoromethyl)pyridin-2-yl]ethanone

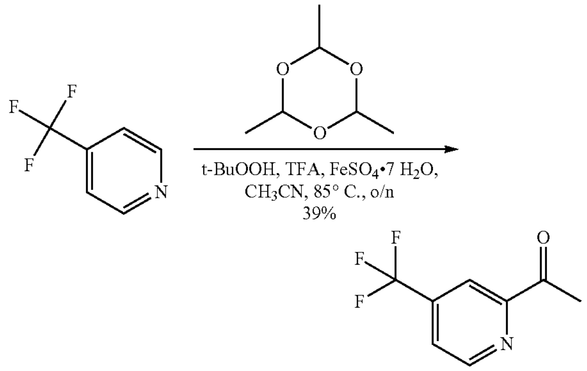

Into a 1-L round-bottom flask purged and maintained with an inert atmosphere of nitrogen, was placed 4-(trifluoromethyl)pyridine (10 g, 68 mmol, 1.0 equiv), $CH_3CN$ (500 mL), paraldehyde (40 g, 306 mmol, 4.5 equiv), TFA (7.8 g, 68 mmol, 1.0 equiv), TBHP (26 g, 291 mmol, 4.3 equiv), $FeSO_4 \cdot 7H_2O$ (0.19 g, 0.68 mmol, 0.01 equiv). The resulting solution was stirred overnight at 85° C. in an oil bath. The reaction mixture was cooled to room temperature. The reaction was then quenched by the addition of 20 g of $Na2SO_3$. The resulting solution was stirred for 0.5 hr at room temperature. The resulting solution was diluted with 1.5 L of $H_2O$. The resulting solution was extracted with 3×600 mL of ethyl acetate and the organic layers combined and concentrated. The residue was applied onto a silica gel column with ethyl acetate/petroleum ether (1/3). This resulted in 5.0 g (39%) of]-[4-(trifluoromethyl)pyridin-2-yl] ethanone as yellow oil.

Synthesis of 2-bromo-1-[4-(trifluoromethyl)pyridin-2-yl]ethanone

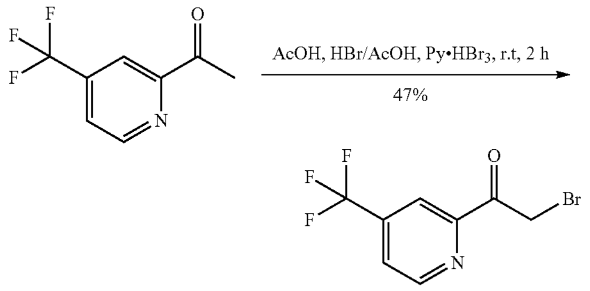

Into a 50-mL round-bottom flask, was placed 1-[4-(trifluoromethyl)pyridin-2-yl]ethanone (500 mg, 2.6 mmol, 1.0 equiv), HOAc (1.5 mL), HBr in AcOH (40%) (1.5 mL), Pyridine hydrobromide (931 mg, 2.9 mmol, 1.1 equiv). The resulting solution was stirred for 2 hr at room temperature. The pH value of the solution was adjusted to 8 with saturated aqueous $NaHCO_3$. The resulting solution was extracted with 3×60 mL of ethyl acetate and the organic layers combined and concentrated. The residue was applied onto a silica gel column with dichloromethane/petroleum ether (1/5-1/3). This resulted in 330 mg (47%) of 2-bromo-1-[4-(trifluoromethyl)pyridin-2-yl]ethanone as a yellow oil.

Synthesis of 5-bromo-3-(ethylsulfanyl)pyridine-2-carboxylic acid

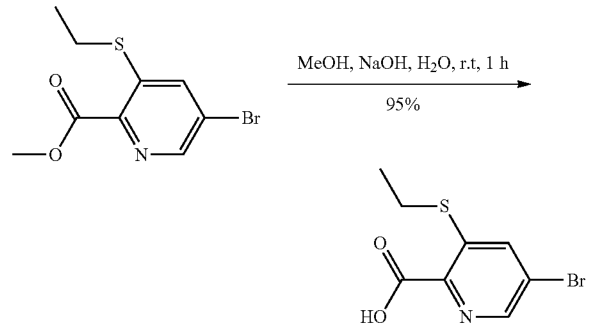

Into a 500-mL round-bottom flask, was placed methyl 5-bromo-3-(ethylsulfanyl)pyridine-2-carboxylate (10 g, 36 mmol, 1.0 equiv), MeOH (150 mL), NaOH (5.8 g, 146 mmol, 4.0 equiv), $H_2O$ (75 mL). The resulting solution was stirred for 1 hr at room temperature. The resulting mixture was concentrated. The resulting solution was diluted with 50 mL of $H_2O$. The pH value of the solution was adjusted to 4-5 with 6M HCl. The solids were collected by filtration. The solid was dried in under infrared light. This resulted in 9.0 g (95%) of 5-bromo-3-(ethylsulfanyl)pyridine-2-carboxylic acid as a light yellow solid.

Synthesis of 5-bromo-3-(ethylsulfanyl)pyridine-2-carboxamide

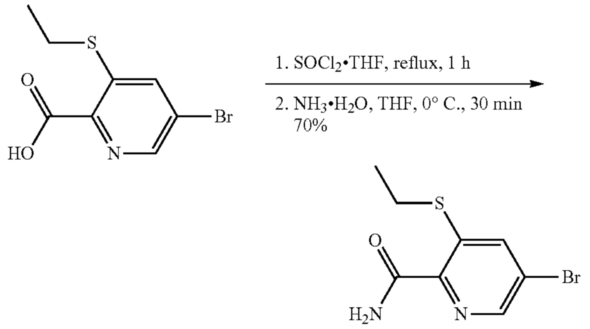

Into a 1-L round-bottom flask, was placed 5-bromo-3-(ethylsulfanyl)pyridine-2-carboxylic acid (10 g, 38 mmol, 1.0 equiv), THF (300 mL), DMF (0.2 mL), $SOCl_2$ (45 g, 382 mmol, 10 equiv).The resulting solution was heated to reflux for 1 hr in an oil bath. The reaction mixture was cooled. The resulting mixture A was concentrated. Into a 1-L round-bottom flask, was placed $NH_3 \cdot H_2O$ (220 g, 1883 mmol, 49 equiv, 30%). This was followed by the addition of A and THF (300 mL) dropwise with stirring at 0° C. The resulting solution was stirred for 0.5 hr at room temperature. The resulting solution was diluted with 1 L of $H_2O$. The solids were collected by filtration. The mixture was dried by infrared light. This resulted in 7.0 g (70%) of 5-bromo-3-(ethylsulfanyl)pyridine-2-carboxamide as yellow oil.

Synthesis of 5-bromo-3-(ethylsulfanyl)pyridine-2-carbonitrile

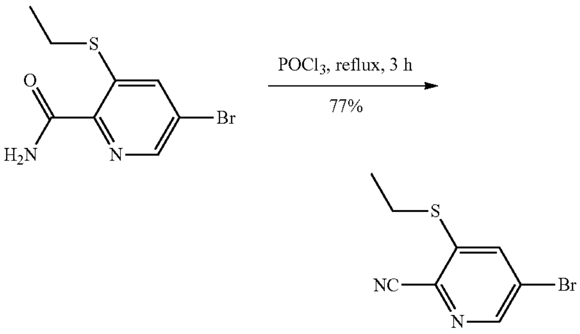

Into a 500-mL round-bottom flask, was placed 5-bromo-3-(ethylsulfanyl)pyridine-2-carboxamide (7.0 g, 26.8 mmol, 1.0 equiv), $POCl_3$ (140 mL). The resulting solution was heated to reflux for 3 hr in an oil bath. The reaction mixture was cooled to room temperature. The resulting mixture was concentrated. The pH value of the solution was adjusted to 8 with saturated aqueous $NaHCO_3$. The resulting solution was extracted with 3×600 mL of ethyl acetate and the organic layers combined and concentrated. The residue was applied onto a silica gel column with ethyl acetate/petroleum ether (1/4). This resulted in 5.0 g (77%) of 5-bromo-3-(ethylsulfanyl)pyridine-2-carbonitrile as a brown solid.

Synthesis of 5-bromo-3-(ethylsulfanyl)-N-hydroxy-pyridine-2-carboximidamide

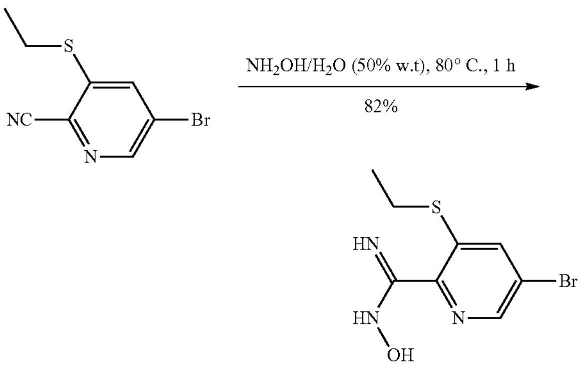

Into a 100-mL round-bottom flask, was placed 5-bromo-3-(ethylsulfanyl)pyridine-2-carbonitrile (3.0 g, 12.3 mmol, 1.0 equiv), $NH_2OH$ (50% in water) (40 mL). The resulting solution was stirred for 1 hr at 80° C. in an oil bath. The reaction mixture was cooled to room temperature. The resulting mixture was concentrated. The crude product was purified by Flash-Prep-HPLC with the following conditions (IntelFlash-1): Column, C1 8 silica gel; mobile phase, $CH_3CN/H_2O$=80%; Detector, 254&220 nm. This resulted in 2.8 g (82%) of 5-bromo-3-(ethylsulfanyl)-N-hydroxypyridine-2-carboximidamide as a white solid.

Synthesis of [5-bromo-3-(ethylsulfanyl)pyridin-2-yl] methanimidamido acetate

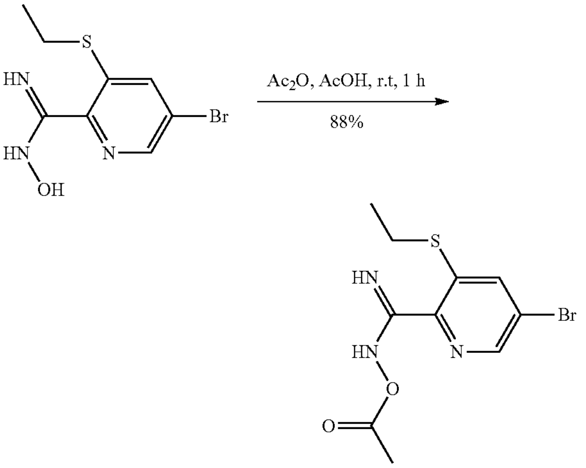

Into a 50-mL round-bottom flask, was placed 5-bromo-3-(ethylsulfanyl)-N-hydroxypyridine-2-carboximidamide (2.75 g, 9.96 mmol, 1.0 equiv), AcOH (27 mL), $Ac_2O$ (5.1 g, 50 mmol, 5.0 equiv). The resulting solution was stirred for 1 hr at room temperature. The pH value of the solution was adjusted to 8 with saturated aqueous $NaHCO_3$. The resulting solution was extracted with 3×150 mL of ethyl acetate and the organic layers combined and concentrated. The residue was applied onto a silica gel column with ethyl acetate/petroleum ether (1/1). This resulted in 2.8 g (88%) of [5-bromo-3-(ethylsulfanyl)pyridin-2-yl]methanimidamido acetate as a white solid.

Synthesis of 5-bromo-3-(ethylsulfanyl)pyridine-2-carboximidamide

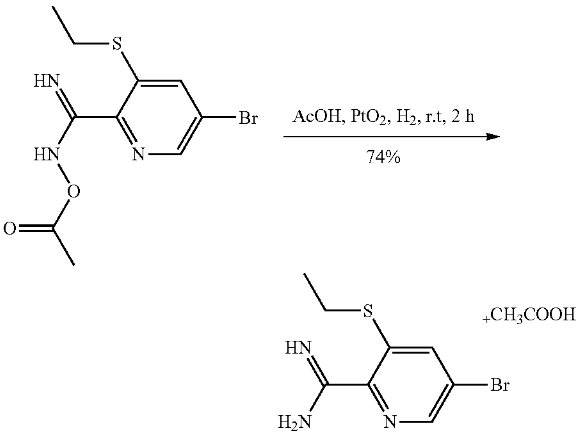

Into a 250-mL round-bottom flask, was placed [5-bromo-3-(ethylsulfanyl)pyridin-2-yl]methanimidamido acetate (2.70 g, 8.5 mmol, 1.0 equiv), AcOH (100 mL), $PtO_2$ (270 mg). The flask was evacuated and flushed three times with nitrogen, followed by flushing with hydrogen. The mixture was stirred 2h at room temperature under an atmosphere of hydrogen (balloon). The solids were filtered out. The resulting mixture was concentrated. The crude product was re-crystallized from EA/PE in the ratio of 1/10(50 mL). This resulted in 2.0 g (74%) of 5-bromo-3-(ethylsulfanyl)pyridine-2-carboximidamide; acetic acid as a yellow solid.

Synthesis of 5-bromo-3-(ethylsulfanyl)-2-[4-[4-(trifluoromethyl)pyridin-2-yl]-3H-imidazol-2-yl]pyridine

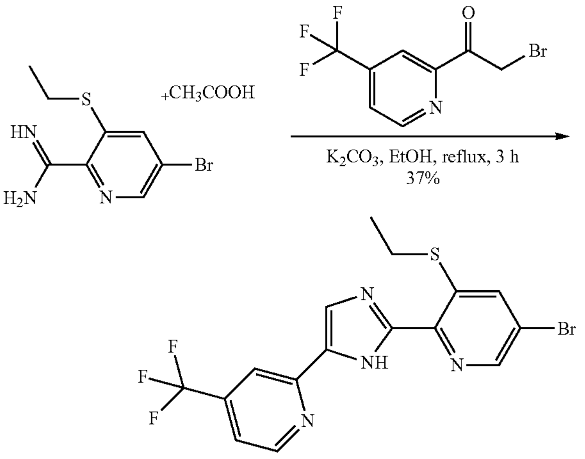

Into a 50-mL round-bottom flask, was placed 5-bromo-3-(ethylsulfanyl)pyridine-2-carboximidamide; acetic acid (400 mg, 1.25 mmol, 1.0 equiv), EtOH (20 mL, 344 mmol, 275 equiv), 2-bromo-1-[4-(trifluoromethyl)pyridin-2-yl]ethanone (368 mg, 1.4 mmol, 1.1 equiv), $K_2CO_3$ (173 mg, 1.25 mmol, 1.0 equiv). The resulting solution was heated to reflux for 3 hr in an oil bath. Then additional 2-bromo-1-[4-(trifluoromethyl)pyridin-2-yl]ethanone (200 mg, 0.75 mmol, 0.6 equiv) was added. The resulting solution was heated to reflux for 3 hr in an oil bath. The reaction mixture was cooled to room temperature. The resulting mixture was concentrated. The resulting solution was diluted with 100 mL of $H_2O$. The resulting solution was extracted with 3×80 mL of ethyl acetate and the organic layers combined and concentrated. The residue was applied onto a silica gel column with ethyl acetate/petroleum ether (1/4-1/2). This resulted in 95 mg (37%) of 5-bromo-3-(ethylsulfanyl)-2-[4-[4-(trifluoromethyl)pyridin-2-yl]-3H-imidazol-2-yl]pyridine as a brown solid.

Synthesis of 5-bromo-3-(ethylsulfanyl)-2-[1-methyl-5-[4-(trifluoromethyl)pyridin-2-yl]imidazol-2-yl]pyridine

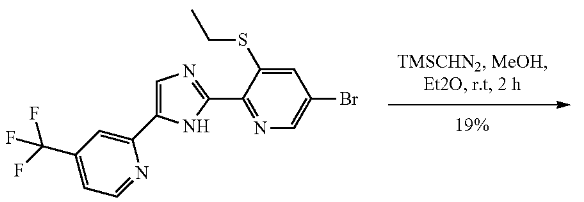

-continued

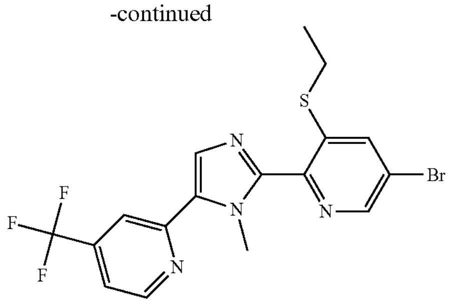

Into a 100-mL round-bottom flask, was placed 5-bromo-3-(ethylsulfanyl)-2-[4-[4-(trifluoromethyl)pyridin-2-yl]-3H-imidazol-2-yl]pyridine (650 mg, 1.5 mmol, 1.0 equiv), MeOH (16 mL), $Et_2O$ (6 mL). This was followed by the addition of $TMSCHN_2$ (11.4 mL, 22.8 mmol, 15 equiv) dropwise with stirring at 0° C. The resulting solution was stirred for 2 hr at room temperature. The resulting mixture was concentrated. The crude product was purified by Flash-Prep-HPLC with the following conditions (IntelFlash-1): Column, C18 silica gel; mobile phase, $CH_3CN$/0.05% TFA=65%; Detector, 254&220 nm. This resulted in 130 mg (19%) of 5-bromo-3-(ethylsulfanyl)-2-[1-methyl-5-[4-(trifluoromethyl)pyridin-2-yl]imidazol-2-yl]pyridine as brown oil.

Synthesis of 5-(4-cyclopropylphenyl)-3-(ethylsulfanyl)-2-[1-methyl-5-[4-(trifluoromethyl)pyridin-2-yl]imidazol-2-yl]pyridine

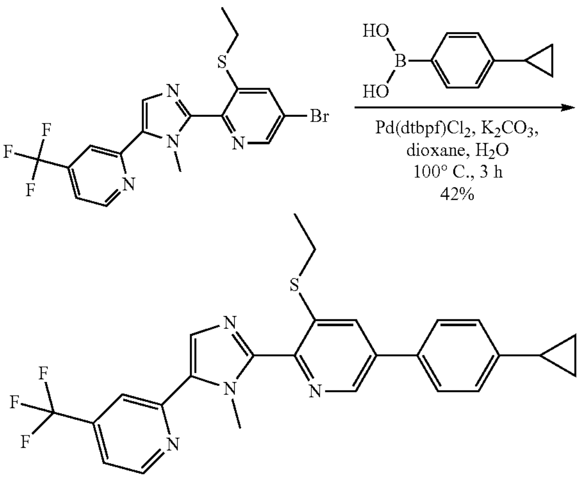

Into a 40-mL vial purged and maintained with an inert atmosphere of nitrogen, was placed 5-bromo-3-(ethylsulfanyl)-2-[1-methyl-5-[4-(trifluoromethyl)pyridin-2-yl]imidazol-2-yl]pyridine (60 mg, 0.14 mmol, 1.0 equiv), dioxane (3 mL), 4-cyclopropylphenylboronic acid (33 mg, 0.2 mmol, 1.5 equiv), $Pd(dtbpf)Cl_2$ (9.0 mg, 0.01 mmol, 0.1 equiv), $K_2CO_3$ (37 mg, 0.27 mmol, 2.0 equiv), $H_2O$ (0.6 mL). The resulting solution was stirred for 3 hr at 100° C. in an oil bath. The resulting mixture was concentrated. The residue was applied onto a silica gel column with ethyl acetate/petroleum ether (1/3). The collected fractions were combined and concentrated. The crude product was purified by Flash-Prep-HPLC with the following conditions (IntelFlash- 1): Column, C18 silica gel; mobile phase, $CH_3CN$/0.05% $NH_3 \cdot H_2O$=95%; Detector, 254&220 nm. This resulted in 27 mg (42%) of 5-(4-cyclopropylphenyl)-3-(ethylsulfanyl)-2-[I-methyl-5-[4-(trifluoromethyl)pyridin-2-yl]imidazol-2-yl] pyridine as brown oil.

Synthesis of 5-(4-cyclopropylphenyl)-3-(ethanesulfonyl)-2-[1-methyl-5-[4-(trifluoromethyl)pyridin-2-yl]imidazol-2-yl]pyridine

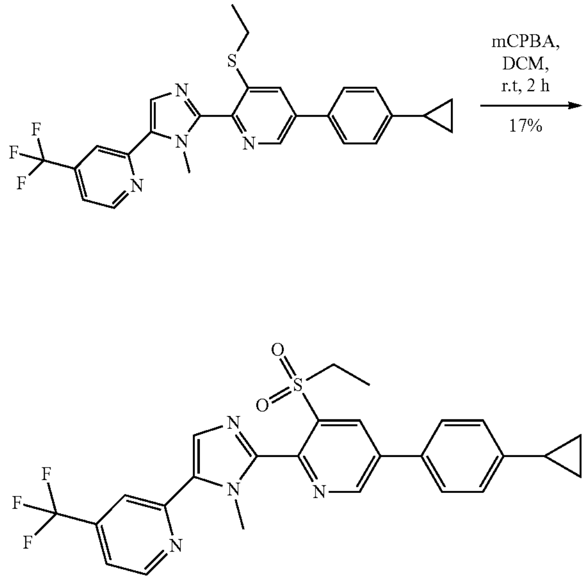

54

Into a 8-mL vial, was placed 5-(4-cyclopropylphenyl)-3-(ethylsulfanyl)-2-[I-methyl-5-[4-(trifluoromethyl)pyridin-2-yl]imidazol-2-yl]pyridine (22 mg, 0.05 mmol, 1.0 equiv), DCM (1.5 mL). This was followed by the addition of mCPBA (23 mg, 0.11 mmol, 2.5 equiv, 85%), in portions at 0° C. The resulting solution was stirred for 2 hr at room temperature. The pH value of the solution was adjusted to 8 with saturated aqueous $NaHCO_3$. The resulting solution was extracted with 3x 10 mL of dichloromethane and the organic layers combined and concentrated. The crude product was purified by Flash-Prep-HPLC with the following conditions (IntelFlash-1): Column, C18 silica gel; mobile phase, $CH_3CN$/0.05% TFA=65%; Detector, 254&220 nm. The product was obtained and concentrated. The crude product was purified by Flash-Prep-HPLC with the following conditions (IntelFlash-1): Column, C18 silica gel; mobile phase, $CH_3CN$/0.05% $NH_3 \cdot H_2O$=100%; Detector, 254&220 nm. This resulted in 3.9 mg (17%) of 5-(4-cyclopropylphenyl)-3-(ethanesulfonyl)-2-[1-methyl-5-[4-(trifluoromethyl)pyridin-2-yl]imidazol-2-yl]pyridine as a white solid.

Synthesis of Compound 55

Synthesis of 5-bromo-3-(ethylsulfanyl)-2-[1-methyl-4-[4-(trifluoromethyl)pyridin-2-yl]imidazol-2-yl] pyridine

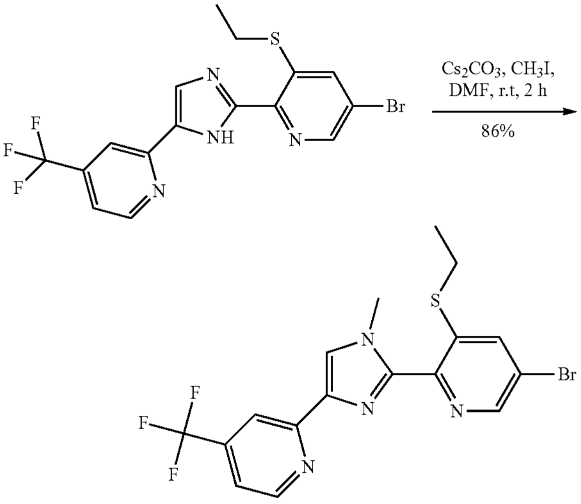

Into a 8-mL vial, was placed 5-bromo-3-(ethylsulfanyl)-2-[4-[4-(trifluoromethyl)pyridin-2-yl]-3H-imidazol-2-yl] pyridine (90 mg, 0.21 mmol, 1.0 equiv), DMF (1.0 mL), $Cs_2CO_3$ (137 mg, 0.25 mmol, 1.2 equiv, 60%), $CH_3I$ (89 mg, 0.6 mmol, 3.0 equiv). The resulting solution was stirred for 2 hr at room temperature. The crude product was purified by Flash-Prep-HPLC with the following conditions (IntelFlash-1): Column, C18 silica gel; mobile phase, $CH_3CN$/0.05% $NH3 \cdot H_2O$=100%; Detector, 254&220 nm. This resulted in 80 mg (86%) of 5-bromo-3-(ethylsulfanyl)-2-[1-methyl-4-[4-(trifluoromethyl)pyridin-2-yl]imidazol-2-yl]pyridine as a brown solid.

Synthesis of 5-(4-cyclopropylphenyl)-3-(ethylsulfanyl)-2-[1-methyl-4-[4-(trifluoromethyl)pyridin-2-yl] imidazol-2-yl]pyridine

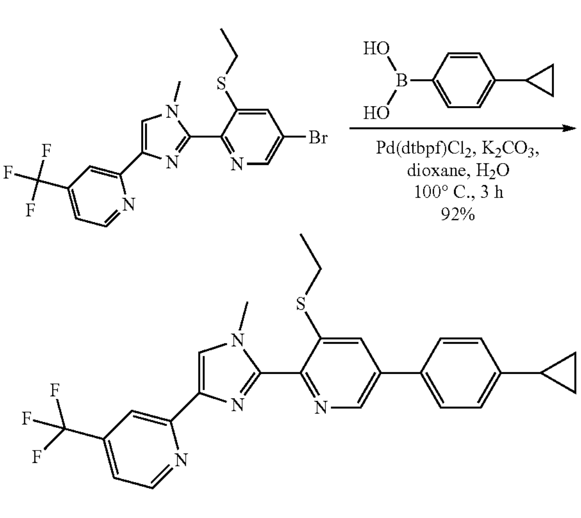

Into a 8-mL vial purged and maintained with an inert atmosphere of nitrogen, was placed 5-bromo-3-20 (ethylsulfanyl)-2-[1-methyl-4-[4-(trifluoromethyl)pyridin-2-yl]imidazol-2-yl]pyridine (80 mg, 0.2 mmol, 1.0 equiv), dioxane (2.0 mL), 4-cyclopropylphenylboronic acid (44 mg, 0.3 mmol, 1.5 equiv), Pd(dtbpf)$Cl_2$ (12 mg, 0.02 mmol, 0.1 equiv), $K2CO_3$ (50 mg, 0.4 mmol, 2.0 equiv), $H_2O$ (0.4 mL). The resulting solution was stirred for 3 hr at 100° C. in an oil bath. The resulting solution was diluted with 10 mL of $H_2O$. The resulting solution was extracted with 3×6 mL of ethyl acetate and the organic layers combined and concentrated. The residue was applied onto a silica gel column with THF/PE (1/4-1/3). This resulted in 80 mg (92%) of 5-(4-cyclopropylphenyl)-3-(ethylsulfanyl)-2-[1-methyl-4-[4-(trifluoromethyl)pyridin-2-yl]imidazol-2-yl]pyridine as a brown solid.

Synthesis of 5-(4-cyclopropylphenyl)-3-(ethanesulfonyl)-2-[1-methyl-4-[4-(trifluoromethyl)pyridin-2-yl]imidazol-2-yl]pyridine

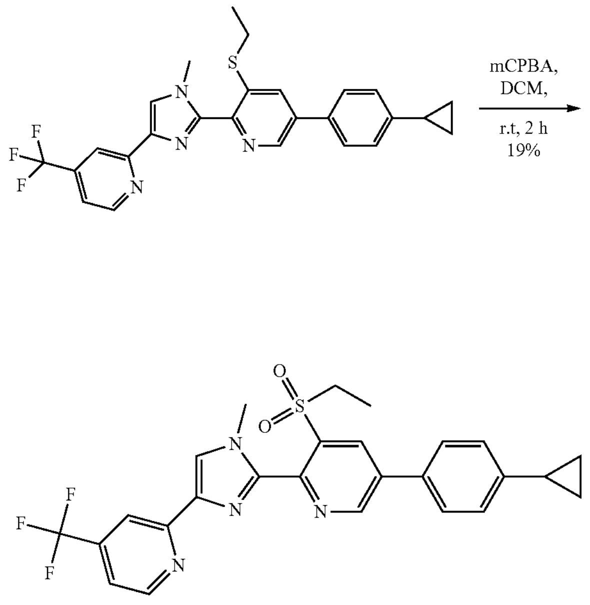

55

Into a 8-mL sealed tube, was placed 5-(4-cyclopropylphenyl)-3-(ethylsulfanyl)-2-[1-methyl-4-[4-(trifluoromethyl)pyridin-2-yl]imidazol-2-yl]pyridine (75 mg, 0.16 mmol, 1.0 equiv), DCM (2.0 mL), mCPBA (79 mg, 0.4 mmol, 2.5 equiv, 85%). The resulting solution was stirred for 2 hr at room temperature. The resulting solution was diluted with 10 mL of saturated aqueous $NaHCO_3$. The resulting solution was stirred for 0.5 hr at room temperature. The resulting solution was extracted with 2×10 mL of dichloromethane and the organic layers combined and concentrated. The crude product was purified by Flash-Prep-HPLC with the following conditions (IntelFlash-1): Column, C18 silica gel; mobile phase, $CH_3CN$/0.05% NH3·$H_2O$=80% increasing to $CH_3CN$/0.05% NH3·$H_2O$=85%; Detector, 254&220 nm. This resulted in 16 mg (19%) of 5-(4-cyclopropylphenyl)-3-(ethanesulfonyl)-2-[I-methyl-4-[4-(trifluoromethyl)pyridin-2-yl]imidazol-2-yl]pyridine as a light yellow solid.

Synthesis of Compound 56

Synthesis of 5-bromo-3-(ethylsulfanyl)pyridine-2-carbonyl chloride

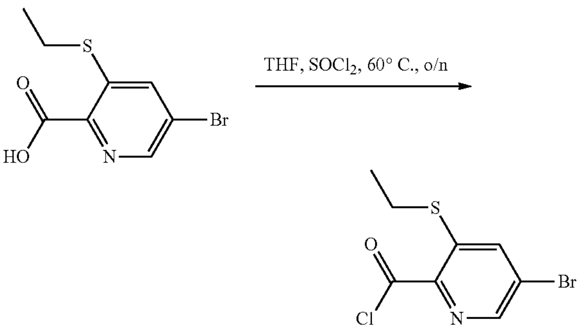

Into a 500-mL round-bottom flask, was placed 5-bromo-3-(ethylsulfanyl)pyridine-2-carboxylic acid (10 g, 38 mmol, 1.0 equiv), THF (200 mL), $SOCl_2$ (5.5 g, 46 mmol, 1.2 equiv). The resulting solution was stirred overnight at 60 degrees C. The resulting mixture was concentrated. The product was used in the next step directly without further purification.

Synthesis of 5-bromo-3-(ethylsulfanyl)-N—methylpyridine-2-carboxamide

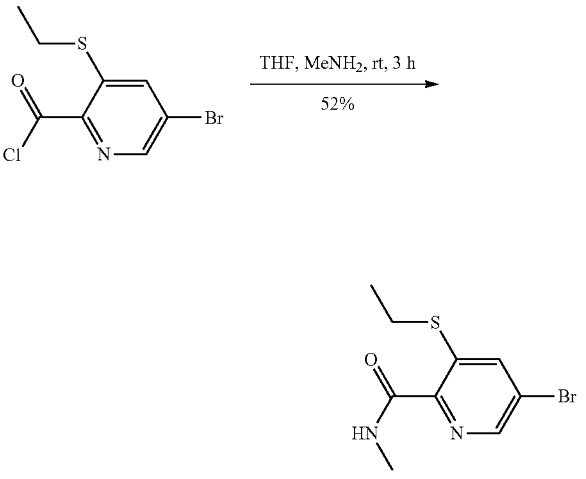

Into a 500-mL round-bottom flask, was placed 5-bromo-3-(ethylthio)picolinoyl chloride (10 g, 38 mmol, 1.0 equiv), THF (200 mL), DIEA (7.4 g, 57 mmol, 1.5 equiv), dimethylamine (2 M in THF) (23 mL, 46 mmol). The resulting solution was stirred for 3 hr at room temperature. The resulting mixture was washed with 200 ml of NaHCO3 and 200 mL of brine. The organic layer was dried over anhydrous sodium sulfate and concentrated. The residue was applied onto a silica gel column with ethyl acetate/petroleum ether (1:4). This resulted in 5.5 g (52%) of 5-bromo-3-(ethylsulfanyl)-N—methylpyridine-2-carboxamide as a yellow solid.

Synthesis of 5-bromo-3-(ethylsulfanyl)-N-methylpyridine-2-carbothioamide

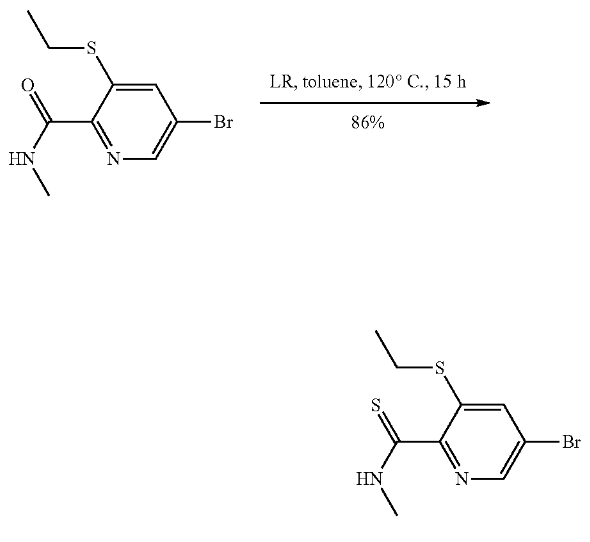

Into a 500-mL round-bottom flask, was placed 5-bromo-3-(ethylsulfanyl)-N-methylpyridine-2-carboxamide (5.5 g, 20 mmol, 1.0 equiv), toluene (55 mL), Lawesson's Reagent (4.9 g, 12 mmol, 0.6 equiv). The resulting solution was stirred for 15 hr at 120 degrees C. The resulting mixture was concentrated. The residue was applied onto a silica gel column with ethyl acetate/petroleum ether (1:4). This resulted in 5.0 g (86%) of 5-bromo-3-(ethylsulfanyl)-N-methylpyridine-2-carbothioamide as yellow oil.

Synthesis of (E)-[[5-bromo-3-(ethylsulfanyl)pyridin-2-yl](methylsulfanyl)methylidene]

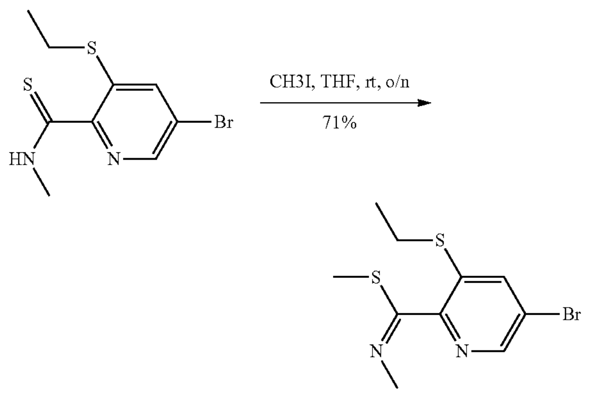

Into a 20-mL vial, was placed 5-bromo-3-(ethylsulfanyl)-N-methylpyridine-2-carbothioamide (5.0 g, 17 mmol, 1.0 equiv), THF (20 mL), $CH_3I$ (24 g, 172 mmol, 10 equiv). The resulting solution was stirred overnight at room temperature. The resulting mixture was concentrated. The residue was applied onto a silica gel column with ethyl acetate/petroleum ether (1:1). This resulted in 3.7 g (71%) of (E)-[[5-bromo-3-(ethylsulfanyl)pyridin-2-yl](methylsulfanyl)methylidene](methyl)amine as yellow oil.

Synthesis of (Z)—N'-amino-5-bromo-3-(ethylsulfanyl)-N-methylpyridine-2-carboximidamide

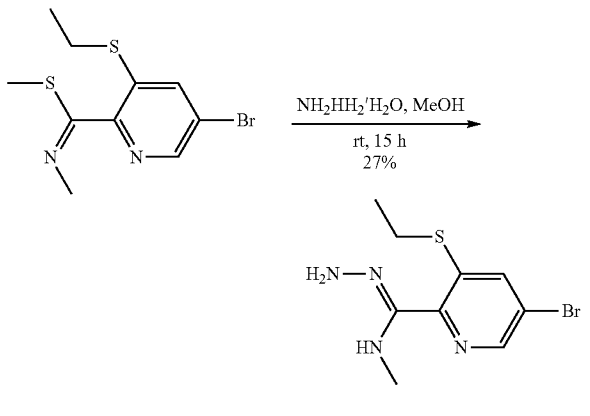

Into a 100-mL round-bottom flask, was placed (E)-[[5-bromo-3-(ethylsulfanyl)pyridin-2-yl](methylsulfanyl)methylidene](methyl)amine (3.5 g, 11.5 mmol, 1.0 equiv), MeOH (15 mL), $NH_2NH_2$—$H_2O$ (0.6 g, 11.5 mmol, 1.0 equiv, 98%). The resulting solution was stirred for 15 hr at room temperature. The crude product was purified by Flash-Prep-HPLC with the following conditions (IntelFlash-1): Column C18, silica gel; mobile phase, ACN/$H_2O$=5%-50%. This resulted in 0.90 g (27%) of (Z)—N'-amino-5-bromo-3-(ethylsulfanyl)-N-methylpyridine-2-carboximidamide as a yellow solid.

Synthesis of N'—[(1Z)-[5-bromo-3-(ethylsulfanyl)pyridin-2-yl](methylamino)methylidene]-3,3,4,4,4-pentafluorobutanehydrazide

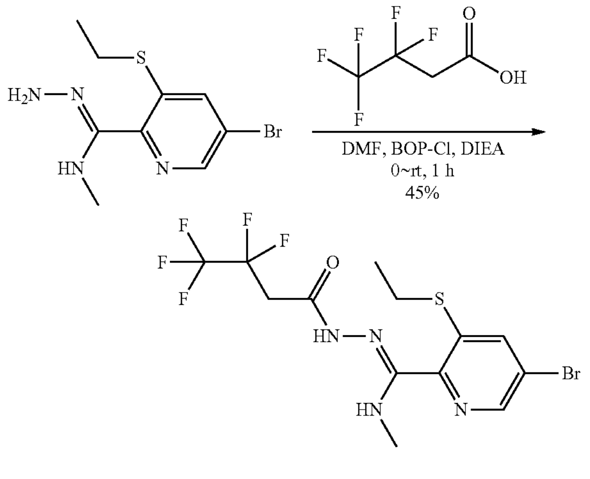

Into a 8-mL vial, was placed (Z)—N'-amino-5-bromo-3-(ethylsulfanyl)-N-methylpyridine-2-carboximidamide 5 (200 mg, 0.7 mmol, 1.0 equiv), 3,3,4,4,4-pentafluorobutanoic acid (410 mg, 1.4 mmol, 2.0 equiv, 60%), DMF (2.0 mL). The resulting solution was cooled to 0 degrees C. To above BOP—Cl (353 mg, 1.4 mmol, 2.0 equiv), DIEA (179 mg, 1.4 mmol, 2.0 equiv) was added. The resulting solution was stirred for 2 hr at room temperature. The resulting solution was diluted with 10 mL of EA. The resulting mixture was washed with 2×10 mL of brine. The mixture was dried over anhydrous sodium sulfate and concentrated. This resulted in 140 mg (45%) of N'—[(1Z)-[5-bromo-3-(ethylsulfanyl)pyridin-2-yl](methylamino)methylidene]-3,3,4,4,4-pentafluorobutanehydrazide as a yellow oil.

Synthesis of 5-bromo-3-(ethylsulfanyl)-2-[4-methyl-5-(2,2,3,3,3-pentafluoropropyl)-1,2,4-triazol-3-yl]pyridine

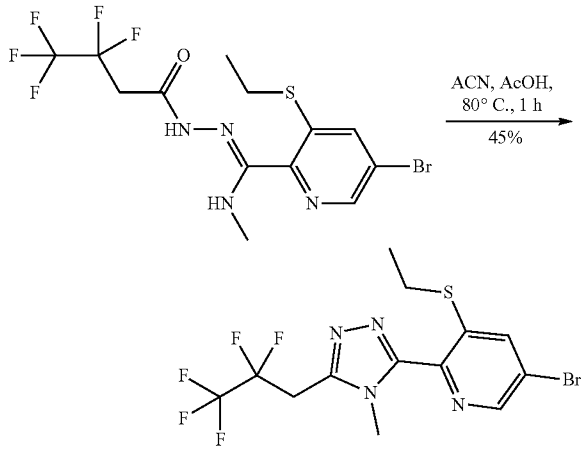

Into a 8-mL vial, was placed N'—[(1Z)-[5-bromo-3-(ethylsulfanyl)pyridin-2-yl](methylamino)methylidene]-3,3,4,4,4-pentafluorobutanehydrazide (140 mg, 0.3 mmol, 1.0 equiv), ACN (2.0 mL), AcOH (1.9 mg, 0.03 mmol, 0.1 equiv). The resulting solution was stirred for 1 hr at 80 degrees C. The resulting mixture was concentrated. The residue was applied onto a silica gel column with ethyl acetate/petroleum ether (1:1). This resulted in 60 mg (45%) of 5-bromo-3-(ethylsulfanyl)-2-[4-methyl-5-(2,2,3,3,3-pentafluoropropyl)-1,2,4-triazol-3-yl]pyridine as a yellow solid.

Synthesis of 5-(4-cyclopropylphenyl)-3-(ethylsulfanyl)-2-[4-methyl-5-(2,2,3,3,3-pentafluoropropyl)-1,2,4-triazol-3-yl]pyridine

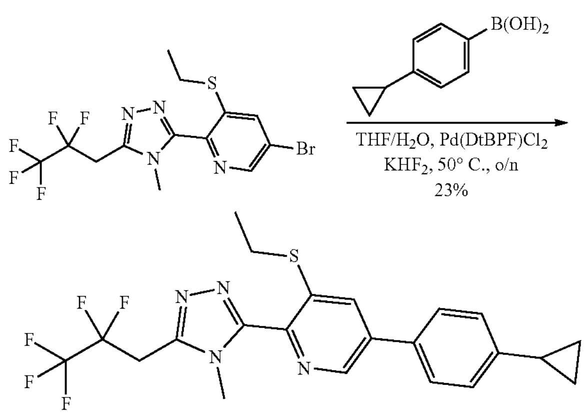

Into a 8-mL vial, was placed 5-bromo-3-(ethylsulfanyl)-2-[4-methyl-5-(2,2,3,3,3-pentafluoropropyl)-1,2,4-triazol-3-yl]pyridine (60 mg, 0.14 mmol, 1.0 equiv), THF (2.0 mL), $H_2O$ (0.20 mL), 4-cyclopropylphenylboronic acid (68 mg, 0.4 mmol, 3.0 equiv), $KHF_2$ (22 mg, 0.27 mmol, 2.0 equiv), Pd(DtBPF)$C_2$ (9 mg, 0.01 mmol, 0.1 equiv). The resulting solution was stirred overnight at 50 degrees C. The resulting mixture was concentrated. The residue was applied onto a silica gel column with ethyl acetate/petroleum ether (1:1). This resulted in 15 mg (23%) of 5-(4-cyclopropylphenyl)-3-(ethylsulfanyl)-2-[4-methyl-5-(2,2,3,3,3-pentafluoropropyl)-1,2,4-triazol-3-yl]pyridine as a yellow solid.

Synthesis of 5-(4-cyclopropylphenyl)-3-(ethanesulfonyl)-2-[4-methyl-5-(2,2,3,3,3-pentafluoropropyl)-1,2,4-triazol-3-yl]pyridine

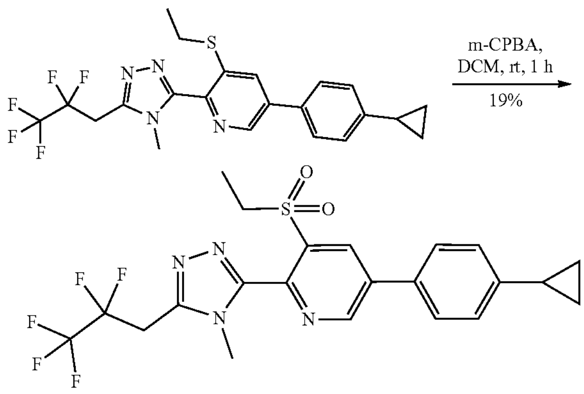

56

Into a 8-mL vial, was placed 5-(4-cyclopropylphenyl)-3-(ethylsulfanyl)-2-[4-methyl-5-(2,2,3,3,3-pentafluoropropyl)-1,2,4-triazol-3-yl]pyridine (15 mg, 0.03 mmol, 1.0 equiv), DCM (2.0 mL), m-CPBA (I1 mg, 0.06 mmol, 2.0 equiv). The resulting solution was stirred for 1 hr at room temperature. The resulting mixture was concentrated. The crude product was purified by Flash-Prep-HPLC with the following conditions (IntelFlash-1): Column C18, silica gel; mobile phase, ACN/$H_2O$=30%-100%; Detector 254 nm. This resulted in 3.1 mg (19%) of 5-(4-cyclopropylphenyl)-3-(ethanesulfonyl)-2-[4-methyl-5-(2,2,3,3,3-pentafluoropropyl)-1,2,4-triazol-3-yl]pyridine as an off-white solid.

Synthesis of Compound 57

Synthesis of 5-(4-cyclopropylphenyl)-3-(ethylsulfanyl)-2-[4-methyl-5-(2,2,3,3,3-pentafluoropropyl)-1,2,4-triazol-3-yl]pyridine

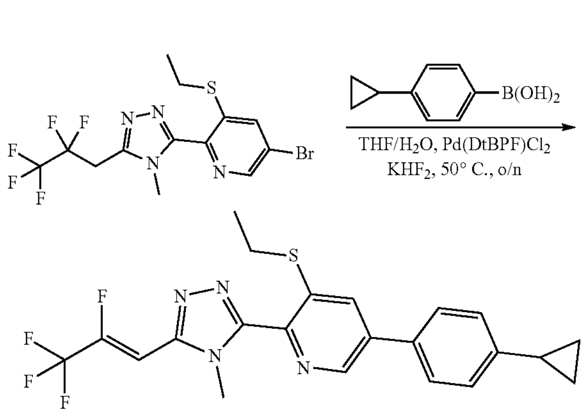

Into a 8-mL vial, was placed 5-bromo-3-(ethylsulfanyl)-2-[4-methyl-5-(2,2,3,3,3-pentafluoropropyl)-1,2,4-triazol-3-yl]pyridine (60 mg, 0.14 mmol, 1.0 equiv), THF (2.0 mL), $H_2O$ (0.2 mL), 4-cyclopropylphenylboronic acid (68 mg, 0.4 mmol, 3.0 equiv), $KHF_2$ (22 mg, 0.28 mmol, 2.0 equiv), $Pd(DtBPF)Cl_2$ (9.0 mg, 0.014 mmol, 0.1 equiv). The resulting solution was stirred overnight at 50 degrees C. The resulting mixture was concentrated. The residue was applied onto a silica gel column with ethyl acetate/petroleum ether (1:1). This resulted in 5 mg of (Z)-5-(4-cyclopropylphenyl)-3-(ethylthio)-2-(4-methyl-5-(2,3,3,3-tetrafluoroprop-1-en-1-yl)-4H-1,2,4-triazol-3-yl)pyridine as a yellow solid.

Synthesis of 5-(4-cyclopropylphenyl)-3-(ethanesulfonyl)-2-[4-methyl-5-(2,2,3,3,3-pentafluoropropyl)-1,2,4-triazol-3-yl]pyridine

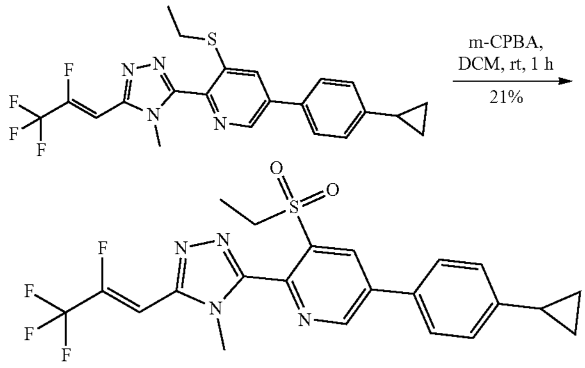

57

Into a 8-mL vial, was placed 5-(4-cyclopropylphenyl)-3-(ethylsulfanyl)-2-[4-methyl-5-[(1Z)-2,3,3,3-tetrafluoroprop-1-en-1-yl]-1,2,4-triazol-3-yl]pyridine(5.0 mg, 0.01 mmol, 1.0 equiv), DCM (1.0 mL), m-CPBA (3.9 mg, 0.02 mmol, 2.0 equiv). The resulting solution was stirred for 1 hr at room temperature. The resulting mixture was concentrated. The crude product was purified by Flash-Prep-HPLC with the following conditions (IntelFlash-1): Column C18, silica gel; mobile phase, $ACN/H_2O$=30%-100%; Detector 254 nm. This resulted in 1.1 mg (21%) of 5-(4-cyclopropylphenyl)-3-(ethanesulfonyl)-2-[4-methyl-5-(2,2,3,3,3-pentafluoropropyl)-1,2,4-triazol-3-yl]pyridine as an off-white solid.

Synthesis of Compound 52

Specifically, the following compounds of formula (I) can be synthesized by adopting the subsequent scheme of Compound 52 by someone who is skilled in the art and employing the starting material described vide supra: 127, 128

Synthesis of 2-bromo-5-(2,2,3,3,3-pentafluoropropoxy)pyridine

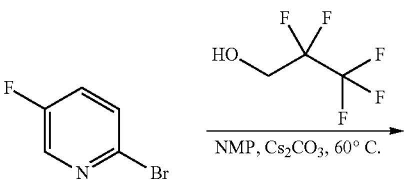

-continued

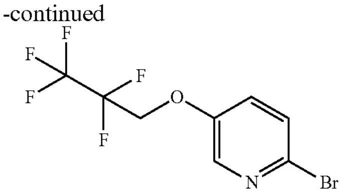

Into a 250-mL round-bottom flask purged and maintained with an inert atmosphere of nitrogen, was placed 2-bromo-5-fluoropyridine (3.0 g, 17 mmol, 1.0 equiv), pentafluoro-1-propanol (5.1 g, 34 mmol, 2.0 equiv), NMP (30 mL), $Cs_2CO_3$ (16 g, 49 mmol, 2.9 equiv). The resulting solution was stirred for 2 hr at 60 degrees C. The reaction mixture was cooled to room temperature. The resulting solution was diluted with 150 mL of $Et_2O$. The reaction was poured into 300 mL of water. The organic mixture was dried over anhydrous sodium sulfate and concentrated under vacuum. This resulted in 1.7 g (33%) of 2-bromo-5-(2,2,3,3,3-pentafluoropropoxy)pyridine as a colorless solid.

Synthesis of 5-(2,2,3,3,3-pentafluoropropoxy)-2-(trimethylstannyl)pyridine

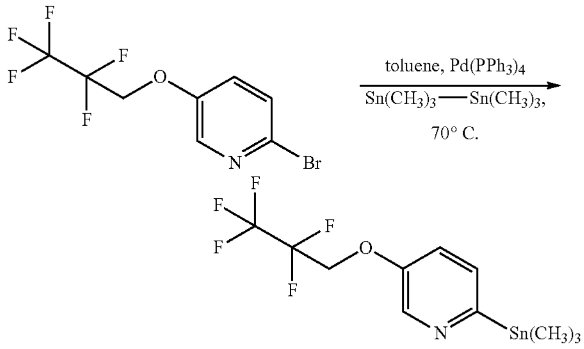

Into a 20-mL vial purged and maintained with an inert atmosphere of nitrogen, was placed 2-bromo-5-(2,2,3,3,3-pentafluoropropoxy)pyridine (500 mg, 1.6 mmol, 1.0 equiv), hexamethyldistannane (1.6 g, 4.9 mmol, 3.0 equiv), toluene (5.0 mL), $Pd(PPh_3)_4$(189 mg, 0.16 mmol, 0.1 equiv). The resulting solution was stirred for 2 hr at 70 degrees C. The reaction mixture was cooled to room temperature. This resulted in 500 mg (crude) of 5-(2,2,3,3,3-pentafluoropropoxy)-2-(trimethylstannyl)pyridine as a black solid.

Synthesis of 2-chloro-5-(4-cyclopropylphenyl)-3-nitropyridine

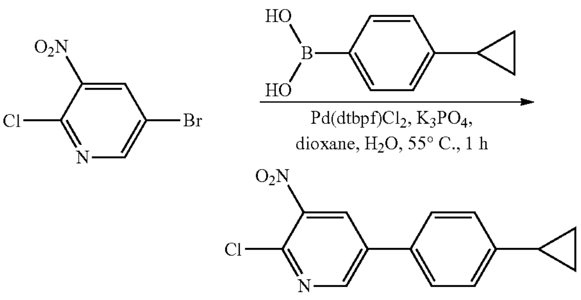

Into a 250-mL round-bottom flask purged and maintained with an inert atmosphere of nitrogen, was placed 5-bromo-2-chloro-3-nitropyridine (2.0 g, 8.4 mmol, 1.0 equiv), 4-cyclopropylphenylboronic acid (1.5 g, 9.3 mmol, 1.1 equiv), $Pd(DtBPF)Cl_2$ (0.55 g, 0.84 mmol, 0.1 equiv), $K_3PO_4$ (3.6 g, 17 mmol, 2.0 equiv), dioxane (40 mL), $H_2O$ (4.0 mL). The resulting solution was stirred for 1 hr at 55 degrees C. The reaction mixture was cooled. The solids were filtered out. The filtrate was concentrated. The crude product was purified by Flash-Prep-HPLC 0.I % $NH_3{\cdot}H_2O$:MeCN=55% increasing to 0.I % NH3$\cdot H_2O$:MeCN=100% within 9 min. This resulted in 1.6 g (69%) of 2-chloro-5-(4-cyclopropylphenyl)-3-nitropyridine as a yellow solid.

Synthesis of 5-(4-cyclopropylphenyl)-3-nitro-5'-(2,2,3,3,3-pentafluoropropoxy)-2,2'-bipyridine

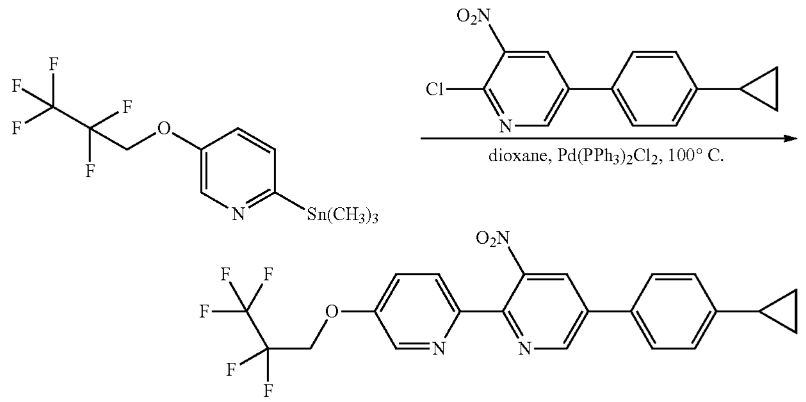

Into a 100-mL round-bottom flask purged and maintained with an inert atmosphere of nitrogen, was placed 5-(2,2,3,3,3-pentafluoropropoxy)-2-(trimethylstannyl)pyridine (500 mg, 1.3 mmol, 1.0 equiv), 2-chloro-5-(4-cyclopropylphenyl)-3-nitropyridine (1.1 g, 4.0 mmol, 3.1 equiv), dioxane (10 mL), CuI (24 mg, 0.13 mmol, 0.1 equiv), $Pd(PPh_3)2Cl_2$ (90 mg, 0.13 mmol, 0.1 equiv). The resulting solution was stirred for 1 hr at 100 degrees C. The reaction mixture was cooled to room temperature. The resulting mixture was concentrated under vacuum. The crude product was purified by Flash-Prep-HPLC with the following conditions (Intel-Flash-1): Column, $C_{18}$ silica gel; mobile phase, $CH_3CN$:$H_2O$=0% increasing to $CH_3CN$:$H_2O$=80% within 30 min. This resulted in 80 mg (13%) of 5-(4-cyclopropylphenyl)-3-nitro-5'-(2,2,3,3,3-pentafluoropropoxy)-2,2'-bipyridine as a white solid.

Synthesis of 5-(4-cyclopropylphenyl)-3-(ethylsulfanyl)-5'-(2,2,3,3,3-pentafluoropropoxy)-2,2'-bipyridine

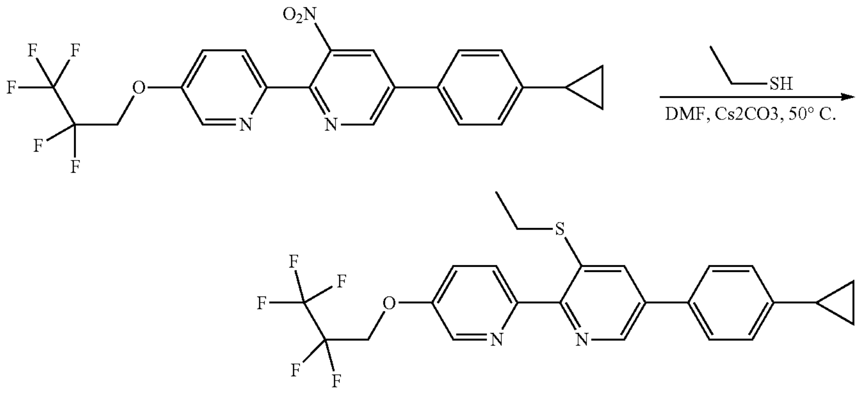

Into a 20-mL vial, was placed 5-(4-cyclopropylphenyl)-3-nitro-5 (100 mg, 0.22 mmol, 1.0 equiv), ethanethiol (27 mg, 0.43 mmol, 2.0 equiv), DMF (5.0 mL), $Cs_2CO_3$ (210 mg, 0.65 mmol, 3.0 equiv). The resulting solution was stirred for 1.5 hr at 50 degrees C. The reaction mixture was cooled to room temperature. The solids were filtered out. The filtrate was purified by Flash-Prep-HPLC with the following conditions (IntelFlash-1): Column, $C_{18}$ silica gel; mobile phase, $CH_3CN$:$H_2O$=0% increasing to $CH_3CN$:$H_2O$=60% within 20 min. This resulted in 25 mg (24%) of 5-(4-cyclopropylphenyl)-3-(ethylsulfanyl)-5'-(2,2,3,3,3-pentafluoropropoxy)-2,2'-bipyridine as a white solid.

Synthesis of 5-(4-cyclopropylphenyl)-3-(ethanesulfonyl)-5'-(2,2,3,3,3-pentafluoropropoxy)-2,2'-bipyridine

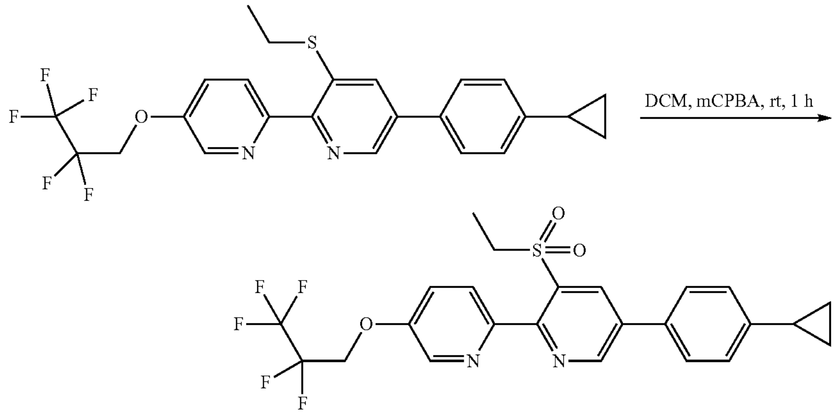

52

Into a 50-mL round-bottom flask, was placed 5-(4-cyclopropylphenyl)-3-(ethylsulfanyl)-5 (25.00 mg, 0.052 mmol, 1.00 equiv), DCM (10.00 mL). This was followed by the addition of mCPBA (31.00 mg, 0.153 mmol, 2.93 equiv, 85%) at 0 degrees C. The resulting solution was stirred for 1 hr at room temperature. The resulting mixture was concentrated under vacuum. The crude product was purified by Flash-Prep-HPLC with the following conditions (IntelFlash-1): Column, C18 silica gel; mobile phase, $CH_3CN$:$H_2O$=0% increasing to $CH_3CN$:$H_2O$=70% within 20 min. This resulted in 7.4 mg (27.75%) of 5-(4-cyclopropylphenyl)-3-(ethanesulfonyl)-5'-(2,2,3,3,3-pentafluoropropoxy)-2,2'-bipyridine as a white solid.

Synthesis of Compound 92

Synthesis of 5-(ethanesulfonyl)-6-[4-ethyl-6-(trifluoromethyl)pyrrolo[3,2-b]pyridin-2-yl]pyridine-3-carbonitrile -continued

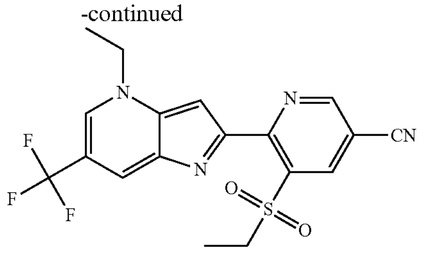

Into a 40-mL vial purged and maintained with an inert atmosphere of nitrogen, was placed 5-bromo-3-(ethanesulfonyl)-2-[4-ethyl-6-(trifluoromethyl)pyrrolo[3,2-b]pyridin-2-yl]pyridine (2.0 g, 4.3 mmol, 1.0 equiv), $Zn(CN)_2$ (40 mg, 0.3 mmol, 0.1 equiv), Zn (120 mg, 1.8 mmol, 0.4 equiv), Dppf (240 mg, 0.4 mmol, 0.1 equiv), $Pd_2(dba)_3$ (200 mg, 0.2 mmol, 0.05 equiv), DMA (20 mL). The resulting solution was stirred for 1.5 hr at 100 degrees C. The reaction mixture was cooled to room temperature. The reaction was then quenched by the addition of 1000 mL of $NaHCO_3$. The resulting solution was extracted with 3×100 mL of ethyl acetate and the organic layers combined and dried over anhydrous sodium sulfate and concentrated under vacuum. The residue was applied onto a silica gel column with dichloromethane/methanol (20:1). This resulted in 580 mg (33%) of 5-(ethanesulfonyl)-6-[4-ethyl-6-(trifluoromethyl)pyrrolo[3,2-b]pyridin-2-yl]pyridine-3-carbonitrile as a yellow solid.

Synthesis of 5-(ethanesulfonyl)-6-[4-ethyl-6-(trifluoromethyl)pyrrolo[3,2-b]pyridin-2-yl]pyridine-3-carboximidamide

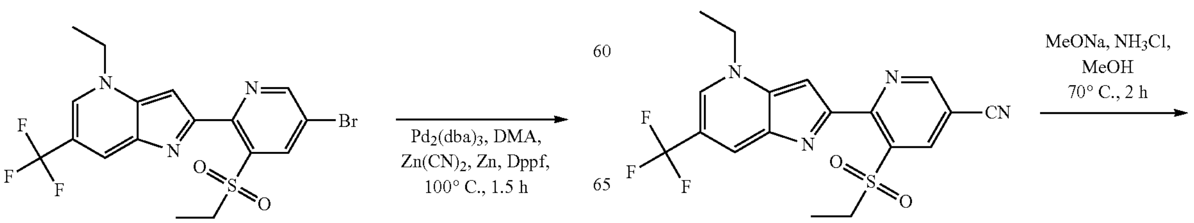

-continued

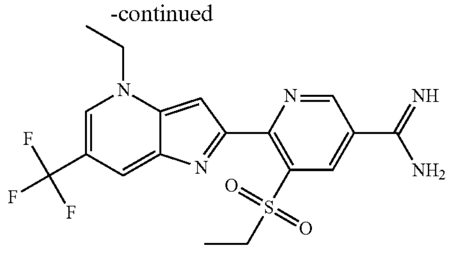

To a stirred solution/mixture of 5-(ethanesulfonyl)-6-[4-ethyl-6-(trifluoromethyl)pyrrolo[3,2-b]pyridin-2-yl]pyridine-3-carbonitrile (2 g, 4.9 mmol, 1.0 equiv) and MeONa (20 g, 111 mmol, 23 equiv) in MeOH (200 mL). The resulting mixture was stirred overnight at room temperature. The final reaction mixture was added $NH_4Cl$ (14 g, 262 mmol, 53 equiv) at 70 degrees C. The resulting mixture was stirred for 2 h at 70 degrees C. under 10 nitrogen atmosphere. The mixture was allowed to cool down to room temperature. The resulting mixture was concentrated under reduced pressure. The residue was purified by reverse flash chromatography with the following conditions: column, C18 silica gel; mobile phase, MeCN in water, 0% to 80% gradient in 40 min; detector, UV 254 nm to afford 5-(ethanesulfonyl)-6-[4-ethyl-6-(trifluoromethyl)pyrrolo[3,2-b]pyridin-2-yl]pyridine-3-carboximidamide (580 mg, 28%) as a yellow solid.

Synthesis of methyl (2E)-2-cyclopropyl-3-(dimethylamino)prop-2-enoate

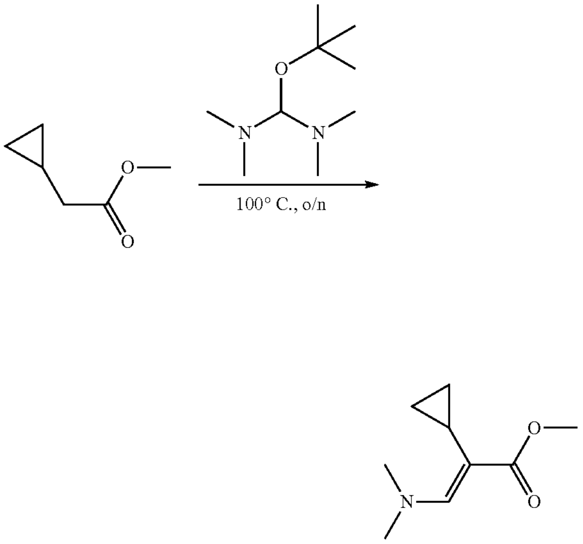

Into a 8-mL sealed tube purged and maintained with an inert atmosphere of nitrogen, was placed methyl 2-cyclopropylacetate (2.0 g, 18 mmol, 1.0 equiv), [tert-butoxy(dimethylamino)methyl]dimethylamine (3.8 g, 22 mmol, 1.25 equiv). The resulting solution was stirred overnight at 100 degrees C. The reaction mixture was cooled to room temperature. The resulting mixture was concentrated under vacuum. This resulted in 2 g (67.45%) of methyl (2E)-2-cyclopropyl-3-(dimethylamino)prop-2-enoate as yellow oil.

Synthesis of 5-cyclopropyl-2-[5-(ethanesulfonyl)-6-[4-ethyl-6-(trifluoromethyl)pyrrolo[3,2-b]pyridin-2-yl]pyridin-3-yl]pyrimidin-4-ol

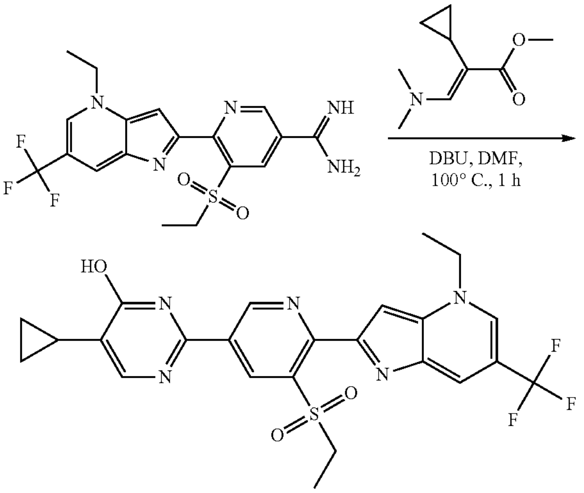

Into a 40 mL vial were added 5-(ethanesulfonyl)-6-[4-ethyl-6-(trifluoromethyl)pyrrolo[3,2-b]pyridin-2-yl]pyridine-3-carboximidamide (100 mg, 0.24 mmol, 1.0 equiv) and methyl (2E)-2-cyclopropyl-3-(dimethylamino)prop-2-enoate (199 mg, 1.18 mmol, 10 equiv), DMF (5.0 mL) and DBU (108 mg, 0.7 mmol, 3.0 equiv) at 100 degrees C. for 1 h under nitrogen atmosphere. The mixture was allowed to cool down to room temperature. The residue was purified by reverse flash chromatography with the following conditions: column, C18 silica gel; mobile phase, MeCN in water, 0% to 100% gradient in 30 min. To afford 5-cyclopropyl-2-[5-(ethanesulfonyl)-6-[4-ethyl-6-(trifluoromethyl)pyrrolo[3,2-b]pyridin-2-yl]pyridin-3-yl]pyrimidin-4-ol (50 mg, 41%) as a yellow solid.

Synthesis of 4-bromo-5-cyclopropyl-2-[5-(ethanesulfonyl)-6-[4-ethyl-6-(trifluoromethyl)pyrrolo[3,2-b]pyridin-2-yl]pyridin-3-yl]pyrimidine

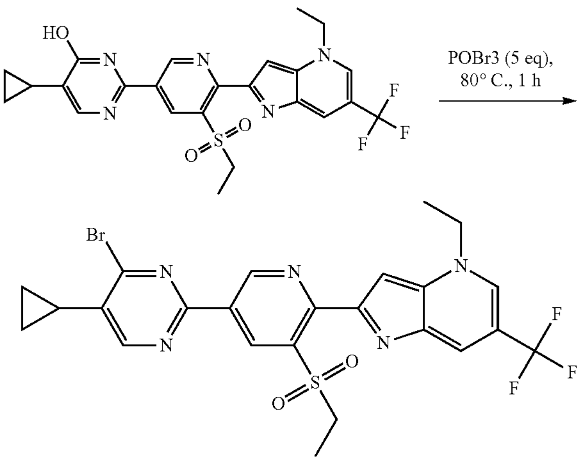

Into a 8 mL vial were added 5-cyclopropyl-2-[5-(ethanesulfonyl)-6-[4-ethyl-6-(trifluoromethyl)pyrrolo [3,2-b]pyridin-2-yl]pyridin-3-yl]pyrimidin-4-ol (50 mg, 0.1 mmol, 1.0 equiv) and $POBr_3$ (125 mg, 0.4 mmol, 4.5 equiv) at 80 degrees C. for 1 h under nitrogen atmosphere. The mixture was allowed to cool down to room temperature. The resulting mixture was diluted with EA (2 mL). The mixture was basified to pH 9 with saturated $NaHCO_3$(aq.). The resulting mixture was extracted with EtOAc (3×2 mL) dried over anhydrous $Na_2SO_4$. After filtration, the filtrate was concentrated under reduced pressure. To afford 4-bromo-5-cyclopropyl-2-[5-(ethanesulfonyl)-6-[4-ethyl-6-(trifluoromethyl) pyrrolo[3,2-b]pyridin-2-yl]pyridin-3-yl]pyrimidine (23 mg, 41%) as a yellow solid.

Synthesis of 5-cyclopropyl-2-[5-(ethanesulfonyl)-6-[4-ethyl-6-(trifluoromethyl)pyrrolo[3,2-b]pyridin-2-yl]pyridin-3-yl]pyrimidine

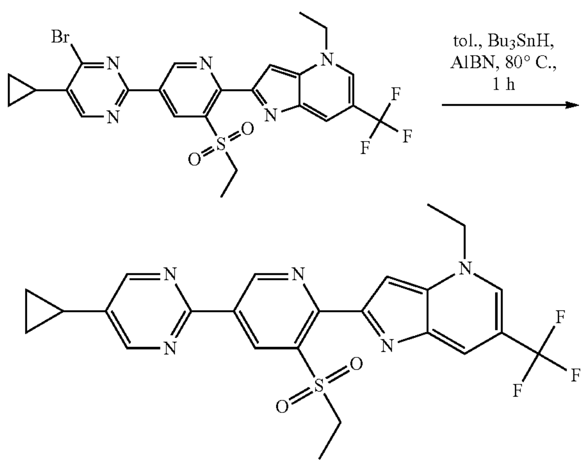

92

Into a 8 mL vial were added 4-bromo-5-cyclopropyl-2-[5-(ethanesulfonyl)-6-[4-ethyl-6-(trifluoromethyl)pyrrolo [3,2-b]pyridin-2-yl]pyridin-3-yl]pyrimidine (20 mg, 0.03 mmol, 1.0 equiv) and 25 tributyltin (26 mg, 0.09 mmol, 2.6 equiv) and AIBN (1 mg, 0.006 mmol, 0.18 equiv) in toluene (2 mL, 18.798 mmol, 545.53 equiv) was stirred for 1 h at 80 degrees C. under nitrogen atmosphere. The mixture was allowed to cool down to room temperature. The resulting mixture was concentrated under reduced pressure. The residue was purified by silica gel column chromatography, eluted with PE/EA (5:1) to afford 5-cyclopropyl-2-[5-(ethanesulfonyl)-6-[4-ethyl-6-(trifluoromethyl)pyrrolo[3,2-b] pyridin-2-yl]pyridin-3-yl]pyrimidine (5.4 mg, 31%) as a yellow solid.

Synthesis of Compound 110

Synthesis of 5-bromo-3-(ethylsulfanyl)pyridine-2-carbonitrile

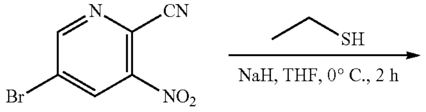

-continued

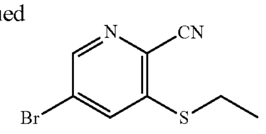

Into a 1000-mL 3-necked round-bottom flask, was placed 5-bromo-3-nitropyridine-2-carbonitrile (15 g, 66 mmol, 1.0 equiv), THF (300 mL), ethanethiol (3.9 g, 63 mmol, 1.0 equiv), NaH (1.7 g, 73 mmol, 1.1 equiv). The resulting solution was stirred for 2 hr at 0 degrees C. The reaction was then quenched by the addition of water. The resulting solution was extracted with 2×500 mL of ethyl acetate dried over anhydrous sodium sulfate and concentrated. The residue was applied onto a silica gel column with ethyl acetate/petroleum ether (1:10). This resulted in 12 g (75%) of 5-bromo-3-(ethylsulfanyl)pyridine-2-carbonitrile as a yellow solid.

Synthesis of 5-bromo-3-(ethylsulfanyl)pyridine-2-carboximidamide

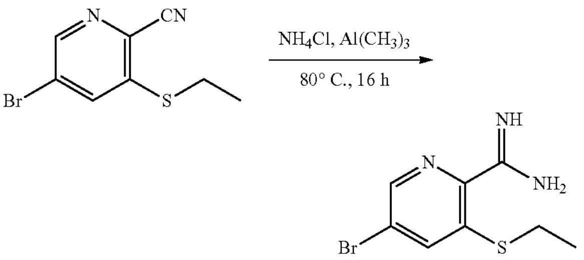

Into a 500-mL 3-necked round-bottom flask, was placed $NH_4Cl$ (2.9 g, 54 mmol, 1.2 equiv), toluene (220 mL, 2070 mmol, 46 equiv), $AlMe_3$ (27 mL, 258 mmol, 5.7 equiv), 5-bromo-3-(ethylsulfanyl)pyridine-2-carbonitrile (11 g, 45 mmol, 1.0 equiv). The resulting solution was stirred for 16 hr at 80 degrees C. The reaction was then quenched by the addition of 100 mL of MeOH. The solids were filtered out. The resulting mixture was concentrated. This resulted in 7 g (59%) of 5-bromo-3-(ethylsulfanyl)pyridine-2-carboximidamide as an off-white solid.

Synthesis of methyl 2-(2,2,3,3,3-pentafluoropropoxy)acetate

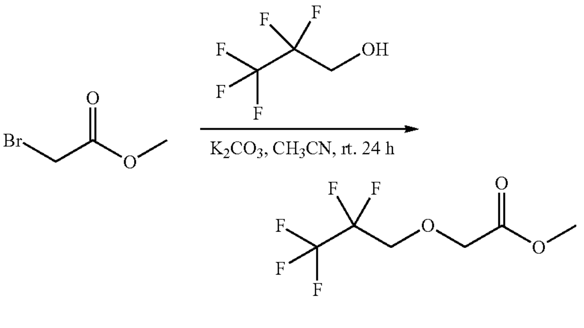

Into a 1000-mL round-bottom flask, was placed methyl 2-bromoacetate (10 g, 65 mmol, 1.0 equiv), $CH_3CN$ (100 mL), $K_2CO_3$ (01 g, 78 mmol, 1.2 equiv), pentafluoro-1-propanol (12 g, 78 mmol, 1.2 equiv). The resulting solution was stirred for 24 hr at room temperature. The solids were filtered out. The filtrate was concentrated. The residue was applied onto a silica gel column with ethyl acetate/petroleum ether (1:10). This resulted in 5 g (34.44%) of methyl 2-(2,2,3,3,3-pentafluoropropoxy)acetate as yellow oil.

Synthesis of methyl (2E)-3-(dimethylamino)-2-(2,2,3,3,3-pentafluoropropoxy)prop-2-enoate

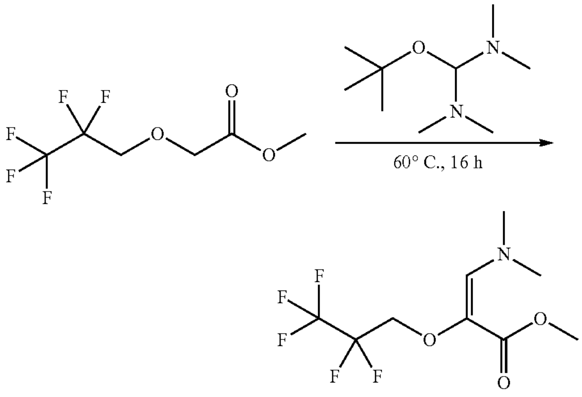

Into a 1000-mL round-bottom flask, was placed methyl 2-(2,2,3,3,3-pentafluoropropoxy)acetate (10 g, 45 mmol, 1.0 equiv), [tert-butoxy(dimethylamino)methyl]dimethylamine (9.4 g, 54 mmol, 1.2 equiv). The resulting solution was stirred for 16 hr at 60 degrees C. The reaction was then quenched by the addition of 50 mL of $NaHCO_3$ in water/ice. The resulting solution was extracted with 2×200 mL of ethyl acetate dried over anhydrous sodium sulfate and concentrated. This resulted in 6 g (48%) of methyl (2E)-3-(dimethylamino)-2-(2,2,3,3,3-pentafluoropropoxy)prop-2-enoate as yellow oil.

Synthesis of methyl 3-oxo-2-(2,2,3,3,3-pentafluoropropoxy)propanoate

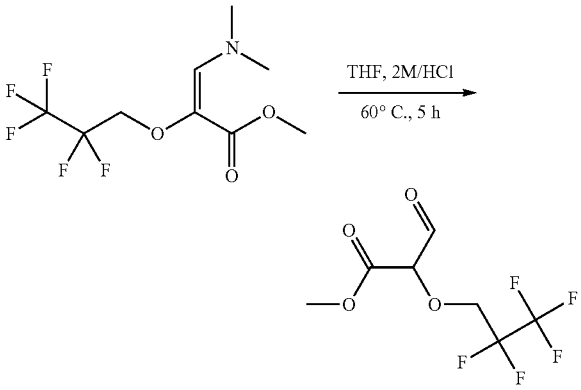

Into a 1000-mL round-bottom flask, was placed methyl (2E)-3-(dimethylamino)-2-(2,2,3,3,3-pentafluoropropoxy) prop-2-enoate (12 g, 43 mmol, 1.0 equiv), THF (240 mL), 2M/HCl (240 mL). The resulting solution was stirred for 5 hr at 60 degrees C. The resulting solution was extracted with 3×500 mL of ethyl acetate dried over anhydrous sodium sulfate and concentrated. This resulted in 7 g (65%) of methyl 3-oxo-2-(2,2,3,3,3-pentafluoropropoxy)propanoate as yellow oil.

Synthesis of 2-[5-bromo-3-(ethylsulfanyl)pyridin-2-yl]-5-(2,2,3,3,3-pentafluoropropoxy)-3H-pyrimidin-4-one

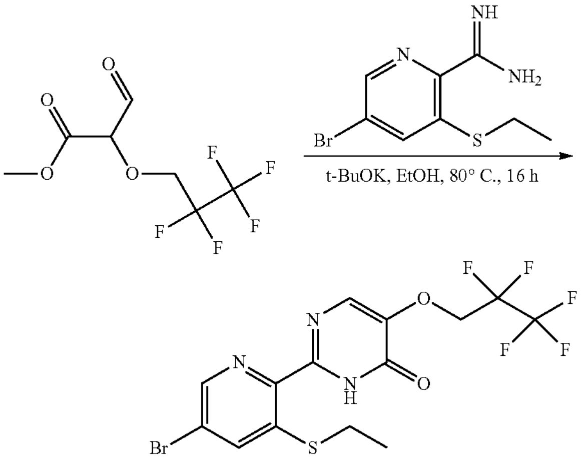

Into a 250-mL round-bottom flask, was placed 5-bromo-3-(ethylsulfanyl)pyridine-2-carboximidamide (4.5 g, 17 mmol, 1.0 equiv), EtOH (90 mL), t-BuOK (3.9 g, 35 mmol, 2.0 equiv), methyl 3-oxo-2-(2,2,3,3,3-pentafluoropropoxy) propanoate (8.7 g, 35 mmol, 2.0 equiv). The resulting solution was stirred for 16 hr at 80 degrees C. The reaction was then quenched by the addition of 500 mL of water. The resulting solution was extracted with 3×500 mL of ethyl acetate dried over anhydrous sodium sulfate and concentrated. The residue was applied onto a silica gel column with ethyl acetate/petroleum ether (1:3). This resulted in 2.8 g (35%) of 2-[5-bromo-3-(ethylsulfanyl)pyridin-2-yl]-5-(2,2,3,3,3-pentafluoropropoxy)-3H-pyrimidin-4-one as a white solid.

Synthesis of 2-[5-bromo-3-(ethylsulfanyl)pyridin-2-yl]-3-methyl-5-(2,2,3,3,3-pentafluoropropoxy)pyrimidin-4-one

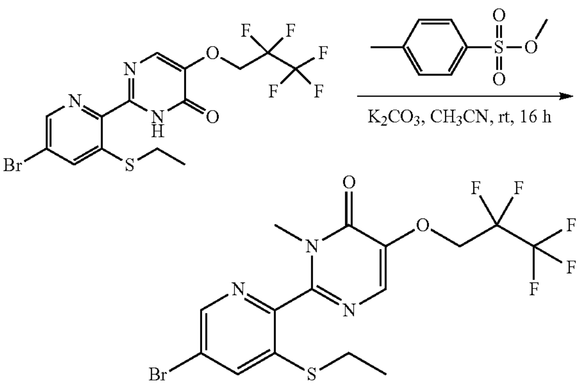

Into a 250-mL round-bottom flask, was placed 2-[5-bromo-3-(ethylsulfanyl)pyridin-2-yl]-5-(2,2,3,3,3-pentafluoropropoxy)-3H-pyrimidin-4-one (2.5 g, 5.4 mmol, 1.0 equiv), $CH_3CN$ (50 mL), $K_2CO_3$ (1.50 g, 11 mmol, 2.0 equiv), methyl 4-methylbenzenesulfonate (1.1 g, 6.05,1.1 equiv). The resulting solution was stirred for 16 hr at room temperature. The reaction was then quenched by the addition of 200 mL of water. The resulting solution was extracted with 2×500 mL of ethyl acetate dried over anhydrous sodium sulfate and concentrated. The residue was applied onto a silica gel column with ethyl acetate/petroleum ether (1:1). This resulted in 2 g (39%) of 2-[5-bromo-3-(ethylsulfanyl)pyridin-2-yl]-3-methyl-5-(2,2,3,3,3-pentafluoropropoxy)pyrimidin-4-one as a white solid.

Synthesis of 2-{15-bromo-3-(ethanesulfonyl)pyridin-2-yl]-3-methyl-5-(2,2,3,3,3-pentafluoropropoxy)pyrimidin-4-one

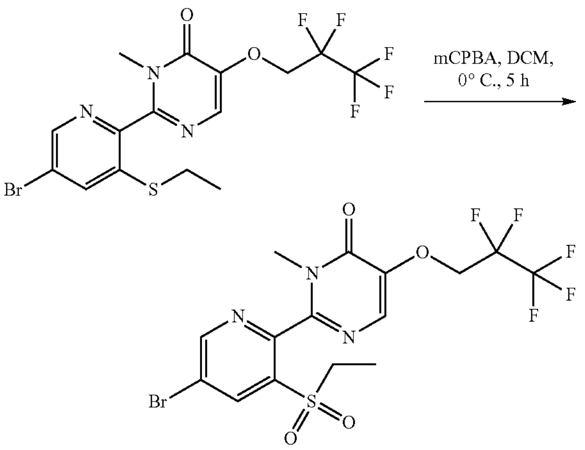

Into a 100-mL round-bottom flask, was placed 2-[5-bromo-3-(ethylsulfanyl)pyridin-2-yl]-3-methyl-5-(2,2,3,3,3-pentafluoropropoxy)pyrimidin-4-one (2.0 g, 4.2 mmol, 1.0 equiv), DCM (40 mL), mCPBA (1.8 g, 11 mmol, 2.5 equiv). The resulting solution was stirred for 5 hr at 0 degrees C. The reaction was then quenched by the addition of water. The resulting solution was extracted with 2×300 mL of ethyl acetate dried over anhydrous sodium sulfate and concentrated. The residue was applied onto a silica gel column with ethyl acetate/petroleum ether (1:4). This resulted in 1.6 g (75%) of 2-[5-bromo-3-(ethanesulfonyl)pyridin-2-yl]-3-methyl-5-(2,2,3,3,3-pentafluoropropoxy)pyrimidin-4-one as a yellow solid.

Synthesis of 2-[5-(4-cyclopropylphenyl)-3-(ethanesulfonyl)pyridin-2-yl]-3-methyl-5-(2,2,3,3,3-pentafluoropropoxy)pyrimidin-4-one

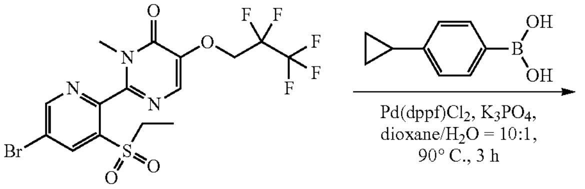

-continued

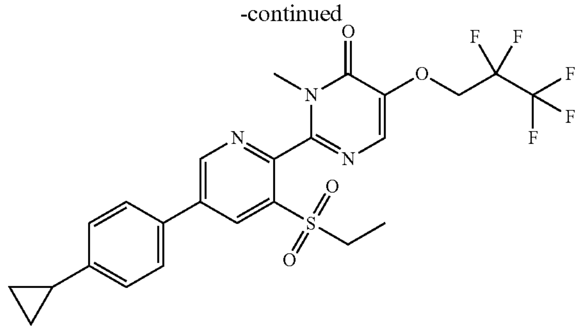

110

Into a 50-mL round-bottom flask purged and maintained with an inert atmosphere of nitrogen, was placed 2-[5-bromo-3-(ethanesulfonyl)pyridin-2-yl]-3-methyl-5-(2,2,3,3,3-pentafluoropropoxy)pyrimidin-4-one (110.00 mg, 0.217 mmol, 1.00 equiv), 4-cyclopropylphenylboronic acid (70 mg, 0.4 mmol, 2.0 equiv), $Pd(dppf)Cl_2$ (16 mg, 0.02 mmol, 0.1 equiv), $K_3PO_4$ (115 mg, 0.5 mmol, 2.5 equiv), dioxane (2.2 mL), $H_2O$ (0.2 mL). The resulting solution was stirred for 3 hr at 90 degrees C. The resulting mixture was concentrated. The residue was applied onto a silica gel column with ethyl acetate/petroleum ether (1:5). The crude product was purified by Flash-Prep-HPLC with the following conditions (IntelFlash-1): Column, C18 silica gel; mobile phase, $CH_3CN$/0.05% $NH_3 \cdot H_2O$=60 increasing to $CH_3CN$/0.05% $NH_3 \cdot H_2O$=95 within 12 min; Detector, 254 nm. This resulted in 50 mg (43%) of 2-[5-(4-cyclopropylphenyl)-3-(ethanesulfonyl)pyridin-2-yl]-3-methyl-5-(2,2,3,3,3-pentafluoropropoxy)pyrimidin-4-one as a white solid.

Synthesis of Compound 123

Synthesis of 2-bromo-5-(2,2,3,3,3-pentafluoropropoxy)pyridine

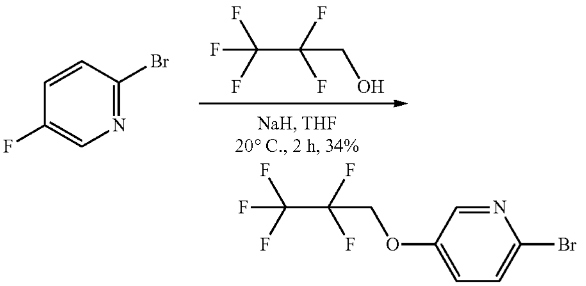

To a solution of pentafluoro-1-propanol (4.3 g, 29 mmol, 1.2 equiv) in THF (50 mL)was added NaH (1.4 g, 36 mmol, 1.5 equiv) at 0 degrees C. The mixture was stirred for 15 min. 2-bromo-5-fluoropyridine (4.2 g, 24 mmol, 1.00 equiv) was added and the mixture was allowed to warm to RT and stirred for 2 h. The reaction mixture was quenched by water and extracted with EA (3*100 mL). The resulting solution was dried over $Na_2SO_4$ and concentrated under vacuum. The residue was purified by silica gel column chromatography, eluted with PE/EA (2/1) to afford 2-bromo-5-(2,2,3,3,3-pentafluoropropoxy)pyridine (2.5 g, 34%) as a white solid.

Synthesis of 5-(2,2,3,3,3-pentafluoropropoxy)-2-(trimethylstannyl)pyridine

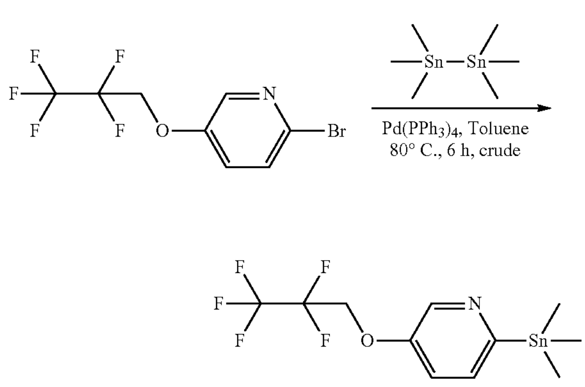

To a solution of 2-bromo-5-(2,2,3,3,3-pentafluoropropoxy)pyridine (100 mg, 0.3 mmol, 1.0 equiv) and hexamethyldistannane (535 mg, 1.6 mmol, 5.0 equiv) in Toluene (5 mL, 47 mmol, 144 equiv) were added($(PPh_3)_4$(38 mg, 0.03 mmol, 0.1 equiv). After stirring for 6 h at 80 degrees C. under a nitrogen atmosphere, the resulting mixture was concentrated under reduced pressure to afford 5-(2,2,3,3,3-pentafluoropropoxy)-2-(trimethylstannyl)pyridine (210 mg, crude) as black solid. The product was used in the next step directly without further purification.

Synthesis of 6-chloro-6'-cyclopropyl-5-(ethanesulfonyl)-3,3'-bipyridine

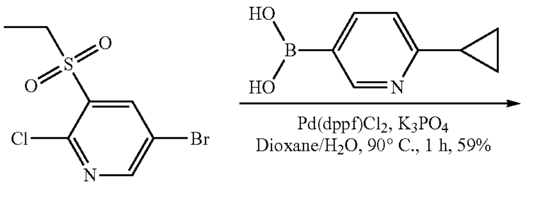

-continued

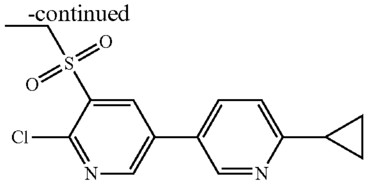

To a solution of 5-bromo-2-chloro-3-(ethanesulfonyl)pyridine (220 mg, 0.8 mmol, 1.0 equiv) and 6-cyclopropylpyridin-3-ylboronic acid (126 mg, 0.8 mmol, 1.0 equiv) in dioxane (4 mL, 47 mmol, 617 equiv) and $H_2O$ (1 mL, 56 mmol, 72 equiv) were added $K_3PO_4$ (328 mg, 1.5 mmol, 2.0 equiv) and Pd(dppf)$Cl_2$ (57 mg, 0.08 mmol, 0.1 equiv). After stirring for 1 h at 90 degrees C. under a nitrogen atmosphere, the resulting mixture was concentrated under reduced pressure. The residue was purified by silica gel column chromatography, eluted with PE/EA (2/1) to afford 6-chloro-6'-cyclopropyl-5-(ethanesulfonyl)-3,3'-bipyridine (148 mg, 59%) as a white solid.

Synthesis of 6'-cyclopropyl-5-(ethanesulfonyl)-6-[5-(2,2,3,3,3-pentafluoropropoxy)pyridin-2-yl]-3,3'-bipyridine

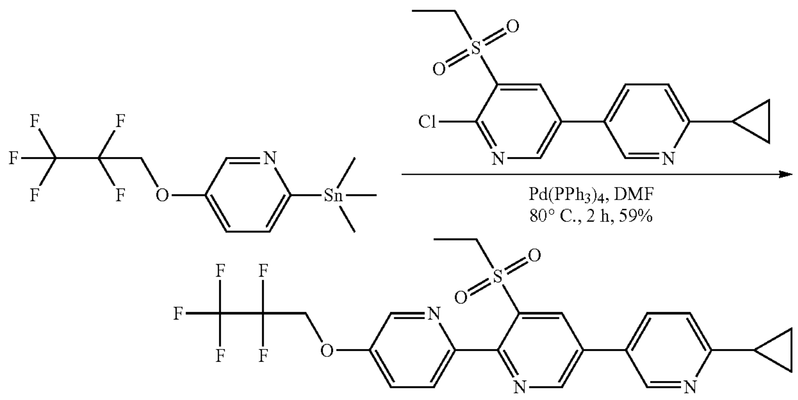

123

Into a 25 mL round-bottom flask, was place 5-(2,2,3,3,3-pentafluoropropoxy)-2-(trimethylstannyl)pyridine (210 mg, 0.539 mmol, 1.00 equiv),6-chloro-6'-cyclopropyl-5-(ethanesulfonyl)-3,3'-bipyridine (86.92 mg, 0.270 mmol, 0.5 equiv),DMF (5 mL, 64.609 mmol, 119.97 equiv), then Pd$(PPh_3)_4$(62.23 mg, 0.054 mmol, 0.1 equiv) was added at $N_2$ protect. Then reaction mixture was stirred at 80 degrees C. for 2 h. The mixture was allowed to cool down to rt. The resulting mixture was diluted with EA (100 mL). The resulting mixture was washed with 3×50 mL of water. The resulting solution was dried and concentrated. The residue was purified by reverse flash chromatography with the following conditions: column, C18 silica gel; mobile phase, MeCN in water, 40% to 80% gradient in 10 min; detector, UV 254 nm. The product was collected and concentrated under reduced pressure. This resulted in 6'-cyclopropyl-5-(ethanesulfonyl)-6-[5-(2,2,3,3,3-pentafluoropropoxy)pyridin-2-yl]-3,3'-bipyridine (17.5 mg, 6.33%) as a white solid.

Synthesis of Compound 126

Specifically, the following compounds of formula (I) can be synthesized by adopting the subsequent scheme of Compound 126 by someone who is skilled in the art and employing the starting material described vide supra: 212, 214 Synthesis of 5-bromo-3-(ethylsulfanyl)-N-methoxy-N-methylpyridine-2-carboxamide

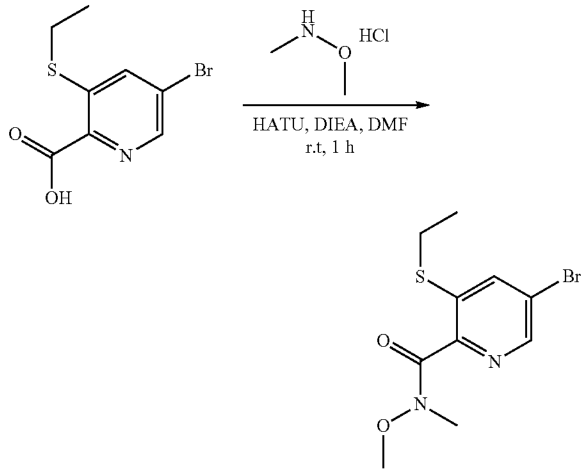

Into a 100 mL round-bottom flask were added 5-bromo-3-(ethylsulfanyl)pyridine-2-carboxylic acid (2 g, 7.6 mmol, 1 equiv), N,O-dimethylhydroxylamine hydrochloride (0.74 g, 7.6 mmol, 1 equiv) and DMF (40 mL, 520 mmol, 68 equiv), DIEA (2.9 g, 23 mmol, 3.0 equiv) at room temperature. To the above mixture was added HATU (4.35 g, 11 mmol, 1.5 equiv) dropwise at 0 degrees C. The resulting mixture was stirred for 1 h at 0 degrees C. The resulting mixture was diluted with water (50 mL). The resulting mixture was extracted with EtOAc (3×40 mL). The combined organic layers were washed with brine (3×30 mL), dried over anhydrous Na2SO4. After filtration, the filtrate was concentrated under reduced pressure. The residue was purified by silica gel column chromatography, eluted with PE/EA (9:1) to afford 5-bromo-3-(ethylsulfanyl)-N-methoxy-N-methylpyridine-2-carboxamide (2.1 g, 90%) as a yellow solid.

Synthesis of 1-[5-bromo-3-(ethylsulfanyl)pyridin-2-yl]ethan-1-one

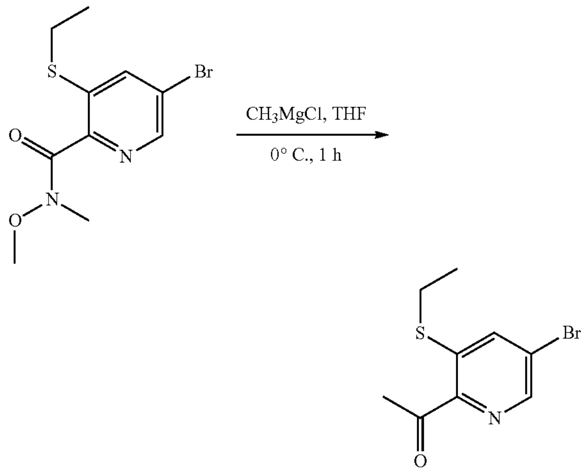

Into a 100 mL 3-necked round-bottom flask were added 5-bromo-3-(ethylsulfanyl)-N-methoxy-N-methylpyridine-2-carboxamide (2 g, 6.6 mmol, 1 equiv) and THF (40 mL, 490 mmol, 75 equiv) at room temperature. To the above mixture was added $CH_3MgCl$ (2.8 mL, 8.4 mmol, 1.3 equiv) dropwise at 0 degrees C. The resulting mixture was stirred for 1 h at 0 degrees C. The reaction was quenched by the addition of sat. NH4Cl (aq.) (50 mL) at room temperature. The resulting mixture was extracted with EtOAc (3×40 mL). The combined organic layers were washed with brine (3×40 mL), dried over anhydrous Na2SO4. After filtration, the filtrate was concentrated under reduced pressure. The residue was purified by silica gel column chromatography, eluted with PE/EA (4:1) to afford 1-[5-bromo-3-(ethylsulfanyl)pyridin-2-yl]ethanone (0.99 g, 57%) as a white solid.

Synthesis of 6-[5-bromo-3-(ethylsulfanyl)pyridin-2-yl]pyridazin-3-ol

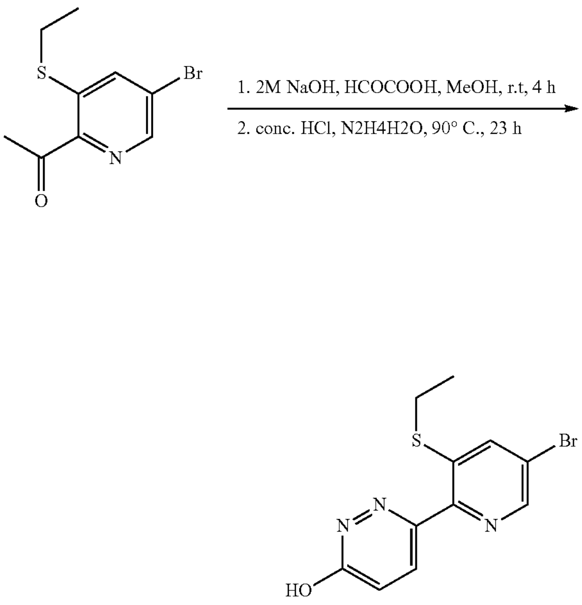

Into a 40 mL round-bottom flask were added 1-[5-bromo-3-(ethylsulfanyl)pyridin-2-yl]ethanone (890 mg, 3.4 mmol, 1 equiv), glyoxalate, glyoxylate hydrate (630 mg, 6.8 mmol, 2 equiv) and MeOH (7.1 mL) at room temperature. To the above mixture was added NaOH (55 mg, 1.4 mmol, 0.4 equiv) in $H_2O$ (6.9 mL, 380 mmol, 112 equiv) dropwise at 0 degrees C. The resulting mixture was stirred for additional 4 h at room temperature. The mixture was allowed to cool down to 0 degrees C. To the above mixture was added conc·HCl (1.8 mL) and hydrazine hydrate (0.74 mL, 15 mmol, 4.3 equiv) dropwise at 0 degrees C. The resulting mixture was stirred for additional 23 h at 90 degrees C. The mixture was allowed to cool down to room temperature. The reaction was quenched by the addition of sat. NH4Cl (aq.) (50 mL) at room temperature. The resulting mixture was extracted with $CH_2Cl2$ (3×50 mL). The combined organic layers were washed with brine (2×50 mL), dried over anhydrous Na2SO4. After filtration, the filtrate was concentrated under reduced pressure. This resulted in 6-[5-bromo-3-(ethylsulfanyl)pyridin-2-yl]pyridazin-3-ol (697 mg, 65%) as a dark red solid.

Synthesis of 3-[5-bromo-3-(ethylsulfanyl)pyridin-2-yl]-6-chloropyridazine

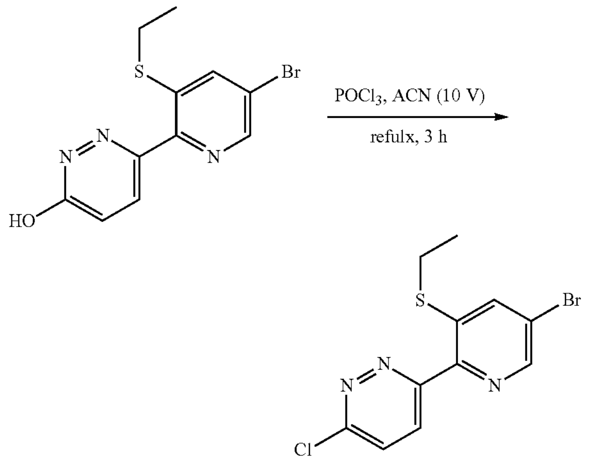

Into a 8 mL round-bottom flask were added 6-[5-bromo-3-(ethylsulfanyl)pyridin-2-yl]pyridazin-3-ol (380 mg, 1.2 mmol, 1 equiv) and ACN (3.7 mL) at room temperature. To the above mixture was added POCl3 (370 mg, 2.4 mmol, 2 equiv) dropwise at 0 degrees C. The resulting mixture was stirred for 3 h at 80 degrees C. The mixture was allowed to cool down to room temperature. The mixture was allowed to cool down to room temperature. The reaction was quenched by the addition of sat. sodium hyposulfite (aq.) (10 mL) at room temperature. The resulting mixture was extracted with EtOAc (3×10 mL). The combined organic layers were washed with brine (3×5 mL), dried over anhydrous Na2SO4. After filtration, the filtrate was concentrated under reduced pressure to afford 3-[5-bromo-3-(ethylsulfanyl)pyridin-2-yl]-6-chloropyridazine (247 mg, 62%) as a dark red solid.

Synthesis of 3-[5-bromo-3-(ethylsulfanyl)pyridin-2-yl]-6-(2,2,3,3,3-pentafluoropropoxy)pyridazine

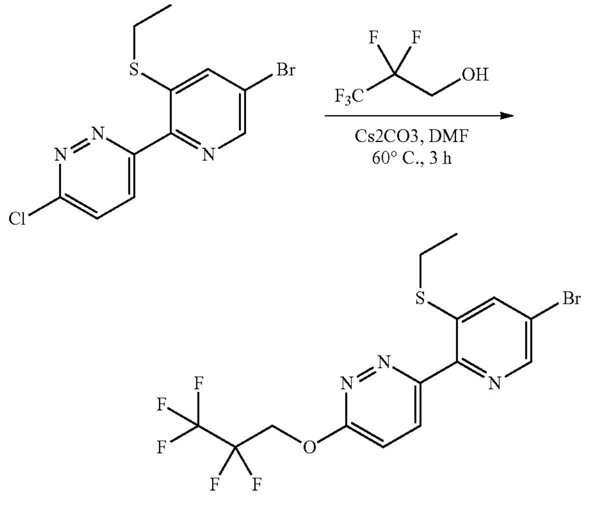

Into a 40 mL round-bottom flask were added 3-[5-bromo-3-(ethylsulfanyl)pyridin-2-yl]-6-chloropyridazine (240 mg, 0.7 mmol, 1 equiv), Cs2CO3 (345 mg, 1.0 mmol, 1.5 equiv) and DMF(10 mL) at room temperature. The resulting mixture was stirred for 3 h at 60 degrees C. The mixture was allowed to cool down to room temperature. The reaction was quenched by the addition of Water (10 mL) at room temperature. The resulting mixture was extracted with EtOAc (3×10 mL). The combined organic layers were washed with brine (2×5 mL), dried over anhydrous Na2SO4. After filtration, the filtrate was concentrated under reduced pressure. The residue was purified by silica gel column chromatography, eluted with PE/EA (97:3) to afford 3-[5-bromo-3-(ethylsulfanyl)pyridin-2-yl]-6-(2,2,3,3,3-pentafluoropropoxy)pyridazine (219 mg, 68%) as a yellow solid.

Synthesis of 3-[5-bromo-3-(ethanesulfonyl)pyridin-2-yl]-6-(2,2,3,3,3-pentafluoropropoxy)pyridazine

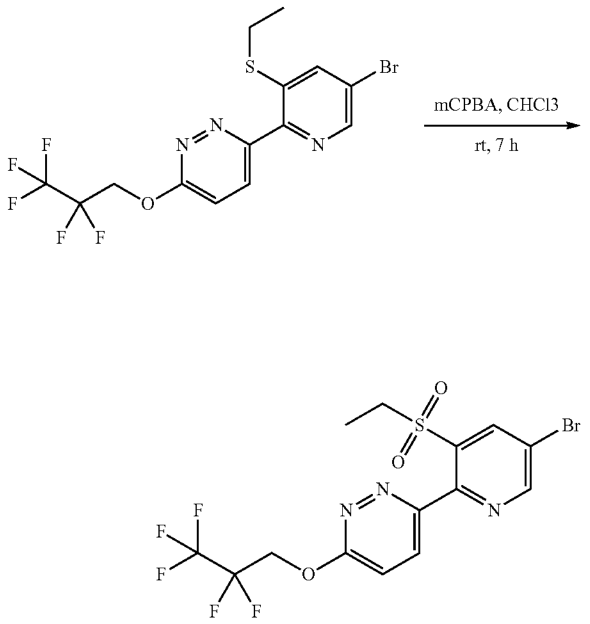 [SMILES: CCSc1cc(Br)cnc1-c1ccc(OCC(F)(F)C(F)(F)F)nn1 ; CCS(=O)(=O)c1cc(Br)cnc1-c1ccc(OCC(F)(F)C(F)(F)F)nn1]

Into a 40 mL round-bottom flask were added 3-[5-bromo-3-(ethylsulfanyl)pyridin-2-yl]-6-(2,2,3,3,3-pentafluoropropoxy)pyridazine (150 mg, 0.3 mmol, 1 equiv) and CHCl3 (6 mL) at room temperature. To the above mixture was added m-CPBA (160 mg, 0.8 mmol, 2.3 equiv) dropwise at 0 degrees C. The resulting mixture was stirred for 7 h at room temperature. The reaction was quenched by the addition of sat. sodium hyposulfite (aq.) (20 mL) at room temperature. The resulting mixture was extracted with EtOAc (3×15 mL). The combined organic layers were washed with water (3×10 mL) and brine (10 mL), dried over anhydrous Na2SO4. After filtration, the filtrate was concentrated under reduced pressure to afford 3-[5-bromo-3-(ethanesulfonyl)pyridin-2-yl]-6-(2,2,3,3,3-pentafluoropropoxy)pyridazine (140 mg, 87%) as a red solid.

Synthesis of 3-[5-(4-cyclopropylphenyl)-3-(ethanesulfonyl)pyridin-2-yl]-6-(2,2,3,3,3-pentafluoropropoxy)pyridazine

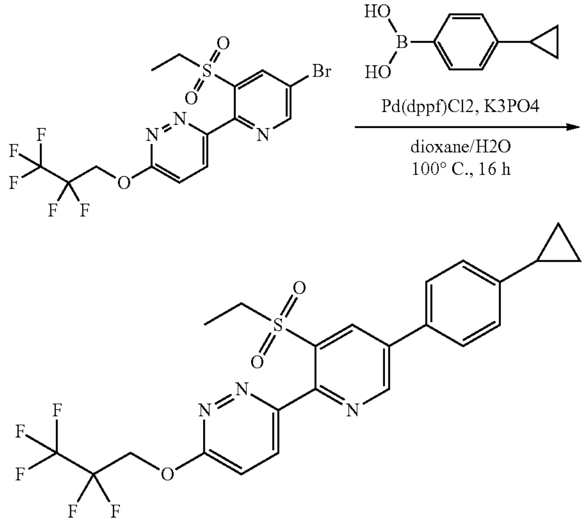

126

Into a 40 mL round-bottom flask were added 3-[5-bromo-3-(ethanesulfonyl)pyridin-2-yl]-6-(2,2,3,3,3-pentafluoropropoxy)pyridazine (118 mg, 0.25 mmol, 1 equiv), (4-cyclopropylphenyl)boronic acid (60 mg, 0.4 mmol, 1.5 equiv), K3PO4 (105 mg, 0.5 mmol, 2.0 equiv), Pd(dppf) Cl2·$CH_2$Cl2 (20 mg, 0.03 mmol, 0.1 equiv), dioxane (2.4 mL) and $H_2O$ (0.4 mL) at room temperature. The resulting mixture was stirred for 16 h at 100 degrees C. under nitrogen atmosphere. The mixture was allowed to cool down to room temperature. The resulting mixture was diluted with water (10 mL). The resulting mixture was extracted with EtOAc (3×10 mL). The combined organic layer was washed with brine (3×5 mL), dried over anhydrous Na2SO4. After filtration, the filtrate was concentrated under reduced pressure. The residue was purified by Prep-TLC (PE/EA 5:1) to afford 3-[5-(4-cyclopropylpheny1)-3-(ethanesulfonyl)pyridin-2-yl]-6-(2,2,3,3,3-pentafluoropropoxy)pyridazine (47 mg, 37%) as a white solid.

Synthesis of Compound 121

Synthesis of 5-bromo-N-methyl-3-nitropyridin-2-amine

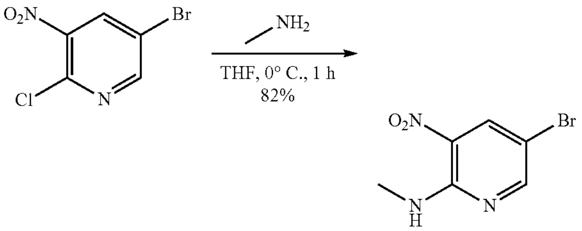

Into a 250-mL round-bottom flask, was placed 5-bromo-2-chloro-3-nitropyridine (6.0 g, 25 mmol, 1.0 equiv), THF (120 mL), methylamine (2.4 g, 76 mmol, 3.0 equiv). The resulting solution was stirred for 1 hr at 0 degrees C. The resulting solution was diluted with 500 mL of $H_2O$. The solids were collected by filtration. The solid was washed three times with water (50 mL). The solid dried by stoving lamp. This resulted in 4.8 g (82%) of 5-bromo-N-methyl-3-nitropyridin-2-amine as a yellow solid.

Synthesis of 5-bromo-N2-methylpyridine-2,3-diamine

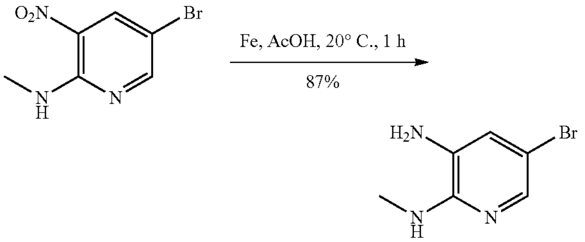

Into a 250-mL round-bottom flask, was placed 5-bromo-N-methyl-3-nitropyridin-2-amine (4.6 g, 20 mmol, 1.0 equiv), AcOH (50 mL), Fe (5.5 g, 99 mmol, 5.0 equiv). The resulting solution was stirred for 1 hr at 20 degrees C. The resulting mixture was concentrated. The resulting solution was diluted with 500 mL of EA. The resulting mixture was washed with 3×200 mL of $Na_2CO_3$ (aq, 2M). The mixture was dried over anhydrous sodium sulfate and concentrated. The residue was applied onto a silica gel column with ethyl acetate/petroleum ether (1/1). The collected fractions were combined and concentrated. This resulted in 3.5 g (87%) of 5-bromo-N2-methylpyridine-2,3-diamine as a brown solid.

Synthesis of N-[5-bromo-2-(methylamino)pyridin-3-yl]-2,2,2-trifluoroacetamide

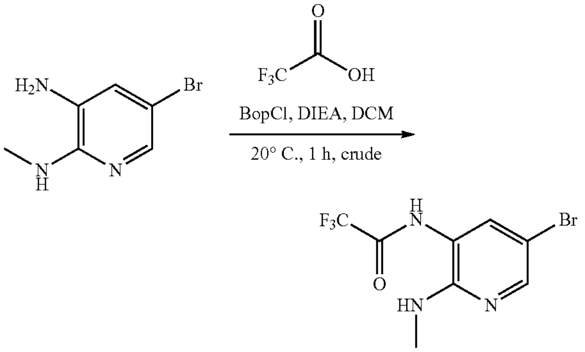

Into a 250-mL round-bottom flask, was placed 5-bromo-N2-methylpyridine-2,3-diamine (3.1 g, 15 mmol, 1.0 equiv), DCM (60 mL), DIEA (5.95 g, 46 mmol, 3.0 equiv), trifluoroacetic acid (2.1 g, 18.4 mmol, 1.2 equiv), BOP—Cl (5.85 g, 23.0 mmol, 1.5 equiv). The resulting solution was stirred for 1 hr at 20 degrees C. The resulting solution was diluted with 300 mL of DCM. The resulting mixture was washed with 3x 100 mL of $H_2O$. The mixture was dried over anhydrous sodium sulfate and concentrated. This resulted in 5.2 g crude of N-[5-bromo-2-(methylamino)pyridin-3-yl]-2,2,2-trifluoroacetamide as a black solid.

Synthesis of 6-bromo-3-methyl-2-(trifluoromethyl)imidazo[4,5-b]pyridine

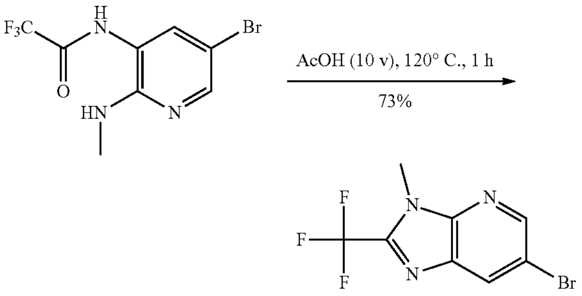

Into a 250-mL round-bottom flask, was placed N-[5-bromo-2-(methylamino)pyridin-3-yl]-2,2,2-trifluoroacetamide (5.2 g, 17 mmol, 1.0 equiv), AcOH (50 mL). The resulting solution was stirred for 1 hr at 120 degrees C. in an oil bath. The reaction mixture was cooled. The resulting mixture was concentrated. The resulting solution was diluted with 500 mL of EA. The resulting mixture was washed with 3×200 mL of $Na_2CO_3$(aq, 2M). The mixture was dried over anhydrous sodium sulfate and concentrated. The residue was applied onto a silica gel column with ethyl acetate/petroleum ether (1/8). The collected fractions were combined and concentrated. This resulted in 3.6 g (73%) of 6-bromo-3-methyl-2-(trifluoromethyl)imidazo[4,5-b]pyridine as a light yellow solid.

Synthesis of 3-methyl-6-(4,4,5,5-tetramethyl-1,3,2-dioxaborolan-2-yl)-2-(trifluoromethyl)imidazo[4,5-b]pyridine

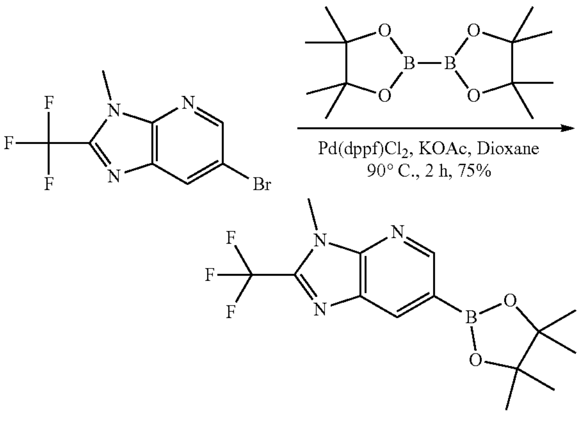

Into a 100-mL round-bottom flask purged and maintained with an inert atmosphere of nitrogen, was placed 6-bromo-3-methyl-2-(trifluoromethyl)imidazo[4,5-b]pyridine (1.0 g, 3.6 mmol, 1.0 equiv), bis(pinacolato)diboron (1.1 g, 4.3 mmol, 1.2 equiv), AcOK (0.7 g, 7.1 mmol, 2.0 equiv), dioxane (50 mL), $Pd(dppf)Cl_2$ (261 mg, 0.4 mmol, 0.1 equiv). The resulting solution was stirred for 2 hr at 90 degrees C. in an oil bath. The reaction mixture was cooled. The resulting mixture was concentrated. The residue was applied onto a silica gel column with ethyl acetate/petroleum ether (1/4). The collected fractions were combined and concentrated. This resulted in 880 mg (75%) of 3-methyl-6-(4,4,5,5-tetramethyl-1,3,2-dioxaborolan-2-yl)-2-(trifluoromethyl)imidazo[4,5-b]pyridine as an off-white solid.

Synthesis of 5-bromo-2-chloropyridin-3-amine

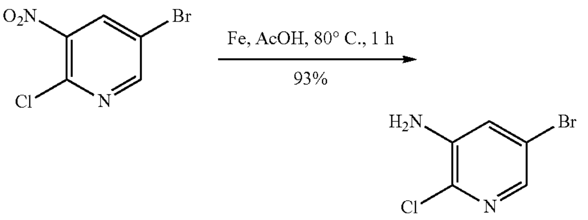

Into a 500-mL round-bottom flask, was placed 5-bromo-2-chloro-3-nitropyridine (10 g, 42 mmol, 1.0 equiv), AcOH (100.00 mL), Fe dust (12 g. 210 mmol, 5.0 equiv). The resulting solution was stirred for 1 hr at 80 degrees C. in an oil bath. The reaction mixture was cooled concentrated. The resulting solution was diluted with 500 mL of EA. The resulting mixture was washed with 3×200 mL of $Na2CO_3$ (aq, 2M). The mixture was dried over anhydrous sodium sulfate and concentrated. This resulted in 8.1 g (93%) of 5-bromo-2-chloropyridin-3-amine as a white solid.

Synthesis of 5-bromo-2-chloro-3-(ethylsulfanyl)pyridine

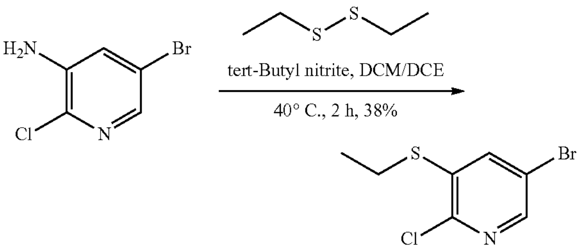

Into a 500-mL round-bottom flask. was placed 5-bromo-2-chloropyridin-3-amine (6.0 g, 29 mmol, 1.0 equiv), DCM (100 mL), DCE (150 mL), diethyl disulfide (3.5 g, 29 mmol, 1.0 equiv), tert-butyl nitrite (3.6 g, 35 mmol, 1.2 equiv). The resulting solution was stirred for 2 hr at 40 degrees C. in an oil bath. The reaction mixture was cooled. The resulting mixture was concentrated. The residue was applied onto a silica gel column with ethyl acetate/petroleum ether (1/4). The collected fractions were combined and concentrated. This resulted in 2.8 g (38%) of 5-bromo-2-chloro-3-(ethylsulfanyl)pyridine as yellow oil.

Synthesis of 5-bromo-2-chloro-3-(ethanesulfonyl)pyridine

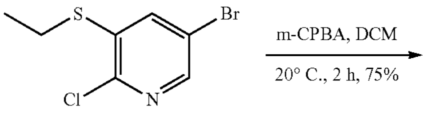

-continued

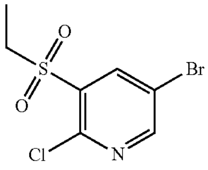

Into a 100-mL round-bottom flask, was placed 5-bromo-2-chloro-3-(ethylsulfanyl)pyridine (2.5 g, 9.9 mmol, 1.0 equiv), DCM (50 mL), m-CPBA (5.1 g, 30 mmol, 3.00 equiv). The resulting solution was stirred for 2 hr at 20 degrees C. The resulting mixture was concentrated. The residue was applied onto a silica gel column with ethyl acetate/petroleum ether (1/5). The collected fractions were combined and concentrated. This resulted in 2.1 g (75%) of 5-bromo-2-chloro-3-(ethanesulfonyl)pyridine as a white solid.

Synthesis of 2-chloro-5-(4-cyclopropylphenyl)-3-(ethanesulfonyl)pyridine

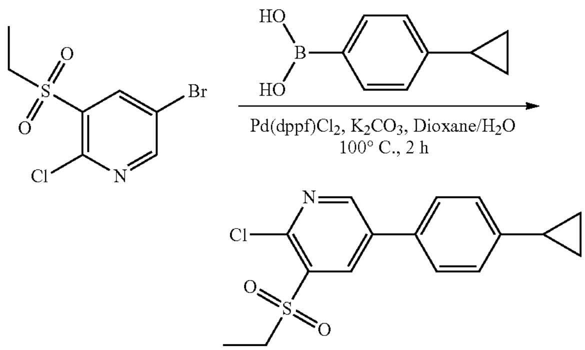

Into a 8-mL vial purged and maintained with an inert atmosphere of nitrogen, was placed 5-bromo-2-chloro-3-(ethanesulfonyl)pyridine (120 mg, 0.4 mmol, 1.0 equiv), 4-cyclopropylphenylboronic acid (82 mg, 0.5 mmol, 1.2 equiv), $K_2CO_3$ (117 mg, 0.8 mmol, 2.0 equiv), dioxane (2.0 mL), $H_2O$ (0.4 mL), $Pd(dppf)Cl_2$ (31 mg, 0.04 mmol, 0.10 equiv). The resulting solution was stirred for 2 hr at 100 degrees C. in an oil bath. The reaction mixture was cooled and used by next step directly.

Synthesis of 5-(4-cyclopropylphenyl)-3-(ethanesulfonyl)-2-[3-methyl-2-(trifluoromethyl) imidazo[4,5-b]pyridin-6-yl]pyridine

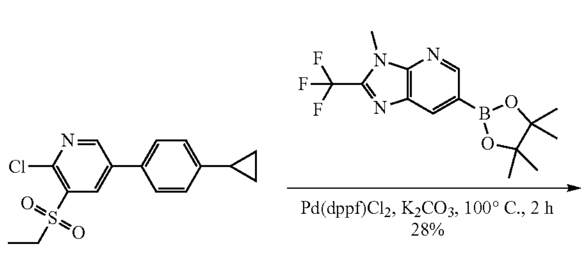

-continued

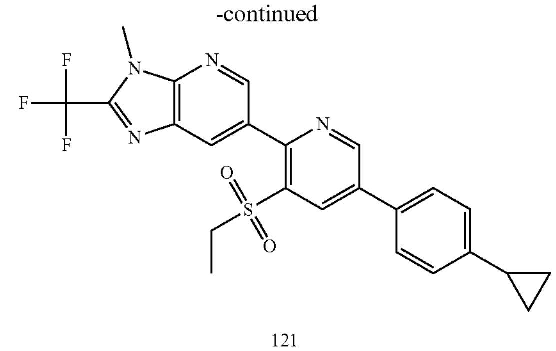

121

The reaction mixture maintained with an inert atmosphere of nitrogen, was placed 3-methyl-6-(4,4,5,5-tetramethyl-1,3,2-dioxaborolan-2-yl)-2-(trifluoromethyl)imidazo[4,5-b]pyridine (122 mg, 0.4 mmol, 1.2 equiv), $Pd(dppf)Cl_2$ (23 mg, 0.03 mmol, 0.1 equiv). The resulting solution was stirred for 2 hr at 100 degrees C. in an oil bath. The reaction mixture was cooled. The resulting solution was diluted with 50 mL of EA. The resulting mixture was washed with 3×20 mL of $H_2O$. The mixture was dried over anhydrous sodium sulfate and concentrated. The crude product was purified by Flash-Prep-HPLC with the following conditions (IntelFlash-1): Column, C18 silica gel; mobile phase, ACN/$H_2O$=0/100 increasing to ACN/$H_2O$=55/45 within 7. The product was obtained and concentrated. This resulted in 42 mg (25%) of 5-(4-cyclopropylphenyl)-3-(ethanesulfonyl)-2-[3-methyl-2-(trifluoromethyl)imidazo(4,5-b]pyridin-6-yl]pyridine as a white solid.

Synthesis of Compound 122

Synthesis of 6-bromo-2-(trifluoromethyl)-1H-pyrrolo[3,2-b]pyridine

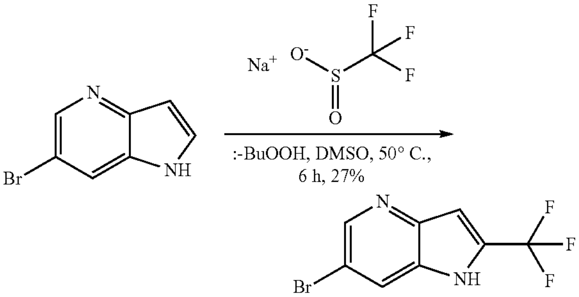

Into a 50-mL round-bottom flask, was placed 6-bromo-1H-pyrrolo[3,2-b]pyridine (700 mg, 3.5 mmol, 1.0 equiv), DMSO (10 mL), t-BuOOH (640 mg, 7.1 mmol, 2.0 equiv), sodium trifluoromethanesulfinate (831 mg, 5.3 mmol, 1.5 equiv). The resulting solution was stirred for 6 hr at 50 degrees C. in an oil bath. The reaction mixture was cooled. The resulting solution was diluted with 200 mL of EA. The resulting mixture was washed with 3×100 mL of $H_2O$. The organic phase was dried over anhydrous sodium sulfate and concentrated. The residue was applied onto a silica gel column with ethyl acetate/petroleum ether (1/2). The collected fractions were combined and concentrated. This resulted in 255 mg (27%) of 6-bromo-2-(trifluoromethyl)-1H-pyrrolo[3,2-b]pyridine as a white solid.

Synthesis of 6-bromo-4-ethyl-2-(trifluoromethyl) pyrrolo[3,2-b]pyridine

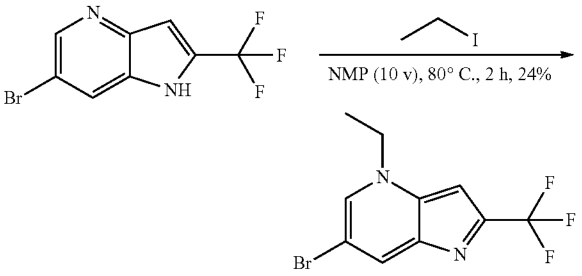

Into a 25-mL round-bottom flask, was placed 6-bromo-2-(trifluoromethyl)-1H-pyrrolo[3,2-b]pyridine (250 mg, 0.9 mmol, 1.0 equiv), NMP (5.0 mL), ethyl iodide (1.5 g, 9.4 mmol, 10 equiv). The resulting solution was stirred for 2 hr at 80 degrees C. in an oil bath. The reaction mixture was cooled. The resulting solution was diluted with 100 mL of EA. The resulting mixture was washed with 3×50 mL of $H_2O$. The mixture was dried over anhydrous sodium sulfate and concentrated. The residue was applied onto a silica gel column with ethyl acetate/petroleum ether (1/1). The collected fractions were combined and concentrated. This resulted in 65 mg (24%) of 6-bromo-4-ethyl-2-(trifluoromethyl)pyrrolo[3,2-b]pyridine as a yellow solid.

Synthesis of [4-ethyl-2-(trifluoromethyl)-4H-pyrrolo [3,2-b]pyridin-6-yl]boronic acid

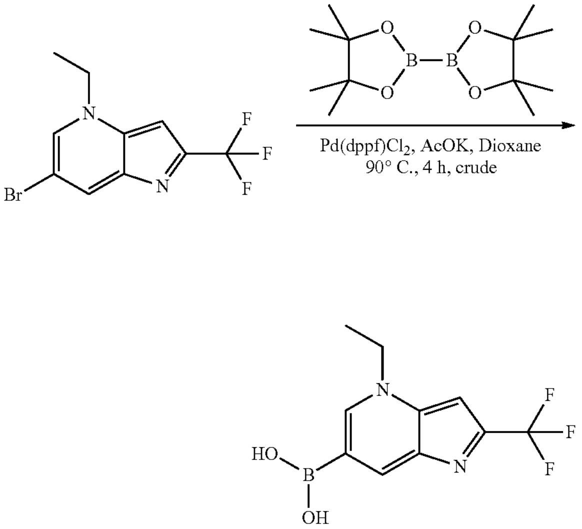

Into a 8-mL vial purged and maintained with an inert atmosphere of nitrogen, was placed 6-bromo-4-ethyl-2-(trifluoromethyl)pyrrolo[3,2-b]pyridine (60 mg, 0.2 mmol, 1.0 equiv), bis(pinacolato)diboron (130 mg, 0.0 mmol, 2.5 equiv), AcOK (80 mg, 0.8 mmol, 4.0 equiv), dioxane (2.0 mL), $Pd(dppf)Cl_2$ (30 mg, 0.04 mmol, 0.2 equiv). The resulting solution was stirred for 4 hr at 90 degrees C. in an oil bath. The reaction mixture was cooled. The reaction mixture was used by next step.

Synthesis of 5-(4-cyclopropylphenyl)-3-(ethanesulfonyl)-2-[4-ethyl-2-(trifluoromethyl)pyrrolo[3,2-b]pyridin-6-yl]pyridine

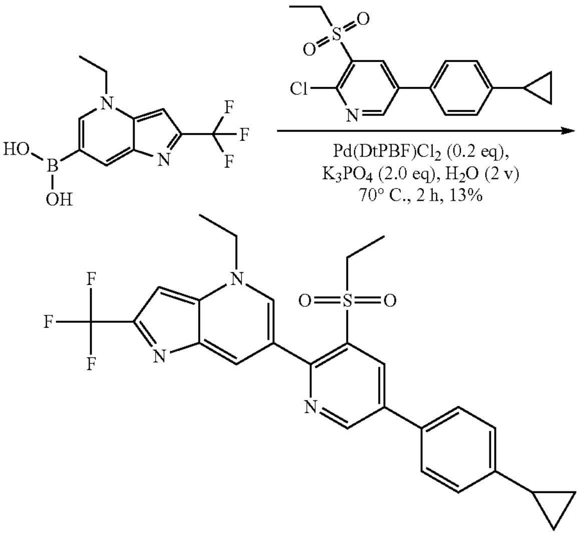

122

The reaction mixture was added 2-chloro-5-(4-cyclopropylphenyl)-3-(ethanesulfonyl)pyridine (66.23 mg, 0.206 mmol, 1.00 equiv), $K_3PO_4$ (174 mg, 0.8 mmol, 4.0 equiv), $H_2O$ (0.5 mL), $Pd(DtBPF)Cl_2$ (13 mg, 0.02 mmol, 0.1 equiv). Under the $N_2$ protect. The reaction mixture was stirred for 2 h at 70 degrees. The mixture was allowed to cool down to rt. The resulting mixture was diluted with EA 50 mL. The resulting mixture was washed with 30 mL of water. The organic phase was dried Na2SO4 and concentrated under vacuum. The crude product was purified by Prep-HPLC with the following conditions ($MeCN/H_2O$=90/10). The resulting mixture was concentrated to get 5-(4-cyclopropylphenyl)-3-(ethanesulfonyl)-2-[4-ethyl-2-(trifluoromethyl)pyrrolo[3,2-b]pyridin-6-yl]pyridine 14 mg (13%) as yellow solid.

Synthesis of Compound 125

Synthesis of 1-ethyl-5-nitro-3-(trifluoromethyl)-1,2-dihydropyridin-2-one

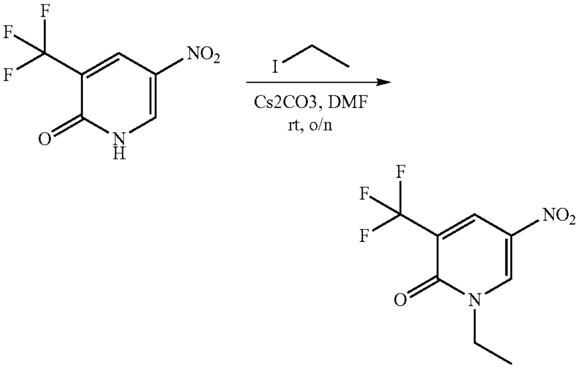

Into a 2 L 4-neck round-bottom flask were added 5-nitro-3-(trifluoromethyl)-1H-pyridin-2-one (21.8 g, 100 mmol, 1 equiv), DMF (I L), Cs2CO3 (97.7 g, 300 mmol, 3 equiv) and ethyl iodide (23.4 g, 150 mmol, 1.5 equiv). The resulting mixture was stirred for 18 h at room temperature. The resulting mixture was diluted with water (2 L). The resulting mixture was extracted with EA (3×1 L). The combined organic layers were washed with water (3×1 L) and brine (1×1 L), dried over anhydrous $Na_2SO_4$. After filtration, the filtrate was concentrated under reduced pressure. The residue was purified by silica gel column chromatography, eluted with PE: EA (3:1) to afford 1-ethyl-5-nitro-3-(trifluoromethyl)pyridin-2-one (12.0 g, 50%) as a yellow solid.

Synthesis of 6-amino-1-ethyl-5-nitro-3-(trifluoromethyl)-1,2-dihydropyridin-2-one

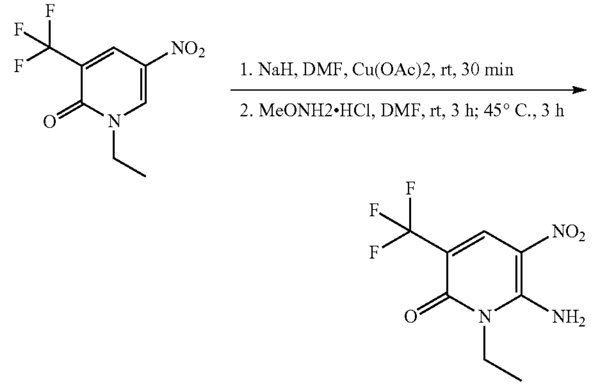

Into a 50 mL round-bottom flask were added 1-ethyl-5-nitro-3-(trifluoromethyl)pyridin-2-one (2.0 g, 8.5 mmol, 1 equiv), Cu(OAc)2 (0.15 g, 0.85 mmol, 0.1 equiv) and DMF (40 mL) at room temperature. To the above mixture was added NaH (2.24 g, 56 mmol, 6.6 equiv, 60%) in portions at 0° C. The resulting mixture was stirred for additional 30 mins at room temperature. To this was added the solution of MeONH2·HCl (1.4 g, 17 mmol, 2.0 equiv) DMF (10 mL) with dropwise at room temperature. The resulting mixture was stirred for 3 h at room temperature and additional 3 h at 45° C. The reaction mixture was poured into 100 mL of NH4Cl (sat.), then extracted with EA (3×100 mL). The combined organic layers were washed with water (3×100 mL) and brine (1×100 mL), dried over anhydrous Na2SO4. After filtration, the filtrate was concentrated under reduced pressure. The residue was purified by silica gel column chromatography, eluted with PE:EA (3:1) to afford 6-amino-1-ethyl-5-nitro-3-(trifluoromethyl)pyridin-2-one (400 mg, 19%) as a yellow solid.

Synthesis of 1-ethyl-6-(methylamino)-5-nitro-3-(trifluoromethyl)-1,2-dihydropyridin-2-one

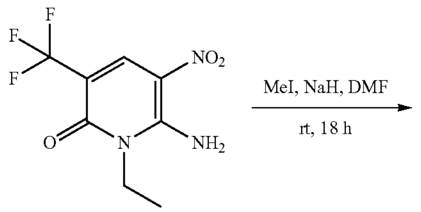

-continued

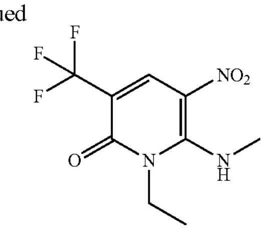

Into a 50 mL round-bottom flask were added 6-amino-1-ethyl-5-nitro-3-(trifluoromethyl)pyridin-2-one (400 mg, 1.6 mmol, 1 equiv), DMF (20 mL) and NaH (320 mg, 8 mmol, 5 equiv). The resulting mixture was stirred for 1 h at room temperature. To the above mixture was added CH3I (1.1 g, 8 mmol, 5 equiv) dropwise at room temperature. The resulting mixture was stirred for additional 18 at room temperature. The reaction mixture was poured into 100 mL of NH4Cl (sat.), then extracted with EA (3×100 mL). The combined organic layers were washed with water (3×100 mL) and brine (1×100 mL), dried over anhydrous Na2SO4. After filtration, the filtrate was concentrated under reduced pressure. The residue was purified by silica gel column chromatography, eluted with PE:EA (4:1) to afford 1-ethyl-6-(methylamino)-5-nitro-3-(trifluoromethyl)pyridin-2-one (80 mg, 19%) as a yellow solid.

Synthesis of 5-amino-1-ethyl-6-(methylamino)-3-(trifluoromethyl)-1,2-dihydropyridin-2-one

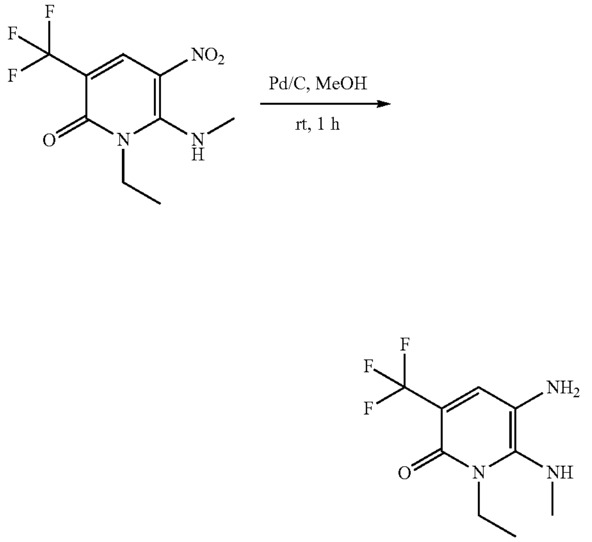

Into a 50-mL round-bottom flask, was placed a solution of 1-ethyl-6-(methylamino)-5-nitro-3-(trifluoromethyl)pyridin-2-one (60 mg, 0.2 mmol, 1 equiv), methanol (6 mL) and Pd/C (7.2 mg, 0.1 mmol, 0.3 equiv). The resulting mixture was stirred for $_1$ h at room temperature under $H_2$ atmosphere. The resulting solution was stirred for 1 h at room temperature. The solids were filtered out. The filtrate was concentrated under. This resulted is 5-amino-1-ethyl-6-(methylamino)-3-(trifluoromethyl)pyridin-2-one (50 mg, crude) as a yellow solid. The crude product was used in the next step directly without further purification.

Synthesis of 5-(4-cyclopropylphenyl)-N-[1-ethyl-2-(methylamino)-6-oxo-5-(trifluoromethyl)-1,6-dihydropyridin-3-yl]-3-(ethylsulfanyl)pyridine-2-carboxamide

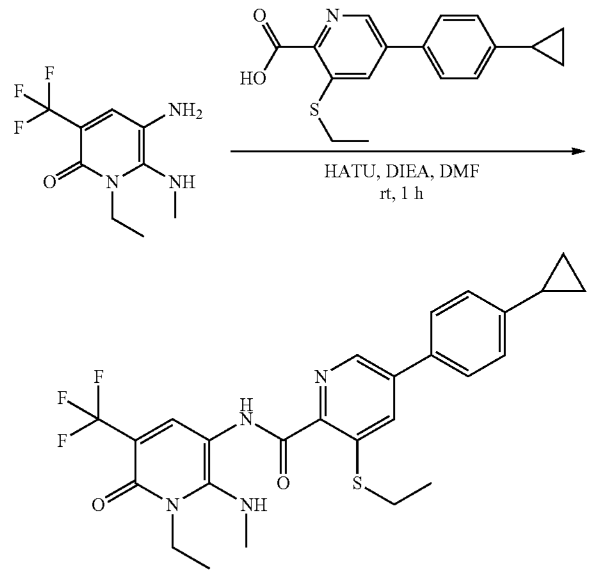

Into a 50 mL round-bottom flask were added 5-amino-1-ethyl-6-(methylamino)-3-(trifluoromethyl)pyridin-2-one (50 mg, 0.2 mmol, 1 equiv), 5-(4-cyclopropylphenyl)-3-(ethylsulfanyl)pyridine-2-carboxylic acid (64 mg, 0.2 mmol, 1 equiv), DMF (5 mL), HATU (162 mg, 0.4 mmol, 2 equiv) and DIEA (82 mg, 0.6 mmol, 3 equiv) at room temperature. The resulting mixture was stirred for 1 h at room temperature. The resulting mixture was diluted with EA (30 mL). The resulting mixture was washed with water (3×30 mL) and brine (1×30 mL). The resulting was dried anhydrous Na2SO4. The residue was purified by silica gel column chromatography, eluted with PE:EA (1:1) to afford 5-(4-cyclopropylphenyl)-N-[1-ethyl-2-(methylamino)-6-oxo-5-(trifluoromethyl)pyridin-3-yl]-3-(ethylsulfanyl)pyridine-2-carboxamide (30 mg, 27%) as a yellow solid.

Synthesis of 6-amino-1-ethyl-5-nitro-3-(trifluoromethyl)-1,2-dihydropyridin-2-one

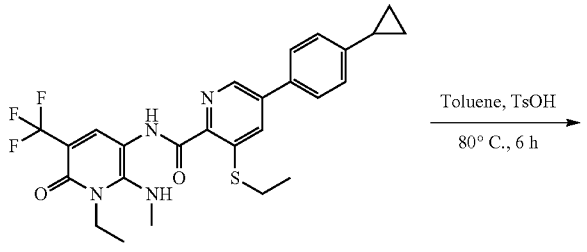

-continued

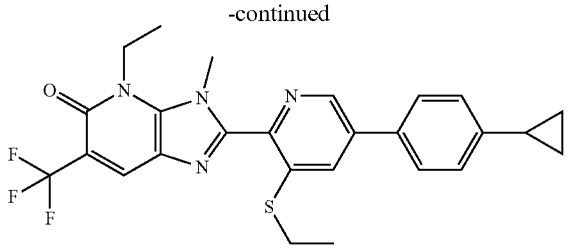

Into a 8 mL vial were added 5-(4-cyclopropylphenyl)-N—[I-ethyl-2-(methylamino)-6-oxo-5-(trifluoromethyl) pyridin-3-yl]-3-(ethylsulfanyl)pyridine-2-carboxamide (30 mg, 0.06 mmol, 1 equiv), toluene (3 mL) and TsOH (2 mg, 0.01 mmol, 0.2 equiv) at room temperature. The resulting mixture was stirred for 6 h at 80° C. The resulting mixture was concentrated under reduced pressure. The residue was purified by silica gel column chromatography, eluted with PE: EA (1:1) to afford 2-[5-(4-cyclopropylphenyl)-3-(ethylsulfanyl)pyridin-2-yl]-4-ethyl-3-methyl-6-(trifluoromethyl) imidazo[4,5-b]pyridin-5-one (10 mg, 34%) as a yellow solid.

Synthesis of 2-[5-(4-cyclopropylphenyl)-3-(ethanesulfonyl)pyridin-2-yl]-4-ethyl-3-methyl-6-(trifluoromethyl)-3H,4H,5H-imidazo[4,5-b]pyridin-5-one

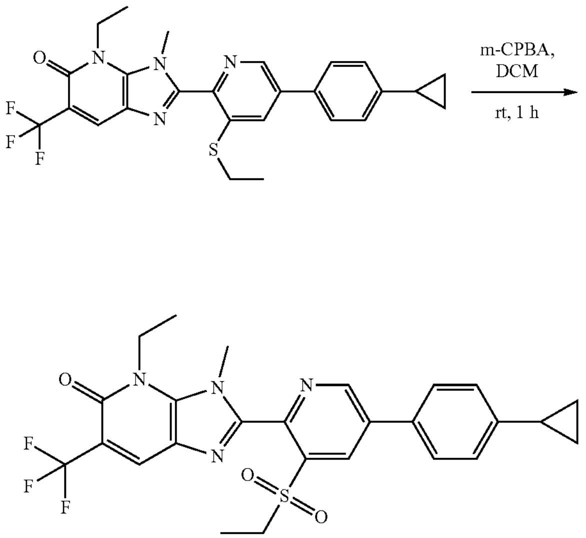

125

Into a 50 mL round-bottom flask were added 2-[5-(4-cyclopropylphenyl)-3-(ethylsulfanyl)pyridin-2-yl]-4-ethyl-3-methyl-6-(trifluoromethyl)imidazo[4,5-b]pyridin-5-one (20 mg, 0.04 mmol, 1 equiv), DCM (2 mL) and m-CPBA (17 mg, 0.10 mmol, 2.5 equiv). The reaction mixture was stirred for 1 h at room temperature. The mixture was purified by silica gel column chromatography, eluted with PE: EA (1:1) to afford 2-[5-(4-cyclopropylphenyl)-3-(ethanesulfonyl) pyridin-2-yl]-4-ethyl-3-methyl-6-(trifluoromethyl)imidazo [4,5-b]pyridin-5-one (8.3 mg, 39%) as a white solid.

Example 2: Physicochemical Characterization of Compounds 1 to 214

| Compound | (ES, m/z) | $^1$H NMR Spectra |
|---|---|---|
| 1 | | (400 MHz, $CDCl_3$, ppm): δ 9.19 (d, J = 2.0 Hz, 1H), 8.80 (d, J = 7.3 Hz, 1H,), 8.69 (d, J = 2.3 Hz, 1H), 8.14 (s, 1H), 7.64-7.60 (m, 2H), 7.33-7.30 (m, 2H), 4.09 (s, 2H), 4.06 (q, J = 7.8 Hz, 2H), 2.01-1.97 (m, 1H), 1.44 (t, J = 7.4 Hz, 3H), 1.10-1.04 (m, 2H), 0.81-0.77 (m, 2H) |
| 2 | | (400 MHz, $CDCl_3$, ppm): δ 9.20-9.19 (m, 1H), 8.83-8.79 (m, 1H), 8.70 (d, J = 2.0 Hz, 1H), 8.15 (s, 1H), 7.74-7.71 (m, 2H), 7.50-7.47 (m, 2H), 7.33 (d, J = 7.1 Hz, 1H), 4.08 (q, J = 7.3 Hz, 2H), 1.85-1.83 (m, 2H), 1.52-1.49 (m, 2H), 1.45 (t, J = 7.5 Hz, 3H) |
| 3 | 539 $[M + H]^+$ | (300 MHz, DMSO-d6, ppm): δ 9.77 (s, 1H), 9.10 (s, 1H), 8.84 (s, 1 H), 8.11 (d, J = 7.5 Hz, 1H), 7.91 (t, J = 7.8 Hz, 1H), 7.48 (d, J = 7.5 Hz, 1H), 4.00 (s, 3H), 3.82 (q, J = 7.5 Hz, 2H), 2.29-2.21 (m, 1 H), 1.25 (t, J = 7.2 Hz, 3H), 1.13-1.02 (m, 4H). |
| 4 | 539 [M + H]+ | (300 MHz, DMSO-d6, ppm): δ 9.85 (s, 1H), 9.19 (s, 1H), 8.83 (s, 1H), 8.63 (d, J = 5.1 Hz, 1H), 8.07 (s, 1H), 7.29 (brs, 1H), 4.01 (s, 3H), 3.82 (q, 7.2 Hz, 2H), 2.18-2.02 (m, 1H), 1.25 (t, J = 7.2 Hz, 3H), 1.25-1.11 (m, 2H), 1.09-0.96 m, 2H). |
| 5 | 539 [M + H]+ | (300 MHz, CDCl3, ppm): δ 9.63 (s, 1H), 9.09 (s, 1H), 8.62 (s, 1H), 8.21 (s, 1H), 7.84 (d, J = 8.1 Hz, 1H), 7.51 (d, J = 8.1 Hz, 1H), 4.10 (s, 3H), 3.87-3.79 (m, 2H), 2.07-1.98 (m, 1H), 1.42 (t, J = 7.5 Hz, 3H), 1.18-1.11 (m, 2H), 0.88-0.83 (m, 2H) |
| 6 | 500 [M + H]+ | (300 MHz, CD3OD, ppm): δ 9.20 (d, J = 2.4 Hz, 1H), 8.73 (d, J = 2.4 Hz, 2H), 8.44 (s, 1H), 7.73-7.30 (m, 4H), 7.20 (s, 1H), 4.87-4.74 (m, 2H), 3.70-3.63 (m, 2H), 2.07-1.98 (m, 1H), 1.72 (t, J = 7.2 Hz, 3H), 1.28 (t, J = 7.5 Hz, 3H), 1.11-1.05 (m, 2H), 0.83-0.78 (m, 2H). |
| 7 | 604 [M + H]+ | (300 MHz, DMSO-d6, ppm): δ 9.33 (d, J = 2.1 Hz, 1H), 8.81 (s, 1H), 8.63 (d, J = 2.1 Hz, 1H), 8.58 (s, 1H), 8.11 (s, 1H), 8.06 (d, J = 8.1 Hz, 1H), 7.37-7.33 (m, 2H), 6.82 (t, J = 57.0 Hz, 1H), 5.31-5.22 (m, 2H), 4.49-4.42 (m, 2H), 2.22 (s, 1H), 1.35-1.31 (m, 3H), 1.17-1.10 (m, 2H), 0.94-0.87 (m, 2H). |
| 8 | 554 [M + H]+ | (300 MHz, CDCl3, ppm) δ 9.10 (d, J = 2.4 Hz, 1H), 8.72 (d, J = 2.1 Hz, 1H), 8.41 (s, 1H), 8.03 (s, 1H), 7.48-7.35 (m, 2H), 7.17 (s, 1H), 7.10-7.04 (m, 1H), 6.38-6.17 (m, 1H), 4.86-4.76 (m, 2H), 4.26-4.21 (m, 2H), 2.24-2.14 (m, 1H), 1.46-1.41 (m, 3H), 1.13-1.07 (m, 2H), 0.86-0.81 (m, 2H). |
| 9 | 554 [M + H]+ | (300 MHz, DMSO-d6, ppm): δ 9.26 (s, 1H), 8.84 (s, 1H), 8.58 (s, 1H), 8.56 (s, 1H), 7.72-7.28 (m, 4H), 6.92-6.48 (m, 1H), 5.35-5.18 (m, 2H), 4.58-4.30 (m, 2H), 2.18-2.11 (m, 1H), 1.31 (t, J = 7.2 Hz, 3H), 1.05-1.02 (m, 2H), 0.95-0.92 (m, 2H). |
| 10 | 604 [M + H]+ | (300 MHz, DMSO-d6, ppm): δ 9.33 (d, J = 2.1 Hz, 1H), 8.82 (s, 1H), 8.63 (d, J = 2.1 Hz, 1H), 8.59 (s, 1H), 7.88-7.81 (m, 2H), 7.56 (s, 1H), 7.34 (s, 1H), 6.81 (t, J = 57.3 Hz, 1H), 5.31-5.22 (m, 2H), 4.49-4.42 (m, 2H), 2.28 (s, 1H), 1.39-1.31 (m, 3H), 1.15-1.09 (m, 4H) |
| 11 | 536 [M + H]+ | (300 MHz, DMSO, ppm) δ 9.27 (d, J = 2.1 Hz, 1H), 8.80 (s, 1H), 8.60 (d, J = 2.1 Hz, 1H), 8.57 (s, 1H), 7.63-7.58 (m, 2H), 7.48-7.43 (m, 1H), 7.33 (s, 1H), 7.21-7.19 (m, 1H), 6.90-6.51 (m, 1H), 5.30-5.20 (m, 2H), 4.49-4.42 (m, 2H), 2.10-2.05 (m, 1H), 1.32 (t, J = 7.5 Hz, 3H), 1.06-0.97 (m, 2H), 0.86-0.78 (m, 2H). |
| 12 | 554 [M + H]+ | (300 MHz, DMSO-d6, ppm): δ 9.31 (d, J = 2.1 Hz, 1H), 8.85 (s, 1H), 8.63 (s, 1H), 8.57 (d, J = 2.4 Hz, 1H), 7.80 (d, J = 8.4 Hz, 2H), 7.30 (d, J = 8.1 Hz, 2H), 6.73 (t, J = 54 Hz, 1H), 5.21 (t, J = 14.4 Hz, 2H), 4.19 (q, J = 7.5 Hz, 2H), 2.08-1.99 (m, 1H), 1.27 (t, J = 7.5 Hz, 3H), 1.07-1.01 (m, 2H), 0.83-0.72 (m, 2H). |
| 13 | 518 [M + H]+ | (300 MHz, CDCl3, ppm): δ 9.18 (s, 1H), 8.68 (d, J = 10.5 Hz, 1H), 8.29 (s, 1H), 7.99 (s, 1H), 7.64 (d, J = 7.8 Hz, 2H), 7.25 (d, J = 10.2 Hz, 2H), 4.70 (q, J = 7.2 Hz, 2H), 4.13 (q, J = 7.2 Hz, 2H), 2.05-1.96 (m, 1H), 1.77 (t, J = 7.2 Hz, 3H), 1.43 (t, J = 7.5 Hz, 3H), 1.21-1.10 (m, 2H), 0.86-0.72 (m, 2H). |
| 14 | 499 [M + H]+ | (300 MHz, Chloroform-d, ppm) δ 9.61 (s, 1H), 9.05 (d, J = 2.1 Hz, 1H), 8.63 (d, J = 5.1 Hz, 1H), 7.62 (s, 1H), 7.46 (s, 1H), 7.16 (s, 1H), 7.04 (dd, J = 5.1, 1.5 Hz, 1H), 3.91 (q, J = 7.5 Hz, 2H), 3.79 (s, 3H), 2.08-2.00 (m, 1H), 1.41 (t, J = 7.5 Hz, 3H), 1.31-1.15 (m, 2H), 0.97-0.87 (m, 2H). |

-continued

| Compound | (ES, m/z) | $^1$H NMR Spectra |
|---|---|---|
| 15 | 498 [M + H]+; | (300 MHz, CDCl3, ppm): δ 9.16 (s, 1H), 8.66 (s, 1H), 7.64 (d, J = 8.4 Hz, 2H), 7.47 (s, 1H), 7.30-7.27 (m, 2H), 7.16 (s, 1H), 3.87 (q, J = 7.5 Hz, 2H), 3.80 (s, 3H), 2.06-1.97 (m, 1H), 1.39 (t, J = 7.5 Hz, 3H), 1.12-1.07 (m, 2H), 0.85-0.82 (m, 2H). |
| 16 | 537 [M + H]+ | (300 MHz, DMSO-d6, ppm) δ 9.62 (d, J = 2.1 Hz, 1H), 9.12 (d, J = 2.1 Hz, 1H), 8.81 (s, 1H), 8.60 (d, J = 5.4 Hz, 2H), 7.97 (s, 1H), 7.35 (s, 1H), 7.22-7.19 (m, 1H), 6.90-6.54 (m, 1H), 5.30-5.20 (m, 2H), 4.49-4.41 (m, 2H), 2.13-2.07 (m, 1H), 1.33-1.28 (m, 3H), 1.16-1.13 (m, 2H), 0.99-0.97 (m, 2H) |
| 17 | 538 [M + H]+ | (300 MHz, DMSO-d6, ppm): δ 9.48 (s, 1H), 8.83 (s, 1H), 8.70 (s, 1H), 7.88 (d, J = 9.1 Hz, 2H), 7.32 (d, J = 9.1 Hz, 2H), 4.00 (s, 3H), 3.82 (q, J = 7.5 Hz, 2H), 2.09-1.92 (m, 1H), 1.26 (t, J = 7.2 Hz, 3H), 1.12-0.99 (m, 2H), 0.85-0.72 (m, 2H). |
| 18 | 563.20 [M + H]+ | (300 MHz, CDCl3, ppm): δ 9.22 (s, 1H), 9.69 (s, 1H), 8.22 (s, 1H), 7.75 (d, J = 8.4 Hz, 2H), 7.52 (d, J = 8.4 Hz, 2H), 4.12 (s, 3H), 3.85 (q, J = 7.5 Hz, 2H), 1.91-1.83 (m, 2H), 1.55-1.48 (m, 2H), 1.42 (t, J = 7.5 Hz, 3H). |
| 19 | 556 [M + H]+ | (300 MHz, CDCl3, ppm): δ 9.23 (d, J = 2.1 Hz, 1H), 8.71 (d, J = 2.1 Hz, 1H), 8.22 (s, 1H), 7.75 (d, J = 8.1 Hz, 2H), 7.46 (d, J = 8.4 Hz, 2H), 4.12 (s, 3H), 3.84 (q, J = 7.5 Hz, 2H), 1.68-1.57 (m, 2H), 1.42 (t, J = 7.5 Hz, 3H), 1.22-1.14 (m, 2H). |
| 20 | 606 [M + H]+ | (300 MHz, Chloroform-d, ppm): δ 9.24 (d, J = 2.1 Hz, 1H), 8.72 (d, J = 2.1 Hz, 1H), 8.24 (s, 1H), 7.79-7.68 (m, 4H), 4.15 (s, 3H), 3.90-3.82 (m, 2H), 1.51-1.39 (m, 5H), 1.14 (s, 2H) |
| 21 | 554 [M + H]+ | (300 MHz, Chloroform-d, ppm) δ 9.25 (d, J = 2.1 Hz, 1H), 8.72 (d, J = 2.1 Hz, 1H), 8.24 (s, 1H), 7.80-7.69 (m, 2H), 7.57-7.49 (m, 2H), 4.14 (s, 3H), 3.86 (q, J = 7.5 Hz, 2H), 1.49-1.38 (m, 5H), 1.31-1.14 (m, 2H) |
| 22 | 525 [M + H]+ | (300 MHz, DMSO-d6, ppm): δ 9.29 (s, 1H), 8.87 (s, 1H), 8.62 (d, J = 1.8 Hz, 1H), 8.51 (s, 1H), 7.92 (d, J = 8.4 Hz, 2H), 7.54 (d, J = 8.4 Hz, 2H), 7.25 (s, 1H), 4.77-4.70 (m, 2H), 4.48-4.40 (m, 2H), 1.87-1.83 (m, 2H), 1.64-1.57 (m, 5H), 1.31 (t, J = 7.2 Hz, 3H) |
| 23 | 516 [M + H]+ | (300 MHz, CDCl3, ppm): δ 9.11 (s, 1H), 8.73 (s, 1H), 8.43 (s, 1H), 8.08 (s, 1H), 7.68 (d, J = 8.1 Hz, 2H), 7.46 (d, J = 8.4 Hz, 2H), 7.19 (s, 1H), 4.67-4.59 (m, 2H), 4.18-4.14 (m, 2H), 1.77 (t, J = 7.2 Hz, 3H), 1.45-1.35 (m, 5H), 1.16-1.12 (m, 2H) |
| 24 | 518 [M + H]+ | (300 MHz, Chloroform-d, ppm) δ 9.17 (s, 1H), 8.75 (d, J = 2.1 Hz, 1H), 8.50 (s, 1H), 8.10 (s, 1H), 7.75 (d, J = 8.4 Hz, 2H), 7.45 (d, J = 8.4 Hz, 2H), 7.22 (s, 1H), 4.64 (q, J = 7.2 Hz, 2H), 4.17 (s, 2H), 1.79 (t, J = 7.2 Hz, 3H), 1.69-1.52 (m, 2H), 1.43 (t, J = 7.5 Hz, 3H), 1.25-1.11 (m, 2H). |
| 25 | 568 [M + H]+ | (300 MHz, Chloroform-d, ppm): δ 9.14 (d, J = 2.2 Hz, 1H), 8.72 (d, J = 2.1 Hz, 1H), 8.48 (s, 1H), 8.08 (s, 1H), 7.76-7.59 (m, 4H), 7.20 (s, 1H), 4.66-4.58 (m, 2H), 4.13 (s, 2H), 1.76 (t, J = 7.3 Hz, 3H), 1.45-1.35 (m, 5H), 1.10 (s, 2H). |
| 26 | 473 [M + H]+ | (300 MHz, CDCl3, ppm): δ 9.44 (s, 1H), 9.02 (d, J = 2.1 Hz, 1H), 8.96 (s, 1H), 8.78 (d, J = 2.1 Hz, 1H), 8.08 (s, 1H), 7.65 (s, 1H), 7.62 (s, 1H), 7.31 (s, 2H), 3.99-3.92 (m, 2H), 2.05-1.97 (m, 1H), 1.50-1.45 (m, 3H), 1.18-1.05 (m, 2H), 0.85-0.79 (m, 2H). |
| 27 | 505 [M + H]+ | (300 MHz, DMSO-d6, ppm): δ 9.43 (dd, J = 6.3, 1.2 Hz, 2H), 9.30 (d, J = 2.4 Hz, 1H), 8.72 (d, J = 2.4 Hz, 1H), 8.27 (s, 1H), 7.85 (d, J = 8.4 Hz, 2H), 7.32 (d, J = 8.4 Hz, 2H), 3.93 (q, J = 7.2 Hz, 2H), 2.07-2.02 (m, 1H), 1.30 (t, J = 7.2 Hz, 3H), 1.08-1.02 (m, 2H), 0.82-0.76 (m, 2H). |
| 28 | 539 [M + H]+ | (300 MHz, DMSO-d6, ppm): δ 9.41-9.39 (m, 2H), 8.77 (d, J = 2.1 Hz, 1H), 8.27 (d, J = 0.9 Hz, 1H), 7.90 (d, J = 8.4 Hz, 2H), 8.32 (d, J = 8.4 Hz, 2H), 3.67 (q, J = 7.2 Hz, 2.H), 2.09-2.03 (m, 1H), 1.21 (t, J = 7.5 Hz, 3H), 1.07-1.04 (m, 2H), 0.82-0.78 (m, 2H). |
| 29 | 521 [M + H]+ | (300 MHz, CDCl3, ppm): δ 9.38 (d, J = 1.2 Hz, 1H), 9.01 (d, J = 2.4 Hz, 2H), 8.79 (d, J = 2.1 Hz, 1H), 8.52 (s, 1H), 7.64 (d, J = 8.4 Hz, 2H), 7.31-7.30 (m, 2H), 3.99 (q, J = 7.5 Hz, 2H), 2.07-1.98 (m, 1H), 1.49 (t, J = 7.5 Hz, 3H), 1.15-1.08 (m, 2H), 0.85-0.80 (m, 2H). |
| 30 | 537 [M + H]+ | (300 MHz, DMSO-d6, ppm): δ 9.66 (d, J = 6.6 Hz, 2H), 9.34 (d, J = 1.8 Hz, 1H), 9.06 (s, 1H), 8.75 (d, J = 2.1 Hz, 1H), 7.86 (d, J = 8.1 Hz, 2H), 7.33 (d, J = 8.4 Hz, 2H), 3.95 (q, J = 6.9 Hz, 2H), 2.07-2.02 (m, 1H), 1.31 (t, J = 7.5 Hz, 3H), 1.09-1.03 (m, 2H), 0.82-0.79 (m, 2H). |
| 31 | 473 [M + H]+ | (300 MHz, CDCl3, ppm): δ 9.18 (s, 1H), 9.12 (brs, 1H), 8.73 (d, J = 1.2 Hz, 1H), 8.45 (s, 1H), 7.98 (s, 1H), 7.61 (d, J = |

-continued

| Compound | (ES, m/z) | $^1$H NMR Spectra |
|---|---|---|
| | | 8.1 Hz, 2H), 7.25 (d, J = 8.4 Hz, 2H), 3.94 (q, J = 7.5 Hz, 2H), 2.00-1.94 (m, 1H), 1.39 (t, J = 7.5 Hz, 3H), 1.10-1.02 (m, 2H), 0.81-0.76 (m, 2H) |
| 32 | 505 [M + H]+ | (300 MHz, CDCl3, ppm): δ 9.09 (s, 2H), 8.69 (d, J = 2.1 Hz, 1H), 8.35 (s, 1H), 7.96 (s, 1H), 7.61 (d, J = 3.9 Hz, 2H), 6.91 (s, 2H), 3.92-3.85 (m, 2H), 2.03-1.94 (m, 1H), 1.39-1.34 (m, 3H), 1.09-1.03 (m, 2H), 0.79-0.88 (m, 2H). |
| 33 | 537 [M + H]+ | (400 MHz, CDCl3, ppm): δ 9.25 (s, 1H), 9.11 (s, 1H), 8.70 (d, J = 3.6 Hz, 1H), 8.58 (s, 1H), 8.51 (s, 1H), 7.62-7.52 (m, 2H), 7.26-7.24 (m, 2H), 4.02-3.96 (m, 2H), 2.02-1.96 (m, 1H), 1.42 (t, J = 7.6 Hz, 3H), 1.13-1.06 (m, 2H), 0.76-0.73 (m, 2H) |
| 34 | 537 [M + H]+ | (300 MHz, Chloroform-d, ppm): δ 9.21 (d, J = 2.2 Hz, 1H), 8.74 (d, J = 2.2 Hz, 1H), 8.58 (d, J = 1.8 Hz, 1H), 8.17 (d, J = 8.7 Hz, 1H), 7.96 (dd, J = 8.7, 0.6 Hz, 1H), 7.67-7.60 (m, 2H), 7.28 (d, J = 2.0 Hz, 2H), 4.08-4.00 (m, 2H), 2.04-1.95 (m, 1H), 1.47 (d, J = 14.9 Hz, 3H), 1.14-1.04 (m, 2H), 0.83-0.77 (m, 2H) |
| 35 | 538 [M + H]+ | (300 MHz, CDCl3, ppm) δ 9.65 (d, J = 2.0 Hz, 1H), 9.14 (d, J = 2.0 Hz, 1H), 8.68-8.58 (m, 2H), 8.24-8.15 (m, 1H), 7.99 (d, J = 8.7 Hz, 1H), 7.64 (s, 1H), 7.05 (d, J = 5.0 Hz, 1H), 4.06 (m, 2H), 2.07-2.04 (m, 1H), 1.30-1.17 (m, 2H), 0.97-0.94 (m, 2H). |
| 36 | 518 [M + H]+ | (300 MHz, CDCl3, ppm): δ 9.21 (d, J = 2.1 Hz, 1H), 8.67 (d, J = 2.1 Hz, 1H), 7.65 (d, J = 8.1 Hz, 2H), 7.41 (s, 1H), 7.29 (d, J = 7.2 Hz, 2H), 5.06 (q, J = 8.4 Hz, 2H), 3.96 (s, 3H), 3.82 (q, J = 7.5 Hz, 2H), 2.07-1.98 (m, 1H), 1.40 (q, J = 7.5 Hz, 3H), 1.15-1.08 (m, 2H), 0.85-0.83 (m, 2H) |
| 37 | 525 [M + H]+ | (300 MHz, CDCl3, ppm): δ 9.29 (d, J = 1.8 Hz, 1H), 8.74 (d, J = 2.1 Hz, 1H), 8.37 (s, 1H), 7.72-7.63 (m, 2H), 7.55-7.29 (m, 2H), 3.96-3.88 (m, 2H), 2.06-1.99 (m, 1H), 1.60-1.32 (m, 3H), 1.16-1.04 (m, 2H), 0.90-0.81 (m, 2H). |
| 38 | 539 [M + H]+ | (300 MHz, Chloroform-d, ppm) δ 9.23 (d, J = 2.1 Hz, 1H), 8.91-8.68 (m, 1H), 8.70 (d, J = 2.1 Hz, 1H), 8.24 (s, 1H), 7.92 (dd, J = 8.4, 2.2 Hz, 1H), 7.39 (d, J = 8.1 Hz, 1H), 4.14 (s, 3H), 3.87 (q, J = 7.5 Hz, 2H), 2.18-2.16 (m, 1H 1.43 (t, J = 7.5 Hz, 3H), 1.23-1.02 (m, 4H). |
| 39 | 488 [M + H]+ | (300 MHz, CDCl3, ppm): δ 9.23 (d, J = 2.4 Hz, 1H), 8.69 (d, J = 2.4 Hz, 1H), 8.21 (s, 1H), 7.68-7.63 (m, 2H), 7.32-7.29 (m, 2H), 4.13 (s, 3H), 3.86 (q, J = 7.5 Hz, 2H), 2.07-1.98 (m, 1H), 1.43 (t, J = 7.5 Hz, 3H), 1.16-1.09 (m, 2H), 0.86-8.22 (m, 2H). |
| 40 | 474 [M + H]+ | (300 MHz, DMSO-d6, ppm): δ 9.47 (d, J = 2.1 Hz, 1H), 9.02 (d, J = 4.4 Hz, 2H), 8.71 (d, J = 2.1 Hz, 1H), 7.88 (d, J = 8.2 Hz, 2H), 7.33 (d, J = 8.2 Hz, 2H), 3.93 (q, J = 7.4 Hz, 2H), 2.12-1.98 (m, 1H), 1.32 (t, J = 7.4 Hz, 3H), 1.13-1.02 (m, 2H), 0.85-0.73 (m, 2H). |
| 41 | 487 [M + H]+ | (300 MHz, CDCl3, ppm): δ 9.20 (d, J = 1.5 Hz, 1H), 8.80 (s, 1H), 8.68 (d, J = 2.1 Hz, 1H), 8.35 (s, 1H), 7.66 (d, J = 8.4 Hz, 2H), 7.30 (d, J = 8.4 Hz, 2H), 3.99-3.86 (m, 5H), 2.07-1.98 (m, 1H), 1.50-1.39 (m, 3H), 1.15-1.10 (m, 2H), 0.89-0.82 (m, 2H). |
| 42 | 550 [M + H]+ | (300 MHz, Chloroform-d, ppm) δ 8.69 (d, J = 2.0 Hz, 1H), 8.26 (s, 1H), 7.89 (d, J = 2.0 Hz, 1H), 7.65 (d, J = 8.4 Hz, 1H), 7.55 (d, J = 8.2 Hz, 2H), 7.48 (d, J = 8.3 Hz, 1H), 7.23 (d, J = 8.2 Hz, 2H), 3.97 (s, 3H), 3.02 (q, J = 7.3 Hz, 2H), 2.02-1.93 (m, 1H), 1.37 (t, J = 7.4 Hz, 3H), 1.10-1.01 (m, 2H), 0.78 (dt, J = 6.6, 4.7 Hz, 2H) |
| 43 | 534 [M + H]+ | (300 MHz, Chloroform-d, ppm) δ 9.71 (s, 1H), 8.50 (d, J = 1.9 Hz, 1H), 7.80 (d, J = 1.9 Hz, 1H), 7.75 (d, J = 2.1 Hz, 1H), 7.52 (d, J = 8.3 Hz, 2H), 7.46 (dd, J = 8.6, 2.2 Hz, 1H), 7.23 (d, J = 8.2 Hz, 2H), 6.98 (s, 1H), 6.75 (d, J = 8.5 Hz, 1H), 3.00 (q, J = 7.4 Hz, 2H), 1.98 (ddd, J = 13.4, 8.8, 5.0 Hz, 1H), 1.45 (t, J = 7.4 Hz, 3H), 1.26 (s, 3H), 1.10-1.02 (m, 2H), 0.81-0.74 (m, 2H) |
| 44 | 537.2 [M + H]+ | (300 MHz, Chloroform-d, ppm) δ: 9.23 (s, 1H), 8.75 (s, 1H), 8.68 (s, 1H), 8.35 (s, 1H), 7.66 (d, J = 8.1 Hz, 2H), 7.31 (s, 2H), 3.93 (d, J = 17.1 Hz, 5H), 2.08-1.96 (m, 1H), 1.42 (t, J = 7.2 Hz, 3H), 1.18-1.05 (m, 2H), 0.88-0.77 (m, 2H). |
| 45 | 543 [M + H]+ | (300 MHz, CDCl3, ppm): δ 9.14 (s, 1H), 8.61 (s, 1H), 7.61 (d, J = 4.2 Hz, 2H), 7.25-7.17 (m, 3H), 4.06 (s, 3H), 3.80 (q, J = 7.5 Hz, 2H), 3.19-3.01 (brs, 1H), 2.02-1.91 (m, 1H), 1.36 (t, J = 7.5 Hz, 3H), 1.39-1.21 (m, 2H), 1.15-1.02 (m, 4H), 0.85-0.72 (m, 2 H). |
| 46 | 472 [M + H]+ | (300 MHz, DMSO-d6, ppm) δ 9.27 (d, J = 2.1 Hz, 1H), 9.16 (d, J = 1.2 Hz, 1H), 8.70 (d, J = 2.1 Hz, 1H), 8.32-8.25 (m, 1H), 8.12 (d, J = 9.0 Hz, 1H), 7.87-7.78 (m, 2H), 7.40-7.39 |

-continued

| Compound | (ES, m/z) | $^1$H NMR Spectra |
|---|---|---|
| | | (m, 1H), 7.36-7.27 (m, 2H), 4.04-4.00 (m, 2H), 2.04-1.98 (m, 1H), 1.35-1.30 (m, 3H), 1.11-0.99 (m, 2H), 0.89-0.73 (m, 2H). |
| 47 | 472 [M + H]+ | (300 MHz, DMSO-d6, ppm) δ 9.28 (d, J = 2.4 Hz, 1H), 8.69-8.67 (m, 2H), 8.36 (s, 1H), 8.20 (d, J = 8.4 Hz, 1H), 7.86-7.76 (m, 2H), 7.67-7.64 (m, 1H), 7.34-7.22 (m, 2H), 4.01-3.94 (rm 2H), 2.03-1.98 (m, 1H), 1.37-1.32 (m, 3H), 1.13-0.93 (m, 2H), 0.83-0.66 (m, 2H) |
| 48 | 473 [M + H]+ | (300 MHz, CDCl3, ppm) δ 9.10 (s, 1H), 9.00 (d, J = 2.1 Hz, 1H), 8.88 (s, 1H), 8.77 (d, J = 2.4 Hz, 1H), 8.47 (s, 1H), 7.62 (d, J = 8.4 Hz, 2H), 7.30 (s, 1H), 4.01 (q, J = 7.2 Hz, 2H), 2.02-1.95 (m, 1H), 1.47 (t, J = 7.5 Hz, 3H), 1.17-1.05 (m, 2H), 0.82-0.79 (m, 2H) |
| 49 | 473 [M + H]+ | (300 MHz, CDCl3, ppm) δ 8.99 (d, J = 2.1 Hz, 1H), 8.95 (d, J = 1.5 Hz, 1H), 8.77 (d, J = 2.4 Hz, 1H), 8.71 (s, 1H), 8.57 (d, J = 0.9 Hz, 1H), 7.60 (d, J = 8.4 Hz, 2H), 7.26 (d, J = 8.4 Hz, 2H), 4.04 (q, J = 7.5 Hz, 2H), 1.98-1.95 (m, 1H), 1.49 (t, J = 7.5 Hz, 3H), 1.18-0.93 (m, 2H), 0.80-0.75 (m, 2H). |
| 50 | 490 [M + H]+ | (300 MHz, DMSO-d6, ppm): δ 9.47 (s, 1H), 9.20 (s, 2H), 8.74 (s, 1H), 8.00-7.70 (m, 2H), 7.45-7.10 (m, 2H), 4.30-4.05 (m, 2H), 2.15-1.91 (m, 1H), 1.46-1.25 (m, 3H), 1.30-1.20 (m, 1H, Nonvolatile solvent), 1.15-0.99 (m, 2H), 0.91-0.71 (m, 2H). |
| 51 | 553 [M + H]+ | (300 MHz, CDCl3, ppm): δ 9.12 (d, J = 2.1 Hz, 1H), 8.81 (d, J = 2.1 Hz, 1H), 8.78 (s, 1H), 8.28 (d, J = 8.4 Hz, 1H), 8.07 (d, J = 8.7 Hz, 1H), 7.65-7.61 (m, 2H), 7.26 (s, 2H), 4.20 (q, J = 7.5 Hz, 2H), 2.04-1.95 (m, 1H), 1.64-1.46 (m, 3H), 1.12-1.05 (m, 2H), 0.82-0.73 (m, 2H). |
| 52 | 513 [M + H]+ | (300 MHz, DMSO-d6, ppm) δ 9.24 (d, J = 2.1 Hz, 1H), 8.54 (d, J = 2.1 Hz, 1H), 8.50 (d, J = 3.0 Hz, 1H), 7.89 (d, J = 8.7 Hz, 1H), 7.77-7.73 (m, 3H), 7.29 (d, J = 8.1 Hz, 2H), 5.12-5.03 (m, 2H), 4.01-3.93 (m, 2H), 2.05-1.97 (m, 1H), 1.31-1.24 (m, 3H), 1.06-1.00 (m, 2H), 0.82-0.72 (m, 2H). |
| 53 | 514 [M + H]+ | (300 MHz, CDCl3, ppm):6 9.21 (d, J = 2.1 Hz, 1H), 8.90 (d, J = 5.1 Hz, 1H), 8.75 (s, 1H), 8.67 (d, J = 2.1 Hz, 1H), 7.66-7.62 (m, 3H), 7.30 (s, 1H), 7.27 (s, 1H), 4.12 (s, 3H), 3.86 (q, J = 7.5 Hz, 2H), 2.06-1.99 (m, 1H), 1.41 (t, J = 7.5 Hz, 3H), 1.14-1.08 (m, 2H), 0.85-0.83 (m, 2H). |
| 54 | 513 [M + H]+ | (300 MHz, DMSO-d6, ppm): δ 9.35 (s, 1H), 8.93 (d, J = 4.8 Hz, 1H), 8.56 (s, 1H), 8.24 (s, 1H), 7.94 (s, 1H), 7.81 (d, J = 7.8 Hz, 2H), 7.70 (d, J = 5.1 Hz, 1H), 7.30 (d, J = 7.8 Hz, 2H), 3.91-3.87 (m, 5H), 2.08-1.99 (m, 1H), 1.24 (t, J = 7.5 Hz, 3H), 1.06-1.03 (m, 2H), 0.79-0.77 (m, 2H). |
| 55 | 513 [M + H]+ | (300 MHz, DMSO-d6, ppm): δ 9.33 (d, 1 = 2.1 Hz, 1H), 8.84 (d, J = 5.1 Hz, 1H), 8.59 (d, J = 2.4 Hz, 1H), 8.14 (s, 1H), 7.98 (s, 1H), 7.81 (d, J = 8.4 Hz, 2H), 7.62 (d, J = 4.2 Hz, 1H), 7.30 (d, J = 8.1 Hz, 2H), 4.04 (q, J = 7.2 Hz, 2H), 3.76 (s, 3H), 2.06-2.01 (m, 1H), 1.28 (t, J = 7.5 Hz, 3H), 1.08-1.01 (m, 2H), 0.80-0.78 (m, 2H). |
| 56 | 501 [M + H]+ | (300 MHz, CDCl3, ppm) δ: 9.16 (s, 1H), 8.65 (s, 1H), 7.63 (d, J = 72 Hz, 2H), 7.27 (d, J = 7.2 Hz, 1H), 3.86-3.69 (m, 4H), 3.65 (s, 3H), 2.00 (m, 1H), 1.38 (t, J = 7.2 Hz, 3H), 1.17-1.06 (m, 2H), 0.87-0.77 (m, 2H). |
| 57 | 481 [M + H]+ | (300 MHz, CDCl3, ppm) δ: 9.16 (s, 1H), 8.66 (s, 1H), 8.04 (d, J = 2.1 Hz, 2H), 7.27 (d, J = 2.1 Hz, 2H), 6.51 (d, J = 30.9 Hz, 1H), 3.84 (t, J = 7.2 Hz, 2H), 3.69 (s, 3H), 2.02 (m, 1H), 1.40 (t, J = 7.2 Hz, 3H), 1.11 (m, 2H), 0.83 (m, 2H). |
| 58 | 501 [M + H]+ | (300 MHz, CDCl3, ppm) δ 9.24 (s, 1H), 8.71 (s, 1H), 8.51 (s, 1H), 8.19 (s, 1H), 7.64 (d, J = 7.8 Hz, 2H), 7.25-7.23 (m, 2H), 4.92 (q, J = 7.2 Hz, 2H), 4.22 (q, J = 7.5 Hz, 2H), 2.00-1.98 m, 1H), 1.78 (t, J = 7.5 Hz, 3H), 1.46 (t, J = 7.5 Hz, 3H), 1.15-1.02 (m, 2H), 0.81-0.79 (m, 2H). |
| 59 | 501 [M + H]+ | (300 MHz, Chloroform-d, ppm): δ 9.20 (d, J = 1.8 Hz, 1H), 8.82-8.76 (m, 1H), 8.69 (d, J = 2.1 Hz, 1H), 8.35 (d, J = 2.1 Hz, 1H), 7.66 (d, J = 8.1 Hz, 2H), 7.30-7.28 (m, 2H), 4.47 (q, J = 7.2 Hz, 2H), 3.94 (q, J = 7.5 Hz, 2H), 2.02-2.00 (m, 1H), 1.45-1.40 (m, 6H), 1.18-1.05 (m, 2H), 0.83-0.80 (m, 2H). |
| 60 | 539 [M + H]+ | (300 MHz, CDCl3, ppm): δ 9.29 (s, 1H), 8.78 (s, 2H), 8.70 (d, J = 3.6 Hz, 1H), 8.26 (s, 1H), 7.63-7.47 (m, 2H), 4.15 (s, 3H), 3.89 (q, J = 4.5 Hz, 1H), 2.29 (s, 1H), 1.45 (t, J = 7.5 Hz 3H), 1.24-1.19 (m, 4H). |
| 61 | 539 [M + H]+ | (300 MHz, CDCl3, ppm): δ 9.26 (s, 1H), 8.89 (s, 1H), 8.74 (s, 1H), 8.59 (s, 1H), 8.24 (s, 1H), 7.93 (m, 1H), 4.14 (s, 3H), 3.91-3.82 (m, 2H), 2.33-2.14 (m, 1H), 1.44-1.37 (m, 3H), 1.34-1.26 (m, 2H), 1.02-0.91 (m, 2H) |
| 62 | 561 [M + H]+ | (300 MHz, DMSO-d6, ppm) δ 9.30 (d, J = 1.8 Hz, 1H), 8.82 (s, 1H), 8.66-8.56 (m, 2H), 7.93 (d, J = 8.4 Hz, 2H), 7.55 (d, |

-continued

| Compound | (ES, m/z) | $^1$H NMR Spectra |
|---|---|---|
| | | J = 8.4 Hz, 21-1), 7.35 (s, 1H), 6.72 (t, J = 54.0 Hz, 1H), 5.26 (t, J = 12.0 Hz, 2H), 4.44 (d, J = 7.5 Hz, 2H), 1.85 (q, J = 4.8 Hz, 2H), 1.62 (q, J = 5.1 Hz, 2H), 1.32 (t, J = 7.5 Hz, 3H). |
| 63 | 604 [M + H]+ | (300 MHz, DMSO-d6, ppm): δ 9.30 (s, 1H), 8.81 (s, 1H), 8.63-8.59 (m, 2H), 7.92 (d, J = 7.8 Hz, 1H), 7.68 (d, J = 7.5 Hz, 2H), 7.35 (s, 1H), 6.72 (t, J = 54.3 Hz, 2H), 5.26 (t, J = 15.3 Hz, 2H), 4.49-4.42 (m, 2H), 1.44-1.40 (m, 2H), 1.32 (t, J = 7.5 Hz, 3H), 1.21 (m, 2H). |
| 64 | 537 [M + H]+ | (300 MHz, DMSO-d6, ppm) δ 9.32 (d, J = 2.1 Hz, 1H), 8.92 (d, J = 2.4 Hz, 1H), 8.81 (s, 1H), 8.66-8.55 (m, 2H), 8.17-8.15 (m, 1H), 7.51 (d, J = 8.1 Hz, 1H), 7.35 (s, 1H), 6.72 (t, J = 54.0 Hz, 1H), 5.26 (t, J = 14.4 Hz, 2H), 4.45 (q, J = 7.5 Hz, 2H), 2.22-2.20 (m, 1H), 1.33 (t, J = 7.5 Hz, 3H), 1.03-1.00 (m, 4H). |
| 65 | 622 [M + H]+ | (300 MHz, DMSO-d6, ppm) δ 9.35 (d, J = 2.1 Hz, 1H), 8.87 (s, 1H), 8.68-8.59 (m, 2H), 7.98-7.90 (m, 2H), 7.69 (d, J = 8.1 Hz, 2H), 6.92-6.58 (m, 1H), 5.22 (t, J = 15.0 Hz, 2H), 4.20 (q, J = 7.5 Hz, 2H), 1.47-1.37 (m, 2H), 1.28 (t, J = 7.5 Hz, 3H), 1.22 (s, 2H). |
| 66 | 586 [M + H]+ | (300 MHz, DMSO-d6, ppm): δ 9.34 (s, 1H), 8.90 (s, 1H), 8.61 (s, 1H), 5.54 (s, 1H), 7.93 (d, J = 8.4 Hz, 2H), 7.68 (d, J = 7.8 Hz, 2H), 4.79-4.74 (m, 2H), 4.24-4.16 (m, 2H), 1.61 (t, J = 7.2 Hz, 3H), 1.44-1.40 (m, 2H), 1.35-1.22 (m, 5H). |
| 67 | 579 [M + H]+ | (300 MHz, DMSO-d6, ppm) δ 9.35 (s, 1H), 8.87 (s, 1H), 8.61 (s, 2H), 7.95 (d, J = 8.1 Hz, 2H), 7.55 (d, J = 7.5 Hz, 2H), 6.74 (t, J = 54.0 Hz, 1H), 6.54 (d, J = 8.3 Hz, 1H), 5.22 (t, J = 15.0 Hz, 2H), 4.20 (d, J = 7.5 Hz, 2H), 1.85 (d, J = 2.4 Hz, 2H), 1.62 (d, J = 3.0 Hz, 2H), 1.28 (t, J = 7.5 Hz, 2H). |
| 68 | 543 [M + H]+ | (300 MHz, DMSO-d6, ppm): δ 9.34 (s, 1H), 8.90 (s, 1H), 8.61-8.54 (m, 2H), 7.94 (d, J = 8.4 Hz, 2H), 7.94 (d, J = 8.1 Hz, 2H), 4.79-4.72 (m, 2H), 4.24-4.16 (m, 2H), 1.87-1.83 (m, 2H), 1.64-1.59 (m, 5H), 1.28 (t, J = 7.5 Hz, 3H). |
| 69 | 555 [M + H]+ | (300 MHz, DMSO-d6, ppm): δ 9.36 (s, 1H), 8.94 (s, 1H), 8.87 (s, 1H), 8.63 (s, 2H), 8.19 (d, J = 8.4 Hz, 1H), 7.52 (d, J = 8.4 Hz, 1H), 6.91-6.56 (m, 1H), 5.27-5.16 (m, 2H), 4.21-4.14 (m, 2H), 2.27-2.18 (m, 1H), 1.31-1.24 (m, 5H), 1.05-1.03 (m, 2H). |
| 70 | 519 [M + H]+ | (300 MHz, DMSO-d6, ppm): δ 9.35 (s, 1H), 8.91 (d, J = 9.9 Hz, 2H), 8.62 (s, 1H), 8.54 (s, 1H), 8.19 (d, J = 8.1 Hz, 1H), 7.51 (d, J = 8.1 Hz, 1H), 4.76-4.72 (m, 2H), 4.22-4.15 (m, 2H), 2.24-2.22 (m, 1H), 1.61 (t, J = 7.2 Hz, 3H), 1.28 (t, J = 7.5 Hz, 3H), 1.05-1.03 (m, 4H) |
| 71 | 564 [M + H]+ | (300 MHz, CDCl3, ppm): δ 9.25 (s, 1H), 8.87 (s, 1H), 8.73 (s, 1H), 8.20 (s, 1H), 8.09 (d, J = 8.1 Hz, 1H), 7.99 (d, J = 7.5 Hz, 1H), 4.16 (s, 3H), 3.93-3.85 (m, 2H), 1.99-1.88 (m, 4H), 1.45 (t, J = 7.5 Hz, 3H). |
| 72 | 607 [M + H]+ | (300 MHz, CDCl3, ppm): δ 9.28 (s, 1H), 9.16 (d, J = 7.5 Hz, 1H), 8.94 (s, 1H), 8.30 (d, J = 3.9 Hz, 1H), 8.26-8.13 (m, 1H), 7.94 (d, J = 7.5 Hz, 1H), 4.16 (s, 3H), 4.02-3.82 (m, 2H), 2.61-2.15 (m, 4H), 1.45 (t, J = 6.6 Hz, 3H). |
| 73 | 541 [M + H]+ | (300 MHz, Chloroform-d, ppm): δ 9.28 (s, 1H), 9.03 (d, J = 2.4 Hz, 1H), 8.77 (d, J = 2.4 Hz, 1H), 8.47 (d, J = 0.9 Hz, 1H), 8.36 (s, 1H), 7.71-7.60 (m, 4H), 4.02 (q, J = 7.5 Hz, 2H), 1.54-1.43 (m, 5H), 1.19-1.09 (m, 2H). |
| 74 | 541 [M + H]+ | (300 MHz, Chloroform-d, ppm) δ9.40 (s, 1H), 9.01 (d, J = 2.1 Hz, 2H), 8.95 (d, J = 2.1 Hz, 1H), 8.78 (d, J = 2.4 Hz, 1H), 8.05 (s, 1H), 7.71-7.65 (m, 4H), 4.32 (q, J = 7.5 Hz, 2H), 1.49-1.43 m, 5H), 1.11-0.93 (m, 2H). |
| 75 | 498 [M + H]+ | (300 MHz, DMSO-d6, ppm): δ 9.43 (s, 1H), 9.02 (s, 1H), 8.89 (s, 1H), 8.79 (s, 1H), 8.08 (s, 1H), 7.73 (d, J = 8.4 Hz, 2H), 7.52 (d, J = 8.4 Hz, 2H), 4.03-3.96 (m, 2H), 1.88 (t, J = 3.9 Hz, 2H), 1.62-1.47 (m, 5H) |
| 76 | 498 [M + H]+ | (300 MHz, DMSO-d6, ppm): δ 9.30 (s, 1H), 9.05 (s, 1H), 8.79 (s, 1H), 8.50 (s, 1H), 8.38 (s, 1H), 7.73 (d, J = 8.1 Hz, 2H), 7.51 (d, J = 8.1 Hz, 2H), 4.06-3.98 (m, 2H), 1.87 (t, J = 3.75 Hz, 2H), 1.55-1.46 (m, 5H) |
| 77 | 474 [M + H]+ | 1H NMR(300 MHz, Chloroform-d, ppm) δ 9.31 (s, 1H), 9.04 (d, J = 2.1 Hz, 1H), 8.82 (d, J = 2.4 Hz, 2H), 8.78 (d, J = 0.9 Hz, 1H), 8.50 (s, 1H), 8.39 (s, 1H), 7.92-7.89 (m, 1H), 7.38 J = 8.1 Hz, 1H), 4.03 (q, J = 7.5 Hz, 2H), 2.22-2.14 (m, 1H), 1.51 (t, J = 7.5 Hz, 3H), 1.22-1.08 (m, 4H) |
| 78 | 474 [M + H]+ | (300 MHz, Chloroform-d, ppm) δ 9.47 (s, 1H), 9.02-8.98 (m, 2H), 8.82-8.78 (m, 2H), 8.08 (s, 1H), 7.91-7.88 (m, 1H), 7.39 (d, J = 8.1 Hz, 1H), 4.01 (q, J = 7.5 Hz, 2H), 2.23-2.19 (m, 1H), 1.49 (t, J = 7.5 Hz, 3H), 1.22-1.11 (m, 4H). |

-continued

| Compound | (ES, m/z) | $^1$H NMR Spectra |
|---|---|---|
| 79 | 605 [M + H]+ | (300 MHz, CDCl3, ppm): δ 9.21 (d, J = 2.1 Hz, 1H), 8.75-8.66 (m, 2H), 8.38 (s, 1H), 7.82-7.34 (m, 4H), 3.97-3.89 (m, 5H), 1.48-1.43 (m, 5H), 1.14 (s, 2H). |
| 80 | 562 [M + H]+ | (300 MHz, CDCl3, ppm): δ 9.21 (s, 1H), 8.76 (s, 1H), 8.70 (s, 1H), 8.35 (s, 1H), 7.76 (d, J = 7.8 Hz, 2H), 7.53 (d, J = 8.1 Hz, 2H), 4.00-3.90 (m, 5H), 2.04-1.89 (m, 2H), 1.55 (t, J = 5.7 Hz, 2H), 1.46-1.35 (m, 3H). |
| 81 | 552 [M + H]+ | (300 MHz, CDCl3, ppm): δ 9.24 (d, J = 2.1 Hz, 1H), 8.75 (d, J = 3.0 Hz, 2H), 7.72-7.63 (m, 2H), 7.32-7.28 (m, 2H), 4.19 (s, 3H), 3.80 (q, J = 7.5 Hz 2H), 2.07-1.99 (m, 1H), 1.69-1.58 (m, 3H), 1.16-1.09 (m, 2H), 0.86-0.74 (m, 2H). |
| 82 | 551.25 [M + H]+ | (300 MHz, CDCl3, ppm): δ 9.22 (s, 1H), 9.11 (s, 1H), 8.74-8.68 (m 2H), 7.71-7.62 (m, 2H), 7.33-7.29 (m, 2H), 3.99 (s, 3H), 3.88 (q, J = 7.5 Hz, 2H), 2.10-1.96 (m, 1H), 1.44 (t, J = 7.5 Hz, 3H), 1.15-1.08 (m, 2H), 0.88-0.80 (m, 2H). |
| 83 | 519.25 [M + H]+ | (300 MHz, CDCl3, ppm): δ 9.20 (s, 1H), 8.76 (s, 1H), 8.68 (s, 1H), 8.44 (s, 1H), 7.67-7.63 (m, 2H), 7.33-7.28 (m, 2H), 3.97-3.85 (m, 5H), 2.21-1.95 (m, 1H), 1.42 (t, J = 7.5 Hz, 3H), 1.17-1.07 (m, 2H), 0.86-0.78 (m, 2H). |
| 84 | 553 [M + H]+ | (300 MHz, CDCl3, ppm): δ 9.24 (d, J = 2.1 Hz, 1H), 8.85 (d, J = 2.1 Hz, 1H), 8.71 (t, J = 2.1 Hz, 2 H), 7.94-7.90 (m, 1H), 7.41-7.39 (m, 1H), 4.20 (s, 3H), 3.85 (q, J = 8.1 Hz 2H), 2.22-2.03 (m, 1H), 1.65-1.42 (m, 3H), 1.29-1.16 (m, 4H). |
| 85 | 577 [M + H]+ | (300 MHz, CDCl3, ppm): δ 9.25 (d, J = 1.8 Hz, 1H), 8.72 (s, 2H), 7.77 (d, J = 8.4 Hz, 2H), 7.55 (d, J = 8.4 Hz, 2H), 4.20 (s, 3H), 3.85 (q, J = 7.5 Hz, 2H), 1.92-1.82 (m, 2H), 1.58-1.48 (m, 2H), 1.45-1.43 (m, 3H). |
| 86 | 620 [M + H]+ | (300 MHz, CDCl3, ppm): δ 9.25 (d, J = 2.1 Hz, 1H), 8.73-7.72 (m, 2H), 7.77-7.71 (m, 4H), 4.20 (s, 3H), 3.85 (q, J = 7.5 Hz 2H), 1.58-1.42 (m, 5H), 1.28-1.14 (m, 2H). |
| 87 | 611 [M + H]+ | (300 MHz, CDCl3, ppm) δ: 9.18 (d, J = 2.1 Hz, 1H), 8.67 (d, J = 2.1 Hz, 1H), 7.71 (d, J = 2.1 Hz, 4H), 7.22 (s, 1H), 4.11 (s, 3H), 3.83 (q, J = 7.5 Hz, 2H), 3.14 (m, 1H), 1.52-1.44 (m, 2H), 1.39 (t, J = 7.5 Hz, 3H), 1.32 (m, 2H), 1.12 (m, 4H) |
| 88 | 568 [M + H]+ | (300 MHz, CDCl3, ppm) δ: 9.17 (d, J = 2.4 Hz, 1H), 8.66 (d, J = 2.4 Hz, 1H), 7.73 (d, J = 8.4 Hz, 2H), 7.52 (d, J = 8.4 Hz, 2H), 7.22 (s, 1H), 4.10 (s, 3H), 3.84 (q, J = 7.5 Hz, 2H), 3.13 (m, 1H), 1.93-1.82 (m, 2H), 1.56-1.48 (m, 2H), 1.40 (t, J = 7.5 Hz, 3H), 1.36-1.28 (m, 2H), 1.10 (m, 2H). |
| 89 | 544 [M + H]+ | (300 MHz, CDCl3, ppm) δ: 9.16 (d, J = 2.4 Hz, 1H), 8.82 (d, J = 2.4 Hz, 1H), 8.65 (d, J = 2.4 Hz, 1H), 7.91 (dd, J = 8.4, 2.4 Hz, 1H), 7.37 (d, J = 8.4 Hz, 1H), 7.22 (s, 1H), 4.11 (s, 3H), 3.84 (q, J = 7.5 Hz, 2H), 3.13 (m, 1H), 2.20 (m, 1H), 1.40 (t, J = 7.5 Hz, 3H), 1.32 (q, J = 7.2 Hz, 2H), 1.21-1.07 (m, 6H). |
| 90 | 538.25 [M + H]+ | (300 MHz, CDCl3, ppm): δ 9.20 (s, 1H), 8.85 (s, 1H), 8.75 (s, 1H), 8.70 (s, 1H), 8.32 (s, 1H), 7.97-7.91 (m, 1H), 7.45-7.28 (m, 1H), 4.05-3.89 (m, 5H), 2.28-2.12 (m, 1H), 1.43 (t, J = 7.5 Hz, 3H), 1.23-1.11 (m, 4H). |
| 91 | 540 [M + H]+ | (300 MHz, CDCl3, ppm): δ 9.98 (s, 1H), 9.50 (s, 1H), 8.64 (s, 2H), 8.22 (s, 1H), 4.11 (s, 3H), 3.82 (q, J = 7.5 Hz, 2H), 2.03-1.94 (m, 1H), 1.43 (t, J = 7.5 Hz, 3H), 1.26-1.18 (m, 2H), 0.94-0.89 (m, 2H). |
| 92 | 502 [M + H]+ | (300 MHz, CDCl3, ppm) δ 9.89 (d, J = 1.9 Hz, 1H), 9.52 (d, J = 1.8 Hz, 1H), 8.62 (s, 2H), 8.45 (s, 1H), 8.08 (s, 1H), 7.21 (s, 1H), 4.64-4.56 (m, 2H), 4.23-4.16 (m, 2H), 1.98-1.90 (m, 1H), 1.78-1.73 (m, 3H), 1.47-1.40 (m, 3H), 1.28-1.15 (m, 2H), 1.00-0.85 (m, 2H). |
| 93 | 540.25 [M + H]+ | (300 MHz, CDCl3, ppm): δ 9.23 (s, 1H), 8.96 (s, 2H), 8.72 (s, 1H), 8.25 (s, 1H), 4.16 (s, 3H), 3.90 (q, J = 7.5 Hz, 2H), 2.47-2.34 (m, 1H), 1.45 (t, J = 7.5 Hz, 3H), 1.36-1.23 (m, 4H) |
| 94 | 502 [M + H]+ | (300 MHz, DMSO-d6, ppm) δ 9.32 (s, 1H), 9.14 (s, 2H), 8.85 (s, 1H), 8.69 (s, 1H), 8.50 (s, 1H), 7.23 (s, 1H), 4.77-4.70 (m, 2H), 4.47-4.40 (m, 2H), 2.33-2.27 (m, 1H), 1.61-1.56 (m, 3H), 1.34-1.29 (m, 3H), 1.15-1.09 (m, 4H). |
| 95 | 536 [M + H]+ | (300 MHz, DMSO-d6, ppm): δ 9.27 (s, 1H), 8.80 (s, 1H), 8.59-8.57 (m, 2H), 7.77 (d, J = 8.1 Hz, 2H), 7.33-7.28 (m, 3H), 6.90-6.54 (m, 1H), 5.30-5.21 (m, 2H), 4.49-4.42 (m, 2H), 2.07-1.98 (m, 1H), 1.32 (t, J = 7.5 Hz, 3H), 1.05-1.01 (m, 2H), 0.78-0.74 (m, 2H). |
| 96 | 526 [M + H]+· | (300 MHz, DMSO-d6, ppm): δ 9.25 (s, 1H), 8.84 (s, 1H), 8.58 (s, 1H), 8.50 (s, 1H), 7.77 (d, J = 8.1 Hz, 2H), 7.31-7.28 (m, 3H), 4.59-4.56 (m, 2H), 4.49-4.42 (m, 2H), 2.07-1.98 (m, 1H), 1.62-1.58 (m, 1H), 1.32 (t, J = 7.5 Hz, 3H), 1.07-1.02 (m, 2H), 0.83-0.77 (m, 2H), 0.62-0.56 (m, 4H). |
| 97 | 522 [M + H]+ | (300 MHz, CDCl3, ppm): δ 9.41 (d, J = 4.2 Hz, 1H), 9.29 (s, 1H), 8.88-8.60 (m, 2H), 8.46-8.09 (m, 1H), 8.07-7.90 (m, |

-continued

| Compound | (ES, m/z) | $^1$H NMR Spectra |
|---|---|---|
| | | 2H), 7.49-7.03 (m, 3H), 4.55-4.39 (m, 2H), 2.14-1.87 (m, 1H), 1.33 (t, J = 6.9 Hz, 3H), 1.10-1.02 (m, 2H), 0.76-0.48 (m, 2H). |
| 98 | 514 [M + H]+ | (300 MHz, CDCl3, ppm): δ 9.20 (s, 1H), 9.08 (s, 1H), 8.92 (s, 1H), 8.66 (s, 1H), 7.65 (d, J = 7.8 Hz, 2H), 7.34 (d, J = 7.8 Hz, 2H), 7.17 (s, 1H), 3.22-3.06 (m, 2H), 2.20 (s, 3H), 2.06-1.98 (m, 1H), 1.33-1.20 (m, 3H), 1.15-1.08 (m, 2H), 0.85-0.80 (m, 2H). |
| 99 | 486 [M + H]+ | (300 MHz, DMSO-d6, ppm): δ 9.25 (s, 1H), 8.79 (s, 1H), 8.58 (s, 1H), 8.49 (s, 1H), 7.77 (d, J = 8.4 Hz, 2H), 7.29 (d, J = 8.4 Hz, 2H), 7.16 (s, 1H), 4.49-4.42 (m, 2H), 4.34 (s, 3H), 2.06-2.02 (m, 1H), 1.31 (t, J = 7.5 Hz, 3H), 1.05-1.01 (m, 2H), 0.78-0.76 (m, 2H) |
| 100 | 514 [M + H]+ | (300 MHz, DMSO-d6, ppm) δ 9.26 (d, J = 2.1 Hz, 1H), 8.76 (s, 1H), 8.58 (d, J = 2.1 Hz, 1H), 8.49 (s, 1H), 7.77 (d, J = 8.1 Hz, 2H), 7.31-7.28 (m, 3H), 5.27-5.22 (m, 1H), 4.45-4.41 (m, 2H), 2.06-2.01 (m, 1H), 1.72 (d, J = 6.6 Hz, 6H), 1.31 (t, J = 7.5 Hz, 3H), 1.07-1.01 (m, 2H), 0.79-0.74 (m, 2H). |
| 101 | 512 [M + H]+ | (300 MHz, CDCl3, ppm) δ: 9.12 (s, 1H), 8.73 (s, 1H), 8.39 (s, 1H), 8.04 (s, 1H), 7.64 (d, J = 8.4 Hz, 2H), 7.26 (d, J = 8.4 Hz, 2H), 7.17 (s, 1H), 6.23-6.08 (m, 1H), 5.60-5.47 (m, 2H), 5.11 (d, J = 6.0 Hz, 2H), 4.20 (q, J = 7.5 Hz, 2H), 2.01 (m, 2H), 1.42 (t, J = 7.5 Hz, 3H), 1.14-1.02 (m, 2H), 0.80 (m, 2H). |
| 102 | 512 [M + H]+ | (300 MHz, CDCl3, ppm) δ: 9.17 (s, 1H), 8.81 (s, 1H), 8.70 (s, 1H), 8.00 (s, 1H), 7.70-7.60 (m, 2H), 7.27-7.20 (m, 2H), 7.07 (s, 1H), 5.95 (m, 1H), 5.22-5.10 (m, 2H), 4.90-4.70 (m, 2H), 3.20 (q, J = 7.5 Hz, 2H), 2.02 (m, 1H), 1.27 (t, J = 7.5 Hz, 3H), 1.11 (m, 2H), 0.83 (m, 2H) |
| 103 | 498 [M + H]+ | (300 MHz, CDCl3, ppm): δ 9.16 (s, 1H), 8.71 (s, 2H), 8.33 (s, 1H), 7.64 (d, J = 7.8 Hz, 2H), 7.55-7.47 (m, 1H), 7.29 (s, 1H), 7.23 (d, J = 7.8 Hz, 2H), 6.03 (d, J = 15.9 Hz, 1H), 5.78 (d, J = 9.3 Hz, 1H), 4.03-3.98 (m, 2H), 2.04-1.98 (m, 1H), 1.41 (t, J = 7.2 Hz, 3H), 1.12.-1.06 (m, 2H), 0.84-0.79 (m, 2H). |
| 104 | 528 [M + H]+ | (300 MHz, CDCl3, ppm): δ 9.12 (s, 1H), 8.73 (s, 1H), 8.38 (s, 1H), 8.32 (s, 1H), 7.64 (d, J = 9.0 Hz, 2H), 7.26 (d, J = 9.0 Hz, 2H), 7.17 (s, 1H), 5.89-5.80 (m, 1H), 5.40-5.30 (m, 2H), 5.30-5.20 (m, 2H), 4.29 (q, J = 9.0 Hz, 2H), 2.05-1.96 (m, 1H), 1.45 (t, J = 9.0 Hz, 3H), 1.11-1.05 (m, 2H), 0.83-0.78 (m, 2H) |
| 105 | 528 [M + H]+ | (300 MHz, CDCl3, ppm): δ 9.17 (s, 1H), 8.88-8.84 (m, 2H), 8.65 (s, 1H), 7.65 (d, J = 9.0 Hz, 2H), 7.30 (d, J = 9.0 Hz, 2H), 6.91 (s, 1H), 5.22-5.14 (m, 4H), 5.11-5.01 (m, 1H), 3.13 (q, J = 9.0 Hz, 2H), 2.07-1.97 (m, 1H), 1.24 (t, J = 9.0 Hz, 3H), 1.14-1.08 (m, 2H), 0.86-0.79 (m, 2H). |
| 106 | 548.15 [M + H]+ | (300 MHz, CDCl3, ppm): δ 9.20 (s, 1H), 8.89 (s, 1H), 8.72 (s, 1H), 8.24 (s, 1H), 7.72-7.62 (m, 2H), 7.46 (s, 1H), 7.30-7.25 (m, 2H), 4.33-4.21 (m, 1H), 3.18 (q, J = 7.2 Hz, 211), 2.10-1.85 (m, 3H), 1.30 (t, J = 7.2 Hz, 3H), 1.18-1.06 (m, 2H), 0.88-0.76 (m, 2H). |
| 107 | 554.15 [M + H]+ | (300 MHz, CDCl3, ppm): δ 9.14 (brs, 1H), 8.75 (s, 1H), 8.38 (s, 1H), 7.99 (s, 1H), 7.68-7.62 (m, 2H), 7.28-7.16 (m, 3H), 5.02 (q, J = 7.8 Hz, 2H), 4.22 (q, J = 7.5 Hz, 2H), 2.08-1.94 (m, 1H), 1.43 (t, J = 7.8 Hz, 3H), 1.15-1.04 (m, 2H), 0.86-0.78 (m, 2H). |
| 108 | 548.15 [M + H]+ | (300 MHz, CDCl3, ppm): δ 9.08 (s, 1H), 8.94 (s, 1H), 8.68 (s, 1H), 8.59 (s, 1H), 7.63-7.60 (m, 2H), 7.34 (s, 1H), 7.20-7.15 (m, 2H), 3.60 (s, 3H), 3.08 (q, J = 7.5 Hz, 2H), 2.03-1.94 (m, 1H), 1.25 (t, J = 7.5 Hz, 3H), 1.10-1.00 (m, 2H), 0.85-0.75 (m, 2H). |
| 109 | 472 [M + H]+ | (300 MHz, DMSO-d6, ppm) δ 12.46 (s, 1H), 9.36 (d, J = 2.1 Hz, 1H), 8.75 (d, J = 1.8 Hz, 1H), 8.66 (d, J = 2.1 Hz, 1H), 8.20 (s, 1H), 7.82 (d, J = 8.4 Hz, 1H), 7.72 (s, 1H), 7.31 (d, J = 8.1 Hz, 1H), 3.49-3.42 (m, 2H), 2.52-2.50 (m, 1H), 2.08-2.01 (m, 1H), 1.13 (t, J = 7.5 Hz, 3H), 1.07-1.04 (m, 2H), 0.80-0.75 (m, 2H). |
| 110 | 544 [M + H]+ | (300 MHz, DMSO-d6, ppm): δ 9.33 (d, J = 2.1 Hz, 1H), 8.58 (d, J = 2.1 Hz, 1H), 7.92 (s, 1H), 7.82 (d, J = 8.4 Hz, 2H), 7.30 (d, J = 8.4 Hz, 2H), 4.95 (t, J = 13.2 Hz, 2H), 3.61-3.52 (m, 1H), 3.33 (s, 3H), 2.08-1.98 (m, 2H), 1.22 (t, J = 7.5 Hz, 3H), 1.07-1.01 (m, 2H), 0.85-0.75 (m, 2H). |
| 111 | 531 [M + H]+ | (400 MHz, CDCl3, ppm): δ 9.14 (d, J = 2.0 Hz, 1H), 8.65 (d, J = 2.0 Hz, 1H), 7.95 (s, 1H), 7.62-7.59 (m, 2 H), 7.28-7.25 (m, 2 H), 4.42-4.35 (m, 2 H), 3.89-3.82 (m, 2 H), 3.81 (s, 3 H), 2.04-1.95 (m, 1 H), 1.44-1.26 (m, 6 H), 1.12-1.08 (m, 2H), 0.82-0.78 (m, 2 H). |

-continued

| Compound | (ES, m/z) | $^1$H NMR Spectra |
|---|---|---|
| 112 | 538 [M + H]+ | (300 MHz, CDCl3, ppm): δ 9.59 (s, 1H), 9.06 (s, 1H), 8.73 (s, 1H), 8.33 (s, 1H), 7.86 (t, J = 5.4 Hz, 1H), 7.71 (d, J = 5.4 Hz, 1H), 7.29 (s, 1H), 3.94 (t, J = 8.7 Hz, 5H), 2.61-2.40 (m, 1H), 1.44 (t, J = 6.6 Hz, 3H), 1.22-1.18 (m, 4H). |
| 113 | 501 [M + H]+ | (300 MHz, DMSO-d6, ppm): δ 9.56 (d, J = 2.1 Hz, 1H), 9.05 (d, J = 2.1 Hz, 1H), 8.86 (s, 1H), 8.51 (s, 1H), 7.98 (d, J = 7.5 Hz, 1H), 7.86 (t, J = 7.8 Hz, 1H), 7.40 (d, J = 7.8 Hz, 1H), 7.25 (s, 1H), 4.77-4.70 (m, 2H), 4.50-4.42 (m, 2H), 2.28-2.22 (m, 1H), 1.59 (t, J = 7.2 Hz, 3H), 1.31 (t, J = 7.5 Hz, 3H), 1.07-1.05 (m, 4H). |
| 114 | 538 [M + H]+ | (300 MHz, CDCl3, ppm): δ 9.61 (s, 1H), 9.02 (s, 2H), 8.14 (s, 1H), 7.76-7.67 (m, 2H), 7.29-7.26 (m, 1H), 3.93 (s, 3H), 3.82 (q, J = 5.4 Hz, 2H), 2.19-2.12 (m, 1H), 1.40 (t, J = 5.4 Hz, 3H), 1.18-1.13 (m, 2H), 1.10-1.08 (m, 2H). |
| 115 | 562 [M + H]+ | (300 MHz, CDCl3, ppm): δ 9.19 (s, 1H), 9.05 (s, 1H), 8.67 (s, 1H), 8.19 (d, J = 8.4 Hz, 1H), 7.73 (d, J = 6.0 Hz, 2H), 7.51 (d, J = 5.7 Hz, 2H), 4.05 (s, 3H), 3.95-3.77 (m, 2H), 1.88-1.81 (m, 2H), 1.58-1.51 (m, 2H), 1.45-1.38 (m, 3H). |
| 116 | 605 [M + H]+ | (300 MHz, CDCl3, ppm): δ 9.24 (d, J = 1.8 Hz, 1H), 9.16 (s, 1H), 8.69 (d, J = 1.8 Hz, 1H), 8.31 (s, 1H), 7.73 (s, 4H), 4.00 (s, 3H), 3.91-3.83 (m, 2H), 1.51-1.42 (m, 5H), 1.15 (s, 2H). |
| 117 | 538 [M + H]+ | (400 MHz, CDCl3, ppm): δ 9.17 (d, J = 2.4 Hz, 1H), 9.02 (s, 1H), 8.81 (d, J = 2.4 Hz, 1H), 8.65 (d, J = 2.0 Hz, 1H), 8.14 (s, 1H), 7.89-7.87 (m, 1H), 7.37-7.35 (m, 1H), 3.94 (s, 3H), 3.88-3.72 (m, 2H), 2.18-2.11 (m, 1H), 1.39 (t, J = 7.6 Hz, 3H), 1.17-1.06 (m, 4H). |
| 118 | 509 [M + H]+ | (300 MHz, CDCl3, ppm) δ: 9.58 (s, 1H), 8.58 (s, 1H), 7.73-7.64 (m, 2H), 7.26-7.20 (m, 2H), 4.07 (s, 3H), 3.82 (q, J = 5.4 Hz, 2H), 3.11 (m, 1H), 2.17-2.11 (m, 1H), 1.38 (t, J = 5.4 Hz, 3H), 1.30-1.25 (m, 2H), 1.25-1.20 (m, 2H), 1.15-1.00 (m, 4H) |
| 119 | 474 [M + H]+ | (300 MHz, Chloroform-d, ppm) δ 9.50 (d, J = 2.1 Hz, 1H), 9.30 (s, 1H), 9.14 (d, J = 2.1 Hz, 1H), 8.49 (d, J = 0.9 Hz, 1H), 8.41 (s, 1H), 7.77-7.72 (m, 1H), 7.68-7.63 (m, 1H), 7.32-7.24 (m, 1H), 4.03 (q, J = 7.5 Hz, 2H), 2.19-2.17 (m, 1H), 1.58-1.52 (m, 3H), 1.35-1.27 (m, 2H), 1.21-1.16 (m, 2H) |
| 120 | 474 [M + H]+ | (300 MHz, Chloroform-d, ppm) δ 9.46-9.43 (m, 2H), 9.14 (d, J = 2.1 Hz, 11-1), 8.98 (s, 1H), 8.08 (s, 1H), 7.78-7.73 (m, 1H), 7.69-7.63 (m, 1H), 7.31 (d, J = 1.2 Hz, 11-1), 4.00 (q, J = 7.4 Hz, 2H), 2.14-2.13 (m, 1H), 1.47-1.45 (m, 3H), 1.27-1.20 (m, 4H). |
| 121 | 487 [M + H]+ | (400 MHz, CDCl3, ppm): δ 9.13 (s, 1H), 8.82 (s, 1H), 8.70 (s, 1H), 8.47 (s, 1H), 7.61 (d, J = 7.6 Hz, 2H), 7.25 (d, J = 8.0 Hz, 2H), 4.12 (s, 3H), 2.81-2.76 (m, 2H), 2.02-1.96 (m, 1H), 1.13-1.06 (m, 5H), 0.85-0.78 (m, 2H). |
| 122 | 500 [M + H]+ | (400 MHz, CDCl3, ppm): δ 9.15 (s, 1H), 8.69 (s, 1H), 8.60 (s, 1H), 8.41 (s, 1H), 7.61 (d, J = 8.0 Hz, 2H), 7.25 (d, J = 7.2 Hz, 2H), 6.84 (s, 1H), 4.63-4.58 (m, 2H), 2.79-2.73 (m, 2H), 1.99 (s, 1H), 1.76-1.72 (m, 3H), 1.09-0.88 (m, 5H), 0.88-0.79 (m, 2H). |
| 123 | 514 [M + H]+ | (400 MHz, CDCl3, ppm): δ 9.04 (s, 1H), 8.77 (s, 1H), 8.63 (d, J = 2.0 Hz, 1H), 8.38 (s, 1H), 7.93 (d, J = 8.4 Hz, 1H), 7.85 (d, J = 8.0 Hz, 1H), 7.45-4.42 (m, 1H), 7.32-7.30 (m, 1H), 4.55 (t, J = 12.0 Hz, 2H), 3.98-3.92 (m, 2H), 2.14 (s, 1H), 1.41 (t, J = 7.6 Hz, 3H), 1.13-1.08 (m, 4H) |
| 124 | 561 [M + H]+ | (300 MHz, CDCl3, ppm): δ 9.17 (d, J = 2.1 Hz, 1H), 8.65 (d, J = 2.1 Hz, 1H), 7.75-7.70 (m, 2H), 7.44 (d, J = 8.4 Hz, 2H), 7.23 (d, J = 19.2 Hz, 1H), 4.08 (s, 3H), 3.85-3.77 (m, 2H), 3.12-3.10 (m, 1H), 1.66-1.55 (m, 2H), 1.40-1.33 (m, 3H), 1.31-1.26 (m, 2H), 1.24-1.15 (m, 2H), 1.10-1.06 (m, 2H) |
| 125 | 531.2 [M + H]+ | (300 MHz, CDCl3, ppm): δ 9.14 (s, 1H), 8.62 (s, 1H), 8.17 (s, 1H), 7.62-7.60 (m, 2H), 7.27-7.26 (m, 2H), 4.51-4.31 (m, 2H), 3.89 (s, 3H), 3.74-3.72 (m, 2H), 2.04-1.95 (m, 1H), 1.59-1.52 (m, 3H), 1.43-1.33 (m, 3H), 1.10-1.06 (m, 2H), 0.80-0.77 (m, 2H) |
| 126 | 514.2 [M + H]+ | (400 MHz, Chloroform-d) δ: 9.11 (d, J = 2.2 Hz, 1H), 8.69 (d, J = 2.1 Hz, 1H), 8.01 (d, J = 9.1 Hz, 1H), 7.66-7.57 (m, 2H), 7.31 (d, J = 9.1 Hz, 1H), 7.27 (d, J = 7.7 Hz, 2H), 5.17-5.05 (m, 2H), 3.94 (q, J = 7.4 Hz, 2H), 2.06-1.95 (m, 1H), 1.45 (t, J = 7.4 Hz, 3H), 1.14-1.03 (m, 2H), 0.81 (dt, J = 6.7, 4.8 Hz, 2H). |
| 127 | 581 [M + H]+ | (400 MHz, CDCl3, ppm): δ 9.10 (s, 1H), 8.69 (s, 1H), 8.42 (s, 1H), 8.00-7.98 (m, 1H), 7.74-7.62 (m, 4H), 7.51-7.48 (m, 1H), 4.61-4.55 (m, 2H), 3.98-3.92 (m, 2H), 1.59-1.41 (m, 5H), 1.17-1.04 (m, 2H). |

-continued

| Compound | (ES, m/z) | $^{1}$H NMR Spectra |
|---|---|---|
| 128 | 538.1 [M + H]+ | (400 MHz, Chloroform-d, ppm) δ: 9.08 (d, J = 2.2 Hz, 1H), 8.68 (d, J = 2.2 Hz, 1H), 8.42 (d, J = 2.9 Hz, 1H), 7.96 (d, J = 8.7 Hz, 1H), 7.74-7.67 (m, 2H), 7.52-7.44 (m, 3H), 4.63-4.53 (m, 2H), 3.97 (q, J = 7.5 Hz, 2H), 1.89-1.81 (m, 2H), 1.56-1.48 (m, 2H), 1.44 (t, J = 7.4 Hz, 3H). |
| 129 | 566 [M + H]+ | (400 MHz, CDCl3, ppm): δ 9.15 (d, J = 2.0 Hz, 1H), 8.66 (d, J = 2.4 Hz, 1H), 7.71-7.65 (m, 4H), 7.43 (s, 1H), 7.14 (s, 1H), 3.89-3.84 (m, 2H), 3.78 (s, 3H), 1.54-1.50 (m, 2H), 1.46-1.43 (m, 3H), 1.11 (s, 2H). |
| 130 | 523 [M + H]+ | (400 MHz, CDCl3, ppm): δ 9.17 (s, 1H), 8.66 (s, 1H), 7.74-7.68 (m, 2H), 7.53-7.50 (m, 3H), 7.18 (s, 1H), 3.89-3.84 (m, 2H), 3.83-3.78 (s, 3H), 1.91-1.83 (m, 2H), 1.56-1.50 (m, 2H), 1.44-1.37 (m, 3H). |
| 131 | 524 [M + H]+ | (400 MHz, CDCl3, ppm): δ 9.14 (d, J = 2.0 Hz, 1H), 8.82 (d, J = 2.4 Hz, 1H), 8.66 (d, J = 2.0 Hz, 1H), 8.04-8.02 (m, 1H), 7.93 (d, J = 8.0 Hz, 1H), 7.43 (s, 1H), 7.14 (s, 1H), 3.94-3.89 (q, J = 7.5 Hz, 2H), 3.80 (s, 3H), 1.95-1.92 (m, 2H), 1.84-1.81 (m, 2H), 1.38 (t, J = 7.5 Hz, 3H). |
| 132 | 612 [M + H]+ | (400 MHz, CDCl3, ppm): δ 9.16 (d, J = 2.0 Hz, 1H), 8.87 (d, J = 2.0 Hz, 1H), 8.64 (d, J = 1.6 Hz, 1H), 8.01-7.98 (m, 1H), 7.77 (d, J = 8.4 Hz, 1H), 7.21 (s, 1H), 4.09 (s, 3H), 3.83 (q, J = 5.4 Hz, 2H), 3.15-3.05 (m, 1H), 1.56-1.43 (m, 4 H), 1.54 (t, J = 10.0 Hz, 3H), 1.32-1.31 (m, 2H), 1.23-1.08 (m, 2H). |
| 133 | 569 [M + H]+ | (400 MHz, CDCl3, ppm): δ 9.15 (d, J = 1.5 Hz, 1H), 8.81 (d, J = 1.5 Hz, 1H), 8.64 (d, J = 1.5 Hz, 1H), 8.04-8.01 (m, 1H), 7.92-7.92 (m 1H), 7.20 (s, 1H), 4.09 (s, 3H), 3.84 (q, J = 7.6 Hz, 2H), 3.12-3.10 (m, 1H), 1.95-1.93 (m, 2H), 1.85-1.80 (m, 2H), 1.40-1.36 (m, 3H), 1.32-1.27 (m, 2H), 1.07-1.00 (m, 2H). |
| 134 | 573 [M + H]+ | (300 MHz, Chloroform-d, ppm): δ 9.22 (d, J = 2.1 Hz, 1H), 8.76 (s, 1H), 8.70 (d, J = 1.8 Hz, 1H), 8.36 (s, 1H), 7.73 (d, J = 8.1 Hz, 2H), 7.47 (d, J = 8.1 Hz, 2H), 4.00-3.86 (m, 5H), 2.93-2.82 (m, 1H), 2.12-1.99 (m, 1H), 1.80-1.70 (m, 1H), 1.43 (t, J = 7.5 Hz, 3H). |
| 135 | 574 [M + H]+ | (300 MHz, Chloroform-d, ppm): δ 9.24 (d, J = 2.1 Hz, 1H), 8.71 (d, J = 2.1 Hz, 1H), 8.24 (s, 1H), 7.74 (d, J = 8.4 Hz, 2H), 7.48 (d, J = 8.4 Hz, 2H), 4.14 (s, 3H), 3.90-3.82 (m, 2H), 2.94-2.83 (m, 1H), 2.03-1.91 (m, 1H), 1.81-1.70 (m, 1H), 1.43 (t, J = 7.5 Hz, 3H). |
| 136 | 538 [M + H]+ | (300 MHz, Chloroform-d, ppm) δ: 9.13 (d, J = 2.0 Hz, 1H), 8.69 (d, J = 2.0 Hz, 1H), 8.22 (s, 1H), 7.60-7.46 (m, 1H), 7.42-7.34 (m, 2H), 7.17-7.14 (d, J = 7.8 Hz, 1H), 4.14 (s, 3H), 3.86-3.78 (m, 2H), 1.88-1.81 (m, 1H), 1.42-1.37 (m, 3H), 1.01-0.94 (m, 2H), 0.82-0.76 (m, 2H). |
| 137 | 539.2 [M + H]+ | (300 MHz, Chloroform-d) δ 9.42 (d, J = 2.0 Hz, 1H), 9.01 (d, J = 2.0 Hz, 1H), 8.75 (s, 1H), 8.35 (s, 1H), 7.75 (d, J = 7.9 Hz, 1H), 7.61 (s, 1H), 4.15 (s, 3H), 4.00-3.85 (m, 2H), 2.05-2.00 (m, 1H), 1.47-1.40 (m, 3H), 1.26-1.20 (m, 2H), 0.95-0.85 (m, 2H). |
| 138 | 539 [M + H]+ | (300 MHz, DMSO-d6, ppm): δ 9.30 (d, J = 2.0 Hz, 1H), 8.85 (s, 1H), 8.64 (d, J = 2.0 Hz, 1H), 8.59 (dd, J = 4.8, 1.7 Hz, 1H), 7.92 (dd, J = 7.7, 1.7 Hz, 1H), 7.38 (dd, J = 7.7, 4.7 Hz, 1H), 4.04 (s, 3H), 3.83 (q, J = 7.4 Hz, 2H), 2.12-2.07 (m, 1H), 1.25 (t, J = 7.4 Hz, 3H), 1.17-1.15 (m, 2H), 0.98-0.94 (m, 2H). |
| 139 | 539 [M + H]+ | (300 MHz, DMSO-d6, ppm) δ 9.31 (d, J = 2.1 Hz, 1H), 8.85 (s, 1H), 8.68 (d, J = 1.8 Hz, 1H), 8.63 (s, 1H), 8.58 (d, J = 5.4 Hz, 1H), 7.15 (d, J = 5.1 Hz, 1H), 4.04 (s, 3H), 3.84 (q, J = 7.5 Hz, 2H), 1.98-1.92 (m, 1H), 1.26 (t, J = 7.5 Hz, 3H), 1.06-1.04 (m, 2H), 0.99-0.96 (m, 2H). |
| 140 | 551 [M + H]+ | (400 MHz, CDCl3, ppm): δ 9.62 (s, 1H), 9.18 (d, J = 1.6 Hz, 1H), 9.05 (s, 1H), 8.80 (d, J = 1.6 Hz, 1H), 7.78-7.74 (m, 1H), 7.70-7.68 (m, 1H), 7.31-7.28 (m, 1H), 3.96 (s, 3H), 3.90-3.88 (m, 2H), 3.82-3.75 (m, 1H), 2.30-2.20 (m, 1H), 1.50-1.38 (m, 3H), 1.19-1.054 (m, 4H). |
| 141 | 540 [M + H]+ | (300 MHz, DMSO-d6, ppm): δ 9.88 (d, J = 1.5 Hz, 1H), 9.28 (d, J = 1.5 Hz, 1H), 9.25 (d, J = 1.5 Hz, 1H), 8.50 (s, 1H), 8.22 (d, J = 1.5 Hz, 1H), 4.02 (s, 3H), 3.85-3.83 (m, 2H), 2.19-2.09 (m, 1H), 1.28-1.25 (m, 5H), 1.16-1.15 (m, 2H). |
| 142 | 554 [M + H]+ | (300 MHz, CDCl3, ppm): δ 9.68 (d, J = 2.1 Hz, 1H), 9.14 (d, J = 2.1 Hz, 1H), 8.23 (s, 1H), 7.52 (s, 1H), 4.11 (s, 3H), 3.85 (q, J = 7.5 Hz, 2H), 2.76 (s, 3H), 2.16-2.08 (m, 1H), 1.43 (t, J = 7.5 Hz, 3H), 1.30-1.26 (m, 2H), 1.25-1.22 (m, 2H). |

-continued

| Compound | (ES, m/z) | $^1$H NMR Spectra |
|---|---|---|
| 143 | 540 [M + H]+ | (300 MHz, CDCl3, ppm) δ 9.97 (d, J = 1.8 Hz, 1H), 9.46 (d, J = 1.8 Hz, 1H), 8.68 (d, J = 5.1 Hz, 1H), 8.22 (s, 1H), 7.24 (s, 1H), 4.11 (s, 3H), 3.83-3.78 (m, 2H), 2.17-2.13 (m, 1H), 1.43 (t, J = 7.5 Hz, 3H), 1.40-1.39 (m, 2H), 1.32-1.31 (m, 2H), 1.24-1.22 (m, 1H). |
| 144 | 606 [M + H]+ | (300 MHz, DMSO-d6, ppm): δ 9.97 (d, J = 1.8 Hz, 1H), 9.10 (d, J = 1.5 Hz, 1H), 8.84 (d, J = 1.8 Hz, 1H), 8.66 (d, J = 1.5 Hz, 1H), 8.30 (d, J = 2.7 Hz, 1H), 8.10 (t, J = 6.0 Hz, 1H), 7.69 (d, J = 6.0 Hz, 1H), 3.92-3.86 (m, 2H), 3.84 (s, 3H), 1.58-1.55 (m, 4H), 1.25 (t, J = 6.0 Hz, 1H). |
| 145 | 607 [M + H]+ | (300 MHz, DMSO-d6, ppm): δ 9.81 (d, J = 1.8 Hz, 1H), 9.12 (d, J = 6.3 Hz, 1H), 8.84 (s, 1H), 8.33 (d, J = 7.5 Hz, 1H), 8.11 (t, J = 8.1 Hz, 1H), 7.71 (d, J = 7.8 Hz, 1H), 4.00 (s, 3H), 3.84-3.82 (m, 2H), 1.59-1.56 (m, 4H), 1.25 (t, J = 7.5 Hz, 3H). |
| 146 | 540 [M + H]+ | (300 MHz, Chloroform-d, ppm) δ 10.06 (d, J = 2.0 Hz, 1H), 9.56 (d, J = 2.0 Hz, 1H), 8.75 (s, 1H), 8.68 (s, 1H), 8.33 (s, 1H), 3.98 (s, 3H), 3.93 (t, J = 7.4 Hz, 2H), 2.31-2.23 (m, 1H), 1.47-1.35 (m, 7H). |
| 147 | 540 [M + H]+ | (300 MHz, Chloroform-d, ppm): δ 9.71 (d, J = 2.1 Hz, 1H), 9.18 (d, J = 2.1 Hz, 1H), 9.04 (s, 1H), 8.76 (d, J = 1.8 Hz, 1H), 8.33 (d, J = 1.8 Hz, 1H), 4.02-3.95 (m, 5H), 2.71-2.62 (m, 1H), 1.48-1.34 (m, 7H). |
| 148 | 540 [M + H]+ | NMR(300 MHz, CDCl3, ppm) δ 10.02 (d, J = 1.5 Hz, 1H), 9.51 (d, J = 1.8 Hz, 1H), 9.22 (s, 1H), 8.76 (s, 1H), 8.35 (s, 1H), 3.95-3.89 (m, 5H), 2.19-2.13 (m, 1H), 1.46-1.41 (m, 7H). |
| 149 | 541 [M + H]+ | (300 MHz, Chloroform-d, ppm): δ 9.72 (d, J = 2.1 Hz, 1H), 9.18 (d, J = 1.8 Hz, 1H), 9.03 (s, 1H), 8.24 (s, 1H), 4.14 (s, 3H), 3.92-3.83 (m, 2H), 2.70-2.61 (m, 1H), 1.46-1.30 (m, 7H). |
| 150 | 541.2 [M + H]+ | (400 MHz, Chloroform-d, ppm) δ 10.09 (d, J = 2.0 Hz, 1H), 9.58 (d, J = 2.0 Hz, 1H), 8.69 (s, 1H), 8.25 (s, 1H), 4.16 (s, 3H), 3.87 (q, J = 7.5 Hz, 2H), 2.29-2.22 (m, 1H), 1.50-1.37 (m, 7H). |
| 151 | 541 [M + H]+ | (300 MHz, CDCl3, ppm) δ 10.04 (d, J = 1.8 Hz, 1H), 9.53 (d, J = 2.1 Hz, 1H), 9.23 (s, 1H), 8.23 (s, 1H), 4.12 (s, 3H), 3.88-3.81 (m, 2H), 2.23-2.14 (m, 1H), 1.46-1.38 (m, 7H). |
| 152 | 540 [M + H]+ | (300 MHz, Chloroform-d, ppm): δ 9.73 (d, J = 2.1 Hz, 1H), 9.11 (d, J = 2.1 Hz, 1H), 8.26 (s, 1H), 8.06 (d, J = 9.0 Hz, 1H), 7.54 (d, J = 9.0 Hz, 1H), 4.13 (s, 3H), 3.89-3.79 (m, 2H), 2.49-2.41 (m, 1H), 1.45-1.30 (m, 7H). |
| 153 | 539 [M + H]+ | (300 MHz, Chloroform-d, ppm): δ 9.71 (s, 1H), 9.10 (s, 1H), 8.76 (s, 1H), 8.36 (s, 1H), 8.00 (d, J = 8.4 Hz, 1H), 7.51 (d, J = 8.4 Hz, 1H), 3.94 (s, 3H), 3.86-3.68 (m, 2H), 2.42-2.36 (m, 1H), 1.43-1.26 (m, 7H). |
| 154 | 552 [M + H]+ | (300 MHz, Chloroform-d, ppm) δ: 9.21 (s, 1H), 8.66 (s, 1H), 8.21 (s, 1H), 7.67 (d, J = 8.3 Hz, 2H), 7.46 (d, J = 8.3 Hz, 2H), 4.11 (s, 3H), 3.86-3.78 (m, 2H), 1.57 (s, 3H), 1.37-1.33 (m, 3H), 0.98-0.93 (m, 2H), 0.90-0.84 (m, 2H). |
| 155 | 568 [M + H]+ | (300 MHz, CDCl3, ppm): δ 9.23 (d, J = 2.4 Hz, 1H), 8.70 (d, J = 8.4 Hz, 1H), 8.29 (s, 1H), 7.73 (d, J = 8.4 Hz, 2H), 7.51 (d, J = 8.4 Hz, 2H), 4.12 (s, 3H), 3.84 (q, J = 7.5 Hz, 2H), 3.32 (s, 3H), 1.44 (t, J = 7.8 Hz, 3H), 1.35-1.32 (m, 2H), 1.10-1.08 (m, 2H). |
| 156 | 622 [M + H]+ | (300 MHz, DMSO-d6, ppm) δ 9.23 (d, J = 2.1 Hz, 1H), 8.70 (d, J = 2.1 Hz, 1H), 8.22 (s, 1H), 7.74 (d, J = 8.4 Hz, 2H), 7.61-7.57 (m, 2H), 5.36-5.33 (m, 1H), 4.12 (s, 3H), 3.88-3.80 (m, 21-1), 2.02-1.97 (m, 1H), 1.70-1.65 (m, 2H), 1.57 (s, 3H). |
| 157 | 552 [M + H1+ | (300 MHz, CDCl3, ppm): δ 9.23-9.20 (m, 1H), 8.70-8.66 (m, 1H), 8.21 (s, 1H), 7.68-7.61 (m, 2H), 7.42-7.22 (m, 2H), 4.11 (s, 3H), 3.86-3.79 (m, 2H), 2.22-1.65 (m, 1H), 1.55 (d, J = 3.0 Hz, 3H), 1.43-0.69 (m, 6H). |
| 158 | 566.3 [M + H]+ | (300 MHz, CDCl3, ppm): δ 9.25 (d, J = 2.1 Hz, 1H), 8.73 (d, J = 2.1 Hz, 1H), 8.23 (s, 1H), 7.67 (d, J = 8.1 Hz, 2H), 7.39 (d, J = 8.1 Hz, 2H), 4.13 (s, 3H), 3.85 (q, J = 7.5 Hz, 2H), 2.04-1.97 m, 1H), 1.44 (t, J = 7.1 Hz, 3H), 1.31 (s, 3H), 0.95-0.90 (m, 2H), 0.89 (s, 3H). |
| 159 | 538.1 [M + H]+ | (300 MHz, Chloroform-d) δ 9.42 (d, J = 2.0 Hz, 1H), 9.01 (d, J = 2.0 Hz, 1H), 8.75 (s, 1H), 8.72 (d, J = 4.8 Hz, 1H), 8.35 (s, 1H), 7.75 (d, J = 7.9 Hz, 1H), 7.61 (s, 1H), 4.02 (d, J = 8.9 Hz, 5H), 2.04 (d, J = 8.4 Hz, 1H), 1.47 (d, J = 14.9 Hz, 3H), 1.26-1.20 (m, 2H), 0.93 (d, J = 5.4 Hz, 2H). |
| 160 | 565 [M + H]+ | (300 MHz, Chloroform-d, ppm): δ 9.23 (d, J = 2.1 Hz, 1H), 8.80 (s, 1H), 8.69 (d, J = 2.1 Hz, 1H), 8.43 (s, 1H), 7.66 (t, J = : 8.4 Hz, 2H), 7.39 (d, J = 8.1 Hz, 2H), 3.96-3.90 (m, 5H), 1.99 (,, J = 7.2 Hz, 1H), 1.44 (t, J = 7.2 Hz, 3H), 1.31 (s, 3H), 0.95-0.92 (m, 5H). |

-continued

| Compound | (ES, m/z) | $^1H$ NMR Spectra |
|---|---|---|
| 161 | 551 [M + H]+· | (300 MHz, CDCl3, ppm): 5 9.21-9.18 (m, 1H), 8.76 (s, 1H), 8.68-8.64 (m, 1H), 8.38 (s, 1H), 7.67-7.61 (m, 2H), 7.41-7.24 (m, 2H), 3.94-3.87 (m, 5H), 2.18-1.65 (m, 1H), 1.41 (t, J = 6.9 Hz, 3H), 1.39-0.69 (m, 6H). |
| 162 | 621 [M + H]+ | (300 MHz, DMSO-d6, ppm) δ 9.20 (d, J = 2.1 Hz, 1H), 8.74 (d, J = 1.8 Hz, 1H), 8.69 (d, J = 2.1 Hz, 1H), 8.33 (d, J = 1.8 Hz, 1H), 7.74 (t, J = 6.6 Hz, 2H), 7.60 (t, J = 2.4 Hz, 2H), 3.94 (s, 3H), 3.92-3.87 (m, 2H), 1.69-1.65 (m, 2H), 1.42 (t, J = 7.2 Hz, 3H), 1.28-1.24 (m, 2H). |
| 163 | 567 [M + H]+ | (400 MHz, CDCl3, ppm): δ 9.20 (d, J = 1.6 Hz, 1H), 8.70 (d, J = 8.4 Hz, 2H), 8.29 (s, 1H), 7.72 (d, J = 8.0 Hz, 2H), 7.50 (d, J = 8.4 Hz, 2H), 3.93-3.87 (m, 5H), 3.32 (s, 3H), 1.40 (t, J = 7.6 Hz, 3H), 1.33-1.30 (m, 2H), 1.26 (s, 2H), 1.09-1.05 (m, 2H). |
| 164 | 551 [M + H]+ | (300 MHz, Chloroform-d, ppm, ppm) δ: 9.18 (s, 1H), 8.76 (s, 1H), 8.65 (s, 1H), 8.39 (s, 1H), 7.66 (d, J = 8.4 Hz, 2H), 7.46 (d, J = 8.4 Hz, 2H), 3.93 (s, 3H), 3.92-3.87 (m, 2H), 1.48 (s, 2H), 1.43-1.38 (m, 3H), 0.98-0.95 (m, 2H), 0.90-0.87 (m, 2H). |
| 165 | 539 [M + H]+ | (300 MHz, CDCl3, ppm) δ 9.95 (d, J = 1.8 Hz, 1H), 9.45 (d, J = 1.8 Hz, 1H), 8.74 (s, 1H), 8.67 (d, J = 5.1 Hz, 1H), 8.35 (s, 1H), 7.23 (d, J = 5.1 Hz, 1H), 4.00 (s, 3H), 3.93-3.80 (m, 2H), 2.15-2.08 (m, 1H), 1.43 (t, J = 7.5 Hz, 3H), 1.36-1.31 (m, 2H), 1.28-1.21 (m, 2H). |
| 166 | 553 [M + H]+ | (300 MHz, CDCl3, ppm): δ 9.66 (d, J = 2.1 Hz, 1H), 9.13 (d, J = 1.8 Hz, 1H), 8.73 (d, J = 1.5 Hz, 1H), 8.31 (d, J = 1.8 Hz, 1H), 7.49 (s, 1H), 3.99-3.92 (m, 5H), 2.86 (s, 3H), 2.40-2.34 (m, 1H), 1.43 (t, J = 7.5 Hz, 3H), 1.32-1.23 (m, 4H). |
| 167 | 539 [M + H]+ | (300 MHz, DMSO-d6, ppm): δ 9.84 (d, J = 2.1 Hz, 1H), 9.25 (t, J = 2.4 Hz, 2H), 8.85 (d, J = 2.1 Hz, 1H), 8.68 (d, J = 1.5 Hz, 1H), 8.21 (d, J = 2.4 Hz, 1H), 3.94-3.87 (m, 2H), 3.85 (s, 3H), 2.20-2.09 (m, 1H), 1.29-1.22 (m, 5H), 1.18-1.14 (m, 2H). |
| 168 | 538 [M + H]+ | (300 MHz, DMSO-d6, ppm) δ 9.28 (d, J = 2.1 Hz, 1H), 8.86 (d, J = 2.1 Hz, 1H), 8.68 (d, J = 2.1 Hz, 1H), 8.63-8.62 (m, 1H), 8.57 (d, J = 5.4 Hz, 1H), 7.17 (d, J = 5.1 Hz, 1H), 3.97-3.84 (q, 2H), 3.86 (s, 1H), 1.95-1.92 (m, 1H), 1.26 (t, J = 7.5 Hz, 3H), 1.06-1.04 (m, 2H), 0.97-0.96 (m, 2H). |
| 169 | 538 [M + H]+ | (300 MHz, DMSO-d6, ppm): δ 9.26 (d, J = 2.0 Hz, 1H), 8.85 (d, J = 2.1 Hz, 1H), 8.66 (d, J = 2.1 Hz, 1H), 8.61-8.57 (m, 2H), 7.91 (dd, J = 7.7, 1.7 Hz, 1H), 7.37 (dd, J = 7.7, 4.8 Hz, 1H), 3.93-3.88 (m, 2H), 3.87 (s, 3H), 2.12-2.06 (m, 1H), 1.25 (t, J = 7.4 Hz, 3H), 1.15-1.13 (m, 2H), 0.98-0.94 (m, 2H). |
| 170 | 537.1 [M + H]+ | (300 MHz, Chloroform-d, ppm) δ: 9.10 (d, J = 2.0 Hz, 1H), 8.67 (s, 1H), 8.66 (d, J = 2.0 Hz, 1H), 8.38 (s, 1H), 7.47-7.41 (m, 1H), 7.38-7.26 (m, 2H), 7.16 (d, J = 7.6 Hz, 1H), 3.97 (s, 3H), 3.92-3.85 (m, 2H), 1.85-1.81 (m, 1H), 1.43-1.40 (m, 3H), 0.93-0.81 (m, 2H), 0.79-0.75 (m, 2H). |
| 171 | 605 [M + H]+ | (300 MHz, CDCl3, ppm) δ 9.58 (d, J = 1.8 Hz, 1H), 9.04 (d, J = 1.8 Hz, 1H), 8.76-8.70 (m, 1H), 8.27 (s, 1H), 7.88-7.79 (m, 2H), 7.68-7.60 (m, 1H), 7.32-729 (m, 1H), 6.60-6.24 (m, 1H), 5.16-4.97 (m, 2H), 4.03-3.89 (m, 2H), 1.62-1.50 (m, 4 H), 1.40-1.35 (m, 3H). |
| 172 | 623 [M + H]+ | (300 MHz, CDCl3, ppm) δ 9.59 (s, 1H), 9.00 (d, J = 1.8 Hz, 1H), 8.47-8.43 (m, 1H), 8.12-8.07 (m, 1H), 7.88-7.78 (m, 2H), 7.69-7.60 (m, 1H), 6.58-6.22 (m, 1H), 4.97-4.93 (m, 2H), 4.16-3.98 (m, 2H), 1.62-1.58 (m, 2H), 1.54-1.50 (m, 2H), 1.45-1.40 (m, 3H). |
| 173 | 492 [M + H]+ | (400 MHz, Chloroform-d, ppm) δ 9.21 (d, J = 2.0 Hz, 1H), 8.84-8.82 (m, 2H), 8.73 (d, J = 2.0 Hz, 1H), 8.16 (s, 1H), 8.06 (d, J = 6.0, 2.4 Hz, 1H), 7.83 (d, J = 8.4 Hz, 1H), 7.34 (dd, J = 7.2, 1.9 Hz, 1H), 4.11 (q, J = 6.4 Hz, 2H), 1.66-1.58 (m, 4H), 1.48 (t, J = 6.4 Hz, 3H). |
| 174 | 542 [M + H]+ | (300 MHz, CD3Cl, ppm): δ 9.22 (s, 1H), 8.92 (s, 1H), 8.83 (t, J = 11.4 Hz, 1H), 8.73 (s, 1H), 8.16 (s, 1H), 8.07 (s, 1H), 7.82 (s, 1H), 7.34 (d, J = 6.6 Hz, 1H), 4.13-4.07 (m, 2H), 1.56 (s, 4H), 1.46 (t, J = 6.3 Hz, 3H). |
| 175 | 499 [M + H]+ | (300 MHz, DMSO-d, ppm): δ 9.44 (s, 1H), 9.36 (d, J = 7.2. Hz, 1H), 9.08 (s, 1H), 8.71 (s, 1H), 8.59 (s, 1H), 8.44-8.40 (m, 1H), 7.75 (d, J = 8.4 Hz, 1H), 7.68-7.65 (m, 1H), 3.98-3.93 (m, 2H), 1.91 (t, J = 3.3 Hz, 2H), 1.80 (t, J = 3.3 Hz, 2H), 1.29 (t, J = 7.5 Hz, 3H). |
| 176 | 562 [M + H]+ | (300 MHz, Chloroform-d, ppm) δ 9.19 (s, 1H), 8.87 (s, 1H), 8.65 (s, 1H), 8.14 (d, J = 8.1 Hz, 1H), 7.92 (d, J = 7.8 Hz, 1H), 7.30-7.26 (m, 1H), 4.09 (s, 3H), 3.89 (q, J = 7.2 Hz, 2H), 3.13 (s, 1H), 1.68 (s, 2H), 1.63 (s, 2H), 1.43 (t, J = 7.2 Hz, 3H), 1.33 (d, J = 7.2 Hz, 2H), 1.09 (s, 2H). |

-continued

| Compound | (ES, m/z) | $^1$H NMR Spectra |
|---|---|---|
| 177 | 569.3 [M + H]+ | (300 MHz, CDCl3, ppm): δ 9.53 (s, 1H), 8.93 (s, 1H), 7.97-7.78 (m, 3H), 7.23 (s, 1H), 4.09 (s, 3H), 3.85 (q, J = 7.4 Hz, 2H), 3.21-3.05 (m, 1H), 2.06-1.95 (m, 2H), 1.90-1.81 (m, 2H), 1.40 (t, J = 7.4 Hz, 3H), 1.35-1.25 (m, 2H), 1.09 (s, 2H). |
| 178 | 562 [M + H]+ | (300 MHz, CDCl3, ppm): δ 9.54 (d, J = 2.1 Hz, 1H), 8.93 (d, J = 2.1 Hz, 1H), 8.10-7.90 (m, 1H), 7.77 (d, J = 7.8 Hz, 2H), 7.26 (s, 1H), 4.07 (s, 3H), 3.86-3.79 (m, 2H), 3.14-3.10 (m, 1H), 1.61-1.52 (m, 4H), 1.39 (t, J = 7.2 Hz, 3H), 1.26 (t, J = 6.9 Hz, 2H), 1.09-1.07 (m, 2H). |
| 179 | 612.3 [M + H]+ | (300 MHz, CDCl3, ppm): δ 9.60 (s, 1H), 8.99 (s, 1H), 7.96-7.79 (m, 2H), 7.75-7.72 (m, 1H), 7.25 (s, 1H), 4.10 (s, 3H), 3.85 (q, J = 7.4 Hz, 2H), 3.18-3.03 (m, 1H), 1.60-1.50 (m, 4H), 1.41 (t, J = 7.5 Hz, 3H), 1.31 (t, J = 7.2 Hz, 2H), 1.10 (brs, 2H). |
| 180 | 605 [M + H]+ | (300 MHz, DMSO-d6, ppm): δ 9.36 (d, J = 2.1 Hz, 1H), 8.94 (d, J = 2.4 Hz, 1H), 8.79 (s, 1H), 8.63 (d, J = 2.1 Hz, 1H), 8.55 (s, 1H), 8.19 (dd, J = 8.1, 2.4 Hz, 1H), 7.52 (d, J = 8.1 Hz, 1H), 6.74 (s, 1H), 5.25 (t, J = 13.5 Hz, 2H), 4.23-4.16 (m, 2H), 2.23-2.21 (m, 1H), 1.28 (t, J = 7.5 Hz, 3H), 1.06-1.02 (m, 4H). |
| 181 | 583 [M + H]+ | (300 MHz, DMSO-d6, ppm): δ 9.36 (d, J = 2.1 Hz, 1H), 8.94 (d, J = 2.4 Hz, 1H), 8.71 (s, 1H), 8.62 (d, J = 2.1 Hz, 1H), 8.46 (s, 1H), 8.19 (dd, J = 8.1, 2.4 Hz, 1H), 7.52 (d, J = 8.1 Hz, 1H), 5.47-5.23 (m, 1H), 4.19-4.17 (m, 2H), 2.13-2.26 (m, 1H), 1.74 (d, J = 6.6 Hz, 6H), 1.28 (t, J = 7.5 Hz, 3H), 1.13-0.95 (m, 4H). |
| 182 | 538.25 [M + H]+ | (300 MHz, CDCl3, ppm): δ 9.67 (s, 1H), 9.10 (s, 1H), 8.75-8.66 (m, 2H), 8.31 (d, J = 2.0 Hz, 1H), 7.70 (s, 1H), 7.26 (s, 1H), 4.08-3.92 (m, 5H), 2.23-2.10 (m, 1H), 1.52-1.38 (m, 5H), 1.13-1.03 (m, 2H). |
| 183 | 565 [M + H]+ | (400 MHz, Chloroform-d) δ 9.73 (d, J = 2.4 Hz, 1H), 9.19 (d, J = 2.0 Hz, 1H), 8.23 (s, 1H), 8.17-8.11 (m, 2H), 4.14 (s, 3H), 3.90 (q, J = 7.2 Hz, 2H), 2.27-2.24 (m, 2H), 2.05-2.00 (m, 2H), 1.49 (t, J = 7.2 Hz, 3H). |
| 184 | 552 [M + H]+ | (300 MHz, DMSO-d6, ppm): δ 9.50 (d, J = 1.8 Hz, 1H), 9.18 (d, J = 2.1 Hz, 1H), 9.06 (d, J = 1.8 Hz, 1H), 9.00 (d, J = 2.1 Hz, 1H), 8.75 (d, J = 1.8 Hz, 1H), 8.27 (dd, J = 8.1, 2.4 Hz, 1H), 7.55 (d, J = 8.1 Hz, 1H), 3.89-3.82 (m, 5H), 2.28-2.20 (m, 1H), 1.26 (t, J = 7.2 Hz, 3H), 1.24-1.04 (m, 4H). |
| 185 | 521 [M + H]+ | (300 MHz, DMSO-d6, ppm): δ 9.48 (d, J = 2.1 Hz, 1H), 8.98 J = 2.1 Hz, 1H), 8.78 (d, J = 1.8 Hz, 1H), 8.72 (d, J = 2.1 Hz, 1H), 8.67 (d, J = 1.8 Hz, 1H), 8.25 (dd, J = 8.1, 2.4 Hz, 1H), 7.54 (d, J = 8.1 Hz, 1H), 3.90-3.82 (m, 2H), 3.80 (s, 3H), 2.28-2.21 (m, 1H), 1.25 (t, J = 7.5 Hz, 3H), 1.06-1.02 (m, 4H). |
| 186 | 521 [M + H]+ | (300 MHz, CDCl3, ppm): δ 9.20 (d, J = 2.1 Hz, 1H), 8.83 (d, J = 2.4 Hz, 1H), 8.67 (d, J = 2.1 Hz, 1H), 8.20 (s, 1H), 7.91 (dd, J = 2.4, 5.7 Hz, 1H), 7.37 (d, J = 8.1 Hz, 1H), 4.08 (s, 3H), 3.84 (q, J = 7.5 Hz, 2H), 2.22-2.13 (m, 1H), 1.41 (t, J = 7.5 Hz, 3H), 1.20-1.10 (m, 4H). |
| 187 | 537 [M + H]+ | (300 MHz, DMSO-d6, ppm): δ 9.50 (d, J = 2.1 Hz, 1H), 9.00-8.98 (m, 2H), 8.76-8.73 (m, 2H), 8.26 (dd, J = 8.4, 2.4 Hz, 1H), 7.54 (d, J = 8.1 Hz, 1H), 3.91-3.82 (m, 5H), 2.28-2.22 (m, 1H), 1.26 (t, J = 7.5 Hz, 3H), 1.09-1.07 (m, 4H). |
| 188 | 537 [M + H]+ | (400 MHz, CDCl3, ppm): δ 9.21 (s, 1H), 8.84 (s, 1H), 8.67 (s, 1H), 8.61 (s, 1H), 7.93 (brs, 1H), 7.38 (d, J = 8.0 Hz, 1H), 4.14 (s, 3H), 3.85 (q, J = 7.2 Hz, 2H), 2.19 (brs, 1H), 1.42 (t, J = 7.6 Hz, 3H), 1.17 (brs, 4H). |
| 189 | 582 [M + H]+ | (400 MHz, DMSO-d6, ppm): δ 9.30 (d, J = 2.0 Hz, 1H), 8.69 (s, 1H), 8.56 (d, J = 2.0 Hz, 1H), 8.44 (s, 1H), 7.79 (d, J = 8.4 Hz, 2H), 7.29 (d, J = 8.4 Hz, 2H), 8.35-5.28 (m, 1H), 4.17 (q, J = 7.2 Hz, 2H), 2.03-1.99 (m, 1H), 1.73 (t, J = 6.4 Hz, 6H), 1.28-1.24 (m, 3H), 1.05-1.01 (m, 2H), 0.81-0.76 (m, 2H). |
| 190 | 604 [M + H]+ | (300 MHz, DMSO-d6, ppm): δ 9.32 (d, J = 2.1 Hz, 1H), 8.80 (s, 1H), 8.56 (d, J = 4.2 Hz, 2H), 7.80 (d, J = 8.4 Hz, 2H), 7.30 (d, J = 8.1 Hz, 2H), 6.92 (s, 1H), 5.26 (t, J = 13.8 Hz, 2H), 4.22-4.15 (m, 2H), 2.08-1.99 (m, 1H), 1.26 (t, J = 7.5 Hz, 3H), 1.07-1.01 (m, 2H), 0.80-0.75 (m, 2H). |
| 191 | 523 [M + H]+ | (400 MHz, Chloroform-d, ppm) δ: 9.09 (d, J = 2.3 Hz, 1H), 8.90 (d, J = 2.0 Hz, 1H), 8.83 (d, J = 2.3 Hz, 1H), 8.73 (s, 1H), 8.45 (s, 1H), 7.62-7.60 (m, 2H), 7.27 (m, 1H), 7.25 (m, 1H), 4.01-3.96 (m, 2H), 2.03-1.96 (m, 1H), 1.48-1.44 (m, 3H), 1.11-1.021 (m, 2H), 0.89-0.88 (m, 2H). |

-continued

| Compound | (ES, m/z) | $^1$H NMR Spectra |
|---|---|---|
| 192 | 542 [M + H]+ | (300 MHz, Chloroform-d) δ 9.56 (s, 1H), 9.07 (d, J = 2.3 Hz, 1H), 8.81 (d, J = 2.2 Hz, 1H), 8.27 (s, 1H), 7.73 (d, J = 8.1 Hz, 2H), 7.46 (d, J = 8.3 Hz, 2H), 4.00-3.93 (m, 2H), 1.69-1.56 (m, 2H), 1.48 (t, J = 7.5 Hz, 3H), 1.23-1.13 (m, 2H). |
| 193 | 549 [M + H]+ | (300 MHz, Chloroform-d) δ 9.56 (d, J = 1.1 Hz, 1H), 9.05 (d,.!-2.2 Hz, 1H), 8.80 (d,.1-2.2 Hz, 1H), 8.27 (d,.1-1.2 Hz, 1H), 7.78-7.68 (m, 2H), 7.57-7.46 (m, 2H), 4.01-3.94 (m, 2H), 1.92-1.82 (m, 2H), 1.55-1.51 (m, 2H), 1.48 (t, J = 7.4 Hz, 3H). |
| 194 | 483 [M + H]+ | (400 MHz, CDCl3, ppm): δ9.17-9.16 (m, 1H), 8.67-8.66 (m, 2H), 8.21-8.20 (m, 1H), 7.64-7.62 (m, 2H), 7.27 (s, 1H), 3.93-3.87 (m, 5H), 2.11-2.02 (m, 3H), 2.01-1.96 (m, 1H), 1.41-1.37 (m, 3H), 1.11-1.07 (m, 2H), 0.82-0.81 (m, 2H). |
| 195 | 539 [M + H]+ | (300 MHz, DMSO-d6) δ: 9.64 (s, 2H), 8.97 (d, J = 2.1 Hz, 1H), 8.86 (s, 1H), 8.68 (d, J = 2.0 Hz, 1H), 8.12 (d, J = 2.2 Hz, 1H), 3.89-3.84 (m, 5H), 2.4 (m, 1H), 1.30-1.18 (m, 7H). |
| 196 | 540 [M + H]+ | 300 MHz, DMSO-d6) δ 9.68 (dd, J = 4.5, 2.1 Hz, 2H), 9.03 (d, J = 2.1 Hz, 1H), 8.86 (s, 1H), 8.13 (d, J = 2.2 Hz, 1H), 4.01 (s, 3H), 3.82 (q, J = 7.4 Hz, 2H), 2.46-2.37 (m, 1H), 1.27 (t, J = 7.4 Hz, 3H), 1.24-1.17 (m, 4H). |
| 197 | 557 [M + H]+ | (300 MHz, Chloroform-d, ppm) δ 9.18 (d, J = 2.1 Hz, 1H), 8.70 (d, J = 2.1 Hz, 1H), 8.32 (s, 1H), 8.13 (s, 1H), 7.78-7.70 (m, 2H), 7.54-7.45 (m, 2H), 5.42 (p, J = 6.9 Hz, 1H), 4.15 (s, 2H), 1.98-1.90 (m, 2H), 1.85-1.83 (dd, J = 16.5, 4.7 Hz, 6H), 1.58-1.48 (m, 2H), 1.43 (t, J = 7.4 Hz, 3H). |
| 198 | 555 [M + H]+ | (300 MHz, Acetonitrile-d3, ppm) δ 9.22 (d, J = 2.1 Hz, 1H), 8.66 (d, J = 21 Hz, 1H), 8.41 (d, J = 2.1 Hz, 2H), 7.90-7.82 (m, 2H), 7.55 (d, J = 8.4 Hz, 2H), 6.23-6.21 (m, 1H), 5.42 (dd, J = 10.4, 1.2 Hz, 2H), 5.38-5.25 (m, 2H), 4.09 (q, J = 7.5 Hz, 2H), 1.87-1.77 (m, 2H), 1.62-1.52 (m, 2H), 1.33 (t, J = 7.5 Hz, 3H). |
| 199 | 555 [M + H]+ | (300 MHz, Chloroform-d, ppm) δ 9.23 (d, J = 2.1 Hz, 1H), 8.78 (d, J = 1.8 Hz, 1H), 8.67 (d, J = 2.1 Hz, 1H), 8.20 (d, J = 2.1 Hz, 1H), 7.8-7.71 (m, 2H), 7.56-7.46 (m, 2H), 3.53-3.40 (m, 1H), 3.29 (dd, J = 7.5, 5.7 Hz, 1H), 3.25 (dd, J = 7.5, 5.6 Hz, 1H), 1.91-1.76 (m, 2H), 1.63-1.47 (m, 2H), 1.32 (t, J = 7.5 Hz, 3H), 1.05-1.03 (m, 1H), 0.99-0.73 (m, 3H). |
| 200 | 569 [M + H]+ | (300 MHz, DMSO-d6, ppm) δ 9.34 (d, J = 2.1 Hz, 1H), 8.92 (s, 1H), 8.64-8.55 (m, 2H), 8.00-7.90 (m, 2H), 7.60-7.50 (m, 2H), 4.60 (d, J = 7.5 Hz, 2H), 4.21 (q, J = 7.5 Hz, 2H), 1.90-1.80 (m, 2H), 1.68-1.57 (m, 3H), 1.28 (t, J = 7.5 Hz, 3H), 0.62 (dd, J = 7.8, 5.7 Hz, 4H). |
| 201 | 501 [M + H]+ | (300 MHz, CDCl3, ppm): δ 9.21-9.20 (m, 1H), 8.733 (s, 1H), 8.68-8.67 (m, 1H), 8.31 (s, 1H), 7.77-7.72 (m, 2H), 7.47-7.44 (m, 2H), 3.93-3.89 (m, 5H), 2.13-1.92 (m, 3H), 1.67-1.56 (m, 2H), 1.50-1.40 (m, 2H). |
| 202 | 562 [M + H]+ | (300 MHz, Chloroform-d, ppm) δ: 9.50 (s, 1H), 9.07 (s, 1H), 9.03 (d, J = 2.1 Hz, 1H), 8.81 (d, J = 2.1 Hz, 1H), 8.73 (s, 1H), 7.75 (d, J = 8.1 Hz, 2H), 7.54 (d, J = 8.4 Hz, 2H), 4.03 (m, 2H), 1.89 (m, 2H), 1.61-1.48 (m, 5H). |
| 203 | 546 [M + H]+ | (300 MHz, Chloroform-d, ppm) δ: 9.37 (s, 1H), 9.08-9.01 (m, 2H), 8.80 (d, J = 2.1 Hz, 1H), 8.51 (s, 1H), 7.74 (d, J = 8.4 Hz, 2H), 7.54 (d, J = 8.4 Hz, 2H), 4.03-3.99 (m, 2H), 2.03 (s, 1H), 1.95-1.86 (m, 2H), 1.55-1.47 (m, 5H). |
| 204 | 530 [M + H]+ | (300 MHz, Chloroform-d, ppm) δ: 9.36 (s, 1H), 8.99 (s, 1H), 8.95 (s, 1H), 8.77 (d, J = 2.1 Hz, 1H), 8.04 (s, 1H), 7.75 (d, J = 8.2 Hz, 2H), 7.53 (d, J = 8.4 Hz, 2H), 4.00-3.93 (m, 2H), 1.88-1.85 (m, 2H), 1.53-1.44 (m, 5H). |
| 205 | 534 [M + H]+ | (300 MHz, CDCl3, ppm) δ 9.20 (s, 1H), 9.19 (s, 1H), 8.79 (s, 1H), 8.37 (s, 1H), 7.73 (d, J = 8.4 Hz, 2H), 7.51 (d, J = 8.4 Hz, 2H), 3.94-3.89 (m, 5H), 1.89-1.86 (m, 2H), 1.55-1.52 (m, 2H), 1.42 (d, J = 7.5 Hz, 3H), 1.25 (s, 1H) 0.92-0.84 (rm 2H), 0.82-0.75 (m, 2H). |
| 206 | 535 [M + H]+ | (300 MHz, DMSO-d6) δ 9.49 (d, J = 2.1 Hz, 1H), 8.72 (d, J = 2.1 Hz, 1H), 8.40 (s, 1H), 8.02 (d, J = 8.4 Hz, 2H), 7.57 (d, J = 8.4 Hz, 2H), 3.96 (s, 3H), 3.86-3.78 (m, 2H), 2.18-2.01 (m, 1H), 1.88-1.84 (m, 2H), 1.66-1.61 (m, 2H), 1.25 (t, J = 7.5 Hz, 3H), 0.81-0.77 (m, 4H). |
| 207 | 508 [M + H]+ | (300 MHz, Chloroform-d, ppm) δ: 9.17 (s, 1H), 8.67 (s, 2H), 8.23 (s, 1H), 7.73 (d, J = 8.1 Hz, 2H), 7.50 (d, J = 8.4 Hz, 2H), 3.96-3.89 (m, 5H), 2.07 (t, J = 18.3 Hz, 3H), 1.88-1.83 (m, 2H), 1.54-1.49 (m, 2H), 1.40 (t, J = 7.5 Hz, 3H). |
| 208 | 502 [M + H]+ | (400 MHz, CDCl3, ppm): δ 9.22 (d, J = 2.4 Hz, 1H), 8.70 (d, J = 2.1 Hz, 1H), 8.20 (s, 1H), 7.74 (d, J = 8.1 Hz, 2H), 7.46 (d, J = 8.1 Hz, 2H), 4.39 (s, 3H), 3.85 (q, J = 7.5 Hz, 2H), 2.31 (t, J = 18.9 Hz, 3H), 1.67-1.56 (m, 2H), 1.43 (d, J = 7.5 Hz, 3H), 1.25-1.16 (m, 2H). |

-continued

| Compound | (ES, m/z) | $^1$H NMR Spectra |
|---|---|---|
| 209 | 484 [M + H]+ | (300 MHz, DMSO-d6) δ 9.46 (d, J = 2.1 Hz, 1H), 8.68 (d, J = 2.1 Hz, 1H), 8.44 (s, 1H), 7.88 (d, J = 8.4 Hz, 2H), 7.33 (d, J = 8.4 Hz, 2H), 3.96 (s, 3H), 3.86-3.79 (m, 2H), 2.26 (t, J = 19.2 Hz, 3H), 2.08-2.01 (m, 1H), 1.26 (t, J = 7.5 Hz, 3H), 1.09-1.04 (m, 2H), 0.85-0.74 (m, 2H). |
| 210 | 509 [M + H]+ | (300 MHz, DMSO-d6, ppm): δ 9.49 (d, J = 2.1 Hz, 1H), 8.72 (d, J = 2.1 Hz, 1H), 8.44 (s, 1H), 8.02 (d, J = 8.4 Hz, 2H), 7.57 (d, J = 8.4 Hz, 2H), 3.96 (s, 3H), 3.83 (q, J = 7.2 Hz, 2H), 2.32-2.19 (m, 3H), 1.89-1.85 (m, 2H), 1.66-1.62 (m, 2H), 1.26 (t, J = 7.2 Hz, 3H). |
| 211 | 555.2 [M + H]+ | (300 MHz, DMSO-$d_6$, ppm) δ 9.49 (d, J = 2.1 Hz, 1H), 8.85 (d, J = 1.8 Hz, 1H), 8.69 (dd, J = 13.2, 2.1 Hz, 2H), 8.01 (d, J = 8.1 Hz, 2H), 7.51 (d, J = 8.4 Hz, 2H), 3.89 (q, J = 7.5 Hz, 2H), 3.84 (s, 3H), 1.67-1.50 (m, 2H), 1.28 (dt, J = 9.5, 7.2 Hz, 5H). |
| 212 | 539 [M + H]+ | (300 MHz, Chloroform-d, ppm) δ: 9.11 (s, 1H), 8.70 (d, J = 1.9 Hz, 1H), 8.02 (d, J = 9.1 Hz, 1H), 7.73 (d, J = 8.1 Hz, 2H), 7.50 (d, J = 8.2 Hz, 2H), 7.32 (d, J = 9.1 Hz, 1H), 5.11 (t, J = 12.8 Hz, 2H), 3.95 (q, J = 7.4 Hz, 2H), 1.86 (q, J = 5.1 Hz, 2H), 1.58-1.40 (m, 5H). |
| 213 | 515 [M + H]+ | (300 MHz, Chloroform-d, ppm) δ: 9.11 (s, 1H), 8.81 (s, 1H), 8.68 (s, 1H), 8.02 (d, J = 9.1 Hz, 1H), 7.92-7.89 (m, 1H), 7.37-7.28 (m, 2H), 5.19-5.04 (m, 2H), 3.99-3.92 (m, 2H), 2.24-2.12 (m, 1H), 1.46 (t, J = 7.4 Hz, 3H), 1.27-1.17 (m, 4H). |
| 214 | 576.2 [M + H]+ | (300 MHz, DMSO-d6, ppm) δ 9.49 (d, J = 2.1 Hz, 1H), 9.19 (d, J = 2.1 Hz, 1H), 9.07 (d, J = 2.1 Hz, 1H), 8.72 (d, J = 2.1 Hz, 1H), 8.03-8.00 (m, 2H), 7.58-7.55 (m, 2H), 3.91-3.83 (m, 5H), 1.89-1.85 (m, 2H), 1.66-1.62 (m, 2H), 1.27 (t, J = 7.5 Hz, 3H). |

Example 3: Screening Method to Test Activity of Compounds of Formula (I) Against Larvae of *Aedes aegypti*

Eight *A. aegypti* L1 larvae in a total volume of 64 μL water were added to 384-well microplates containing compounds formulated in 100% DMSO. The plates were incubated for 48 h at 27° C. Individual well images were acquired and analyzed using a pipeline to quantitatively assess the amount of larvae biomass accumulating at the bottom of the well. The efficacy of a compound at a given dose is expressed as "percentage of mortality" and determined by comparison to average biomass descriptors of positive and negative control wells containing 1.0 μM Fipronil or DMSO only, respectively. Dose response assay were conducted to determine an $EC_{50}$ value. Compounds 10, 61, 70, 81, 84, 89, 120, 201 exhibited $EC_{50}$ values of between 50 nM and 40 nM. Compounds 1, 2, 3, 12, 13, 17, 18, 19, 20, 22, 25, 26, 27, 29, 30, 32, 34, 38, 41, 42, 43, 44, 45, 52, 60, 65, 66, 67, 68, 71, 72, 79, 80, 82, 83, 85, 86, 87, 88, 90, 91, 112, 114, 115, 116, 117, 202, 203, 204, 207, 212 exhibited $EC_{50}$ values of less than 40 nM.

Example 4: Screening method to test contact activity of compounds of formula (I) against Adult *Ctenocephalides felis*

Compounds of formula (I) dissolved in 100% DMSO were diluted in acetone to a desired concentration. The resulting formulation was used to coat the fibers of a 0.5-inch-long piece of pipe cleaner placed in a glass scintillation vial. The vial was capped with a rubber gasket and filter paper insert. After the acetone had evaporated, ten adult *Ctenocephalides felis* fleas were added to each vial. The vials were then incubated at 22° C., 80% relative humidity, and 12 hours of light/]2 hours of dark until a visual evaluation for mortality was performed at 72 hours post-treatment. Compound efficacy at a given dose is expressed as percentage mortality and adjusted to remove background mortality observed in control vials containing DMSO only. A dose response series of treated vials was implemented to determine $EC_{50}$ values. Compounds 44, 117, 118 exhibited $EC_{50}$ values of between 100 μM and 10 μM. Compounds 71, 90 exhibited $EC_{50}$ values of less than 10 μM.

Example 5: Screening Method to Test Contact Activity of Compounds of Formula (I) Against Adult *Rhipicephalus sanguineus*

Compounds of formula (I) formulated in 100% DMSO were diluted in a solution containing acetone and Triton X-100 (0.02%). The resulting formulation was used to coat the inner walls of glass scintillation vials and the filter paper covering the cap of the vial. Once dried, ten adult *R. sanguineus* ticks were added to the vials. The vials were incubated at 24° C., 95% relative humidity, and 12 hours of light/12 hours of dark until evaluation. Ticks were visually evaluated for mortality at 48 hours post-treatment. Compound efficacy at a given dose is expressed as percentage mortality. A dose response series was implemented to determine $EC_{50}$ values. Compounds 1, 13, 31, 38, 44, 46, 60, 61, 80, 81, 84, 88, 112, 115, 133, 134, 135, 147, 153, 154, 155, 157, 163, 165, 166, 167, 169, 176, 177, 178, 179, 182, 188, 189, 194, 197, 201, 211 exhibited $EC_{50}$ values of between 100 μM and 10 μM. Compounds 27, 45, 52, 96, 100, 101, 126, 128, 185, 187, 207, 213 exhibited $EC_{50}$ values of less than 10 μM.

Example 6: Screening Method to Test Ingestion Activity of Compounds of Formula (I) Against Adult *Ctenocephalides felis*

Compounds of formula (I) dissolved in 100% DMSO were added to bovine blood and offered via an artificial membrane feeding system to adult *C. felis* fleas. The motility of fleas was then recorded by machine vision 24h post treatment. Efficacy is expressed in % motility reduction compared to controls containing blood treated with DMSO only. A dose response series was implemented to determine $EC_{80}$ values. Compounds 9, 10, 12, 16, 20, 22, 35, 42, 43, 44, 45, 46, 62, 70, 72, 86, 88, 90, 93, 107, 112, 124, 129, 130, 131, 132, 133, 134, 135, 140, 142, 145,147, 148, 149, 150, 160, 161, 162, 163, 164, 169, 171, 172, 173, 174, 175, 176, 178, 181, 189, 190, 192, 196, 198 exhibited $EC_{8}o$ values of between 10 μM and 1 μM. Compounds 2, 18, 19, 25, 63, 65, 66, 67, 68, 71, 80, 85, 115, 138, 143, 146, 151, 153, 156, 165, 166, 177, 179, 180, 182, 183, 184, 185, 187, 193, 195, 197, 200, 201, 211, 214 exhibited $EC_{80}$ values of less than 1 μM.

Example 7: Screening Method to Test Contact Activity of Compounds of Formula (I) Against Adult *Ctenocephalides felis*

Adult *C. felis* fleas were distributed on a surface treated with compounds of formula (I) or compound carrier vehicle and incubated for 24h. Motility of the fleas were then quantified by machine vision. Efficacy was expressed in % motility reduction compared to negative controls containing compound carrier only. A dose response series was implemented to determine $EC_{80}$ values. Compounds 1, 6, 8, 9, 10, 12, 13, 14, 15, 16, 17, 19, 21, 24, 25, 26, 27, 29, 30, 34, 38, 39, 40, 41, 42, 43, 44, 48, 58, 60, 62, 63, 65, 66, 72, 79, 81, 82, 83, 84, 86, 87, 88, 89, 92, 100, 107, 110, 124, 125, 127, 128, 129, 131, 133, 134, 135, 136, 139, 142, 144, 154, 158, 166, 170, 171 exhibited $EC_{80}$ values of between 10 μM and 1 μM. Compounds 2, 4, 18, 35, 67, 70, 71, 80, 85, 90, 93, 112, 115, 118, 120,130, 137, 138, 143, 152, 153, 159, 165, 168, 169 exhibited $EC_{80}$ values of less than 1 μM.

Example 8: Screening Method to Test Contact Activity of Compounds of Formula (I) Against Larvae of *Rhipicephalus sanguineus*

Tick eggs were distributed on a surface treated with compounds of formula (I) or carrier vehicle and incubated for approximately one month until the larvae hatch. Motility of the larvae was quantified by machine vision. Efficacy is expressed in % motility reduction compared to negative controls containing compound vehicle only. A dose response series was implemented to determine $EC_{80}$ values. Compounds 79 and 88 exhibited $EC_{80}$ values of less than 500 $\mu M/m^2$.

Example 9: Comparison of Selected Specific Compounds of Formula (I) with the Four Structurally Closest Prior Art Compounds (A), (B), (C) and (D) Specifically Excluded from the Scope of Formula (I)

The four structurally closest prior art compounds (A), (B), (C) and (D) specifically excluded from the scope of formula (I) were characterized vis-a-vis selected compounds of formula (I) with regard to their potency in in vitro screening assays against fleas (Ctenocehalides *felis*) and ticks (*Rhipicephalus sanguineus*).

It is important to note that compounds that show better activity versus ticks are more desirable in the animal health field, as ticks are more difficult to control than fleas. Noteworthy, in particular with regard to fleas the illustrated comparative data are based on a flea membrane feeding (ingestion, blood feeding) assay. Data from this assay are more relevant for compounds intended to be delivered systemically to an animal via oral or injectable routes. Membrane feeding assays differ to primary screening laboratory contact assays in that the latter only measure the effect of the direct contact of selected compounds on the parasite, such as the flea or the tick. The information derived from laboratory contact assays is strictly limited to the ability of the compound to be absorbed through the parasite surface and to reach its molecular target, and no information can be gleaned from these contact assays as to whether the compound would also be active when presented orally to the ectoparasite itself in a blood meal, such as with the membrane feeding assay, and certainly not when administered orally to an animal host (e.g. "in vivo") with subsequent exposure to the ectoparasite.

Profiling of the four structurally closest prior art compounds (A), (B), (C) and (D) specifically excluded from the scope of formula (I) in the flea membrane feeding (ingestion, blood feeding) assay as well as the flea and tick contact assays show some activity of these compounds against fleas, but no activity against ticks (an entry of >100 μM signifies that the respective tested compound was found to not be active at the top concentration administered in the assay). However, as explained above, spectrum of action against this range of species (i.e. fleas and ticks) is a desirable property of ectoparasiticides for veterinary use. In the following table 1 comparative experimental data of the in vitro assays are shown regarding flea membrane feeding (ingestion, blood feeding) activity against *Ctenocephalides felis* and contact activity against *Rhipicephalus sanguineus*. The results of these two in vitro assays demonstrate the superior potency/efficacy of selected compounds of formula (I) over the four structurally closest prior art compounds (A), (B), (C) and (D) specifically excluded from the scope of formula (I): on the one hand, these results suggest the unsuitability of such structurally closest prior art compounds against ticks, such as *R. sanguineus*, for administration methods that require the direct absorption through the parasite surface for efficacy (e.g. topical). On the other hand, the selected compounds of formula (I) show increased activity and potency against the desired spectrum of fleas and ticks while exhibiting better suitability for administration methods that require either ingestion of the compound in the blood meal, e.g. oral or other systemic route, or its direct absorption through the parasite surface by residue contact, e.g. topical.

TABLE 1

| Compound | *C. felis* membrane feeding (ingestion/blood feeding) activity $EC_{80}$ (μM) | *R. sanguineus* contact activity $EC_{50}$ (μM) |
|---|---|---|
| (A) | >10 | >100 |
| (B) | >10 | >100 |
| (C) | >10 | >100 |
| (D) | >10 | >100 |
| 12 | <1 | 10-100 |
| 19 | <1 | 10-100 |
| 44 | 1-10 | 10-100 |
| 45 | 1-10 | <10 |
| 46 | 1-10 | 10-100 |
| 80 | <1 | 10-100 |
| 88 | 1-10 | 10-100 |
| 89 | 1-10 | 10-100 |
| 96 | 1-10 | 10-100 |
| 97 | <1 | 10-100 |
| 112 | 1-10 | 10-100 |
| 115 | <1 | 10-100 |
| 124 | 1-10 | 10-100 |
| 133 | 1-10 | 10-100 |

TABLE 1-continued

| Compound | *C. felis* membrane feeding (ingestion/blood feeding) activity $EC_{80}$ (μM) | *R. sanguineus* contact activity $EC_{50}$ (μM) |
|---|---|---|
| 134 | 1-10 | 10-100 |
| 135 | 1-10 | 10-100 |
| 142 | 1-10 | 10-100 |
| 153 | 1-10 | 10-100 |
| 165 | <1 | 10-100 |
| 166 | <1 | 10-100 |
| 169 | 1-10 | 10-100 |
| 186 | <1 | <10 |

Example 10: Comparison of Oral Rat-Tick Efficacy Data for Selected Specific Compounds of Formula (I) Against Nymphs of *Dermacentor variabilis* Ticks On Day −1, rats were sedated, fitted with an Elizabethan collar, and infested with approximately 35 nymphal stage *D. variabilis* ticks. On Day 0, each rat was treated via oral gavage with the appropriate formulation of placebo, positive control, or test compound at the appropriate dose. On Day 3, all rats were euthanized, and ticks were removed, counted, and disposed of. In Table 2 efficacy is expressed in % mortality compared to negative controls containing compound vehicle only.

TABLE 2

| Compound | Observed efficacy | Oral dose |
|---|---|---|
| 19 | >95% | 10 mg/kg |
| 44 | >95% | 10 mg/kg |
| 67 | >95% | 10 mg/kg |

Example 11: Insecticidal Test on *Spodoptera litura*

The compounds of formula (I) of the present invention or salts thereof were separately dispersed in water and diluted to 500 ppm. Cabbage leaves were dipped in the dispersion for about 30 seconds. After air dried, the leaves were placed in a plastic Petri dish with a diameter of 9 cm and inoculated with ten 2nd-instar larvae of *Spodoptera litura*, after which the dish was closed and then allowed to stand in a room at 25° C. 8 days after the inoculation, the numbers of the dead and alive insects were counted. The corrected mortality rate was calculated according to the following formula and the insecticidal activity was evaluated according to the following criteria.

Corrected mortality rate (%)=100×(Survival rate in an untreated plot−Survival rate in a treated plot)/Survival rate in an untreated plot A: the corrected mortality rate is 100%
B: the corrected mortality rate is 90 to 99%
C: the corrected mortality rate is 80 to 89%
D: the corrected mortality rate is 50 to 79%

As a result, the compounds 2, 3, 4, 5, 10, 17, 18, 19, 20, 25, 35, 38, 41, 42, 43, 44, 45, 63, 66, 67, 68, 69, 70, 71, 79, 85, 86, 87, 88, 89, 90, 91, 96, 107, 112, 114, 115, 117, 118, 123, 124, 127, 128, 129, 130, 131, 132, 133, 135, 136, 141, 142, 143, 144, 145, 146, 149, 150, 153, 156, 160, 161, 162, 165, 166, 167, 169, 170, 171, 172, 174, 177, 180, 181, 182, 185, 186, 187, 188, 192 and 194 showed the activity level evaluated as A.

Example 12: Insecticidal Test on *Plutella xylostella*

The compounds of formula (I) of the present invention or salts thereof were separately dispersed in water and diluted to 500 ppm. Ten adults of *Plutella xylostella* were released onto Chinese cabbage seedlings and allowed to lay eggs thereon. 2 days after the release of the adults, the seedling was dipped in the dispersion for about 30 seconds. After air dried, the seedling was kept in a room at 25° C. 6 days after the dip treatment, the numbers of the dead and alive insects were counted. The corrected mortality rate was calculated according to the following formula and the insecticidal activity was evaluated according to the following criteria.

Corrected mortality rate (%)=100×(Survival rate in an untreated plot−Survival rate in a treated plot)/Survival rate in an untreated plot A: the corrected mortality rate is 100%
B: the corrected mortality rate is 90 to 99%
C: the corrected mortality rate is 80 to 89%
D: the corrected mortality rate is 50 to 79%

As a result, the compounds 2, 3, 4, 5, 6, 8, 9, 10, 11, 15, 16, 17, 18, 19, 20, 21, 24, 25, 31, 32, 34, 35, 38, 39, 40, 41, 42, 43, 44, 45, 52, 55, 60, 63, 64, 66, 67, 68, 69, 70, 71, 79, 82, 83, 85, 86, 87, 88, 89, 90, 91, 92, 94, 96, 97, 100,112, 113,114, 115, 117, 118, 123, 124, 126, 127, 128, 129,130, 131,132,133,134,135, 136, 138, 140,141, 142, 143, 144, 145, 146, 149, 150, 153, 154, 156, 157, 158, 160, 161, 162, 164, 165, 166, 167, 168, 169, 170, 171, 174, 177, 180, 181, 182, 185, 186, 187, 188, 189, 190, 191, 192, 194, 195 and 196 showed the activity level evaluated as A.

Example 13: Insecticidal Test on *Laodelphax striatellus*

The compounds of formula (I) of the present invention or salts thereof were separately dispersed in water and diluted to 500 ppm. Rice plant seedlings were dipped in the dispersion for about 30 seconds. After air dried, the seedlings were put into a separate glass test tube and inoculated with ten 3rd-instar nymphs of *Laodelphax striatellus* and then the glass test tube was kept in a room at 25° C. 8 days after the inoculation, the numbers of the dead and alive insects were counted. The corrected mortality rate was calculated according to the following formula and the insecticidal activity was evaluated according to the following criteria.

Corrected mortality rate (%)=100×(Survival rate in an untreated plot−Survival rate in a treated plot)/Survival rate in an untreated plot A: the corrected mortality rate is 100%
B: the corrected mortality rate is 90 to 99%
C: the corrected mortality rate is 80 to 89%
D: the corrected mortality rate is 50 to 79%

As a result, the compounds 2, 3, 4, 5, 15, 18, 20, 38, 39, 41, 44, 45, 52, 55, 60, 69, 71, 82, 83, 85, 88, 89, 96, 100, 115, 117, 118, 123, 124, 126, 128, 129, 130, 131, 133, 134, 135, 138, 141, 142, 143, 149, 150, 153, 156, 157, 158, 160, 161, 164, 165, 166, 167, 169, 174, 177, 180, 182, 185, 186, 187, 188, 194, 195 and 196 showed the activity level evaluated as A.

Example 14: Insecticidal Test on *Myzus persicae*

The compounds of formula (I) of the present invention or salts thereof were separately dispersed in water and diluted to 500 ppm. Chinese cabbage plants were planted in plastic pots (diameter: 8 cm, height: 8 cm). Aphids (*Myzus persi-*

*cae*) were propagated on the plants and then the number of surviving aphids was counted. The dispersion was applied to the foliage of the potted plants. After the plants were air dried, these were kept in a greenhouse. 6 days after the application, the number of the alive insects was counted on the plants. The control rate was calculated according to the following formula and the control efficacy was evaluated according to the following criteria.

$$\text{Control rate } (\%)=100-\{(T\times Ca)/(Ta\times C)\}\times 100$$

Ta: the number of alive insects before the foliar application in a treated plot

T: the number of alive insects after the foliar application in a treated plot

Ca: the number of alive insects before the foliar application in an untreated plot C: the number of alive insects after the foliar application in an untreated plot A: the control rate is 100%

B: the control rate is 90 to 99%

C: the control rate is 80 to 89%

D: the control rate is 50 to 79%

As a result, the compounds 2, 3, 5, 15, 17, 18, 20, 21, 32, 38, 39, 41, 43, 44, 45, 52, 55, 69, 71, 83, 85, 87, 88, 89, 90, 92, 96, 112, 115, 117, 118, 123, 124, 125, 126, 128, 130, 131, 132, 133, 134, 135, 138, 141, 142, 144, 145, 146, 149, 150, 153, 154, 156, 157, 160,161, 162, 164, 165, 166, 167, 168, 169, 170, 174, 177, 180, 181, 182, 185, 186, 188, 194 and 196 showed the control efficacy level evaluated as A.

REFERENCES

The following references, to the extent that they provide exemplary procedural or other details supplementary to those set forth herein, are specifically incorporated herein by reference.

(1) JP 2018/076354
(2) US 2020/0361940
(3) WO 2016/030229
(4) WO 2017/146221
(5) WO 2020/178789
(6) WO 2021/033141
(7) WO 2021/049595
(8) WO 2021/049596

EMBODIMENTS

The following clauses are also part of the disclosure and are comprised by the spirit and scope of the present invention:

1. A compound of formula (I)

(I)

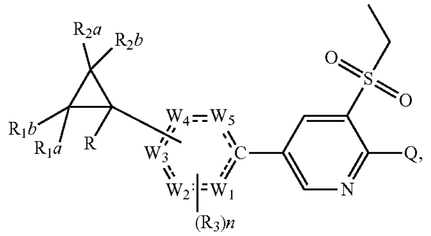

wherein:

W1, W2, W3, W4, W5 are each independently N, C or C—H, wherein at most three of W1, W2, W3, W4, W5 are N;

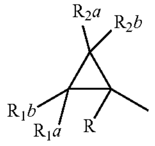

is attached to a C atom;

R, R1a, R1b, R2a, R2b, R3 are each independently hydrogen, halogen, such as F, Cl, Br, I, $C_1$-$C_6$-alkyl, such as $CH_3$, $C_1$-$C_6$-haloalkyl, such as $CF_3$, $CHF_2$, $CH_2$—$CF_3$, $CH_2$—$CHF_2$, $CH_2$—$CH_2F$, $CF_2$—$CH_3$, $CH_2F$, $CF_2$—$CF_3$, $CF_2$—$CHF_2$, $C_3$-$C_8$-cycloalkyl, such as cyclopropyl, aryl, such as phenyl, $C_1$-$C_6$-alkoxy, such as methoxy, ethoxy, propoxy, $C_1$-$C_6$-haloalkoxy, such as O—$CF_3$, OH, CN, C(O)OR, $S(O)_1$—($C_1$-$C_6$-alkyl), such as S—$CH_3$, S(O)—$CH_3$, $S(O)_2$—$CH_3$, S(O),—($C_1$-$C_6$-haloalkyl), such as S—$CF_3$, S(O)—$CF_3$, $S(O)_2$—$CF_3$, $S(O)_r$—R.; $S(O)_2$—$N(R_x)(R_y)$; S(O)—(R,)=N—$R_z$; and wherein R3, if present once or more times, in each occurrence is independently attached to a C atom; or wherein R together with R1a or R1b forms an unsubstituted or substituted carbocycle or an unsubstituted or substituted heterocycle, wherein preferably such carbocycle or heterocycle if substituted is independently substituted with one, two or three substituents each independently selected from the group consisting of: halogen, such as F, Cl, Br, I, alkyl, such as $CH_3$, $C_1$-$C_6$-haloalkyl, such as $CF_3$, $CHF_2$, $CH_2$—$CF_3$, CH—$CHF_2$, $CH_2$—$CH_2F$, $CF_2$—$CH_3$, $CH_2F$, $CF_2$—$CF_3$, $CF_2$—$CHF_2$, $C_3$-$C_5$-cycloalkyl, such as cyclopropyl, aryl, such as phenyl, $C_1$-$C_6$-alkoxy, such as methoxy, ethoxy, propoxy, $C_1$-$C_6$-haloalkoxy, such as O—$CF_3$, OH, CN, $C(O)OR_x$, S(O)—($C_1$-$C_6$-alkyl), such as S—$CH_3$, S(O)—$CH_3$, $S(O)_2$—$CH_3$, S(O),—($C_1$-$C_6$-haloalkyl), such as S—$CF_3$, S(O)—$CF_3$, $S(O)_2$—$CF_3$;

Q is selected from the group consisting of: Q1, Q2, Q3, wherein:

Q1 is an unsubstituted or substituted monocyclic, preferably 5- or 6-membered, heteroaryl or heterocyclyl containing one, two or three heteroatoms, which are each independently selected from the group consisting of N, O, S, S(O), $S(O)_2$; wherein preferably Q1 if substituted is substituted with one, two, three or four substituents each independently selected from the group consisting of: halogen, such as F, Cl, Br, I, $C_1$-$C_6$-alkyl, such as methyl, ethyl, isopropyl, $C_2$-$C_6$-alkenyl, such as ethenyl, $C_1$-$C_6$-haloalkyl, such as $CF_3$, $C_2FS$, $CH_2$—$CHF_2$, $CH_2$—$CF_3$, $CHF_2$, $C_2$-$C_6$-haloalkenyl, such as CH═CF—$CF_3$, $C_1$-$C_6$-haloalkoxy, such as O—$CH_2$—$CF_3$, O—$CH_2$—$C_2F_5$, $C_3$-$C_5$-cycloalkyl, such as cyclopropyl, $C_3$-$C_5$-cycloalkyl-alkyl, such as cyclopropyl-methyl, $C_3$-$C_5$-cycloalkyl substituted with one or more halogens, such as cyclopropyl substituted with one or more F, heterocyclyl, such as aziridinyl, oxetanyl, heteroaryl, such as pyridine or pyridine substituted with one or more $C_1$-$C_6$-haloalkyl or $C_1$-$C_6$-haloalkoxy, such as $CF_3$, $CH_2$—$CF_2$—$CF_3$, or O—$CH_2$—$CF_2$—$CF_3$, =O;

Q2 is an unsubstituted or substituted fused bicyclic, preferably 9- or 10-membered, heteroaryl or heterocyclyl containing one, two, three, four or five heteroatoms, which are each independently selected from the group consisting of N, O, S, S(O), $S(O)_2$: wherein preferably Q2 if substituted is substituted with one, two, three, four, five or six substituents each independently selected from the group consisting of: halogen, such as F, Cl, Br, I, $C_1$-$C_6$-alkyl, such as methyl, ethyl, isopropyl, $C_2$-$C_6$-alkenyl, such as ethenyl, $C_1$-$C_6$-haloalkyl, such as $CF_3$, $C_2F_5$, $CH_2$—$CHF_2$, $CH_2$—$CF_3$, $CHF_2$, $C_2$—C-haloalkenyl, such as CH═CF—$CF_3$, $C_1$-$C_6$-haloalkoxy, such as O—$CH_2$—$CF_3$, 0—$CH_2$—$C_2F_5$, $C_3$-$C_x$-cycloalkyl, such as cyclopropyl, $C_3$-$C_5$-cycloalkyl-alkyl, such as cyclopropyl-methyl, $C_3$-$C_5$-cycloalkyl substituted with one or more halogens, such as cyclopropyl substituted with one or more F, C(O)—($C_1$-$C_6$-alkyl), such as C(O)-methyl, heterocyclyl, such as aziridinyl, oxetanyl, $S(O)_r(C_1$-$C_6$-alkyl), such as S-methyl; S(O)-methyl, $S(O)_2$-methyl; $S(O)_s$—($C_1$-$C_6$-haloalkyl), such as S—$CF_3$, S(O)—$CF_3$, $S(O)_2$—$CF_3$, =O;

Q3 is an unsubstituted or substituted fused tricyclic, preferably 12- or 13-membered, heteroaryl or heterocyclyl containing one, two, three, four, five, six or seven heteroatoms, which are each independently selected from the group consisting of N, O S, S(O), $S(O)_2$; wherein preferably Q3 if substituted is substituted with one, two, three, four, five, six, seven or eight substituents each independently selected from the group consisting of: halogen, such as F, Cl, Br, I, $C_1$-$C_6$-alkyl, such as methyl, ethyl, isopropyl, $C_2$-$C_6$-alkenyl, such as ethenyl, $C_1$-$C_6$-haloalkyl, such as $CF_3$, $C_2F_5$, $CH_2$—$CHF_2$, $CH_2$—$CF_3$, $CHF_2$, $C_2$-$C_6$-haloalkenyl, such as CH═CF—$CF_3$, $C_1$-$C_6$-haloalkoxy, such as O—$CH_2$—$CF_3$, O—$CH_2$—$C_2F_5$, $C_3$-$C_a$-cycloalkyl, such as cyclopropyl, $C_3$-$C_5$-cycloalkyl-alkyl, such as cyclopropyl-methyl, $C_3$-$C_5$-cycloalkyl substituted with one or more halogens, such as cyclopropyl substituted with one or more F, C(O)—($C_1$-$C_6$-alkyl), such as C(O)-methyl, heterocyclyl, such as aziridinyl, oxetanyl, $S(O)_r$—($C_1$-$C_6$-alkyl), such as S-methyl; S(O)-methyl, $S(O)_2$-methyl; $S(O)_r$—($C_1$-$C_6$-haloalkyl), such as S—$CF_3$, S(O)—$CF_3$, $S(O)_2$—$CF_3$, =O;

$R_v$, $R_w$, $R_x$, $R_y$, $R_z$ in each occurrence are independently selected from the group consisting of: hydrogen, halogen, such as F, Cl, Br, I, $C_1$-$C_6$-alkyl, such as methyl, ethyl, $C_1$-$C_6$-haloalkyl, such as $CF_3$;

n is 0, 1, 2, 3, 4;

r, s, t in each occurrence independently are 0, 1 or 2;

the dashed bond (...) signifies a single or double bond;

or a pharmaceutically acceptable salt thereof;

with the proviso that the following compounds are excluded from the scope of the compound of formula (I):

(A)

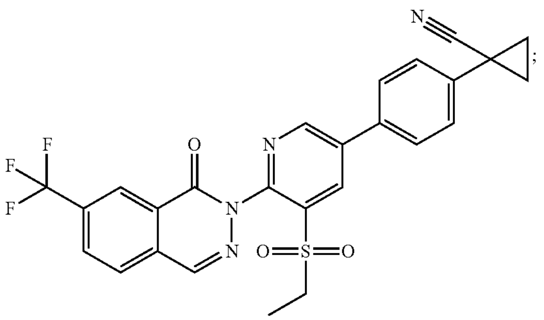

-continued (B)

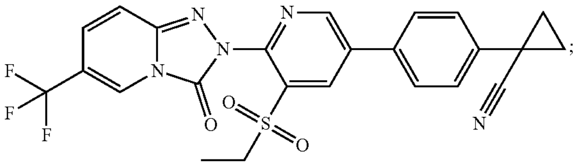

(C)

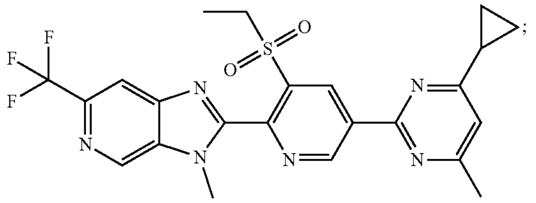

(D)

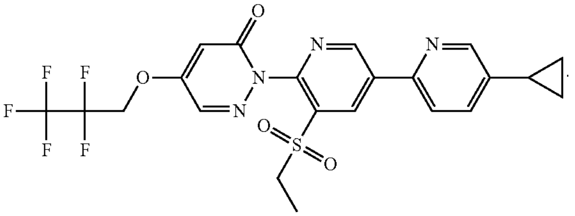

2. The compound according to clause 1, wherein Q1, Q2, Q3 are independently selected from the group consisting of:

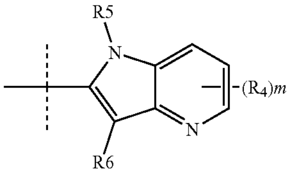

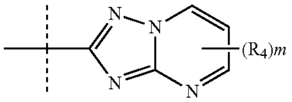

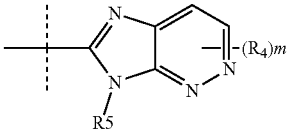

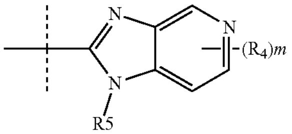

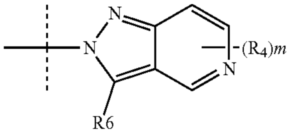

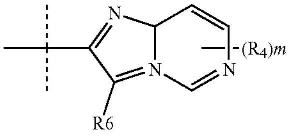

-continued
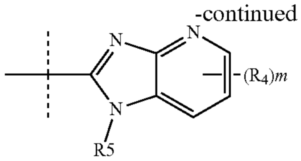
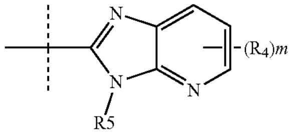
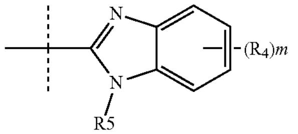
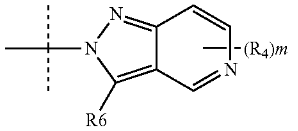
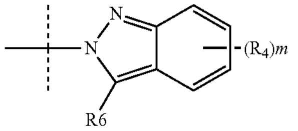
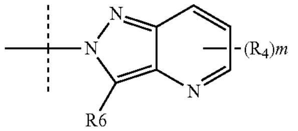
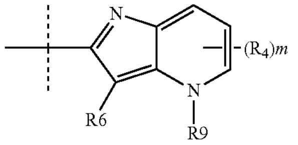
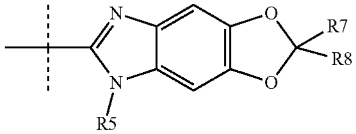
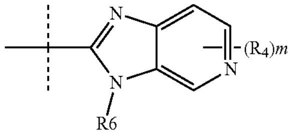
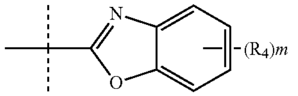
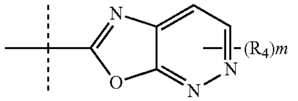
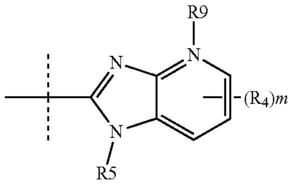
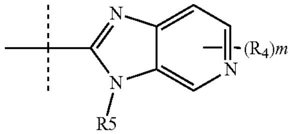
-continued
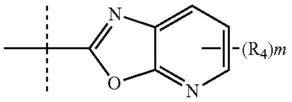
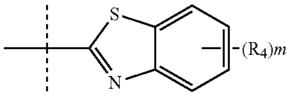
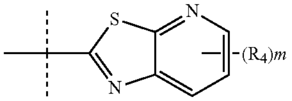
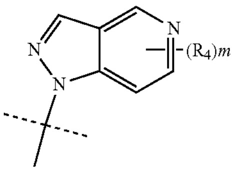
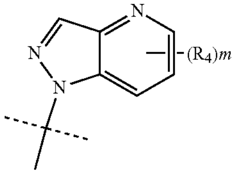
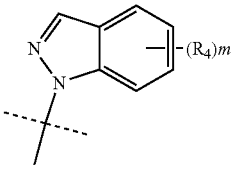
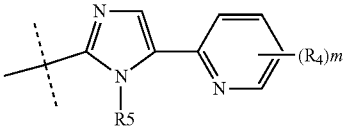
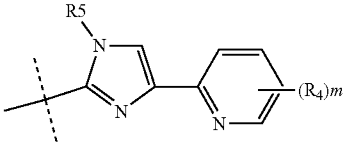
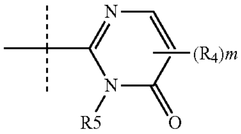
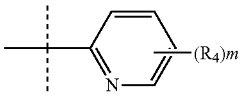
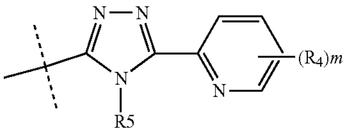
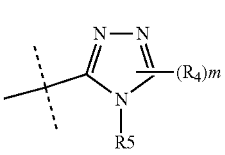
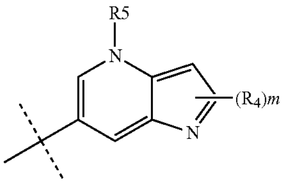
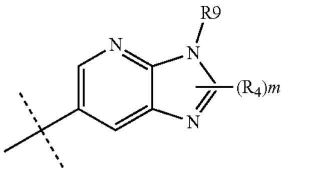
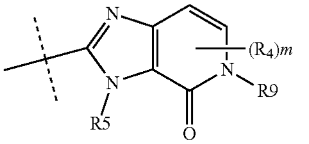

-continued

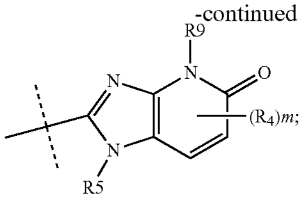

wherein:

R4 is $C_1$-$C_6$-haloalkyl, such as $CF_3$, $C_2F_5$, $C_2$-$C_6$-haloalkenyl, such as CH═CF—$CF_3$, $C_1$-$C_6$-haloalkoxy, such as O—$CH_2$—$CF_3$, 0—$CH_2$—$C_2F_5$, S(O),—($C_1$-$C_6$-alkyl), such as S-methyl, S(O)-methyl; $S(O)_2$-methyl; S(O)y ($C_1$-$C_6$-haloalkyl), such as S—$CF_3$, S(O)—$CF_3$, $S(O)_2$—$CF_3$, =O, wherein R4, if present once or more times, in each occurrence is independently attached to a C atom;

R5, R9 are each independently hydrogen, $C_1$-$C_6$-alkyl, such as methyl, ethyl, isopropyl, $C_2$-$C_5$-alkenyl, such as ethenyl, $C_1$-$C_6$-haloalkyl, such as $CF_3$, $CH_2$—$CHF_2$, $CH_2$—$CF_3$, $CHF_2$, $C_3$-$C_8$-cycloalkyl, such as cyclopropyl, $C_3$-$C_s$-cycloalkyl-alkyl, such as cyclopropylmethyl, $C_3$-$C_5$-cycloalkyl substituted with one or more haloalkyl, such as cyclopropyl substituted with one or more $CF_3$, $C_3$-$C_5$-cycloalkyl substituted with one or more halogens, such as cyclopropyl substituted with one or more F, C(O)—($C_1$-$C_6$-alkyl), such as C(O)-methyl, heterocyclyl, such as aziridinyl, oxetanyl, S(O) p-($C_1$-$C_6$-alkyl), such as S-methyl, S(O)-methyl; S(O) $_2$-methyl; S(O)y-($C_1$-$C_6$-haloalkyl), such as S—$CF_3$, S(O)—$CF_3$, $S(O)_2$—$CF_3$;

R6, R7, R8 are each independently hydrogen, halogen, such as F, Cl, Br, I;

m is 0, 1 or 2;

p, q in each occurrence independently are 0, 1 or 2;

or a pharmaceutically acceptable salt thereof.

3. The compound according to any one of clauses 1 to 2, wherein the following Q radicals are excluded from the scope of the compound of formula (I):

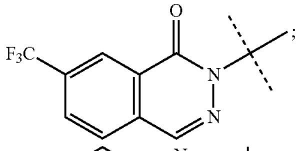

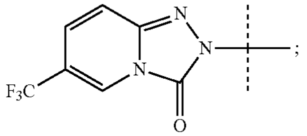

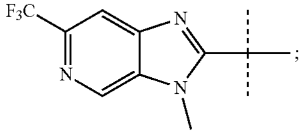

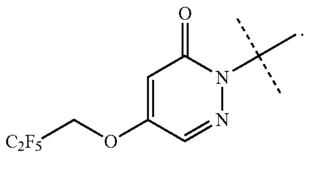

4. The compound according to any one of clauses 1 to 3, wherein

W1, W2, W3, W4, W5 are independently C or C—H;

or a pharmaceutically acceptable salt thereof.

5. The compound according to any one of clauses 1 to 3, wherein

W1 is an N atom, and

W2, W3, W4, W5 are independently C or C—H;

or a pharmaceutically acceptable salt thereof.

6. The compound according to any one of clauses 1 to 3, wherein

W2 is an N atom, and

W1, W3, W4, W5 are independently C or C—H;

or a pharmaceutically acceptable salt thereof.

7. The compound according to any one of clauses 1 to 3, wherein

W3 is an N atom, and

W1, W2, W4, W5 are independently C or C—H;

or a pharmaceutically acceptable salt thereof.

8. The compound according to any one of clauses 1 to 3, wherein

W1, W5 are both N atoms, and

W2, W3, W4 are independently C or C—H;

or a pharmaceutically acceptable salt thereof.

9. The compound according to any one of clauses 1 to 3, wherein

W2, W4 are both N atoms, and

W1, W3, W5 are independently C or C—H;

or a pharmaceutically acceptable salt thereof.

10. The compound according to any one of clauses 1 to 3, wherein

W1, W2 are both N atoms, and

W3, W4, W5 are independently C or C—H;

or a pharmaceutically acceptable salt thereof.

11. The compound according to any one of clauses 1 to 3, wherein

W1, W2, W4 are all N atoms, and

W3, W5 are independently C or C—H;

or a pharmaceutically acceptable salt thereof.

12. The compound according to any one of clauses 1 to 3, wherein

W1, W2, W5 are all N atoms, and

W3, W4 are independently C or C—H;

or a pharmaceutically acceptable salt thereof.

13. The compound according to any one of clauses 1 to 12, wherein

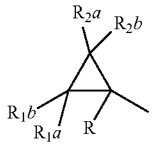

is attached to W3, wherein W3 is a C atom, wherein R, R1a, R1b, R2a, R2b are as defined in any one of the preceding clauses;

or a pharmaceutically acceptable salt thereof.

14. The compound according to any one of clauses 1 to 12, wherein

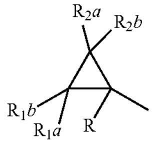

is attached to W2, wherein W2 is a C atom, wherein R, R1a, R1b, R2a, R2b are as defined in any one of the preceding clauses;

or a pharmaceutically acceptable salt thereof.

15. The compound according to any one of clauses 1 to 12, wherein

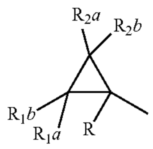

is attached to W4, wherein W4 is a C atom, wherein R, R1a, R1b, R2a, R2b are as defined in any one of the preceding clauses;

or a pharmaceutically acceptable salt thereof.

16. The compound according to any one of clauses 1 to 12, wherein

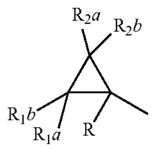

is attached to W1, wherein W1 is a C atom, wherein R, R1a, R1b, R2a, R2b are as defined in any one of the preceding clauses;

or a pharmaceutically acceptable salt thereof.

17. The compound according to any one of clauses 1 to 12, wherein

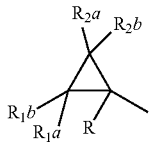

is attached to W5, wherein W5 is a C atom, wherein R, R1a, R1b, R2a, R2b are as defined in any one of the preceding clauses;

or a pharmaceutically acceptable salt thereof.

18. The compound according to any one of clauses 1 to 17, wherein n is 0 or 1;

or a pharmaceutically acceptable salt thereof.

19. The compound according to any one of clauses 1 to 18, wherein m is 1 or 2;

or a pharmaceutically acceptable salt thereof.

20. The compound according to any one of clauses 1 to 19, wherein Q1, Q2, Q3 independently are selected from the group consisting of:

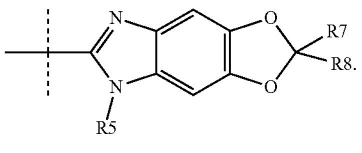

wherein R5, R7, R8 are as defined in any one of the preceding clauses, such as R5 is "methyl" and R7 and R8 are both "F";

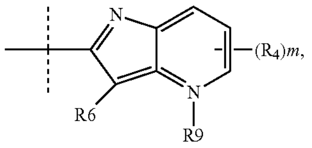

wherein R4, R6, R9, m are as defined in any one of the preceding clauses, such as R6 is "hydrogen", R9 is "$CH_2$—$CHF_2$" or "ethyl", m is 1 and R4 is "$CF_3$";

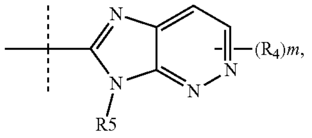

wherein R4, R5, m are as defined in any one of the preceding clauses, such as R5 is "methyl", m is 1 and R4 is "$CF_2$—$CF_3$" or "$S(O)_2$—$CF_3$";

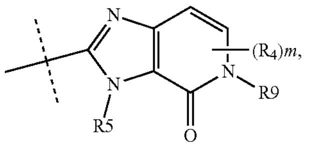

wherein R4, R5, R9, m are as defined in any one of the preceding clauses, such as R5 is "methyl", R9 is "cyclopropyl", m is 1 and R4 is "$CF_3$";

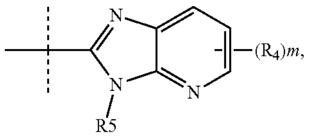

wherein R4, R5, m are as defined in any one of the preceding clauses, such as R5 is "methyl", m is 1 and R4 is "$CF_2$—$CF_3$";

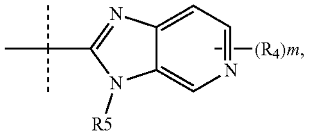

wherein R4, R5, m are as defined in any one of the preceding clauses, such as R5 is "methyl", m is 1 and R4 is "$CF_2$—$CF_3$";

or a pharmaceutically acceptable salt thereof.

21. The compound according to any one of clauses 1 to 20 selected from the group consisting of:

1
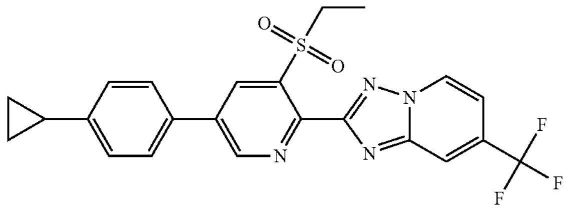
2
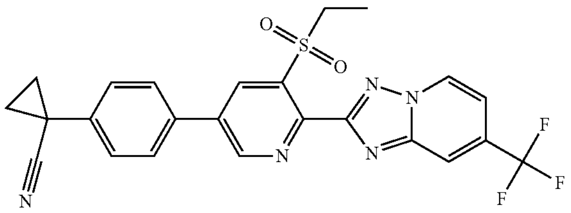
3
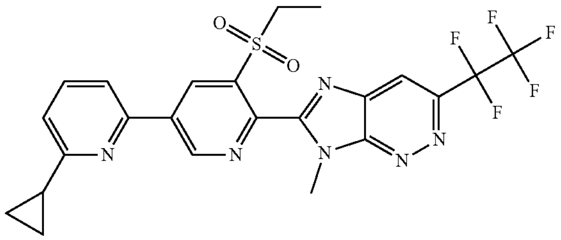
4
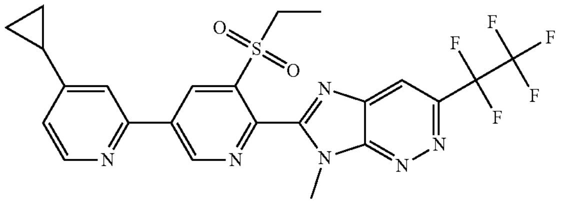
5
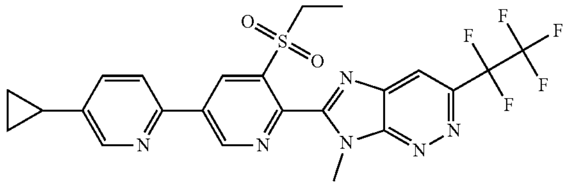
6
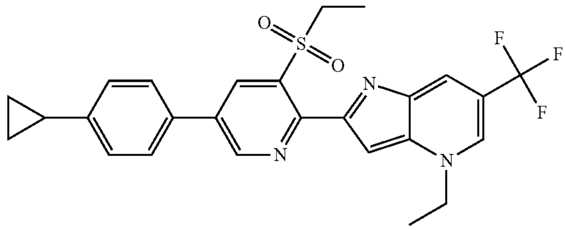
-continued
7
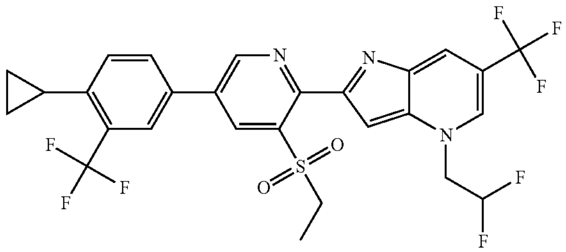
8
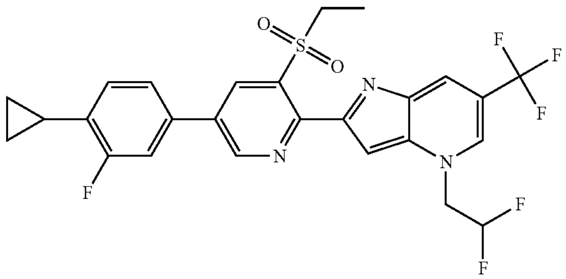
9
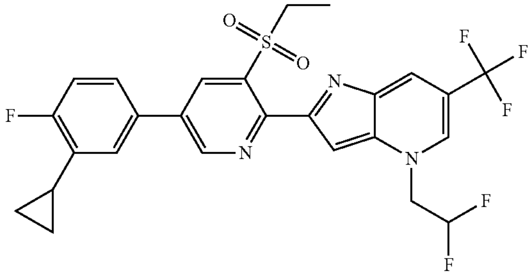
10
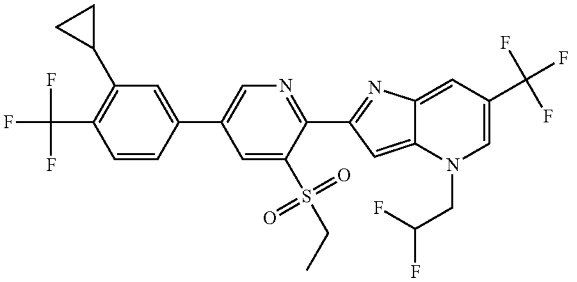
11
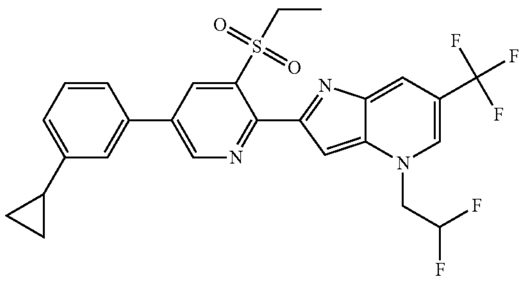

-continued
12
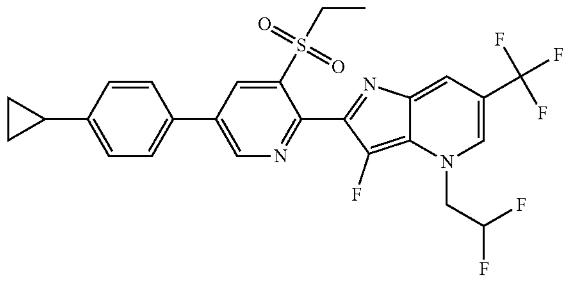
13
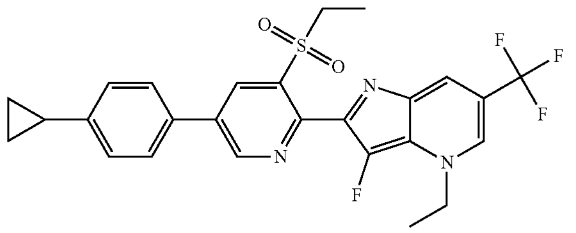
14
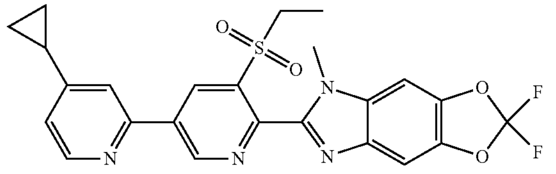
15
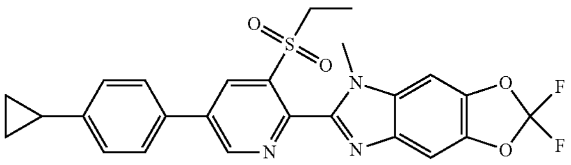
16
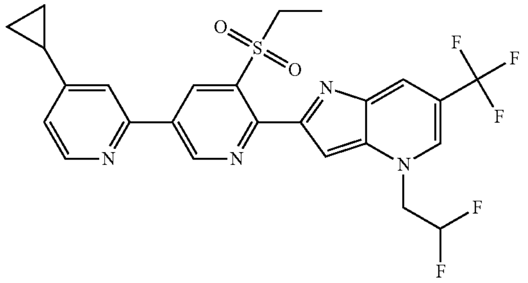
17
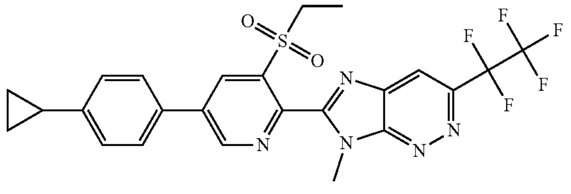
-continued
18
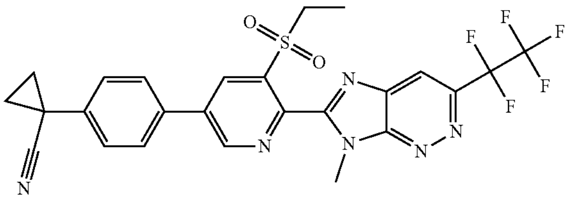
19
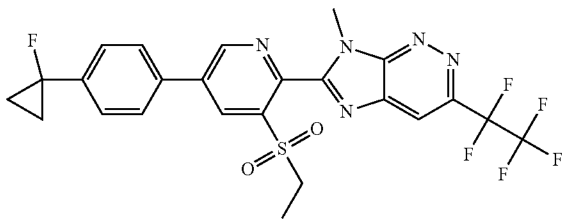
20
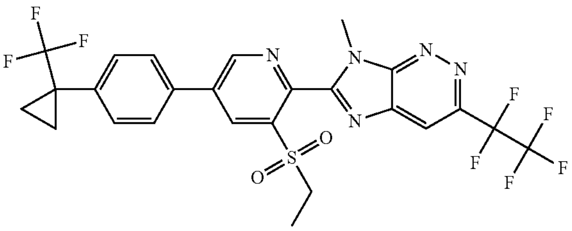
21
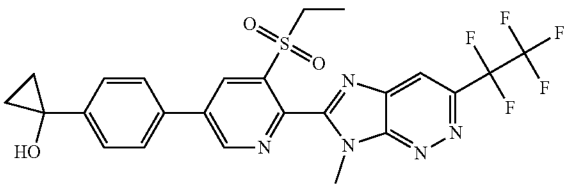
22
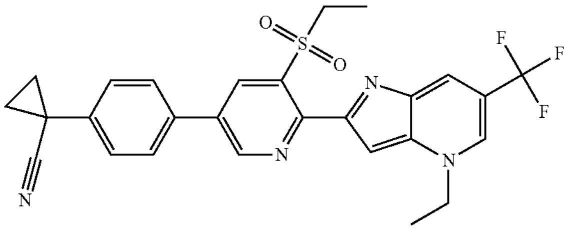
23
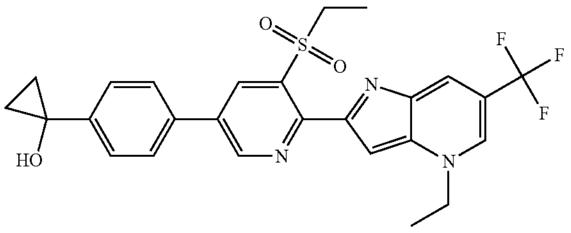

-continued
24
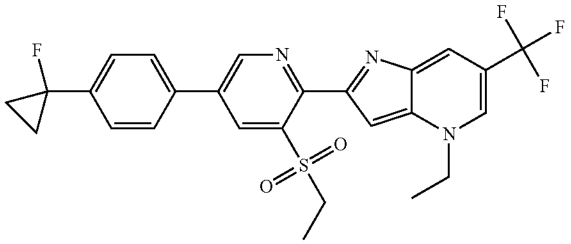
25
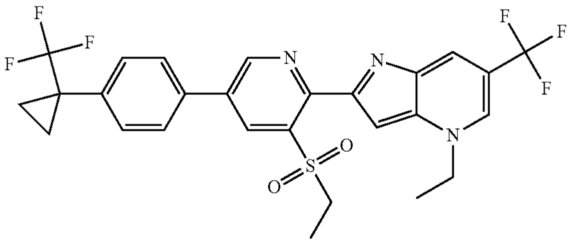
26
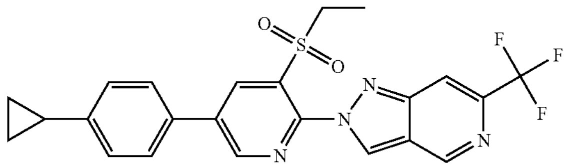
27
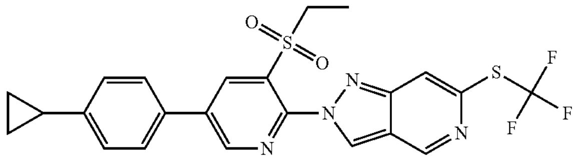
28
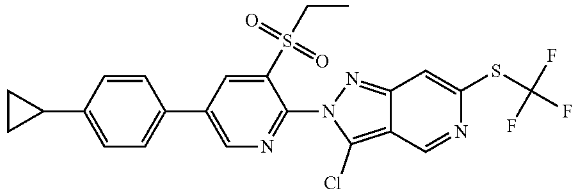
29
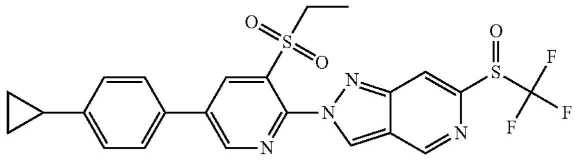
30
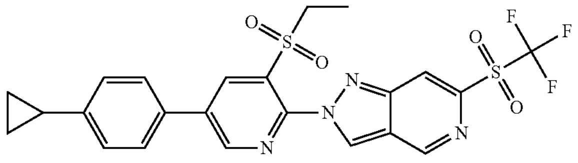
-continued
31
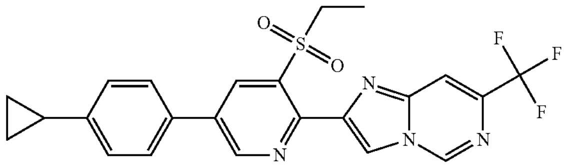
32
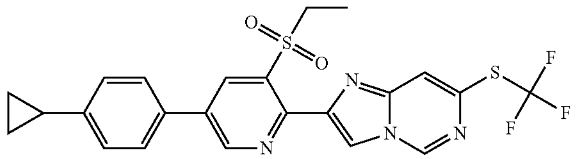
33
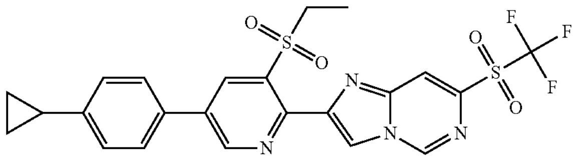
34
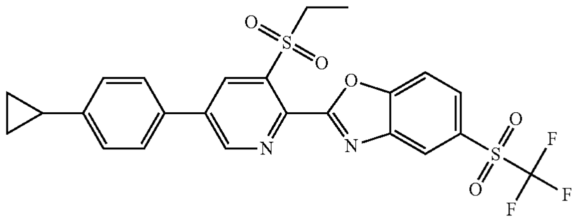
35
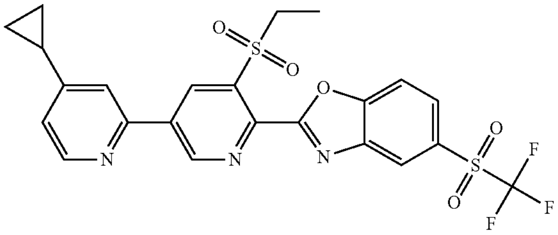
36
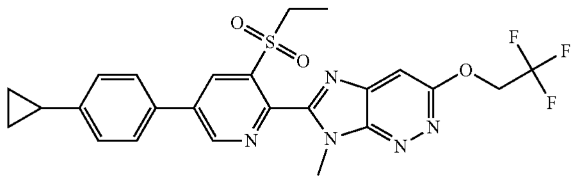
37
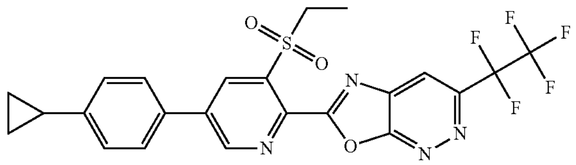

-continued
38
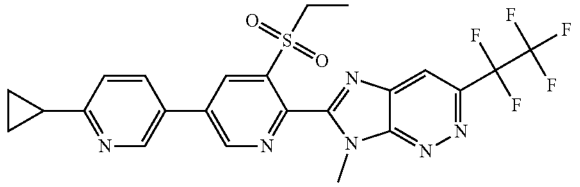
39
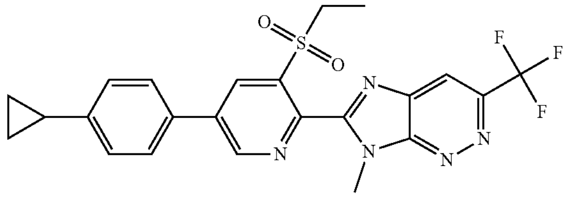
40
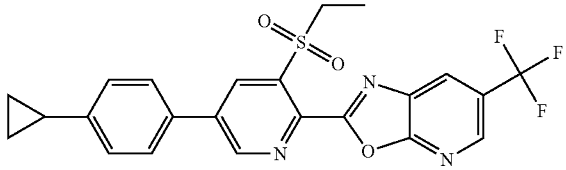
41
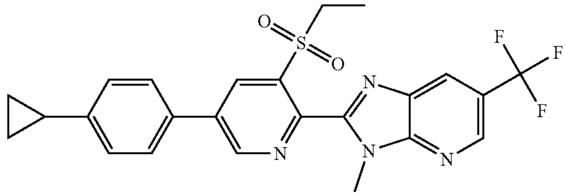
42
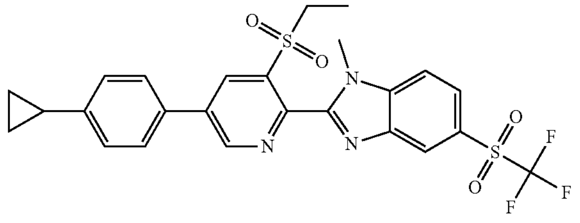
43
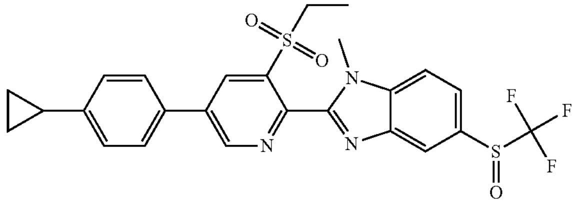
44
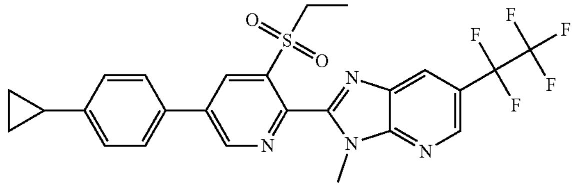
-continued
45
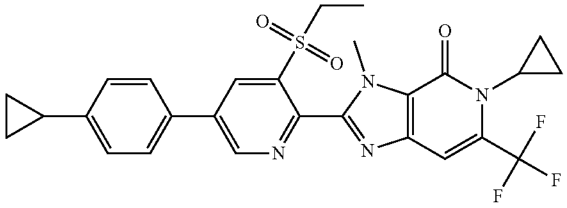
46
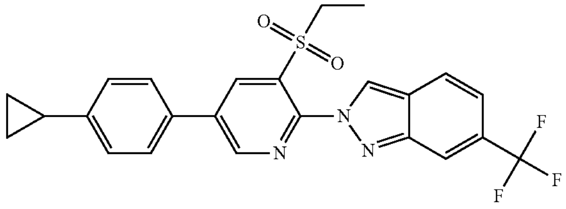
47
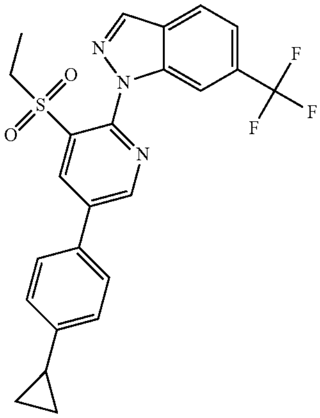
48
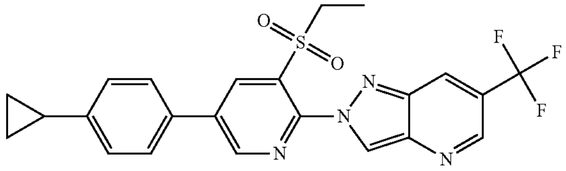
49
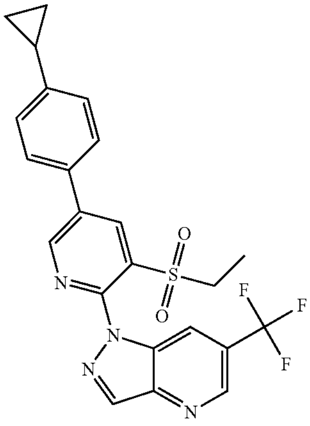

-continued
50
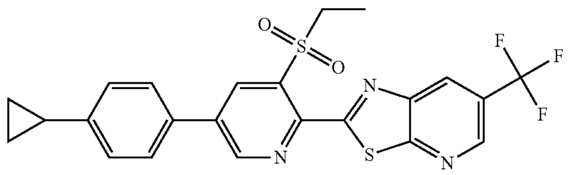
51
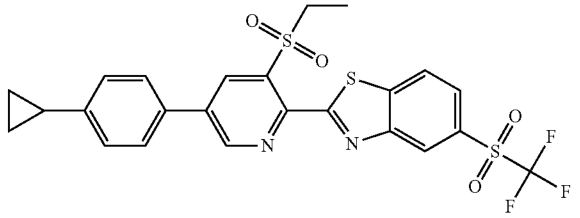
52
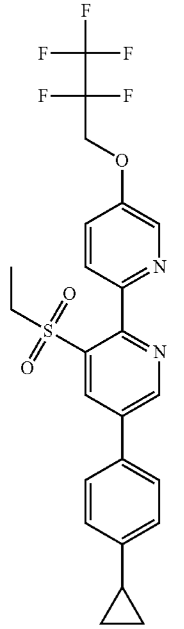
53
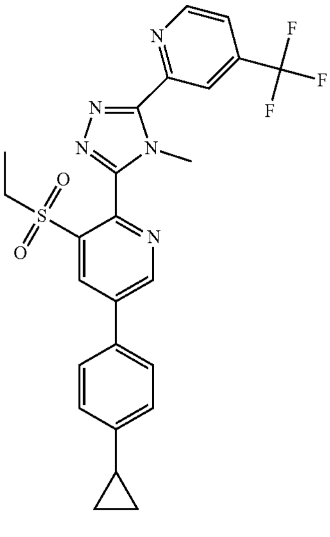
-continued
54
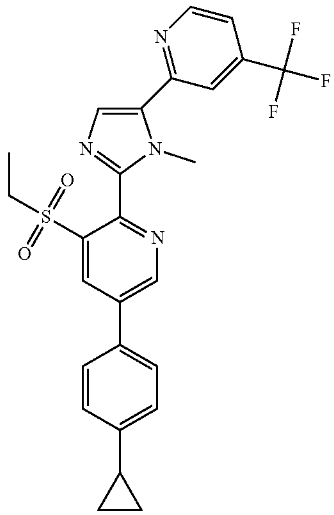
55
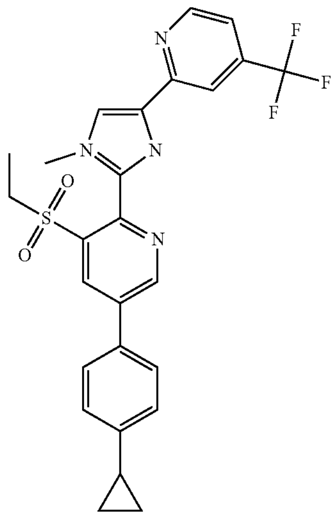
56
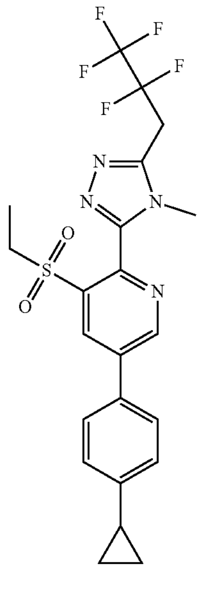

-continued
57
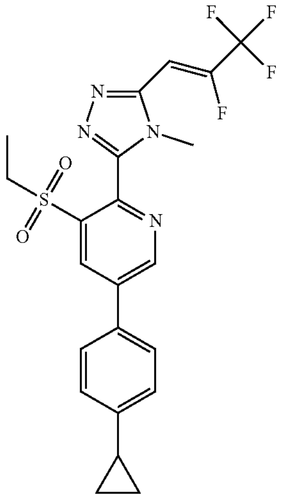
58
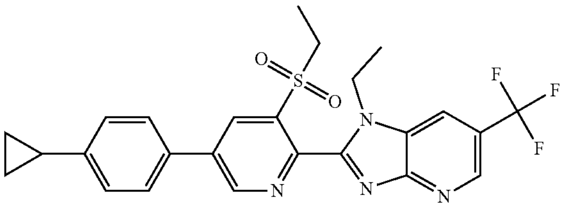
59
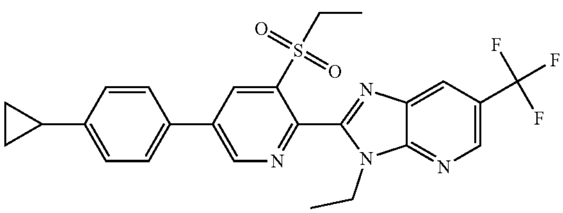
60
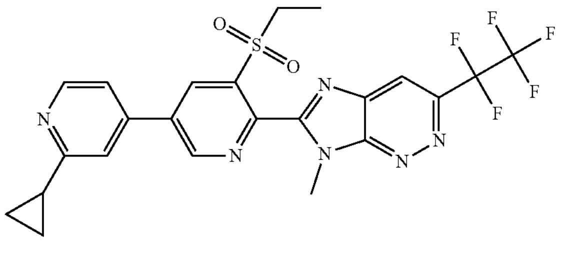
61
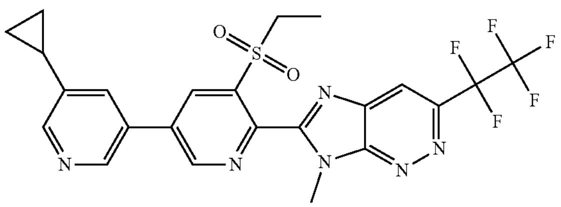
-continued
62
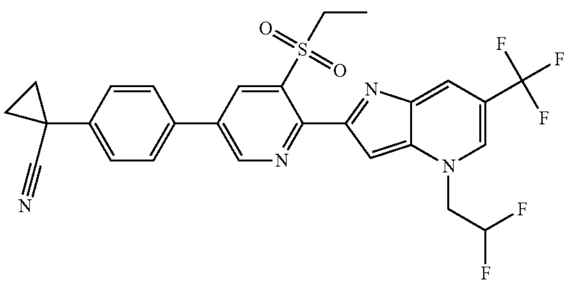
63
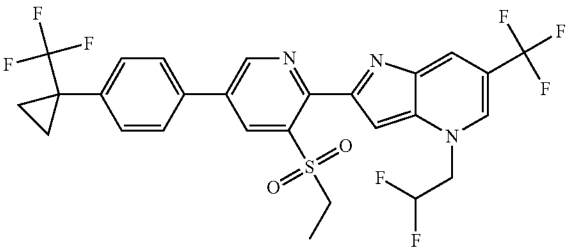
64
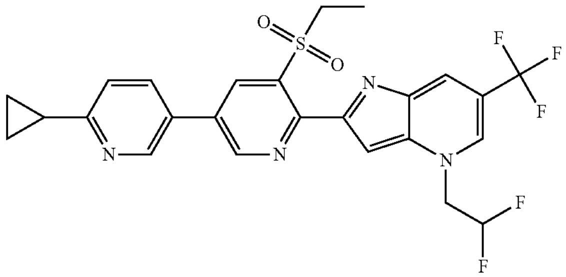
65
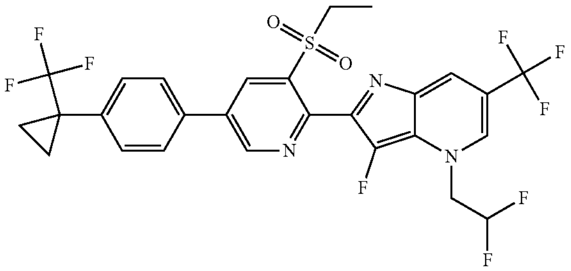
66
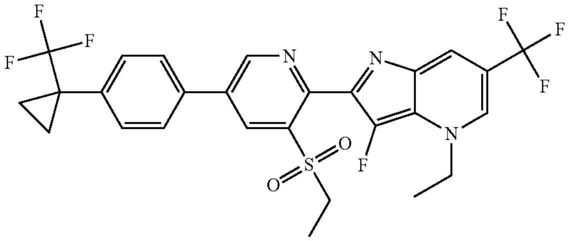

-continued
67
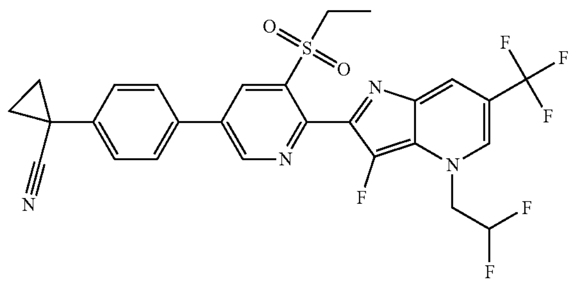
68
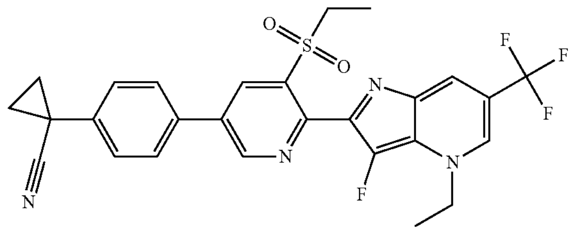
69
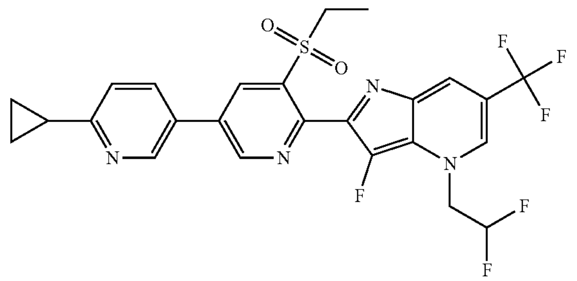
70
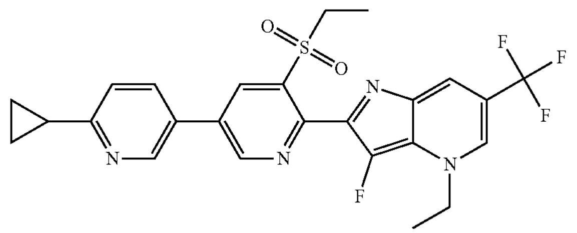
71
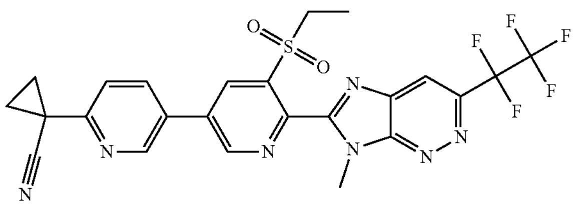
72
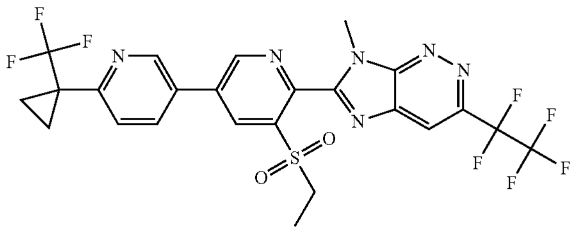
-continued
73
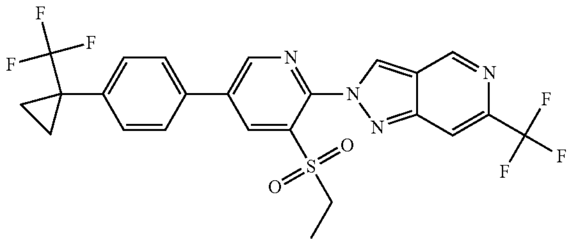
74
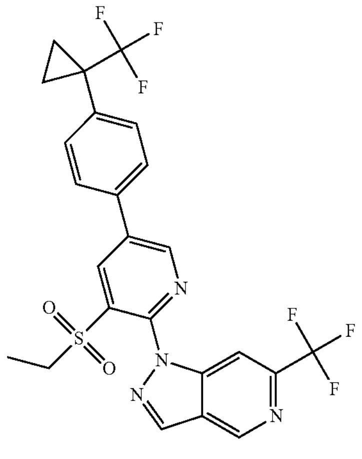
75
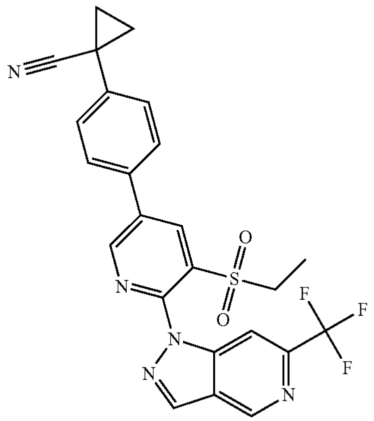
76
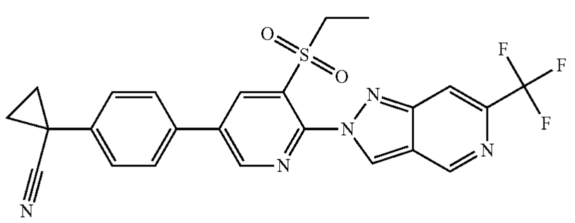
77
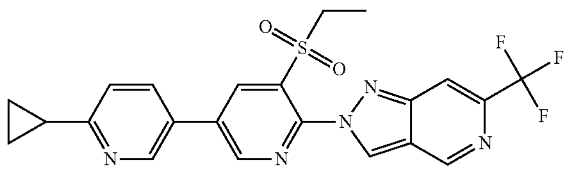

-continued
78
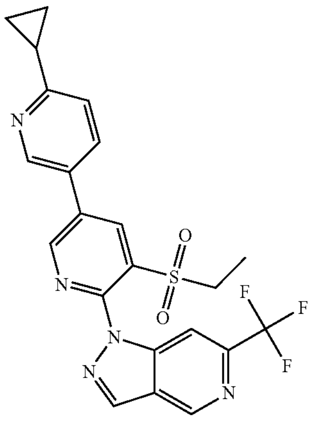
79
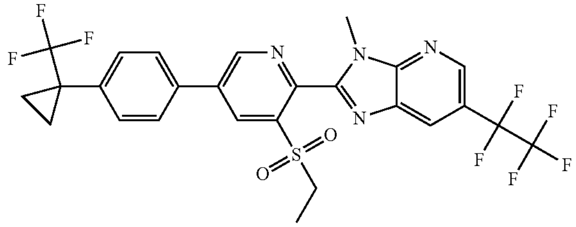
80
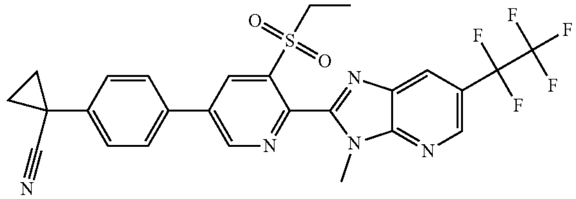
81
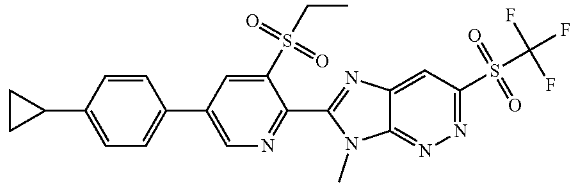
82
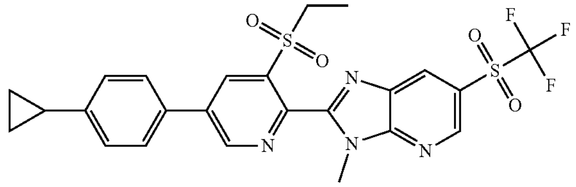
83
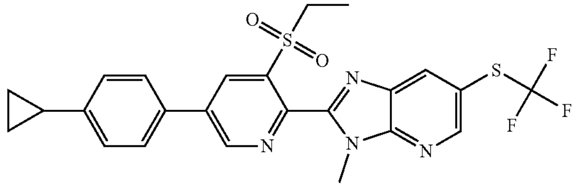
-continued
84
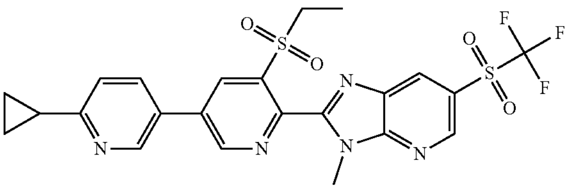
85
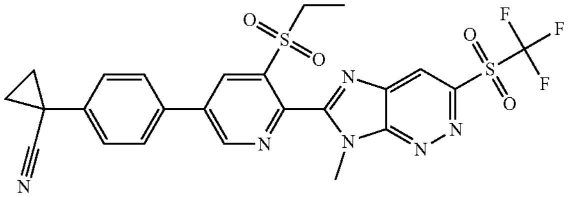
86
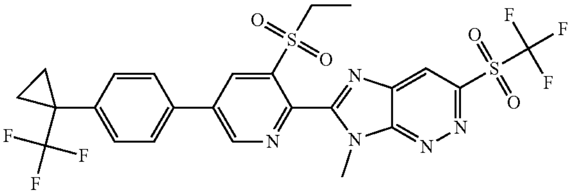
87
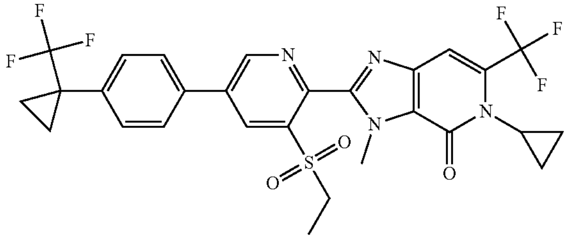
88
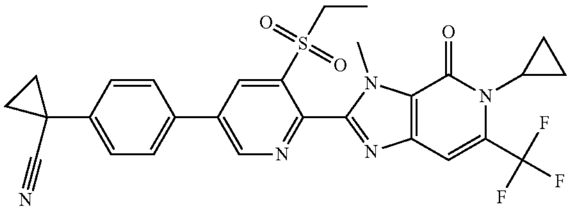
89
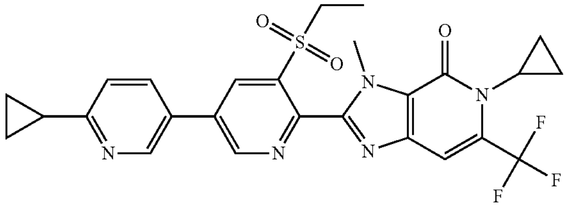

90
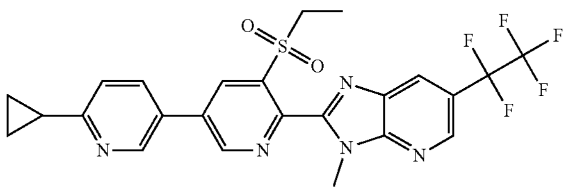
91
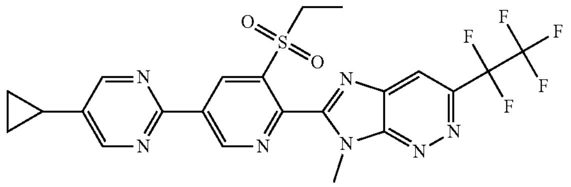
92
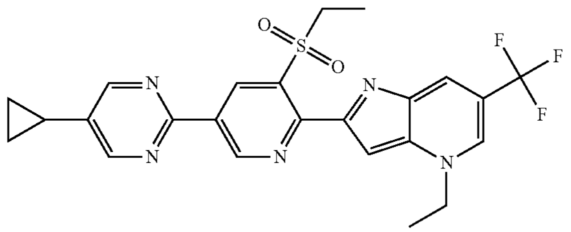
93
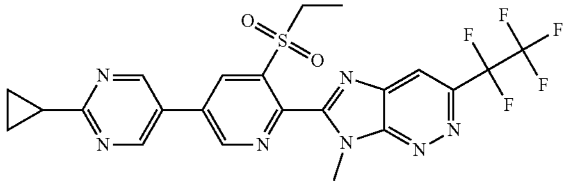
94
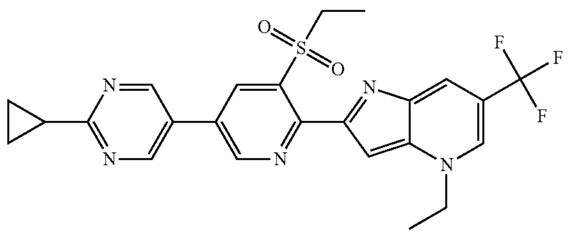
95
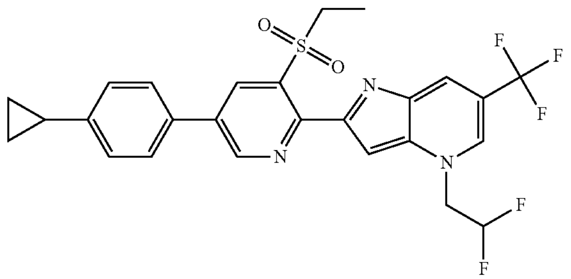
96
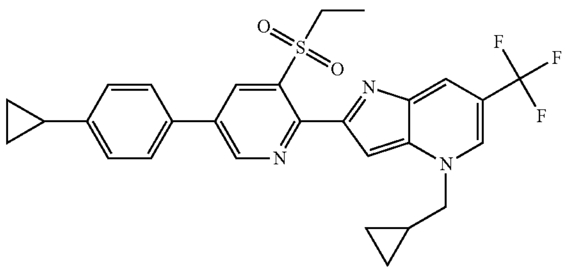
97
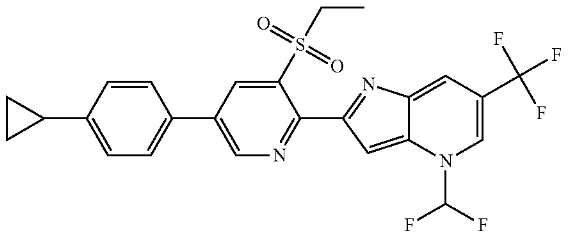
98
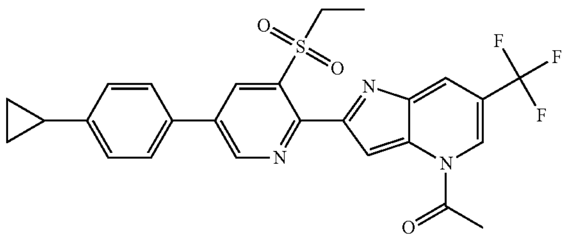
99
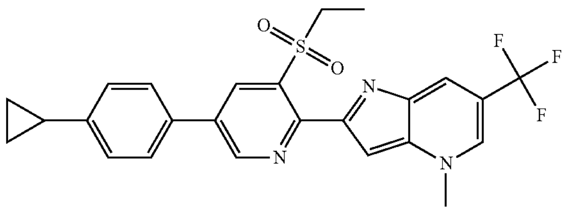
100
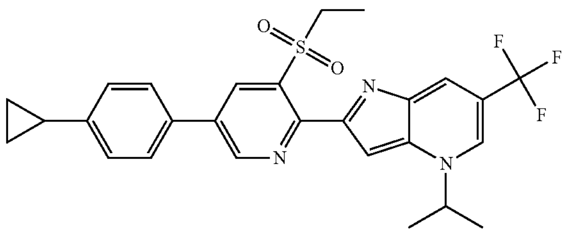
101
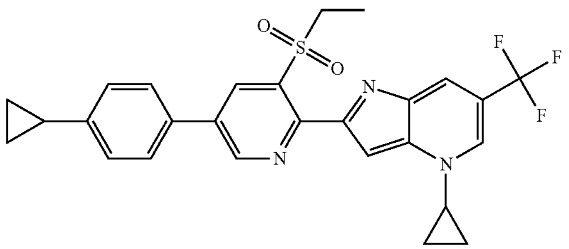

-continued
102
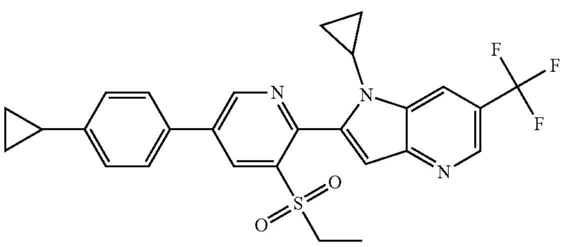
103
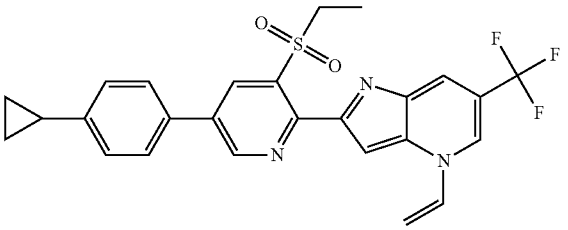
104
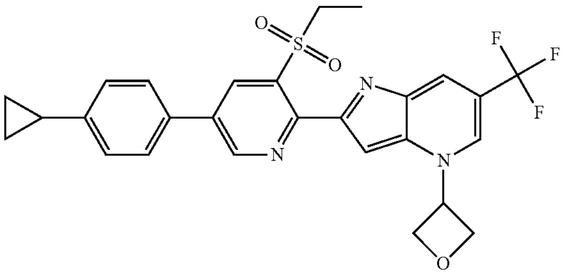
105
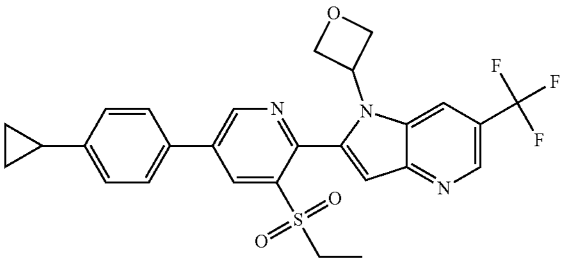
106
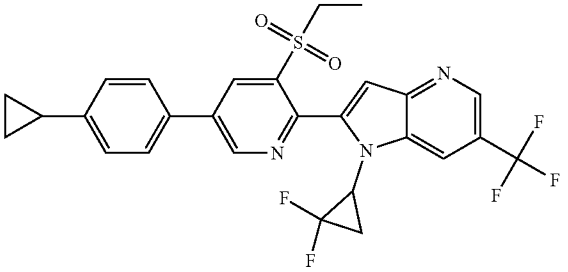
-continued
107
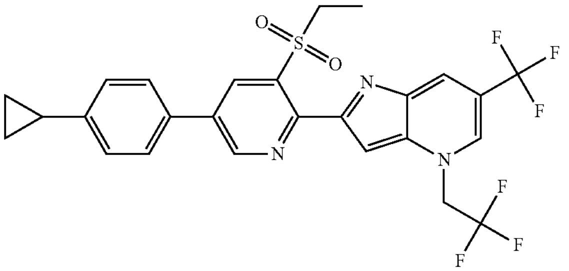
108
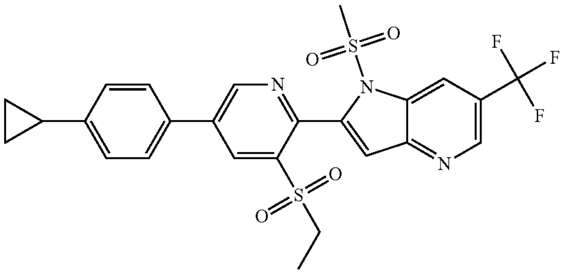
109
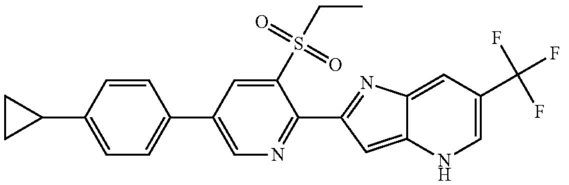
110
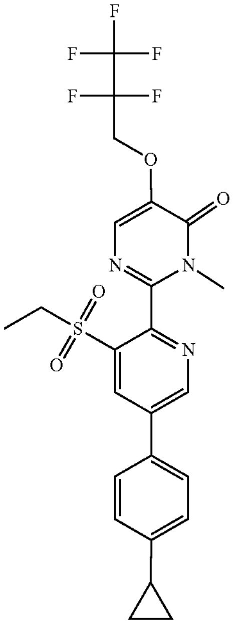

-continued
111
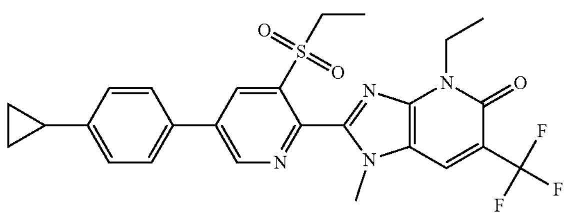
112
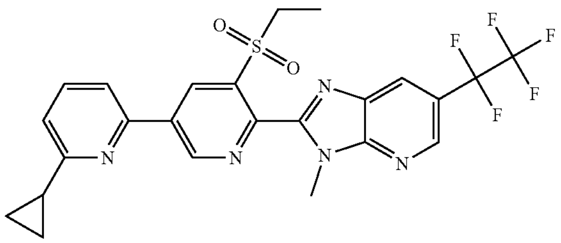
113
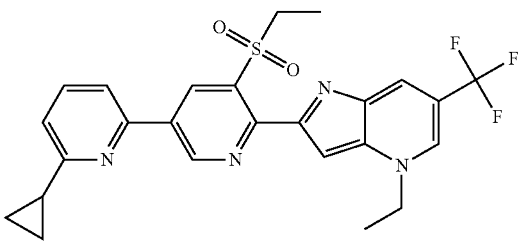
114
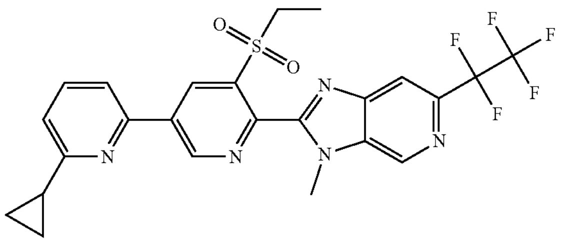
115
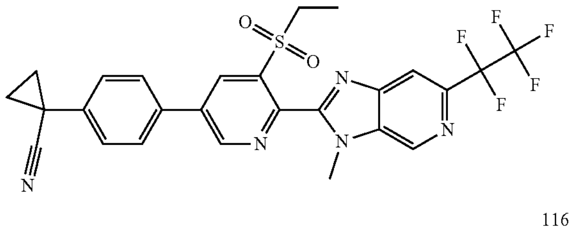
116
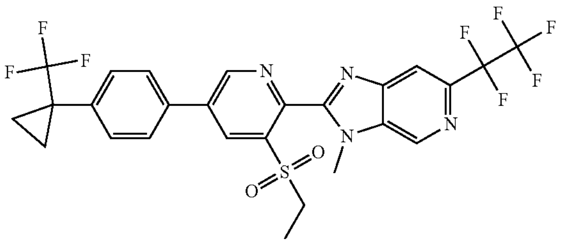
-continued
117
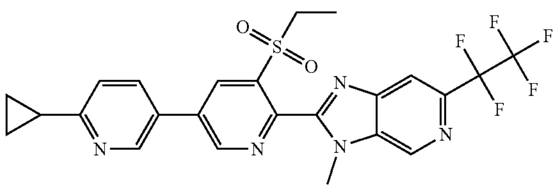
118
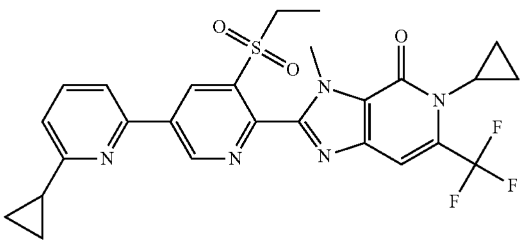
119
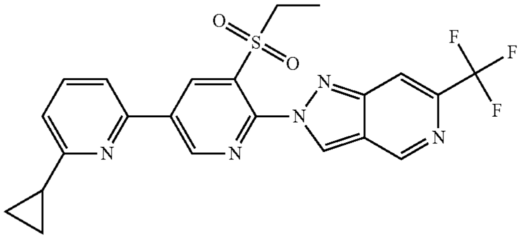
120
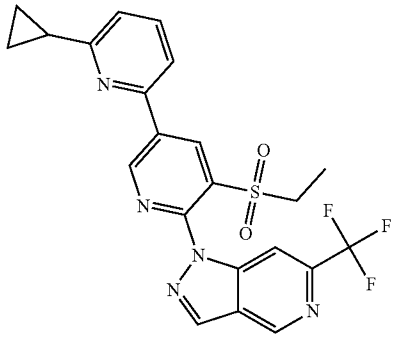
121
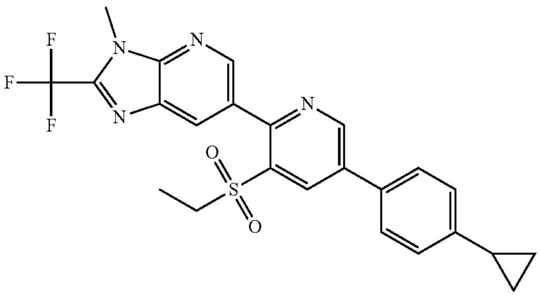

-continued

122

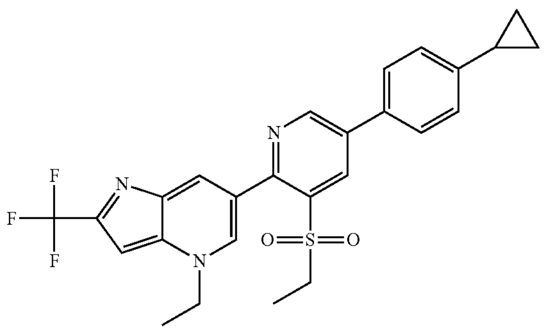

123

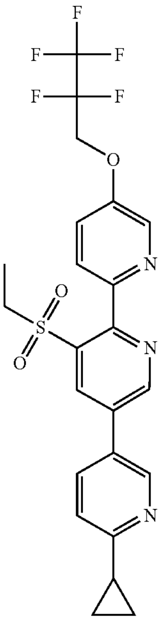

124

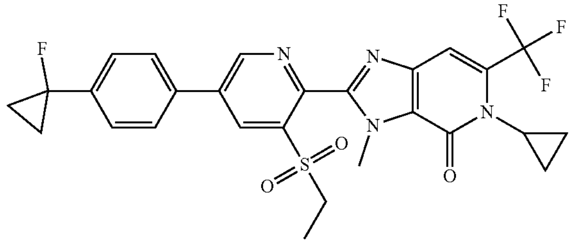

or a pharmaceutically acceptable salt thereof.

22. A pharmaceutical composition comprising one or more compound(s) of formula (I) according to any one of clauses 1 to 21 or a pharmaceutically acceptable salt thereof and one or more pharmaceutically acceptable excipient(s).

23. A pharmaceutical composition comprising one or more compound(s) of formula (I) according to any one of clauses 1 to 21 or a pharmaceutically acceptable salt thereof, one or more additional pharmaceutically active agent(s), and one or more pharmaceutically acceptable excipient(s).

24. A compound of formula (1) according to any one of clauses 1 to 21 or a pharmaceutically acceptable salt thereof or a pharmaceutical composition according to any one of clauses 22 to 23 for use as a medicament, preferably for use as an antiparasitic medicament.

25. The compound of formula (I) according to any one of clauses 1 to 21 or a pharmaceutically acceptable salt thereof or a pharmaceutical composition according to any one of clauses 22 to 23 for use in a method of treatment, prevention and/or control of a parasitic infection and/or infestation in an animal.

The invention claimed is:

1. A compound of formula (I)

(I)

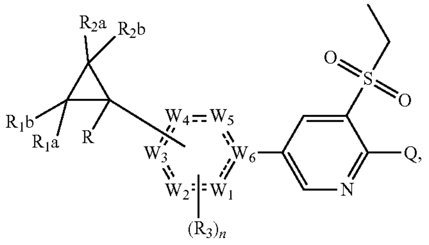

wherein:

W1, W2, W3, W4, W5 are each independently N, C or C—H, wherein at most three of W1, W2, W3, W4, W5 are N;

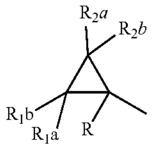

is attached to a C atom;

R, R1a, R1b, R2a, R2b, R3 are each independently hydrogen, halogen, $C_1$-$C_6$-alkyl, $C_1$-$C_6$-haloalkyl, C3-C8-cycloalkyl, aryl, $C_1$-$C_6$-alkoxy, $C_1$-$C_6$-haloalkoxy, $S(O)_r$—($C_1$-$C_6$-alkyl), $S(O)_s$—($C_1$-$C_6$-haloalkyl), $S(O)_t$—$R_w$, $S(O)_2$—$N(R_x)(R_y)$, or S(O)—$(R_w)$=N—$R_z$; and wherein R3, if present once or more times, in each occurrence is independently attached to a C atom; or wherein R together with R1a or R1b forms an unsubstituted or substituted carbocycle or an unsubstituted or substituted heterocycle, wherein the carbocycle or heterocycle if substituted is independently substituted with one, two or three substituents each independently selected from the group consisting of halogen, alkyl, $C_1$-$C_6$-haloalkyl, $C_3$-$C_8$-cycloalkyl, aryl, $C_1$-$C_6$-alkoxy, $C_1$-$C_6$-haloalkoxy, OH, CN, $C(O)OR_x$, $S(O)_r$—($C_1$-$C_6$-alkyl), and $S(O)_s$—($C_1$-$C_6$-haloalkyl);

Q is selected from the group consisting of:

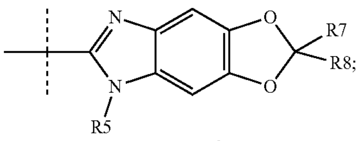

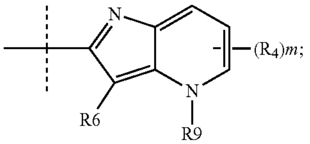

-continued

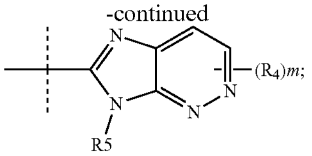

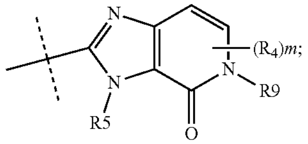

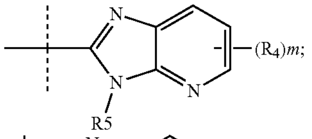

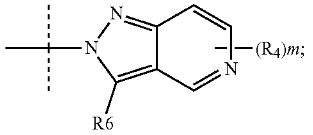

and

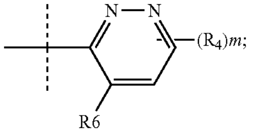

wherein:

R4 is selected from the group consisting of $C_1$-$C_6$-haloalkyl, $C_2$-$C_6$-haloalkenyl, $C_1$-$C_6$-haloalkoxy, $S(O)_p$—($C_1$-$C_6$-alkyl), $S(O)_q$—($C_1$-$C_6$-haloalkyl), and =O, wherein, if R4 is present once or more times, in each occurrence is independently attached to a C atom;

R5, R9 are each independently selected from the group consisting of hydrogen, $C_1$-$C_6$-alkyl, $C_2$-$C_6$-alkenyl, $C_1$-$C_6$-haloalkyl, $C_3$-$C_8$-cycloalkyl, $C_3$-$C_8$-cycloalkyl-alkyl, $C_3$-$C_8$-cycloalkyl substituted with one or more haloalkyl, $C_3$-$C_8$-cycloalkyl substituted with one or more halogens, C(O)—($C_1$-$C_6$-alkyl), heterocyclyl, $S(O)_p$—($C_1$-$C_6$-alkyl), and $S(O)_q$—($C_1$-$C_6$-haloalkyl);

R6, R7, R8 are each independently selected from the group consisting of hydrogen, F, Cl, Br, and I;

m is 0, 1 or 2; and p, q in each occurrence independently are 0, 1 or 2;

$R_v$, $R_w$, $R_x$, $R_y$, $R_z$ in each occurrence are independently selected from the group consisting of hydrogen, halogen, $C_1$-$C_6$-alkyl, and $C_1$-$C_6$-haloalkyl;

n is 0, 1, 2, 3, or 4;

r, s, t in each occurrence independently are 0, 1 or 2; and the dashed bond (- - - - -) signifies a single or double bond;

or a pharmaceutically acceptable salt thereof.

2. The compound according to claim 1, wherein: W1, W2, W3, W4, W5 are independently C or C—H; or a pharmaceutically acceptable salt thereof.

3. The compound according to claim 1, wherein: W1 is an N atom, and W2, W3, W4, W5 are independently C or C—H; or a pharmaceutically acceptable salt thereof.

4. The compound according to claim 1, wherein: W2 is an N atom, and W1, W3, W4, W5 are independently C or C—H; or a pharmaceutically acceptable salt thereof.

5. The compound according to claim 1, wherein: W3 is an N atom, and W1, W2, W4, W5 are independently C or C—H; or a pharmaceutically acceptable salt thereof.

6. The compound according to claim 1, wherein: W1, W3 are both N atoms, and W2, W4, W5 are independently C or C—H; or a pharmaceutically acceptable salt thereof.

7. The compound according to claim 1, wherein: W1, W5 are both N atoms, and W2, W3, W4 are independently C or C—H; or a pharmaceutically acceptable salt thereof.

8. The compound according to claim 1, wherein: W2, W3 are both N atoms, and W1, W4, W5 are independently C or C—H; or a pharmaceutically acceptable salt thereof.

9. The compound according to claim 1, wherein: W2, W4 are both N atoms, and W1, W3, W5 are independently C or C—H; or a pharmaceutically acceptable salt thereof.

10. The compound according to claim 1, wherein: W1, W2 are both N atoms, and W3, W4, W5 are independently C or C—H; or a pharmaceutically acceptable salt thereof.

11. The compound according to claim 1, wherein: W1, W2, W4 are all N atoms, and W3, W5 are independently C or C—H; or a pharmaceutically acceptable salt thereof.

12. The compound according to claim 1, wherein: W1, W2, W5 are all N atoms, and W3, W4 are independently C or C—H; or a pharmaceutically acceptable salt thereof.

13. The compound according to claim 1, wherein:

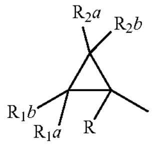

is attached to W3, wherein W3 is a C atom; or a pharmaceutically acceptable salt thereof.

14. The compound according to claim 1, wherein;

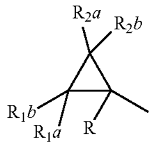

is attached to W2, wherein W2 is a C atom; or a pharmaceutically acceptable salt thereof.

15. The compound according to claim 1, wherein:

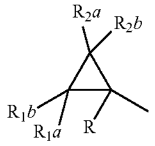

is attached to W4, wherein W4 is a C atom; or a pharmaceutically acceptable salt thereof.

16. The compound according to claim 1, wherein:

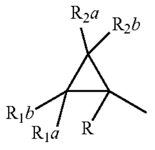

is attached to W1, wherein W1 is a C atom;

or a pharmaceutically acceptable salt thereof.

17. The compound according to claim 1, wherein:

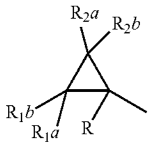

is attached to W5, wherein W5 is a C atom;

or a pharmaceutically acceptable salt thereof.

18. The compound according to claim 1, wherein:

n is 0 or 1;

or a pharmaceutically acceptable salt thereof.

19. The compound according to claim 1, wherein:

m is 1 or 2;

or a pharmaceutically acceptable salt thereof.

20. A compound selected from the group consisting of:

1

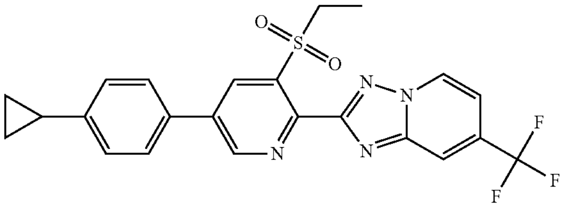

2

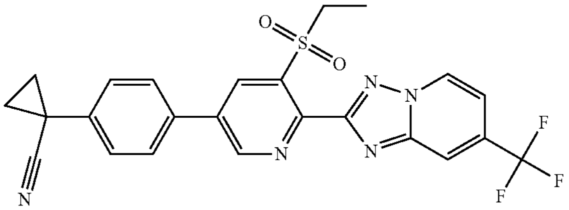

3

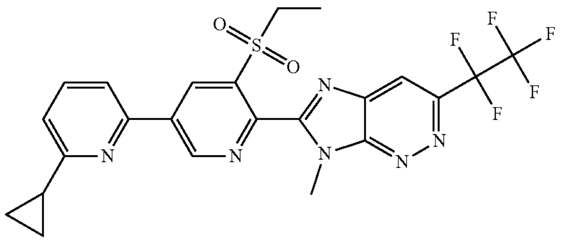

-continued

4

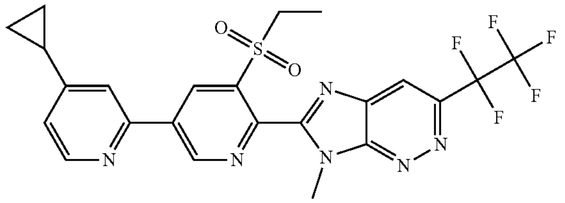

5

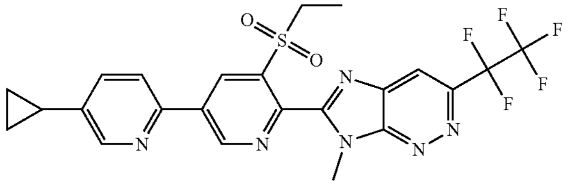

6

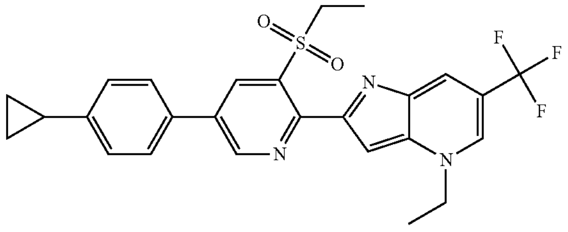

7

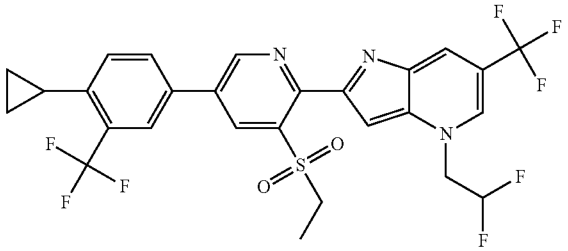

8

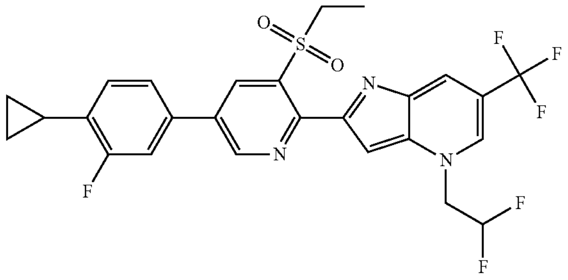

9

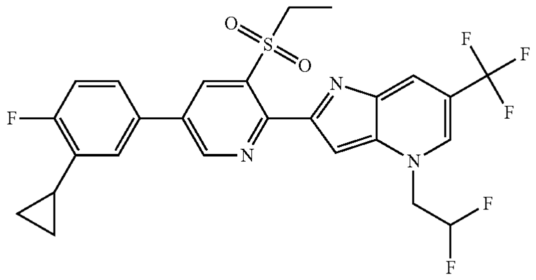

-continued
10
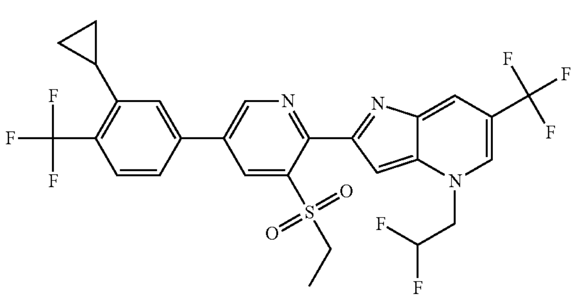
11
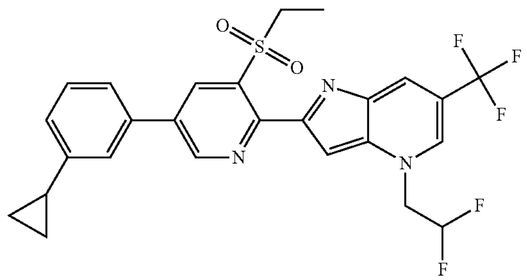
12
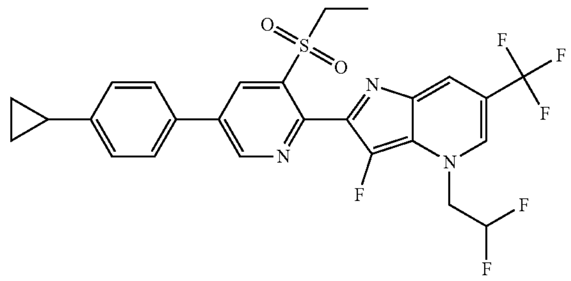
13
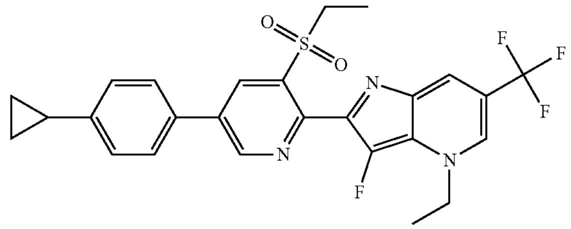
14
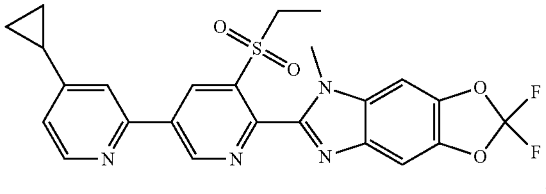
15
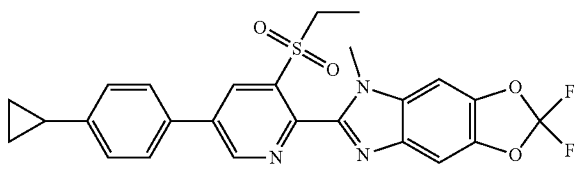
-continued
16
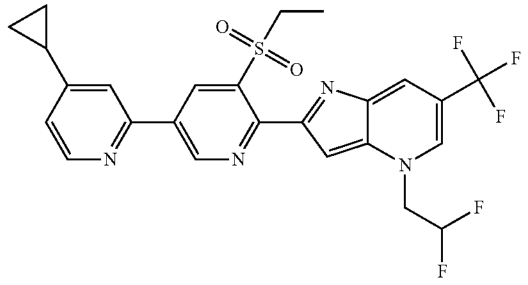
17
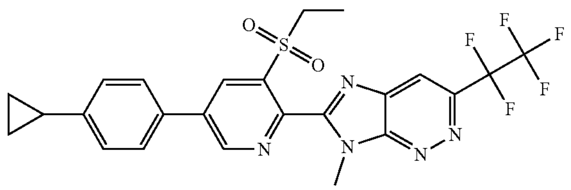
18
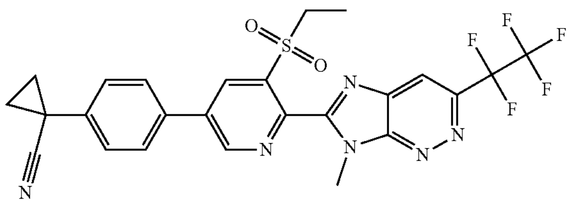
19
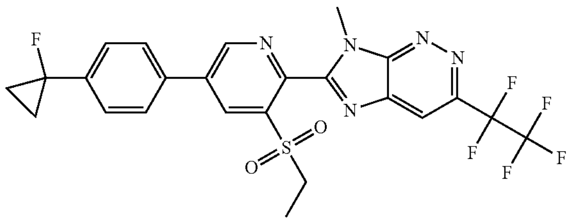
20
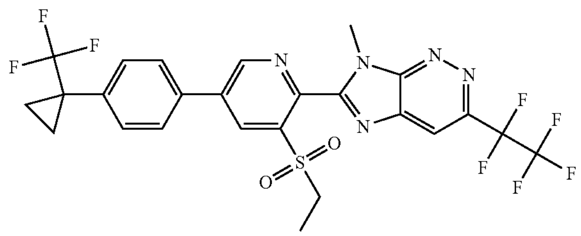
21
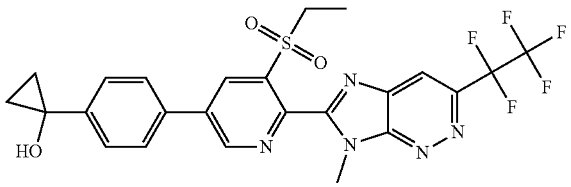

-continued
22
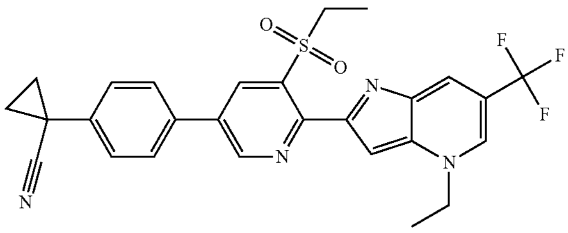
23
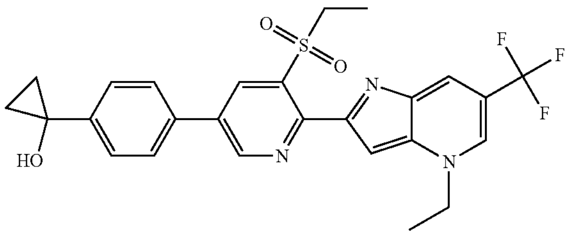
24
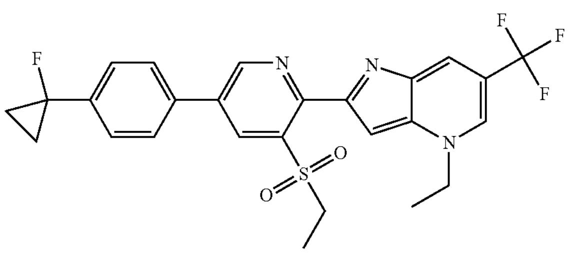
25
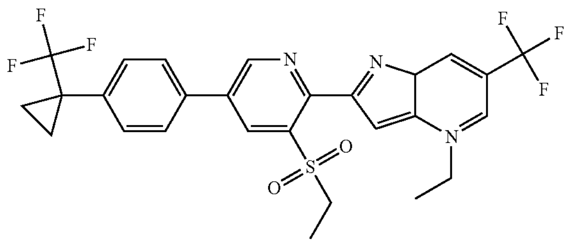
26
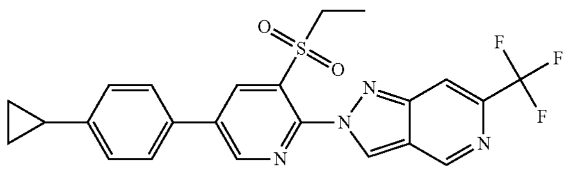
27
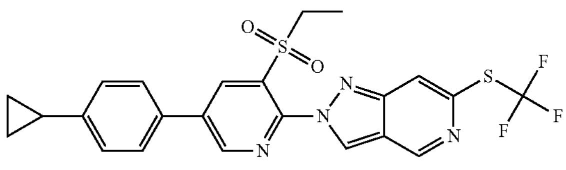
-continued
28
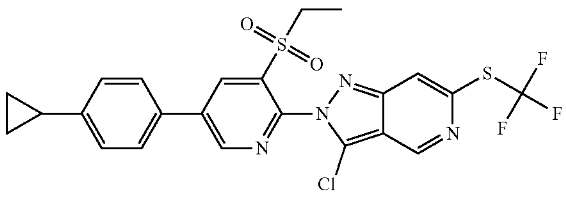
29
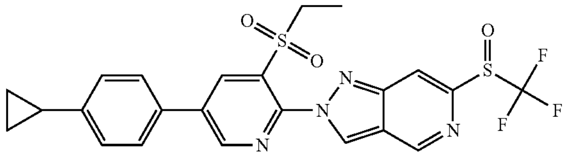
30
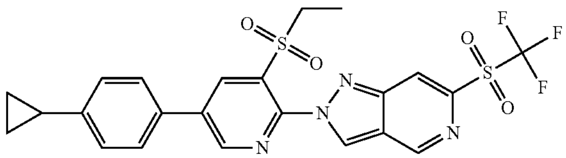
31
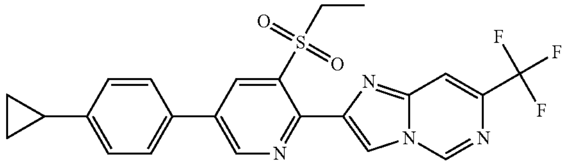
32
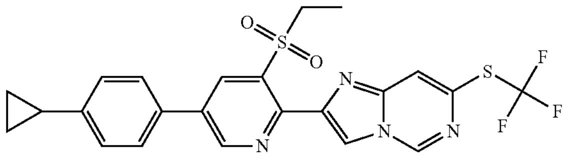
33
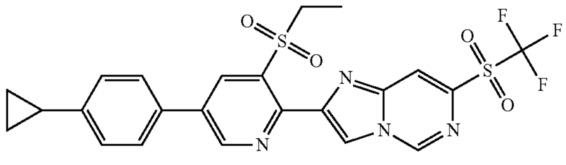
34
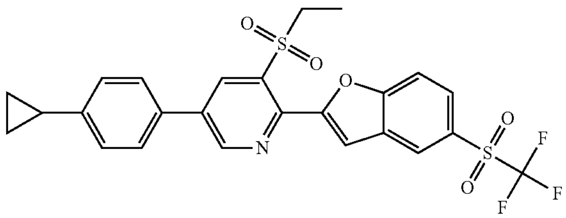

-continued
35
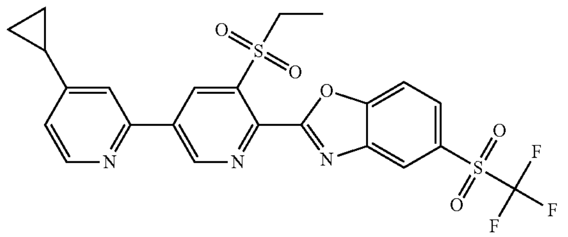
36
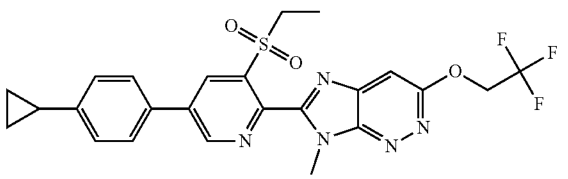
37
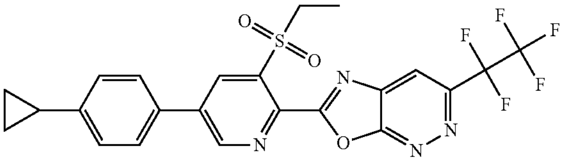
38
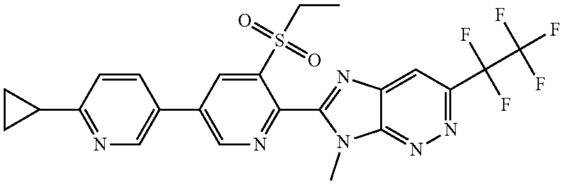
39
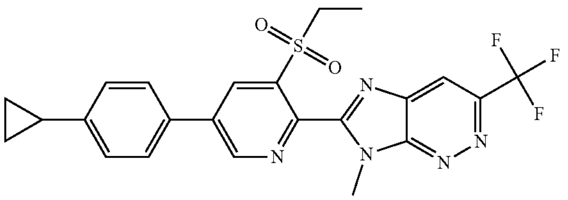
40
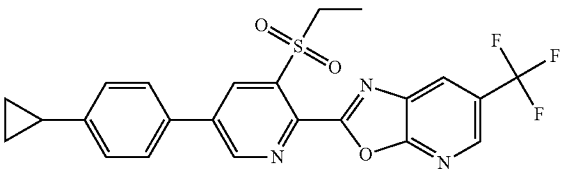
41
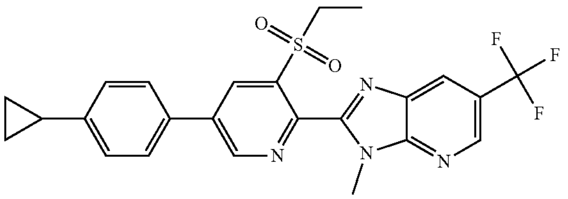
-continued
42
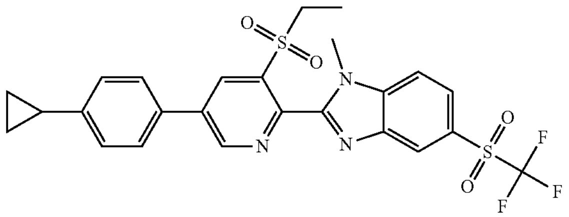
43
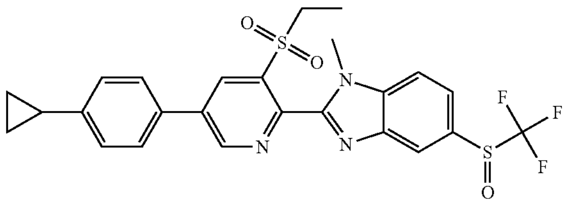
44
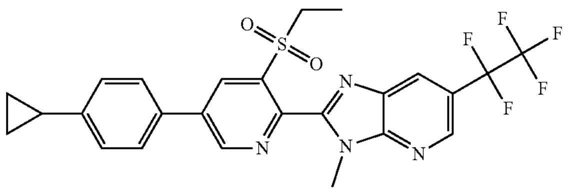
45
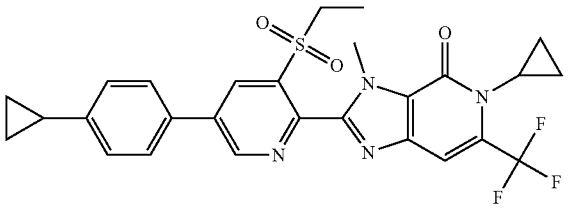
46
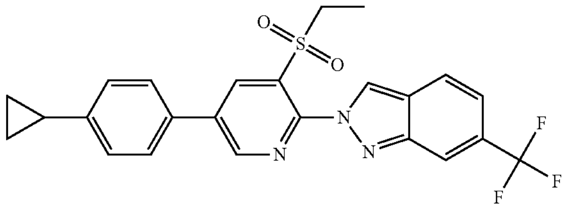
47
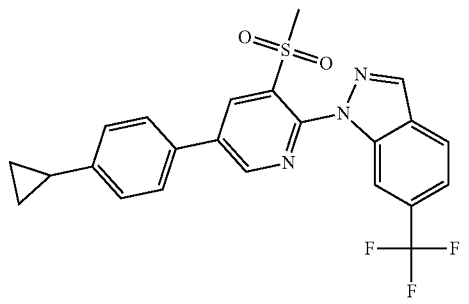

-continued
48
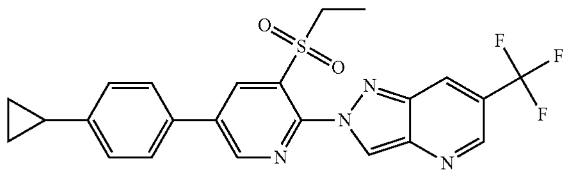
49
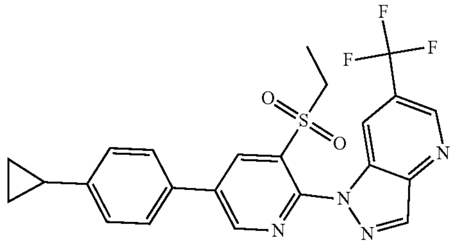
50
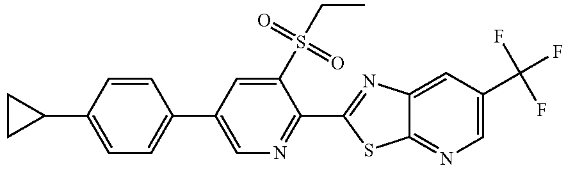
51
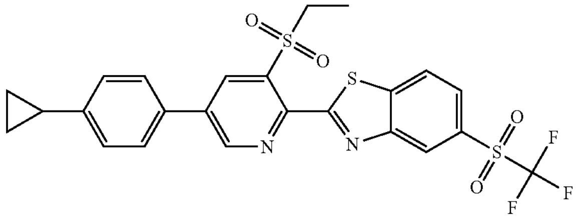
52
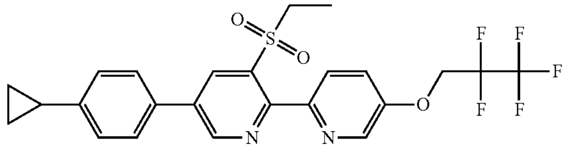
53
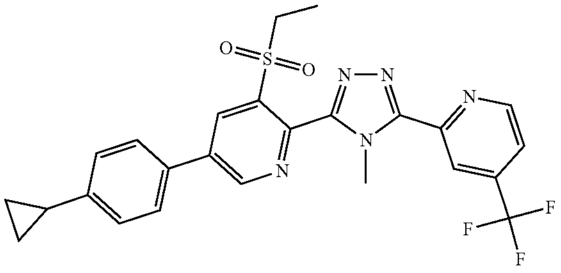
-continued
54
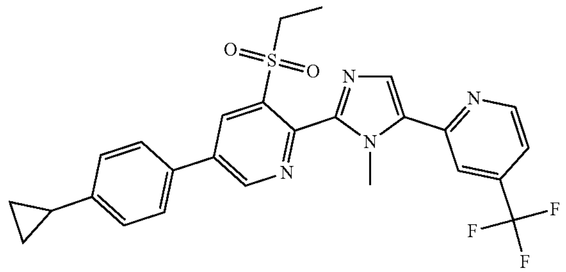
55
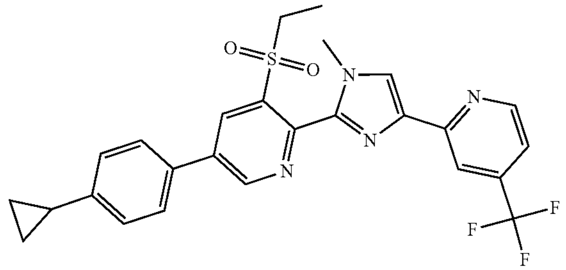
56
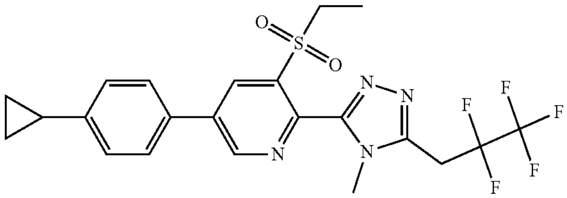
57
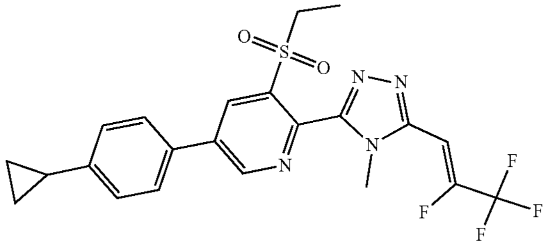
58
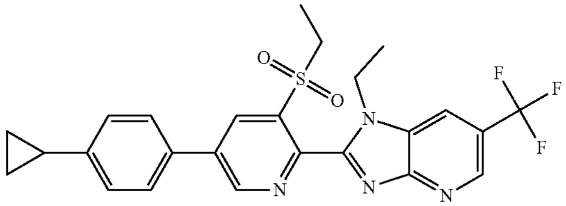
59
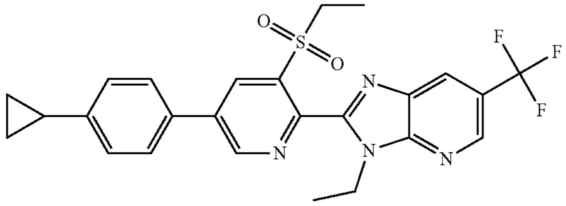

-continued
60
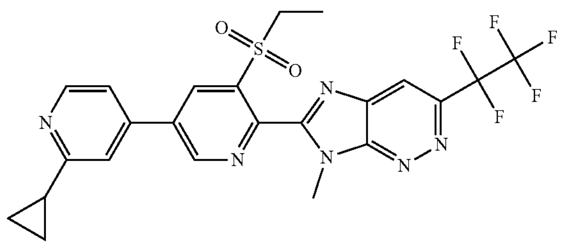
61
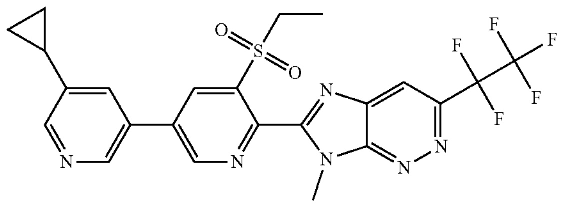
62
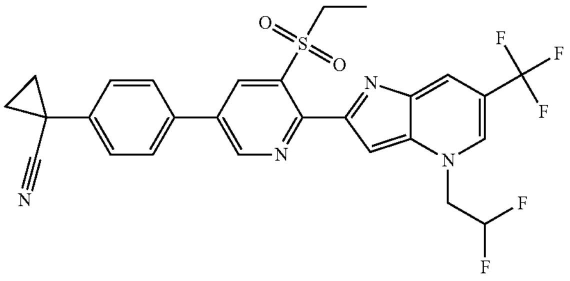
63
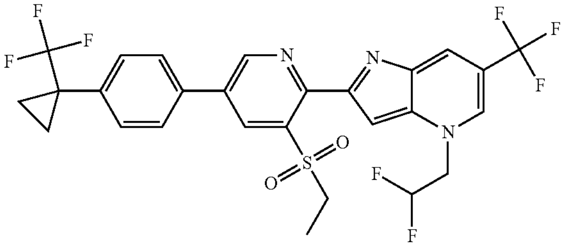
64
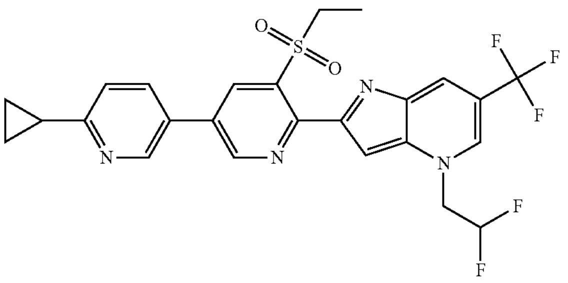
-continued
65
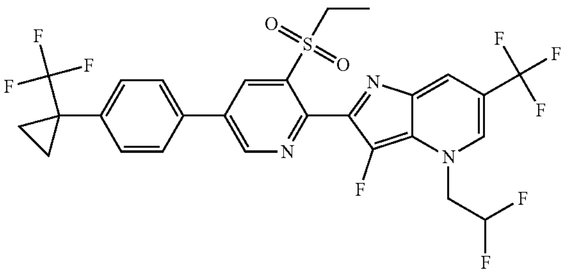
66
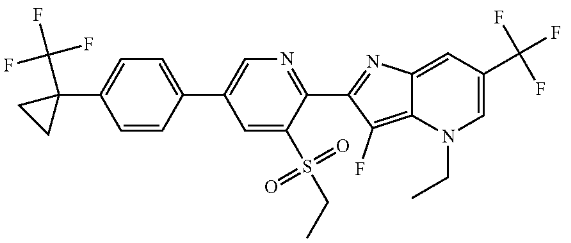
67
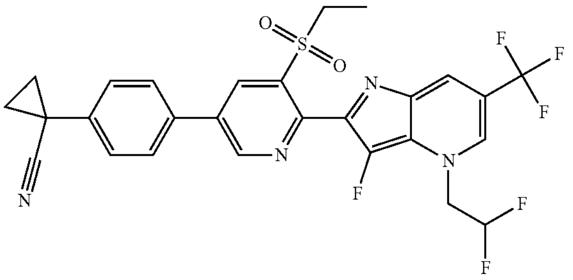
68
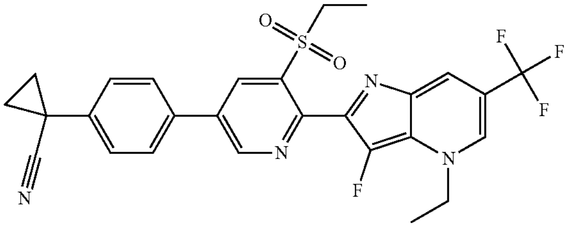
69
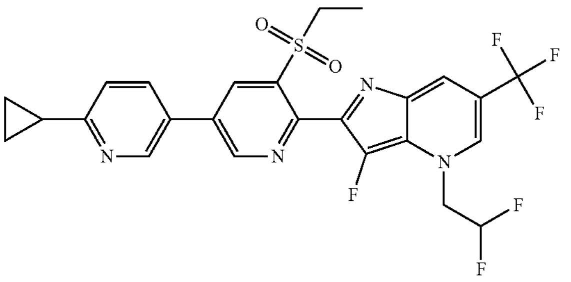

-continued
70
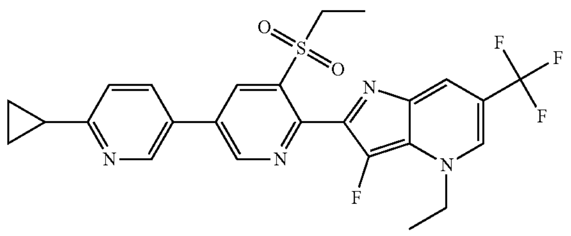
71
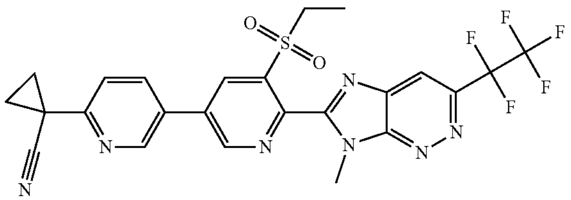
72
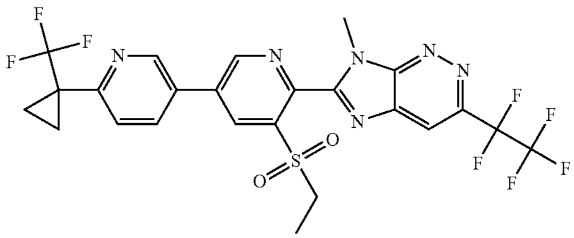
73
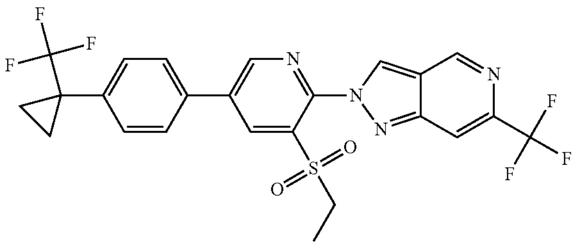
74
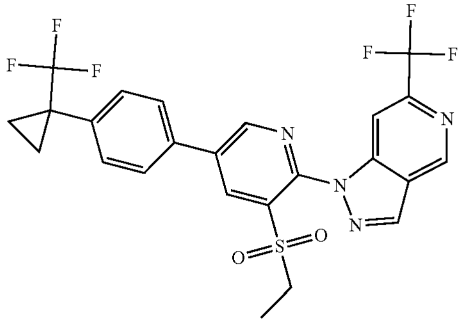
-continued
75
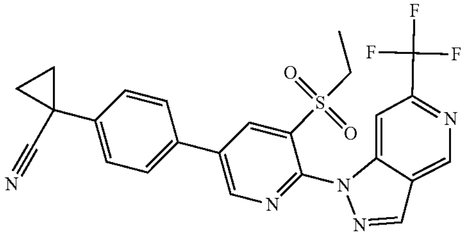
76
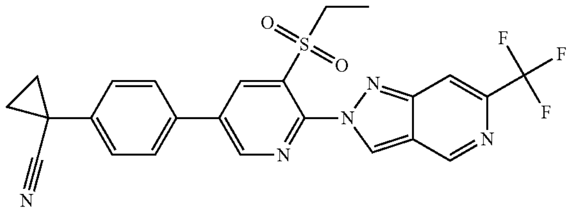
77
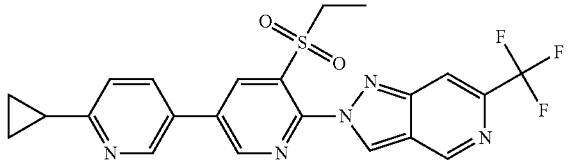
78
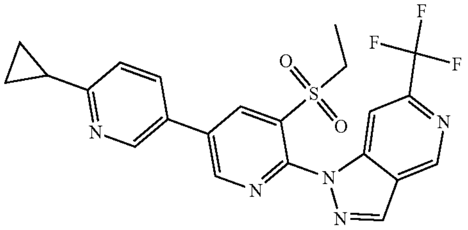
79
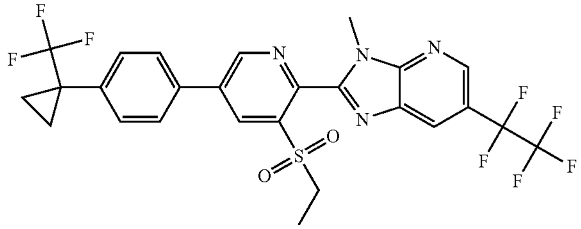
80
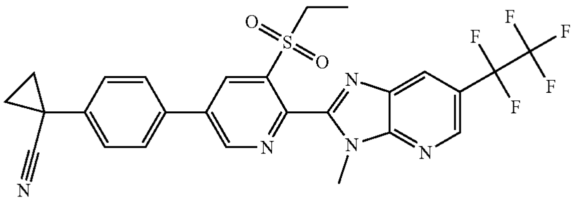
81
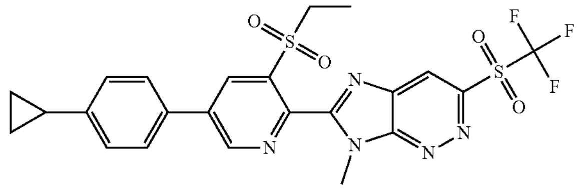

-continued
82
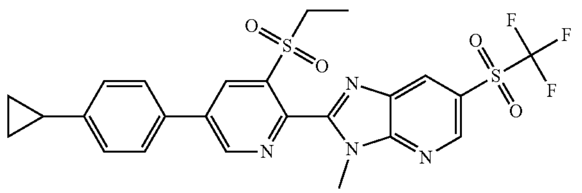
83
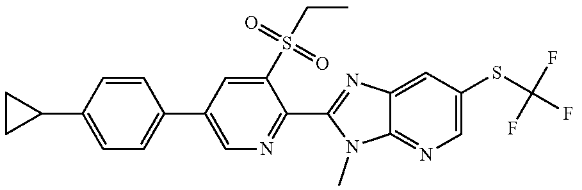
84
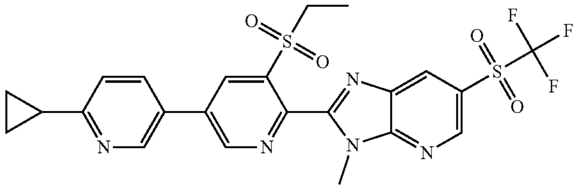
85
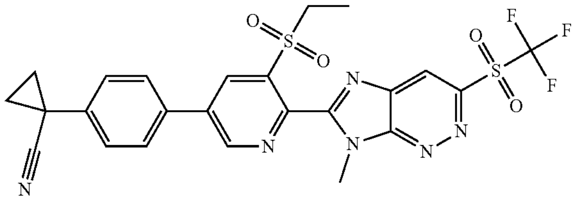
86
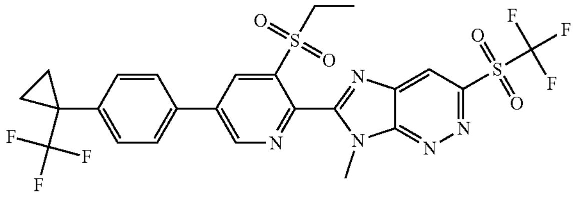
87
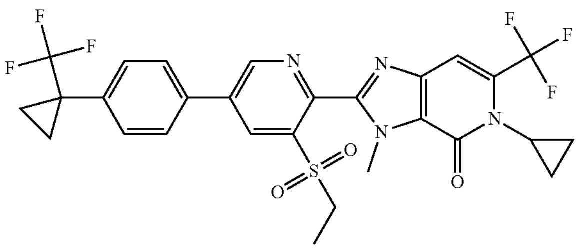
88
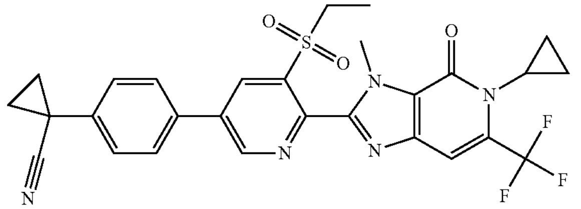
-continued
89
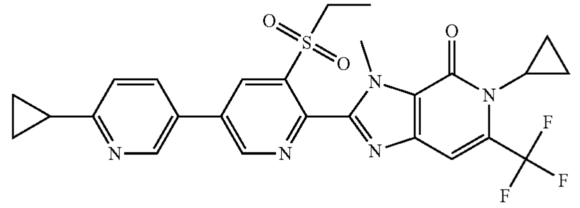
90
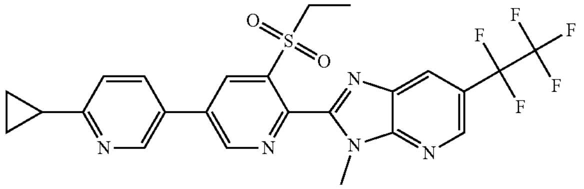
91
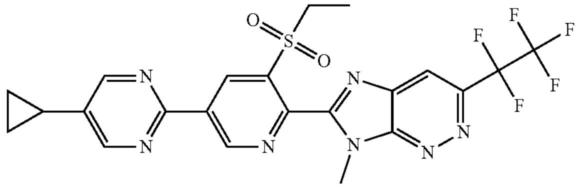
92
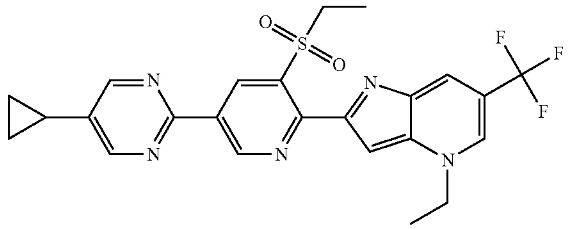
93
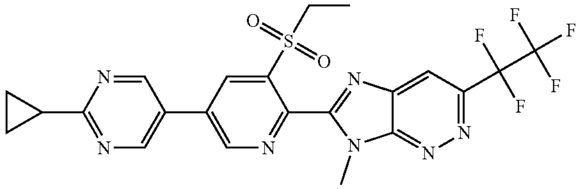
94
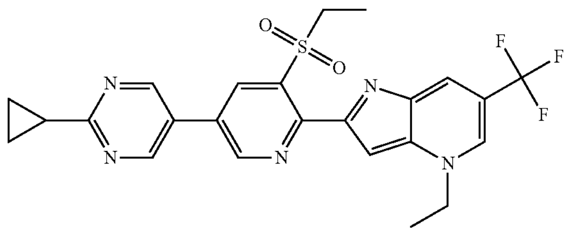

-continued
95
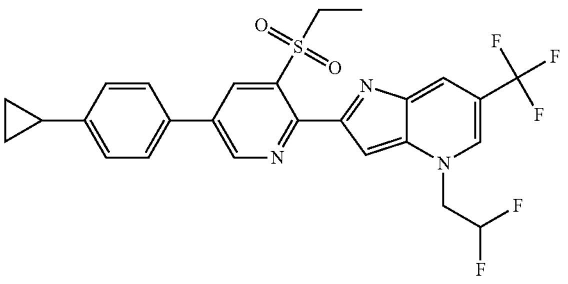
96
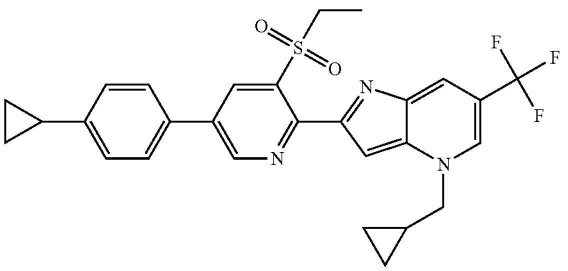
97
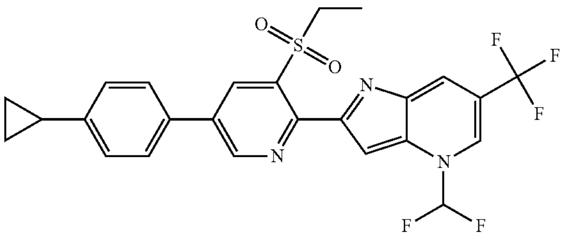
98
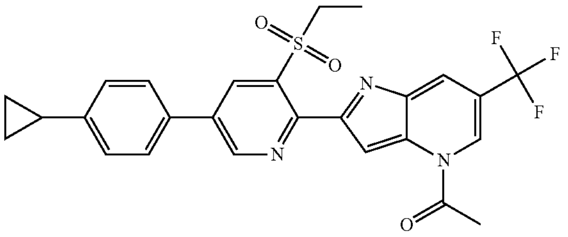
99
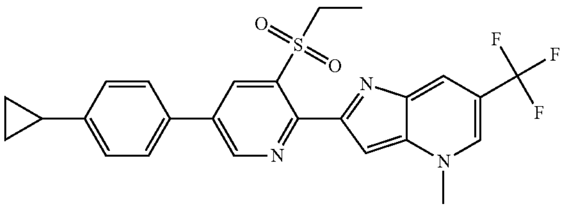
-continued
100
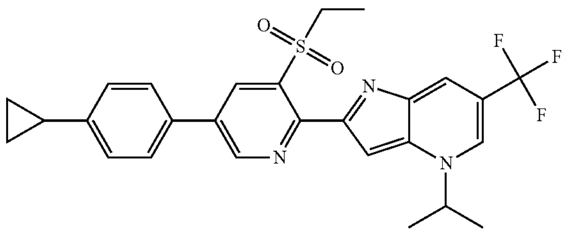
101
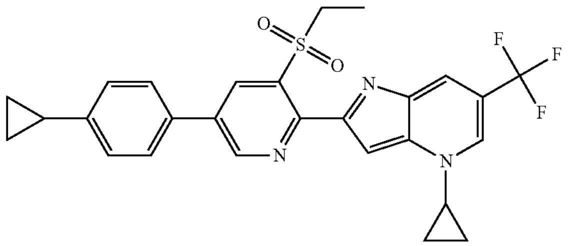
102
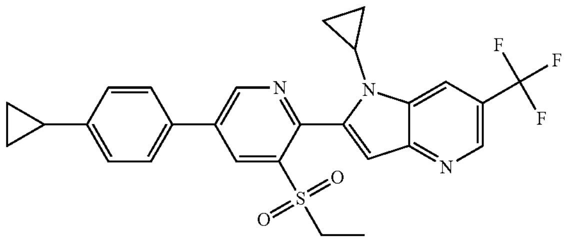
103
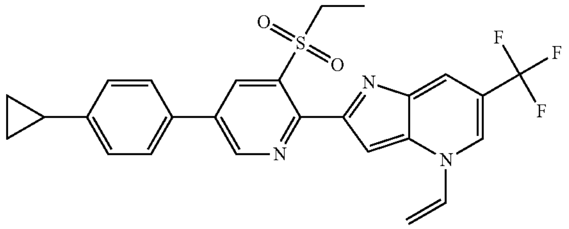
104
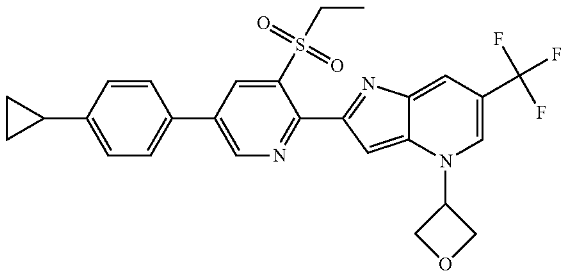
105
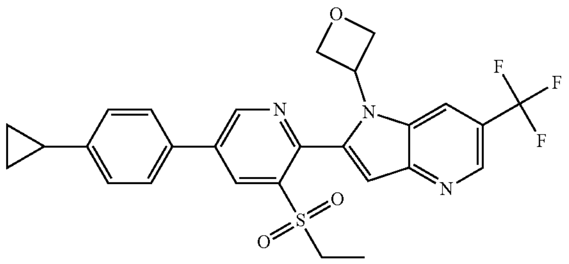

-continued
106
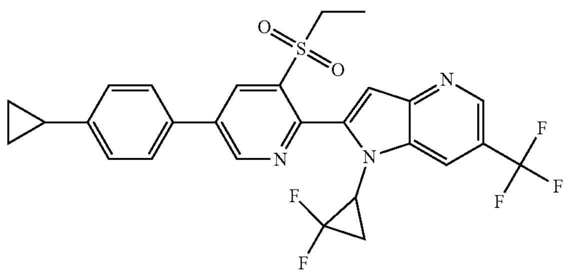
107
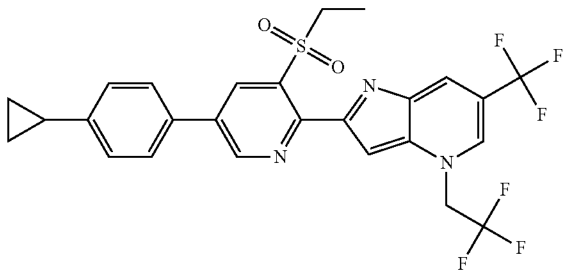
108
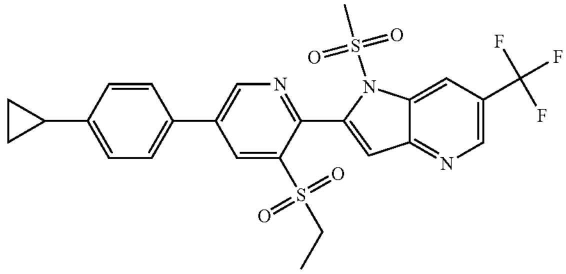
109
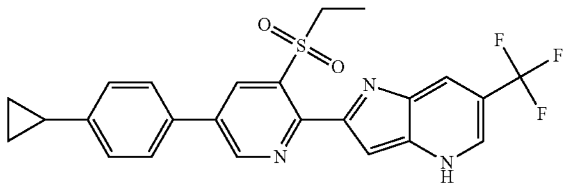
110
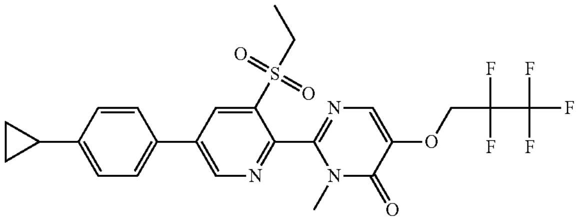
111
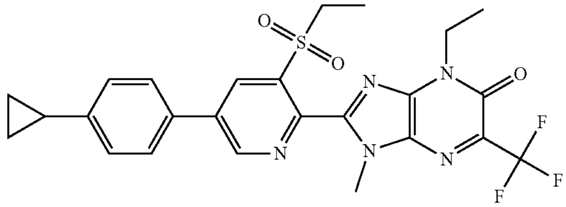
-continued
112
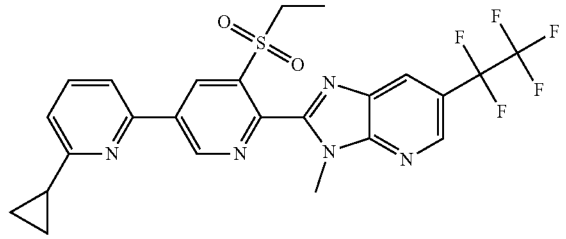
113
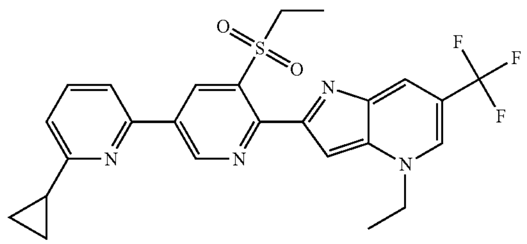
114
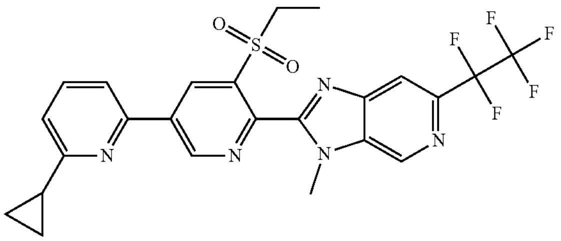
115
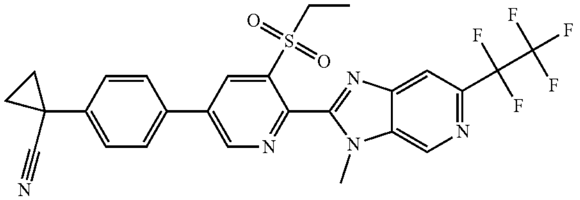
116
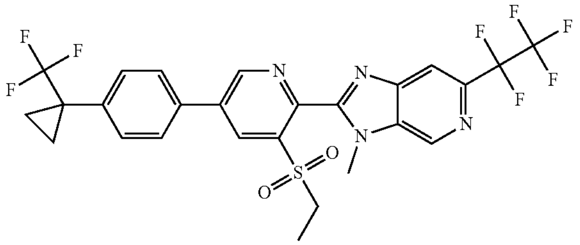
117
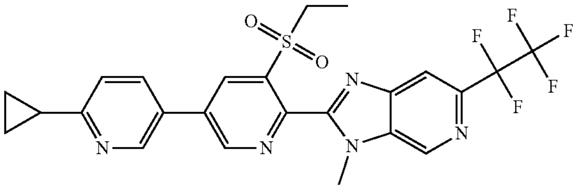

118
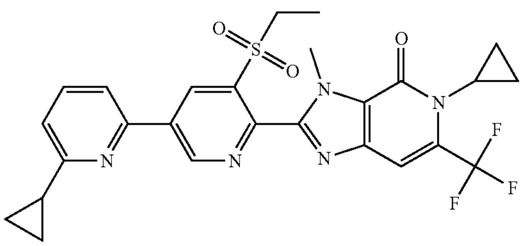
119
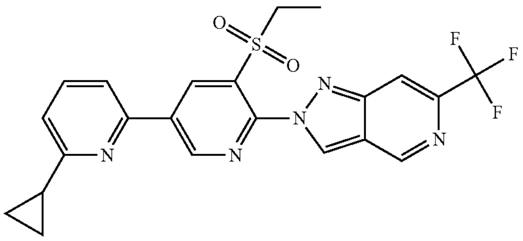
120
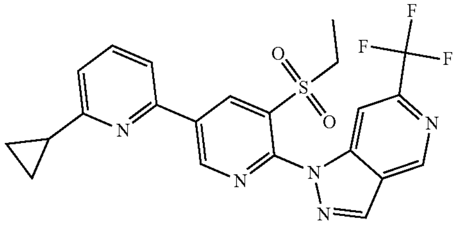
121
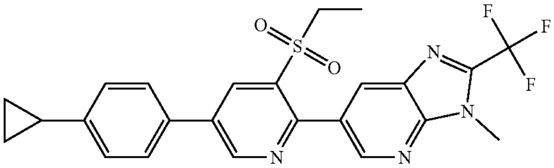
122
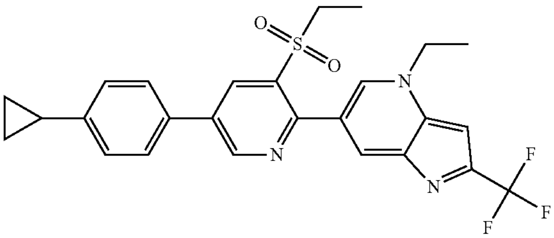
123
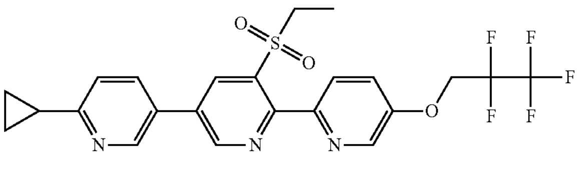
124
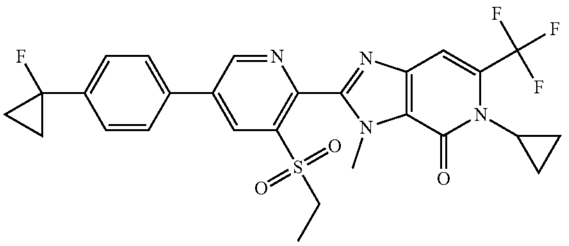
125
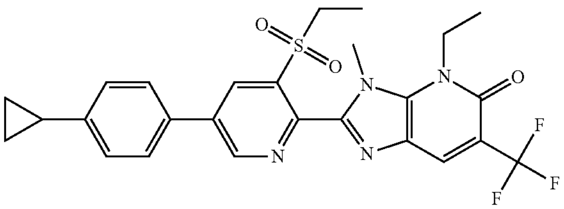
126
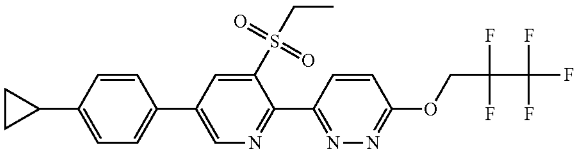
127
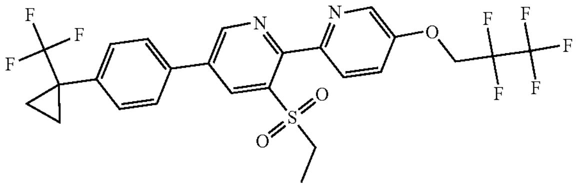
128
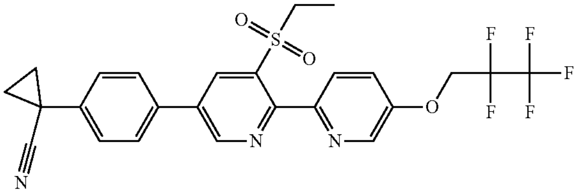
129
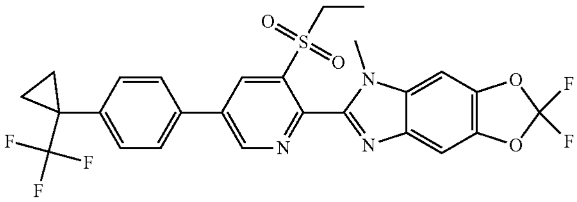
130
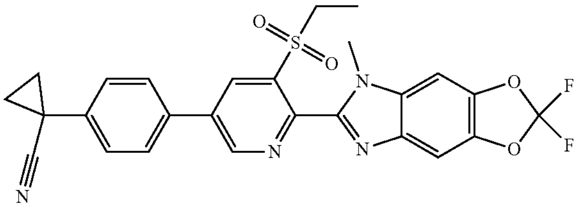

131
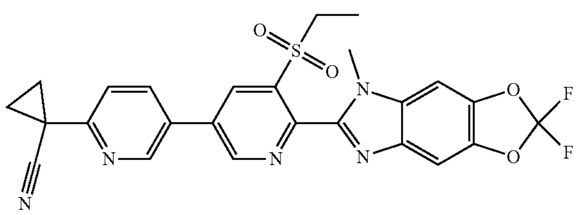
132
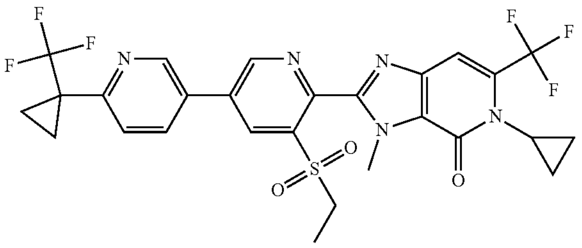
133
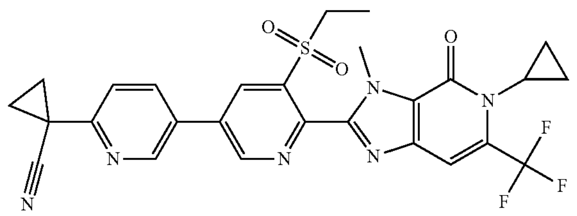
134
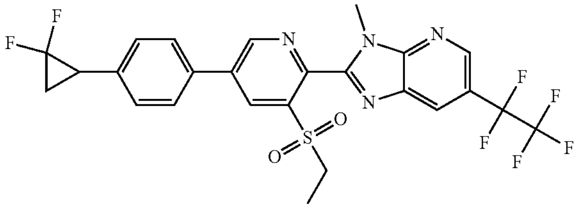
135
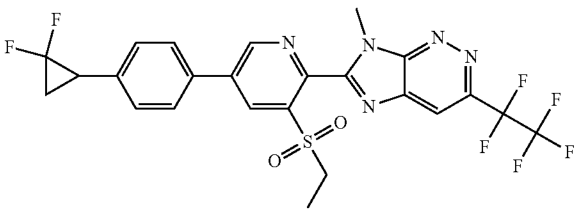
136
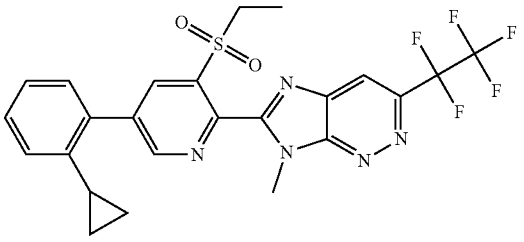
137
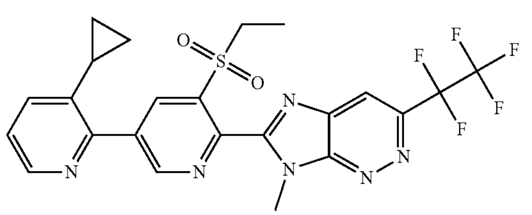
138
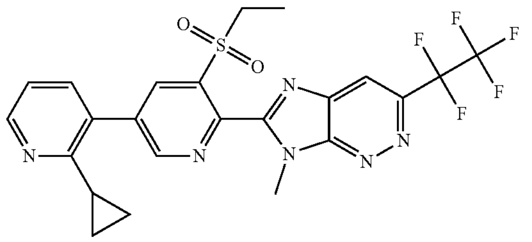
139
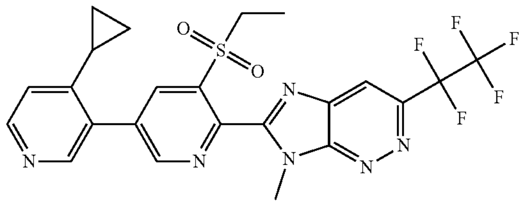
140
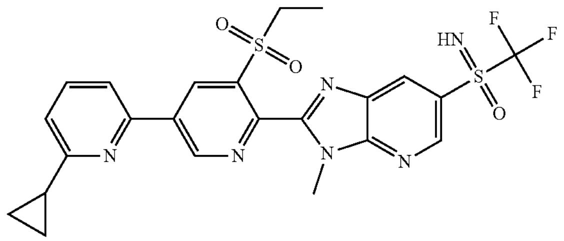
141
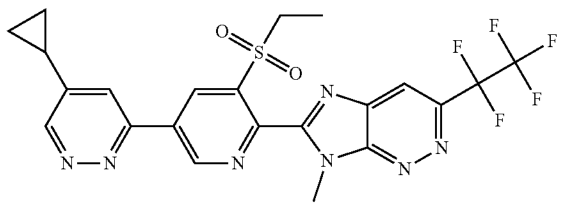
142
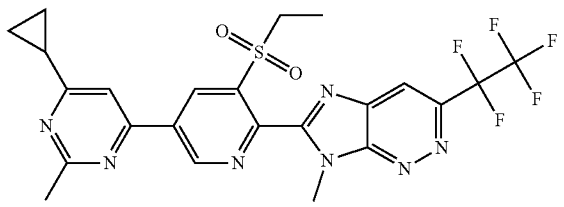

-continued
143
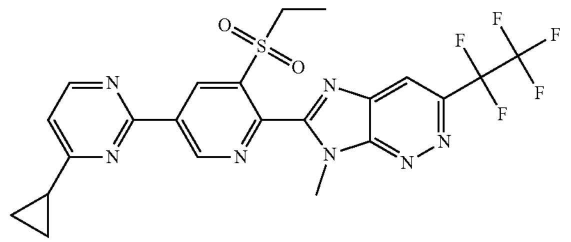
144
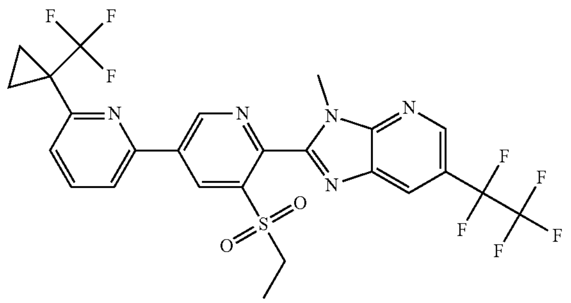
145
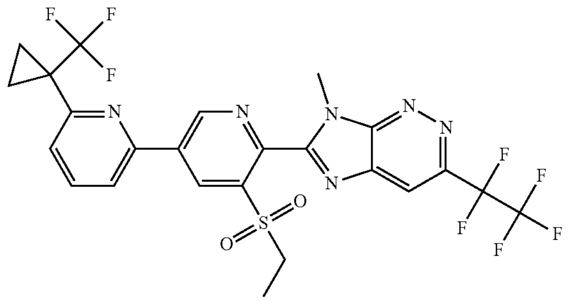
146
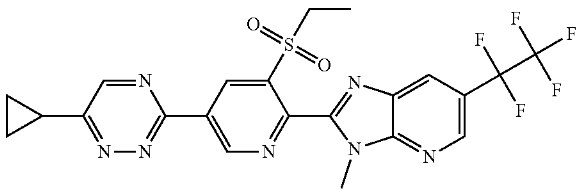
147
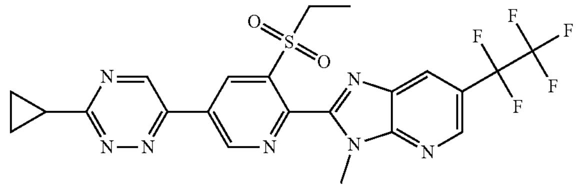
-continued
148
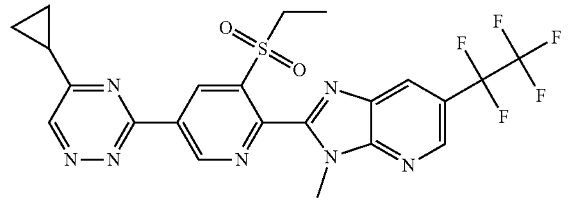
149
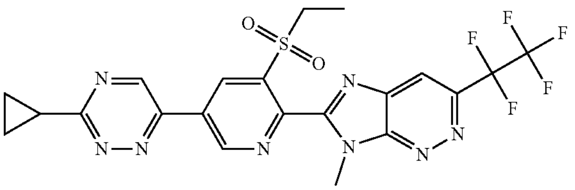
150
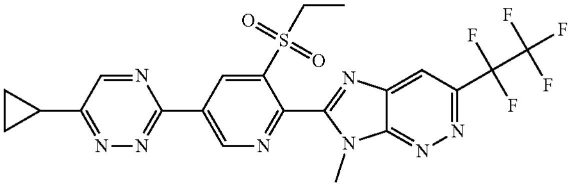
151
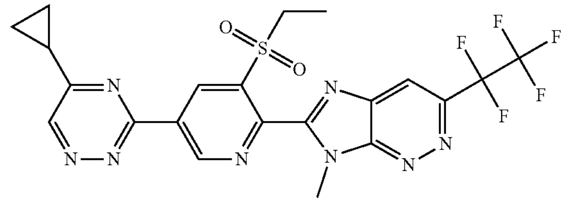
152
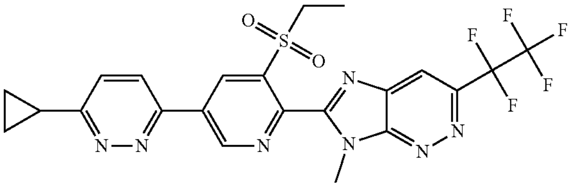
153
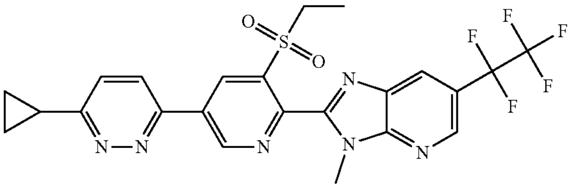
154
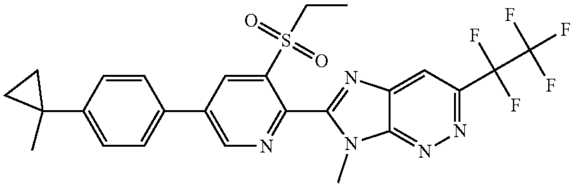

-continued
155
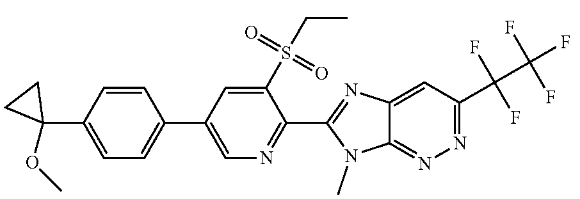
156
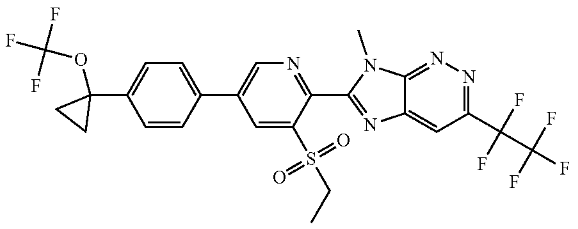
157
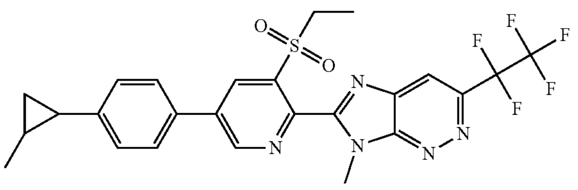
158
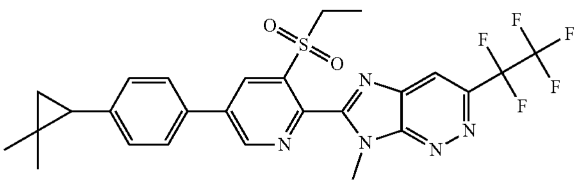
159
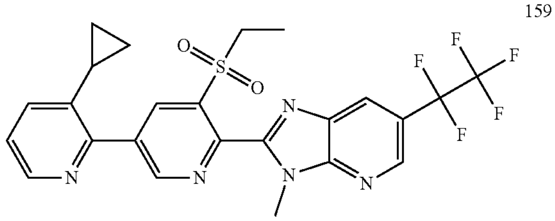
160
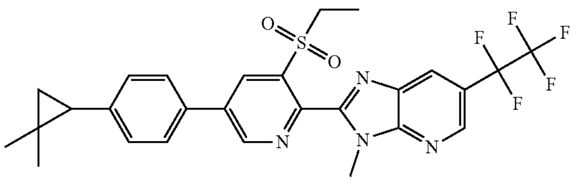
161
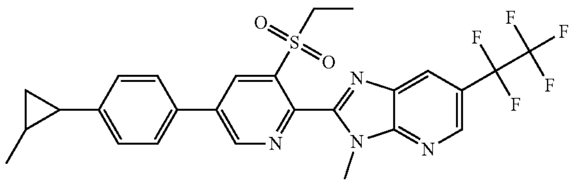
-continued
162
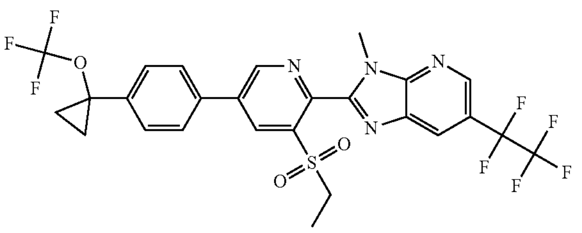
163
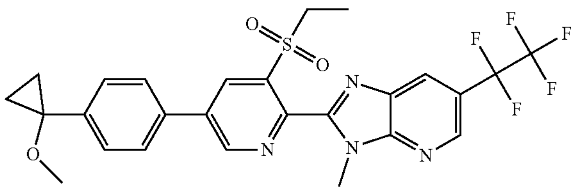
164
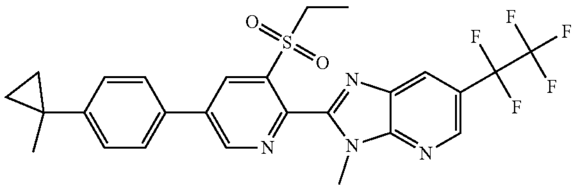
165
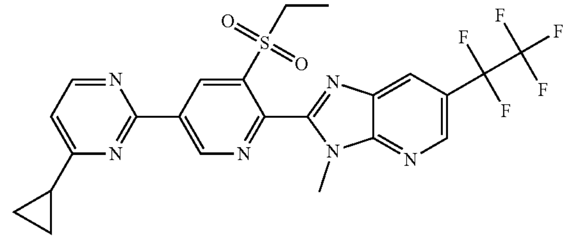
166
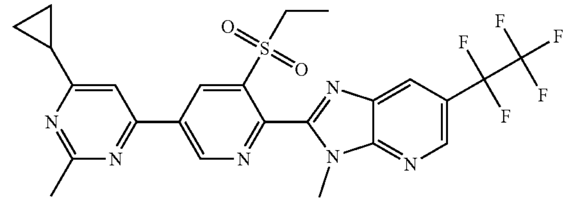
167
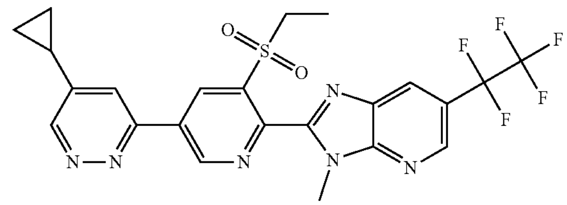
168
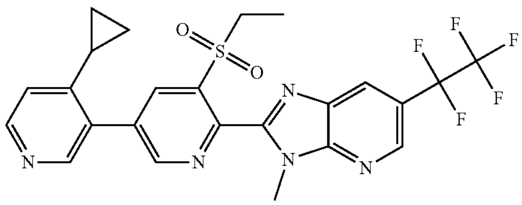

-continued
169
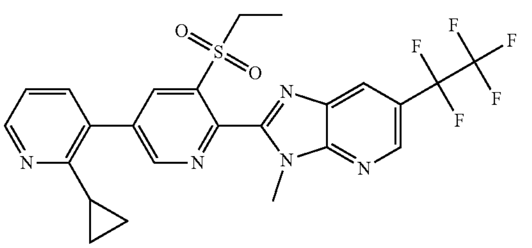
170
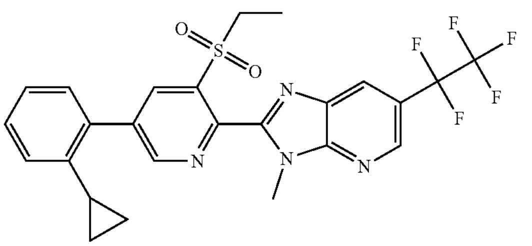
171
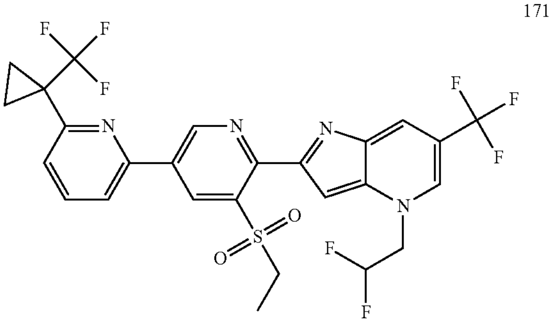
172
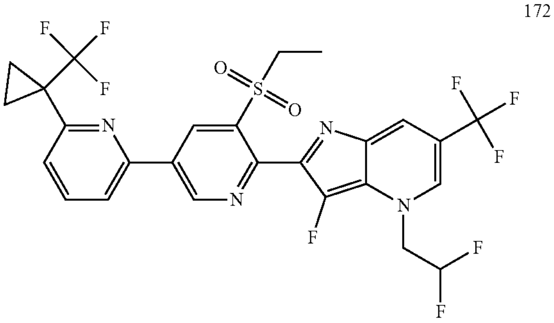
173
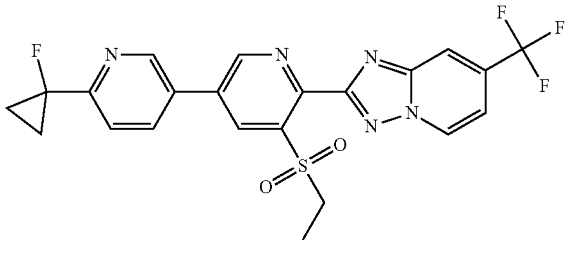
-continued
174
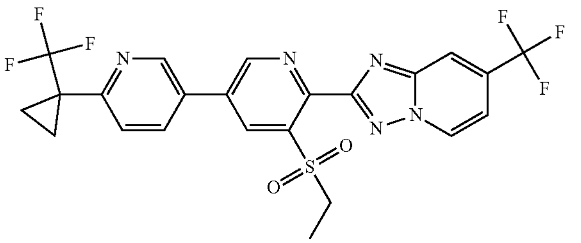
175
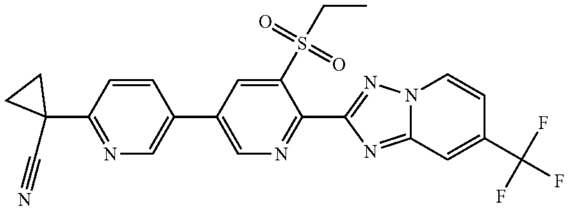
176
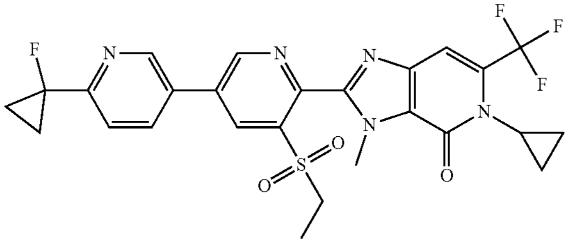
177
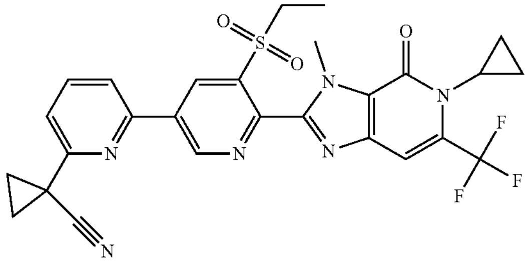
178
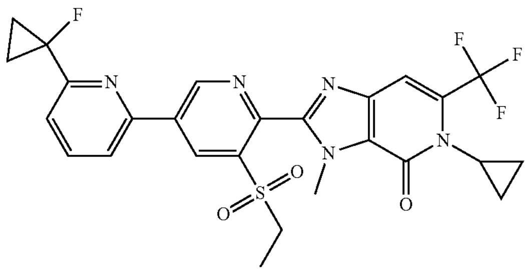
179
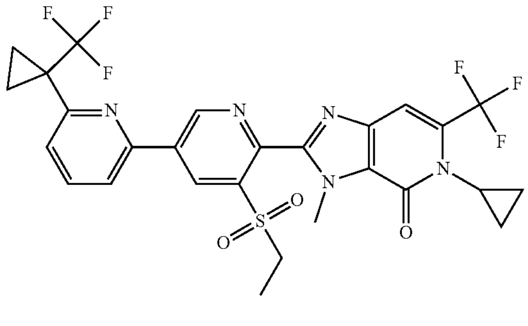

-continued
180
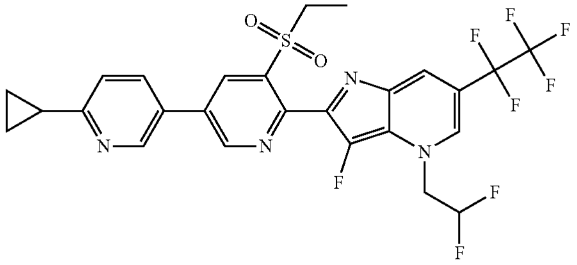
181
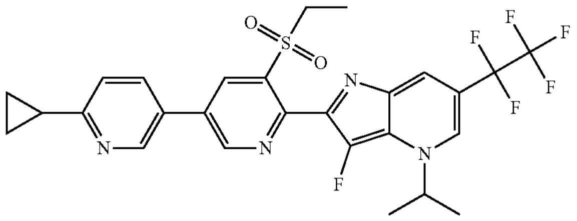
182
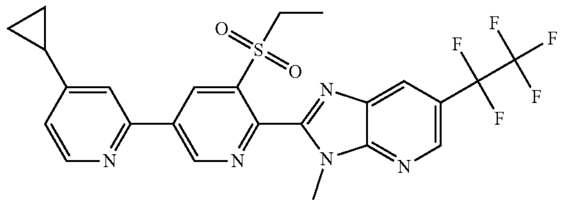
183
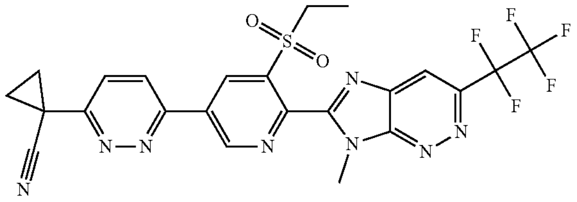
184
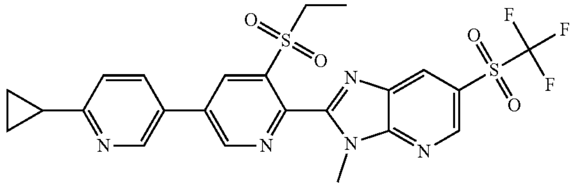
185
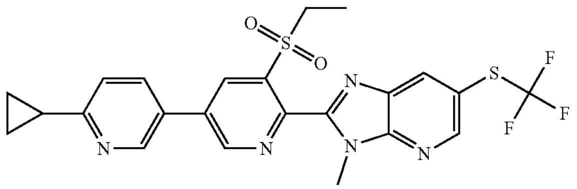
186
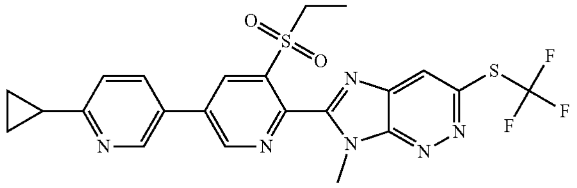
-continued
187
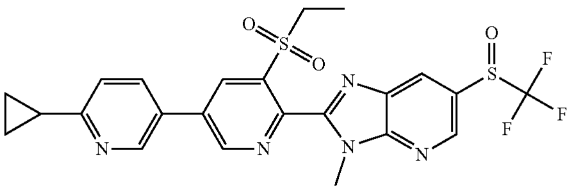
188
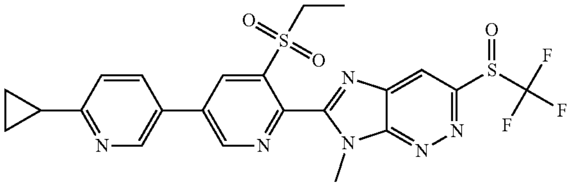
189
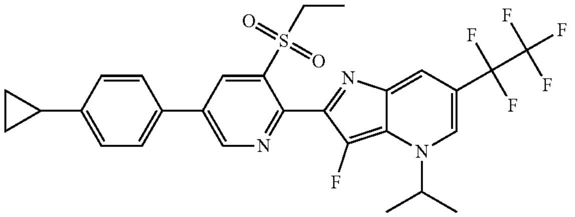
190
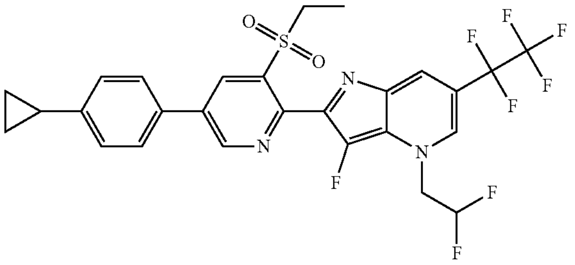
191
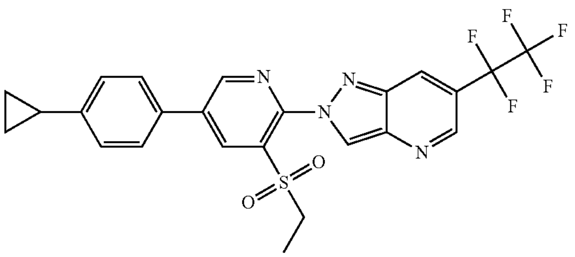
192
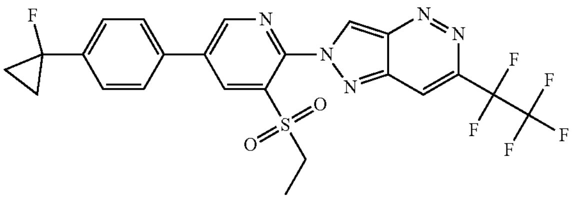

-continued
193
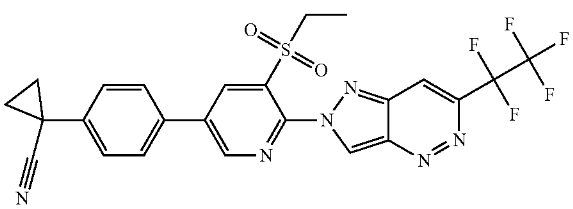
194
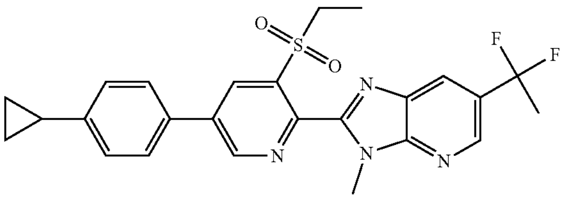
195
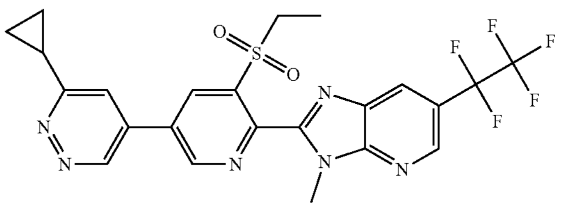
196
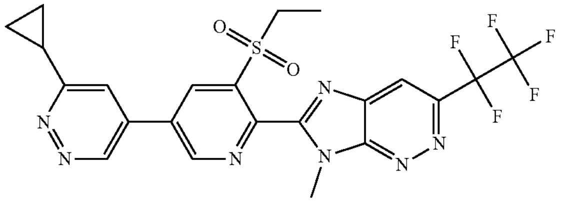
197
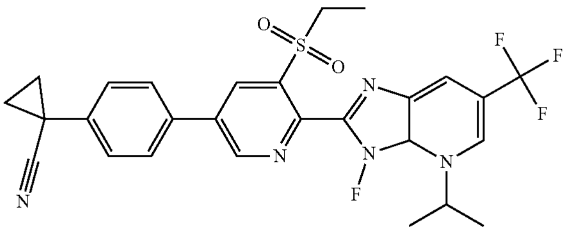
198
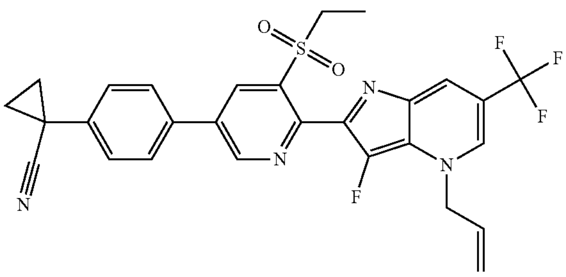
-continued
199
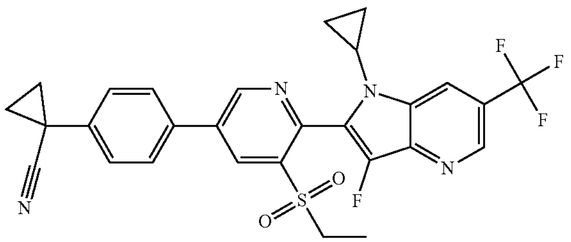
200
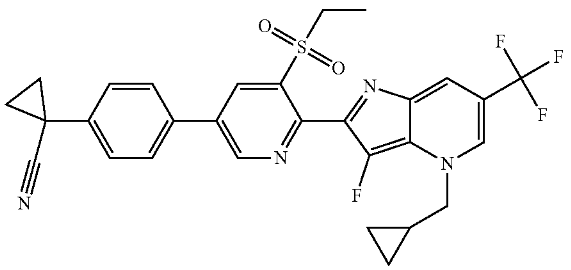
201
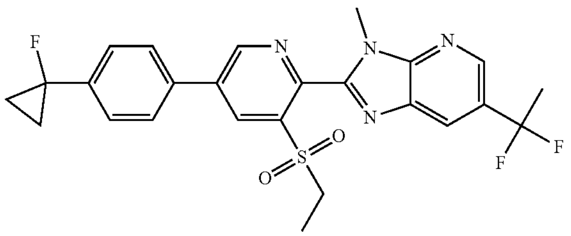
202
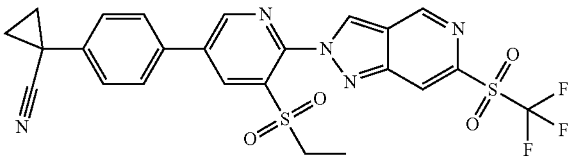
203
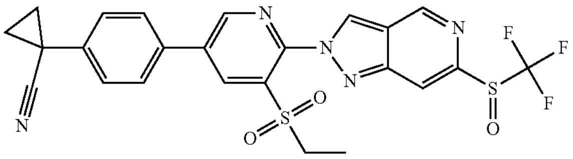
204
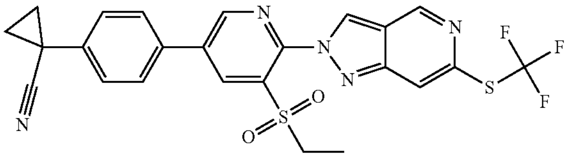
205
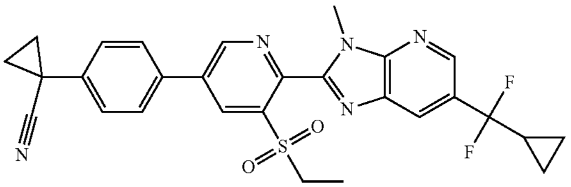

-continued

206

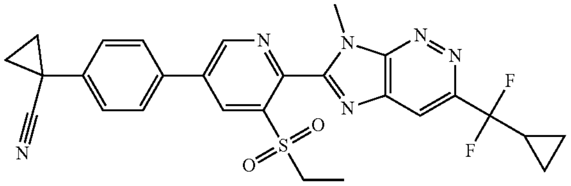

207

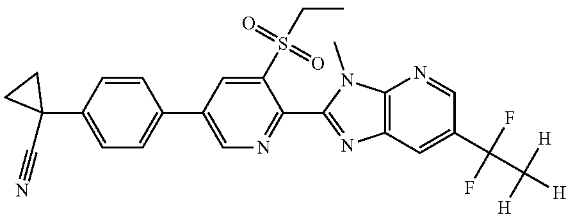

208

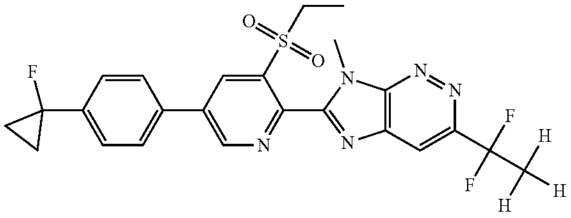

209

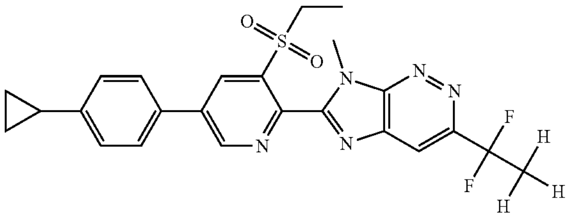

210

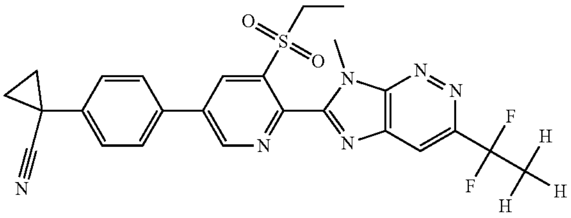

211

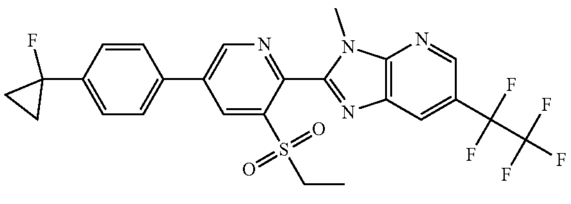

212

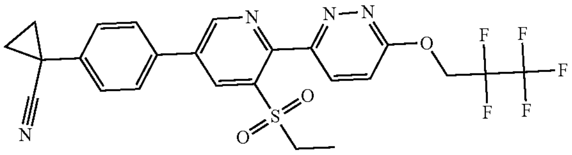

-continued

213

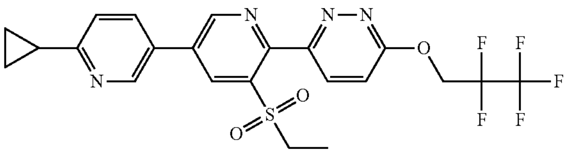

214

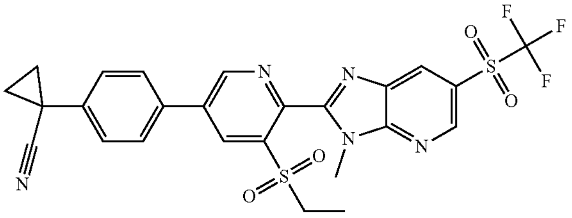

or a pharmaceutically acceptable salt thereof.

21. The compound according to claim 1, wherein:

W1, W2, W3, W4, W5 are independently C or C—H;

or

W1 is an N atom, and

W2, W3, W4, W5 are independently C or C—H;

or

W2 is an N atom, and

W1, W3, W4, W5 are independently C or C—H;

or

W1, W2 are independently an N atom, and

W3, W4, W5 are independently C or C—H;

or

W1, W3 are independently an N atom, and

W2, W4, W5 are independently C or C—H;

and n is 0 or 1;

and

Q is selected from the group consisting of:

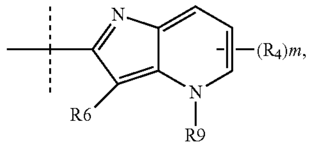

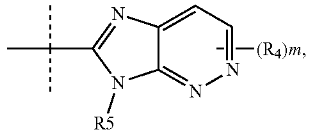

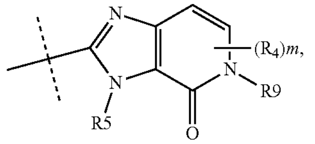

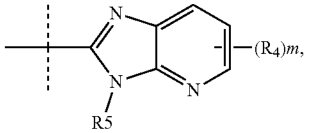
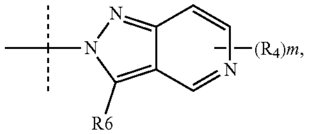
and
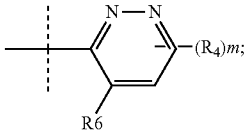
or a pharmaceutically acceptable salt thereof.
22. A compound selected from the group consisting of:
12
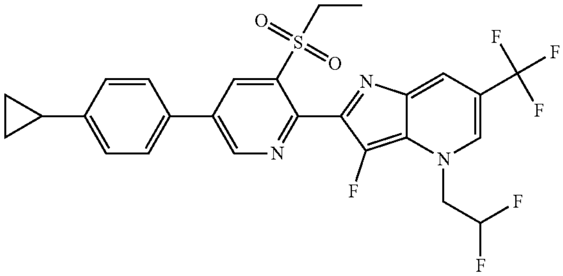
19
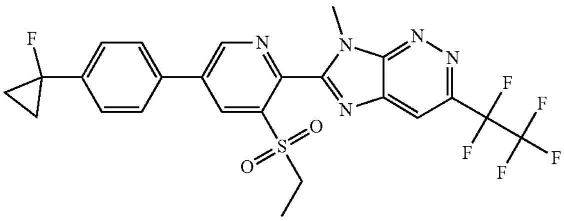
44
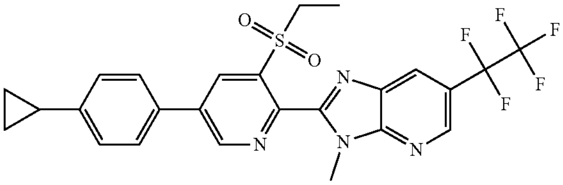
-continued
45
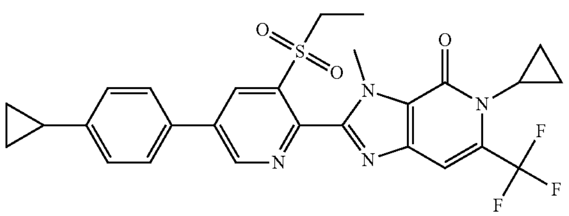
46
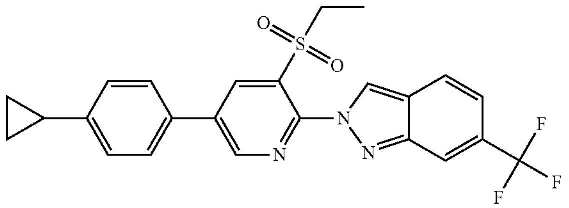
67
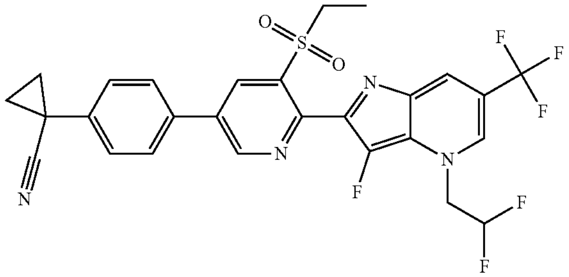
76
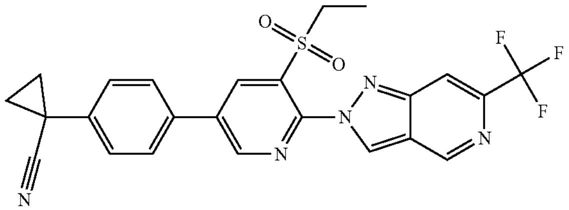
80
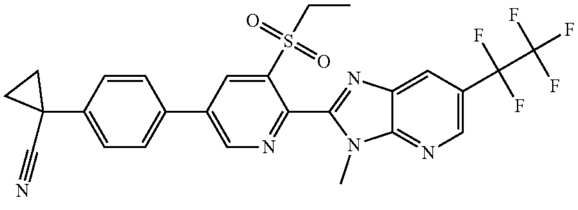
88
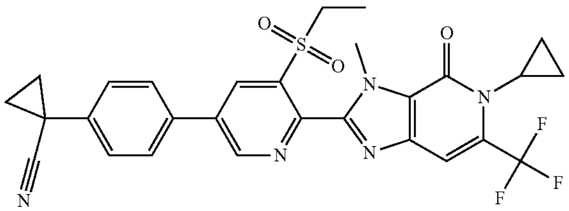

-continued
89
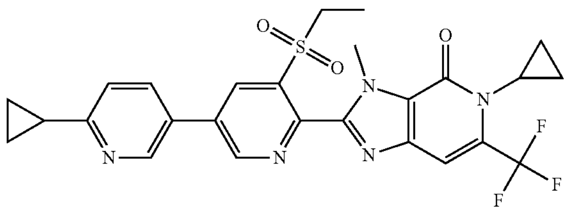
96
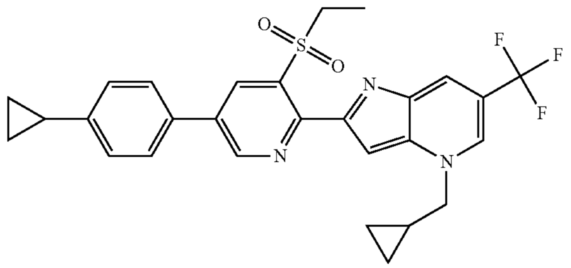
97
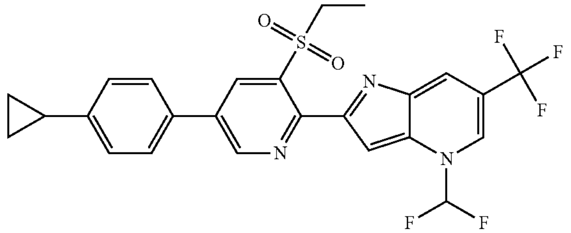
112
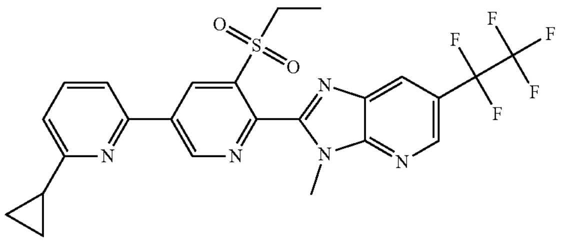
115
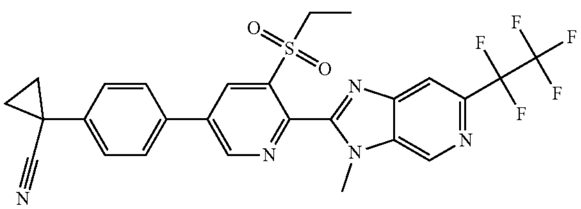
124
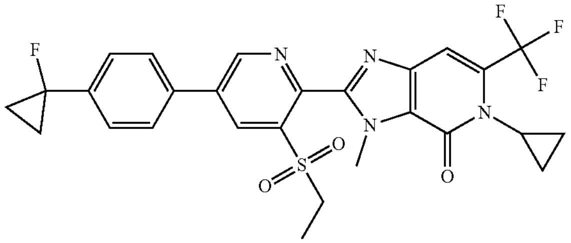
-continued
133
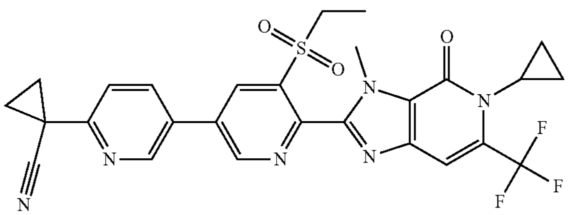
134
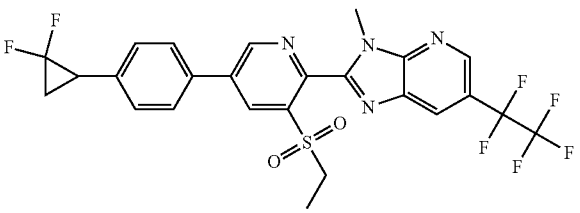
135
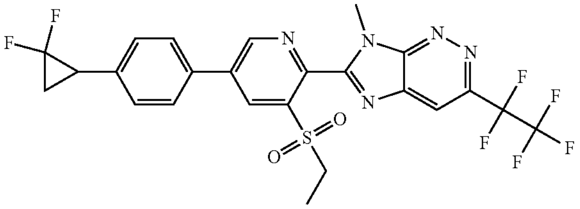
142
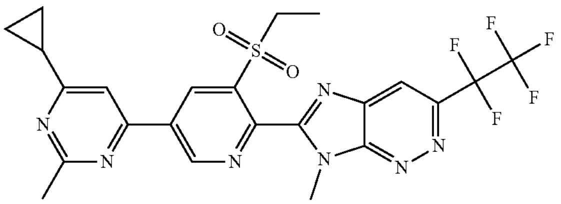
153
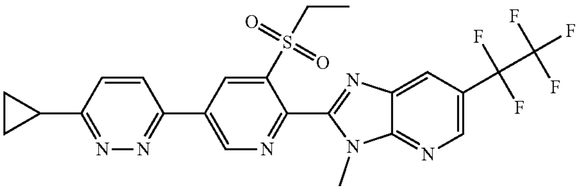
166
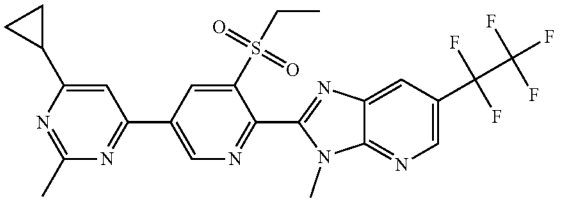

169
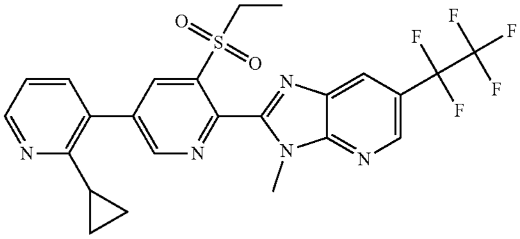
186
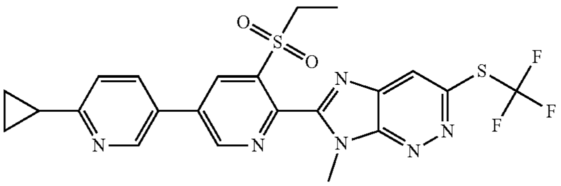
197
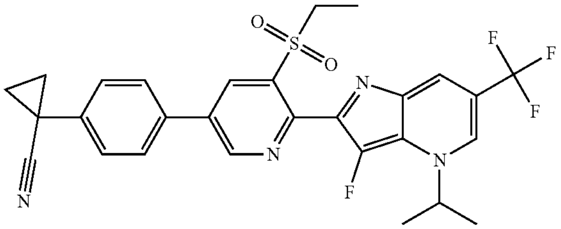
200
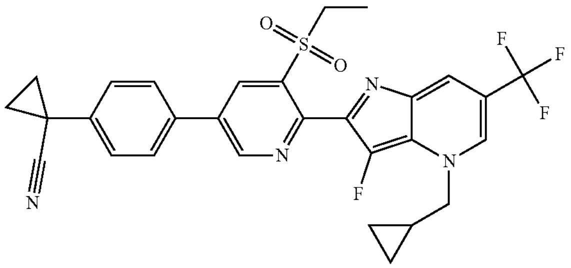
202
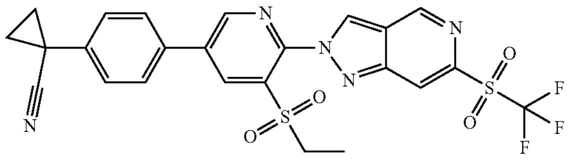
203
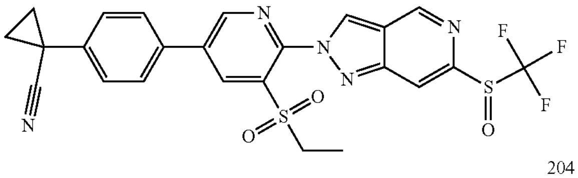
204
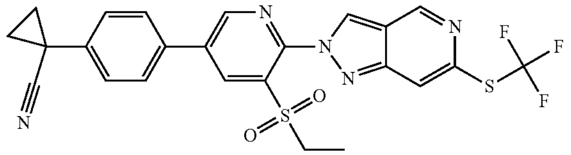
205
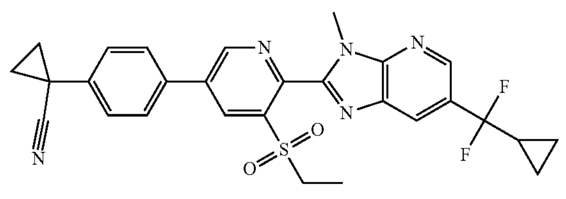
206
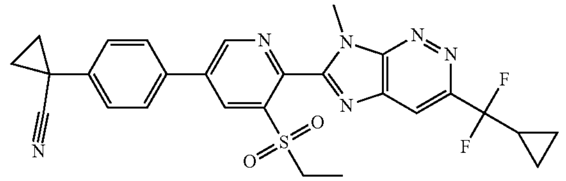
207
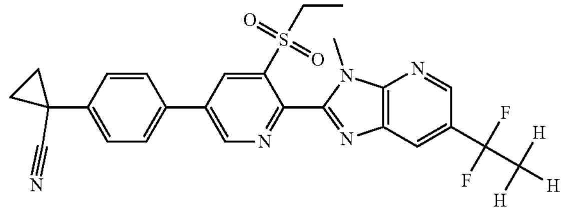
208
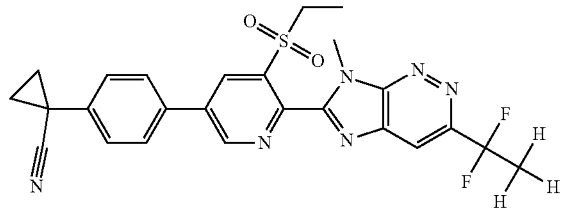
209
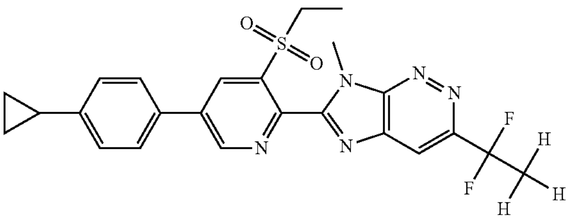
210
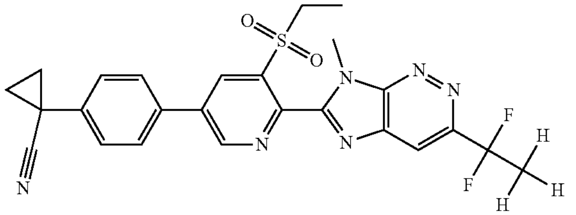
211
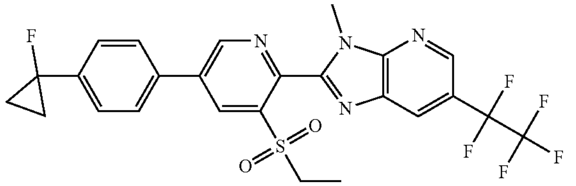

-continued

212

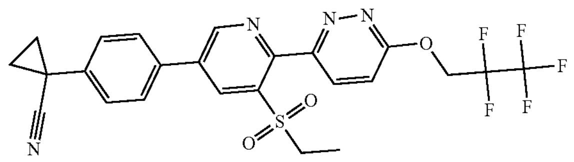

213

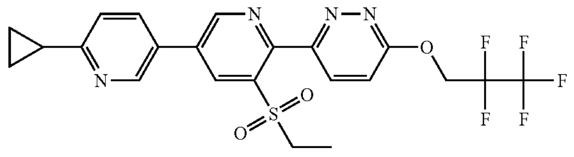

214

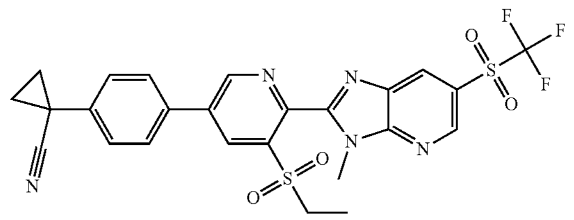

or a pharmaceutically acceptable salt thereof.

23. A pharmaceutical composition comprising one or more compound(s) according to claim 1, or a pharmaceutically acceptable salt thereof and one or more pharmaceutically acceptable excipient(s).

24. The pharmaceutical composition of claim 23, further comprising one or more additional pharmaceutically active agent(s), and one or more pharmaceutically acceptable excipient(s).

25. An antiparasitic medicament comprising the pharmaceutical composition of claim 23.

26. A method of treatment, prevention and/or control of a parasitic infection and/or infestation in an animal, the method comprising administering to an animal the pharmaceutical composition of claim 23.

27. The method of claim 26, wherein the method further comprises treatment of an ectoparasitic infection and/or infestation in the animal.

28. The method of claim 26, wherein the animal has an infestation of fleas and/or ticks.

29. The compound according to claim 1, wherein:

R4 is selected from the group consisting of $CF_3$, $C_2F_5$, CH═CF—$CF_3$, O—$CH_2$—$CF_3$, O—$CH_2$—$C_2F_5$, S-methyl, S(O)-methyl; $S(O)_2$-methyl, S—$CF_3$, S(O)—$CF_3$, and $S(O)_2$—$CF_3$; and R5 and R9 are each independently selected from the group consisting of methyl, ethyl, isopropyl, ethenyl, $CF_3$, $CH_2$—$CHF_2$, $CH_2$—$CF_3$, $CHF_2$, cyclopropyl, cyclopropyl-methyl, cyclopropyl substituted with one or more $CF_3$, cyclopropyl substituted with one or more F, C(O)-methyl, aziridinyl, oxetanyl, S-methyl, S(O)-methyl, $S(O)_2$-methyl, S—$CF_3$, S(O)—$CF_3$, and $S(O)_2$—$CF_3$; and $R_v$, $R_w$, $R_x$, $R_y$, $R_z$ are each independently selected from the group consisting of F, Cl, Br, I, methyl, ethyl, and $CF_3$; and R, R1a, R1b, R2a, R2b, R3 are each independently selected from the group consisting of F, Cl, Br, I, $CH_3$, $CF_3$, $CHF_2$, $CH_2$—$CF_3$, $CH_2$—$CHF_2$, $CH_2$—$CH_2F$, $CF_2$—$CH_3$, $CH_2F$, $CF_2$—$CF_3$, $CF_2$—$CHF_2$, cyclopropyl, phenyl, methoxy, ethoxy, propoxy, O—$CF_3$, S—$CH_3$, S(O)—$CH_3$, $S(O)_2$—$CH_3$, S—$CF_3$, S(O)—CF, and $S(O)_2$—$CF_3$; or R together with R1a or R1b forms an unsubstituted or substituted carbocycle or an unsubstituted or substituted heterocycle, and the carbocycle or heterocycle if substituted is independently substituted with one, two or three substituents each independently selected from the group consisting of F, Cl, Br, I, $CH_3$, $CF_3$, $CHF_2$, $CH_2$—$CF_3$, $CH_2$—$CHF_2$, $CH_2$—$CH_2F$, $CF_2$—$CH_3$, $CH_2F$, $CF_2$—$CF_3$, $CF_2$—$CHF_2$, cyclopropyl, phenyl, methoxy, ethoxy, propoxy, O—$CF_3$, S—$CH_3$, S(O)—$CH_3$, $S(O)_2$—$CH_3$, S—$CF_3$, S(O)—$CF_3$, and $S(O)_2$—$CF_3$.

30. The compound according to claim 1 wherein Q is:

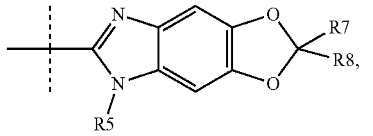

and

R5 is methyl and R7 and R8 are each F; or

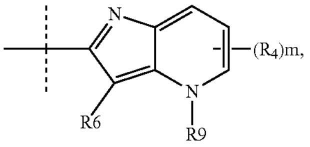

and

R6 is hydrogen or F, R9 is $CHF_2$ or $CH_2$—$CHF_2$ or ethyl or $CH_2$-cyclopropyl, m is 1, and R4 is $CF_3$; or

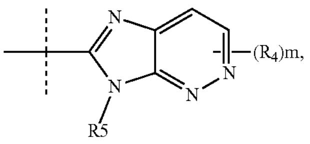

and

R5 is methyl, m is 1, and R4 is $CF_2$-cyclopropyl or $CF_2$—$CF_3$ or S—$CF_3$ or $S(O)_2$—$CF_3$; or

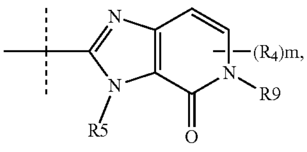

and

R5 is methyl, R9 is cyclopropyl, m is 1, and R4 is $CF_3$; or

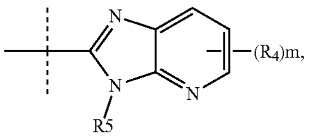

and

R5 is methyl, m is 1, and R4 is $CF_2$—$CF_3$ or $CF_2$-cyclopropyl or $S(O)_2$—$CF_3$; or

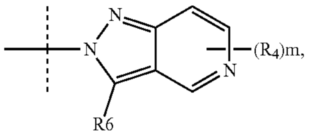

and

R6 is hydrogen or F, m is 1, and R4 is $CF_3$ or $CF_2$—$CF_3$ or S—$CF_3$ or S(O)—$CF_3$ or $S(O)_2$—$CF_3$; or

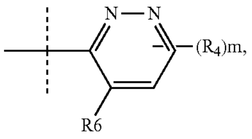

and

R6 is hydrogen, m is 1, and R4 is —O—$CF_2$—$CF_3$.

31. The compound according to claim 21, wherein:

W1 is a C atom, and

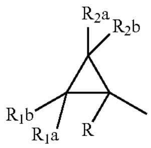

is attached to W1; or

W2 is a C atom, and

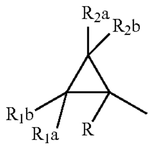

is attached to W2; or

W3 is a C atom, and

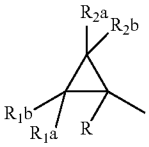

is attached to W3; or

W4 is a C atom, and

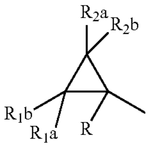

is attached to W4; and

R1a, R1b, R2a, R2b are independently hydrogen or F.

32. The compound according to claim 21, wherein Q is:

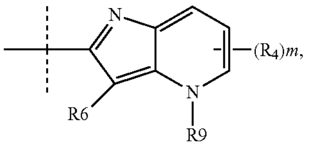

and

R6 is hydrogen or F, R9 is $CHF_2$ or $CH_2$—$CHF_2$ or ethyl or $CH_2$-cyclopropyl, m is 1 and R4 is $CF_3$; or

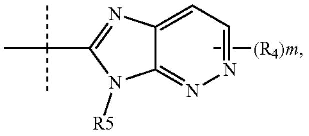

and

R5 is methyl, m is 1 and R4 is $CF_2$-cyclopropyl or $CF_2$—$CF_3$ or S—$CF_3$ or $S(O)_2$—$CF_3$; or

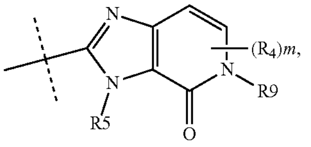

and

R5 is methyl, R9 is cyclopropyl, m is 1 and R4 is $CF_3$; or

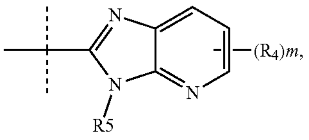

and
R5 is methyl, m is 1 and R4 is $CF_2$—$CF_3$ or $CF_2$-cyclopropyl or S(O),—$CF_3$; or
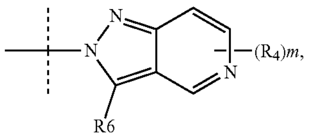
and
R6 is hydrogen or F, m is 1 and R4 is $CF_3$ or $CF_2$—$CF_3$ or S—$CF_3$ or S(O)—$CF_3$ or S(O)—$CF_3$; or
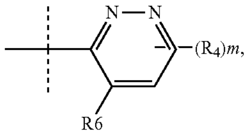
and
R6 is hydrogen, m is 1 and R4 is —O—$CF_2$—$CF_3$.
* * * * *